(12) United States Patent
Amishiro et al.

(10) Patent No.: US 8,673,908 B2
(45) Date of Patent: Mar. 18, 2014

(54) KYNURENINE PRODUCTION INHIBITOR

(75) Inventors: Nobuyoshi Amishiro, Sakai (JP); Yuichi Fukuda, Sunto-gun (JP); Keisuke Kimpara, Sunto-gun (JP); Motoya Mie, Sunto-gun (JP); Hisashi Tagaya, Sunto-gun (JP); Takeshi Takahashi, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 281 days.

(21) Appl. No.: 13/128,516

(22) PCT Filed: Nov. 9, 2009

(86) PCT No.: PCT/JP2009/069065
§ 371 (c)(1),
(2), (4) Date: May 10, 2011

(87) PCT Pub. No.: WO2010/053182
PCT Pub. Date: May 14, 2010

(65) Prior Publication Data
US 2011/0237584 A1 Sep. 29, 2011

(30) Foreign Application Priority Data

Nov. 10, 2008 (JP) ................................ 2008-287256

(51) Int. Cl.
| A61K 31/535 | (2006.01) |
| A01N 43/58 | (2006.01) |
| A01N 43/60 | (2006.01) |
| A61K 31/495 | (2006.01) |
| A61K 31/50 | (2006.01) |
| C07D 413/00 | (2006.01) |
| C07D 491/00 | (2006.01) |
| C07D 241/02 | (2006.01) |

(52) U.S. Cl.
USPC ........ 514/234.8; 514/249; 544/119; 544/350; 544/408

(58) Field of Classification Search
USPC .................... 514/234.8, 249, 252.11, 255.05; 544/119, 350, 357, 405
See application file for complete search history.

(56) References Cited

U.S. PATENT DOCUMENTS

| 5,250,549 | A | 10/1993 | Yoshino et al. |
| 5,292,758 | A | 3/1994 | Yoshino et al. |
| 5,332,751 | A | 7/1994 | Yoshino et al. |
| 5,434,172 | A | 7/1995 | Yoshino et al. |
| 5,610,304 | A | 3/1997 | Yoshino et al. |
| 5,610,320 | A | 3/1997 | Yoshino et al. |
| 5,861,401 | A | 1/1999 | Bradbury |
| 6,083,951 | A | 7/2000 | Bradbury |
| 6,927,214 | B1 | 8/2005 | Teng et al. |
| 7,410,972 | B2 | 8/2008 | Baxter et al. |
| 7,662,825 | B2 | 2/2010 | Baxter et al. |
| 7,732,442 | B2 | 6/2010 | Habashita et al. |
| 2005/0075346 | A1 | 4/2005 | Baxter et al. |
| 2006/0004010 | A1 | 1/2006 | Habashita et al. |
| 2006/0025423 | A1 | 2/2006 | Baxter et al. |
| 2007/0093491 | A1 | 4/2007 | Baxter et al. |
| 2007/0254886 | A1 | 11/2007 | Habashita et al. |

(Continued)

FOREIGN PATENT DOCUMENTS

| EP | 0 472 053 | 2/1992 |
| EP | 1541563 | * 6/2005 |

(Continued)

OTHER PUBLICATIONS

Supplementary European Search Report dated May 22, 2012 issued in EP Application No. 09824879.2.

(Continued)

*Primary Examiner* — Sreeni Padmanabhan
*Assistant Examiner* — Uma Ramachandran
(74) *Attorney, Agent, or Firm* — Wenderoth, Lind & Ponack, L.L.P.

(57) ABSTRACT

Provided is a kynurenine production inhibitor comprising a nitrogen-containing heterocyclic compound represented by formula (I):

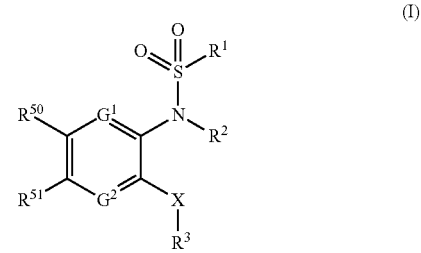

(wherein $R^{50}$ and $R^{51}$ may be the same or different and each represent a hydrogen atom or the like, $G^1$ and $G^2$ may be the same or different and each represent a nitrogen atom or the like, X represents formula (III):

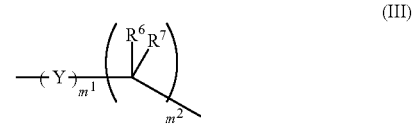

(wherein $m^1$ and $m^2$ may be the same or different and each represent an integer of 0 or 1, Y represents an oxygen atom or the like, and $R^6$ and $R^7$ may be the same or different and each represent a hydrogen atom or the like),
$R^1$ represents optionally substituted lower alkyl or the like, $R^2$ represents a hydrogen atom or the like, and $R^3$ represents optionally substituted lower alkyl or the like), and the like.

17 Claims, No Drawings

(56) References Cited

U.S. PATENT DOCUMENTS

| | | |
|---|---|---|
| 2009/0082356 A1 | 3/2009 | Gaillard et al. |
| 2010/0075947 A1 | 3/2010 | Aftab et al. |
| 2010/0081670 A1 | 4/2010 | Baxter et al. |
| 2010/0087440 A1 | 4/2010 | Bajjalieh et al. |
| 2010/0137308 A1 | 6/2010 | Gaillard et al. |
| 2010/0266539 A1 | 10/2010 | Habashita et al. |

FOREIGN PATENT DOCUMENTS

| | | |
|---|---|---|
| JP | 5-39256 | 2/1993 |
| JP | 9-510987 | 11/1997 |
| JP | 2006-137723 | 6/2006 |
| WO | 95/26957 | 10/1995 |
| WO | 97/32858 | 9/1997 |
| WO | 00/42026 | 7/2000 |
| WO | 03/051870 | 6/2003 |
| WO | 03/059893 | 7/2003 |
| WO | 2004/007472 | 1/2004 |
| WO | 2005/021513 | 3/2005 |
| WO | 2005/023771 | 3/2005 |
| WO | 2006/038594 | 4/2006 |
| WO | 2007/023186 | 3/2007 |
| WO | 2007/044729 | 4/2007 |
| WO | 2008/021389 | 2/2008 |
| WO | 2008/101979 | 8/2008 |
| WO | 2008/127594 | 10/2008 |
| WO | 2011/142316 | 11/2011 |

OTHER PUBLICATIONS

L. Chio et al., "Identification of a Class of Sulfonamides Highly Active Against Dihydropteroate Synthase from *Toxoplasma gondii*, *Pneumocystis carinii*, and *Mycobacterium avium*", Antimicrobial Agents and Chemotherapy, American Society for Microbiology, vol. 40, No. 3, pp. 727-733, Mar. 1, 1996.

English Translation of International Preliminary Report on Patentability and Written Opinion dated Jun. 21, 2011.

S. V. Litvinenko et al. "Synthesis, Structure, and Chemical Properties of Some N-(3-Chloro-2-Quinoxalyl)Arylsulfonamides", Chemistry of Heterocyclic Compounds, vol. 30, No. 3, pp. 340-344, 1994.

R. H. Bradbury et al., "New Non-Peptide Endothelin-A Receptor Antagonists: Synthesis, Biological Properties, and Structure-Activity Relationships of 5-(Dimethylamino)-*N*-pyridyl-, -*N*-pyrimidinyl-, -*N*-pyridazinyl-, and -*N*-pyrazinyl-1-naphthalenesulfonamides", J. Med. Chem., vol. 40, pp. 996-1004, 1997.

* cited by examiner

KYNURENINE PRODUCTION INHIBITOR

This application is a U.S. national stage of International Application No. PCT/JP2009/069065 filed Nov. 9, 2009.

TECHNICAL FIELD

The present invention relates to a kynurenine production inhibitor, a nitrogen-containing heterocyclic compound or a pharmaceutically acceptable salt thereof having an inhibitory effect on kynurenine production, and the like.

BACKGROUND ART

Cancer cells excessively express tumor-associated antigens. The host immune system is considered to respond to the tumor-associated antigens and then exert cellular immunity to eliminate tumors. However, various immune escape mechanisms are present in microenvironment, such as tumor, or in the whole body, and when hosts fail to eliminate tumors, the tumors grow.

Recently, it has been reported that indoleamine 2,3-dioxygenase (IDO), a tryptophan-metabolizing enzyme, inhibits the proliferation of T cells and NK cells and activates regulatory T cells, thereby causing the depression of the host immune system. The expression of IDO is increased in the tumor tissue, and IFN-γ stimulation induces expression of IDO in cancer cells and dendritic cells (for example, the Journal of Clinical Investigation (J. Clin. Invest.), vol. 117, No. 5, pp. 1147-1154 (2007)). In a human, in the kynurenine pathway, in which IDO is involved as the initiation step, 90% of tryptophan, an essential amino acid, is metabolized into kynurenine, and subsequently into 3OH-kynurenine, quinolinic acid, and the like. Activation of IDO decreases the tryptophan concentration and increases the kynurenine concentration in a local or systemic manner, and tryptophan metabolites containing kynurenine induce the death of T cells and NK cells (for example, the Journal of Experimental Medicine (J. Exp. Med.), vol. 196, No. 4, pp. 447-457 (2002)). The tryptophan metabolism induces conversion of CD4$^+$CD25$^-$ T cells into regulatory T cells (for example, Blood, vol. 109, No. 7, pp. 2871-2877 (2007)). In the culture supernatant of dendritic cells in which expression of IDO has been induced by INF-γ, the tryptophan concentration is decreased and the kynurenine concentration is increased. In co-culture of T cells with such dendritic cells, T cell proliferation is suppressed compared to co-culture with unstimulated dendritic cells (for example, the Journal of Experimental Medicine (J. Exp. Med.), vol. 196, No. 4, pp. 447-457 (2002)).

From the above facts, in the tumor environment with an increased expression of IDO, the increased kynurenine concentration induced by tryptophan metabolism suppresses antitumor effector cells, which is considered to be one of the immune escape mechanisms in tumors (for example, the Journal of Clinical Investigation (J. Clin. Invest.), vol. 117, No. 5, pp. 1147-1154 (2007)).

An increased expression of IDO in the tumor tissue of colorectal cancer and prostate cancer has been reported (for example, Clinical Cancer Research (Clin. Cancer Res.), vol. 12, No. 4, pp. 1144-1151 (2006); and European Journal of Cancer (Eur. J. Cancer), vol. 44, No. 15, pp. 2266-2275 (2008)). In acute myeloid leukemia cells, IDO is constitutively expressed (for example, Leukemia, vol. 21, pp. 353-355 (2007)). It is reported that endometrial cancer, melanoma and ovarian cancer patients with an increased expression of IDO have a poor prognosis (for example, British Journal of Cancer (Br. J. Cancer), vol. 95, No. 11, 1555-1561 (2006); the Journal of Clinical Investigation (J. Clin. Invest.), vol. 114, No. 2, 280-290 (2004); and Clinical Cancer Research (Clin. Cancer Res.), vol. 11, No. 16, 6030-6039 (2005)). In adult T cell leukemia lymphoma and acute myeloid leukemia, the kynurenine/tryptophan ratio in the blood is increased (for example, Leukemia Research (Leuk. Res.), vol. 33, No. 1, pp. 39-45 (2009); and Leukemia Research (Leuk. Res.), vol. 33, No. 3, pp. 490-494 (2009)). It is reported that melanoma patients with an increased kynurenine/tryptophan ratio in the blood have a poor prognosis (for example, Dermatology, vol. 214, No. 1, pp. 8-14 (2007)). As mentioned above, it is thought that IDO and/or kynurenine is involved in many solid cancers and blood cancers.

1-methyltryptophan (1-MT), a tryptophan derivative, competes with tryptophan and thereby inhibits kynurenine production (for example, Cancer Research (Cancer Res.), vol. 67, No. 2, pp. 792-800 (2007)). Suppression of T cell proliferation in the presence of IDO-expressing cancer cells and dendritic cells is cancelled by 1-MT (for example, Cancer Research (Cancer Res.), vol. 67, No. 2, pp. 792-800 (2007)). Further, 1-MT induces major histocompatibility complex (MHC)-restricted rejection in allogeneic pregnant mice (for example, Nature Immunology (Nat. Immunol.), vol. 2, No. 1, pp. 64-68 (2001)). These results suggest that inhibition of IDO suppresses kynurenine production and induces immunity.

In mice bearing mouse melanoma cells, 1-MT shows an antitumor effect. This effect disappears in immunodeficient mice (for example, Cancer Research (Cancer Res.), vol. 67, No. 2, pp. 792-800 (2007)). These results suggest that the antitumor effect of 1-MT is based on immunostimulation caused by IDO inhibition-mediated inhibitory effect on kynurenine production.

On the other hand, it is reported that, in HIV positive patients, the IDO expression in PBMC and the viral load correlate with each other (for example, Blood, vol. 109, pp. 3351-3359 (2007)). It is also reported that, in chronic hepatitis C patients, the IDO mRNA level in the liver is increased, and the kynurenine/tryptophan ratio in the serum is increased (for example, the Journal of Virology (J. Virol.), vol. 81, No. 7, pp. 3662-3666 (2007)).

As mentioned above, it is thought that IDO inhibitors and/or kynurenine production inhibitors are promising as a preventive or therapeutic agent for diseases in which kynurenine production is involved, such as cancer, AIDS, AIDS dementia, Alzheimer's disease, depression, infections, and immune diseases.

On the other hand, pyrazine derivatives having an endothelin antagonistic effect are known (see patent literature 1 and nonpatent literature 1).

As a therapeutic agent for diseases in which chemokines are involved, N-pyrazinyl-2-thiophenesulfonamide derivatives (see patent literature 2), N-pyrazinylbenzenesulfonamide derivatives (see patent literature 3) N-(2-quinoxalinyl) benzenesulfonamide derivatives (see patent literature 4), and the like are known. As a chemokine receptor antagonist, N-pyrazinylbenzenesulfonamide derivatives, N-(2-quinoxalinyl)benzenesulfonamide derivatives (see patent literatures 5 and 6), pyridopyrazin-2-on-3-ylmethanesulfonamide derivatives (see patent literature 7), and the like are known. As a functional modulator of thymus and activation-regulated chemokine (TARC; CC chemokine ligand 17 (CCL17)) and/or of macrophage-derived chemokine (MDC; CC chemokine ligand 22 (CCL22)), N-pyrazinylbenzenesulfonamide derivatives, N-(2-pyridopyrazinyl)benzenesulfonamide derivatives (see patent literature 8), and the like are known.

N-(2-quinoxalinyl)benzenesulfonamide derivatives (see patent literatures 9 and 10) having an inhibitory activity against phosphatidylinositol-3-kinase (PI3K), and the like are known.

PRIOR ART

Patent Literature

Patent Literature 1: Published Japanese Translations of PCT International Publication for Patent Application No. 510987/1997
Patent Literature 2: WO 03/051870
Patent Literature 3: WO 03/059893
Patent Literature 4: WO 05/021513
Patent Literature 5: WO 04/007472
Patent Literature 6: WO 05/023771
Patent Literature 7: WO 97/032858
Patent Literature 8: Japanese Published Unexamined Patent Application (Kokai) No. 137723/2006
Patent Literature 9: WO 07/044,729
Patent Literature 10: WO 07/023,186

Nonpatent Literature

Non Patent Literature 1:
Journal of Medicinal Chemistry, 1997, vol. 40, p. 996

SUMMARY OF INVENTION

Problems to be Solved by Invention

An object of the present invention is to provide a kynurenine production inhibitor, and a nitrogen-containing heterocyclic compound or a pharmaceutically acceptable salt thereof having an inhibitory effect on kynurenine production, and the like.

Means for Solving Problems

The present invention relates to the following (1) to (41).
(1) A kynurenine production inhibitor comprising, as an active ingredient, a nitrogen-containing heterocyclic compound represented by formula (I):

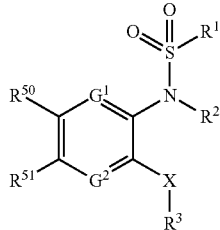

(I)

{wherein $R^{50}$ and $R^{51}$ may be the same or different and each represent a hydrogen atom, optionally substituted lower alkoxy or halogen, or $R^{50}$ and $R^{51}$ are combined together with the two respective adjacent carbon atoms to form ring A selected from a benzene ring, a naphthalene ring and a pyridine ring (wherein the ring A may have a substituent(s), the number of which is from 1 to the substitutable number, and the substituent(s) may be the same or different and each is halogen, optionally substituted lower alkyl or optionally substituted lower alkoxy), $G^1$ and $G^2$ may be the same or different and each represent a nitrogen atom or CH with the proviso that $G^1$ and $G^2$ do not represent CH at the same time,
X represents formula (III):

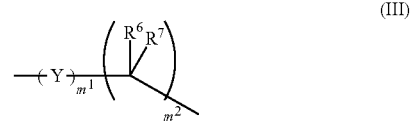

(III)

[wherein $m^1$ and $m^2$ may be the same or different and each represent an integer of 0 or 1,
Y represents an oxygen atom, —S(O)$m^3$- (wherein $m^3$ represents an integer from 0 to 2) or —NR$^8$— (wherein R$^8$ represents a hydrogen atom or optionally substituted lower alkyl), and
$R^6$ and $R^7$ may be the same or different and each represent a hydrogen atom, halogen, cyano, carboxy, optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{12}$R$^{13}$ (wherein $R^{12}$ and $R^{13}$ may be the same or different and each represent a hydrogen atom or optionally substituted lower alkyl, or $R^{12}$ and $R^{13}$ are combined together with the adjacent nitrogen atom to form an optionally substituted nitrogen-containing heterocyclic group)],
$R^1$ represents optionally substituted lower alkyl, optionally substituted lower alkenyl, optionally substituted lower alkynyl, optionally substituted cycloalkyl, optionally substituted aryl, an optionally substituted heterocyclic group or —NR$^{24}$R$^{25}$ (wherein $R^{24}$ and $R^{25}$ may be the same or different and each represent a hydrogen atom, optionally substituted lower alkyl, optionally substituted lower alkenyl, optionally substituted lower alkynyl or optionally substituted cycloalkyl),
$R^2$ represents a hydrogen atom or optionally substituted lower alkyl, or $R^1$ and $R^2$ are combined together with the adjacent sulfur atom and nitrogen atom to form an optionally substituted sulfur-containing and nitrogen-containing heterocyclic group, and
$R^3$ represents optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{28}$R$^{29}$ (wherein $R^{28}$ and $R^{29}$ may be the same or different and each represent a hydrogen atom or optionally substituted lower alkyl, or $R^{28}$ and $R^{29}$ are combined together with the adjacent nitrogen atom to form an optionally substituted nitrogen-containing heterocyclic group)},
or a pharmaceutically acceptable salt thereof.
(2) The kynurenine production inhibitor according to (1), wherein $G^1$ and $G^2$ are nitrogen atoms.
(3) The kynurenine production inhibitor according to (1) or (2), wherein $R^2$ is a hydrogen atom.
(4) The kynurenine production inhibitor according to any one of (1) to (3), wherein $m^1$ and $m^2$ are 1 and Y is an oxygen atom.
(5) The kynurenine production inhibitor according to any one of (1) to (4), wherein either $R^6$ or $R^7$ is a hydrogen atom.
(6) The kynurenine production inhibitor according to any one of (1) to (4), wherein $R^6$ is optionally substituted lower alkyl.
(7) The kynurenine production inhibitor according to any one of (1) to (6), wherein $R^1$ is optionally substituted lower alkyl, optionally substituted lower alkenyl, optionally substituted lower alkynyl, optionally substituted cycloalkyl, optionally substituted aryl or an optionally substituted heterocyclic group.

(8) The kynurenine production inhibitor according to any one of (1) to (7), wherein $R^3$ is optionally substituted lower alkyl, optionally substituted cycloalkyl, optionally substituted aryl or an optionally substituted heterocyclic group.

(9) A nitrogen-containing heterocyclic compound represented by formula (II):

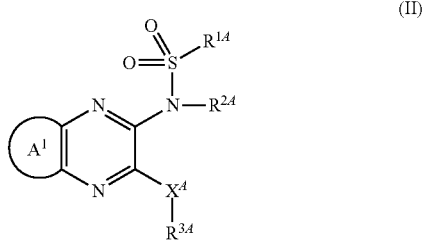

(II)

{wherein ring $A^1$ represents a benzene ring, a naphthalene ring or a pyridine ring (wherein the ring $A^1$ may have a substituent (s), the number of which is from 1 to the substitutable number, and the substituent(s) may be the same or different and each is halogen, optionally substituted lower alkyl or optionally substituted lower alkoxy),
$X^A$ represents formula (IV):

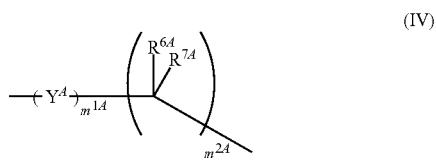

(IV)

[wherein $m^{1A}$ and $m^{2A}$ may be the same or different and each represent an integer of 0 or 1,
$Y^A$ represents an oxygen atom, —S(O)$m^{3A}$- (wherein $m^{3A}$ represents an integer from 0 to 2) or —NR$^{8A}$— (wherein R$^{8A}$ represents a hydrogen atom or optionally substituted lower alkyl), and R$^{6A}$ and R$^{7A}$ may be the same or different and each represent a hydrogen atom, halogen, cyano, carboxy, optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{12A}$R$^{13A}$ (wherein R$^{12A}$ and R$^{13A}$ may be the same or different and each represent a hydrogen atom or optionally substituted lower alkyl, or R$^{12A}$ and R$^{13A}$ are combined together with the adjacent nitrogen atom to form an optionally substituted nitrogen-containing heterocyclic group)],
R$^{1A}$ represents optionally substituted lower alkyl, optionally substituted lower alkenyl, optionally substituted lower alkynyl, optionally substituted cycloalkyl, optionally substituted aryl, an optionally substituted heterocyclic group or —NR$^{24A}$R$^{25A}$ (wherein R$^{24A}$ and R$^{25A}$ may be the same or different and each represent a hydrogen atom, optionally substituted lower alkyl, optionally substituted lower alkenyl, optionally substituted lower alkynyl or optionally substituted cycloalkyl),
R$^{2A}$ represents a hydrogen atom or optionally substituted lower alkyl, or R$^{1A}$ and R$^{2A}$ are combined together with the adjacent sulfur atom and nitrogen atom to form an optionally substituted sulfur-containing and nitrogen-containing heterocyclic group, and
R$^{3A}$ represents optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{28A}$R$^{29A}$ (wherein R$^{28A}$ and R$^{29A}$ may be the same or different and each represent a hydrogen atom or optionally substituted lower alkyl, or R$^{28A}$ and R$^{29A}$ are combined together with the adjacent nitrogen atom to form an optionally substituted nitrogen-containing heterocyclic group)},
or a pharmaceutically acceptable salt thereof.

(10) The nitrogen-containing heterocyclic compound or a pharmaceutically acceptable salt thereof according to (9), wherein R$^{1A}$ is optionally substituted lower alkyl, optionally substituted lower alkenyl, optionally substituted lower alkynyl or —NR$^{24AA}$R$^{25AA}$ (wherein R$^{24AA}$ and R$^{25AA}$ may be the same or different and each represent a hydrogen atom, optionally substituted lower alkyl, optionally substituted lower alkenyl or optionally substituted lower alkynyl).

(11) The nitrogen-containing heterocyclic compound or a pharmaceutically acceptable salt thereof according to (9), wherein R$^{1A}$ is optionally substituted aryl or an optionally substituted heterocyclic group.

(12) The nitrogen-containing heterocyclic compound or a pharmaceutically acceptable salt thereof according to any one of (9) to (11), wherein ring $A^1$ is a benzene ring or a pyridine ring.

(13) The nitrogen-containing heterocyclic compound or a pharmaceutically acceptable salt thereof according to any one of (9) to (12), wherein $m^{1A}$ is 1.

(14) The nitrogen-containing heterocyclic compound or a pharmaceutically acceptable salt thereof according to (13), wherein $Y^A$ is an oxygen atom.

(15) The nitrogen-containing heterocyclic compound or a pharmaceutically acceptable salt thereof according to any one of (9) to (14), wherein $m^{2A}$ is 1.

(16) The nitrogen-containing heterocyclic compound or a pharmaceutically acceptable salt thereof according to (15), wherein R$^{7A}$ is a hydrogen atom.

(17) The nitrogen-containing heterocyclic compound or a pharmaceutically acceptable salt thereof according to (15) or (16), wherein R$^{6A}$ is halogen, cyano, carboxy, optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{12A}$R$^{13A}$ (wherein R$^{12A}$ and R$^{13A}$ have the same meanings as defined above, respectively).

(18) The nitrogen-containing heterocyclic compound or a pharmaceutically acceptable salt thereof according to (15) or (16), wherein R$^{6A}$ is optionally substituted lower alkyl or an optionally substituted heterocyclic group.

(19) The nitrogen-containing heterocyclic compound or a pharmaceutically acceptable salt thereof according to (15) or (16), wherein R$^{6A}$ is fluorine-substituted lower alkyl.

(20) The nitrogen-containing heterocyclic compound or a pharmaceutically acceptable salt thereof according to (15) or (16), wherein R$^{6A}$ is trifluoromethyl.

(21) The nitrogen-containing heterocyclic compound or a pharmaceutically acceptable salt thereof according to any one of (9) to (20), wherein R$^{3A}$ is optionally substituted lower alkyl.

(22) The nitrogen-containing heterocyclic compound or a pharmaceutically acceptable salt thereof according to any one of (9) to (20), wherein R$^{3A}$ is optionally substituted cycloalkyl, optionally substituted aryl, an optionally substituted heterocyclic group, optionally substituted lower alkanoyl, optionally substituted lower alkoxycarbonyl or —CONR$^{28A}$R$^{29A}$ (wherein R$^{28A}$ and R$^{29A}$ have the same meanings as defined above, respectively).

(23) The nitrogen-containing heterocyclic compound or a pharmaceutically acceptable salt thereof according to any one of (9) to (20), wherein R$^{3A}$ is optionally substituted aryl or an optionally substituted heterocyclic group.

(24) The nitrogen-containing heterocyclic compound or a pharmaceutically acceptable salt thereof according to any one of (9) to (23), wherein R$^{2A}$ is a hydrogen atom.

(25) A pharmaceutical composition comprising, as an active ingredient, the nitrogen-containing heterocyclic compound or a pharmaceutically acceptable salt thereof described in anyone of (9) to (24).

(26) A kynurenine production inhibitor comprising, as an active ingredient, the nitrogen-containing heterocyclic compound or a pharmaceutically acceptable salt thereof described in any one of (9) to (24).

(27) A method for inhibiting kynurenine production, comprising a step of administering an effective amount of the nitrogen-containing heterocyclic compound or a pharmaceutically acceptable salt thereof described in any one of (9) to (24).

(28) Use of the nitrogen-containing heterocyclic compound or a pharmaceutically acceptable salt thereof described in anyone of (9) to (24) for the manufacture of a kynurenine production inhibitor.

(29) The nitrogen-containing heterocyclic compound or a pharmaceutically acceptable salt thereof according to any one of (9) to (24) for use in inhibiting kynurenine production.

(30) A preventive or therapeutic agent for a disease in which kynurenine production is involved, comprising, as an active ingredient, the nitrogen-containing heterocyclic compound or a pharmaceutically acceptable salt thereof described in anyone of (1) to (8).

(31) A preventive or therapeutic agent for a disease in which kynurenine production is involved, comprising, as an active ingredient, the nitrogen-containing heterocyclic compound or a pharmaceutically acceptable salt thereof described in any one of (9) to (24).

(32) The preventive or therapeutic agent according to (30) or (31), wherein the disease in which kynurenine production is involved is cancer.

(33) A method for preventing or treating a disease in which kynurenine production is involved, comprising a step of administering an effective amount of the nitrogen-containing heterocyclic compound or a pharmaceutically acceptable salt thereof described in any one of (1) to (8).

(34) A method for preventing or treating a disease in which kynurenine production is involved, comprising a step of administering an effective amount of the nitrogen-containing heterocyclic compound or a pharmaceutically acceptable salt thereof described in any one of (9) to (24).

(35) The method according to (33) or (34), wherein the disease in which kynurenine production is involved is cancer.

(36) Use of the nitrogen-containing heterocyclic compound or a pharmaceutically acceptable salt thereof described in any one of (1) to (8) for the manufacture of a preventive or therapeutic agent for a disease in which kynurenine production is involved.

(37) Use of the nitrogen-containing heterocyclic compound or a pharmaceutically acceptable salt thereof described in any one of (9) to (24) for the manufacture of a preventive or therapeutic agent for a disease in which kynurenine production is involved.

(38) The use of the nitrogen-containing heterocyclic compound or a pharmaceutically acceptable salt thereof according to (36) or (37), wherein the disease in which kynurenine production is involved is cancer.

(39) The nitrogen-containing heterocyclic compound or a pharmaceutically acceptable salt thereof described in any one of (1) to (8) for use in preventing or treating a disease in which kynurenine production is involved.

(40) The nitrogen-containing heterocyclic compound or a pharmaceutically acceptable salt thereof according to any one of (9) to (24) for use in preventing or treating a disease in which kynurenine production is involved.

(41) The nitrogen-containing heterocyclic compound or a pharmaceutically acceptable salt thereof according to (39) or (40), wherein the disease in which kynurenine production is involved is cancer.

Effects of Invention

The present invention provides a kynurenine production inhibitor, and a nitrogen-containing heterocyclic compound or a pharmaceutically acceptable salt thereof having an inhibitory effect on kynurenine production, and the like.

MODES FOR CARRYING OUT INVENTION

Hereinafter, the compounds represented by the above formulae (I) and (II) are referred to as Compounds (I) and (II), respectively. The same applies to other compounds having different formula numbers.

The definitions of the respective groups and their substituents in the formulae (I) and (II) are as follows.

(i) Examples of the halogen include each atom of fluorine, chlorine, bromine and iodine. Preferred examples of the halogen include a fluorine atom, a chlorine atom, and the like.

(ii) Examples of the lower alkyl moieties of the lower alkyl, the lower alkoxy, the lower alkoxycarbonyl and the lower alkylsulfonyl include linear or branched alkyl having 1 to 10 carbon atoms. More specific examples thereof include methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, and the like. Preferred examples thereof include linear or branched alkyl having 1 to 4 carbon atoms, and the like. More preferred examples thereof include methyl, ethyl, n-propyl, isopropyl, n-butyl, isobutyl, sec-butyl, tert-butyl, and the like.

(iii) Examples of the cycloalkyl include cycloalkyl having 3 to 10 carbon atoms. More specific examples thereof include cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl, bicyclo[3.3.1]nonyl, and the like. Preferred examples thereof include cycloalkyl having 3 to 6 carbon atoms, and the like. More preferred examples thereof include cyclopropyl, cyclobutyl, cyclopentyl, cyclohexyl, and the like.

The cycloalkyl may be, for example, cycloalkyl condensed with aryl. More specific examples thereof include tetrahydronaphthalenyl, and the like.

(iv) Examples of the lower alkenyl include linear or branched alkenyl having 2 to 10 carbon atoms. More specific examples thereof include vinyl, allyl, 1-propenyl, 1-butenyl, 3-butenyl, 2-pentenyl, 4-pentenyl, 2-hexenyl, 5-hexenyl, 2-decenyl, 9-decenyl, and the like. Preferred examples thereof include linear or branched alkenyl having 2 to 3 carbon atoms, and the like. More preferred examples thereof include allyl, and the like.

(v) Examples of the lower alkynyl include linear or branched alkynyl having 2 to 10 carbon atoms. More specific examples thereof include ethynyl, 1-propynyl, 2-propynyl, 3-butynyl, 4-pentynyl, 5-hexynyl, 9-decynyl, and the like. Preferred examples thereof include linear or branched alkynyl having 2 to 3 carbon atoms, and the like. More preferred examples thereof include 2-propynyl, and the like.

(vi) Examples of the aryl include monocyclic aryl and condensed aryl in which two or more rings are fused. More specific examples thereof include aryl having 6 to 14 ring carbon atoms, such as phenyl, naphthyl, indenyl, and anthranil. Preferred examples thereof include aryl having 6 to 10 carbon atoms, and the like. More preferred examples thereof include phenyl, naphthyl, and the like.

(vii) Examples of the lower alkanoyl include linear or branched lower alkanoyl having 1 to 8 carbon atoms. More specific examples thereof include formyl, acetyl, propionyl, butyryl, isobutyryl, valeryl, isovaleryl, pivaloyl, hexanoyl, heptanoyl, octanoyl, and the like. Preferred examples thereof include linear or branched lower alkanoyl having 1 to 3 carbon atoms, and the like. More preferred examples thereof include formyl, acetyl, propionyl, and the like.

(viii) Examples of the heterocyclic group include an aromatic heterocyclic group, an aliphatic heterocyclic group, and the like.

Examples of the aromatic heterocyclic group include a 5- or 6-membered monocyclic aromatic heterocyclic group which contains at least one heteroatom selected from a nitrogen atom, an oxygen atom and a sulfur atom, a bicyclic or tricyclic condensed aromatic heterocyclic group in which 3- to 8-membered rings are fused and which contains at least one heteroatom selected from a nitrogen atom, an oxygen atom and a sulfur atom, and the like. More specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridyl-1-oxide, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, and the like. Preferred examples thereof include a 5- or 6-membered monocyclic aromatic heterocyclic group which contains at least one nitrogen atom, a 5- or 6-membered monocyclic aromatic heterocyclic group which contains 1 or 2 heteroatoms selected from an oxygen atom and a sulfur atom, a bicyclic or tricyclic condensed aromatic heterocyclic group in which 5- or 6-membered rings are fused and which contains at least one heteroatom selected from a nitrogen atom, an oxygen atom and a sulfur atom, and the like. More preferred examples thereof include imidazolyl, pyrazolyl, isoxazolyl, thiazolyl, pyrazinyl, pyridyl, pyridyl-1-oxide, thienyl, furyl, benzofuranyl, benzothiophenyl, indolyl, quinolinyl, benzotriazolyl, and the like.

Examples of the aliphatic heterocyclic group include a 5- or 6-membered monocyclic aliphatic heterocyclic group which contains at least one heteroatom selected from a nitrogen atom, an oxygen atom and a sulfur atom, a bicyclic or tricyclic condensed aliphatic heterocyclic group in which 3- to 8-membered rings are fused and which contains at least one heteroatom selected from a nitrogen atom, an oxygen atom and a sulfur atom, and the like. More specific examples thereof include aziridinyl, azetidinyl, pyrrolidinyl, piperidino, piperidinyl, quinuclidinyl, azepanyl, 1,2,5,6-tetrahydropyridyl, 1,2-dihydropyridyl, imidazolidinyl, pyrazolidinyl, piperazinyl, homopiperazinyl, pyrazolinyl, oxiranyl, oxetanyl, tetrahydrofuranyl, tetrahydro-2H-pyranyl, 5,6-dihydro-2H-pyranyl, 1,4-dioxanyl, 1,3-dioxanyl, tetrahydro-2H-thiopyranyl, tetrahydro-2H-thiopyranyl-1,1-dioxide, tetrahydro-2H-thiopyranyl-1-oxide, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, 3,4-dihydro-2H-benzo[b][1,4]oxazinyl, tetrahydroquinolyl, tetrahydroisoquinolyl, chromanyl, thiochromanyl, tetrahydroquinoxalinyl, tetrahydroquinazolinyl, dihydrobenzodioxanyl, and the like. Preferred examples thereof include a 5- or 6-membered monocyclic aliphatic heterocyclic group which contains at least one heteroatom selected from a nitrogen atom and an oxygen atom, a 6-membered monocyclic aliphatic heterocyclic group which contains one sulfur atom, a bicyclic condensed aliphatic heterocyclic group in which 5- or 6-membered rings are fused and which contains at least one heteroatom selected from a nitrogen atom, an oxygen atom and a sulfur atom, and the like. More preferred examples thereof include tetrahydro-2H-pyranyl, morpholino, morpholinyl, pyrrolidinyl, tetrahydro-2H-thiopyranyl, tetrahydro-2H-thiopyranyl-1,1-dioxide, tetrahydro-2H-thiopyranyl-1-oxide, tetrahydrofuranyl, 3,4-dihydro-2H-benzo[b][1,4]oxazinyl, piperidino, piperidinyl, quinuclidinyl, thiochromanyl, 1,3-dioxanyl, 1,2-dihydropyridyl, and the like.

Examples of the nitrogen-containing heterocyclic group formed together with the adjacent nitrogen atom include a 5- or 6-membered monocyclic heterocyclic group which contains at least one nitrogen atom (the monocyclic heterocyclic group may further contain another nitrogen atom, an oxygen atom or a sulfur atom), a bicyclic or tricyclic condensed heterocyclic group in which 3- to 8-membered rings are fused and which contains at least one nitrogen atom (the condensed heterocyclic group may further contain another nitrogen atom, an oxygen atom or a sulfur atom), and the like. More specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl, and the like. Preferred examples thereof include a 5- or 6-membered monocyclic heterocyclic group which contains at least one nitrogen atom. Morpholino is particularly preferred.

(x) Examples of the sulfur-containing and nitrogen-containing heterocyclic group formed together with the adjacent nitrogen atom and sulfur atom include a 5- or 6-membered monocyclic heterocyclic group which contains at least one sulfur atom and at least one nitrogen atom (the monocyclic heterocyclic group may further contain another nitrogen atom, an oxygen atom or another sulfur atom), a bicyclic or tricyclic condensed heterocyclic group in which 3- to 8-membered rings are fused and which contains at least one sulfur atom and at least one nitrogen atom (the condensed heterocyclic group may further contain another nitrogen atom, an oxygen atom or another sulfur atom), and the like. More specific examples thereof include 1,1-dioxoisothiazolidinyl, and the like.

(xi) The substituents of the optionally substituted lower alkyl, the optionally substituted lower alkoxy, the optionally substituted cycloalkyl, the optionally substituted lower alkoxycarbonyl and the optionally substituted lower alkanoyl may be the same or different and the number thereof is, for example, 1 to the substitutable number, preferably 1 to 3, and examples thereof include (xi-a) halogen,
(xi-b) hydroxy,
(xi-c) cyano,
(xi-d) carboxy,
(xi-e) optionally substituted lower alkoxycarbonyl (the number of the substituent of the substituted lower alkoxycarbonyl is, for example, 1 to 3, and examples thereof include halogen, hydroxy, cyano, lower alkoxy, optionally substituted aryl (the number of the substituent of the substituted aryl is, for example, 1 to 3, and examples thereof include halogen, hydroxy, cyano, lower alkyl, lower alkoxy, and the like), and the like),
(xi-f) optionally substituted cycloalkyl (the number of the substituent of the substituted cycloalkyl is, for example, 1 to 3, and examples thereof include halogen, hydroxy, lower alkoxy, optionally substituted lower alkyl (the number of the substituent of the substituted lower alkyl is, for example, 1 to 3, and examples thereof include halogen, hydroxy, cyano, lower alkoxy, and the like), and the like),
(xi-g) optionally substituted lower alkoxy (the number of the substituent of the substituted lower alkoxy is, for example, 1 to 3, and examples thereof include halogen, hydroxy, lower alkoxy, and the like),
(xi-h) optionally substituted aryl (the number of the substituent of the substituted aryl is, for example, 1 to 3, and examples thereof include halogen, carboxy, lower alkoxycarbonyl, and the like),
(xi-i) an optionally substituted heterocyclic group {the number of the substituent of the substituted heterocyclic group is, for example, 1 to 3, and examples thereof include halogen, hydroxy, oxo, lower alkoxy, lower alkoxycarbonyl, lower alkylsulfonyl, lower alkanoyl, optionally substituted lower alkyl (the number of the substituent of the substituted lower alkyl is, for example, 1 to 3, and examples thereof include halogen, hydroxy, cyano, optionally substituted lower alkoxy (the number of the substituent of the substituted lower alkoxy is, for example, 1 to 3, and examples thereof include halogen, hydroxy, and the like), and the like), optionally substituted aryl (the number of the substituent of the substituted aryl is, for example, 1 to 3, and examples thereof include halogen, hydroxy, cyano, lower alkyl, lower alkoxy, and the like), an optionally substituted heterocyclic group (the number of the substituent of the substituted heterocyclic group is, for example, 1 to 3, and examples thereof include halogen, hydroxy, cyano, lower alkyl, lower alkoxy, and the like), and the like},
(xi-j) —$NR^{31}R^{32}$ {wherein $R^{31}$ and $R^{32}$ may be the same or different and each represent a hydrogen atom, lower alkoxycarbonyl, lower alkenyl, lower alkynyl, lower alkanoyl, optionally substituted lower alkyl (the number of the substituent of the substituted lower alkyl is, for example, 1 to 3, and examples thereof include halogen, amino, hydroxy, carboxy, carbamoyl, lower alkanoyl, optionally substituted lower alkoxy (the number of the substituent of the substituted lower alkoxy is, for example, 1 to 3, and examples thereof include halogen, hydroxy, and the like), lower alkoxycarbonyl, optionally substituted cycloalkyl (the number of the substituent of the substituted cycloalkyl is, for example, 1 to 3, and examples thereof include halogen, hydroxy, optionally substituted lower alkyl (the number of the substituent of the substituted lower alkyl is, for example, 1 to 3, and examples thereof include halogen, hydroxy, and the like), and the like), mono- or di-lower alkylamino, an optionally substituted heterocyclic group (the number of the substituent of the substituted heterocyclic group is, for example, 1 to 3, and examples thereof include halogen, hydroxy, cyano, lower alkoxy, and the like), optionally substituted aryl (the number of the substituent of the substituted aryl is, for example, 1 to 3, and examples thereof include halogen, hydroxy, cyano, lower alkoxy, and the like), and the like), optionally substituted cycloalkyl (the number of the substituent of the substituted cycloalkyl is, for example, 1 to 3, and examples thereof include halogen, amino, hydroxy, and the like), optionally substituted aryl (the number of the substituent of the substituted aryl is, for example, 1 to 3, and examples thereof include halogen, amino, hydroxy, optionally substituted lower alkyl (the number of the substituent of the substituted lower alkyl is, for example, 1 to 3, and examples thereof include halogen, hydroxy, and the like), an optionally substituted heterocyclic group (the number of the substituent of the substituted heterocyclic group is, for example, 1 to 3, and examples thereof include halogen, hydroxy, lower alkyl, lower alkoxy, and the like), and the like), or an optionally substituted heterocyclic group (the number of the substituent of the substituted heterocyclic group is, for example, 1 to 3, and examples thereof include halogen, amino, hydroxy, optionally substituted lower alkyl (the number of the substituent of the substituted lower alkyl is, for example, 1 to 3, and examples thereof include halogen, hydroxy, and the like), an optionally substituted heterocyclic group (the number of the substituent of the substituted heterocyclic group is, for example, 1 to 3, and examples thereof include halogen, hydroxy, lower alkyl, lower alkoxy, and the like), and the like)},
(xi-k) —$CONR^{33}R^{34}$ {wherein $R^{33}$ and $R^{34}$ may be the same or different and each represent a hydrogen atom, optionally substituted lower alkyl (the number of the substituent of the substituted lower alkyl is, for example, 1 to 3, and examples thereof include halogen, amino, hydroxy, carboxy, carbamoyl, optionally substituted lower alkoxy (the number of the substituent of the substituted lower alkoxy is, for example, 1 to 3, and examples thereof include halogen, hydroxy, and the like), lower alkoxycarbonyl, optionally substituted cycloalkyl (the number of the substituent of the substituted cycloalkyl is, for example, 1 to 3, and examples thereof include halogen, hydroxy, and the like), mono- or di-lower alkylamino, a heterocyclic group, and the like), optionally substituted cycloalkyl (the number of the substituent of the substituted cycloalkyl is, for example, 1 to 3, and examples thereof include halogen, amino, hydroxy, and the like), or lower alkanoyl, or $R^{33}$ and $R^{34}$ are combined together with the adjacent nitrogen atom to form a nitrogen-containing heterocyclic group},
(xi-l) optionally substituted lower alkylsulfonyl (the number of the substituent of the substituted lower alkylsulfonyl is, for example, 1 to 3, and examples thereof include halogen, hydroxy, cyano, lower alkoxy, and the like),
(xi-m) tri-(lower alkyl)silyloxy, and the like.

In the above (xi), the halogen has the same meaning as defined in the above (i), the lower alkyl moieties of the lower alkyl, the lower alkoxy, the lower alkoxycarbonyl and the lower alkylsulfonyl have the same meanings as defined in the above (ii), the cycloalkyl has the same meaning as defined in the above (iii), the lower alkenyl has the same meaning as defined in the above (iv), the lower alkynyl has the same meaning as defined in the above (v), the aryl has the same meaning as defined in the above (vi), the lower alkanoyl has the same meaning as defined in the above (vii), the heterocyclic group has the same meaning as defined in the above (viii), and the nitrogen-containing heterocyclic group formed together with the adjacent nitrogen atom has the same meaning as defined in the above (ix).

The lower alkyl moiety of the mono- or di-lower alkylamino has the same meaning as defined in the above (ii), and the two lower alkyl moieties of the di-lower alkylamino may be the same or different.

The lower alkyl moiety of the tri-(lower alkyl) silyloxy has the same meaning as defined in the above (ii), and the three lower alkyl moieties of the tri-(lower alkyl) silyloxy may be the same or different.

(xii) The substituents of the substituted aryl, the substituted heterocyclic group and the substituted nitrogen-containing heterocyclic group formed together with the adjacent nitrogen atom may be the same or different and the number thereof is, for example, 1 to 3, and examples thereof include
(xii-a) halogen,
(xii-b) hydroxy,
(xii-c) cyano,
(xii-d) formyl,
(xii-e) carboxy,
(xii-f) lower alkoxycarbonyl,
(xii-g) optionally substituted lower alkyl (the substituent of the optionally substituted lower alkyl has the same meaning as defined in the above (xi)),
(xii-h) optionally substituted lower alkoxy (the substituent of the optionally substituted lower alkoxy has the same meaning as defined in the above (xi)),
(xii-i) optionally substituted lower alkanoyl (the substituent of the optionally substituted lower alkanoyl has the same meaning as defined in the above (xi)),
(xii-j) optionally substituted lower alkylsulfonyl (the substituent of the optionally substituted lower alkylsulfonyl has the same meaning as defined in the above (xi)),
(xii-k) optionally substituted aryl (the substituent of the optionally substituted aryl has the same meaning as defined in the above (xi)),
(xii-l) an optionally substituted heterocyclic group (the number of the substituent of the substituted heterocyclic group is, for example, 1 to 3, and examples thereof include halogen, nitro, hydroxy, cyano, carboxy, lower alkanoyl, lower alkoxycarbonyl, optionally substituted lower alkyl (the number of the substituent of the substituted lower alkyl is, for example, 1 to 3, and examples thereof include hydroxy, and the like), optionally substituted lower alkoxy (the number of the substituent of the substituted lower alkoxy is, for example, 1 to 3, and examples thereof include hydroxy, and the like), and the like),
(xii-m) $NR^{35}R^{36}$ {wherein $R^{35}$ and $R^{36}$ may be the same or different and each represent a hydrogen atom, optionally substituted lower alkyl (the substituent of the substituted lower alkyl has the same meaning as defined in the above (xi)), optionally substituted lower alkanoyl (the substituent of the substituted lower alkanoyl has the same meaning as defined in the above (xi)), or optionally substituted aryl (the substituent of the substituted aryl has the same meaning as that of the substituted heterocyclic group in the above (xii-l))},
(xii-n) —$CONR^{37}R^{38}$ {wherein $R^{37}$ and $R^{38}$ may be the same or different and each represent a hydrogen atom, optionally substituted lower alkyl (the substituent of the substituted lower alkyl has the same meaning as defined in the above (xi)), or optionally substituted aryl (the substituent of the substituted aryl has the same meaning as that of the substituted heterocyclic group in the above (xii-l)), or $R^{37}$ and $R^{38}$ are combined together with the adjacent nitrogen atom to form an optionally substituted nitrogen-containing heterocyclic group (the substituent of the substituted nitrogen-containing heterocyclic group formed together with the adjacent nitrogen atom has the same meaning as that of the substituted heterocyclic group in the above (xii-l))},
(xii-o) optionally substituted cycloalkyl (the substituent of the substituted cycloalkyl has the same meaning as defined in the above (xi)),
and the like.

The number of the substituent of the substituted heterocyclic group and the substituted nitrogen-containing heterocyclic group formed together with the adjacent nitrogen atom is, for example, 1 to 3, and examples thereof include, in addition to the above (xii-a) to (xii-o), following (xii-p), (xii-q), (xii-r), and the like: (xii-p) oxo,
(xii-q) —$O(CR^{38}R^{40})_nO$— (wherein $R^{39}$ and $R^{40}$ may be the same or different and each represent a hydrogen atom, lower alkyl, or the like, n represents 1 to 3, and the two terminal oxygen atoms are bound to the same carbon atom in the substituted heterocyclic group or the substituted nitrogen-containing heterocyclic group formed together with the adjacent nitrogen atom),
(xii-r) optionally substituted cycloalkylcarbonyl (the number of the substituent of the substituted cycloalkylcarbonyl is, for example, 1 to 3, and examples thereof include halogen, amino, hydroxy, and the like),
and the like.

In the above (xii), the halogen has the same meaning as defined in the above (i), the lower alkyl moieties of the lower alkyl, the lower alkoxy, the lower alkoxycarbonyl and the lower alkylsulfonyl have the same meanings as defined in the above (ii) the cycloalkyl has the same meaning as defined in the above (iii), the aryl has the same meaning as defined in the above (vi), the lower alkanoyl has the same meaning as defined in the above (vii), the heterocyclic group has the same meaning as defined in the above (viii), and the nitrogen-containing heterocyclic group formed together with the adjacent nitrogen atom has the same meaning as defined in the above (ix). (xiii) Examples of the fluorine-substituted lower alkyl include lower alkyl substituted with a fluorine atom (s), the number of which is from 1 to the substitutable number, and the like. Specifically, trifluoromethyl, (1-fluoro-1-methyl)ethyl, 1,1,2,2,2-pentafluoroethyl, and the like are preferred. (xiv) The number of the substituent of the optionally substituted lower alkenyl is, for example, 1 to 3, and examples thereof include halogen, hydroxy, cyano, carboxy, and the like. (xv) The number of the substituent of the optionally substituted lower alkynyl is, for example, 1 to 3, and examples thereof include halogen, hydroxy, cyano, carboxy, and the like. (xvi) The number of the substituent of the optionally substituted sulfur-containing and nitrogen-containing heterocyclic group is, for example, 1 to 3, and examples thereof include halogen, hydroxy, oxo, cyano, carboxy, and the like.

Examples of the pharmaceutically acceptable salt of Compounds (I) and (II) include pharmaceutically acceptable acid addition salts, metal salts, ammonium salts, organic amine addition salts, amino acid addition salts, and the like. Examples of the pharmaceutically acceptable acid addition salts include inorganic acid salts such as hydrochlorides, sulfates, and phosphates; organic acid salts such as acetates, trifluoroacetates, maleates, fumarates, tartrates, citrates, and lactates; and the like. Examples of the pharmaceutically acceptable metal salts include alkali metal salts such as sodium salts and potassium salts; alkaline earth metal salts such as magnesium salts and calcium salts; aluminum salts; zinc salts; and the like. Examples of the pharmaceutically acceptable ammonium salts include salts of ammonium, tetramethylammonium, or the like. Examples of the pharmaceutically acceptable organic amine addition salts include addition salts of morpholine, piperidine, or the like. Examples of the pharmaceutically acceptable amino acid addition salts include addition salts of lysine, glycine, phenylalanine, aspartic acid, glutamic acid, or the like.

After one or more kinds selected from Compound (I) used in the present invention, Compound (II) of the present invention, and pharmaceutically acceptable salts thereof are (1) added to cells and the like in an in vitro system, or (2) administered to a living body such as mammals and the like, inhibition of kynurenine production is observed in comparison with the case where the compound or a pharmaceutically acceptable salt thereof is not administered. That is, Compounds (I), (II) and pharmaceutically acceptable salts thereof have an inhibitory effect on kynurenine production, and thus has an inhibitory effect on increase in the kynurenine concentration. Compounds (I), (II) and pharmaceutically acceptable salts thereof have an excellent inhibitory effect on kynurenine production, and thus are useful for prevention or treatment of, for example, a disease in which IDO and/or kynurenine is involved. Compounds (I), (II) and pharmaceutically acceptable salts thereof are preferably suitable in particular as an active ingredient of a preventive or therapeutic agent for a disease in which kynurenine production is involved, for example, a disease in which the local or systemic level of kynurenine is increased, and as an active ingredient of a kynurenine production inhibitor.

"Treatment" refers to alleviating or curing a condition or a disease and/or its accompanying symptom, or to alleviating the same. "Prevention" refers to delaying or preventing the development of a condition or a disease and its accompanying symptom, or to reducing the subject's risk of developing a condition or a disease.

Examples of the disease in which IDO and/or kynurenine production is involved include cancer (tumor), immune diseases, neurodegenerative diseases, infections, and the like.

Examples of the cancer include cancer derived from hematopoietic tumor, multiple myeloma, breast cancer, ovarian cancer, endometrial cancer, cervical cancer, prostate cancer, bladder cancer, renal cancer, gastric cancer, esophagus cancer, hepatic cancer, biliary tract cancer, colon cancer, rectal cancer, pancreatic cancer, lung cancer, head and neck cancer, osteosarcoma, melanoma, cancer derived from brain tumor, and the like. Compounds (I), (II) and pharmaceutically acceptable salts thereof are preferably suitable for prevention or treatment of cancer, in particular, gastric cancer, breast cancer, or the like.

Examples of the neurodegenerative disease include AIDS dementia, Alzheimer's disease, depression, and the like.

Examples of the infection include viral infection, bacterial infection, fungal infection, chlamydial infection, rickettsial infection, and the like.

Examples of the immune disease (immune disease) include acquired immune deficiency syndrome (AIDS), bronchial asthma, pollen allergy, allergic rhinitis, atopic dermatitis, rheumatoid arthritis, ulcerative colitis, Crohn's disease, multiple sclerosis, amyotrophic lateral sclerosis, graft versus host disease, and the like.

The above Compounds (I), (II) and pharmaceutically acceptable salts thereof are preferably suitable in particular as an active ingredient of a preventive or therapeutic agent for cancer (tumor) or the like.

Hereinafter, production methods of Compounds (I) and (II) will be described.

In the production methods described below, in the case where a defined group changes under the conditions of the production methods or is not suitable for carrying out the production methods, it is possible to produce a desired compound by use of a method commonly used in synthetic organic chemistry such as the methods for introducing and removing a protective group (for example, the method described in T. W. Greene, Protective Groups in Organic Synthesis, 3rd edition, John Wiley & Sons Inc. (1999), or the like). The order of reaction steps, such as introduction of a substituent, may be changed as necessary.

Compound (I) or (II) can be produced, for example, according to the following production methods 1 to 5.

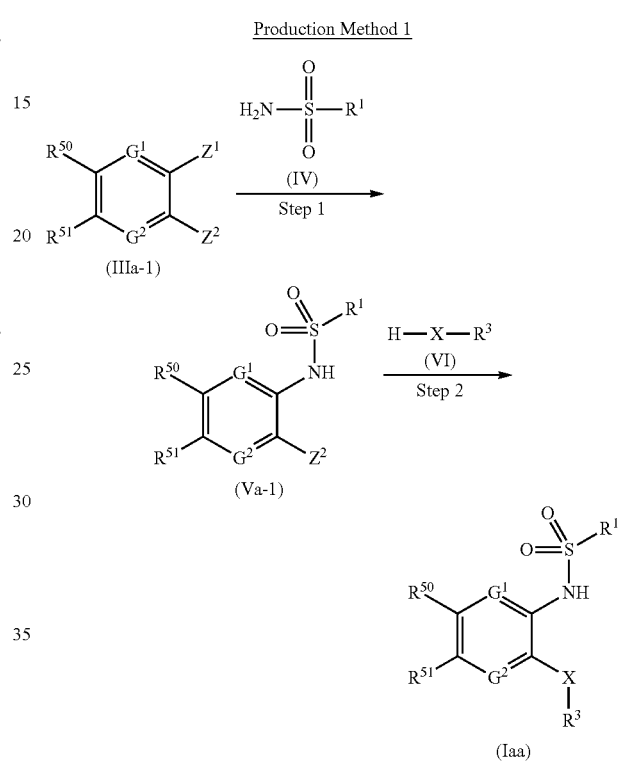

(In the formula, $R^1$, $R^3$, $R^{50}$, $R^{51}$, $G^1$, $G^2$ and X have the same meanings as defined above, respectively, and $Z^1$ and $Z^2$ may be the same or different and each represent a leaving group, such as a chlorine atom, a bromine atom, an iodine atom, methanesulfonyloxy, p-toluenesulfonyloxy, and trifluoromethanesulfonyloxy.)

Step 1

Compound (Va-1) can be produced by reacting Compound (IIIa-1), in the absence of a solvent or in a solvent inert to the reaction, with Compound (IV) of which the amount is 1 to 10 equivalents, preferably 1 equivalent, in the presence of a suitable base of which the amount is 1 to 100 equivalents, preferably 1 to 5 equivalents, at a temperature between −10° C. and 200° C., preferably between 30° C. and 180° C., for 5 minutes to 72 hours.

Examples of the solvent inert to the reaction include tetrahydrofuran (THF), dioxane, 1,2-dimethoxyethane, benzene, toluene, xylene, N,N-dimethylformamide (DMF), N,N-dimethylacetamide (DMA), dimethyl sulfoxide (DMSO), N-methylpyrrolidone (NMP), pyridine, chloroform, dichloromethane, ethyl acetate, acetonitrile, and the like. These solvents can be used alone or as a mixture thereof. Particularly, DMSO or DMF is preferred.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as lithium diisopropylamide (LDA) and lithium hexamethyldisilazane (LiHMDS); alkali metal salts, such as sodium hydroxide, potassium hydroxide, lithium hydroxide, sodium carbonate and potassium carbonate; organic bases, such as pyridine, triethylamine, diisopropylethylamine, 1,8-diazabicyclo[5.4.0]undec-7-ene (DBU), 1,5-diazabicyclo[4.3.0]non-5-ene (DBN), N,N-dimethylaminopyridine (DMAP) and N-methylmorpholine; solid bases, such as AMBERLYST A-21 (manufactured by Rohm and Haas Company), AG1-X8 (manufactured by Bio-Rad Laboratories, Inc.), polyvinylpyridine and morpholinomethyl polystyrene; and the like. Particularly, alkali metal hydrides or alkali metal salts are preferred. Particularly, sodium hydride or potassium carbonate is more preferred.

Compound (IIIa-1) can be obtained, for example, as a commercial product, or according to known methods (for example, the method described in WO2003/059893).

Compound (IV) can be obtained, for example, as a commercial product.

Step 2

Compound (Iaa) can be produced by reacting Compound (Va-1), in the absence of a solvent or in a solvent inert to the reaction, in the presence of a suitable base of which the amount is 1 to 100 equivalents, preferably 1 to 10 equivalents, with Compound (VI) of which the amount is 1 to 20 equivalents, preferably 1 to 4 equivalents, at a temperature between −20° C. and 200° C., preferably between room temperature and 80° C., for 5 minutes to 72 hours.

Examples of the solvent inert to the reaction include THF, dioxane, 1,2-dimethoxyethane, benzene, toluene, xylene, DMF, DMA, NMP, pyridine, chloroform, dichloromethane, ethyl acetate, acetonitrile, and the like. These solvents can be used alone or as a mixture thereof. Particularly, THF or DMF is preferred.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (manufactured by Rohm and Haas Company), AG1-X8 (manufactured by Bio-Rad Laboratories, Inc.), polyvinylpyridine and morpholinomethyl polystyrene; and the like. Particularly, alkali metal hydrides or metal alkoxides are preferred. Particularly, sodium hydride or potassium tert-butoxide is more preferred.

Compound (VI) can be obtained according to known methods (Journal of the American Chemical Society, vol. 111, p. 393 (1989)), or as a commercial product.

Production Method 2

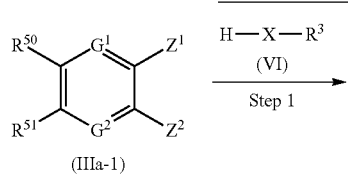

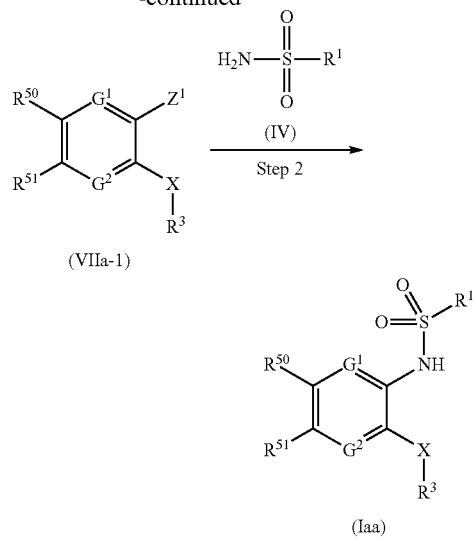

(In the formula, $R^1$, $R^3$, $R^{50}$, $R^{51}$, $Z^1$, $Z^2$, $G^1$, $G^2$ and X have the same meanings as defined above, respectively.)

Step 1

Compound (VIIa-1) can be produced from Compound (IIIa-1) in a similar manner to Step 2 of Production Method 1.

Step 2

Compound (Iaa) can be produced from Compound (VIIa-1) in a similar manner to Step 1 of Production Method 1.

Production Method 3

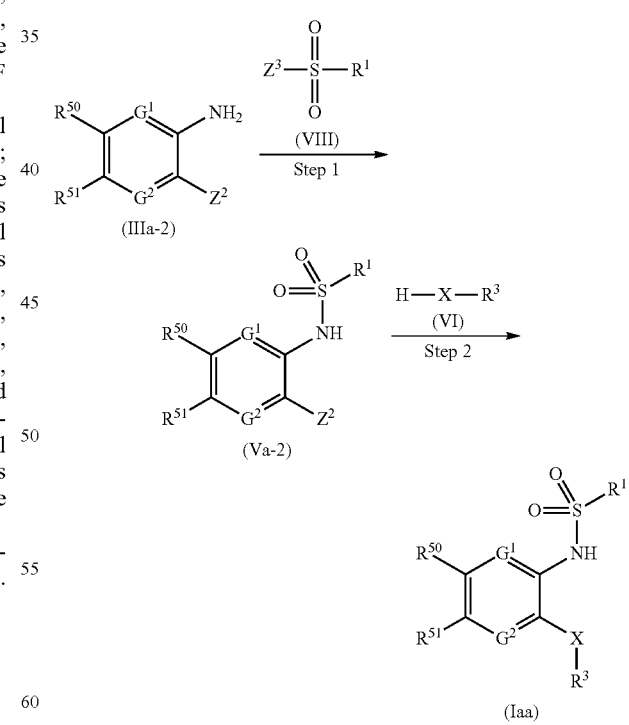

(In the formula, $R^1$, $R^3$, $R^{50}$, $R^{51}$, $Z^2$, $G^1$, $G^2$ and X have the same meanings as defined above, respectively, and $Z^3$ represents a leaving group, such as a chlorine atom, a bromine atom, an iodine atom, methanesulfonyloxy, p-toluenesulfonyloxy, and trifluoromethanesulfonyloxy.)

Step 1

Compound (Va-2) can be produced by reacting Compound (IIIa-2), in the absence of a solvent or in a solvent inert to the reaction, with Compound (VIII) of which the amount is 1 to 10 equivalents, preferably 1 equivalent, in the presence of a suitable base of which the amount is 1 to 100 equivalents, preferably 1 to 5 equivalents, at a temperature between −10° C. and 200° C., preferably between 30° C. and 180° C., for 5 minutes to 72 hours.

Examples of the solvent inert to the reaction include THF, dioxane, 1,2-dimethoxyethane, benzene, toluene, xylene, DMF, DMA, DMSO, NMP, pyridine, chloroform, dichloromethane, ethyl acetate, acetonitrile, and the like. These solvents can be used alone or as a mixture thereof. Particularly, DMSO or DMF is preferred.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (manufactured by Rohm and Haas Company), AG1-X8 (manufactured by Bio-Rad Laboratories, Inc.), polyvinylpyridine and morpholinomethyl polystyrene; and the like. Particularly, alkali metal hydrides are preferred. Particularly, sodium hydride is more preferred.

Compound (IIIa-2) can be obtained, for example, as a commercial product, or according to known methods (for example, the method described in U.S. Pat. No. 3,898,216).

Compound (VIII) can be obtained, for example, as a commercial product.

Step 2

Compound (Iaa) can be produced by reacting Compound (Va-2), in the absence of a solvent or in a solvent inert to the reaction, in the presence of a suitable base of which the amount is 1 to 100 equivalents, preferably 1 to 10 equivalents, with Compound (VI) of which the amount is 1 to 20 equivalents, preferably 1 to 4 equivalents, at a temperature between −20° C. and 200° C., preferably between room temperature and 80° C., for 5 minutes to 72 hours.

Examples of the solvent inert to the reaction include THF, dioxane, 1,2-dimethoxyethane, benzene, toluene, xylene, DMF, DMA, NMP, pyridine, chloroform, dichloromethane, ethyl acetate, acetonitrile, and the like. These solvents can be used alone or as a mixture thereof. Particularly, THF or DMF is preferred.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (manufactured by Rohm and Haas Company), AG1-X8 (manufactured by Bio-Rad Laboratories, Inc.), polyvinylpyridine and morpholinomethyl polystyrene; and the like. Particularly, alkali metal hydrides or metal alkoxides are preferred. Particularly, sodium hydride or potassium tert-butoxide is more preferred.

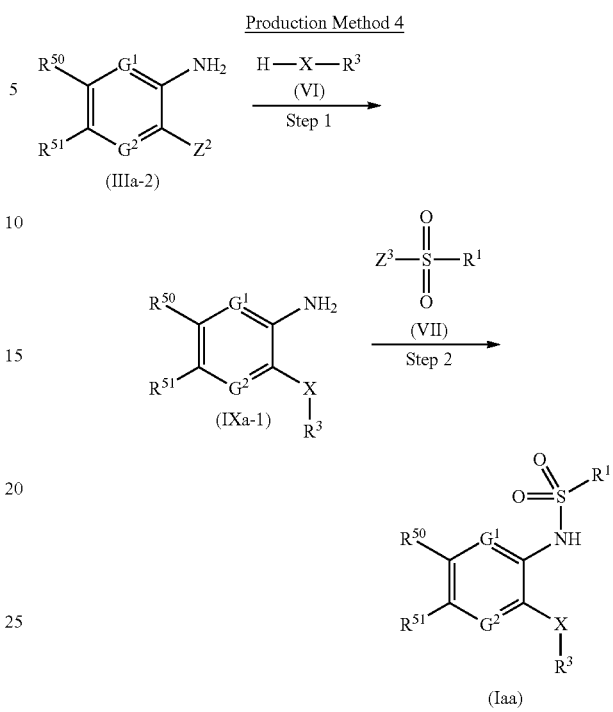

(In the formula, $R^1$, $R^3$, $R^{50}$, $R^{51}$, $Z^2$, $Z^3$, $G^1$, $G^2$ and X have the same meanings as defined above, respectively.)

Step 1

Compound (IXa-1) can be produced from Compound (IIIa-2) in a similar manner to Step 2 of Production Method 3.

Step 2

Compound (Iaa) can be produced from Compound (IXa-1) in a similar manner to Step 1 of Production Method 3.

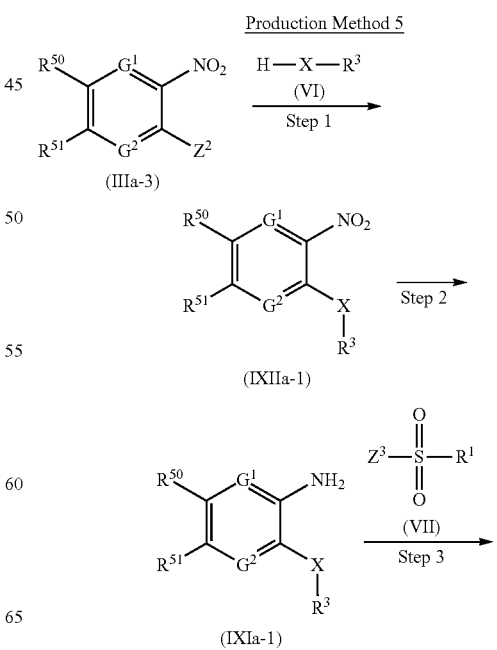

-continued

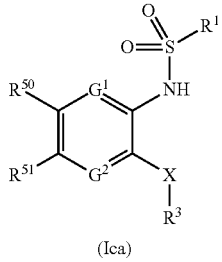

(In the formula, $R^1$, $R^3$, $R^{50}$, $R^{51}$, $Z^2$, $Z^3$, $G^1$, $G^2$, and X have the same meanings as defined above, respectively.)

Step 1

Compound (IXIIa-1) can be produced from Compound (IIIa-3) in a similar manner to Step 2 of Production Method 3.

Step 2

Compound (IXIa-1) can be produced by reacting Compound (IXIIa-1), for example in the absence of a solvent or in a solvent inert to the reaction, with a reducing agent of which the amount is 10 to 100% by weight relative to the weight of Compound (IXIIa-1), at a temperature between −20° C. and 200° C., preferably between room temperature and 80° C., for 5 minutes to 72 hours.

Examples of the solvent inert to the reaction include water, acetic acid, hydrochloric acid, trifluoroacetic acid, trifluoromethanesulfonic acid, methanol, ethanol, propanol, THF, dioxane, ether, 1,2-dimethoxyethane, benzene, toluene, xylene, DMF, DMA, NMP, pyridine, and the like. These solvents can be used alone or as a mixture thereof. Particularly, water, acetic acid or a combination thereof is preferred.

Examples of the reducing agent include iron(0), tin(0), tin(II) dichloride, tin(II) dichloride dihydrate, zinc, sodium hydrosulfite, and the like. Particularly, iron(0) is preferred.

Step 3

Compound (Ica) can be produced from Compound (IXIa-1) in a similar manner to Step 1 of Production Method 3.

Compounds (I) and (II) in which $R^2$ is optionally substituted lower alkyl can be produced by reacting Compound (Iaa) or (Ica), for example in the absence of a solvent or in a solvent inert to the reaction, with a suitable alkylating agent of which the amount is 1 to 100 equivalents, preferably 1 to 10 equivalents, at a temperature between −20° C. and 200° C., preferably between room temperature and 80° C., for 5 minutes to 72 hours.

Examples of the alkylating agent include trimethylsilyldiazomethane, $R^{100}$-$Z^4$ (wherein $R^{100}$ represents optionally substituted lower alkyl, and $Z^4$ represents a leaving group, such as a chlorine atom, a bromine atom, an iodine atom, methanesulfonyloxy, p-toluenesulfonyloxy, and trifluoromethanesulfonyloxy), and the like. Preferred examples thereof include trimethylsilyldiazomethane.

Examples of the solvent inert to the reaction include methanol, ethanol, acetonitrile, THF, dioxane, 1,2-dimethoxyethane, benzene, toluene, xylene, DMF, DMA, NMP, pyridine, chloroform, dichloromethane, ethyl acetate, and the like. These solvents can be used alone or as a mixture thereof. Particularly, methanol or acetonitrile is preferred.

When this reaction is performed, 1 to 100 equivalents, preferably 1 to 10 equivalents of a suitable base may be added.

Examples of the suitable base include alkali metal hydrides, such as sodium hydride and potassium hydride; metal alkoxides, such as sodium methoxide, sodium ethoxide and potassium tert-butoxide; alkali metal salts, such as sodium hydroxide, potassium hydroxide, lithium hydroxide, sodium carbonate, potassium carbonate, cesium carbonate, sodium hydrogen carbonate and potassium hydrogen carbonate; organic bases, such as pyridine, triethylamine, diisopropylethylamine, DBU, DBN, DMAP and N-methylmorpholine; solid bases, such as AMBERLYST A-21 (manufactured by Rohm and Haas Company), AG1-X8 (manufactured by Bio-Rad Laboratories, Inc.), polyvinylpyridine and morpholinomethyl polystyrene; and the like.

Isolation and purification of the products in the above-described respective Production Methods can be performed by an appropriate combination of methods generally employed in organic synthesis, for example, filtration, extraction, washing, drying, concentration, crystallization, various types of chromatography, and the like. The intermediates can be subjected to the subsequent reaction without any particular purification.

Some of Compounds (I) and (II) exist as isomers such as stereoisomers, regioisomers, geometric isomers and optical isomers. All possible isomers and mixtures containing the isomers at any ratio are also used and included in the present invention.

A salt of Compounds (I) and (II) can be obtained as follows. When Compounds (I) and (II) are obtained in the form of a salt, the salt may be simply purified as it is. When Compounds (I) and (II) are obtained in a free form, the compound may be dissolved or suspended in a suitable solvent, and then an acid, a base, or the like may be added thereto for salt formation.

Compounds (I) and (II) or pharmaceutically acceptable salts thereof may exist in the form of adducts with water or any of various solvents in some cases, and these adducts are also included in the present invention.

Specific examples of the compounds used in the present invention are shown in Tables 1 to 6. However, the scope of the present invention is not limited to these compounds. The compounds shown in Tables 2 to 6 below are the ones produced in the respective Examples described later.

In the following Tables, Me, MeO, EtO and Et represent methyl, methoxy, ethoxy and ethyl, respectively.

TABLE 1

| Compound | Structure | Instrumental analysis data (MS m/z) |
|---|---|---|
| 1 | 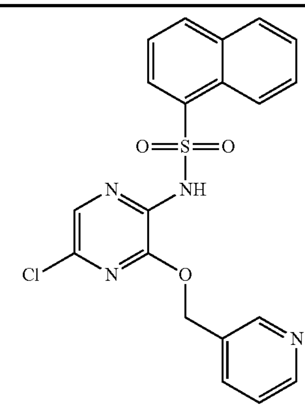 | 427 [M + H]+ |

TABLE 1-continued

| Compound | Structure | Instrumental analysis data (MS m/z) |
|---|---|---|
| 2 | 2,3-dichloro-N-(5-chloro-3-((4-methoxybenzyl)oxy)pyrazin-2-yl)benzenesulfonamide | 474 [M + H]+ |
| 3 | 2,3-dichloro-N-(5-chloro-3-(naphthalen-2-ylmethoxy)pyrazin-2-yl)benzenesulfonamide | 494 [M + H]+ |
| 4 | 2,3-dichloro-N-(3-((1-methyl-1H-benzo[d][1,2,3]triazol-5-yl)methoxy)pyrido[2,3-b]pyrazin-2-yl)benzenesulfonamide | 516 [M + H]+ |
| 5 | 2,3-dichloro-N-(3-((4-methoxybenzyl)oxy)pyrido[2,3-b]pyrazin-2-yl)benzenesulfonamide | 491 [M + H]+ |

TABLE 2

| Example No. | Compound No. | R¹ | X—R³ |
|---|---|---|---|
| 1 | 6 | 2,3-dichlorophenyl | 3-pyridylmethoxy |
| 2 | 7 | 1-naphthyl | 3-pyridazinylmethoxy |

TABLE 2-continued
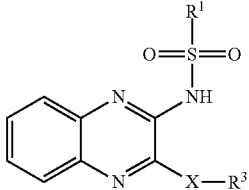
| Example No. | Compound No. | R¹ | X—R³ |
|---|---|---|---|
| 3 | 8 | 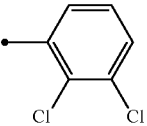 | 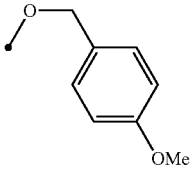 |
| 4 | 9 | 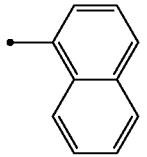 | 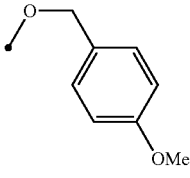 |
| 5 | 10 | 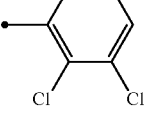 | 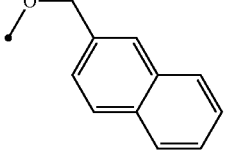 |
| 6 | 11 | 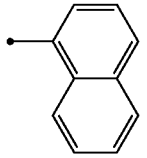 | 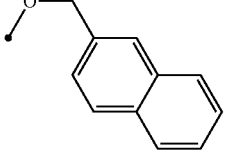 |
| 7 | 12 | 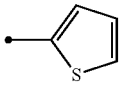 | 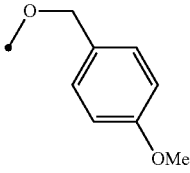 |
| 8 | 13 | 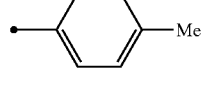 | 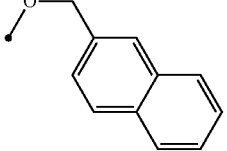 |
| 9 | 14 | 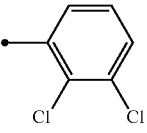 | 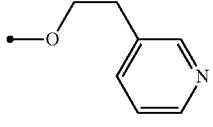 |

TABLE 2-continued

| Example No. | Compound No. | R¹ | X—R³ |
|---|---|---|---|
| 10 | 15 | 3,5-dichlorophenyl | 2-naphthylmethoxy |
| 11 | 16 | 2,3-dichlorophenyl | 1-(pyridin-3-yl)ethoxy (Me) |
| 12 | 17 | 2,3-dichlorophenyl | 2-(trifluoromethyl)benzyloxy |
| 13 | 18 | 2,3-dichlorophenyl | 3-(trifluoromethyl)benzyloxy |
| 14 | 19 | 2,3-dichlorophenyl | 4-(trifluoromethyl)benzyloxy |
| 15 | 20 | 2,3-dichlorophenyl | 2,2,2-trifluoro-1-(pyridin-3-yl)ethoxy |
| 16 | 21 | 2-(trifluoromethyl)phenyl | 2-naphthylmethoxy |
| 17 | 22 | 3-(trifluoromethyl)phenyl | 2-naphthylmethoxy |

TABLE 2-continued
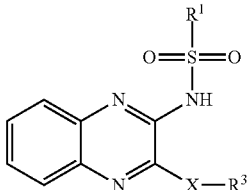
| Example No. | Compound No. | R¹ | X—R³ |
|---|---|---|---|
| 18 | 23 |  | 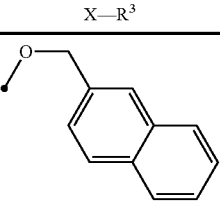 |
| 19 | 24 | 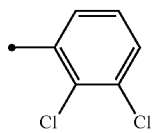 | 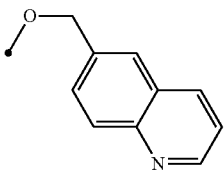 |
| 20 | 25 | 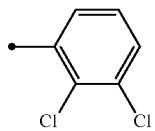 | 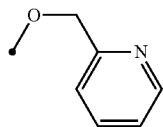 |
| 21 | 26 | 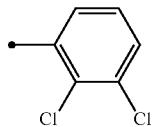 | 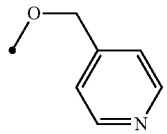 |
| 22 | 27 | 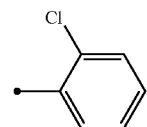 | 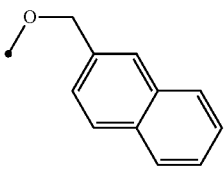 |
| 23 | 28 | 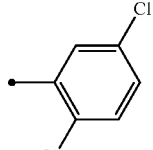 | 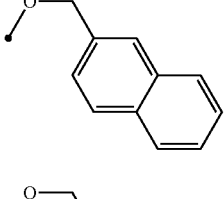 |
| 24 | 29 | 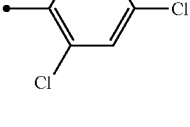 | 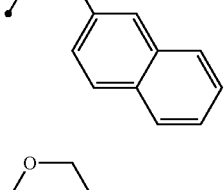 |
| 25 | 30 | 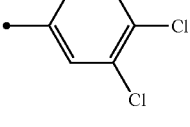 | 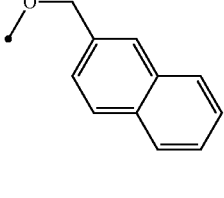 |

TABLE 2-continued

| Example No. | Compound No. | R¹ | X—R³ |
|---|---|---|---|
| 26 | 31 | 2,3-diClPh | OCH(Et)(3-pyridyl) |
| 27 | 32 | 2,3-diClPh | OCH₂Ph |
| 28 | 33 | 2,3-diClPh | OCH₂(pyrazin-2-yl) |
| 29 | 34 | 2,3-diClPh | OCH(iPr)(3-pyridyl) |
| 30 | 35 | 2-CF₃Ph | OCH(CF₃)(4-CF₃Ph) |
| 31 | 36 | 2,3-diClPh | OCH(CF₃)(4-CF₃Ph) |
| 32 | 37 | 2,3-diClPh | OC(Me)₂(3-pyridyl)... |

TABLE 2-continued
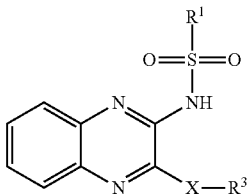
| Example No. | Compound No. | R¹ | X—R³ |
|---|---|---|---|
| 33 | 38 | 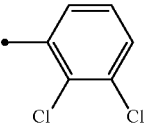 | 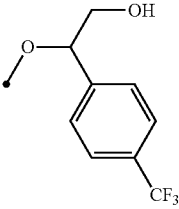 |
| 34 | 39 | 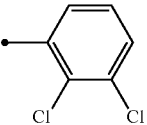 | 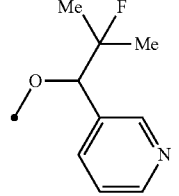 |
| 35 | 40 | 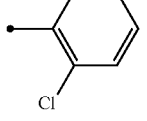 | 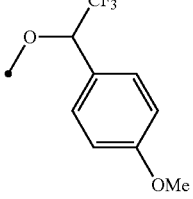 |
| 36 | 41 | 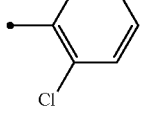 | 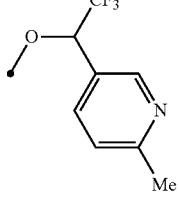 |
| 37 | 42 | 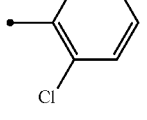 | 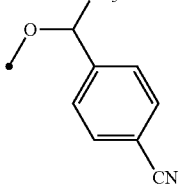 |
| 38 | 43 | 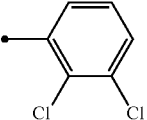 | 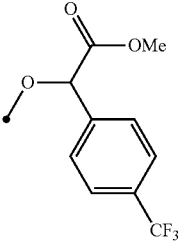 |

TABLE 2-continued
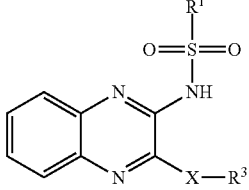
| Example No. | Compound No. | R¹ | X—R³ |
|---|---|---|---|
| 39 | 44 | 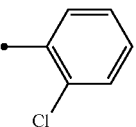 | 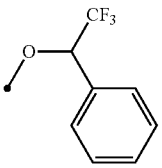 |
| 40 | 45 | 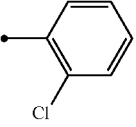 | 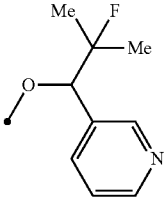 |
| 41 | 46 | 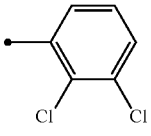 | 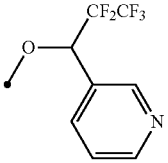 |
| 42 | 47 | 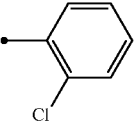 | 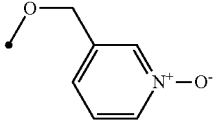 |
| 43 | 48 | 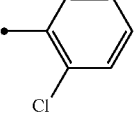 | 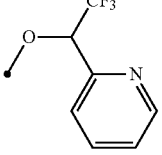 |
| 44 | 49 | 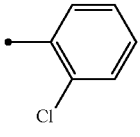 | 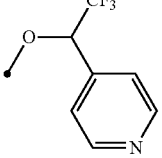 |
| 45 | 50 | 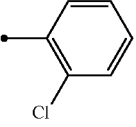 | 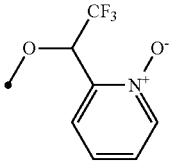 |

TABLE 2-continued
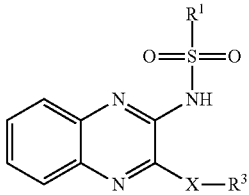
| Example No. | Compound No. | R¹ | X—R³ |
|---|---|---|---|
| 46 | 51 | 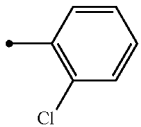 | 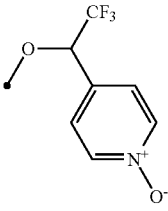 |
| 47 | 52 | 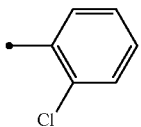 | 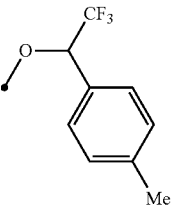 |
| 48 | 53 | 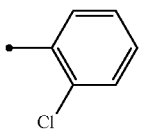 | 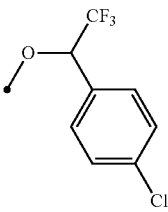 |
| 49 | 54 | 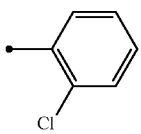 | 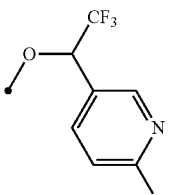 |
| 50 | 55 | 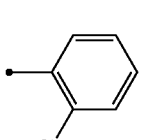 | 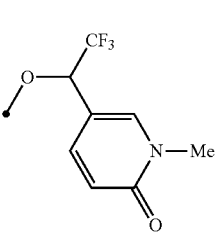 |
| 51 | 56 | 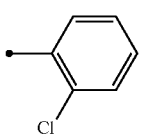 | 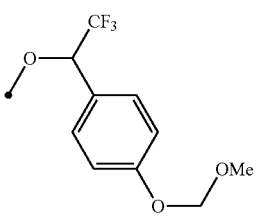 |

TABLE 2-continued
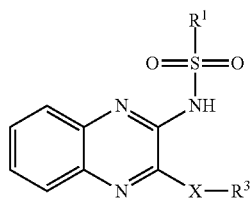
| Example No. | Compound No. | R¹ | X—R³ |
|---|---|---|---|
| 52 | 57 | 2-Cl-phenyl | -O-CH(CF₃)-(4-CH(OEt)₂-phenyl) |
| 53 | 58 | 2-Cl-phenyl | -O-CH(CF₃)-(4-CHO-phenyl) |
| 54 | 59 | 2-Cl-phenyl | -O-CH(CF₃)-(4-F-phenyl) |
| 55 | 60 | 2-Cl-phenyl | -O-CH(CF₃)-(4-CH₂OH-phenyl) |
| 56 | 61 | 2-Cl-phenyl | -O-CH(CF₃)-(4-CO₂H-phenyl) |
| 57 | 62 | 2-Cl-phenyl | -O-CH(CF₃)-(4-CH₂NMe₂-phenyl) |

TABLE 2-continued

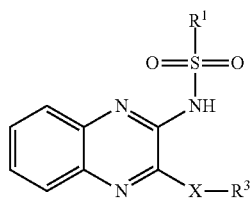

| Example No. | Compound No. | R¹ | X—R³ |
|---|---|---|---|
| 58 | 63 | 2-Cl-phenyl | 4-(CONMe₂)-phenyl-CH(OCF₃... )-O- [1-(4-dimethylcarbamoylphenyl)-2,2,2-trifluoroethoxy] |
| 59 | 64 | 2-Cl-phenyl | [1-(6-methoxypyridin-3-yl)-2,2,2-trifluoroethoxy] |
| 60 | 65 | 2-Cl-phenyl | [1-(2-methyl-1-oxidopyridin-5-yl)-2,2,2-trifluoroethoxy] |
| 61 | 66 | 2-Cl-phenyl | [1-(1-oxidopyridin-3-yl)-2-fluoro-2-methylpropoxy] |
| 62 | 67 | 2-Cl-phenyl | [1-(pyridin-3-yl)-2-cyano-2-methylpropoxy] |
| 63 | 68 | 2-Cl-phenyl | [1-(1-oxidopyridin-3-yl)-2-cyano-2-methylpropoxy] |

TABLE 2-continued
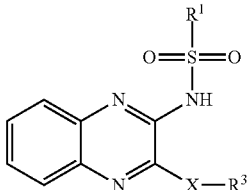
| Example No. | Compound No. | R¹ | X—R³ |
|---|---|---|---|
| 64 | 69 | 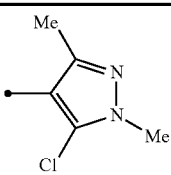 | 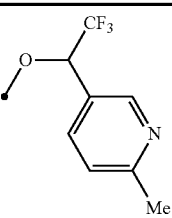 |
| 65 | 70 | 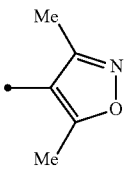 | 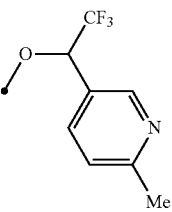 |
| 66 | 71 | 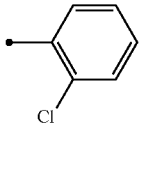 | 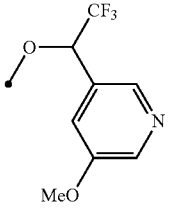 |
| 67 | 72 | 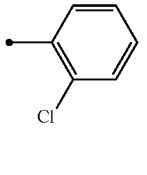 | 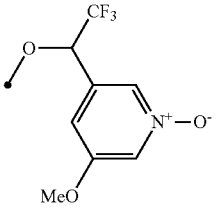 |
| 68 | 73 | 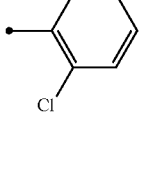 | 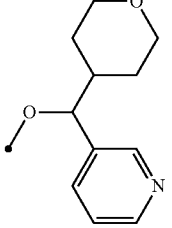 |
| 69 | 74 | 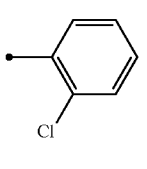 | 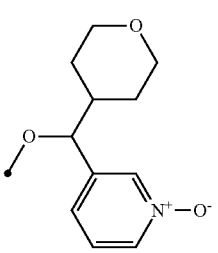 |

TABLE 2-continued

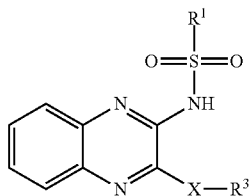

| Example No. | Compound No. | R¹ | X—R³ |
|---|---|---|---|
| 70 | 75 | 5-chloro-1,3-dimethyl-1H-pyrazol-4-yl | 2-fluoro-2-methyl-1-(pyridin-3-yl)propoxy (Me, F, Me) |
| 71 | 76 | 3,5-dimethylisoxazol-4-yl | 2-fluoro-2-methyl-1-(pyridin-3-yl)propoxy (Me, F, Me) |
| 72 | 77 | 2-chlorophenyl | 1-[4-(morpholinomethyl)phenyl]-2,2,2-trifluoroethoxy |
| 73 | 78 | 2-chlorophenyl | (4-fluorotetrahydro-2H-pyran-4-yl)(pyridin-3-yl)methoxy |
| 74 | 79 | 2-chlorophenyl | (4-fluorotetrahydro-2H-pyran-4-yl)(1-oxidopyridin-3-yl)methoxy |
| 75 | 80 | 2-chlorophenyl | 2-methyl-2-(methylsulfonyl)-1-(pyridin-3-yl)propoxy (Me, SO₂Me, Me) |

TABLE 2-continued
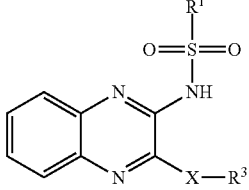
| Example No. | Compound No. | R¹ | X—R³ |
|---|---|---|---|
| 76 | 81 | 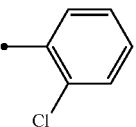 | 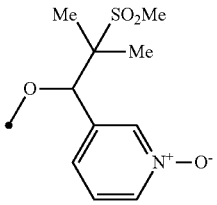 |
| 77 | 82 | 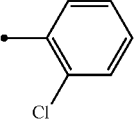 | 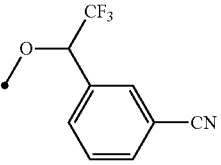 |
| 78 | 83 | 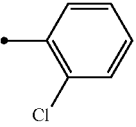 | 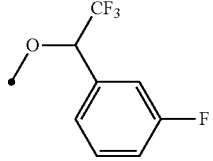 |
| 79 | 84 | 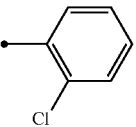 | 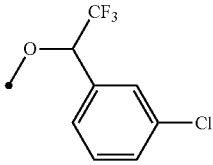 |
| 80 | 85 | 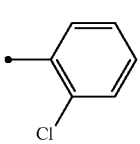 | 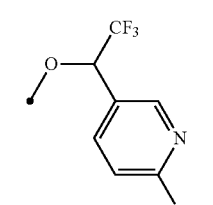 |
| 81 | 86 | 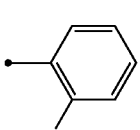 | 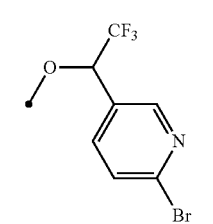 |

TABLE 2-continued
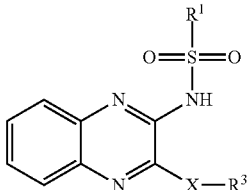
| Example No. | Compound No. | R¹ | X—R³ |
|---|---|---|---|
| 82 | 87 | 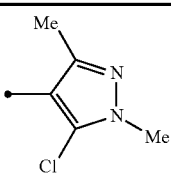 |  |
| 83 | 88 | 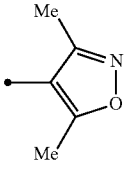 |  |
| 84 | 89 | 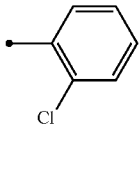 | 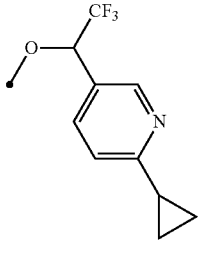 |
| 85 | 90 | 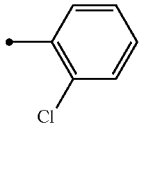 | 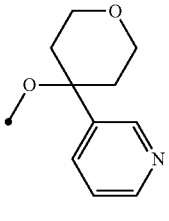 |
| 86 | 91 | 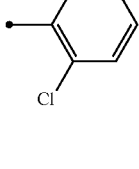 | 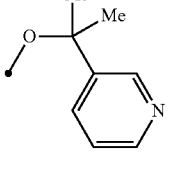 |
| 87 | 92 | 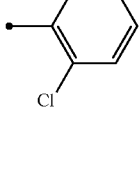 | 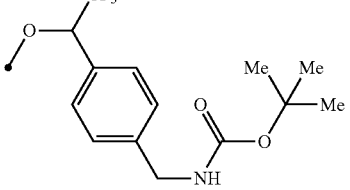 |

TABLE 2-continued
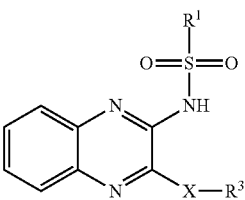
| Example No. | Compound No. | R¹ | X—R³ |
|---|---|---|---|
| 88 | 93 | 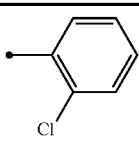 | 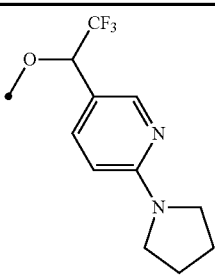 |
| 89 | 94 | 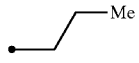 | 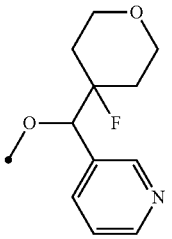 |
| 90 | 95 | 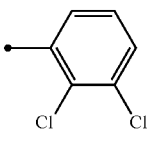 | 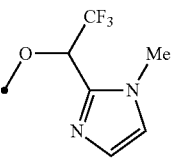 |
| 91 | 96 | 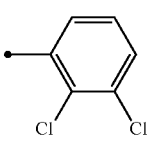 | 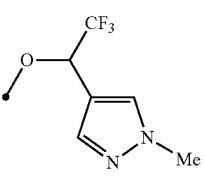 |
| 92 | 97 | 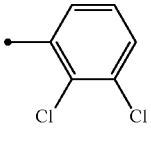 | 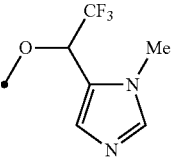 |
| 93 | 98 | 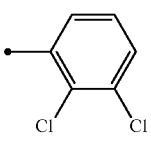 | 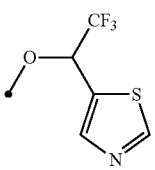 |
| 94 | 99 | 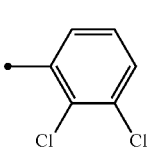 | 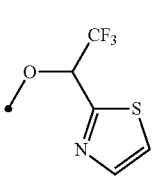 |

TABLE 2-continued
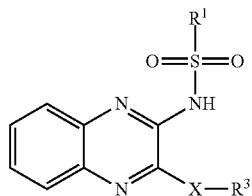
| Example No. | Compound No. | R¹ | X—R³ |
|---|---|---|---|
| 95 | 100 | 2,3-dichlorophenyl | —O—CH(CF₃)-(2-thienyl) |
| 96 | 101 | 2,3-dichlorophenyl | —O—CH(CF₃)-(3-thienyl) |
| 97 | 102 | 2,3-dichlorophenyl | —O—CH(CF₃)-cyclohexyl |
| 98 | 103 | 2,3-dichlorophenyl | —O—CH(CF₃)-(1-methyl-1H-indol-2-yl) |
| 99 | 104 | 2-chlorophenyl | —O—CH(CF₃)-(benzofuran-2-yl) |
| 100 | 105 | 2-chlorophenyl | —O—CH(COOH)-phenyl |
| 101 | 106 | 2-chlorophenyl | —O—CH(CF₃)-(2,4-dimethylthiazol-5-yl) |

TABLE 2-continued
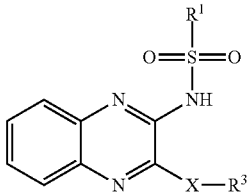
| Example No. | Compound No. | R¹ | X—R³ |
|---|---|---|---|
| 102 | 107 | 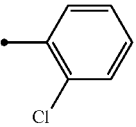 | 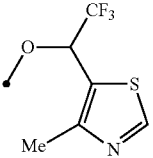 |
| 103 | 108 | 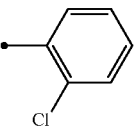 | 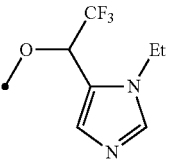 |
| 104 | 109 | 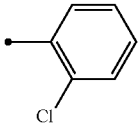 | 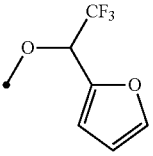 |
| 105 | 110 | 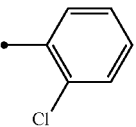 | 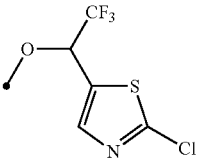 |
| 106 | 111 | 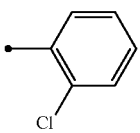 | 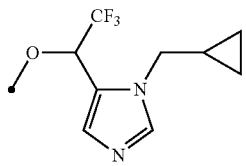 |
| 107 | 112 | 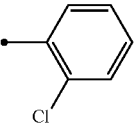 | 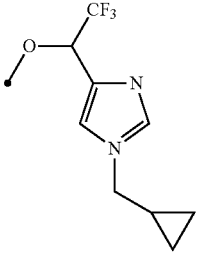 |
| 108 | 113 | 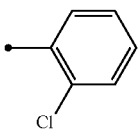 | 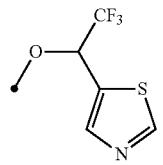 |

TABLE 2-continued

| Example No. | Compound No. | R¹ | X—R³ |
|---|---|---|---|
| 109 | 114 | 2-chlorophenyl | OCH(CF₃)-(2-morpholino-thiazol-5-yl) |
| 110 | 115 | 2-chlorophenyl | OCH(CF₃)-(1,2-dimethyl-1H-imidazol-5-yl) |
| 111 | 116 | 2-chlorophenyl | OCH(CF₃)-(tetrahydropyran-4-yl) |
| 112 | 117 | 2-chlorophenyl | OCH(CF₃)-cyclopropyl |
| 113 | 118 | 2-chlorophenyl | OCH(CF₃)-cyclohexyl |
| 114 | 119 | 3,5-dimethylisoxazol-4-yl | OCH(CF₃)-(tetrahydropyran-4-yl) |
| 115 | 120 | 5-chloro-1,3-dimethyl-1H-pyrazol-4-yl | OCH(CF₃)-(tetrahydropyran-4-yl) |

TABLE 2-continued
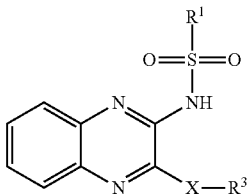
| Example No. | Compound No. | R¹ | X—R³ |
|---|---|---|---|
| 116 | 121 | 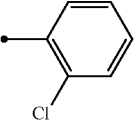 | 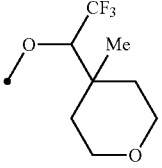 |
| 117 | 122 | 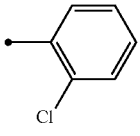 | 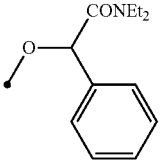 |
| 118 | 123 | 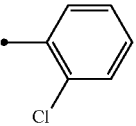 | 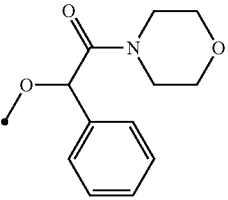 |
| 119 | 124 | 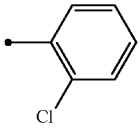 | 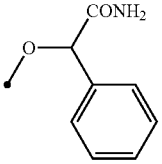 |
| 120 | 125 | 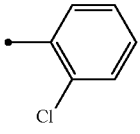 | 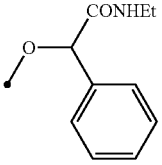 |
| 121 | 126 | 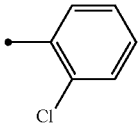 | 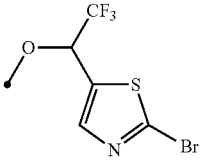 |
| 122 | 127 | 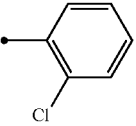 | 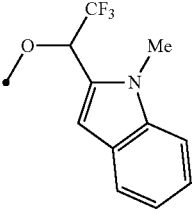 |

TABLE 2-continued
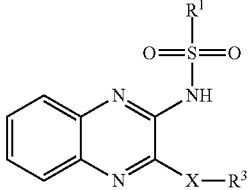
| Example No. | Compound No. | R¹ | X—R³ |
|---|---|---|---|
| 123 | 128 | 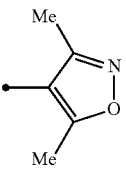 | 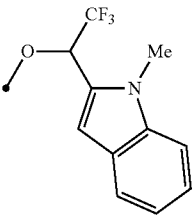 |
| 124 | 129 | 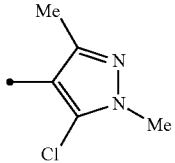 | 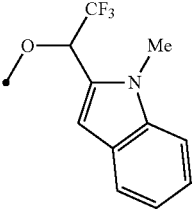 |
| 125 | 130 | 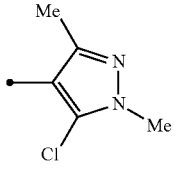 | 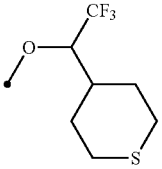 |
| 126 | 131 | 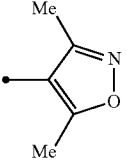 | 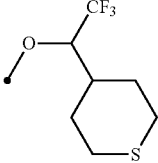 |
| 127 | 132 | 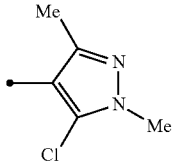 | 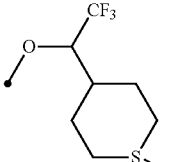 |
| 128 | 133 | 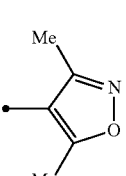 | 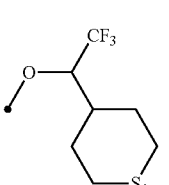 |

TABLE 2-continued

| Example No. | Compound No. | R¹ | X—R³ |
|---|---|---|---|
| 129 | 134 | 2-chlorophenyl | -OCH(CF₃)-(2-phenylthiazol-5-yl) |
| 130 | 135 | n-propyl (CH₂CH₂Me) | -OCH(CF₃)-(1-methylindol-2-yl) |
| 131 | 136 | 2-chlorophenyl | -OCH(CF₃)-(tetrahydrofuran-3-yl) |
| 132 | 137 | phenyl | -OCH(CF₃)-(pyridin-3-yl) |
| 133 | 138 | 2-chlorophenyl | -OCH(CF₃)-(pyridin-3-yl) |
| 134 | 139 | pyridin-3-yl | -OCH(CF₃)-(pyridin-3-yl) |
| 135 | 140 | thiophen-2-yl | -OC(CF₃)-(pyridin-3-yl) |

TABLE 2-continued
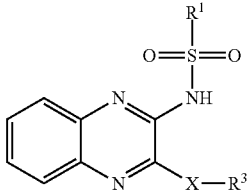
| Example No. | Compound No. | R¹ | X—R³ |
|---|---|---|---|
| 136 | 141 | 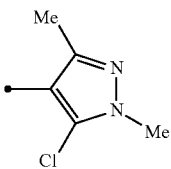 | 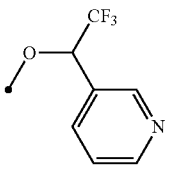 |
| 137 | 142 | 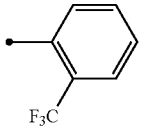 | 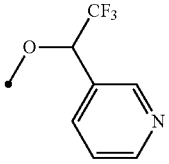 |
| 138 | 143 | 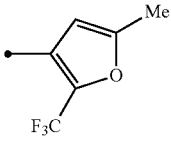 | 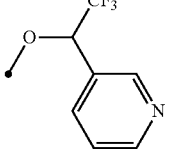 |
| 139 | 144 | 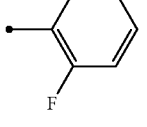 | 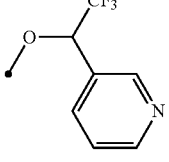 |
| 140 | 145 | 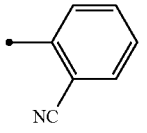 | 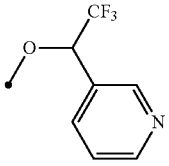 |
| 141 | 146 | 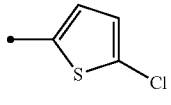 | 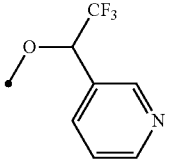 |
| 142 | 147 | 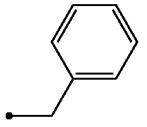 | 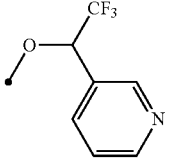 |

TABLE 2-continued

| Example No. | Compound No. | R¹ | X—R³ |
|---|---|---|---|
| 143 | 148 | —Me | -OCH(CF₃)(3-pyridyl) |
| 144 | 149 | —CF₃ | -OCH(CF₃)(3-pyridyl) |
| 145 | 150 | cyclopropyl | -OCH(CF₃)(3-pyridyl) |
| 146 | 151 | 2-(CF₃O)phenyl | -OCH(CF₃)(3-pyridyl) |
| 147 | 152 | 3,5-dichlorophenyl | -OCH(CF₃)(3-pyridyl) |
| 148 | 153 | 3,5-difluorophenyl | -OCH(CF₃)(3-pyridyl) |
| 149 | 154 | 1,2-dimethyl-1H-imidazol-4-yl | -OCH(CF₃)(3-pyridyl) |

TABLE 2-continued

| Example No. | Compound No. | R¹ | X—R³ |
|---|---|---|---|
| 150 | 155 | 3,5-dimethylisoxazol-4-yl | OCH(CF₃)-(pyridin-3-yl) |
| 151 | 156 | 2-methylphenyl | OCH(CF₃)-(pyridin-3-yl) |
| 152 | 157 | 2-aminophenyl | OCH(CF₃)-(pyridin-3-yl) |
| 153 | 158 | 2-methoxyphenyl | OCH(CF₃)-(pyridin-3-yl) |
| 154 | 159 | 2,3-dichlorophenyl | O(CH₂)₃-(pyridin-3-yl) |
| 155 | 160 | pyridin-2-yl | OCH(CF₃)-(pyridin-3-yl) |
| 156 | 161 | thiophen-3-yl | OCH(CF₃)-(pyridin-3-yl) |
| 157 | 162 | 2,5-dimethylthiophen-3-yl | OCH(CF₃)-(pyridin-3-yl) |

TABLE 2-continued
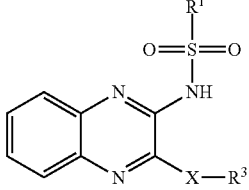
| Example No. | Compound No. | R¹ | X—R³ |
|---|---|---|---|
| 158 | 163 | 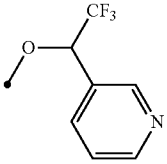 | 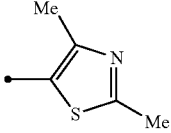 |
| 159 | 164 | 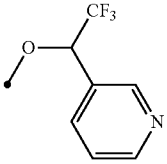 | 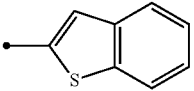 |
| 160 | 165 | 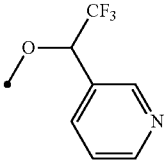 | 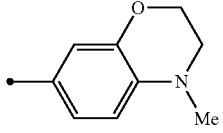 |
| 161 | 166 | 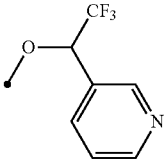 | 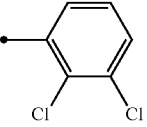 |
| 162 | 167 | 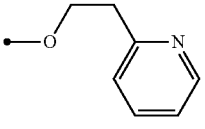 | 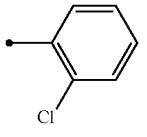 |
| 163 | 168 | 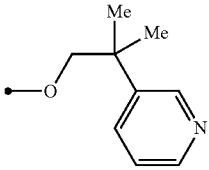 |  |
| 164 | 169 | 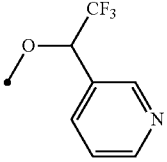 | 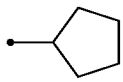 |

TABLE 2-continued

| Example No. | Compound No. | R¹ | X—R³ |
|---|---|---|---|
| 165 | 170 | 5-chloro-1,3-dimethyl-1H-pyrazol-4-yl | 1-(1-methyl-1H-imidazol-5-yl)-2,2,2-trifluoroethoxy |
| 166 | 171 | 3,5-dimethylisoxazol-4-yl | 1-(1-methyl-1H-imidazol-5-yl)-2,2,2-trifluoroethoxy |
| 167 | 172 | 2-chlorophenyl | 1,1,1-trifluoro-4-(pyridin-3-yl)butan-2-yloxy |
| 168 | 173 | 2-chlorobenzyl | 2,2,2-trifluoro-1-(pyridin-3-yl)ethoxy |
| 169 | 174 | dimethylamino | 2,2,2-trifluoro-1-(pyridin-3-yl)ethoxy |
| 170 | 175 | 2-chlorophenyl | 1-(1-methyl-1H-imidazol-5-yl)-2,2,2-trifluoroethoxy |
| 171 | 176 | 2-chlorophenyl | 2-methyl-3-(pyridin-3-yl)propoxy |
| 172 | 177 | 2-chlorophenyl | 3-(pyridin-3-yl)butoxy |

TABLE 2-continued

| Example No. | Compound No. | R¹ | X—R³ |
|---|---|---|---|
| 173 | 178 | 3,5-dimethylisoxazol-4-yl | 1-(thiazol-5-yl)-2,2,2-trifluoroethoxy |
| 174 | 179 | n-propyl | 1-(pyridin-3-yl)-2,2,2-trifluoroethoxy |
| 175 | 180 | isobutyl | 1-(pyridin-3-yl)-2,2,2-trifluoroethoxy |
| 176 | 181 | 3-chlorophenyl | 1-(pyridin-3-yl)-2,2,2-trifluoroethoxy |
| 177 | 182 | 4-chlorophenyl | 1-(pyridin-3-yl)-2,2,2-trifluoroethoxy |
| 178 | 183 | cyclohexyl | 1-(pyridin-3-yl)-2,2,2-trifluoroethoxy |
| 179 | 184 | 5-chloro-1,3-dimethylpyrazol-4-yl | 1-phenyl-2,2,2-trifluoroethoxy |

TABLE 2-continued

| Example No. | Compound No. | R¹ | X—R³ |
|---|---|---|---|
| 180 | 185 | 3,5-dimethylisoxazol-4-yl | -OCH(CF₃)(phenyl) |
| 181 | 186 | 5-chloro-1,3-dimethyl-1H-pyrazol-4-yl | -OCH(CF₃)(thiazol-5-yl) |
| 182 | 187 | isobutyl | -OCH(CF₃)(pyridin-3-yl) |
| 183 | 188 | morpholin-4-yl | -OCH(CF₃)(pyridin-3-yl) |
| 184 | 189 | -NH-cyclopropyl | -OCH(CF₃)(pyridin-3-yl) |
| 185 | 190 | Et | -OCH(CF₃)(pyridin-3-yl) |
| 186 | 191 | n-butyl | -OCH(CF₃)(pyridin-3-yl) |

TABLE 2-continued

| Example No. | Compound No. | R¹ | X—R³ |
|---|---|---|---|
| 187 | 192 | —CH₂CH₂Me | —OCH(CF₃)-(6-Me-pyridin-3-yl) |
| 188 | 193 | —CH₂CH₂CF₃ | —OCH(CF₃)-(pyridin-3-yl) |
| 189 | 194 | —NHCH₂CH₂Me | —OCH(CF₃)-(pyridin-3-yl) |
| 190 | 195 | —NHEt | —OCH(CF₃)-(pyridin-3-yl) |
| 191 | 196 | —CH₂CH₂Me | —OCH(CF₃)-(2-Cl-thiazol-5-yl) |
| 192 | 197 | —CH₂CH₂Me | —OCH(CF₃)-(4-CH₂NMe₂-phenyl) |
| 193 | 198 | 3,5-dimethylisoxazol-4-yl | —OCH(CF₃)-(2-Cl-thiazol-5-yl) |

TABLE 2-continued
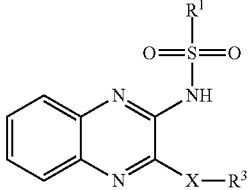
| Example No. | Compound No. | R¹ | X—R³ |
|---|---|---|---|
| 194 | 199 | 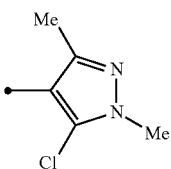 | 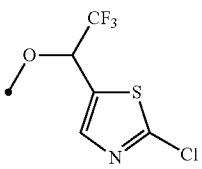 |
| 195 | 200 | 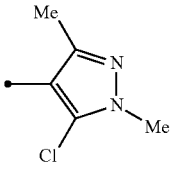 | 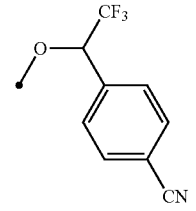 |
| 196 | 201 | 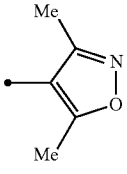 | 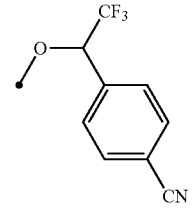 |
| 197 | 202 | 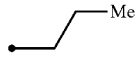 | 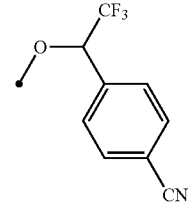 |
| 198 | 203 | 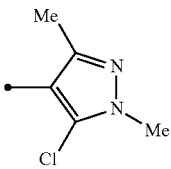 | 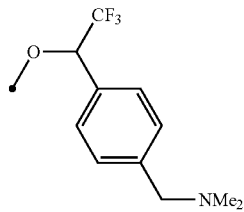 |
| 199 | 204 | 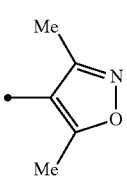 | 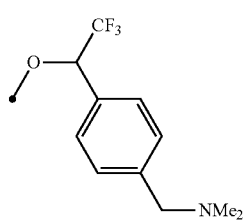 |

TABLE 2-continued

| Example No. | Compound No. | R¹ | X—R³ |
|---|---|---|---|
| 200 | 205 | —NH—CH₂CH₂—OMe | —O—CH(CF₃)-(3-pyridyl) |
| 201 | 206 | —NH—CH₂CH₂CH₂—OMe | —O—CH(CF₃)-(3-pyridyl) |
| 202 | 207 | —NH—CH₂CH₂—OEt | —O—CH(CF₃)-(3-pyridyl) |
| 203 | 208 | 4-(NHBoc-CH₂CH₂)-phenyl | —O—CH(CF₃)-(3-pyridyl) |
| 204 | 209 | 4-(NH₂-CH₂CH₂)-phenyl | —O—CH(CF₃)-(3-pyridyl) |
| 205 | 210 | —CH₂CH₂Me | —O—CH(CHMe₂)-(3-pyridyl) |
| 206 | 211 | —CH₂CH₂Me | —O—CH(CHMe₂)-(3-pyridyl N-oxide) |

TABLE 2-continued
| Example No. | Compound No. | R¹ | X—R³ |
|---|---|---|---|
| 207 | 212 | 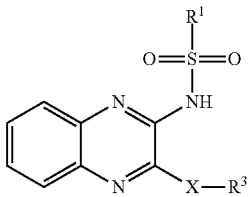 | 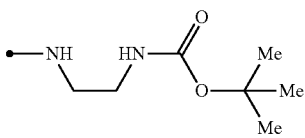 |
| 208 | 213 | 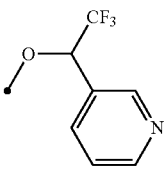 | 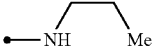 |
| 209 | 214 | 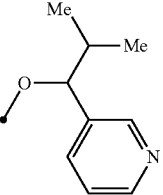 |  |
| 210 | 215 | 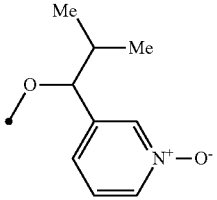 | 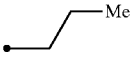 |
| 211 | 216 | 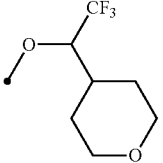 | 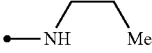 |
| 212 | 217 | 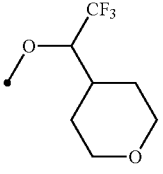 | 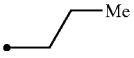 |
| 213 | 218 | 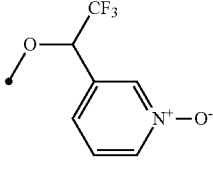 | 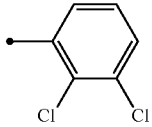 |

TABLE 2-continued
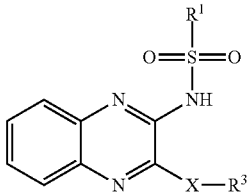
| Example No. | Compound No. | R¹ | X—R³ |
|---|---|---|---|
| 214 | 219 | 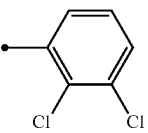 | 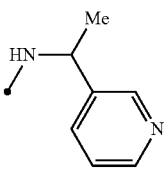 |
| 215 | 220 | 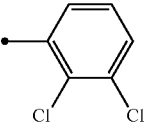 | 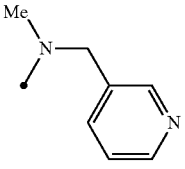 |
| 216 | 221 | 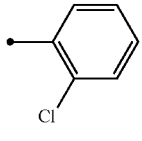 | 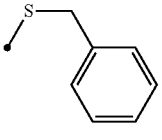 |
| 217 | 222 | 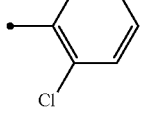 | 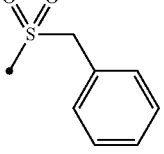 |
| 218 | 223 | 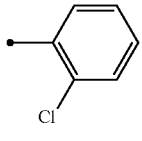 | 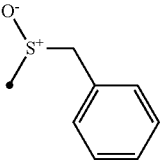 |
| 219 | 224 | 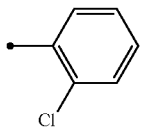 | 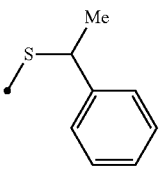 |
| 220 | 225 | 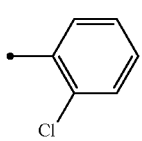 | 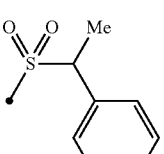 |
| 221 | 226 | 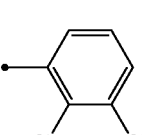 | 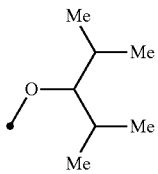 |

TABLE 2-continued

| Example No. | Compound No. | R¹ | X—R³ |
|---|---|---|---|
| 222 | 227 | 2,3-dichlorophenyl | 1,2,3,4-tetrahydronaphthalen-1-yloxy |
| 223 | 228 | 2-chlorophenyl | thiochroman-4-yloxy |
| 224 | 229 | 2-chlorophenyl | tetrahydro-2H-pyran-4-yl |
| 225 | 230 | 2-chlorophenyl | 1-methyl-2-morpholinoethoxy |
| 226 | 231 | 2-chlorophenyl | 3,3-dimethyl-2-methoxybutyl (OCH(Me)C(Me)₃... ) |
| 227 | 232 | 2-chlorophenyl | 1-methyl-2-ethoxyethoxy |
| 228 | 233 | 2-chlorophenyl | 1,3-bis(dimethylamino)propan-2-yloxy |
| 229 | 234 | 2-chlorophenyl | tetrahydrofuran-3-yloxy |
| 230 | 235 | 2-chlorophenyl | 1-methylpiperidin-4-yloxy |

TABLE 2-continued
| Example No. | Compound No. | R¹ | X—R³ |
|---|---|---|---|
| 231 | 236 | 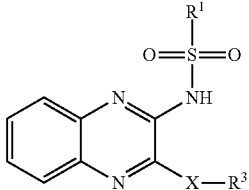 2-Cl-phenyl | 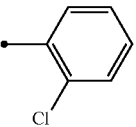 quinuclidinyloxy |
| 232 | 237 | 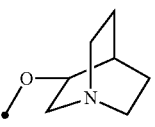 2-Cl-phenyl | 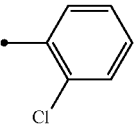 |
| 233 | 238 | 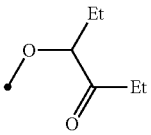 2-Cl-phenyl | 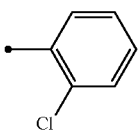 |
| 234 | 239 | 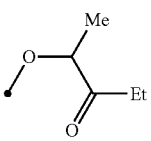 2-Cl-phenyl | 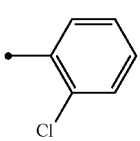 |
| 235 | 240 | 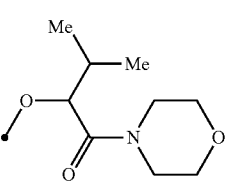 2-Cl-phenyl | 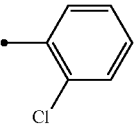 |
| 236 | 241 | 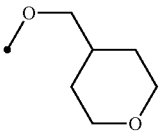 2-Cl-phenyl | 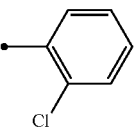 |
| 237 | 242 | 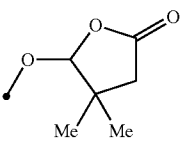 2-Cl-phenyl | 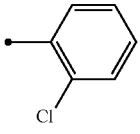 |

TABLE 2-continued

| Example No. | Compound No. | R¹ | X—R³ |
|---|---|---|---|
| 238 | 243 | 2-chlorophenyl | methoxy(pyridin-3-yl)(thiazol-5-yl)methyl |
| 239 | 244 | 2-chlorophenyl | 2-(2-oxopyrrolidin-1-yl)ethoxy |
| 240 | 245 | 2-chlorophenyl | (4-ethyltetrahydro-2H-pyran-4-yl)methoxy |
| 241 | 246 | 2-chlorophenyl | (4-methyltetrahydro-2H-pyran-4-yl)methoxy |
| 242 | 247 | 2-chlorophenyl | (4-methoxytetrahydro-2H-pyran-4-yl)methoxy |
| 243 | 248 | 2-chlorophenyl | (5-oxomorpholin-3-yl)methoxy |
| 244 | 249 | 2-chlorophenyl | (5-oxomorpholin-2-yl)methoxy |

TABLE 2-continued
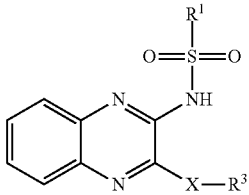
| Example No. | Compound No. | R¹ | X—R³ |
|---|---|---|---|
| 245 | 250 | 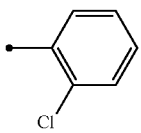 | 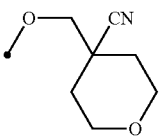 |
| 246 | 251 | 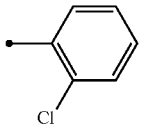 | 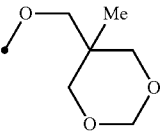 |
TABLE 3
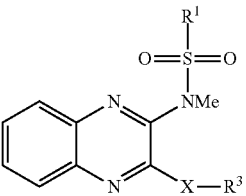
| Example No. | Compound No. | R¹ | X—R³ |
|---|---|---|---|
| 247 | 252 | 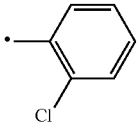 | 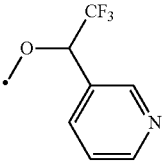 |
| 248 | 253 | 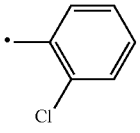 | 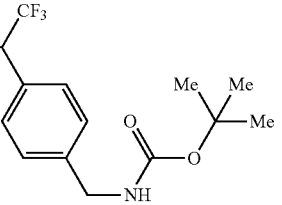 |

TABLE 4

| Example No. | Compound No. | Structure |
|---|---|---|
| 249 | 254 | (2,3-dichlorophenylsulfonyl)amino-5-chloro-3-[1-(pyridin-3-yl)-2,2,2-trifluoroethoxy]pyrazine |
| 250 | 255 | (2,3-dichlorophenylsulfonyl)amino-6-methoxy-2-[1-(pyridin-3-yl)-2,2,2-trifluoroethoxy]pyridine |
| 251 | 256 | (2,3-dichlorophenylsulfonyl)amino-5-chloro-3-[1-(pyridin-3-yl)propoxy]pyrazine |

TABLE 4-continued

| Example No. | Compound No. | Structure |
|---|---|---|
| 252 | 257 | (2,3-dichlorophenylsulfonyl)amino-pyrido[2,3-b]pyrazine with [1-(pyridin-3-yl)-2,2,2-trifluoroethoxy] |
| 253 | 258 | (2,3-dichlorophenylsulfonyl)amino-pyrido[3,2-b]pyrazine with [1-(pyridin-3-yl)-2,2,2-trifluoroethoxy] |
| 254 | 259 | (2,3-dichlorophenylsulfonyl)amino-5-chloro-3-[1-(4-methoxyphenyl)-2,2,2-trifluoroethoxy]pyrazine |

TABLE 4-continued
| Example No. | Compound No. | Structure |
|---|---|---|
| 255 | 260 | 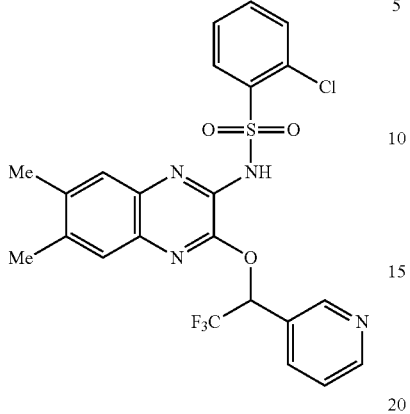 |
| 256 | 261 | 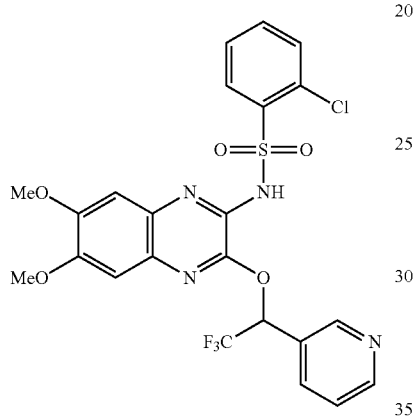 |
| 257 | 262 | 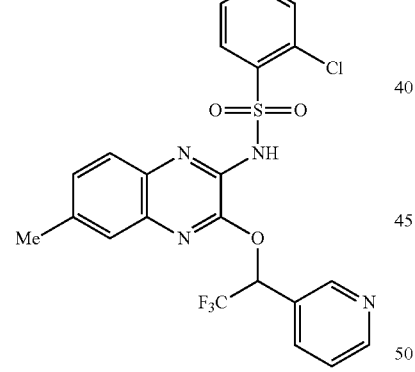 |
| 258 | 263 | 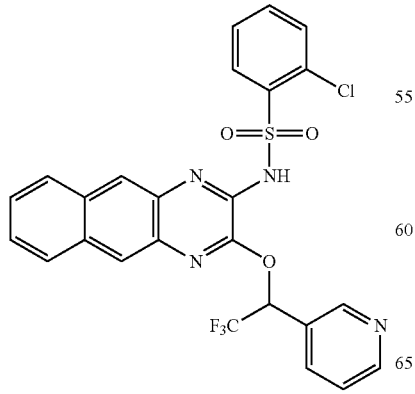 |
| 259 | 264 | 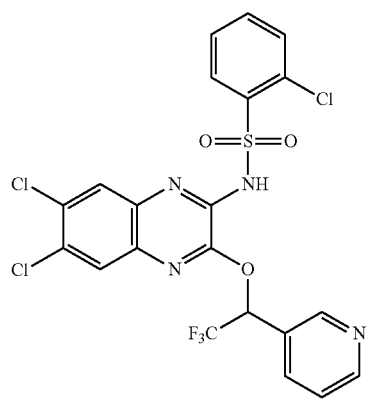 [SMILES: O=S(=O)(Nc1nc2cc(Cl)c(Cl)cc2nc1OC(c1cccnc1)C(F)(F)F)c1ccccc1Cl] |
| 260 | 265 | 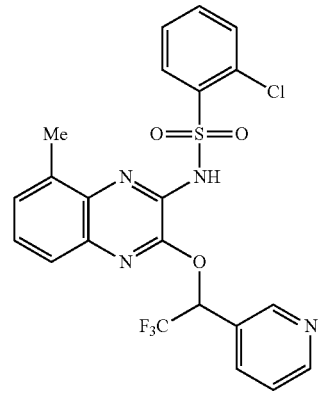 [SMILES: Cc1cccc2nc(OC(c3cccnc3)C(F)(F)F)c(NS(=O)(=O)c3ccccc3Cl)nc12] |
| 261 | 266 | 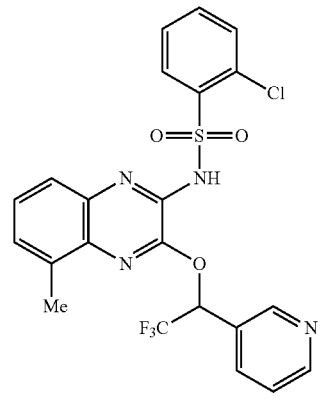 [SMILES: Cc1cccc2nc(NS(=O)(=O)c3ccccc3Cl)c(OC(c3cccnc3)C(F)(F)F)nc12] |

TABLE 5
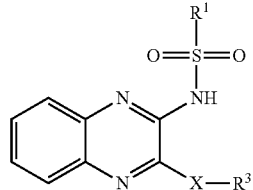
| Example No. | Compound No. | R¹ | X—R³ |
|---|---|---|---|
| 262 | 267 | 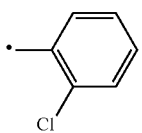 | 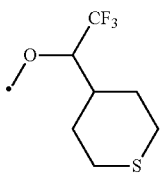 |
| 263 | 268 | 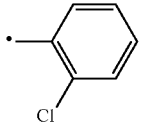 | 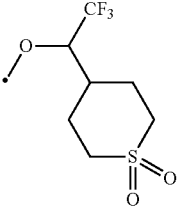 |
| 264 | 269 | 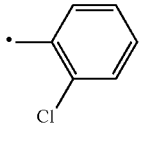 | 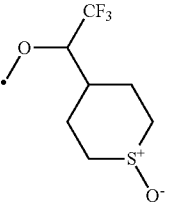 |
| 264 | 270 | 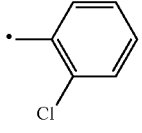 | 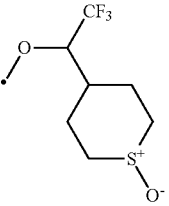 |
| 265 | 271 | 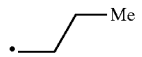 | 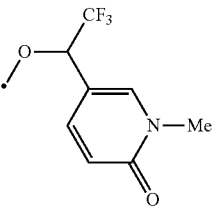 |
| 266 | 272 | 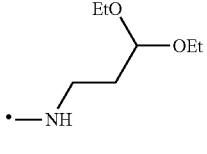 | 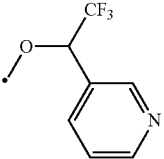 |

TABLE 5-continued
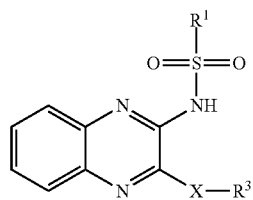
| Example No. | Compound No. | R¹ | X—R³ |
|---|---|---|---|
| 267 | 273 | 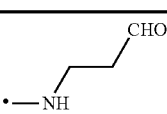 | 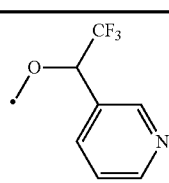 |
| 268 | 274 | 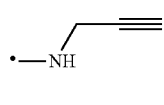 | 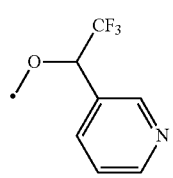 |
| 269 | 275 | 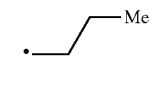 | 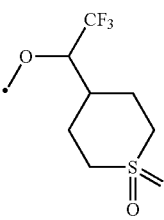 |
| 270 | 276 | 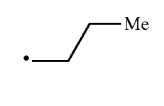 | 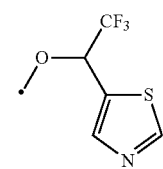 |
| 271 | 277 | 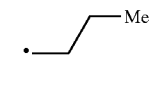 | 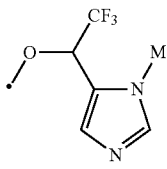 |
| 272 | 278 | 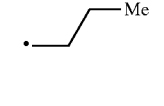 | 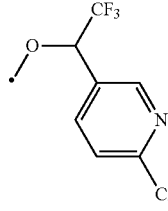 |
| 273 | 279 | 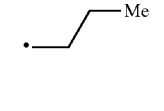 | 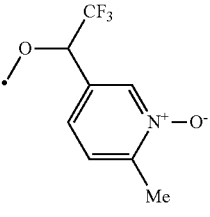 |

TABLE 5-continued
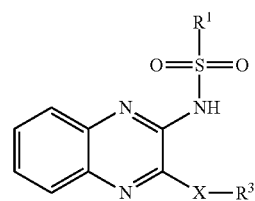
| Example No. | Compound No. | R¹ | X—R³ |
|---|---|---|---|
| 274 | 280 | •—NH—CH₂—Me (ethylamino) | O-CH(CF₃)-(6-methylpyridin-3-yl) |
| 275 | 281 | •—NH—CH₂—Me (ethylamino) | O-CH(CF₃)-(thiazol-5-yl) |
| 276 | 282 | •—NH—CH₂—Me (ethylamino) | O-CH(CF₃)-(1-methyl-1H-imidazol-5-yl) |
| 277 | 283 | •—NH—CH₂—Me (ethylamino) | O-CH(CF₃)-(6-chloropyridin-3-yl) |
| 278 | 284 | •—NH—CH₂—Me (ethylamino) | O-CH(CF₃)-(6-methylpyridin-3-yl 1-oxide) |
| 279 | 285 | •—NH-cyclopropyl | O-CH(CF₃)-(6-methylpyridin-3-yl) |

US 8,673,908 B2

TABLE 5-continued

| Example No. | Compound No. | R¹ | X—R³ |
|---|---|---|---|
| 280 | 286 | —NH-cyclopropyl | —O—CH(CF₃)-(thiazol-5-yl) |
| 281 | 287 | —NH-cyclopropyl | —O—CH(CF₃)-(1-methyl-1H-imidazol-5-yl) |
| 282 | 288 | —NH-cyclopropyl | —O—CH(CF₃)-(6-chloropyridin-3-yl) |
| 283 | 289 | —NH-cyclopropyl | —O—CH(CF₃)-(6-methylpyridin-3-yl 1-oxide) |
| 284 | 290 | —CH₂CH₂CH₂Me (propyl) | —O—CH(CF₃)-(3-cyanophenyl) |
| 285 | 291 | —NH-CH₂CH₂Me | —O—CH(CF₃)-(3-cyanophenyl) |
| 286 | 292 | —NH-CH₂CH₂Me | —O—CH(CF₃)-(4-cyanophenyl) |

TABLE 5-continued
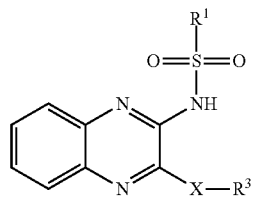
| Example No. | Compound No. | R¹ | X—R³ |
|---|---|---|---|
| 287 | 293 | 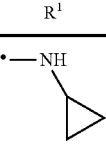 | 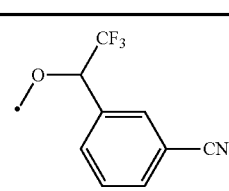 |
| 288 | 294 | 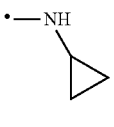 | 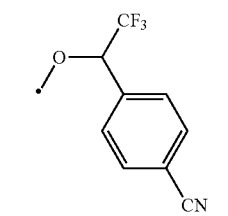 |
| 289 | 295 | 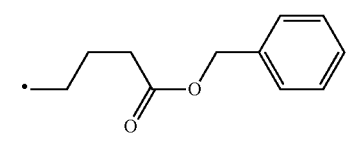 | 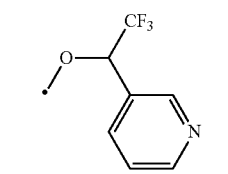 |
| 290 | 296 | 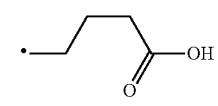 | 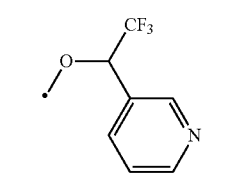 |
| 291 | 297 | 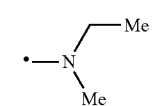 | 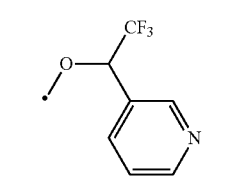 |
| 292 | 298 | 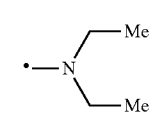 | 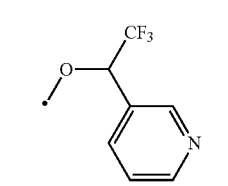 |
| 293 | 299 | 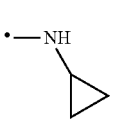 | 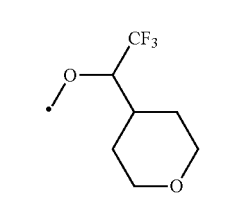 |

TABLE 5-continued
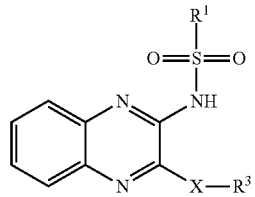
| Example No. | Compound No. | R¹ | X—R³ |
|---|---|---|---|
| 294 | 300 | CH₂CH₂OMe | OCH(CF₃)-(3-pyridyl) |
| 295 | 301 | CH₂CH₂CH₂OMe | OCH(CF₃)-(3-pyridyl) |
| 296 | 302 | CH₂CH₂Me | OCH(CF₃)-(4-chlorophenyl) |
| 297 | 303 | CH₂-cyclopropyl | OCH(CF₃)-(3-pyridyl) |
| 298 | 304 | allyl | OCH(CF₃)-(3-pyridyl) |
| 299 | 305 | CH₂-cyclopropyl | OCH(CF₃)-(6-methyl-3-pyridyl) |
| 300 | 306 | CH₂-cyclopropyl | OCH(CF₃)-(2-methyl-thiazol-5-yl) |

TABLE 5-continued

| Example No. | Compound No. | R¹ | X—R³ |
|---|---|---|---|
| 301 | 307 | cyclopropylmethyl | (S)-1-methoxy-2,2,2-trifluoro-1-(pyridin-3-yl)ethyl |
| 302 | 308 | cyclopropylmethyl | (S)-1-methoxy-2,2,2-trifluoro-1-(6-chloropyridin-3-yl)ethyl |
| 303 | 309 | cyclopropylmethyl | (S)-1-methoxy-2,2,2-trifluoro-1-(3-cyanophenyl)ethyl |
| 304 | 310 | 2-chlorophenyl | (S)-1-methoxy-2,2,2-trifluoro-1-phenylethyl |
| 305 | 311 | 2-chlorophenyl | (R)-1-methoxy-2,2,2-trifluoro-1-phenylethyl |
| 306 | 312 | n-propyl | (S)-1-methoxy-2,2,2-trifluoro-1-(pyridin-3-yl)ethyl |
| 307 | 313 | n-propyl | (R)-1-methoxy-2,2,2-trifluoro-1-(pyridin-3-yl)ethyl |

TABLE 5-continued
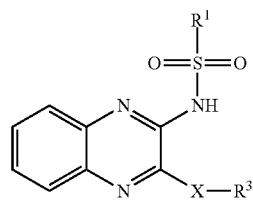
| Example No. | Compound No. | R¹ | X—R³ |
|---|---|---|---|
| 308 | 314 | 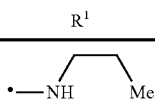 | 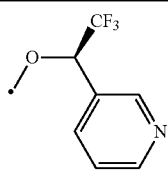 |
| 309 | 315 | 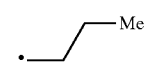 | 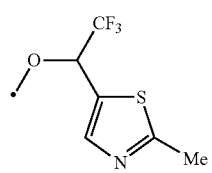 |
| 310 | 316 | 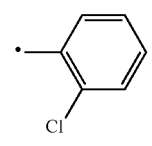 | 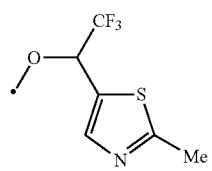 |
| 311 | 317 | 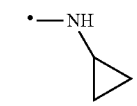 | 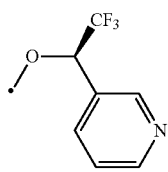 |
| 312 | 318 | 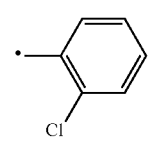 | 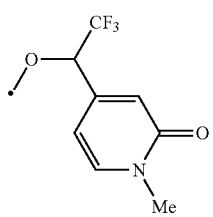 |
| 313 | 319 | 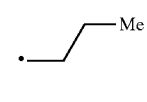 | 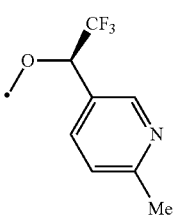 |
| 314 | 320 | 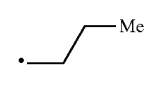 | 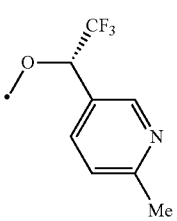 |

TABLE 5-continued
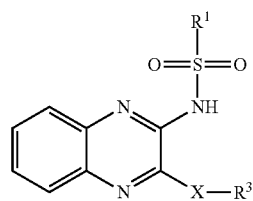
| Example No. | Compound No. | R¹ | X—R³ |
|---|---|---|---|
| 315 | 321 | 2-chlorophenyl | —O—CH(CF₃)₂ |
| 316 | 322 | n-propyl | —O—CH(CF₃)₂ |
| 317 | 323 | —NH-ethyl | —O—CH(CF₃)-(2-methylthiazol-5-yl) |
| 318 | 324 | —NH-cyclopropyl | —O—CH(CF₃)-(2-methylthiazol-5-yl) |
| 319 | 325 | 2-chlorophenyl | —O—CH(CF₃)-(1-methylpiperidin-4-yl) |
| 320 | 326 | n-propyl | —O—CH(CF₃)-(1-methylpiperidin-4-yl) |
| 321 | 327 | n-propyl | —O—CH(CF₃)-(piperidin-4-yl) |

TABLE 5-continued

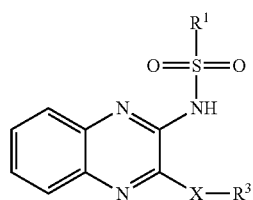

| Example No. | Compound No. | R¹ | X—R³ |
|---|---|---|---|
| 322 | 328 | •—NH—CH₂CH₂—Me | 4-(1-methoxy-2,2,2-trifluoroethyl)-1-methylpiperidine |
| 323 | 329 | •—NH-cyclopropyl | 4-(1-methoxy-2,2,2-trifluoroethyl)-1-methylpiperidine |
| 324 | 330 | •—CH₂CH₂—Me | 4-(1-methoxy-2,2,2-trifluoroethyl)-1-acetylpiperidine |
| 325 | 331 | •—CH₂CH₂—Me | 3-(1-methoxy-2,2,2-trifluoroethyl)-5-methylpyridine |
| 326 | 332 | •—CH₂CH₂—Me | 3-(1-methoxy-2,2,2-trifluoroethyl)-5-fluoropyridine |
| 327 | 333 | •—CH₂CH₂—Me | 4-(1-methoxy-2,2,2-trifluoroethyl)-1-methyl-2-pyridone |

TABLE 5-continued

| Example No. | Compound No. | R¹ | X—R³ |
|---|---|---|---|
| 328 | 334 | propyl (Me) | 1-(5-methoxypyridin-3-yl)-2,2,2-trifluoroethoxy |
| 329 | 335 | propyl (Me) | 1-(5-chloropyridin-3-yl)-2,2,2-trifluoroethoxy |
| 330 | 336 | propyl (Me) | 1-(1-methanesulfonylpiperidin-4-yl)-2,2,2-trifluoroethoxy |
| 331 | 337 | propyl (Me) | 1-(1-methoxycarbonylpiperidin-4-yl)-2,2,2-trifluoroethoxy |
| 332 | 338 | 2-chlorophenyl | 1-(5-chloropyridin-3-yl)-2,2,2-trifluoroethoxy |
| 333 | 339 | 2-chlorophenyl | 1-(5-fluoropyridin-3-yl)-2,2,2-trifluoroethoxy |

TABLE 5-continued

| Example No. | Compound No. | R¹ | X—R³ |
|---|---|---|---|
| 334 | 340 | propyl | 1-propionyl-4-(1-methoxy-2,2,2-trifluoroethyl)piperidine |
| 335 | 341 | propyl | 1-(cyclopropylcarbonyl)-4-(1-methoxy-2,2,2-trifluoroethyl)piperidine |
| 336 | 342 | propyl | 5-[(S)-1-methoxy-2,2,2-trifluoroethyl]-2-methylthiazole |
| 337 | 343 | propyl | 5-(1-methoxy-2,2,2-trifluoroethyl)-2-methylthiazole |
| 338 | 344 | propyl | 4-(1-methoxy-2,2,2-trifluoroethyl)-2-methylthiazole |
| 339 | 345 | propyl | 5-(methoxymethyl)-2-methylthiazole |
| 340 | 346 | propyl | (S)-4-(1-methoxy-2,2,2-trifluoroethyl)tetrahydropyran |

TABLE 5-continued
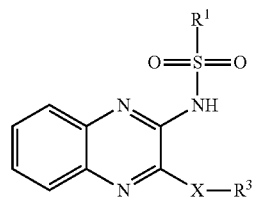
| Example No. | Compound No. | R¹ | X—R³ |
|---|---|---|---|
| 340 | 347 | –CH₂CH₂Me | (S)-OCH(CF₃)-(tetrahydropyran-4-yl) |
| 341 | 348 | –CH₂CH₂Me | (S)-OCH(CF₃)-(6-chloropyridin-3-yl) |
| 342 | 349 | –CH₂CH₂Me | (S)-OCH(CF₃)-(3-cyanophenyl) |
| 343 | 350 | –CH₂CH₂Me | OCH(CF₃)-(4-fluorotetrahydropyran-4-yl) |
| 344 | 351 | –CH₂CH₂Me | OCH(CF₃)-(4-cyanotetrahydropyran-4-yl) |
| 345 | 352 | –CH₂CH₂Me | OCH(CF₃)-(4-hydroxytetrahydropyran-4-yl) |
| 346 | 353 | –CH₂CH₂Me | OCH(CF₃)-(4-methoxytetrahydropyran-4-yl) |

TABLE 5-continued
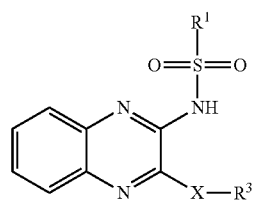
| Example No. | Compound No. | R¹ | X—R³ |
|---|---|---|---|
| 347 | 354 | ⸱⁀⁀Me (propyl) | piperidine with 4-F, 4-[CH(CF₃)(OMe)], N-acetyl |
| 348 | 355 | ⸱⁀⁀Me (propyl) | piperidine with 4-F, 4-[CH(CF₃)(OMe)], N-SO₂Me |
| 349 | 356 | ⸱⁀⁀Me (propyl) | piperidine with 4-Me, 4-[CH(CF₃)(OMe)], N-acetyl |
| 350 | 357 | ⸱⁀⁀Me (propyl) | piperidine with 4-Me, 4-[CH(CF₃)(OMe)], N-SO₂Me |

TABLE 6

| Example No. | Compound No. | Structure |
|---|---|---|
| 351 | 358 | 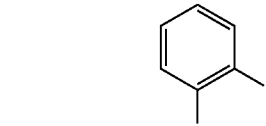 |
| 352 | 359 | 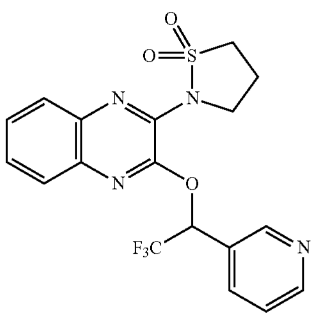 [SMILES: O=S1(=O)CCCN1c1nc2ccccc2nc1OC(c1cccnc1)C(F)(F)F] |
| 353 | 360 | 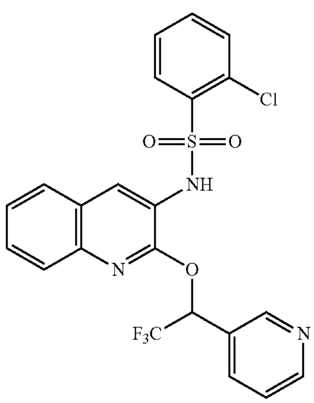 [SMILES: O=S(=O)(Nc1cc2ccccc2nc1OC(c1cccnc1)C(F)(F)F)c1ccccc1Cl] |
| 354 | 361 | 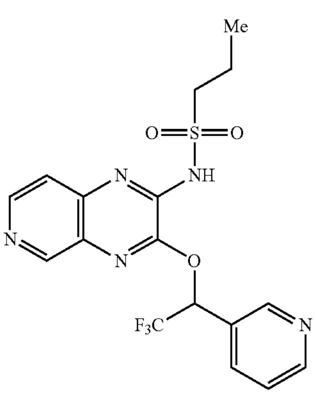 [SMILES: CCCS(=O)(=O)Nc1nc2ccncc2nc1OC(c1cccnc1)C(F)(F)F] |

TABLE 6-continued

| Example No. | Compound No. | Structure |
|---|---|---|
| 355 | 362 | 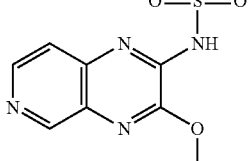 |

Next, pharmacological effects of some of Compounds (I) and (II) will be described with reference to Test Examples.

TEST EXAMPLE 1

Inhibitory Activity on Kynurenine Production

This assay was performed according to a method modified from the method described in the Journal of Biological Chemistry (J. Biol. Chem.), vol. 263, pp. 2041-2048 (1988). Culture of KATO-III derived from human gastric cancer cells was performed by use of RPMI 1640 (GIBCO, 11875) supplemented with 10 vol % FBS (GIBCO, 10091-148, lot. 665285). 1 μL of a DMSO solution of the test substance was diluted with 199 μL of the culture medium, and the diluted solution was added to wells of a 384 well plate (10 μL/well). Then, IFN-γ (Sigma, 1-3265) was added to the culture medium so that the concentration of IFN-γ was 31.25 ng/mL, and the KATO-III cells were suspended at 50,000 cells/ml, in the culture medium. 40 μL of the suspension was added to each well (2,000 cells/well), and culture of the KATO-III cells was performed at 37° C. under a 5% $CO_2$ atmosphere for 96 hours. The final concentration of DMSO was limited to 0.1 vol % or less so that DMSO itself might not affect the kynurenine concentration measured by this assay. After the culture, 10 μL of a 30 w/v % aqueous trichloroacetic acid solution was added to each well, and incubation was performed at 65° C. for 30 minutes. The plate was centrifuged at 2,500×g for 5 minutes, and then 15 μL of the supernatant in each well was transferred into another 384 well plate. To each of the transferred supernatants, 15 μL of a 2 w/v % solution of p-dimethylaminobenzaldehyde in acetic acid was added, incubation was performed at 65° C. for 20 minutes, and then the absorbance at 480 nm was measured.

$$\text{Inhibition rate } (\%) = \frac{(\text{Control} - \text{Sample})}{(\text{Control} - \text{Blank})} \times 100$$

Sample: the absorbance value of the well to which a DMSO solution containing the test substance was added and in which cells were treated with IFN-γ.

Blank: the absorbance value of the well to which only DMSO, not the test substance was added and in which cells were treated with IFN-γ.

Control: the absorbance value of the well to which only DMSO, not the test substance was added and in which cells were not treated with IFN-γ.

The inhibition rates at various concentrations of each test substance were measured, and the $IC_{50}$ value was calculated as a concentration which gives an inhibition rate of 50%. The results showed that the $IC_{50}$ values of Compounds 10, 11, 15, 16, 18, 20 to 24, 27 to 29, 31, 34 to 37, 39 to 49, 51 to 60, 62 to 80, 82 to 90, 92 to 94, 96 to 104, 106 to 113, 115 to 121, 126 to 144, 146, 147, 150 to 153, 155 to 159, 161 to 165, 167 to 208, 210, 211, 213 to 217, 224, 226, 230, 237, 242, 243, 245, 246, 253, 262 to 271, 272, 274 to 276, 278 to 286, 288, 290 to 295, 297 to 312, 314 to 319, 321 to 325, 330 to 342, 344, 347 to 351 and 353 to 357 were less than 1 μmol/L, and that the $IC_{50}$ values of Compounds 2, 3, 5, 6, 13, 26, 30, 32, 91, 125, 148, 221, 231, 232, 239, 247, 250, 251, 260, 273, 277, 287, 289, 313, 326, 328, 343, 345, 346, 352, 358, 360 and 362 were 1 to 10 μmol/L.

That is, it became clear that Compound (I) of the present invention has an inhibitory activity on kynurenine production.

In this assay, expression of IDO in KATO-III cells is induced by IFN-γ treatment and then kynurenine in the culture medium is quantified. It is known that the kynurenine concentration in a culture medium increases in proportion to the enzymatic activity of intracellular IDO (for example, the Journal of Biological Chemistry (J. Biol. Chem.), vol. 263, pp. 2041-2048 (1988)). The compounds of the present invention showed an inhibitory effect on kynurenine production. It is known that kynurenine production is inhibited by IDO inhibitors (for example, the Journal of Clinical Investigation (J. Clin. Invest.), vol. 117, No. 5, pp. 1147-1154 (1988)), and thus it is expected that Compound (I) also has an inhibitory effect on IDO.

It is known that compounds having an inhibitory effect on kynurenine production and/or on IDO are useful as an antitumor agent, an anti-AIDS agent, an anti-AIDS dementia agent, an anti-Alzheimer's disease agent, an antidepressant, or the like (for example, the Journal of Clinical Investigation (J. Clin. Invest.), vol. 117, pp. 1147-1154 (2007); the Journal of Virology (J. Virol.), vol. 81, pp. 11593-11603 (2007); Neuropathology and Applied Neurobiology (Neuropathol. Appl. Neurobiol.), vol. 31, pp. 395-404 (2005); Neuroscience Letters (Neurosci. Lett.), vol. 187, pp. 9-12 (1995); and Neuropsychopharmacology, vol. 33, 2341-2351 (2008)). It is known that such compounds also have an immunostimulatory activity (for example, Nature Immunology (Nat. Immunol.), vol. 2, pp. 64-68 (2001)). Therefore, Compound (I) of the present invention can be expected as an antitumor agent, an anti-AIDS agent, an anti-AIDS dementia agent, an anti-Alzheimer's disease agent, an antidepressant, an immunostimulator, or the like.

TEST EXAMPLE 2

Antitumor Effect 5-week-old BALB/c mice (male, supplied from CLEA Japan, Inc.) were purchased. After quarantine and stabilization, mice which favorably gained their weight and had no apparent abnormalities were used in the test. The test started from 6 weeks of age. The mice were housed in groups of 6 mice per plastic cage with free access to commercial solid feed and water in a breeding room in which the room temperature was 19° C. to 25° C., the humidity was 30 to 70% and the light was kept on for 12 hours a day (7:00 a.m. to 7:00 p.m.).

The abdominal hair of the BALB/c mice was shaved on the day before the test. Transplantation was performed by subcutaneous injection of a suspension containing $1\times10^6$ 4T1 mouse breast cancer cells in 100 μL of phosphate buffered saline (PBS) from the shaved region of each mouse.

When the tumor volume reached 30 to 80 mm$^3$, the mice were divided into groups so that the average tumor volume of each group was equal. The test compound was suspended in 0.5% (w/v) methylcellulose 400 cP (manufactured by Wako Pure Chemical Industries, Ltd.), and the suspension was orally administered to each mouse of the corresponding group once or twice daily. The tumor volume was calculated using the formula $(a \times b^2)/2$ (a: tumor major axis, b: tumor minor axis). The tumor volume (V) was measured twice or three times a week, and the tumor growth rate ($V/V_0$) was calculated by division of the tumor volume (V) by the tumor volume on the day of the first administration ($V_0$). The T/C (treatment group/control group) value was calculated by division of the $V/V_0$ value of the test compound treatment group by the $V/V_0$ value of the control group, based on which the antitumor effect was evaluated.

Statistical analysis was performed on the tumor volumes of the control group and the treatment group, using student's T-test. If the p value was <0.05, we considered the difference significant. The results are shown in the following Tables 7 and 8.

TABLE 7

| Compound No. | Dose (mg/kg) | Day 3 T/C | Day 3 p value | Day 7 T/C | Day 7 p value |
|---|---|---|---|---|---|
| 16 | 100 | 0.62 | 0.032 | 0.58 | 0.091 |

TABLE 8

| Compound No. | Dose (mg/kg) | Day 4 T/C | Day 4 p value | Day 7 T/C | Day 7 p value |
|---|---|---|---|---|---|
| 20 | 10 | 0.68 | 0.028 | 0.69 | 0.072 |
| 179 | 0.1 | 0.76 | 0.040 | 0.50 | 0.000032 |

The results show that Compound 16 significantly inhibited tumor growth on Day 3 and Day 7 after administration, and that Compounds 20 and 179 significantly inhibited tumor growth on Day 4 and Day 7 after administration. From the above results, it became clear that Compound (I) of the present invention, such as Compounds 16, 20, 179 and the like, can be used as an antitumor agent.

Compounds (I) and (II) or pharmaceutically acceptable salts thereof can be used as they are or in various forms of pharmaceuticals depending on the pharmacological effect, the purpose of administration, and the like. The pharmaceutical composition of the present invention can be usually produced by homogeneously mixing a pharmaceutically acceptable carrier with an effective amount of Compound (I) or (II) or a pharmaceutically acceptable salt thereof as an active ingredient. The carrier can be in a wide range of forms depending on the dosage form suitable for administration. The pharmaceutical composition is preferably in a dosage unit form suitable for oral administration or parenteral administration such as injection and the like.

For example, for preparation of tablets, excipients, such as lactose and mannitol; disintegrants, such as starch; lubricants, such as magnesium stearate; binders, such as polyvinylalcohol and hydroxypropylcellulose; surfactants, such as sucrose fatty acid ester and sorbitol fatty acid ester; and the like can be used in a usual manner. It is preferable that 1 to 200 mg of the active ingredient is contained per tablet.

For preparation of injections, water; saline; vegetable oils, such as olive oil and peanut oil; solvents, such as ethyl oleate and propylene glycol; solubilizing agents, such as sodium benzoate, sodium salicylate and urethane; tonicity agents, such as salts and glucose; preservatives, such as phenol, cresol, p-hydroxybenzoic acid esters and chlorobutanol; antioxidants, such as ascorbic acid and sodium pyrosulfite; and the like can be used in a usual manner.

Compounds (I) and (II) or pharmaceutically acceptable salts thereof can be administered orally or parenterally (example: injections and the like). The effective dose and dose frequency vary depending on the dosage form, the age, body weight and condition of a patient, and the like, but in general, the daily dose is preferably 0.01 to 100 mg/kg.

Subjects to which Compounds (I) and (II) or pharmaceutically acceptable salts thereof are administered are preferably patients with the above-described diseases in which kynurenine production is involved. Particularly, patients with cancer (tumor), neurodegenerative diseases, infections, immune diseases, or the like are preferably suitable, and patients with cancer (tumor) or the like are more preferably suitable. These patients can be selected by use of a known diagnosis method. Also, for prevention of the onset of the diseases, the above-mentioned compound can be administered to mammals which may develop the diseases. Compounds (I) and (II) or their pharmaceutically acceptable salts or a composition thereof can be administered orally or parenterally to humans and non-human mammals (example: a mouse, a rat, a hamster, a guinea pig, a rabbit, a cat, a dog, a pig, a cow, a horse, a sheep, a monkey, and the like).

Hereinafter, the present invention will be illustrated in more detail by way of Examples and Reference Examples, but is not limited thereto.

Regarding a proton nuclear magnetic resonance spectrum ($^1$H-NMR), in some compounds and measurement conditions, exchangeable protons are not clearly observed. As the notations of the multiplicity of signals, those generally employed are used, and the symbol "br" represents an apparent broad signal.

The instrumental data of the compounds in the respective Reference Examples and Examples below were measured by use of the following devices.

$^1$H-NMR: JEOL JNM-EX270 (270 MHz) or JEOL JNM-AL300 (300 MHz) MS: JEOL SX-102AQQ (the FAB method), JEOL JMS-DX303 (the FAB method), Micromass Quattro (the APCI method) or Micromass LCT (ESI, the APCI Method)

Unless otherwise noted, the symbol "%" regarding the concentration means "% by mass", and the ratio of solvents means the volume ratio of the solvents.

EXAMPLE 1

2,3-dichloro-N-{3-[(pyridin-3-yl)methoxy]quinoxalin-2-yl}-benzenesulfonamide (Compound 6)

2-Amino-3-[(pyridin-3-yl)methoxy]quinoxaline (Compound BA) (383 mg, 1.52 mmol) was dissolved in tetrahydrofuran (10.0 mL). To this, 60% sodium hydride (in oil) (182 mg, 4.55 mmol) was added under a nitrogen atmosphere at 0° C. and the mixture was stirred at the same temperature for 15 minutes. To this, 2,3-dichlorobenzenesulfonyl chloride (954 mg, 4.55 mmol) was added and the mixture was stirred at room temperature for 12 hours. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol=9/1).

Further, slurry purification was performed using diisopropyl ether, to give 2,3-dichloro-N-{3-[(pyridin-3-yl)methoxy]quinoxalin-2-yl}-benzenesulfonamide (Compound 6) (172 mg, yield: 25%).

ESIMS m/z: 461 (M+H)$^+$; $^1$H-NMR (300 MHz, CDCl$_3$, δ): 5.62 (s, 2H), 7.14-7.52 (m, 5H), 7.65-7.75 (m, 2H), 7.88-8.33 (m, 2H), 8.67 (dd, J=1.1, 4.8 Hz, 1H), 8.88 (d, J=1.8 Hz, 1H).

EXAMPLE 2

N-{3-[(pyridin-3-yl)methoxy]quinoxalin-2-yl}-1-naphthalenesulfonamide (Compound 7)

2-Amino-3-[(pyridin-3-yl)methoxy]quinoxaline (Compound BA) (60.0 mg, 0.238 mmol) and 1-naphthalenesulfonyl chloride (189 mg, 0.834 mmol) were dissolved in pyridine (0.6 mL). The mixture was stirred under a nitrogen atmosphere at room temperature for 72 hours. Then, a saturated aqueous sodium bicarbonate solution was added to the reaction mixture, and extraction with ethyl acetate was performed, followed by washing with brine and drying over anhydrous sodium sulfate. The solvent was evaporated off under reduced pressure, and the residue was purified by preparative thin-layer chromatography (chloroform/methanol=9/1). Further, slurry purification was performed using diisopropyl ether, to give N-{3-[(pyridin-3-yl)methoxy]quinoxalin-2-yl}-1-naphthalenesulfonamide (Compound 7) (39.8 mg, yield: 38%).

ESIMS m/z: 253 (M+H)$^+$; $^1$H-NMR (300 MHz, DMSO-d$_6$, δ): 5.56 (s, 2H), 7.41-7.77 (m, 8H), 7.98 (d, J=7.3 Hz, 1H), 8.06 (d, J=7.71 Hz, 1H), 8.24 (d, J=8.1 Hz, 1H), 8.56-8.59 (m, 2H), 8.81-8.87 (m, 2H).

EXAMPLE 3

2,3-dichloro-N-{3-[(4-methoxyphenyl)methoxy]quinoxalin-2-yl}benzenesulfonamide (Compound 8)

According to Example 1, by use of 2-amino-3-[(4-methoxyphenyl)methoxy]quinoxaline (Compound BB) (68.8 mg, 0.242 mmol), 2,3-dichlorobenzenesulfonyl chloride (178 mg, 0.725 mmol), 60% sodium hydride (in oil) (19.4 mg, 0.484 mmol) and tetrahydrofuran (1.4 mL), the mixture was stirred and reacted at room temperature for 92 hours. After purification by preparative thin-layer chromatography (hexane/ethyl acetate=7/3), slurry purification was further performed using diisopropyl ether, to give 2,3-dichloro-N-{3-[(4-methoxyphenyl)methoxy]quinoxalin-2-yl}benzenesulfonamide (Compound 8) (49.9 mg, yield: 42%).

ESIMS m/z: 490 (M+H)$^+$; $^1$H-NMR (300 MHz, DMSO-d$_6$, δ): 3.34 (s, 3H), 5.48 (s, 2H), 6.95 (d, J=8.4 Hz, 2H), 7.48-8.32 (m, 9H).

EXAMPLE 4

N-{3-[(4-methoxyphenyl)methoxy]quinoxalin-2-yl}-1-naphthalenesulfonamide (Compound 9)

According to Example 1, by use of 2-amino-3-[(4-methoxyphenyl)methoxy]quinoxaline (Compound BB) (69.4 mg, 0.247 mmol), 1-naphthalenesulfonyl chloride (168 mg, 0.740 mmol), 60% sodium hydride (in oil) (24.7 mg, 0.618 mmol) and tetrahydrofuran (1.4 mL), the mixture was stirred and reacted at room temperature for 28.5 hours. After purification by preparative thin-layer chromatography (hexane/ethyl acetate=7/3), slurry purification was further performed using diisopropyl ether, to give N-{3-[(4-methoxyphenyl) methoxy]quinoxalin-2-yl}-1-naphthalenesulfonamide (Compound 9) (11.6 mg, yield: 10%).

ESIMS m/z: 472 (M+H)$^+$; $^1$H-NMR (300 MHz, DMSO-$d_6$, δ): 3.75 (s, 3H), 5.47 (s, 2H), 6.94 (d, J=8.1 Hz, 2H), 7.45-8.90 (m, 13H), 11.86 (br s, 1H).

EXAMPLE 5

2,3-dichloro-N-{3-[(2-naphthyl) methoxy]quinoxalin-2-yl}-benzenesulfonamide (Compound 10)

According to Example 1, by use of 2-amino-3-[(2-naphthyl) methoxy]quinoxaline (Compound BC) (71.5 mg, 0.237 mmol), 2,3-dichlorobenzenesulfonyl chloride (175 mg, 0.712 mmol), 60% sodium hydride (in oil) (23.7 mg, 0.593 mmol) and tetrahydrofuran (1.4 mL), the mixture was stirred and reacted at room temperature for 28.5 hours. After purification by preparative thin-layer chromatography (hexane/ethyl acetate=7/3), slurry purification was further performed using diisopropyl ether, to give 2,3-dichloro-N-{3-[(2-naphthyl)methoxy]quinoxalin-2-yl}-benzenesulfonamide (Compound 10) (61.9 mg, yield: 50%).

ESIMS m/z: 510 (M+H)$^+$; $^1$H-NMR (300 MHz, DMSO-$d_6$, δ): 5.73 (s, 2H), 7.52-8.30 (m, 14H).

EXAMPLE 6

N-{3-[(2-naphthyl)methoxy]quinoxalin-2-yl}-1-naphthalenesulfonamide (Compound 11)

According to Example 1, by use of 2-amino-3-[(2-naphthyl)methoxy]quinoxaline (Compound BC) (72.7 mg, 0.241 mmol), 1-naphthalenesulfonyl chloride (164 mg, 0.724 mmol), 60% sodium hydride (in oil) (24.1 mg, 0.603 mmol) and tetrahydrofuran (1.4 mL), the mixture was stirred and reacted at room temperature for 28.5 hours. After purification by preparative thin-layer chromatography (hexane/ethyl acetate=7/3), slurry purification was further performed using diisopropyl ether, to give N-{3-[(2-naphthyl)methoxy]quinoxalin-2-yl}-1-naphthalenesulfonamide (Compound 11) (37.4 mg, yield: 32%).

ESIMS m/z: 492 (M+H)$^+$; $^1$H-NMR (300 MHz, DMSO-$d_6$, δ): 5.72 (s, 2H), 7.46-8.92 (m, 18H), 11.93 (br s, 1H).

EXAMPLE 7

N-{3-[(4-methoxyphenyl)methoxy]quinoxalin-2-yl}-1-thiophenesulfonamide (Compound 12)

According to Example 1, by use of 2-amino-3-[(4-methoxyphenyl)methoxy]quinoxaline (Compound BB) (72.2 mg, 0.257 mmol), 1-thiophenesulfonyl chloride (141 mg, 0.770 mmol), 60% sodium hydride (in oil) (30.8 mg, 0.770 mmol) and tetrahydrofuran (1.4 mL), the mixture was stirred and reacted at room temperature for 28.5 hours. After purification by preparative thin-layer chromatography (hexane/ethyl acetate=7/3), slurry purification was further performed using diisopropyl ether, to give N-{3-[(4-methoxyphenyl) methoxy]quinoxalin-2-yl}-1-thiophenesulfonamide (Compound 12) (9.2 mg, yield: 8%).

ESIMS m/z: 428 (M+H)$^+$; $^1$H-NMR (300 MHz, DMSO-$d_6$, δ): 3.76 (s, 3H), 5.46 (s, 2H), 6.94-6.99 (m, 2H), 7.17 (t, J=4.4 Hz, 1H), 7.52-7.99 (m, 8H), 11.54 (br s, 1H).

EXAMPLE 8

N-{3-[(2-naphthyl)methoxy]quinoxalin-2-yl}-4-toluenesulfonamide (Compound 13)

N-(3-Chloroquinoxalin-2-yl)-4-toluenesulfonamide (Compound AB) (70.0 mg, 0.210 mmol) and 2-naphthaleneethanol (40.0 mg, 252 mmol) were dissolved in tetrahydrofuran (1.5 mL). To this, 60% sodium hydride (in oil) (18.5 mg, 0.462 mmol) was added under a nitrogen atmosphere at 0° C. and the mixture was stirred at room temperature for 2 hours. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was subjected to slurry purification using methanol, to give N-{3-[(2-naphthyl)methoxy]quinoxalin-2-yl}-4-toluenesulfonamide (Compound 13) (79.0 mg, yield: 83%).

ESIMS m/z: 446 (M+H)$^+$; $^1$H-NMR (300 MHz, DMSO-$d_6$, δ): 2.34 (s, 3H), 5.70 (s, 2H), 7.40 (d, J=8.1 Hz, 2H), 7.53-7.56 (m, 4H), 7.71-8.12 (m, 9H), 11.33 (br s, 1H).

EXAMPLE 9

2,3-dichloro-N-{3-[2-(pyridin-3-yl)ethoxy]quinoxalin-2-yl}-benzenesulfonamide (Compound 14)

According to Example 8, by use of 2,3-dichloro-N-(3-chloroquinoxalin-2-yl)benzenesulfonamide (Compound AA) (70.0 mg, 0.180 mmol), 3-(2-hydroxyethyl)pyridine (33.4 mg, 0.270 mmol), 60% sodium hydride (in oil) (18.0 mg, 0.450 mmol) and tetrahydrofuran (1.5 mL), the mixture was stirred and reacted at room temperature for 4 hours. Then, slurry purification was performed using methanol, to give 2,3-dichloro-N-{3-[2-(pyridin-3-yl)ethoxy]quinoxalin-2-yl}-benzenesulfonamide (Compound 14) (20.6 mg, yield: 24%).

ESIMS m/z: 475 (M+H)$^+$; $^1$H-NMR (270 MHz, DMSO-$d_6$, δ): 3.16 (t, J=6.3 Hz, 2H), 4.61 (t, J=6.3 Hz, 2H), 7.27-7.36 (m, 4H), 7.54-7.60 (m, 2H), 7.82-7.84 (m, 2H), 8.27 (d, J=7.6 Hz, 1H), 8.44 (d, J=3.6 Hz, 1H), 8.60 (s, 1H).

EXAMPLE 10

3,5-dichloro-N-{3-[(2-naphthyl)methoxy]quinoxalin-2-yl}-benzenesulfonamide (Compound 15)

According to Example 1, by use of 2-amino-3-[(2-naphthyl)methoxy]quinoxaline (Compound BC) (47.9 mg, 0.159 mmol), 3,5-dichlorobenzenesulfonyl chloride (117 mg, 0.477=1), 60% sodium hydride (in oil) (15.9 mg, 0.398 mmol) and tetrahydrofuran (1.5 mL), the mixture was stirred and reacted at room temperature for 12 hours. After purification by preparative thin-layer chromatography (hexane/ethyl acetate=4/1), slurry purification was further performed using diisopropyl ether, to give 3,5-dichloro-N-{3-[(2-naphthyl) methoxy]quinoxalin-2-yl}-benzenesulfonamide (Compound 15) (10.5 mg, yield: 13%).

ESIMS m/z: 510 (M+H)$^+$; $^1$H-NMR (270 MHz, DMSO-$d_6$, δ): 5.71 (s, 2H), 7.51-8.13 (m, 14H).

EXAMPLE 11

2,3-dichloro-N-{3-[1-(pyridin-3-yl)ethoxy]quinoxalin-2-yl}-benzenesulfonamide (Compound 16)

According to Example 8, by use of 2,3-dichloro-N-(3-chloroquinoxalin-2-yl)benzenesulfonamide (Compound AA) (70.0 mg, 0.180 mmol), Compound CA (33.4 mg, 0.270 mmol), 60% sodium hydride (in oil) (18.0 mg, 0.450 mmol) and tetrahydrofuran (1.5 mL), the mixture was stirred and reacted at room temperature for 2 hours. After purification by preparative thin-layer chromatography (chloroform/methanol=19/1), slurry purification was further performed using diisopropyl ether, to give 2,3-dichloro-N-{3-[1-(pyridin-3-yl)ethoxy]quinoxalin-2-yl}-benzenesulfonamide (Compound 16) (57.0 mg, yield: 67%).

ESIMS m/z: 475 (M+H)$^+$; $^1$H-NMR (300 MHz, DMSO-d$_6$, δ): 1.72 (d, J=6.3 Hz, 3H), 6.42 (q, J=6.3 Hz, 1H), 7.40-7.67 (m, 6H), 7.93 (dd, J=1.1, 8.1 Hz, 1H), 8.04 (d, J=7.7 Hz, 1H), 8.34 (d, J=8.0 Hz, 1H), 8.51 (dd, J=1.1, 4.8 Hz, 1H), 8.83 (d, J=1.5 Hz, 1H).

EXAMPLE 12

2,3-dichloro-N-{3-[(2-trifluoromethylphenyl)methoxy]-quinoxalin-2-yl}benzenesulfonamide (Compound 17)

According to Example 8, by use of 2,3-dichloro-N-(3-chloroquinoxalin-2-yl)benzenesulfonamide (Compound AA) (70.0 mg, 0.180 mmol), 2-(trifluoromethyl)benzyl alcohol (35.9 μL, 0.270 mmol), 60% sodium hydride (in oil) (18.0 mg, 0.450 mmol) and tetrahydrofuran (1.5 mL), the mixture was stirred and reacted at room temperature for 2 hours. After purification by preparative thin-layer chromatography (hexane/ethyl acetate=7/3), slurry purification was further performed using diisopropyl ether, to give 2,3-dichloro-N-{3-[(2-trifluoromethylphenyl)methoxy]-quinoxalin-2-yl}benzenesulfonamide (Compound 17) (61.7 mg, yield: 65%).

ESIMS m/z: 528 (M+H)$^+$; $^1$H-NMR (300 MHz, DMSO-d$_6$, δ): 5.71 (s, 2H), 7.50-7.94 (m, 10H), 8.30 (br s, 1H).

EXAMPLE 13

2,3-dichloro-N-{3-[(3-trifluoromethylphenyl)methoxy]-quinoxalin-2-yl}benzenesulfonamide (Compound 18)

According to Example 8, by use of 2,3-dichloro-N-(3-chloroquinoxalin-2-yl)benzenesulfonamide (Compound AA) (70.0 mg, 0.180 mmol), 3-(trifluoromethyl)benzyl alcohol (36.7 μL, 0.270 mmol), 60% sodium hydride (in oil) (18.0 mg, 0.450 mmol) and tetrahydrofuran (1.5 mL), the mixture was stirred and reacted at room temperature for 2 hours. Then, slurry purification was performed using methanol, to give 2,3-dichloro-N-{3-[(3-trifluoromethylphenyl)methoxy]-quinoxalin-2-yl}benzenesulfonamide (Compound 18) (43.8 mg, yield: 46%).

ESIMS m/z: 528 (M+H)$^+$; $^1$H-NMR (300 MHz, DMSO-d$_6$, δ): 5.64 (s, 2H), 7.49-7.94 (m, 10H), 8.31 (br s, 1H).

EXAMPLE 14

2,3-dichloro-N-{3-[(4-trifluoromethylphenyl)methoxy]-quinoxalin-2-yl}benzenesulfonamide (Compound 19)

According to Example 8, by use of 2,3-dichloro-N-(3-chloroquinoxalin-2-yl)benzenesulfonamide (Compound AA) (70.0 mg, 0.180 mmol), 4-(trifluoromethyl)benzyl alcohol (37.0 μL, 0.270 mmol), 60% sodium hydride (in oil) (18.0 mg, 0.450 mmol) and tetrahydrofuran (1.5 mL), the mixture was stirred and reacted at room temperature for 2 hours. Then, slurry purification was performed using methanol, to give 2,3-dichloro-N-{3-[(4-trifluoromethylphenyl)methoxy]-quinoxalin-2-yl}benzenesulfonamide (Compound 19) (48.3 mg, yield: 51%).

ESIMS m/z: 528 (M+H)$^+$; $^1$H-NMR (300 MHz, DMSO-d$_6$, δ): 5.65 (s, 2H), 7.50-7.95 (m, 10H), 8.31 (br s, 1H).

EXAMPLE 15

2,3-dichloro-N-{3-[2,2,2-trifluoro-1-(pyridin-3-yl)ethoxy]-quinoxalin-2-yl}benzenesulfonamide (Compound 20)

According to Example 8, by use of 2,3-dichloro-N-(3-chloroquinoxalin-2-yl)benzenesulfonamide (Compound AA) (83.7 mg, 0.215 mmol), Compound CB (57.2 mg, 0.323 mmol), 60% sodium hydride (in oil) (21.5 mg, 0.538 mmol) and tetrahydrofuran (2.0 mL), the mixture was stirred and reacted at room temperature for 17 hours. After purification by preparative thin-layer chromatography (chloroform/methanol=19/1), slurry purification was further performed using diisopropyl ether, to give 2,3-dichloro-N-{3-[2,2,2-trifluoro-1-(pyridin-3-yl)ethoxy]-quinoxalin-2-yl}benzenesulfonamide (Compound 20) (74.8 mg, yield: 66%).

ESIMS m/z: 529 (M+H)$^+$; $^1$H-NMR (300 MHz, DMSO-d$_6$, δ): 7.19 (q, J=6.6 Hz, 1H), 7.52-7.68 (m, 6H), 7.94 (dd, J=1.5, 8.1 Hz, 1H), 8.28-8.37 (m, 2H), 8.67 (d, J=4.4 Hz, 1H), 9.06 (s, 1H).

EXAMPLE 16

2-(trifluoromethyl)-N-{3-[(2-naphthyl)methoxy]quinoxalin-2-yl}benzenesulfonamide (Compound 21)

According to Example 1, by use of 2-amino-3-[(2-naphthyl)methoxy]quinoxaline (Compound BC) (70.0 mg, 0.232 mmol), 2-(trifluoromethyl)benzenesulfonyl chloride (107 μL, 0.696 mmol), 60% sodium hydride (in oil) (23.2 mg, 0.580 mmol) and tetrahydrofuran (1.5 mL), the mixture was stirred and reacted at room temperature for 12 hours. After purification by preparative thin-layer chromatography (hexane/ethyl acetate=7/3), slurry purification was further performed using diisopropyl ether, to give 2-(trifluoromethyl)-N-{3-[(2-naphthyl)methoxy]quinoxalin-2-yl}benzenesulfonamide (Compound 21) (55.7 mg, yield: 47%).

ESIMS m/z: 510 (M+H)$^+$; $^1$H-NMR (270 MHz, DMSO-d$_6$, δ): 5.72 (s, 2H), 7.49-8.09 (m, 14H), 8.48 (br s, 1H).

EXAMPLE 17

3-(trifluoromethyl)-N-{3-[(2-naphthyl)methoxy]quinoxalin-2-yl}benzenesulfonamide (Compound 22)

According to Example 1, by use of 2-amino-3-[(2-naphthyl)methoxy]quinoxaline (Compound BC) (70.0 mg, 0.232 mmol), 3-(trifluoromethyl)benzenesulfonyl chloride (112 μL, 0.696 mmol), 60% sodium hydride (in oil) (23.2 mg, 0.580 mmol) and tetrahydrofuran (1.5 mL), the mixture was stirred and reacted at room temperature for 12 hours. After purification by preparative thin-layer chromatography (hexane/ethyl acetate=7/3), slurry purification was further performed using diisopropyl ether, to give 3-(trifluoromethyl)-N-{3-[(2-naphthyl)methoxy]quinoxalin-2-yl}benzenesulfonamide (Compound 22) (16.3 mg, yield: 14%).

ESIMS m/z: 510 (M+H)$^+$; $^1$H-NMR (270 MHz, DMSO-$d_6$, δ): 5.71 (s, 2H), 7.51-8.11 (m, 13H), 8.43-8.54 (m, 2H).

EXAMPLE 18

4-(trifluoromethyl)-N-{3-[(2-naphthyl)methoxy]quinoxalin-2-yl}benzenesulfonamide (Compound 23)

According to Example 1, by use of 2-amino-3-[(2-naphthyl)methoxy]quinoxaline (Compound BC) (70.0 mg, 0.232 mmol), 4-(trifluoromethyl)benzenesulfonyl chloride (170 mg, 0.696 mmol), 60% sodium hydride (in oil) (23.2 mg, 0.580 mmol) and tetrahydrofuran (1.5 mL), the mixture was stirred and reacted at room temperature for 12 hours. After purification by preparative thin-layer chromatography (hexane/ethyl acetate=7/3), slurry purification was further performed using methanol, to give 4-(trifluoromethyl)-N-{3-[(2-naphthyl)methoxy]quinoxalin-2-yl}benzenesulfonamide (Compound 23) (22.5 mg, yield: 19%).

ESIMS m/z: 510 (M+H)$^+$; $^1$H-NMR (270 MHz, DMSO-$d_6$, δ): 5.72 (s, 2H), 7.53-8.11 (m, 13H), 8.37-8.40 (m, 2H).

EXAMPLE 19

2,3-dichloro-N-{3-[(quinolin-6-yl)methoxy]quinoxalin-2-yl}-benzenesulfonamide (Compound 24)

According to Example 8, by use of 2,3-dichloro-N-(3-chloroquinoxalin-2-yl)benzenesulfonamide (Compound AA) (78.1 mg, 0.201 mmol), 6-quinolinemethanol (64.0 mg, 0.402 mmol), 60% sodium hydride (in oil) (24.1 mg, 0.603 mmol) and tetrahydrofuran (1.5 mL), the mixture was stirred and reacted at room temperature for 24 hours. Then, slurry purification was performed using methanol, to give 2,3-dichloro-N-{3-[(quinolin-6-yl)methoxy]quinoxalin-2-yl}-benzenesulfonamide (Compound 24) (63.2 mg, yield: 61%).

ESIMS m/z: 511 (M+H)$^+$; $^1$H-NMR (270 MHz, DMSO-$d_6$, δ): 5.67 (s, 2H), 7.07-7.22 (m, 3H), 7.41-7.47 (m, 2H), 7.55 (dd, J=4.3, 8.3 Hz, 1H), 7.63 (dd, J=1.3, 7.9 Hz, 1H), 7.92 (dd, J=1.7, 8.6 Hz, 1H), 8.03-8.08 (m, 2H), 8.23 (dd, J=1.3, 7.9 Hz, 1H), 8.36 (d, J=7.9 Hz, 1H), 8.90 (dd, J=1.7, 4.3 Hz, 1H).

EXAMPLE 20

2,3-dichloro-N-{3-[(pyridin-2-yl)methoxy]quinoxalin-2-yl}-benzenesulfonamide (Compound 25)

According to Example 8, by use of 2,3-dichloro-N-(3-chloroquinoxalin-2-yl)benzenesulfonamide (Compound AA) (70.0 mg, 0.180 mmol), 2-pyridinemethanol (26.1 μL, 0.270 mmol), 60% sodium hydride (in oil) (18.0 mg, 0.450 mmol) and tetrahydrofuran (1.5 mL), the mixture was stirred and reacted at room temperature for 24 hours. Then, slurry purification was performed using methanol, to give 2,3-dichloro-N-{3-[(pyridin-2-yl)methoxy]quinoxalin-2-yl}-benzenesulfonamide (Compound 25) (57.5 mg, yield: 69%).

ESIMS m/z: 460 (M+H)$^+$; $^1$H-NMR (270 MHz, DMSO-$d_6$, δ): 5.58 (s, 2H), 7.63-7.37 (m, 4H), 7.52-7.61 (m, 3H), 7.79-7.86 (m, 2H), 8.27 (dd, J=1.7, 7.9 Hz, 1H), 8.58 (ddd, J=1.0, 1.7, 5.0 Hz, 1H).

EXAMPLE 21

2,3-dichloro-N-{3-[(pyridin-4-yl)methoxy]quinoxalin-2-yl}-benzenesulfonamide (Compound 26)

According to Example 8, by use of 2,3-dichloro-N-(3-chloroquinoxalin-2-yl)benzenesulfonamide (Compound AA) (70.0 mg, 0.180 mmol), 4-pyridinemethanol (29.5 mg, 0.270 mmol), 60% sodium hydride (in oil) (18.0 mg, 0.450 mmol) and tetrahydrofuran (1.5 mL), the mixture was stirred and reacted at room temperature for 24 hours. Then, slurry purification was performed using methanol, to give 2,3-dichloro-N-{3-[(pyridin-4-yl)methoxy]quinoxalin-2-yl}-benzenesulfonamide (Compound 26) (41.7 mg, yield: 50%).

ESIMS m/z: 460 (M+H)$^+$; $^1$H-NMR (270 MHz, DMSO-$d_6$, δ): 5.62 (s, 2H), 7.43-7.51 (m, 2H), 7.56-7.68 (m, 5H), 7.92 (dd, J=1.7, 7.9 Hz, 1H), 8.31 (dd, J=1.3, 8.3 Hz, 1H), 8.60-8.62 (m, 2H).

EXAMPLE 22

2,6-dichloro-N-{3-[(2-naphthyl)methoxy]quinoxalin-2-yl}-benzenesulfonamide (Compound 27)

According to Example 1, by use of 2-amino-3-[(2-naphthyl)methoxy]quinoxaline (Compound BC) (70.0 mg, 0.232 mmol), 2,6-dichlorobenzenesulfonyl chloride (171 mg, 0.696 mmol), 60% sodium hydride (in oil) (23.2 mg, 0.580 mmol) and tetrahydrofuran (1.5 mL), the mixture was stirred and reacted at room temperature for 24 hours. After purification by preparative thin-layer chromatography (hexane/ethyl acetate=7/3), slurry purification was further performed using methanol, to give 2,6-dichloro-N-{3-[(2-naphthyl)methoxy]quinoxalin-2-yl}-benzenesulfonamide (Compound 27) (29.6 mg, yield: 25%).

ESIMS m/z: 510 (M+H)$^+$; $^1$H-NMR (270 MHz, DMSO-$d_6$, δ): 5.75 (s, 2H), 7.49-7.73 (m, 10H), 7.91-7.97 (m, 3H), 8.07 (s, 1H).

EXAMPLE 23

2,5-dichloro-N-{3-[(2-naphthyl)methoxy]quinoxalin-2-yl}-benzenesulfonamide (Compound 28)

According to Example 1, by use of 2-amino-3-[(2-naphthyl)methoxy]quinoxaline (Compound BC) (70.0 mg, 0.232 mmol), 2,5-dichlorobenzenesulfonyl chloride (171 mg, 0.696 mmol), 60% sodium hydride (in oil) (23.2 mg, 0.580 mmol) and tetrahydrofuran (1.5 mL), the mixture was stirred and reacted at room temperature for 24 hours. After purification by preparative thin-layer chromatography (hexane/ethyl acetate=7/3), slurry purification was further performed using methanol, to give 2,5-dichloro-N-{3-[(2-naphthyl)methoxy]quinoxalin-2-yl}-benzenesulfonamide (Compound 28) (40.2 mg, yield: 25%).

ESIMS m/z: 510 (M+H)$^+$; $^1$H-NMR (270 MHz, DMSO-$d_6$, δ): 5.72 (s, 2H), 7.50-7.73 (m, 9H), 7.91-7.96 (m, 3H), 8.07 (s, 1H), 8.28 (s, 1H).

EXAMPLE 24

2,4-dichloro-N-{3-[(2-naphthyl)methoxy]quinoxalin-2-yl}-benzenesulfonamide (Compound 29)

According to Example 1, by use of 2-amino-3-[(2-naphthyl)methoxy]quinoxaline (Compound BC) (70.0 mg, 0.232 mmol), 2,4-dichlorobenzenesulfonyl chloride (171 mg, 0.696 mmol), 60% sodium hydride (in oil) (23.2 mg, 0.580 mmol) and tetrahydrofuran (1.5 mL), the mixture was stirred and reacted at room temperature for 24 hours. After purification by preparative thin-layer chromatography (hexane/ethyl acetate=7/3), slurry purification was further performed using methanol, to give 2,4-dichloro-N-{3-[(2-naphthyl)methoxy]quinoxalin-2-yl}-benzenesulfonamide (Compound 29) (43.5 mg, yield: 37%).

ESIMS m/z: 510 $(M+H)^+$; $^1$H-NMR (270 MHz, DMSO-$d_6$, δ): 5.73 (s, 2H), 7.50-8.07 (m, 13H), 8.31 (s, 1H).

EXAMPLE 25

3,4-dichloro-N-{3-[(2-naphthyl)methoxy]quinoxalin-2-yl}-benzenesulfonamide (Compound 30)

According to Example 1, by use of 2-amino-3-[(2-naphthyl)methoxy]quinoxaline (Compound BC) (70.0 mg, 0.232 mmol), 3,4-dichlorobenzenesulfonyl chloride (171 mg, 0.696 mmol), 60% sodium hydride (in oil) (23.2 mg, 0.580 mmol) and tetrahydrofuran (1.5 mL), the mixture was stirred and reacted at room temperature for 24 hours. Then, slurry purification was performed using methanol, to give 3,4-dichloro-N-{3-[(2-naphthyl)methoxy]quinoxalin-2-yl}-benzenesulfonamide (Compound 30) (37.1 mg, yield: 31%).

ESIMS m/z: 510 $(M+H)^+$; $^1$H-NMR (270 MHz, DMSO-$d_6$, δ): 5.71 (s, 2H), 7.53-7.99 (m, 12H), 8.11 (s, 1H), 8.37 (s, 1H).

EXAMPLE 26

2,3-dichloro-N-{3-[1-(pyridin-3-yl)propoxy]quinoxalin-2-yl}benzenesulfonamide (Compound 31)

According to Example 8, by use of 2,3-dichloro-N-(3-chloroquinoxalin-2-yl)benzenesulfonamide (Compound AA) (70.0 mg, 0.180 mmol), Compound CC (37.0 mg, 0.270 mmol), 60% sodium hydride (in oil) (18.0 mg, 0.450 mmol) and tetrahydrofuran (1.5 mL), the mixture was stirred and reacted at room temperature for 2 hours. After purification by preparative thin-layer chromatography (chloroform/methanol=9/1), slurry purification was further performed using diisopropyl ether, to give 2,3-dichloro-N-{3-[1-(pyridin-3-yl)propoxy]quinoxalin-2-yl}benzenesulfonamide (Compound 31) (60.1 mg, yield: 68%).

ESIMS m/z: 489 $(M+H)^+$; $^1$H-NMR (270 MHz, DMSO-$d_6$, δ): 0.97 (t, J=7.6 Hz, 3H), 1.91-2.10 (m, 1H), 2.12-2.22 (m, 1H), 6.20 (dd, J=5.9, 8.0 Hz, 1H), 7.39-7.68 (m, 6H), 7.91-8.02 (m, 2H), 8.35 (dd, J=1.0, 7.9 Hz, 1H), 8.49 (dd, J=1.3, 5.0 Hz, 1H), 8.81 (d, J=2.0 Hz, 1H).

EXAMPLE 27

2,3-dichloro-N-(3-benzyloxyquinoxalin-2-yl)benzenesulfonamide (Compound 32)

According to Example 8, by use of 2,3-dichloro-N-(3-chloroquinoxalin-2-yl)benzenesulfonamide (Compound AA) (70.0 mg, 0.180 mmol), benzyl alcohol (27.9 μL, 0.270 mmol), 60% sodium hydride (in oil) (18.0 mg, 0.450 mmol) and tetrahydrofuran (1.5 mL), the mixture was stirred and reacted at room temperature for 12 hours. After purification by preparative thin-layer chromatography (hexane/ethyl acetate=5/1), slurry purification was further performed using diisopropyl ether, to give 2,3-dichloro-N-(3-benzyloxyquinoxalin-2-yl)benzenesulfonamide (Compound 32) (59.7 mg, yield: 72%).

ESIMS m/z: 460 $(M+H)^+$; $^1$H-NMR (270 MHz, DMSO-$d_6$, δ): 5.56 (s, 2H), 7.31-7.71 (m, 10H), 7.93 (dd, J=1.0, 8.3 Hz, 1H), 8.29 (s, 1H).

EXAMPLE 28

2,3-dichloro-N-{3-[(pyrazin-2-yl)methoxy]quinoxalin-2-yl}-benzenesulfonamide (Compound 33)

According to Example 8, by use of 2,3-dichloro-N-(3-chloroquinoxalin-2-yl)benzenesulfonamide (Compound AA) (53.2 mg, 0.137 mmol), Compound CD (18.1 mg, 0.164 mmol), 60% sodium hydride (in oil) (12.4 mg, 0.301 mmol) and tetrahydrofuran (1.0 mL), the mixture was stirred and reacted at room temperature for 18 hours. Then, slurry purification was performed using methanol, to give 2,3-dichloro-N-{3-[(pyrazin-2-yl)methoxy]quinoxalin-2-yl}-benzenesulfonamide (Compound 33) (34.2 mg, yield: 54%).

ESIMS m/z: 462 $(M+H)^+$; $^1$H-NMR (270 MHz, DMSO-$d_6$, δ): 5.59 (s, 2H), 7.02-7.23 (m, 3H), 7.38-7.47 (m, 2H), 7.64 (dd, J=1.3, 7.9 Hz, 1H), 8.23 (dd, J=1.7, 7.9 Hz, 1H), 8.62 (d, J=2.6 Hz, 1H), 8.67 (dd, J=1.3, 2.6 Hz, 1H), 8.81 (d, J=1.3 Hz, 1H).

EXAMPLE 29

2,3-dichloro-N-{3-[2-methyl-1-(pyridin-3-yl)propoxy]-quinoxalin-2-yl}benzenesulfonamide (Compound 34)

According to Example 8, by use of 2,3-dichloro-N-(3-chloroquinoxalin-2-yl)benzenesulfonamide (Compound AA) (70.0 mg, 0.180 mmol) Compound CE (40.8 mg, 0.270 mmol), 60% sodium hydride (in oil) (18.0 mg, 0.450 mmol) and tetrahydrofuran (1.5 mL), the mixture was stirred and reacted at room temperature for 24 hours. After purification by preparative thin-layer chromatography (chloroform/methanol=9/1), slurry purification was further performed using diisopropyl ether, to give 2,3-dichloro-N-{3-[2-methyl-1-(pyridin-3-yl)propoxy]-quinoxalin-2-yl}benzenesulfonamide (Compound 34) (23.8 mg, yield: 26%).

ESIMS m/z: 503 $(M+H)^+$; $^1$H-NMR (270 MHz, CDCl$_3$, δ): 1.13 (d, J=5.6 Hz, 6H), 2.28-2.45 (m, 1H), 5.87-5.95 (m, 1H), 7.40-7.75 (m, 9H), 8.51 (d, J=4.0 Hz, 1H), 8.71 (s, 1H).

EXAMPLE 30

2-(trifluoromethyl)-N-{3-[2,2,2-trifluoro-1-(4-trifluoromethylphenyl)ethoxy]quinoxalin-2-yl}benzenesulfonamide (Compound 35)

According to Example 8, by use of 2-(trifluoromethyl)-N-(3-chloroquinoxalin-2-yl)benzenesulfonamide (Compound AC) (30.0 mg, 0.077 mmol), Compound CF (28.2 mg, 0.116 mmol), 60% sodium hydride (in oil) (7.7 mg, 0.193 mmol) and tetrahydrofuran (1.0 mL), the mixture was stirred and reacted at room temperature for 12 hours. After purification by preparative thin-layer chromatography (hexane/ethyl acetate=7/3), slurry purification was further performed using hexane, to give 2-(trifluoromethyl)-N-{3-[2,2,2-trifluoro-1-(4-trifluoromethylphenyl)ethoxy]quinoxalin-2-yl}benzenesulfonamide (Compound 35) (25.8 mg, yield: 56%).

ESIMS m/z: 596 (M+H)$^+$; $^1$H-NMR (270 MHz, DMSO-d$_6$, δ): 7.18-7.20 (m, 1H), 7.53-7.63 (m, 4H), 7.85-8.09 (m, 7H), 8.55 (d, J=7.9 Hz, 1H).

EXAMPLE 31

2,3-dichloro-N-{3-[2,2,2-trifluoro-1-(4-trifluoromethyl-phenyl)ethoxy]quinoxalin-2-yl}benzenesulfonamide (Compound 36)

According to Example 8, by use of 2,3-dichloro-N-(3-chloroquinoxalin-2-yl)benzenesulfonamide (Compound AA) (57.0 mg, 0.147 mmol), Compound CF (43.0 mg, 0.176 mmol), 60% sodium hydride (in oil) (13.0 mg, 0.323 mmol) and tetrahydrofuran (1.5 mL), the mixture was stirred and reacted at room temperature for 12 hours. After purification by preparative thin-layer chromatography (hexane/ethyl acetate=7/3), slurry purification was further performed using hexane, to give 2,3-dichloro-N-{3-[2,2,2-trifluoro-1-(4-trifluoromethyl-phenyl)ethoxy]quinoxalin-2-yl}benzenesulfonamide (Compound 36) (18.9 mg, yield: 22%).

ESIMS m/z: 596 (M+H)$^+$; $^1$H-NMR (270 MHz, DMSO-d$_6$, δ): 7.19-7.22 (m, 1H), 7.53-7.69 (m, 5H), 7.85-7.96 (m, 5H), 8.36 (d, J=7.9 Hz, 1H).

EXAMPLE 32

2,3-dichloro-N-{3-[2,2-dimethyl-1-(pyridin-3-yl)propoxy]-quinoxalin-2-yl}benzenesulfonamide (Compound 37)

According to Example 8, by use of 2,3-dichloro-N-(3-chloroquinoxalin-2-yl)benzenesulfonamide (Compound AA) (97.2 mg, 0.250 mmol), Compound CG (62.0 mg, 0.375 mmol), 60% sodium hydride (in oil) (25.0 mg, 0.625 mmol) and tetrahydrofuran (2.0 mL), the mixture was stirred and reacted at room temperature for 24 hours. After purification by preparative thin-layer chromatography (chloroform/methanol=19/1), slurry purification was further performed using hexane, to give 2,3-dichloro-N-{3-[2,2-dimethyl-1-(pyridin-3-yl)propoxy]-quinoxalin-2-yl}benzenesulfonamide (Compound 37) (62.6 mg, yield: 48%).

ESIMS m/z: 517 (M+H)$^+$; $^1$H-NMR (300 MHz, DMSO-d$_6$, δ): 1.02 (s, 9H), 6.11 (s, 1H), 7.36-7.54 (m, 5H), 7.65 (dd, J=7.7, 8.4 Hz, 1H), 7.92-7.98 (m, 2H), 8.34 (dd, J=1.1, 8.1 Hz, 1H), 8.49 (dd, J=1.5, 4.8 Hz, 1H), 8.76 (s, 1H).

EXAMPLE 33

2,3-dichloro-N-{3-[2-hydroxy-1-(4-trifluoromethylphenyl)-ethoxy]quinoxalin-2-yl}benzenesulfonamide (Compound 38)

Step 1

According to Example 8, by use of 2,3-dichloro-N-(3-chloroquinoxalin-2-yl)benzenesulfonamide (Compound AA) (82.2 mg, 0.211 mmol), Compound CM (115 mg, 0.3175 mmol), 60% sodium hydride (in oil) (21.1 mg, 0.528 mmol) and tetrahydrofuran (2.0 mL), the mixture was stirred and reacted at room temperature for 1 hour. Then, purification by silica gel column chromatography (hexane/ethyl acetate=19/1) was performed to give 2,3-dichloro-N-{3-[2-triisopropylsiloxy-1-(4-trifluoromethylphenyl)ethoxy]quinoxalin-2-yl}benzenesulfonamide (117 mg, yield: 78%).

ESIMS m/z: 714 (M+H)$^+$

Step 2

2,3-Dichloro-N-{3-[2-triisopropylsiloxy-1-(4-trifluoromethylphenyl)ethoxy]quinoxalin-2-yl}benzenesulfonamide (113 mg, 0.159 mmol) was suspended in methanol (1.0 mL). To this, a 10% solution of hydrogen chloride in methanol (1.0 mL) was added at room temperature and the mixture was stirred for 2 hours. Then, tetrahydrofuran (1.0 mL) was added to the reaction mixture and the mixture was stirred at room temperature for 18.5 hours. The reaction mixture was concentrated and the residue was purified by preparative thin-layer chromatography (hexane/ethyl acetate=7/3). Further, slurry purification was performed using hexane, to give 2,3-dichloro-N-{3-[2-hydroxy-1-(4-trifluoromethylphenyl)-ethoxy]quinoxalin-2-yl}benzenesulfonamide (Compound 38) (20.0 mg, yield: 23%).

ESIMS m/z: 558 (M+H)$^+$; $^1$H-NMR (300 MHz, DMSO-d$_6$, δ): 4.32 (br s, 1H), 4.64 (br s, 1H), 5.25 (br s, 1H), 6.12 (br s, 1H), 7.47-7.99 (m, 10H), 8.41 (br s, 1H), 11.76 (br s, 1H).

EXAMPLE 34

2,3-dichloro-N-{3-[2-fluoro-2-methyl-1-(pyridin-3-yl)-propoxy]quinoxalin-2-yl}benzenesulfonamide (Compound 39)

According to Example 8, by use of 2,3-dichloro-N-(3-chloroquinoxalin-2-yl)benzenesulfonamide (Compound AA) (70.0 mg, 0.180 mmol), Compound CI (45.7 mg, 0.270 mmol), 60% sodium hydride (in oil) (18.0 mg, 0.450 mmol) and tetrahydrofuran (1.5 mL), the mixture was stirred and reacted at 50° C. for 8 hours. After purification by preparative thin-layer chromatography (chloroform/methanol=19/1), slurry purification was further performed using methanol, to give 2,3-dichloro-N-{3-[2-fluoro-2-methyl-1-(pyridin-3-yl)-propoxy]quinoxalin-2-yl}benzenesulfonamide (Compound 39) (68.3 mg, yield: 73%).

ESIMS m/z: 521 (M+H)$^+$; $^1$H-NMR (300 MHz, DMSO-d$_6$, δ): 1.43 (d, J=7.0 Hz, 3H), 1.50 (J=7.0 Hz, 3H), 6.40 (d, J=15.8 Hz, 1H), 7.40-7.67 (m, 6H), 7.93 (dd, J=1.5, 8.1 Hz, 1H), 8.06 (br s, 1H), 8.35 (d, J=8.1 Hz, 1H), 8.53 (dd, J=1.5, 4.8 Hz, 1H), 8.84 (s, 1H).

EXAMPLE 35

2-chloro-N-{3-[2,2,2-trifluoro-1-(4-methoxyphenyl)ethoxy]-quinoxalin-2-yl}benzenesulfonamide (Compound 40)

According to Example 8, by use of 2-chloro-N-(3-chloroquinoxalin-2-yl)benzenesulfonamide (Compound AD) (70.0 mg, 0.198 mmol), Compound CJ (61.1 mg, 0.296 mmol), 60% sodium hydride (in oil) (19.8 mg, 0.495 mmol) and tetrahydrofuran (1.5 mL), the mixture was stirred and reacted at room temperature for 14 hours and successively at 50° C. for hours. After purification by preparative thin-layer chromatography (hexane/ethyl acetate=3/1), slurry purification was further performed using methanol, to give 2-chloro-N-{3-[2,2,2-trifluoro-1-(4-methoxyphenyl)ethoxy]-quinoxalin-2-yl}benzenesulfonamide (Compound 40) (17.5 mg, yield: 17%).

ESIMS m/z: 523 (M+H)+; $^1$H-NMR (270 MHz, DMSO-$d_6$, δ): 3.76 (s, 3H), 6.94-7.02 (m, 3H), 7.50-7.80 (m, 9H), 8.37 (s, 1H), 12.46 (br s, 1H).

EXAMPLE 36

2-chloro-N-{3-[2,2,2-trifluoro-1-(6-methylpyridin-3-yl)-ethoxy]quinoxalin-2-yl}benzenesulfonamide (Compound 41)

According to Example 8, by use of 2-chloro-N-(3-chloroquinoxalin-2-yl)benzenesulfonamide (Compound AD) (70.0 mg, 0.198 mmol), Compound CK (56.8 mg, 0.297 mmol), 60% sodium hydride (in oil) (31.7 mg, 0.495 mmol) and tetrahydrofuran (1.5 mL), the mixture was stirred and reacted at room temperature for 16.5 hours and successively at 50° C. for hours. After purification by preparative thin-layer chromatography (chloroform/methanol=19/1), slurry purification was further performed using diisopropyl ether, to give 2-chloro-N-{3-[2,2,2-trifluoro-1-(6-methylpyridin-3-yl)-ethoxy]quinoxalin-2-yl}benzenesulfonamide (Compound 41) (38.8 mg, yield: 39%).

ESIMS m/z: 509 (M+H)+; $^1$H-NMR (270 MHz, DMSO-$d_6$, δ): 2.48 (s, 3H), 7.12 (q, J=6.6 Hz, 1H), 7.39 (d, J=7.9 Hz, 1H), 7.52-7.65 (m, 7H), 8.17 (br s, 1H), 8.34-8.38 (m, 1H), 8.90 (s, 1H).

EXAMPLE 37

2-chloro-N-{3-[2,2,2-trifluoro-1-(4-cyanophenyl)ethoxy]-quinoxalin-2-yl}benzenesulfonamide (Compound 42)

2-Chloro-3-[2,2,2-trifluoro-1-(4-cyanophenyl)ethoxy]-quinoxaline (Compound BO) (42.6 mg, 0.117 mmol) was dissolved in dimethyl sulfoxide (1.0 mL). To this, 2-chlorobenzenesulfonamide (22.4 mg, 0.117 mmol) and potassium carbonate (16.2 mg, 0.117 mmol) were added at room temperature and the mixture was stirred at 150° C. for 2 hours. The reaction mixture was allowed to cool down to room temperature, a 1% aqueous acetic acid solution (1.0 mL) was added thereto, and the precipitate was collected by filtration. The obtained solid was purified by preparative thin-layer chromatography (hexane/ethyl acetate=1/1). Further, slurry purification was performed using diisopropyl ether, to give 2-chloro-N-{3-[2,2,2-trifluoro-1-(4-cyanophenyl)ethoxy]-quinoxalin-2-yl}benzenesulfonamide (Compound 42) (20.6 mg, yield: 34%).

ESIMS m/z: 518 (M+H)+; $^1$H-NMR (270 MHz, DMSO-$d_6$, δ): 7.22 (br s, 1H), 7.52-7.66 (m, 7H), 7.97-8.13 (m, 4H), 8.38 (br s, 1H), 12.52 (br s, 1H).

EXAMPLE 38

2,3-dichloro-N-{3-{methoxycarbonyl[4-(trifluoromethyl)-phenyl]methoxy}quinoxalin-2-yl}benzenesulfonamide (Compound 43)

According to Example 37, by use of 2-chloro-3-{methoxycarbonyl[4-(trifluoromethyl)phenyl]-methoxy}quinoxaline (Compound BR) (50.1 mg, 0.126 mmol), dimethyl sulfoxide (1.0 mL), 2,3-dichlorobenzenesulfonamide (28.5 mg, 0.126 mmol) and potassium carbonate (17.4 mg, 0.126 mmol), the mixture was stirred and reacted at 150° C. for 1 hour. After purification by preparative thin-layer chromatography (hexane/ethyl acetate=1/1), slurry purification was further performed using diisopropyl ether, to give 2,3-dichloro-N-{3-{methoxycarbonyl[4-(trifluoromethyl)-phenyl]methoxy}quinoxalin-2-yl}benzenesulfonamide (Compound 43) (3.7 mg, yield: 5%).

ESIMS m/z: 585 (M+H)+; $^1$H-NMR (300 MHz, DMSO-$d_6$, δ): 3.69 (s, 3H), 6.56 (s, 1H), 7.54-7.67 (m, 5H), 7.84-7.99 (m, 5H), 8.31 (br s, 1H).

EXAMPLE 39

2-chloro-N-[3-(2,2,2-trifluoro-1-phenylethoxy)quinoxalin-2-yl]benzenesulfonamide (Compound 44)

According to Example 8, by use of 2-chloro-N-(3-chloroquinoxalin-2-yl)benzenesulfonamide (Compound AD) (70.0 mg, 0.198 mmol), α-(trifluoromethyl)benzyl alcohol (52.3 mg, 0.297 mmol), 60% sodium hydride (in oil) (19.8 mg, 0.495 mmol) and tetrahydrofuran (1.5 mL), the mixture was stirred and reacted at room temperature for 16.5 hours and successively at 50° C. for 7 hours. After purification by preparative thin-layer chromatography (hexane/ethyl acetate=2/1), slurry purification was further performed using hexane, to give 2-chloro-N-[3-(2,2,2-trifluoro-1-phenylethoxy)quinoxalin-2-yl]benzenesulfonamide (Compound 44) (24.0 mg, yield: 25%).

ESIMS m/z: 493 (M+H)+; $^1$H-NMR (270 MHz, DMSO-$d_6$, δ): 7.03 (br s, 1H), 7.44-7.87 (m, 12H), 8.37 (br s, 1H), 12.51 (br s, 1H).

EXAMPLE 40

2-chloro-N-{3-[2-fluoro-2-methyl-1-(pyridin-3-yl)ethoxy]-quinoxalin-2-yl}benzenesulfonamide (Compound 45)

According to Example 8, by use of 2-chloro-N-(3-chloroquinoxalin-2-yl)benzenesulfonamide (Compound AD) (70.0 mg, 0.198 mmol), Compound CI (50.3 mg, 0.297 mmol), 60% sodium hydride (in oil) (19.8 mg, 0.495 mmol) and tetrahydrofuran (1.5 mL), the mixture was stirred and reacted at 50° C. for 1 hour. After purification by preparative thin-layer chromatography (chloroform/methanol=19/1), slurry purification was further performed using diisopropyl ether, to give 2-chloro-N-{3-[2-fluoro-2-methyl-1-(pyridin-3-yl)ethoxy]-quinoxalin-2-yl}benzenesulfonamide (Compound 45) (66.1 mg, yield: 69%).

ESIMS m/z: 487 (M+H)+; $^1$H-NMR (270 MHz, DMSO-$d_6$, δ): 1.43 (d, J=5.3 Hz, 3H), 1.51 (d, J=5.3 Hz, 3H), 6.44 (d, J=15.9 Hz, 1H), 7.40-7.65 (m, 8H), 8.06 (d, J=6.9 Hz, 1H), 8.35-8.38 (m, 1H), 8.53 (dd, J=1.3, 5.0 Hz, 1H), 8.85 (s, 1H).

EXAMPLE 41

2,3-dichloro-N-{3-[3,3,3,2,2-pentafluoro-1-(pyridin-3-yl)-propoxy]quinoxalin-2-yl}benzenesulfonamide (Compound 46)

According to Example 8, by use of 2,3-dichloro-N-(3-chloroquinoxalin-2-yl)benzenesulfonamide (Compound AA) (70.0 mg, 0.180 mmol). 3-(3,3,3,2,2-pentafluoro-1-hydroxypropyl)pyridine (61.3 mg, 0.270 mmol), 60% sodium hydride (in oil) (18.0 mg, 0.450 mmol) and tetrahydrofuran (1.5 mL), the mixture was stirred and reacted at room temperature for 12 hours and successively at 50° C. for 5 hours. After purification by preparative thin-layer chromatography (chloroform/methanol=19/1), slurry purification was further performed using methanol, to give 2,3-dichloro-N-{3-[3,3,3, 2,2-pentafluoro-1-(pyridin-3-yl)-propoxy]quinoxalin-2-yl}benzenesulfonamide (Compound 46) (28.8 mg, yield: 28%).

ESIMS m/z: 578 (M+H)$^+$; $^1$H-NMR (270 MHz, DMSO-d$_5$, δ): 7.23 (dd, J=5.9, 19.8 Hz, 1H), 7.52-7.69 (m, 6H), 7.94 (dd, J=1.3, 8.3 Hz, 1H), 8.33-8.36 (m, 2H), 8.68 (dd, J=1.7, 5.0 Hz, 1H), 9.07 (s, 1H).

EXAMPLE 42

3-{1-[3-(2-chlorobenzenesulfonamide)quinoxalin-2-yloxy]-2,2,2-trifluoroethyl}pyridine 1-oxide (Compound 47)

2-Chloro-N-{3-[2,2,2-trifluoro-1-(pyridin-3-yl)ethoxy]-quinoxalin-2-yl}benzenesulfonamide (Compound 138) (50.0 mg, 0.101 mmol) was dissolved in dichloromethane (2.0 mL). To this, meta-chloroperbenzoic acid (26.1 mg, 0.152 mmol) was added under a nitrogen atmosphere at 0° C. and the mixture was stirred at the same temperature for 2.5 hours. The reaction mixture was concentrated and the residue was purified by preparative thin-layer chromatography (chloroform/methanol=19/1). Further, slurry purification was performed using diisopropyl ether, to give 3-{1-[3-(2 chlorobenzenesulfonamide)quinoxalin-2-yloxy]-2,2,2-trifluoroethyl}pyridine 1-oxide (Compound 47) (44.6 mg, yield: 86%).

ESIMS m/z: 511 (M+H)$^+$; $^1$H-NMR (270 MHz, DMSO-d$_6$, δ): 7.27 (br s, 1H), 7.52-7.91 (m, 9H), 8.29-8.38 (m, 1H), 9.06 (br s, 1H).

EXAMPLE 43

2-chloro-N-{3-[2,2,2-trifluoro-1-(pyridin-2-yl)ethoxy]-quinoxalin-2-yl}benzenesulfonamide (Compound 48)

According to Example 8, by use of 2-chloro-N-(3-chloro-quinoxalin-2-yl)benzenesulfonamide (Compound AD) (150 mg, 0.423 mmol), Compound CN (113 mg, 0.635 mmol), 60% sodium hydride (in oil) (42.3 mg, 1.06 mmol) and tetrahydrofuran (5.0 mL), the mixture was stirred and reacted at 50° C. for 96 hours. After purification by preparative thin-layer chromatography (chloroform/methanol=19/1), slurry purification was further performed using diisopropyl ether, to give 2-chloro-N-{3-[2,2,2-trifluoro-1-(pyridin-2-yl)ethoxy]-quinoxalin-2-yl}benzenesulfonamide (Compound 48) (74.2 mg, yield: 35%).

ESIMS m/z: 494 (M+H)$^+$; $^1$H-NMR (300 MHz, DMSO-d$_6$, δ): 6.98 (br s, 1H), 7.47-7.64 (m, 8H), 7.93-8.12 (m, 2H), 8.64-8.67 (m, 1H).

EXAMPLE 44

2-chloro-N-{3-[2,2,2-trifluoro-1-(pyridin-2-yl)ethoxy]-quinoxalin-4-yl}benzenesulfonamide (Compound 49)

According to Example 37, by use of 2-chloro-3-[2,2,2-trifluoro-1-(pyridin-3-yl)ethoxy]-quinoxaline (Compound BD) (223 mg, 0.659 mmol), dimethyl sulfoxide (4.0 mL), 2-chlorobenzenesulfonamide (126 mg, 0.659 mmol) and potassium carbonate (91.1 mg, 0.659 mmol), the mixture was stirred and reacted at 150° C. for 0.5 hour. After purification by preparative thin-layer chromatography (hexane/ethyl acetate=1/1), slurry purification was further performed using diisopropyl ether, to give 2-chloro-N-{3-[2,2,2-trifluoro-1-(pyridin-2-yl)ethoxy]-quinoxalin-4-yl}benzenesulfonamide (Compound 49) (95.2 mg, yield: 29%).

ESIMS m/z: 494 (M+H)$^+$; $^1$H-NMR (300 MHz, DMSO-d$_6$, δ): 7.15 (q, J=6.2 Hz, 1H), 7.52-7.65 (m, 7H), 7.87 (br s, 2H), 8.35-8.38 (m, 1H), 8.69-8.71 (m, 2H).

EXAMPLE 45

2-{1-[3-(2-chlorobenzenesulfonamide)quinoxalin-2-yloxy]-2,2,2-trifluoroethyl}pyridine 1-oxide (Compound 50)

According to Example 42, by use of 2-chloro-N-{3-[2,2,2-trifluoro-1-(pyridin-2-yl)ethoxy]quinoxalin-2-yl}benzenesulfonamide (Compound 48) (50.0 mg, 0.101 mmol), dichloromethane (2.0 mL) and meta-chloroperbenzoic acid (43.7 mg, 0.253 mmol), the mixture was stirred and reacted at room temperature for 6.5 hours. After purification by preparative thin-layer chromatography (chloroform/methanol=19/1), slurry purification was further performed using diisopropyl ether, to give 2-{1-[3-(2 chlorobenzenesulfonamide)quinoxalin-2-yloxy]-2,2,2-trifluoroethyl}pyridine 1-oxide (Compound 50) (39.7 mg, yield: 77%).

ESIMS m/z: 510 (M+H)$^+$; $^1$H-NMR (270 MHz, DMSO-d$_6$, δ): 7.52-7.65 (m, 9H), 7.82 (br s, 1H), 8.37-8.45 (m, 3H), 12.41 (br s, 1H).

EXAMPLE 46

4-{1-[3-(2 chlorobenzenesulfonamide)quinoxalin-2-yloxy]-2,2,2-trifluoroethyl}pyridine 1-oxide (Compound 51)

According to Example 42, by use of 2-chloro-N-{3-[2,2,2-trifluoro-1-(pyridin-4-yl)ethoxy]quinoxalin-2-yl}benzenesulfonamide (Compound 49) (50.0 mg, 0.101 mmol), dichloromethane (2.0 mL) and meta-chloroperbenzoic acid (43.7 mg, 0.253 mmol), the mixture was stirred and reacted at room temperature for 5 hours. After purification by preparative thin-layer chromatography (chloroform/methanol=19/1), slurry purification was further performed using diisopropyl ether, to give 4-{1-[3-(2 chlorobenzenesulfonamide)quinoxalin-2-yloxy]-2,2,2-trifluoroethyl}pyridine 1-oxide (Compound 51) (45.5 mg, yield: 88%).

ESIMS m/z: 510 (M+H)$^+$; $^1$H-NMR (270 MHz, DMSO-d$_6$, δ): 7.20 (br s, 1H), 7.52-7.65 (m, 8H), 7.96 (br s, 2H), 8.35 (d, J=6.6 Hz, 2H), 12.47 (br s, 1H).

EXAMPLE 47

2-chloro-N-{3-[2,2,2-trifluoro-1-(4-toluoyl)ethoxy]-quinoxalin-2-yl}benzenesulfonamide (Compound 52)

According to Example 8, by use of 2-chloro-N-(3-chloro-quinoxalin-2-yl)benzenesulfonamide (Compound AD) (70.0 mg, 0.198 mmol), Compound DE (75.3 mg, 0.369 mmol), 60% sodium hydride (in oil) (23.7 mg, 0.594 mmol) and tetrahydrofuran (1.5 mL), the mixture was stirred and reacted at 50° C. for 3 hours. After purification by preparative thin-layer chromatography (hexane/ethyl acetate=3/1), slurry purification was further performed using diisopropyl ether, to give 2-chloro-N-{3-[2,2,2-trifluoro-1-(4-toluoyl)ethoxy]-quinoxalin-2-yl}benzenesulfonamide (Compound 52) (57.6 mg, yield: 57%).

ESIMS m/z: 508 (M+H)⁺; ¹H-NMR (300 MHz, CDCl₃, δ): 2.36 (s, 3H), 6.61-6.75 (m, 1H), 7.18-7.62 (m, 11H), 8.20-8.54 (m, 2H).

EXAMPLE 48

2-chloro-N-{3-[2,2,2-trifluoro-1-(4-chlorophenyl)ethoxy]-quinoxalin-2-yl}benzenesulfonamide (Compound 53)

According to Example 8, by use of 2-chloro-N-(3-chloro-quinoxalin-2-yl)benzenesulfonamide (Compound AD) (70.0 mg, 0.198 mmol), Compound CP (83.4 mg, 0.369 mmol), 60% sodium hydride (in oil) (23.7 mg, 0.594 mmol) and tetrahydrofuran (1.5 mL), the mixture was stirred and reacted at 50° C. for 3 hours. After purification by preparative thin-layer chromatography (hexane/ethyl acetate=3/1), slurry purification was further performed using diisopropyl ether, to give 2-chloro-N-{3-[2,2,2-trifluoro-1-(4-chlorophenyl)ethoxy]-quinoxalin-2-yl}benzenesulfonamide (Compound 53) (59.7 mg, yield: 57%).

ESIMS m/z: 527 (M+H)⁺; ¹H-NMR (300 MHz, CDCl₃, δ): 6.61-6.74 (m, 1H), 7.33-7.64 (m, 11H), 8.18-8.54 (m, 2H).

EXAMPLE 49

2-chloro-N-{3-[2,2,2-trifluoro-1-(6-cyanopyridin-3-yl)-ethoxy]quinoxalin-2-yl}benzenesulfonamide (Compound 54)

According to Example 37, by use of 2-chloro-3-[2,2,2-trifluoro-1-(6-cyanopyridin-3-yl)ethoxy]-quinoxaline (Compound BS) (70.0 mg, 0.192 mmol), dimethyl sulfoxide (2.0 mL), 2-chlorobenzenesulfonamide (40.5 mg, 0.211 mmol) and potassium carbonate (29.2 mg, 0.211 mmol), the mixture was stirred and reacted at 150° C. for 2 hours. After purification by preparative thin-layer chromatography (hexane/ethyl acetate=7/3), slurry purification was further performed using hexane, to give 2-chloro-N-{3-[2,2,2-trifluoro-1-(6-cyanopyridin-3-yl)-ethoxy]quinoxalin-2-yl}benzenesulfonamide (Compound 54) (9.4 mg, yield: 9%).

ESIMS m/z: 520 (M+H)⁺; ¹H-NMR (270 MHz, DMSO-d₆, δ): 7.42-7.65 (m, 8H), 8.24 (d, J=7.7 Hz, 1H), 8.39 (s, 1H), 8.68 (br s, 1H), 9.33 (s, 1H), 12.48 (br s, 1H).

EXAMPLE 50

2-chloro-N-{3-[2,2,2-trifluoro-1-(1-methyl-2(1H)pyridon-5-yl)ethoxy]quinoxalin-2-yl}benzenesulfonamide (Compound 55)

According to Example 37, by use of 2-chloro-3-[2,2,2-trifluoro-1-(1-methyl-2(1H)pyridon-5-yl)-ethoxy]quinoxaline (Compound BT) (70.0 mg, 0.190 mmol), dimethyl sulfoxide (2.0 mL), 2-chlorobenzenesulfonamide (39.9 mg, 0.208 mmol) and potassium carbonate (28.7 mg, 0.208 mmol), the mixture was stirred and reacted at 150° C. for 1.5 hours. After purification by silica gel column chromatography (hexane/ethyl acetate=1/1), slurry purification was further performed using methanol, to give 2-chloro-N-{3-[2,2,2-trifluoro-1-(1-methyl-2(1H)pyridon-5-yl)ethoxy]quinoxalin-2-yl}benzenesulfonamide (Compound 55) (36.7 mg, yield: 37%).

ESIMS m/z: 520 (M+H)⁺; ¹H-NMR (270 MHz, DMSO-d₆, δ): 3.44 (s, 3H), 6.50 (d, J=9.5 Hz, 1H), 6.91 (br s, 1H), 7.48-7.72 (m, 7H), 8.01 (br s, 1H), 8.37 (br s, 2H), 12.30 (br s, 1H).

EXAMPLE 51

2-chloro-N-{3-[2,2,2-trifluoro-1-(4-methoxymethoxyphenyl)-ethoxy]quinoxalin-2-yl}benzenesulfonamide (Compound 56)

According to Example 8, by use of 2-chloro-N-(3-chloro-quinoxalin-2-yl)benzenesulfonamide (Compound AD) (150 mg, 0.423 mmol), Compound CQ (150 mg, 0.635 mmol), 60% sodium hydride (in oil) (42.3 mg, 1.06 mmol) and tetrahydrofuran (5.0 mL), the mixture was stirred and reacted at 50° C. for 2 hours. After purification by preparative thin-layer chromatography (hexane/ethyl acetate=3/1), slurry purification was further performed using diisopropyl ether, to give 2-chloro-N-{3-[2,2,2-trifluoro-1-(4-methoxymethoxyphenyl)-ethoxy]quinoxalin-2-yl}benzenesulfonamide (Compound 56) (115 mg, yield: 49%).

ESIMS m/z: 553 (M+H)⁺; ¹H-NMR (300 MHz, CDCl₃, δ): 5.17 (s, 3H), 6.71 (s, 2H), 6.58-6.76 (m, 1H), 7.00-7.09 (m, 2H), 7.29-7.66 (m, 9H), 8.20-8.54 (m, 2H).

EXAMPLE 52

2 chloro-N-{3-[2,2,2-trifluoro-1-(4-diethoxymethyloxy-phenyl)ethoxy]quinoxalin-2-yl}benzenesulfonamide (Compound 57)

According to Example 8, by use of 2-chloro-N-(3-chloro-quinoxalin-2-yl)benzenesulfonamide (Compound AD) (500 mg, 1.41 mmol), Compound CR (589 mg, 2.12 mmol), 60% sodium hydride (in oil) (141 mg, 3.53 mmol) and tetrahydrofuran (10 mL), the mixture was stirred and reacted at 50° C. for 5 hours. Then, purification by silica gel column chromatography (hexane/ethyl acetate=7/3) was performed to give 2-chloro-N-{3-[2,2,2-trifluoro-1-(4-diethoxymethyloxyphenyl)ethoxy]quinoxalin-2-yl}benzenesulfonamide (Compound 57) (789 mg, yield: 94%).

ESIMS m/z: 596 (M+H)⁺; ¹H-NMR (300 MHz, CDCl₃, δ): 1.20-1.29 (m, 6H), 3.53-3.65 (m, 4H), 5.47-5.56 (m, 2H), 7.26-7.73 (m, 11H), 8.18-8.53 (m, 2H).

EXAMPLE 53

2-chloro-N-{3-[2,2,2-trifluoro-1-(4-formylphenyl)ethoxy]-quinoxalin-2-yl}benzenesulfonamide (Compound 58)

2-Chloro-N-{3-[2,2,2-trifluoro-1-(4-diethoxymethyloxy-phenyl)ethoxy]quinoxalin-2-yl}benzenesulfonamide (Compound 57) (506 mg, 0.894 mmol) was dissolved in tetrahydrofuran (10 mL). To this, a 1 mol/L aqueous hydrogen chloride solution (10 mL) was added and the mixture was stirred at room temperature for 1 hour. Then, the reaction mixture was neutralized with a saturated aqueous sodium bicarbonate solution, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=7/3). Further, slurry purification was performed using methanol, to give 2-chloro-N-{3-[2,2,2-trifluoro-1-(4-formylphenyl)ethoxy]quinoxalin-2-yl}benzenesulfonamide (Compound 58) (282 mg, yield: 64%).

ESIMS m/z: 521 (M+H)⁺; ¹H-NMR (300 MHz, CDCl₃, δ): 6.71-6.82 (m, 1H), 7.32-7.97 (m, 11H), 8.23-8.55 (m, 2H), 10.04 (s, 1H).

EXAMPLE 54

2-chloro-N-{3-[2,2,2-trifluoro-1-(4-fluorophenyl)ethoxy]-quinoxalin-2-yl}benzenesulfonamide (Compound 59)

Compound CS (478 mg, 2.51 mmol) and 2,3-dichloroquinoxaline (618 mg, 3.11 mmol) were dissolved in tetrahydrofuran (10 mL). To this, 60% sodium hydride (in oil) (124 mg, 3.11 mmol) was added under a nitrogen atmosphere at 0° C. and the mixture was stirred at room temperature for 1 hour. Then, saturated ammonium chloride was added to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=9/1) to give a mixture (702 mg) of 2-chloro-3-[2,2,2-trifluoro-1-(4-fluorophenyl)ethoxy]-quinoxaline and 2,3-dichloroquinoxaline. This mixture was dissolved in dimethyl sulfoxide (7.0 mL). To this, 2-chlorobenzenesulfonamide (455 mg, 2.37 mmol) and potassium carbonate (328 mg, 2.37 mmol) were added at room temperature and the mixture was stirred at 150° C. for 30 minutes. The reaction mixture was allowed to cool down to room temperature, a 1% aqueous acetic acid solution (1.0 mL) was added thereto, and the precipitate was collected by filtration. The obtained solid was purified by preparative thin-layer chromatography (hexane/ethyl acetate=7/3). Further, slurry purification was performed using diisopropyl ether, to give 2-chloro-N-{3-[2,2,2-trifluoro-1-(4-fluorophenyl)ethoxy]-quinoxalin-2-yl}benzenesulfonamide (Compound 59) (541 mg, yield: 42%).

ESIMS m/z: 511 (M+H)$^+$; $^1$H-NMR (300 MHz, CDCl$_3$, δ): 6.63-6.78 (m, 1H), 7.05-7.15 (m, 2H), 7.31-7.61 (m, 9H), 8.20-8.54 (m, 2H).

EXAMPLE 55

2-chloro-N-{3-[2,2,2-trifluoro-1-(4-hydroxymethylphenyl)-ethoxy]quinoxalin-2-yl}benzenesulfonamide (Compound 60)

2-Chloro-N-{3-[2,2,2-trifluoro-1-(4-formylphenyl)-ethoxy]quinoxalin-2-yl}benzenesulfonamide (Compound 58) (52.0 mg, 0.100 mmol) was dissolved in tetrahydrofuran (1.0 mL) and methanol (0.5 mL). To this, sodium borohydride (5.7 mL) was added under a nitrogen atmosphere at 0° C. and the mixture was stirred at the same temperature for 1 hour. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was subjected to slurry purification using diisopropyl ether, to give 2-chloro-N-{3-[2,2,2-trifluoro-1-(4-hydroxymethylphenyl)-ethoxy]quinoxalin-2-yl}benzenesulfonamide (Compound 60) (26.7 mg, yield: 51%).

ESIMS m/z: 523 (M+H)$^+$; $^1$H-NMR (270 MHz, DMSO-d$_6$, δ): 4.48 (d, J=4.0 Hz, 1H), 5.20 (br s, 1H), 6.92-7.68 (m, 11H), 8.29 (br s, 1H).

EXAMPLE 56

2-chloro-N-{3-[2,2,2-trifluoro-1-(4-carboxyphenyl)ethoxy]-quinoxalin-2-yl}benzenesulfonamide (Compound 61)

2-Chloro-N-{3-[2,2,2-trifluoro-1-(4-formylphenyl)-ethoxy]quinoxalin-2-yl}benzenesulfonamide (Compound 58) (102 mg, 0.189 mmol) was dissolved in acetone (5.0 mL). To this, the Jones reagent was added dropwise at room temperature until the solution showed a permanent yellow color. After addition of 2-propanol, the reaction mixture was filtered through Celite. The filtrate was concentrated and the residue was purified by silica gel column chromatography (methanol/chloroform=9/1). Further, slurry purification was performed using diisopropyl ether, to give 2-chloro-N-{3-[2,2,2-trifluoro-1-(4-carboxyphenyl)ethoxy]-quinoxalin-2-yl}benzenesulfonamide (Compound 61) (85.4 mg, yield: 84%).

ESIMS m/z: 537 (M+H)$^+$; $^1$H-NMR (300 MHz, CDCl$_3$, δ): 6.78 (q, J=6.6 Hz, 1H), 7.44-7.53 (m, 6H), 7.59-7.63 (m, 1H), 7.72 (d, J=8.1 Hz, 2H), 8.14 (d, J=8.1 Hz, 2H), 8.45 (br s, 1H).

EXAMPLE 57

2-chloro-N-{3-[2,2,2-trifluoro-1-(4-dimethylaminomethyl-phenyl)ethoxy]quinoxalin-2-yl}benzenesulfonamide (Compound 62)

2-Chloro-N-{3-[2,2,2-trifluoro-1-(4-formylphenyl)-ethoxy]quinoxalin-2-yl}benzenesulfonamide (Compound 58) (50.0 mg, 0.096 mmol) was dissolved in acetonitrile (1.0 mL). To this, dimethylamine (a 2.0 mol/L solution in tetrahydrofuran, 0.48 mL, 0.958 mmol) and acetic acid (54.8 µL, 0.958=1) were added under a nitrogen atmosphere at room temperature and the mixture was stirred at the same temperature for 30 minutes. To this, sodium triacetoxyborohydride (61.0 mg, 0.288 mmol) was further added and the mixture was stirred for 4 hours. Then, a saturated aqueous sodium bicarbonate solution was added to the reaction mixture, and extraction with chloroform was performed, followed by drying over anhydrous sodium sulfate. The solvent was evaporated off under reduced pressure, and the residue was purified by preparative thin-layer chromatography (chloroform/methanol=9/1). Further, slurry purification was performed using diisopropyl ether, to give 2-chloro-N-{3-[2,2,2-trifluoro-1-(4-dimethylaminomethyl-phenyl)ethoxy]quinoxalin-2-yl}benzenesulfonamide (Compound 62) (48.2 mg, yield: 91%).

ESIMS m/z: 551 (M+H)$^+$; $^1$H-NMR (270 MHz, CDCl$_3$, δ): 2.25 (s, 6H), 3.45 (s, 2H), 6.75 (q, J=6.6 Hz, 1H), 7.35-7.64 (m, 11H), 8.44-8.48 (m, 1H).

EXAMPLE 58

2-chloro-N-{3-[2,2,2-trifluoro-1-(4-dimethylcarbamoyl-phenyl)ethoxy]quinoxalin-2-yl}benzenesulfonamide (Compound 63)

2-Chloro-N-{3-[2,2,2-trifluoro-1-(4-carboxyphenyl)-ethoxy]quinoxalin-2-yl}benzenesulfonamide (Compound 61) (46.0 mg, 0.171 mmol) was dissolved in N,N-dimethylformamide. To this, dimethylamine (a 2.0 mol/L solution in tetrahydrofuran, 85.5 µL, 0.171 mmol) and 1-hydroxybenzotriazole monohydrate (13.1 mg, 0.086 mmol) were added under a nitrogen atmosphere at room temperature. To this, 1-ethyl-3-(3-dimethylaminopropyl)carbodiimide hydrochloride (32.8 mg, 0.171 mmol) was further added at 0° C. and the mixture was stirred at room temperature for 4 hours. Then, water was added to the reaction mixture, and the resulting solid was collected by filtration and then dried at 50° C. Thus, 2-chloro-N-{3-[2,2,2-trifluoro-1-(4-dimethylcarbamoyl-phenyl)ethoxy]quinoxalin-2-yl}benzenesulfonamide (Compound 63) (45.1 mg, yield: 93%) was obtained.

ESIMS m/z: 565 (M+H)+; 1H-NMR (270 MHz, CDCl3, δ): 2.96 (s, 3H), 3.11 (s, 3H), 6.76 (q, J=6.6 Hz, 1H), 7.41-7.52 (m, 9H), 7.60-7.65 (m, 3H), 8.44-8.47 (m, 1H).

EXAMPLE 59

2-chloro-N-{3-[2,2,2-trifluoro-1-(6-methoxypyridin-3-yl)-ethoxy]quinoxalin-2-yl}benzenesulfonamide (Compound 64)

According to Example 8, by use of 2-chloro-N-(3-chloroquinoxalin-2-yl)benzenesulfonamide (Compound AD) (70.0 mg, 0.198 mmol), Compound CT (61.5 mg, 0.297 mmol), 60% sodium hydride (in oil) (15.8 mg, 0.396 mmol) and tetrahydrofuran (1.5 mL), the mixture was stirred and reacted at 50° C. for 5 hours. After purification by preparative thin-layer chromatography (hexane/ethyl acetate=5/1), slurry purification was further performed using diisopropyl ether, to give 2-chloro-N-{3-[2,2,2-trifluoro-1-(6-methoxypyridin-3-yl)-ethoxy]quinoxalin-2-yl}benzenesulfonamide (Compound 64) (78.9 mg, yield: 76%).

ESIMS m/z: 525 (M+H)+; 1H-NMR (300 MHz, CDCl3, δ): 3.94 (s, 3H), 6.63-6.82 (m, 2H), 7.28-7.67 (m, 7H), 7.82 (d, J=7.3 Hz, 1H), 8.20-8.52 (m, 3H).

EXAMPLE 60

3-{1-[3-(2-chlorobenzenesulfonamide)quinoxalin-2-yloxy]-2,2,2-trifluoroethyl}-6-methylpyridine 1-oxide (Compound 65)

According to Example 42, by use of 2-chloro-N-{3-[2,2,2-trifluoro-1-(6-methylpyridin-3-yl)ethoxy]quinoxalin-2-yl}benzenesulfonamide (Compound 41) (49.3 mg, 0.097 mmol), dichloromethane (2.0 mL) and meta-chloroperbenzoic acid (41.8 mg, 0.242 mmol), the mixture was stirred and reacted at room temperature for 3.5 hours. After purification by preparative thin-layer chromatography (chloroform/methanol=19/1), slurry purification was further performed using diisopropyl ether, to give 3-{1-[3-(2-chlorobenzenesulfonamide)quinoxalin-2-yloxy]-2,2,2-trifluoroethyl}-6-methylpyridine 1-oxide (Compound 65) (43.2 mg, yield: 85%).

ESIMS m/z: 525 (M+H)+; 1H-NMR (270 MHz, DMSO-d6, δ): 2.36 (s, 3H), 7.24 (br s, 1H), 7.53-7.76 (m, 10H), 8.38 (br s, 1H), 9.11 (br s, 1H).

EXAMPLE 61

3-{1-[3-(2-chlorobenzenesulfonamide)quinoxalin-2-yloxy]-2-fluoro-2-methylpropyl}pyridine 1-oxide (Compound 66)

According to Example 42, by use of 2-chloro-N-{3-[2-fluoro-2-methyl-1-(pyridin-3-yl)ethoxy]quinoxalin-2-yl}benzenesulfonamide (Compound 45) (45.0 mg, 0.092 mmol), dichloromethane (2.0 mL) and meta-chloroperbenzoic acid (39.9 mg, 0.242 mmol), the mixture was stirred and reacted at room temperature for 3.5 hours. After purification by preparative thin-layer chromatography (chloroform/methanol=19/1), slurry purification was further performed using diisopropyl ether, to give 3-{1-[3-(2 chlorobenzenesulfonamide)quinoxalin-2-yloxy]-2-fluoro-2-methylpropyl}pyridine 1-oxide (Compound 66) (47.3 mg, yield: quantitative).

ESIMS m/z: 503 (M+H)+; 1H-NMR (270 MHz, DMSO-d6, δ): 1.45 (s, 3H), 1.53 (s, 3H), 6.51 (d, J=14.9 Hz, 1H), 7.41-7.63 (m, 9H), 8.18 (d, J=6.3 Hz, 1H), 8.39 (br s, 1H), 8.84 (br s, 1H), 12.28 (br s, 1H).

EXAMPLE 62

2-chloro-N-{3-[2-cyano-2-methyl-1-(pyridin-3-yl) propoxy]-quinoxalin-2-yl}benzenesulfonamide (Compound 67)

According to Example 8, by use of 2-chloro-N-(3-chloroquinoxalin-2-yl)benzenesulfonamide (Compound AD) (100 mg, 0.282 mmol), Compound CU (74.6 mg, 0.423 mmol), 60% sodium hydride (in oil) (28.2 mg, 0.705 mmol) and tetrahydrofuran (2.0 mL), the mixture was stirred and reacted at 50° C. for 3 hours. After purification by preparative thin-layer chromatography (chloroform/methanol=19/1), slurry purification was further performed using diisopropyl ether, to give 2-chloro-N-{3-[2-cyano-2-methyl-1-(pyridin-3-yl)propoxy]-quinoxalin-2-yl}benzenesulfonamide (Compound 67) (99.9 mg, yield: 72%).

ESIMS m/z: 494 (M+H)+; 1H-NMR (300 MHz, DMSO-d6, δ): 1.43 (s, 3H), 1.54 (s, 3H), 6.41 (s, 1H), 7.43-7.67 (m, 9H), 8.10 (br s, 1H), 8.36-8.39 (m, 1H), 8.56 (dd, J=1.8, 4.8 Hz, 1H), 8.88 (br s, 1H).

EXAMPLE 63

3-{1-[3-(2-chlorobenzenesulfonamide)quinoxalin-2-yloxy]-2-cyano-2-methylpropyl}pyridine 1-oxide (Compound 68)

According to Example 42, by use of 2-chloro-N-{3-[2-cyano-2-methyl-1-(pyridin-3-yl)propoxy]quinoxalin-2-yl}benzenesulfonamide (Compound 67) (50.0 mg, 0.101 mmol), dichloromethane (2.0 mL) and meta-chloroperbenzoic acid (43.7 mg, 0.253 mmol), the mixture was stirred and reacted at room temperature for 3 hours. After purification by preparative thin-layer chromatography (chloroform/methanol=19/1), slurry purification was further performed using diisopropyl ether, to give 3-{1-[3-(2 chlorobenzenesulfonamide)quinoxalin-2-yloxy]-2-cyano-2-methylpropyl}pyridine 1-oxide (Compound 68) (51.1 mg, yield: 99%).

ESIMS m/z: 509 (M+H)+; 1H-NMR (300 MHz, DMSO-d6, δ): 4.48 (s, 3H), 1.52 (s, 3H), 6.53 (s, 1H), 7.47-7.91 (m, 9H), 8.21 (d, J=5.9 Hz, 1H), 8.38 (br s, 1H), 8.87 (br s, 1H), 12.31 (br s, 1H).

EXAMPLE 64

5-chloro-1,3-dimethyl-N-{3-[2,2,2-trifluoro-1-(6-methylpyridin-3-yl)ethoxy]quinoxalin-2-yl}-1H-pyrazole-4-sulfonamide (Compound 69)

5-Chloro-1,3-dimethyl-N-(3-chloroquinoxalin-2-yl)-1H-pyrazole-4-sulfonamide (Compound AF) (70.0 mg, 0.188 mmol) and Compound CK (53.9 mg, 0.282 mmol) were dissolved in 1,2-dimethoxyethane (1.5 mL). To this, 60% sodium hydride (in oil) (18.8 mg, 0.470 mmol) was added under a nitrogen atmosphere at 0° C. and the mixture was stirred at 80° C. for 2 hours. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by preparative thin-layer chromatography (chloroform/methanol=19/1). Further, slurry purification was performed using diisopropyl ether, to give 5-chloro-1,3-dimethyl-N-{3-[2,2,2-trifluoro-1-(6-methylpyridin-3-yl)ethoxy]quinoxalin-2-yl}-1H-pyrazole-4-sulfonamide (Compound 69) (69.0 mg, yield: 70%).

ESIMS m/z: 526 (M+H)$^+$; $^1$H-NMR (300 MHz, DMSO-d$_6$, δ): 2.47 (s, 3H), 2.49 (s, 3H), 3.74 (s, 3H), 7.12 (q, J=7.0 Hz, 1H), 7.38 (d, J=8.4 Hz, 1H), 7.53-7.70 (m, 4H), 8.21 (d, J=8.4 Hz, 1H) 8.92 (s, 1H).

EXAMPLE 65

3,5-dimethyl-N-{3-[2,2,2-trifluoro-1-(6-methylpyridin-3-yl)ethoxy]quinoxalin-2-yl}isoxazole-4-sulfonamide (Compound 70)

According to Example 64, by use of 3,5-dimethyl-N-(3-chloroquinoxalin-2-yl)isoxazole-4-sulfonamide (Compound AG) (70.0 mg, 0.207 mmol), Compound CK (59.2 mg, 0.310 mmol), 60% sodium hydride (in oil) (20.7 mg, 0.518 mmol) and 1,2-dimethoxyethane (1.5 mL), the mixture was stirred and reacted at 80° C. for 3 hours. After purification by preparative thin-layer chromatography (chloroform/methanol=9/1), slurry purification was further performed using diisopropyl ether, to give 3,5-dimethyl-N-{3-[2,2,2-trifluoro-1-(6-methylpyridin-3-yl)ethoxy]quinoxalin-2-yl}isoxazole-4-sulfonamide (Compound 70) (76.7 mg, yield: 75%).

ESIMS m/z: 494 (M+H)$^+$; $^1$H-NMR (300 MHz, DMSO-d$_6$, δ): 2.48 (s, 3H), 2.49 (s, 3H), 3.34 (s, 3H), 7.11 (q, J=7.3 Hz, 1H), 7.39 (d, J=8.1 Hz, 1H), 7.55-7.70 (m, 4H), 8.18 (dd, J=1.5, 8.1 Hz, 1H), 8.92 (d, J=1.5 Hz, 1H).

EXAMPLE 66

2-chloro-N-{3-[2,2,2-trifluoro-1-(5-methoxypyridin-3-yl)-ethoxy]quinoxalin-2-yl}benzenesulfonamide (Compound 71)

According to Example 8, by use 2-chloro-N-{3-chloroquinoxalin-2-yl}benzenesulfonamide (Compound AD) (100 mg, 0.282 mmol), Compound CV (87.6 mg, 0.423 mmol), 60% sodium hydride (in oil) (28.2 mg, 0.705 mmol) and tetrahydrofuran (2.0 mL), the mixture was stirred and reacted at 50° C. for 3 hours. After purification by preparative thin-layer chromatography (chloroform/methanol=19/1), slurry purification was further performed using diisopropyl ether, to give 2-chloro-N-{3-[2,2,2-trifluoro-1-(5-methoxypyridin-3-yl)-ethoxy]quinoxalin-2-yl}benzenesulfonamide (Compound 71) (138 mg, yield: 93%).

ESIMS m/z: 525 (M+H)$^+$; $^1$H-NMR (300 MHz, DMSO-d$_6$, δ): 3.87 (s, 3H), 7.16-7.23 (m, 1H), 7.52-7.65 (m, 7H), 7.98 (br s, 1H), 8.36-8.38 (m, 2H), 8.65 (s, 1H).

EXAMPLE 67

3-{1-[3-(2 chlorobenzenesulfonamide)quinoxalin-2-yloxy]-2,2,2-trifluoroethyl}-5-methoxypyridine 1-oxide (Compound 72)

According to Example 42, by use of 2-chloro-N-{3-[2,2,2-trifluoro-1-(5-methoxypyridin-3-yl)ethoxy]quinoxalin-2-yl}benzenesulfonamide (Compound 71) (54.0 mg, 0.103 mmol), dichloromethane (2.0 mL) and meta-chloroperbenzoic acid (44.4 mg, 0.257 mmol), the mixture was stirred and reacted at room temperature for 2.5 hours. After purification by preparative thin-layer chromatography (chloroform/methanol=19/1), slurry purification was further performed using diisopropyl ether, to give 3-{1-[3-(2-chlorobenzenesulfonamide)quinoxalin-2-yloxy]-2,2,2-trifluoroethyl}-5-methoxypyridine 1-oxide (Compound 72) (48.4 mg, yield: 87%).

ESIMS m/z: 525 (M+H)$^+$; $^1$H-NMR (300 MHz, DMSO-d$_6$, δ): 3.87 (s, 3H), 7.16-7.23 (m, 1H), 7.52-7.65 (m, 7H), 7.98 (br s, 1H), 8.36-8.38 (m, 2H), 8.65 (s, 1H).

EXAMPLE 68

2-chloro-N-{3-[tetrahydropyran-4-yl(pyridin-3-yl)methoxy]-quinoxalin-2-yl}benzenesulfonamide (Compound 73)

According to Example 37, by use of 2-chloro-3-[tetrahydropyran-4-yl(pyridin-3-yl)methoxy]-quinoxaline (Compound BE) (176 mg, 0.495 mmol), dimethyl sulfoxide (4.0 mL), 2-chlorobenzenesulfonamide (94.9 mg, 0.495 mmol) and potassium carbonate (68.4 mg, 0.495 mmol), the mixture was stirred and reacted at 150° C. for 1 hour. Then, slurry purification was performed using diisopropyl ether, to give 2-chloro-N-{3-[tetrahydropyran-4-yl(pyridin-3-yl)methoxy]-quinoxalin-2-yl}benzenesulfonamide (Compound 73) (191 mg, yield: 76%).

ESIMS m/z: 510 (M+H)$^+$; $^1$H-NMR (270 MHz, DMSO-d$_6$, δ): 1.13-1.40 (m, 1H), 1.30-1.50 (m, 2H), 1.94-1.98 (m, 1H), 2.33-3.36 (m, 1H), 3.21-3.36 (m, 2H), 3.80-3.96 (m, 2H), 7.38-7.48 (m, 4H), 7.54-7.66 (m, 4H), 8.01 (d, J=7.6 Hz, 1H), 8.38 (dd, J=3.6, 6.0 Hz, 1H), 8.48 (dd, J=1.7, 4.6 Hz, 1H), 8.79 (d, J=1.7 Hz, 1H), 12.15 (br s, 1H).

EXAMPLE 69

3-{[3-(2-chlorobenzenesulfonamide)quinoxalin-2-yloxy]tetrahydropyran-4-yl)}methylpyridine 1-oxide (Compound 74)

According to Example 42, by use of 2-chloro-N-{3-[tetrahydropyran-4-yl(pyridin-3-yl)methoxy]quinoxalin-2-yl}benzenesulfonamide (Compound 73) (93.0 mg, 0.182 mmol), dichloromethane (3.0 mL) and meta-chloroperbenzoic acid (78.5 mg, 0.455 mmol), the mixture was stirred and reacted at room temperature for 2 hours. After purification by preparative thin-layer chromatography (chloroform/methanol=19/1), slurry purification was further performed using diisopropyl ether, to give 3-{[3-(2-chlorobenzenesulfonamide)quinoxalin-2-yloxy]tetrahydropyran-4-yl)}methylpyridine 1-oxide (Compound 74) (84.0 mg, yield: 88%).

ESIMS m/z: 527 (M+H)$^+$; $^1$H-NMR (270 MHz, DMSO-d$_6$, δ): 1.20-1.25 (m, 1H), 1.34-1.50 (m, 2H), 1.83-1.88 (m, 1H), 2.27-3.31 (m, 1H), 3.22-3.33 (m, 2H), 3.84-3.94 (m, 2H), 7.38-7.64 (m, 9H), 8.13 (d, J=5.9 Hz, 1H), 8.39 (br s, 1H), 8.68 (br s, 1H), 12.09 (br s, 1H).

EXAMPLE 70

5-chloro-1,3-dimethyl-N-{3-[2-fluoro-2-methyl-1-(pyridin-3-yl)ethoxy]quinoxalin-2-yl}-1H-pyrazole-4-sulfonamide (Compound 75)

According to Example 64, by use of 5-chloro-1,3-dimethyl-N-(3-chloroquinoxalin-2-yl)-1H-pyrazole-4-sulfonamide (Compound AF) (70.0 mg, 0.188 mmol), Compound CI (40.7 mg, 0.241 mmol), 60% sodium hydride (in oil) (17.1 mg, 0.429 mmol) and 1,2-dimethoxyethane (1.5 mL), the mixture was stirred and reacted at 80° C. for 3 hours. After purification by preparative thin-layer chromatography (chloroform/methanol=19/1), slurry purification was further performed using diisopropyl ether, to give 5-chloro-1,3-dimethyl-N-{3-[2-fluoro-2-methyl-1-(pyridin-3-yl)ethoxy]quinoxalin-2-yl}-1H-pyrazole-4-sulfonamide (Compound 75) (73.4 mg, yield: 77%).

ESIMS m/z: 504 (M+H)$^+$; $^1$H-NMR (270 MHz, DMSO-$d_6$, δ): 1.45 (d, J=10.6 Hz, 3H), 1.53 (d, J=10.6 Hz, 3H), 2.50 (s, 3H), 3.73 (s, 3H), 6.46 (d, J=17.5 Hz, 1H), 7.43 (dd, J=5.0, 7.6 Hz, 1H), 7.48-7.66 (m, 4H), 8.12 (d, J=7.6 Hz, 1H), 8.52 (dd, J=1.7, 5.0 Hz, 1H), 8.87 (d, J=1.7 Hz, 1H), 11.99 (br s, 1H).

EXAMPLE 71

3,5-dimethyl-N-{3-[2-fluoro-2-methyl-1-(pyridin-3-yl)-ethoxy]quinoxalin-2-yl}isoxazole-4-sulfonamide (Compound 76)

According to Example 64, by use of 3,5-dimethyl-N-(3-chloroquinoxalin-2-yl) isoxazole-4-sulfonamide (Compound AG) (70.0 mg, 0.207 mmol), Compound CI (41.0 mg, 0.242 mmol), 60% sodium hydride (in oil) (18.0 mg, 0.449 mmol) and 1,2-dimethoxyethane (1.5 mL), the mixture was stirred and reacted at 80° C. for 3 hours. After purification by preparative thin-layer chromatography (chloroform/methanol 9/1), slurry purification was further performed using diisopropyl ether, to give 3,5-dimethyl-N-{3-[2-fluoro-2-methyl-1-(pyridin-3-yl)-ethoxy]quinoxalin-2-yl}isoxazole-4-sulfonamide (Compound 76) (82.4 mg, yield: 84%).

ESIMS m/z: 471 (M+H)$^+$; $^1$H-NMR (270 MHz, DMSO-$d_6$, δ): 1.45 (d, J=21.1 Hz, 3H), 1.53 (d, J=21.1 Hz, 3H), 2.50 (s, 3H), 2.84 (s, 3H), 6.42 (d, J=17.8 Hz, 1H), 7.43 (dd, J=4.6, 7.6 Hz, 1H), 7.49-7.67 (m, 4H), 8.11 (d, J=7.6 Hz, 1H), 8.53 (dd, J=1.7, 4.6 Hz, 1H), 8.87 (d, J=1.7 Hz, 1H).

EXAMPLE 72

2-chloro-N-{3-{2,2,2-trifluoro-1-[4-(morpholin-1-yl)methyl-phenyl]ethoxy}quinoxalin-2-yl}benzenesulfonamide (Compound 77)

According to Example 57, by use of 2-chloro-N-{3-[2,2,2-trifluoro-1-(4-formylphenyl)ethoxy]-quinoxalin-2-yl}benzenesulfonamide (Compound 58) (32.0 mg, 0.061 mmol), acetonitrile (1.0 mL), morpholine (53.5 μL, 0.613 mmol), acetic acid (33.6 μL, 0.613 mmol) and sodium triacetoxyborohydride (39.9 mg, 0.184 mmol), the mixture was stirred and reacted at room temperature for 5 hours. After purification by preparative thin-layer chromatography (chloroform/methanol=9/1), slurry purification was further performed using hexane, to give 2-chloro-N-{3-{2,2,2-trifluoro-1-[4-(morpholin-1-yl)methyl-phenyl]ethoxy}quinoxalin-2-yl}benzenesulfonamide (Compound 77) (28.9 mg, yield: 80%).

ESIMS m/z: 593 (M+H)$^+$; $^1$H-NMR (270 MHz, DMSO-$d_6$, δ): 2.76 (br s, 4H), 3.65 (br s, 4H), 3.92 (br s, 2H), 7.02 (q, J=7.3 Hz, 1H), 7.28-7.50 (m, 9H), 7.81 (d, J=7.3 Hz, 2H), 8.29-8.32 (m, 1H).

EXAMPLE 73

2-chloro-N-{3-[4-fluorotetrahydropyran-4-yl(pyridin-3-yl)-methoxy]quinoxalin-2-yl}benzenesulfonamide (Compound 78)

According to Example 37, by use of 2-chloro-3-[4-fluorotetrahydropyran-4-yl(pyridin-3-yl)-methoxy]quinoxaline (Compound BF) (100 mg, 0.268 mmol), dimethyl sulfoxide (2.0 mL), 2-chlorobenzenesulfonamide (51.3 mg, 0.268 mmol) and potassium carbonate (37.0 mg, 0.268 mmol), the mixture was stirred and reacted at 150° C. for 1 hour. After purification by preparative thin-layer chromatography (chloroform/methanol=19/1), slurry purification was further performed using diisopropyl ether, to give 2-chloro-N-{3-[4-fluorotetrahydropyran-4-yl(pyridin-3-yl)-methoxy]quinoxalin-2-yl}benzenesulfonamide (Compound 78) (138 mg, yield: 97%).

ESIMS m/z: 529 (M+H)$^+$; $^1$H-NMR (300 MHz, DMSO-$d_6$, δ): 1.53-1.61 (m, 1H), 1.94-2.17 (m, 3H), 3.46-3.64 (m, 2H), 3.78-3.85 (m, 2H), 6.42 (d, J=17.6 Hz, 1H), 7.40-7.65 (m, 8H), 8.06 (d, J=6.6 Hz, 1H), 8.35-8.38 (m, 1H), 8.53 (dd, J=1.5, 4.8 Hz, 1H).

EXAMPLE 74

3-{[3-(2-chlorobenzenesulfonamide)quinoxalin-2-yloxy]fluoro(tetrahydropyran-4-yl)}methylpyridine 1-oxide (Compound 79)

According to Example 42, by use of 2-chloro-N-{3-[4-fluorotetrahydropyran-4-yl(pyridin-3-yl)methoxy]quinoxalin-2-yl}benzenesulfonamide (Compound 78) (55.0 mg, 0.104 mmol), dichloromethane (2.0 mL) and meta-chloroperbenzoic acid (44.9 mg, 0.260 mmol), the mixture was stirred and reacted at room temperature for 2.5 hours. After purification by preparative thin-layer chromatography (chloroform/methanol=19/1), slurry purification was further performed using diisopropyl ether, to give 3-{[3-(2-chlorobenzenesulfonamide)quinoxalin-2-yloxy]fluoro (tetrahydropyran-4-yl)}methylpyridine 1-oxide (Compound 79) (49.9 mg, yield: 88%).

ESIMS m/z: 545 (M+H)$^+$; $^1$H-NMR (300 MHz, DMSO-$d_6$, δ): 1.60-1.68 (m, 1H), 1.92-2.15 (m, 3H), 3.47-3.54 (m, 2H), 3.80-3.83 (m, 2H), 6.48 (d, J=18.7 Hz, 1H), 7.41-7.63 (m, 8H), 8.18 (d, J=5.9 Hz, 1H), 8.38 (br s, 1H), 8.77 (br s, 1H), 12.32 (br s, 1H).

EXAMPLE 75

2-chloro-N-{3-[2-methanesulfonyl-2-methyl-1-(pyridin-3-yl)-propoxy]quinoxalin-2-yl}benzenesulfonamide (Compound 80)

According to Example 8, by use of 2-chloro-N-(3-chloroquinoxalin-2-yl)benzenesulfonamide (Compound AD) (100 mg, 0.282 mmol), Compound CY (86.7 mg, 0.378 mmol), 60% sodium hydride (in oil) (26.4 mg, 0.660 mmol) and tetrahydrofuran (2.0 mL), the mixture was stirred and reacted at 50° C. for 2 hours. After purification by preparative thin-layer chromatography (chloroform/methanol=19/1), slurry purification was further performed using diisopropyl ether, to give 2-chloro-N-{3-[2-methanesulfonyl-2-methyl-1-(pyridin-3-yl)-propoxy]quinoxalin-2-yl}benzenesulfonamide (Compound 80) (110 mg, yield: 71%).

ESIMS m/z: 547 (M+H)$^+$; $^1$H-NMR (300 MHz, DMSO-$d_6$, δ): 1.21 (s, 3H), 1.61 (brs, 3H), 3.10 (br s, 3H), 6.67 (brs, 1H), 7.42-7.65 (m, 8H), 8.08 (br s, 1H), 8.34 (br s, 1H), 8.54 (dd, J=1.5, 4.8 Hz, 1H), 8.85 (br s, 1H).

EXAMPLE 76

3-{1-[3-(2 chlorobenzenesulfonamide)quinoxalin-2-yloxy]-2-methanesulfonyl-2-methylpropyl}pyridine 1-oxide (Compound 81)

According to Example 42, by use of 2-chloro-N-{3-[2-methanesulfonyl-2-methyl-1-(pyridin-3-yl)propoxy]quinoxalin-2-yl}benzenesulfonamide (Compound 80) (55.0 mg, 0.101 mmol), dichloromethane (2.0 mL) and meta-chloroperbenzoic acid (43.7 mg, 0.253 mmol), the mixture was stirred and reacted at room temperature for 2 hours. After purification by preparative thin-layer chromatography (chloroform/methanol=19/1), slurry purification was further performed using diisopropyl ether, to give 3-{1-[3-(2 chlorobenzenesulfonamide)quinoxalin-2-yloxy]-2-methanesulfonyl-2-methylpropyl}pyridine 1-oxide (Compound 81) (39.8 mg, yield: 70%).

ESIMS m/z: 562 (M+H)$^+$; $^1$H-NMR (300 MHz, DMSO-d$_6$, δ): 1.28 (s, 3H), 1.66 (br s, 3H), 3.16 (br s, 3H), 6.75 (br s, 1H), 7.42-7.63 (m, 9H), 8.19 (d, J=6.2 Hz, 1H), 8.37 (br s, 1H), 8.87 (br s, 1H), 12.24 (br s, 1H).

EXAMPLE 77

2-chloro-N-{3-[2,2,2-trifluoro-1-(3-cyanophenyl) ethoxy]-quinoxalin-2-yl}benzenesulfonamide (Compound 82)

According to Example 8, by use of 2-chloro-N-(3-chloroquinoxalin-2-yl)benzenesulfonamide (Compound AD) (70.0 mg, 0.198 mmol) Compound CZ (59.5 mg, 0.296 mmol), 60% sodium hydride (in oil) (19.8 mg, 0.495 mmol) and tetrahydrofuran (1.5 mL), the mixture was stirred and reacted at room temperature for 12 hours. After purification by preparative thin-layer chromatography (hexane/ethyl acetate=3/1), slurry purification was further performed using diisopropyl ether, to give 2-chloro-N-{3-[2,2,2-trifluoro-1-(3-cyanophenyl)ethoxy]-quinoxalin-2-yl}benzenesulfonamide (Compound 82) (68.2 mg, yield: 66%).

ESIMS m/z: 519 (M+H)$^+$; $^1$H-NMR (300 MHz, DMSO-d$_6$, δ): 7.25 (br s, 1H), 7.52-7.74 (m, 8H), 7.96 (d, J=7.7 Hz, 1H), 8.25 (br s, 1H), 8.40 (br s, 1H), 8.59 (br s, 1H), 12.45 (br s, 1H).

EXAMPLE 78

2-chloro-N-{3-[2,2,2-trifluoro-1-(3-fluorophenyl) ethoxy]-quinoxalin-2-yl}benzenesulfonamide (Compound 83)

Compound DA (100 mg, 0.515 mmol) and 2,3-dichloroquinoxaline (103 mg, 0.515 mmol) were dissolved in tetrahydrofuran (2.0 mL). To this, 60% sodium hydride (in oil) (30.9 mg, 0.773 mmol) was added under a nitrogen atmosphere at 0° C. and the mixture was stirred at room temperature for 2 hours. Then, saturated ammonium chloride was added to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=9/1) to give a mixture (170 mg) of 2-chloro-3-[2,2,2-trifluoro-1-(3-fluorophenyl)ethoxy]-quinoxaline and 2,3-dichloroquinoxaline. This mixture was dissolved in dimethyl sulfoxide (3.0 mL). To this, 2-chlorobenzenesulfonamide (91.3 mg, 0.477 mmol) and potassium carbonate (65.9 mg, 0.477 mmol) were added at room temperature and the mixture was stirred at 150° C. for 1 hour. The reaction mixture was allowed to cool down to room temperature, a 1% aqueous acetic acid solution (1.0 mL) was added thereto, and the precipitate was collected by filtration. The obtained solid was purified by preparative thin-layer chromatography (hexane/ethyl acetate=7/3). Further, slurry purification was performed using diisopropyl ether, to give 2-chloro-N-{3-[2,2,2-trifluoro-1-(3-fluorophenyl) ethoxy]-quinoxalin-2-yl}benzenesulfonamide (Compound 83) (129 mg, yield: 49%).

ESIMS m/z: 512 (M+H)$^+$; $^1$H-NMR (300 MHz, DMSO-d$_6$, δ): 7.15 (br s, 1H), 7.28-7.34 (m, 1H), 7.52-7.92 (m, 10H), 8.38 (br s, 1H), 12.48 (br s, 1H).

EXAMPLE 79

2-chloro-N-{3-[2,2,2-trifluoro-1-(3-chlorophenyl) ethoxy]-quinoxalin-2-yl}benzenesulfonamide (Compound 84)

Compound DB (100 mg, 0.475 mmol) and 2,3-dichloroquinoxaline (95.4 mg, 0.475 mmol) were dissolved in tetrahydrofuran (2.0 mL). To this, 60% sodium hydride (in oil) (28.5 mg, 0.713 mmol) was added under a nitrogen atmosphere at 0° C. and the mixture was stirred at room temperature for 2 hours. Then, saturated ammonium chloride was added to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=9/1) to give a mixture (153 mg) of 2-chloro-3-[2,2,2-trifluoro-1-(3-chlorophenyl)ethoxy]-quinoxaline and 2,3-dichloroquinoxaline. This mixture was dissolved in dimethyl sulfoxide (3.0 mL). To this, 2-chlorobenzenesulfonamide (78.6 mg, 0.410 mmol) and potassium carbonate (56.7 mg, 0.410 mmol) were added at room temperature and the mixture was stirred at 150° C. for 1 hour. The reaction mixture was allowed to cool down to room temperature, a 1% aqueous acetic acid solution (1.0 mL) was added thereto, and the precipitate was collected by filtration. The obtained solid was purified by preparative thin-layer chromatography (hexane/ethyl acetate=7/3). Further, slurry purification was performed using diisopropyl ether, to give 2-chloro-N-{3-[2,2,2-trifluoro-1-(3-chlorophenyl)ethoxy]-quinoxalin-2-yl}benzenesulfonamide (Compound 84) (110 mg, yield: 44%).

ESIMS m/z: 528 (M+H)$^+$; $^1$H-NMR (300 MHz, DMSO-d$_6$, δ): 7.16 (br s, 1H), 7.48-7.65 (m, 9H), 7.84 (br s, 1H), 8.15 (br s, 1H), 8.39 (br s, 1H), 12.53 (br s, 1H).

EXAMPLE 80

2-chloro-N-{3-[2,2,2-trifluoro-1-(6-chloropyridin-3-yl)-ethoxy]quinoxalin-2-yl}benzenesulfonamide (Compound 85)

According to Example 8, by use of 2-chloro-N-(3-chloroquinoxalin-2-yl)benzenesulfonamide (Compound AD) (100 mg, 0.282 mmol), Compound DC (89.5 mg, 0.423 mmol), 60% sodium hydride (in oil) (28.2 mg, 0.705 mmol) and tetrahydrofuran (2.0 mL), the mixture was stirred and reacted at room temperature for 28 hours. After purification by preparative thin-layer chromatography (hexane/ethyl acetate=3/1), slurry purification was further performed using diisopropyl ether, to give 2-chloro-N-{3-[2,2,2-trifluoro-1-(6-chloropyridin-3-yl)-ethoxy]quinoxalin-2-yl}benzenesulfonamide (Compound 85) (68.8 mg, yield: 46%).

ESIMS m/z: 528 (M+H)$^+$; $^1$H-NMR (270 MHz, DMSO-d$_6$, δ): 7.67 (br s, 1H), 7.90-8.10 (m, 8H), 8.75-8.84 (m, 2H), 9.34 (br s, 1H), 12.82 (br s, 1H).

EXAMPLE 81

2-chloro-N-{3-[2,2,2-trifluoro-1-(6-bromopyridin-3-yl)-ethoxy]quinoxalin-2-yl}benzenesulfonamide (Compound 86)

According to Example 8, by use of 2-chloro-N-(3-chloroquinoxalin-2-yl)benzenesulfonamide (Compound AD) (300 mg, 0.847 mmol), Compound DD (325 mg, 1.27 mmol), 60% sodium hydride (in oil) (84.7 mg, 2.12 mmol) and tetrahydrofuran (6.0 mL), the mixture was stirred and reacted at 50° C. for 5 hours. After purification by silica gel column chromatography (hexane/ethyl acetate=3/1), slurry purification was further performed using diisopropyl ether, to give 2-chloro-N-{3-[2,2,2-trifluoro-1-(6-bromopyridin-3-yl)-ethoxy]quinoxalin-2-yl}benzenesulfonamide (Compound 86) (306 mg, yield: 63%).

ESIMS m/z: 575 (M+H)$^+$; $^1$H-NMR (300 MHz, DMSO-d$_6$, δ): 7.26 (br s, 1H), 7.53-7.66 (m, 7H), 7.85 (d, J=8.1 Hz, 1H), 8.38 (br s, 2H), 8.94 (br s, 1H), 12.46 (br s, 1H).

EXAMPLE 82

5-chloro-1,3-dimethyl-N-{3-[4-fluorotetrahydropyran-4-yl-(pyridin-3-yl)methoxy]quinoxalin-2-yl}-1H-pyrazole-4-sulfonamide (Compound 87)

According to Example 37, by use of 2-chloro-3-[4-fluorotetrahydropyran-4-yl(pyridin-3-yl)-methoxy]quinoxaline (Compound BF) (70.0 mg, 0.187 mmol), dimethyl sulfoxide (1.5 mL), Compound FB (39.3 mg, 0.187 mmol) and potassium carbonate (25.8 mg, 0.187 mmol), the mixture was stirred and reacted at 150° C. for 2 hours. After purification by preparative thin-layer chromatography (chloroform/methanol=19/1), slurry purification was further performed using diisopropyl ether, to give 5-chloro-1,3-dimethyl-N-{3-[4-fluorotetrahydropyran-4-yl-(pyridin-3-yl)methoxy]quinoxalin-2-yl}-1H-pyrazole-4-sulfonamide (Compound 87) (64.6 mg, yield: 63%).

ESIMS m/z: 547 (M+H)$^+$; $^1$H-NMR (270 MHz, DMSO-d$_6$, δ): 1.52-1.60 (m, 1H), 1.92-2.13 (m, 3H), 2.50 (s, 3H), 3.46-3.64 (m, 2H), 3.73 (s, 3H), 3.78-3.86 (m, 2H), 6.44 (d, J=19.4 Hz, 1H), 7.43 (dd, J=4.9, 7.9 Hz, 1H), 7.50-7.66 (m, 4H), 8.19 (d, J=7.3 Hz, 1H), 8.52 (d, J=3.9 Hz, 1H), 8.85 (s, 1H).

EXAMPLE 83

3,5-dimethyl-N-{3-[4-fluorotetrahydropyran-4-yl(pyridin-3-yl)methoxy]quinoxalin-2-yl}isoxazole-4-sulfonamide (Compound 88)

According to Example 37, by use of 2-chloro-3-[4-fluorotetrahydropyran-4-yl(pyridin-3-yl)-methoxy]quinoxaline (Compound BF) (70.0 mg, 0.187 mmol), dimethyl sulfoxide (1.5 mL), Compound FC (32.9 mg, 0.187 mmol) and potassium carbonate (25.8 mg, 0.187 mmol), the mixture was stirred and reacted at 150° C. for 2 hours. After purification by preparative thin-layer chromatography (chloroform/methanol=19/1), slurry purification was further performed using diisopropyl ether, to give 3,5-dimethyl-N-{3-[4-fluorotetrahydropyran-4-yl(pyridin-3-yl)methoxy]quinoxalin-2-yl}isoxazole-4-sulfonamide (Compound 88) (66.2 mg, yield: 69%).

ESIMS m/z: 514 (M+H)$^+$; $^1$H-NMR (270 MHz, DMSO-d$_6$, δ): 1.46-1.55 (m, 1H), 1.94-2.12 (m, 3H), 2.50 (s, 3H), 2.84 (s, 3H), 3.43-3.60 (m, 2H), 3.78-3.87 (m, 2H), 6.42 (d, J=20.4 Hz, 1H), 7.44 (dd, J=4.6, 8.2 Hz, 1H), 7.51-7.66 (m, 4H), 8.09 (d, J=7.2 Hz, 1H), 8.52 (d, J=4.6 Hz, 1H), 8.86 (s, 1H).

EXAMPLE 84

2-chloro-N-{3-[2,2,2-trifluoro-1-(6-cyclopropylpyridin-3-yl)ethoxy]quinoxalin-2-yl}benzenesulfonamide (Compound 89)

2-Chloro-N-{3-[2,2,2-trifluoro-1-(6-bromopyridin-3-yl)-ethoxy]quinoxalin-2-yl}benzenesulfonamide (Compound 86) (50.0 mg, 0.087 mmol), [bis(diphenylphosphino)ferrocene]dichloropalladium (7.1 mg, 0.0087 mmol) and sodium carbonate (27.7 mg, 0.261 mmol) were suspended in 1,4-dioxane (1.0 mL) and water (0.5 mL). To this, cyclohexyl pinacolborane (23.8 μL, 0.131 mmol) was added under a nitrogen atmosphere at room temperature and the mixture was stirred at 100° C. for 24 hours. Then, saturated ammonium chloride was added to the reaction mixture, and extraction with ethyl acetate was performed, followed by washing with brine and drying over anhydrous sodium sulfate. The solvent was evaporated off under reduced pressure, and the residue was purified by preparative thin-layer chromatography (hexane/ethyl acetate=7/3). Further, slurry purification was performed using hexane, to give 2-chloro-N-{3-[2,2,2-trifluoro-1-(6-cyclopropylpyridin-3-yl)ethoxy]quinoxalin-2-yl}benzenesulfonamide (Compound 89) (14.2 mg, yield: 31%).

ESIMS m/z: 535 (M+H)$^+$; $^1$H-NMR (300 MHz, DMSO-d$_6$, δ): 0.93-0.98 (m, 4H), 2.07-2.16 (m, 1H), 7.11 (br s, 1H), 7.40-7.64 (m, 8H), 8.17-8.84 (m, 3H).

EXAMPLE 85

2-chloro-N-{3-{[4-(pyridin-3-yl)tetrahydropyran-4-yl]oxy}-quinoxalin-2-yl}benzenesulfonamide (Compound 90)

According to Example 37, by use of 2-chloro-3-{[4-(pyridin-3-yl)tetrahydropyran-4-yl]oxy}-quinoxaline (Compound BH) (21.8 mg, 0.064 mmol), dimethyl sulfoxide (0.6 mL), 2-chlorobenzenesulfonamide (18.3 mg, 0.096 mmol) and potassium carbonate (13.3 mg, 0.096 mmol), the mixture was stirred and reacted at 150° C. for 1 hour. After purification by preparative thin-layer chromatography (chloroform/methanol=19/1), slurry purification was further performed using diisopropyl ether, to give 2-chloro-N-{3-{[4-(pyridin-3-yl)tetrahydropyran-4-yl]oxy}-quinoxalin-2-yl}benzenesulfonamide (Compound 90) (16.3 mg, yield: 75%).

ESIMS m/z: 497 (M+H)$^+$; $^1$H-NMR (300 MHz, DMSO-d$_6$, δ): 2.17-2.51 (m, 2H), 2.93-2.98 (m, 2H), 3.82-3.85 (m, 4H), 7.26-7.37 (m, 5H), 7.62-7.65 (m, 3H), 7.92 (d, J=8.1 Hz, 1H), 8.36-8.42 (m, 2H), 8.76 (s, 1H).

EXAMPLE 86

2-chloro-N-{3-[1-methyl-1-(pyridin-3-yl)ethoxy]quinoxalin-2-yl}benzenesulfonamide (Compound 91)

According to Example 37, by use of 2-chloro-3-[1-methyl-1-(pyridin-3-yl)ethoxy]quinoxaline (Compound BI) (50.0 mg, 0.167 mmol), dimethyl sulfoxide (1.5 mL), 2-chlorobenzenesulfonamide (47.9 mg, 0.250 mmol) and potassium carbonate (34.6 mg, 0.250 mmol), the mixture was stirred and reacted at 150° C. for 2 hours. After purification by preparative thin-layer chromatography (chloroform/methanol=19/1), slurry purification was further performed using diisopropyl ether, to give 2-chloro-N-{3-[1-methyl-1-(pyridin-3-yl)ethoxy]quinoxalin-2-yl}benzenesulfonamide (Compound 91) (17.7 mg, yield: 23%).

ESIMS m/z: 455 (M+H)$^+$; $^1$H-NMR (300 MHz, DMSO-d$_6$, δ): 2.01 (s, 6H), 7.24-7.38 (m, 5H), 7.59-7.67 (m, 3H), 7.86 (d, J=8.1 Hz, 1H), 8.32-8.41 (m, 2H), 8.71 (d, J=2.2 Hz, 1H).

EXAMPLE 87

2-chloro-N-{3-[2,2,2-trifluoro-1-(tert-butoxycarbonyl-aminomethylphenyl)ethoxy]quinoxalin-2-yl}benzenesulfonamide (Compound 92)

2-Chloro-N-{3-[2,2,2-trifluoro-1-(4-formylphenyl)-ethoxy]quinoxalin-2-yl}benzenesulfonamide (Compound 58) (238 mg, 0.456 mmol) and tert-butyl carbamate (320 mg, 2.74 mmol) were dissolved in acetonitrile (5.0 mL). To this, triethyl silane (369 μL, 2.74 μmol) and trifluoroacetic acid (141 mL, 1.82 mmol) were added under a nitrogen atmosphere at room temperature and the mixture was stirred at the same temperature for 48 hours. Then, saturated sodium bicarbonate was added to the reaction mixture, and extraction with ethyl acetate was performed, followed by washing with brine and drying over anhydrous sodium sulfate. The solvent was evaporated off under reduced pressure, and the residue was purified by preparative thin-layer chromatography (hexane/ethyl acetate=4/1) to give 2-chloro-N-{3-[2,2,2-trifluoro-1-(tert-butoxycarbonyl-aminomethylphenyl)ethoxy]quinoxalin-2-yl}benzenesulfonamide (Compound 92) (174 mg, yield: 61%).

ESIMS m/z: 637 (M+H)$^+$; $^1$H-NMR (270 MHz, DMSO-d$_6$, δ): 1.44 (s, 9H), 3.57 (s, 3H), 4.31 (d, J=5.5 Hz, 2H), 4.84 (br s, 1H), 6.76 (q, J=6.6 Hz, 1H), 7.30-7.76 (m, 11H), 8.18 (d, J=7.0 Hz, 1H).

EXAMPLE 88

2-chloro-N-{3-{2,2,2-trifluoro-1-[6-(pyrrolidin-1-yl)-pyridin-3-yl]ethoxy}quinoxalin-2-yl}benzenesulfonamide (Compound 93)

According to Example 8, by use of 2-chloro-N-(3-chloroquinoxalin-2-yl)benzenesulfonamide (Compound AD) (70.0 mg, 0.198 mmol), Compound DH (73.0 mg, 0.296 mmol), 60% sodium hydride (in oil) (19.8 mg, 0.495 mmol) and tetrahydrofuran (1.5 mL), the mixture was stirred and reacted at 50° C. for 3.5 hours. After purification by silica gel column chromatography (hexane/ethyl acetate=5/1), slurry purification was further performed using diisopropyl ether, to give 2-chloro-N-{3-{2,2,2-trifluoro-1-[6-(pyrrolidin-1-yl)-pyridin-3-yl]ethoxy}quinoxalin-2-yl}benzenesulfonamide (Compound 93) (60.2 mg, yield: 54%).

ESIMS m/z: 564 (M+H)$^+$; $^1$H-NMR (270 MHz, DMSO-d$_6$, δ): 1.89-1.94 (m, 4H), 3.37 (br s, 4H), 6.53 (d, J=9.3 Hz, 1H), 6.88 (q, J=7.3 Hz, 1H), 7.49-7.68 (m, 7H), 8.33-8.37 (m, 1H), 8.43 (d, J=2.0 Hz, 1H).

EXAMPLE 89

N-{3-[4-fluorotetrahydropyran-4-yl(pyridin-3-yl)methoxy]-quinoxalin-2-yl}propane-1-sulfonamide (Compound 94)

According to Example 37, by use of 2-chloro-3-[4-fluorotetrahydropyran-4-yl(pyridin-3-yl)-methoxy]quinoxaline (Compound BF) (70.0 mg, 0.187 mmol), dimethyl sulfoxide (1.5 mL), Compound FS (23.0 mg, 0.187 mmol) and potassium carbonate (25.8 mg, 0.187 mmol), the mixture was stirred and reacted at 150° C. for 2 hours. After purification by preparative thin-layer chromatography (chloroform/methanol 19/1), slurry purification was further performed using diisopropyl ether, to give N-{3-[4-fluorotetrahydropyran-4-yl(pyridin-3-yl)methoxy]-quinoxalin-2-yl}propane-1-sulfonamide (Compound 94) (36.5 mg, yield: 52%).

ESIMS m/z: 461 (M+H)$^+$; $^1$H-NMR (270 MHz, DMSO-d$_6$, δ): 1.02 (t, J=7.3 Hz, 3H), 1.51-1.60 (m, 1H), 1.70-2.19 (m, 5H), 3.38-3.59 (m, 2H), 3.74-3.87 (m, 4H), 6.41 (d, J=19.2 Hz, 1H), 7.42 (dd, J=4.6, 7.9 Hz, 1H), 7.54-7.63 (m, 3H), 7.77-7.81 (m, 1H), 8.07 (d, J=7.6 Hz, 1H), 8.52 (dd, J=1.7, 4.6 Hz, 1H), 8.85 (s, 1H), 11.22 (br s, 1H).

EXAMPLE 90

2,3-dichloro-N-{3-[2,2,2-trifluoro-1-(1-methyl-1H-imidazol-2-yl)ethoxy]quinoxalin-2-yl}benzenesulfonamide (Compound 95)

Sixty percent sodium hydride (in oil) (15.5 mg, 0.387 mmol) was suspended in tetrahydrofuran (1.0 mL). To this, a tetrahydrofuran solution (1.5 mL) of Compound DI (46.5 mg, 0.258 mmol) was added under a nitrogen atmosphere at room temperature and the mixture was stirred at the same temperature for 15 minutes. To this, 2,3-dichloro-N-(3-chloroquinoxalin-2-yl)benzenesulfonamide (Compound AA) (50.0 mg, 0.129 mmol) was added and the mixture was stirred for 3.5 hours. After water was added to the reaction mixture, extraction with ethyl acetate was performed, followed by washing with brine and drying over anhydrous sodium sulfate. The solvent was evaporated off under reduced pressure, and the residue was purified by preparative thin-layer chromatography (chloroform/methanol=15/1) to give 2,3-dichloro-N-{3-[2,2,2-trifluoro-1-(1-methyl-1H-imidazol-2-yl)ethoxy]quinoxalin-2-yl}benzenesulfonamide (Compound 95) (52.0 mg, yield: 76%).

ESIMS m/z: 532 (M+H)$^+$; $^1$H-NMR (300 MHz, CDCl$_3$, δ): 3.86 (s, 3H), 6.92 (s, 1H), 7.08 (m, 2H), 7.38-7.47 (m, 4H), 7.62-7.67 (m, 2H), 8.35 (br s, 1H).

EXAMPLE 91

2,3-dichloro-N-{3-[2,2,2-trifluoro-1-(1-methyl-1H-pyrazol-4-yl)ethoxy]quinoxalin-2-yl}benzenesulfonamide (Compound 96)

According to Example 90, by use of 60% sodium hydride (in oil) (23.3 mg, 0.581 mmol), tetrahydrofuran (3.5 mL), Compound DJ (46.5 mg, 0.258 mmol) and 2,3-dichloro-N-(3-chloroquinoxalin-2-yl)benzenesulfonamide (Compound AA) (50.0 mg, 0.129 mmol), the mixture was stirred and reacted at 50° C. for 1.6 hours. Then, purification by preparative thin-layer chromatography (chloroform/methanol=20/1) was performed to give 2,3-dichloro-N-{3-[2,2,2-trifluoro-1-(1-methyl-1H-pyrazol-4-yl)ethoxy]quinoxalin-2-yl}benzenesulfonamide (Compound 96) (38.7 mg, yield: 56%).

ESIMS m/z: 534, 532 (M+H)$^+$; $^1$H-NMR (300 MHz, CDCl$_3$+CD$_3$OD, δ): 3.89 (s, 3H), 6.92 (q, J=6.8 Hz, 1H), 7.35 (s, 1H), 7.42-7.59 (m, 5H), 7.67-7.69 (m, 1H), 7.71 (dd, J=1.5, 8.1 Hz, 1H), 8.34 (dd, J=1.6, 7.9 Hz, 1H).

EXAMPLE 92

2,3-dichloro-N-{3-[2,2,2-trifluoro-1-(1-methyl-1H-imidazol-5-yl)ethoxy]quinoxalin-2-yl}benzenesulfonamide (Compound 97)

According to Example 90, by use of 60% sodium hydride (in oil) (23.3 mg, 0.581 mmol), tetrahydrofuran (3.5 mL), Compound DK (46.5 mg, 0.258 mmol) and 2,3-dichloro-N-(3-chloroquinoxalin-2-yl)benzenesulfonamide (Compound AA) (50.0 mg, 0.129 mmol), the mixture was stirred and reacted at 50° C. for 1.6 hours. Then, purification by preparative thin-layer chromatography (chloroform/methanol=15/1) was performed to give 2,3-dichloro-N-{3-[2,2,2-trifluoro-1-(1-methyl-1H-imidazol-5-yl)ethoxy]quinoxalin-2-yl}benzenesulfonamide (Compound 97) (31.3 mg, yield: 46%).

ESIMS m/z: 532, 530 (M−H)$^−$; $^1$H-NMR (270 MHz, CDCl$_3$, δ): 3.90 (s, 3H), 6.82 (m, 1H), 7.40-7.50 (m, 4H), 7.63-7.73 (m, 4H), 8.40 (br s, 1H).

EXAMPLE 93

2,3-dichloro-N-{3-[2,2,2-trifluoro-1-(thiazol-5-yl)ethoxy]-quinoxalin-2-yl}benzenesulfonamide (Compound 98)

According to Example 90, by use of 60% sodium hydride (in oil) (15.5 mg, 0.387 mmol), tetrahydrofuran (2.5 mL), Compound 2,3-dichloro-N-(3-chloroquinoxalin-2-yl)benzenesulfonamide (Compound AA) (50.0 mg, 0.129 mmol), the mixture was stirred and reacted at a temperature of room temperature to 50° C. for 1.8 hours. Then, purification by preparative thin-layer chromatography (chloroform/methanol=15/1) was performed to give 2,3-dichloro-N-{3-[2,2,2-trifluoro-1-(thiazol-5-yl)ethoxy]-quinoxalin-2-yl}benzenesulfonamide (Compound 98) (43.5 mg, yield: 63%).

ESIMS m/z: 535, 533 (M−H)$^−$; $^1$H-NMR (270 MHz, CDCl$_3$, δ): 7.19 (m, 1H), 7.40-7.50 (m, 4H), 7.67 (dd, J=1.3, 8.3 Hz, 1H), 7.69 (m, 1H), 8.19 (s, 1H), 8.38 (br s, 1H), 8.91 (s, 1H).

EXAMPLE 94

2,3-dichloro-N-{3-[2,2,2-trifluoro-1-(thiazol-2-yl)ethoxy]-quinoxalin-2-yl}benzenesulfonamide (Compound 99)

According to Example 90, by use of 60% sodium hydride (in oil) (31.0 mg, 0.774 mmol), tetrahydrofuran (4.0 mL), Compound DM (94.0 mg, 0.516 mmol) and 2,3-dichloro-N-(3-chloroquinoxalin-2-yl)benzenesulfonamide (Compound AA) (50.0 mg, 0.129 mmol), the mixture was stirred and reacted at a temperature of room temperature to 50° C. for hours. Then, purification by preparative thin-layer chromatography (chloroform/methanol=15/1) was performed to give 2,3-dichloro-N-{3-[2,2,2-trifluoro-1-(thiazol-2-yl)ethoxy]-quinoxalin-2-yl}benzenesulfonamide (Compound 99) (12.3 mg, yield: 18%).

ESIMS m/z: 535, 533 (M−H)$^−$; $^1$H-NMR (270 MHz, CDCl$_3$, δ): 7.26 (br s, 1H), 7.40-7.50 (m, 5H), 7.65-7.71 (m, 2H), 7.91 (d, J=3.0 Hz, 1H), 8.39 (br s, 1H).

EXAMPLE 95

2,3-dichloro-N-{3-[2,2,2-trifluoro-1-(thiophen-2-yl)-ethoxy]quinoxalin-2-yl}benzenesulfonamide (Compound 100)

According to Example 90, by use of 60% sodium hydride (in oil) (21.0 mg, 0.516 mmol), tetrahydrofuran (2.5 mL), Compound DN (70.0 mg, 0.387 mmol) and 2,3-dichloro-N-(3-chloroquinoxalin-2-yl)benzenesulfonamide (Compound AA) (50.0 mg, 0.129 mmol), the mixture was stirred and reacted at 50° C. for 5.3 hours. Then, purification by preparative thin-layer chromatography (chloroform/methanol=100/1) was performed to give 2,3-dichloro-N-{3-[2,2,2-trifluoro-1-(thiophen-2-yl)-ethoxy]quinoxalin-2-yl}benzenesulfonamide (Compound 100) (37.4 mg, yield: 54%).

ESIMS m/z: 536, 534 (M+H)$^+$; $^1$H-NMR (270 MHz, CDCl$_3$, δ): 7.04 (dd, J=4.0, 5.0 Hz, 1H), 7.10 (br s, 1H), 7.40-7.49 (m, 7H), 7.66 (dd, J=1.7, 8.3 Hz, 1H), 7.69-7.73 (m, 1H), 8.41 (br s, 1H).

EXAMPLE 96

2,3-dichloro-N-{3-[2,2,2-trifluoro-1-(thiophen-3-yl)-ethoxy]quinoxalin-2-yl}benzenesulfonamide (Compound 101)

According to Example 90, by use of 60% sodium hydride (in oil) (21.0 mg, 0.516 mmol), tetrahydrofuran (2.5 mL), Compound DO (70.0 mg, 0.387 mmol) and 2,3-dichloro-N-(3-chloroquinoxalin-2-yl)benzenesulfonamide (Compound AA) (50.0 mg, 0.129 mmol), the mixture was stirred and reacted at a temperature of room temperature to 50° C. for 3.8 hours. Then, purification by preparative thin-layer chromatography (chloroform/methanol=100/1) was performed to give 2,3-dichloro-N-{3-[2,2,2-trifluoro-1-(thiophen-3-yl)-ethoxy]quinoxalin-2-yl}benzenesulfonamide (Compound 101) (43.7 mg, yield: 63%).

ESIMS m/z: 534 (M+H)$^+$; $^1$H-NMR (300 MHz, CDCl$_3$, δ): 6.93 (br s, 1H), 7.29-7.48 (m, 7H), 7.63 (br s, 1H), 7.67 (dd, J=1.5, 8.1 Hz, 1H), 7.68 (m, 1H), 8.41 (br s, 1H).

EXAMPLE 97

2,3-dichloro-N-[3-(1-cyclohexyl-2,2,2-trifluoroethoxy)-quinoxalin-2-yl]benzenesulfonamide (Compound 102)

According to Example 90, by use of 60% sodium hydride (in oil) (21.0 mg, 0.516 mmol), tetrahydrofuran (2.5 mL), Compound DP (70.5 mg, 0.387 mmol) and 2,3-dichloro-N-(3-chloroquinoxalin-2-yl)benzenesulfonamide (Compound AA) (50.0 mg, 0.129 mmol), the mixture was stirred and reacted at 50° C. for 2.6 hours. Then, purification by preparative thin-layer chromatography (hexane/ethyl acetate=4/1) was performed to give 2,3-dichloro-N-[3-(1-cyclohexyl-2,2,2-trifluoroethoxy)-quinoxalin-2-yl]benzenesulfonamide (Compound 102) (43.3 mg, yield: 63%).

ESIMS m/z: 536, 534 (M+H)$^+$; $^1$H-NMR (270 MHz, CDCl$_3$, δ): 1.12-1.34 (m, 4H), 1.71-1.90 (m, 6H), 2.05 (m, 1H), 5.88 (br s, 1H), 7.41-7.50 (m, 4H), 7.65-7.70 (m, 2H), 8.10-8.43 (m, 2H).

EXAMPLE 98

2,3-dichloro-N-{3-[2,2,2-trifluoro-1-(1-methyl-1H-indol-2-yl)ethoxy]quinoxalin-2-yl}benzenesulfonamide (Compound 103)

According to Example 90, by use of 60% sodium hydride (in oil) (15.0 mg, 0.387 mmol), tetrahydrofuran (2.5 mL), Compound DQ (59.0 mg, 0.258 mmol) and 2,3-dichloro-N-(3-chloroquinoxalin-2-yl)benzenesulfonamide (Compound AA) (50.0 mg, 0.129 mmol), the mixture was stirred and reacted at 50° C. for 2.3 hours. Then, purification by preparative thin-layer chromatography (chloroform/methanol=15/1) was performed to give 2,3-dichloro-N-{3-[2,2,2-trifluoro-1-(1-methyl-1H-indol-2-yl)ethoxy]quinoxalin-2-yl}benzenesulfonamide (Compound 103) (60.7 mg, yield: 81%).

ESIMS m/z: 581, 579 (M−H)$^-$; $^1$H-NMR (270 MHz, CDCl$_3$, δ): 3.95 (s, 3H), 6.87 (br s, 1H), 7.00 (m, 1H), 7.10 (dd, J=6.9, 7.3 Hz, 1H), 7.26-7.45 (m, 7H), 7.60-7.66 (m, 3H), 8.35 (br s, 1H).

EXAMPLE 99

2-chloro-N-{3-[2,2,2-trifluoro-1-(benzofuran-2-yl)ethoxy]-quinoxalin-2-yl}benzenesulfonamide (Compound 104)

According to Example 90, by use of 60% sodium hydride (in oil) (25.5 mg, 0.635 mmol), tetrahydrofuran (3.5 mL), Compound DR (91.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 3.2 hours. Then, purification by preparative thin-layer chromatography (chloroform/methanol=30/1) was performed to give 2-chloro-N-{3-[2,2,2-trifluoro-1-(benzofuran-2-yl)ethoxy]-quinoxalin-2-yl}benzenesulfonamide (Compound 104) (38.4 mg, yield: 51%).

ESIMS m/z: 536, 534 (M+H)$^+$; $^1$H-NMR (270 MHz, CDCl$_3$, δ): 7.08 (m, 2H), 7.23-7.61 (m, 10H), 7.71 (m, 1H), 8.30-8.49 (m, 2H).

EXAMPLE 100

2-[3-(2-chlorophenylsulfonamide)quinoxalin-2-yloxy]-2-phenylacetic acid (Compound 105)

According to Example 90, by use of 60% sodium hydride (in oil) (45.0 mg, 1.13 mmol), tetrahydrofuran (6.0 mL), 2-hydroxy-2-phenylacetic acid (93.3 mg, 0.610 mmol) and 2-chloro-N-(3-chloroquinoxalin-2-yl)benzenesulfonamide (Compound AD) (80.0 mg, 0.226 mmol), the mixture was stirred and reacted at 50° C. for 3.7 hours. Then, purification by preparative thin-layer chromatography (chloroform/methanol=5/1) was performed to give 2-[3-(2-chlorophenylsulfonamide)quinoxalin-2-yloxy]-2-phenylacetic acid (Compound 105) (79.4 mg, yield: 75%).

ESIMS m/z: 472, 470 (M+H)$^+$; $^1$H-NMR (270 MHz, CDCl$_3$, δ): 6.53 (s, 1H), 7.15-7.63 (m, 12H), 8.32 (br s, 1H), 8.98 (br s, 1H).

EXAMPLE 101

2-chloro-N-{3-[2,2,2-trifluoro-1-(2,4-dimethylthiazol-5-yl)ethoxy]quinoxalin-2-yl}benzenesulfonamide (Compound 106)

According to Example 90, by use of 60% sodium hydride (in oil) (23 mg, 0.564 mmol), tetrahydrofuran (2.5 mL), Compound DS (89.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.7 hours. Then, purification by preparative thin-layer chromatography (chloroform/methanol=30/1) was performed to give 2-chloro-N-{3-[2,2,2-trifluoro-1-(2,4-dimethylthiazol-5-yl)ethoxy]quinoxalin-2-yl}benzenesulfonamide (Compound 106) (47.4 mg, yield: 64%).

ESIMS m/z: 531, 529 (M+H)$^+$; $^1$H-NMR (300 MHz, CDCl$_3$, δ): 2.62 (s, 3H), 2.65 (s, 3H), 7.00 (m, 1H), 7.40-7.63 (m, 7H), 8.25 (br s, 1H), 8.50 (br s, 1H).

EXAMPLE 102

2-chloro-N-{3-[2,2,2-trifluoro-1-(4-methylthiazol-5-yl)-ethoxy]quinoxalin-2-yl}benzenesulfonamide (Compound 107)

According to Example 90, by use of 60% sodium hydride (in oil) (23 mg, 0.564 mmol), tetrahydrofuran (2.5 mL), Compound DT (83.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.7 hours. Then, purification by preparative thin-layer chromatography (chloroform/methanol=30/1) was performed to give 2-chloro-N-{3-[2,2,2-trifluoro-1-(4-methylthiazol-5-yl)-ethoxy]quinoxalin-2-yl}benzenesulfonamide (Compound 107) (41.6 mg, yield: 57%).

ESIMS m/z: 517, 515 (M+H)$^+$; $^1$H-NMR (270 MHz, CDCl$_3$, δ): 2.72 (s, 3H), 7.08 (m, 1H), 7.46-7.51 (m, 7H), 7.66 (m, 1H), 8.45 (br s, 1H), 8.79 (s, 1H).

EXAMPLE 103

2-chloro-N-{3-[2,2,2-trifluoro-1-(1-ethyl-1H-imidazol-5-yl)ethoxy]quinoxalin-2-yl}benzenesulfonamide (Compound 108)

According to Example 90, by use of 60% sodium hydride (in oil) (23 mg, 0.564 mmol), tetrahydrofuran (3.0 mL), Compound DU (84.7 mg, 0.436 mmol) and 2-chloro-N-(3-chloroquinoxalin-2-yl)benzenesulfonamide (Compound AD) (50.0 mg, 0.141 mmol), the mixture was stirred and reacted at 50° C. for 1.8 hours. Then, purification by preparative thin-layer chromatography (chloroform/methanol=15/1) was performed to give 2-chloro-N-{3-[2,2,2-trifluoro-1-(1-ethyl-1H-imidazol-5-yl)ethoxy]quinoxalin-2-yl}benzenesulfonamide (Compound 108) (51.0 mg, yield: 71%).

ESIMS m/z: 514, 512 (M+H)$^+$; $^1$H-NMR (270 MHz, CDCl$_3$+CD$_3$OD, δ): 1.51 (t, J=7.3 Hz, 3H), 4.19-4.39 (m, 2H), 6.92 (q, J=6.6 Hz, 1H), 7.36-7.67 (m, 9H), 8.41 (m, 1H).

EXAMPLE 104

2-chloro-N-{3-[2,2,2-trifluoro-1-(furan-2-yl)ethoxy]-quinoxalin-2-yl}benzenesulfonamide (Compound 109)

According to Example 90, by use of 60% sodium hydride (in oil) (23 mg, 0.564 mmol), tetrahydrofuran (2.5 mL), 2,2,2-trifluoro-1-(furan-2-yl)ethanol (70.0 mg, 0.423 mmol) and 2-chloro-N-(3-chloroquinoxalin-2-yl)benzenesulfonamide (Compound AD) (50.0 mg, 0.141 mmol), the mixture was stirred and reacted at room temperature for 2.0 hours. Then, purification by preparative thin-layer chromatography (chloroform/methanol=40/1) was performed to give 2-chloro-N-{3-[2,2,2-trifluoro-1-(furan-2-yl)ethoxy]-quinoxalin-2-yl}benzenesulfonamide (Compound 109) (43.3 mg, yield: 63%).

ESIMS m/z: 486, 484 (M+H)$^+$; $^1$H-NMR (300 MHz, CDCl$_3$, δ): 6.44 (s, 1H), 6.72 (d, J=3.3 Hz, 1H), 7.01 (m, 1H), 7.43-7.51 (m, 7H), 7.71 (m, 1H), 8.20 (m, 1H), 8.48 (br s, 1H).

EXAMPLE 105

2-chloro-N-{3-[2,2,2-trifluoro-1-(2-chlorothiazol-5-yl)-ethoxy]quinoxalin-2-yl}benzenesulfonamide (Compound 110)

According to Example 90, by use of 60% sodium hydride (in oil) (23 mg, 0.564 mmol), tetrahydrofuran (2.5 mL), Compound DV (92.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2.0 hours. Then, purification by preparative thin-layer chromatography (chloroform/methanol=40/1) was performed to give 2-chloro-N-{3-[2,2,2-trifluoro-1-(2-chlorothiazol-5-yl)-ethoxy]quinoxalin-2-yl}benzenesulfonamide (Compound 110) (21.1 mg, yield: 28%).

ESIMS m/z: 537, 535 (M+H)$^+$; $^1$H-NMR (270 MHz, CDCl$_3$, δ): 7.02 (br s, 1H), 7.49-7.52 (m, 7H), 7.70 (m, 1H), 7.72 (s, 1H), 8.45 (br s, 1H).

EXAMPLE 106

2-chloro-N-{3-[2,2,2-trifluoro-1-(1-cyclopropylmethyl-1H-imidazol-5-yl)ethoxy]quinoxalin-2-yl}benzenesulfonamide (Compound 111)

According to Example 90, by use of 60% sodium hydride (in oil) (23 mg, 0.564 mmol), tetrahydrofuran (2.5 mL), Compound DW (93.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2.0 hours. Then, purification by preparative thin-layer chromatography (chloroform/methanol=15/1) was performed to give 2-chloro-N-{3-[2,2,2-trifluoro-1-(1-cyclopropylmethyl-1H-imidazol-5-yl)ethoxy]quinoxalin-2-yl}benzenesulfonamide (Compound 111) (58.6 mg, yield: 77%).

ESIMS m/z: 540, 538 (M+H)$^+$; $^1$H-NMR (270 MHz, CDCl$_3$, δ): 0.36-0.45 (m, 2H), 0.69 (m, 2H), 1.27 (m, 1H), 3.98 (dd, J=6.9, 14.2 Hz, 1H), 4.04 (dd, J=7.3, 14.2 Hz, 1H), 6.97 (q, J=6.6 Hz, 1H), 7.29 (s, 1H), 7.41-7.59 (m, 7H), 7.62 (m, 1H), 7.77 (s, 1H), 8.45 (m, 1H).

EXAMPLE 107

2-chloro-N-{3-[2,2,2-trifluoro-1-(1-cyclopropylmethyl-1H-imidazol-4-yl)ethoxy]quinoxalin-2-yl}benzenesulfonamide (Compound 112)

According to Example 90, by use of 60% sodium hydride (in oil) (21.0 mg, 0.527 mmol), tetrahydrofuran (3.0 mL), Compound DX (85.2 mg, 0.386 mmol) and 2-chloro-N-(3-chloroquinoxalin-2-yl)benzenesulfonamide (Compound AD) (50.0 mg, 0.141 mmol), the mixture was stirred and reacted at 50° C. for 2.2 hours. Then, purification by preparative thin-layer chromatography (chloroform/methanol=15/1) was performed to give 2-chloro-N-{3-[2,2,2-trifluoro-1-(1-cyclopropylmethyl-1H-imidazol-4-yl)ethoxy]quinoxalin-2-yl}benzenesulfonamide (Compound 112) (63.3 mg, yield: 83%).

ESIMS m/z: 540, 538 (M+H)$^+$; $^1$H-NMR (270 MHz, CDCl$_3$, δ): 0.37 (m, 2H), 0.71 (m, 2H), 1.25 (m, 1H), 3.79 (d, J=6.9 Hz, 2H), 7.07 (q, J=6.8 Hz, 1H), 7.30 (s, 1H), 7.43-7.49 (m, 7H), 7.57 (s, 1H), 7.71 (m, 1H), 8.48 (br s, 1H).

EXAMPLE 108

2-chloro-N-{3-[2,2,2-trifluoro-1-(thiazol-5-yl)ethoxy]-quinoxalin-2-yl}benzenesulfonamide (Compound 113)

According to Example 90, by use of 60% sodium hydride (in oil) (23 mg, 0.564 mmol), tetrahydrofuran (2.5 mL), Compound DL (77.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2.0 hours. Then, purification by preparative thin-layer chromatography (chloroform/methanol=15/1) was performed to give 2-chloro-N-{3-[2,2,2-trifluoro-1-(thiazol-5-yl)ethoxy]-quinoxalin-2-yl}benzenesulfonamide (Compound 113) (44.0 mg, yield: 62%).

ESIMS m/z: 503, 501 (M+H)$^+$; $^1$H-NMR (270 MHz, CDCl$_3$, δ): 7.21 (br s, 1H), 7.47-7.51 (m, 7H), 7.70 (m, 1H), 8.19 (m, 1H), 8.46 (br s, 1H), 8.90 (s, 1H).

EXAMPLE 109

2-chloro-N-{3-[2,2,2-trifluoro-1-(2-morpholinothiazol-5-yl)ethoxy]quinoxalin-2-yl}benzenesulfonamide (Compound 114)

According to Example 90, by use of 60% sodium hydride (in oil) (17.0 mg, 0.417 mmol), tetrahydrofuran (3.0 mL), Compound DY (79.8 mg, 0.298 mmol) and 2-chloro-N-(3-chloroquinoxalin-2-yl)benzenesulfonamide (Compound AD) (42.0 mg, 0.119 mmol), the mixture was stirred and reacted at room temperature for 3.0 hours. Then, purification by preparative thin-layer chromatography (chloroform/methanol=15/1, 50/1) was performed to give 2-chloro-N-{3-[2,2,2-trifluoro-1-(2-morpholinothiazol-5-yl)ethoxy]quinoxalin-2-yl}benzenesulfonamide (Compound 114) (7.0 mg, yield: 10%).

ESIMS m/z: 586, 584 (M–H)$^-$; $^1$H-NMR (270 MHz, CDCl$_3$, δ): 3.44 (m, 4H), 3.79 (m, 4H), 6.77 (m, 1H), 7.24 (m, 4H), 8.48 (br s, 1H), 8.88 (br s, 1H).

EXAMPLE 110

2-chloro-N-{3-[2,2,2-trifluoro-1-(1,2-dimethyl-1H-imidazol-5-yl)ethoxy]quinoxalin-2-yl}benzenesulfonamide (Compound 115)

According to Example 90, by use of 60% sodium hydride (in oil) (23 mg, 0.564 mmol), tetrahydrofuran (3.5 mL), Compound DZ (82.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2.5 hours. Then, purification by preparative thin-layer chromatography (chloroform/methanol=15/1) was performed to give 2-chloro-N-{3-[2,2,2-trifluoro-1-(1,2-dimethyl-1H-imidazol-5-yl)ethoxy]quinoxalin-2-yl}benzenesulfonamide (Compound 115) (53.8 mg, yield: 75%).

ESIMS m/z: 514, 512 (M+H)⁺; ¹H-NMR (300 MHz, CDCl₃, δ): 2.38 (s, 3H), 3.72 (s, 3H), 6.88 (q, J=6.8 Hz, 1H), 7.20 (s, 1H), 7.45-7.57 (m, 7H), 7.66 (m, 1H), 8.41 (m, 1H).

EXAMPLE 111

2-chloro-N-{3-[2,2,2-trifluoro-1-(tetrahydro-2H-pyran-4-yl)ethoxy]quinoxalin-2-yl}benzenesulfonamide (Compound 116)

According to Example 90, by use of 60% sodium hydride (in oil) (28.0 mg, 0.705 mmol), tetrahydrofuran (3.5 mL), Compound EA (104 mg, 0.564 mmol) and 2-chloro-N-(3-chloroquinoxalin-2-yl)benzenesulfonamide (Compound AD) (50.0 mg, 0.141 mmol), the mixture was stirred and reacted at 50° C. for 1.2 hours. Then, purification by preparative thin-layer chromatography (chloroform/methanol=20/1) was performed to give 2-chloro-N-{3-[2,2,2-trifluoro-1-(tetrahydro-2H-pyran-4-yl)ethoxy]quinoxalin-2-yl}benzenesulfonamide (Compound 116) (54.3 mg, yield: 77%).

ESIMS m/z: 504, 502 (M+H)⁺; ¹H-NMR (270 MHz, CDCl₃, δ): 1.60-1.81 (m, 4H), 2.33 (m, 1H), 3.43 (m, 2H), 4.00 (m, 2H), 5.94 (br s, 1H), 7.49-7.71 (m, 7H), 8.25 (br s, 1H), 8.52 (br s, 1H).

EXAMPLE 112

2-chloro-N-[3-(1-cyclopropyl-2,2,2-trifluoroethoxy)-quinoxalin-2-yl]benzenesulfonamide (Compound 117)

According to Example 90, by use of 60% sodium hydride (in oil) (28.0 mg, 0.705 mmol), tetrahydrofuran (2.5 mL), Compound EB (79.0 mg, 0.564 mmol) and 2-chloro-N-(3-chloroquinoxalin-2-yl)benzenesulfonamide (Compound AD) (50.0 mg, 0.141 mmol), the mixture was stirred and reacted at 500 for 1.2 hours. Then, purification by preparative thin-layer chromatography (hexane/ethyl acetate=4/1) was performed to give 2-chloro-N-[3-(1-cyclopropyl-2,2,2-trifluoroethoxy)-quinoxalin-2-yl]benzenesulfonamide (Compound 117) (30.7 mg, yield: 48%).

ESIMS m/z: 460, 458 (M+H)⁺; ¹H-NMR (270 MHz, CDCl₃, δ): 0.61-0.67 (m, 4H), 1.38 (m, 1H), 5.39 (m, 1H), 7.45-7.66 (m, 7H), 8.21 (br s, 1H), 8.52 (br s, 1H).

EXAMPLE 113

2-chloro-N-[3-(1-cyclohexyl-2,2,2-trifluoroethoxy)-quinoxalin-2-yl]benzenesulfonamide (Compound 118)

According to Example 90, by use of 60% sodium hydride (in oil) (28.0 mg, 0.692 mmol), tetrahydrofuran (3.0 mL), Compound DP (94.5 mg, 0.519 mmol) and 2-chloro-N-(3-chloroquinoxalin-2-yl)benzenesulfonamide (Compound AD) (61.3 mg, 0.173 mmol), the mixture was stirred and reacted at 50° C. for 1.5 hours. Then, purification by preparative thin-layer chromatography (hexane/ethyl acetate=4/1) was performed to give 2-chloro-N-[3-(1-cyclohexyl-2,2,2-trifluoroethoxy)-quinoxalin-2-yl]benzenesulfonamide (Compound 118) (55.2 mg, yield: 64%).

ESIMS m/z: 502, 500 (M+H)⁺; ¹H-NMR (300 MHz, CDCl₃, δ): 1.23-1.29 (m, 4H), 1.71-2.05 (m, 6H), 2.34 (m, 1H), 5.91 (br s, 1H), 7.46-7.59 (m, 6H), 7.68 (m, 1H), 8.19 (br s, 1H), 8.52 (br s, 1H).

EXAMPLE 114

3,5-dimethyl-N-{3-[2,2,2-trifluoro-1-(tetrahydro-2H-pyran-4-yl)ethoxy]quinoxalin-2-yl}isoxazole-4-sulfonamide (Compound 119)

According to Example 90, by use of 60% sodium hydride (in oil) (16.0 mg, 0.396 mmol), tetrahydrofuran (3.0 mL), Compound DP (52.0 mg, 0.283 mmol) and N-(3-chloroquinoxalin-2-yl)-3,5-dimethylisoxazole-4-sulfonamide (Compound AG) (38.0 mg, 0.113 mmol), the mixture was stirred and reacted at 50° C. for 2 hours. Then, purification by preparative thin-layer chromatography (chloroform/methanol 20/1) was performed to give 3,5-dimethyl-N-{3-[2,2,2-trifluoro-1-(tetrahydro-2H-pyran-4-yl)ethoxy]quinoxalin-2-yl}isoxazole-4-sulfonamide (Compound 119) (29.7 mg, yield: 54%).

ESIMS m/z: 485 (M–H)⁻; ¹H-NMR (270 MHz, CDCl₃, δ): 1.52-1.81 (m, 4H), 2.35 (m, 1H), 2.52 (s, 3H), 2.91 (br s, 3H), 3.44 (m, 2H), 4.01 (m, 2H), 5.95 (m, 1H), 7.56 (m, 2H), 7.72 (m, 2H), 8.12 (br s, 1H).

EXAMPLE 115

5-chloro-1,3-dimethyl-N-{3-[2,2,2-trifluoro-1-(tetrahydro-2H-pyran-4-yl)ethoxy]quinoxalin-2-yl}-1H-pyrazole-4-sulfonamide (Compound 120)

According to Example 90, by use of 60% sodium hydride (in oil) (16.0 mg, 0.402 mmol), tetrahydrofuran (3.5 mL), Compound DP (52.0 mg, 0.283 mmol) and 5-chloro-N-(3-chloroquinoxalin-2-yl)-1,3-dimethyl-1H-pyrazole-4-sulfonamide (Compound AF) (42.0 mg, 0.113 mmol), the mixture was stirred and reacted at 50° C. for 2 hours. Then, purification by preparative thin-layer chromatography (chloroform/methanol=20/1) was performed to give 5-chloro-1,3-dimethyl-N-{3-[2,2,2-trifluoro-1-(tetrahydro-2H-pyran-4-yl)ethoxy]quinoxalin-2-yl}-1H-pyrazole-4-sulfonamide (Compound 120) (35.6 mg, yield: 61%).

ESIMS m/z: 522, 520 (M+H)⁺; ¹H-NMR (270 MHz, CDCl₃, δ): 1.55-1.76 (m, 4H), 2.34 (m, 1H), 2.68 (s, 3H), 3.47 (m, 2H), 3.77 (s, 3H), 4.00 (m, 2H), 5.96 (m, 1H), 7.52-7.56 (m, 2H), 7.70-7.75 (m, 2H), 8.19 (br s, 1H).

EXAMPLE 116

2-chloro-N-{3-[2,2,2-trifluoro-1-(4-methyltetrahydro-2H-pyran-4-yl]ethoxy}quinoxalin-2-yl)benzenesulfonamide (Compound 121)

According to Example 90, by use of 60% sodium hydride (in oil) (46.3 mg, 1.16 mmol), tetrahydrofuran (4.6 mL), Compound EC (119 mg, 0.602 mmol) and 2-chloro-N-(3-chloroquinoxalin-2-yl)benzenesulfonamide (Compound AD) (68.0 mg, 0.192 mmol), the mixture was stirred and reacted from 50° C. to reflux temperature for 6 hours. Then, purification by preparative thin-layer chromatography (chloroform/methanol=20/1, hexane/ethyl acetate=3/1) was performed to give 2-chloro-N-{3-[2,2,2-trifluoro-1-(4-methyltetrahydro-2H-pyran-4-yl)ethoxy]quinoxalin-2-yl}benzenesulfonamide (Compound 121) (5.5 mg, yield: 6%).

ESIMS m/z: 518, 516 (M+H)⁺; ¹H-NMR (270 MHz, CDCl₃, δ): 1.37 (br s, 3H), 1.59 (m, 2H), 1.76-1.95 (m, 2H), 4.11 (m, 2H), 4.14 (m, 2H), 6.00 (br s, 1H), 7.45-7.50 (m, 6H), 7.70 (m, 1H), 8.15-8.50 (m, 2H).

EXAMPLE 117

2-[3-(2-chlorophenylsulfonamide)quinoxalin-2-yloxy]-N,N-diethyl-2-phenylacetamide (Compound 122)

According to Example 90, by use of 60% sodium hydride (in oil) (23.0 mg, 0.564 mmol), tetrahydrofuran (2.5 mL), Compound ED (88.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2.8 hours. Then, purification by preparative thin-layer chromatography (chloroform/methanol=20/1) was performed to give 2-[3-(2-chlorophenylsulfonamide)quinoxalin-2-yloxy]-N,N-diethyl-2-phenylacetamide (Compound 122) (46.1 mg, yield: 62%).

ESIMS m/z: 527, 525 (M+H)$^+$; $^1$H-NMR (270 MHz, CDCl$_3$, δ): 1.10 (t, J=6.9 Hz, 3H), 1.25 (t, J=7.1 Hz, 3H), 3.27-3.58 (m, 4H), 6.70 (s, 1H), 7.29-7.61 (m, 12H), 8.48 (br s, 1H), 8.98 (br s, 1H).

EXAMPLE 118

2-chloro-N-[3-(2-morpholino-2-oxy-1-phenylethoxy)-quinoxalin-2-yl]benzenesulfonamide (Compound 123)

2-[3-(2-Chlorophenylsulfonamide)quinoxalin-2-yloxy]-2-phenylacetic acid (Compound 105) (29.1 mg, 0.0619 mmol) obtained in Example 100 was dissolved in tetrahydrofuran (1.75 mL). To this, 1-ethyl-3-(3-dimethylaminopropyl)carbodiimide hydrochloride (24.0 mg, 0.124 mmol), 1-hydroxybenzotriazole monohydrate (4.3 mg, 0.031 mmol) and N,N-dimethylaminopyridine (DMAP) (3.8 mg, 0.031 mmol) were added and the mixture was stirred at 0° C. for 15 minutes. To this, N,N-dimethylformamide (0.8 mL), 1-ethyl-3-(3-dimethylaminopropyl)carbodiimide hydrochloride (24.0 mg, 0.124 mmol), 1-hydroxybenzotriazole monohydrate (4.3 mg, 0.031 mmol), N,N-dimethylaminopyridine (3.8 mg, 0.031 mmol) and morpholine (0.0324 mL, 0.371 mmol) were further added and the mixture was stirred at room temperature for 18.7 hours. After water and 1 mol/L hydrochloric acid were added to the reaction mixture, extraction with ethyl acetate was performed, followed by washing with brine and drying over anhydrous sodium sulfate. The solvent was evaporated off under reduced pressure, and the residue was purified by preparative thin-layer chromatography (chloroform/methanol=50/1) to give 2-chloro-N-[3-(2-morpholino-2-oxy-1-phenylethoxy)-quinoxalin-2-yl]benzenesulfonamide (Compound 123) (9.1 mg, yield: 27%).

ESIMS m/z: 541, 539 (M+H)$^+$; $^1$H-NMR (300 MHz, CDCl$_3$, δ): 3.64 (m, 8H), 6.76 (s, 1H), 7.41-7.65 (m, 13H), 8.48 (br s, 1H).

EXAMPLE 119

2-[3-(2-chlorophenylsulfonamide)quinoxalin-2-yloxy]-2-phenylacetamide (Compound 124)

According to Example 90, by use of 60% sodium hydride (in oil) (16.9 mg, 0.423 mmol), tetrahydrofuran (2.5 mL), 2-hydroxy-2-phenylacetamide (42.6 mg, 0.282 mmol) and 2-chloro-N-(3-chloroquinoxalin-2-yl)benzenesulfonamide (Compound AD) (50.0 mg, 0.141 mmol), the mixture was stirred and reacted at 50° C. for 2.5 hours. Then, purification by preparative thin-layer chromatography (chloroform/methanol=15/1) was performed to give 2-[3-(2-chlorophenylsulfonamide)quinoxalin-2-yloxy]-2-phenylacetamide (Compound 124) (43.0 mg, yield: 65%).

ESIMS m/z: 469, 467 (M+H)$^+$; $^1$H-NMR (300 MHz, CDCl$_3$, δ): 3.78 (br s, 2H), 6.74 (br s, 1H), 7.32-7.52 (m, 12H), 7.64 (br d, J=6.6 Hz, 2H), 8.44 (br s, 1H).

EXAMPLE 120

2-[3-(2-chlorophenylsulfonamide)quinoxalin-2-yloxy]-N-ethyl-2-phenylacetamide (Compound 125)

According to Example 90, by use of 60% sodium hydride (in oil) (23.0 mg, 0.564 mmol), tetrahydrofuran (2.5 mL), Compound EF (76.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 3.2 hours. Then, purification by preparative thin-layer chromatography (chloroform/methanol=20/1) was performed to give 2-[3-(2-chlorophenylsulfonamide)quinoxalin-2-yloxy]-N-ethyl-2-phenylacetamide (Compound 125) (45.2 mg, yield: 65%).

ESIMS m/z: 497, 495 (M−H)$^−$; $^1$H-NMR (270 MHz, CDCl$_3$, δ): 1.03 (t, J=7.3 Hz, 3H), 3.23-3.29 (m, 2H), 6.66 (s, 1H), 7.05 (br s, 1H), 7.26-7.51 (m, 10H), 7.57 (m, 2H), 7.64 (m, 1H), 8.38 (br s, 1H).

EXAMPLE 121

2-chloro-N-{3-[2,2,2-trifluoro-1-(2-bromothiazol-5-yl)-ethoxy]quinoxalin-2-yl}benzenesulfonamide (Compound 126)

According to Example 90, by use of 60% sodium hydride (in oil) (42.3 mg, 1.06 mmol), tetrahydrofuran (7.5 mL), Compound EG (166 mg, 0.635 mmol) and 2-chloro-N-(3-chloroquinoxalin-2-yl)benzenesulfonamide (Compound AD) (150.0 mg, 0.423 mmol), the mixture was stirred and reacted at 50° C. for 3 hours. Then, purification by preparative thin-layer chromatography (chloroform/methanol=50/1) was performed to give 2-chloro-N-{3-[2,2,2-trifluoro-1-(2-bromothiazol-5-yl)-ethoxy]quinoxalin-2-yl}benzenesulfonamide (Compound 126) (83.3 mg, yield: 34%).

ESIMS m/z: 583, 581, 579 (M+H)$^+$: $^1$H-NMR (300 MHz, CDCl$_3$, δ): 7.06 (br s, 1H), 7.30-7.62 (m, 7H), 7.69 (m, 1H), 7.85 (s, 1H), 8.45 (br s, 1H).

EXAMPLE 122

2-chloro-N-{3-[2,2,2-trifluoro-1-(1-methyl-1H-indol-2-yl)-ethoxy]quinoxalin-2-yl}benzenesulfonamide (Compound 127)

According to Example 90, by use of 60% sodium hydride (in oil) (17.0 mg, 0.423 mmol), tetrahydrofuran (2.5 mL), Compound DQ (65.0 mg, 0.282 mmol) and 2-chloro-N-(3-chloroquinoxalin-2-yl)benzenesulfonamide (Compound AD) (50.0 mg, 0.141 mmol), the mixture was stirred and reacted at 50° C. for 3.3 hours. Then, purification by preparative thin-layer chromatography (chloroform/methanol=40/1) was performed to give 2-chloro-N-{3-[2,2,2-trifluoro-1-(1-methyl-1H-indol-2-yl)-ethoxy]quinoxalin-2-yl}benzenesulfonamide (Compound 127) (65.5 mg, yield: 85%).

ESIMS m/z: 547, 545 (M−H)$^−$; $^1$H-NMR (270 MHz, CDCl$_3$+CD$_3$OD, δ): 3.98 (s, 3H), 6.89 (br s, 1H), 7.05 (br s,

1H), 7.11 (ddd, J=0.7, 6.9, 7.6 Hz, 1H), 7.27 (ddd, J=1.2, 7.1, 8.3 Hz, 1H), 7.36 (m, 1H), 7.44-7.52 (m, 7H), 7.62 (m, 2H), 8.43 (br s, 1H).

EXAMPLE 123

3,5-dimethyl-N-{3-[2,2,2-trifluoro-1-(1-methyl-1H-indol-2-yl)ethoxy]quinoxalin-2-yl}isoxazole-4-sulfonamide (Compound 128)

According to Example 90, by use of 60% sodium hydride (in oil) (18.0 mg, 0.444 mmol), tetrahydrofuran (2.5 mL), Compound DQ (68.0 mg, 0.296 mmol) and N-(3-chloroquinoxalin-2-yl)-3,5-dimethylisoxazole-4-sulfonamide (Compound AG) (50.0 mg, 0.148 mmol), the mixture was stirred and reacted at 50° C. for 1.7 hours. Then, purification by preparative thin-layer chromatography (chloroform/methanol=20/1) was performed to give 3,5-dimethyl-N-{3-[2,2,2-trifluoro-1-(1-methyl-1H-indol-2-yl)ethoxy]quinoxalin-2-yl}isoxazole-4-sulfonamide (Compound 128) (46.6 mg, yield: 59%).

ESIMS m/z: 530 (M−H)−; $^1$H-NMR (270 MHz, CDCl$_3$+CD$_3$OD, δ): 2.54 (s, 3H), 2.87 (s, 3H), 4.01 (s, 3H), 6.90 (br s, 1H), 7.12 (dd, J=6.9, 6.9 Hz, 1H), 7.14 (br s, 1H), 7.28 (dd, J=6.9, 7.3 Hz, 1H), 7.38 (m, 1H), 7.53-7.67 (m, 5H).

EXAMPLE 124

5-chloro-1,3-dimethyl-N-{3-[2,2,2-trifluoro-1-(1-methyl-1H-indol-2-yl)ethoxy]quinoxalin-2-yl}-1H-pyrazole-4-sulfonamide (Compound 129)

According to Example 90, by use of 60% sodium hydride (in oil) (16.0 mg, 0.402 mmol), tetrahydrofuran (2.5 mL), Compound DQ (52.0 mg, 0.268 mmol) and 5-chloro-N-(3-chloroquinoxalin-2-yl)-1,3-dimethyl-1H-pyrazole-4-sulfonamide (Compound AF) (50.0 mg, 0.134 mmol), the mixture was stirred and reacted at 50° C. for 1.5 hours. Then, purification by preparative thin-layer chromatography (chloroform/methanol=100/1) was performed to give 5-chloro-1,3-dimethyl-N-{3-[2,2,2-trifluoro-1-(1-methyl-1H-indol-2-yl)ethoxy]quinoxalin-2-yl}-1H-pyrazole-4-sulfonamide (Compound 129) (53.2 mg, yield: 70%).

ESIMS m/z: 565, 563 (M−H)−; $^1$H-NMR (270 MHz, CDCl$_3$, δ): 2.66 (s, 3H), 3.73 (s, 3H), 3.99 (s, 3H), 6.89 (s, 1H), 7.05 (m, 1H), 7.11 (dd, J=6.9, 7.9 Hz, 1H), 7.27 (dd, J=6.9, 7.9 Hz, 1H), 7.35 (d, J=8.3 Hz, 1H), 7.50-7.73 (m, 5H), 8.31 (br s, 1H).

EXAMPLE 125

5-chloro-1,3-dimethyl-N-{3-[2,2,2-trifluoro-1-(tetrahydro-2H-thiopyran-4-yl)ethoxy]quinoxalin-2-yl}-1H-pyrazole-4-sulfonamide (Compound 130)

According to Example 90, by use of 60% sodium hydride (in oil) (21.0 mg, 0.536 mmol), tetrahydrofuran (2.5 mL), Compound EH (80.5 mg, 0.402 mmol) and 5-chloro-N-(3-chloroquinoxalin-2-yl)-1,3-dimethyl-1H-pyrazole-4-sulfonamide (Compound AF) (50.0 mg, 0.134 mmol), the mixture was stirred and reacted at 50° C. for 2.2 hours. Then, purification by preparative thin-layer chromatography (hexane/ethyl acetate=4/1 to 3/1) was performed to give 5-chloro-1,3-dimethyl-N-{3-[2,2,2-trifluoro-1-(tetrahydro-2H-thiopyran-4-yl)ethoxy]quinoxalin-2-yl}-1H-pyrazole-4-sulfonamide (Compound 130) (35.3 mg, yield: 49%).

ESIMS m/z: 538, 536 (M+H)+; $^1$H-NMR (270 MHz, CDCl$_3$, δ): 1.66-1.75 (m, 2H), 2.10-2.24 (m, 3H), 2.59-2.78 (m, 7H), 3.77 (s, 3H), 5.95 (m, 1H), 7.54 (m, 2H), 7.71 (m, 2H), 8.17 (br, 1H).

EXAMPLE 126

3,5-dimethyl-N-{3-[2,2,2-trifluoro-1-(tetrahydro-2H-thiopyran-4-yl)ethoxy]quinoxalin-2-yl}isoxazole-4-sulfonamide (Compound 131)

According to Example 90, by use of 60% sodium hydride (in oil) (24.0 mg, 0.592 mmol), tetrahydrofuran (2.5 mL), Compound EH (89.0 mg, 0.444 mmol) and N-(3-chloroquinoxalin-2-yl)-3,5-dimethylisoxazole-4-sulfonamide (Compound AG) (50.0 mg, 0.148 mmol), the mixture was stirred and reacted at 50° C. for 2.5 hours. Then, purification by preparative thin-layer chromatography (hexane/ethyl acetate=4/1) was performed to give 3,5-dimethyl-N-{3-[2,2,2-trifluoro-1-(tetrahydro-2H-thiopyran-4-yl)ethoxy]quinoxalin-2-yl}isoxazole-4-sulfonamide (Compound 131) (39.9 mg, yield: 54%).

ESIMS m/z: 503 (M+H)+; $^1$H-NMR (270 MHz, CDCl$_3$, δ): 1.62-1.75 (m, 2H), 2.15-2.24 (m, 3H), 2.52 (s, 3H), 2.63-2.78 (m, 4H), 2.90 (s, 3H), 5.93 (m, 1H), 7.55 (m, 2H), 7.65 (br s, 1H), 7.73 (m, 2H).

EXAMPLE 127

5-chloro-1,3-dimethyl-N-{3-[2,2,2-trifluoro-1-(tetrahydro-2H-thiopyran-1,1-dioxide-4-yl)ethoxy]quinoxalin-2-yl}-1H-pyrazole-4-sulfonamide (Compound 132)

5-Chloro-1,3-dimethyl-N-{3-[2,2,2-trifluoro-1-(tetrahydro-2H-thiopyran-4-yl)ethoxy]quinoxalin-2-yl}-1H-pyrazole-4-sulfonamide (Compound 130) (24.6 mg, 0.0459 mmol) obtained in Example 125 was dissolved in dichloromethane (2.0 mL). To this, meta-chloroperbenzoic acid (24.0 mg, 0.138 mmol) was added and the mixture was stirred under a nitrogen atmosphere at room temperature for 2.8 hours. After water was added to the reaction mixture, extraction with ethyl acetate was performed, followed by washing with brine and drying over anhydrous sodium sulfate. The solvent was evaporated off under reduced pressure, and the residue was purified by preparative thin-layer chromatography (chloroform/methanol=30/1) to give 5-chloro-1,3-dimethyl-N-{3-[2,2,2-trifluoro-1-(tetrahydro-2H-thiopyran-1,1-dioxide-4-yl)ethoxy]quinoxalin-2-yl}-1H-pyrazole-4-sulfonamide (Compound 132) (18.6 mg, yield: 71%).

ESIMS m/z: 570, 568 (M+H)+; $^1$H-NMR (270 MHz, CDCl$_3$, δ): 2.19-2.22 (m, 2H), 2.33-2.39 (m, 3H), 2.67 (s, 3H), 3.00-3.10 (m, 4H), 3.78 (s, 3H), 6.06 (m, 1H), 7.63 (m, 2H), 7.74 (m, 2H), 8.32 (br s, 1H).

EXAMPLE 128

3,5-dimethyl-N-{3-[2,2,2-trifluoro-1-(tetrahydro-2H-thiopyran-1,1-dioxide-4-yl)ethoxy]quinoxalin-2-yl}-isoxazole-4-sulfonamide (Compound 133)

According to the step of Example 127, by use of 3,5-dimethyl-N-{3-[2,2,2-trifluoro-1-(tetrahydro-2H-thiopyran-4-yl)ethoxy]quinoxalin-2-yl}isoxazole-4-sulfonamide (Compound 131) (27.0 mg, 0.0537 mmol) obtained in Example 126 and dissolved in dichloromethane (2.2 mL), and meta-chloroperbenzoic acid (37.3 mg, 0.215 mmol), the mixture was stirred and reacted under a nitrogen atmosphere at room temperature for 3.3 hours. Then, purification by preparative thin-layer chromatography (chloroform/methanol=30/1) was performed to give 3,5-dimethyl-N-{3-[2,2,2-trifluoro-1-(tetrahydro-2H-thiopyran-1,1-dioxide-4-yl)ethoxy]quinoxalin-2-yl}-isoxazole-4-sulfonamide (Compound 133) (23.6 mg, yield: 82%).

ESIMS m/z: 535 (M+H)$^+$; $^1$H-NMR (270 MHz, CDCl$_3$, δ): 2.23-2.32 (m, 5H), 2.51 (s, 3H), 2.88 (s, 3H), 3.06-3.16 (m, 4H), 6.04 (m, 1H), 7.57 (m, 3H), 7.71 (m, 2H).

EXAMPLE 129

2-chloro-N-{3-[2,2,2-trifluoro-1-(2-phenylthiazol-5-yl)-ethoxy]quinoxalin-2-yl}benzenesulfonamide (Compound 134)

According to Example 90, by use of 60% sodium hydride (in oil) (10.0 mg, 0.251 mmol), tetrahydrofuran (2.5 mL), Compound EI (43.2 mg, 0.167 mmol) and 2-chloro-N-(3-chloroquinoxalin-2-yl)benzenesulfonamide (Compound AD) (29.6 mg, 0.0835 mmol), the mixture was stirred and reacted at 50° C. for 5 hours. Then, purification by preparative thin-layer chromatography (chloroform/acetone=100/1) was performed to give 2-chloro-N-{3-[2,2,2-trifluoro-1-(2-phenylthiazol-5-yl)-ethoxy]quinoxalin-2-yl}benzenesulfonamide (Compound 134) (23.6 mg, yield: 49%).

ESIMS m/z: 579, 577 (M+H)$^+$; $^1$H-NMR (270 MHz, CDCl$_3$, δ): 7.18 (br s, 1H), 7.44-7.57 (m, 9H), 7.72 (m, 1H), 7.92 (m, 2H), 8.09 (s, 1H), 8.20 (br s, 1H), 8.49 (br s, 1H).

EXAMPLE 130

N-{3-[2,2,2-trifluoro-1-(1-methyl-1H-indol-2-yl)ethoxy]-quinoxalin-2-yl}propane-1-sulfonamide (Compound 135)

According to Example 90, by use of 60% sodium hydride (in oil) (17.0 mg, 0.420 mmol), tetrahydrofuran (2 mL), Compound DQ (64.0 mg, 0.280 mmol) and N-(3-chloroquinoxalin-2-yl)propane-1-sulfonamide (Compound AH) (40.0 mg, 0.140 mmol), the mixture was stirred and reacted at 50° C. for 2 hours. Then, purification by preparative thin-layer chromatography (chloroform/acetone=100/1) was performed to give N-{3-[2,2,2-trifluoro-1-(1-methyl-1H-indol-2-yl)ethoxy]-quinoxalin-2-yl}propane-1-sulfonamide (Compound 135) (54.5 mg, yield: 81%).

ESIMS m/z: 477 (M−H)$^-$; $^1$H-NMR (270 MHz, CDCl$_3$, δ): 1.10 (t, J=7.4 Hz, 3H), 1.98 (m, 2H), 3.76 (m, 2H), 4.02 (s, 3H), 6.91 (s, 1H), 7.09 (br s, 1H), 7.12 (dd, J=6.9, 7.9 Hz, 1H), 7.28 (dd, J=6.9, 8.6 Hz, 1H), 7.36 (d, J=8.3 Hz, 1H), 7.56 (m, 2H), 7.62 (d, J=7.9 Hz, 1H), 7.74 (m, 1H), 7.86 (br s, 1H).

EXAMPLE 131

2-chloro-N-{3-[2,2,2-trifluoro-1-(tetrahydrofuran-3-yl)-ethoxy]quinoxalin-2-yl}benzenesulfonamide (Compound 136)

According to Example 90, by use of 60% sodium hydride (in oil) (16.0 mg, 0.396 mmol), tetrahydrofuran (3.2 mL), Compound EJ (44.0 mg, 0.260 mmol) and 2-chloro-N-(3-chloroquinoxalin-2-yl)benzenesulfonamide (Compound AD) (40.0 mg, 0.113 mmol), the mixture was stirred and reacted at 50° C. for 2.5 hours. Then, purification by preparative thin-layer chromatography (chloroform/methanol=30/1) was performed to give 2-chloro-N-{3-[2,2,2-trifluoro-1-(tetrahydrofuran-3-yl)-ethoxy]quinoxalin-2-yl}benzenesulfonamide (Compound 136) (16.6 mg, yield: 30%).

ESIMS m/z: 490, 488 (M+H)$^+$; $^1$H-NMR (300 MHz, CDCl$_3$, δ): 1.90 (m, 1H), 2.17 (m, 1H), 2.93 (m, 1H), 3.76-4.14 (m, 4H), 6.11 (br s, 1H), 7.49-7.71 (m, 7H), 8.26 (br s, 1H), 8.53 (br s, 1H).

EXAMPLE 132

N-{3-[2,2,2-trifluoro-1-(pyridin-3-yl)ethoxy]quinoxalin-2-yl}benzenesulfonamide (Compound 137)

2-Chloro-3-[2,2,2-trifluoro-1-(pyridin-3-yl)ethoxy]-quinoxaline (Compound BJ) (73 mg, 0.21 mmol) was dissolved in dimethyl sulfoxide (2 mL). To this, benzenesulfonamide (33 mg, 0.21 mmol) and potassium carbonate (29 mg, 0.21 mmol) were added at room temperature and the mixture was stirred at 150° C. for 2 hours. The reaction mixture was allowed to cool down to room temperature, a 1% aqueous acetic acid solution (20 mL) was added thereto, and the precipitate was collected by filtration. The obtained solid was subjected to slurry purification using methanol, to give N-{3-[2,2,2-trifluoro-1-(pyridin-3-yl)ethoxy]quinoxalin-2-yl}benzenesulfonamide (Compound 137) (31 mg, 320).

ESIMS m/z: 461 (M+H)$^+$; $^1$H-NMR (270 MHz, DMSO-d$_6$, δ): 7.16 (q, J=7.0 Hz, 1H), 7.46-7.79 (m, 8H), 8.15-8.35 (m, 3H), 8.64 (d, J=5.0 Hz, 1H), 9.06 (s, 1H), 11.92 (br s, 1H).

EXAMPLE 133

2-chloro-N-{3-[2,2,2-trifluoro-1-(pyridin-3-yl)ethoxy]-quinoxalin-2-yl}benzenesulfonamide (Compound 138)

According to Example 132, by use of 2-chloro-3-[2,2,2-trifluoro-1-(pyridin-3-yl)ethoxy]-quinoxaline (Compound BJ) (80 mg, 0.24 mmol), dimethyl sulfoxide (2 mL), 2-chlorobenzenesulfonamide (45 mg, 0.24 mmol) and potassium carbonate (33 mg, 0.24 mmol), 2-chloro-N-{3-[2,2,2-trifluoro-1-(pyridin-3-yl)ethoxy]-quinoxalin-2-yl}benzenesulfonamide (Compound 138) (68 mg, yield: 58%) was obtained.

ESIMS m/z: 495 (M+H)$^+$; $^1$H-NMR (270 MHz, DMSO-d$_6$, δ): 7.20 (q, J=6.8 Hz, 1H), 7.49-7.67 (m, 8H), 8.26-8.42 (m, 2H), 8.66 (dd, J=1.5, 4.8 Hz, 1H), 9.07 (s, 1H).

EXAMPLE 134

N-{3-[2,2,2-trifluoro-1-(pyridin-3-yl)ethoxy]quinoxalin-2-yl}pyridine-3-sulfonamide (Compound 139)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FA (33 mg, 0.21 mmol) and potassium carbonate (28 mg, 0.21 mmol), the mixture was stirred and reacted at 150° C. for 1.5 hours. Thus, N-{3-[2,2,2-trifluoro-1-(pyridin-3-yl)ethoxy]quinoxalin-2-yl}pyridine-3-sulfonamide (Compound 139) (55 mg, yield: 59%) was obtained.

ESIMS m/z: 462 (M+H)$^+$; $^1$H-NMR (270 MHz, CDCl$_3$, δ): 6.75 (q, J=5.4 Hz, 1H), 7.29-8.05 (m, 8H), 8.45-8.91 (m, 4H), 9.45 (br s, 1H).

EXAMPLE 135

N-{3-[2,2,2-trifluoro-1-(pyridin-3-yl)ethoxy]quinoxalin-2-yl}thiophene-2-sulfonamide (Compound 140)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), thiophene-2-sulfonamide (34 mg, 0.21 mmol) and potassium carbonate (28 mg, 0.21 mmol), the mixture was stirred and reacted at 150° C. for 1.5 hours. Thus, N-{3-[2,2,2-trifluoro-1-(pyridin-3-yl)ethoxy]quinoxalin-2-yl}thiophene-2-sulfonamide (Compound 140) (71 mg, yield: 74%) was obtained.

ESIMS m/z: 467 (M+H)$^+$; $^1$H-NMR (270 MHz, CDCl$_3$, δ): 6.78 (q, J=5.4 Hz, 1H), 7.06-7.75 (m, 6H), 7.86-8.17 (m, 3H), 8.67 (d, J=5.4 Hz, 1H), 8.87 (s, 1H).

EXAMPLE 136

5-chloro-1,3-dimethyl-N-{3-[2,2,2-trifluoro-1-(pyridin-3-yl)ethoxy]quinoxalin-2-yl}-1H-pyrazole-4-sulfonamide (Compound 141)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FB (43 mg, 0.21 mmol) and potassium carbonate (28 mg, 0.21 mmol), the mixture was stirred and reacted at 150° C. for 1.5 hours. Thus, 5-chloro-1,3-dimethyl-N-{3-[2,2,2-trifluoro-1-(pyridin-3-yl)ethoxy]quinoxalin-2-yl}-1H-pyrazole-4-sulfonamide (Compound 141) (67 mg, yield: 70%) was obtained.

ESIMS m/z: 513 (M+H)$^+$; $^1$H-NMR (270 MHz, CDCl$_3$, δ): 2.68 (s, 3H), 3.77 (s, 3H), 6.80 (q, J=6.6 Hz, 1H), 7.34-7.80 (m, 5H), 7.95 (d, J=7.6 Hz, 1H), 8.68 (d, J=3.6 Hz, 1H), 8.86 (s, 1H).

EXAMPLE 137

N-{3-[2,2,2-trifluoro-1-(pyridin-3-yl)ethoxy]quinoxalin-2-yl}-2-(trifluoromethyl)benzenesulfonamide (Compound 142)

According to Example 132, by use of 2-chloro-3-[2,2,2-trifluoro-1-(pyridin-3-yl)ethoxy]-quinoxaline (Compound BJ) (100 mg, 0.29 mmol), dimethyl sulfoxide (2 mL), 2-(trifluoromethyl)benzenesulfonamide (66 mg, 0.29 mmol) and potassium carbonate (40 mg, 0.29 mmol), the mixture was stirred and reacted at 150° C. for 1 hour. Thus, N-{3-[2,2,2-trifluoro-1-(pyridin-3-yl)ethoxy]quinoxalin-2-yl}-2-(trifluoromethyl)benzenesulfonamide (Compound 142) (104 mg, yield: 68%) was obtained.

ESIMS m/z: 486 (M+H)$^+$; $^1$H-NMR (270 MHz, CDCl$_3$, δ): 6.83 (q, J=6.1 Hz, 1H), 7.12-8.12 (m, 10H), 8.66 (dd, J=1.5, 4.8 Hz, 1H), 8.84 (d, J=1.5 Hz, 1H).

EXAMPLE 138

5-methyl-N-{3-[2,2,2-trifluoro-1-(pyridin-3-yl)ethoxy]-quinoxalin-2-yl}-2-(trifluoromethyl)furan-3-sulfonamide (Compound 143)

According to Example 132, by use of 2-chloro-3-[2,2,2-trifluoro-1-(pyridin-3-yl)ethoxy]-quinoxaline (Compound BJ) (73 mg, 0.21 mmol), dimethyl sulfoxide (2 mL), Compound FD (47 mg, 0.21 mmol) and potassium carbonate (28 mg, 0.21 mmol), the mixture was stirred and reacted at 150° C. for 1.5 hours. Then, purification by silica gel column chromatography (chloroform/methanol=1/0 to 50/1) was performed to give 5-methyl-N-{3-[2,2,2-trifluoro-1-(pyridin-3-yl)ethoxy]-quinoxalin-2-yl}-2-(trifluoromethyl) furan-3-sulfonamide (Compound 143) (41 mg, 38%).

ESIMS m/z: 533 (M+H)$^+$; $^1$H-NMR (270 MHz, CDCl$_3$, δ): 2.88 (s, 3H), 6.77 (br s, 1H), 7.21-7.76 (m, 5H), 7.95 (d, J=7.7 Hz, 1H), 8.68 (dd, J=1.5, 4.8 Hz, 1H), 8.88 (d, J=1.5 Hz, 1H).

EXAMPLE 139

2-fluoro-N-{3-[2,2,2-trifluoro-1-(pyridin-3-yl)ethoxy]-quinoxalin-2-yl}benzenesulfonamide (Compound 144)

According to Example 90, by use of 60% sodium hydride (in oil) (35 mg, 0.87 mmol), tetrahydrofuran (3 mL), Compound CB (78 mg, 0.44 mmol) and N-(3-chloroquinoxalin-2-yl)-2-fluorobenzenesulfonamide (Compound AE) (100 mg, 0.29 mmol), the mixture was stirred and reacted at room temperature for 4 hours. Then, purification by silica gel column chromatography (chloroform/methanol=1/0 to 100/1) was performed to give 2-fluoro-N-{3-[2,2,2-trifluoro-1-(pyridin-3-yl)ethoxy]-quinoxalin-2-yl}benzenesulfonamide (Compound 144) (51 mg, yield: 37%).

ESIMS m/z: 479 (M+H)$^+$; $^1$H-NMR (270 MHz, CDCl$_3$, δ): 6.76 (br s, 1H), 7.11-7.74 (m, 9H), 7.96 (d, J=7.3 Hz, 1H), 8.67 (d, J=5.4 Hz, 1H), 8.86 (s, 1H).

EXAMPLE 140

2-cyano-N-{3-[2,2,2-trifluoro-1-(pyridin-3-yl)ethoxy]-quinoxalin-2-yl}benzenesulfonamide (Compound 145)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), 2-cyanobenzenesulfonamide (38 mg, 0.21 mmol) and potassium carbonate (28 mg, 0.21 mmol), the mixture was stirred and reacted at 150° C. for 1.5 hours. The reaction mixture was allowed to cool down to room temperature, a 1% aqueous acetic acid solution was added thereto, and extraction with ethyl acetate was performed. The organic layer was washed with a saturated aqueous sodium chloride solution and dried over anhydrous magnesium sulfate, and then the solvent was evaporated off under reduced pressure. The residue was subjected to slurry purification using methanol, to give 2-cyano-N-{3-[2,2,2-trifluoro-1-(pyridin-3-yl)ethoxy]-quinoxalin-2-yl}benzenesulfonamide (Compound 145) (70 mg, 70%).

ESIMS m/z: 486 (M+H)$^+$; $^1$H-NMR (270 MHz, CDCl$_3$, δ): 6.84 (br s, 1H), 7.35-8.30 (m, 10H), 8.70 (m, 1H), 8.98 (s, 1H).

EXAMPLE 141

5-chloro-N-{3-[2,2,2-trifluoro-1-(pyridin-3-yl)ethoxy]-quinoxalin-2-yl}thiophene-2-sulfonamide (Compound 146)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), 5-chlorothiophene-2-sulfonamide (41 mg, 0.21 mmol) and potassium carbonate (28 mg, 0.21 mmol), the mixture was stirred and reacted at 150° C. for 1.5 hours. Thus, 5-chloro-N-{3-[2,2,2-trifluoro-1-(pyridin-3-yl)ethoxy]-quinoxalin-2-yl}thiophene-2-sulfonamide (Compound 146) (61 mg, yield: 59%) was obtained.

ESIMS m/z: 501 (M+H)$^+$; $^1$H-NMR (270 MHz, CDCl$_3$, δ): 6.77 (q, J=6.6 Hz, 1H), 6.94 (d, J=4.0 Hz, 1H), 7.20-7.89 (m, 6H), 7.96 (d, J=8.1 Hz, 1H), 8.67 (dd, J=1.6, 4.9 Hz, 1H), 8.87 (s, J=1.6 Hz, 1H).

EXAMPLE 142

1-phenyl-N-{3-[2,2,2-trifluoro-1-(pyridin-3-yl)ethoxy]-quinoxalin-2-yl}methanesulfonamide (Compound 147)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), α-toluenesulfonamide (35 mg, 0.21 mmol) and potassium carbonate (28 mg, 0.21 mmol), the mixture was stirred and reacted at 150° C. for 1.5 hours. Thus, 1-phenyl-N-{3-[2,2,2-trifluoro-1-(pyridin-3-yl)ethoxy]-quinoxalin-2-yl}methanesulfonamide (Compound 147) (56 mg, yield: 57%) was obtained.

ESIMS m/z: 475 (M+H)$^+$; $^1$H-NMR (270 MHz, CDCl$_3$, δ): 5.04 (s, 2H), 6.70 (br s, 1H), 6.98-8.07 (m, 11H), 8.68 (d, J=4.6 Hz, 1H), 8.83 (s, 1H).

EXAMPLE 143

N-{3-[2,2,2-trifluoro-1-(pyridin-3-yl)ethoxy]quinoxalin-2-yl}methanesulfonamide (Compound 148)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), methanesulfonamide (20 mg, 0.21 mmol) and potassium carbonate (28 mg, 0.21 mmol), the mixture was stirred and reacted at 150° C. for 1.5 hours. Then, slurry purification was performed using isopropyl ether, to give N-{3-[2,2,2-trifluoro-1-(pyridin-3-yl)ethoxy]quinoxalin-2-yl}methanesulfonamide (Compound 148) (40 mg, yield: 33%).

ESIMS m/z: 399 (M+H)$^+$; $^1$H-NMR (270 MHz, CDCl$_3$, δ): 3.62 (s, 3H), 6.81 (br s, 1H), 7.73-8.01 (m, 6H), 8.68 (dd, J=1.5, 4.8 Hz, 1H), 8.89 (d, J=1.5 Hz, 1H).

EXAMPLE 144

1,1,1-trifluoro-N-{3-[2,2,2-trifluoro-1-(pyridin-3-yl)-ethoxy]quinoxalin-2-yl}methanesulfonamide (Compound 149)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), trifluoromethanesulfonamide (31 mg, 0.21 mmol) and potassium carbonate (28 mg, 0.21 mmol), the mixture was stirred and reacted at 150° C. for 1.5 hours. The reaction mixture was allowed to cool down to room temperature, a 1% aqueous acetic acid solution was added thereto, and extraction with ethyl acetate was performed. The organic layer was washed with a saturated aqueous sodium chloride solution and dried over anhydrous magnesium sulfate, and then the solvent was evaporated off under reduced pressure. The residue was purified by silica gel column chromatography (chloroform/methanol=1/0 to 20/1). Further, slurry purification was performed using isopropyl ether, to give 1,1,1-trifluoro-N-{3-[2,2,2-trifluoro-1-(pyridin-3-yl)-ethoxy]quinoxalin-2-yl}methanesulfonamide (Compound 149) (13 mg, 14%).

ESIMS m/z: 453 (M+H)$^+$; $^1$H-NMR (270 MHz, CDCl$_3$, δ): 6.73 (q, J=6.5 Hz, 1H), 7.36-7.79 (m, 5H), 8.02 (d, J=8.1 Hz, 1H), 8.69 (dd, J=1.6, 4.9 Hz, 1H), 8.86 (s, J=1.6 Hz, 1H).

EXAMPLE 145

N-{3-[2,2,2-trifluoro-1-(pyridin-3-yl)ethoxy]quinoxalin-2-yl}cyclopropanesulfonamide (Compound 150)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), cyclopropanesulfonamide (25 mg, 0.21 mmol) and potassium carbonate (28 mg, 0.21 mmol), the mixture was stirred and reacted at 150° C. for 1.5 hours. Thus, N-{3-[2,2,2-trifluoro-1-(pyridin-3-yl)ethoxy]quinoxalin-2-yl}cyclopropanesulfonamide (Compound 150) (21 mg, yield: 24%) was obtained.

ESIMS m/z: 425 (M+H)$^+$; $^1$H-NMR (270 MHz, CDCl$_3$, δ): 1.06-1.69 (m, 5H), 6.83 (q, J=6.2 Hz, 1H), 7.34-8.02 (m, 6H), 8.69 (d, J=4.8 Hz, 1H), 8.90 (s, 1H).

EXAMPLE 146

N-{3-[2,2,2-trifluoro-1-(pyridin-3-yl)ethoxy]quinoxalin-2-yl}-2-(trifluoromethoxy)benzenesulfonamide (Compound 151)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), 2-(trifluoromethoxy)benzenesulfonamide (50 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}-2-(trifluoromethoxy)benzenesulfonamide (Compound 151) (26 mg, yield: 23%) was obtained.

ESIMS m/z: 545 (M+H)$^+$; $^1$H-NMR (270 MHz, DMSO-d$_6$, δ): 7.19 (br s, 1H), 7.40-7.84 (m, 9H), 8.20-8.21 (m, 1H), 8.65 (d, J=5.4 Hz, 1H), 9.03 (s, 1H).

EXAMPLE 147

3,5-dichloro-N-{3-[2,2,2-trifluoro-1-(pyridin-3-yl)ethoxy]-quinoxalin-2-yl}benzenesulfonamide (Compound 152)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FE (47 mg, 0.21 mmol) and potassium carbonate (28 mg, 0.21 mmol), the mixture was stirred and reacted at 150° C. for 1 hour. Thus, 3,5-dichloro-N-{3-[2,2,2-trifluoro-1-(pyridin-3-yl)ethoxy]-quinoxalin-2-yl}benzenesulfonamide (Compound 152) (69 mg, yield: 56%) was obtained.

ESIMS m/z: 530 (M+H)$^+$; $^1$H-NMR (270 MHz, DMSO-d$_6$, δ): 7.15 (q, J=7.1 Hz, 1H), 7.49-7.75 (m, 5H), 7.98 (t, J=2.0 Hz, 1H), 8.16 (d, J=2.0 Hz, 2H), 8.25 (d, J=7.9 Hz, 1H), 8.65 (dd, J=1.6, 4.9 Hz, 1H), 9.03 (s, J=1.6 Hz, 1H).

EXAMPLE 148

3,5-difluoro-N-{3-[2,2,2-trifluoro-1-(pyridin-3-yl)ethoxy]-quinoxalin-2-yl}benzenesulfonamide (Compound 153)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FF (40 mg, 0.21 mmol) and potassium carbonate (28 mg, 0.21 mmol), the mixture was stirred and reacted at 150° C. for 1 hour. Thus, 3,5-difluoro-N-{3-[2,2,2-trifluoro-1-(pyridin-3-yl)ethoxy]-quinoxalin-2-yl}benzenesulfonamide (Compound 153) (20 mg, yield: 20%) was obtained.

ESIMS m/z: 497 (M+H)$^+$; $^1$H-NMR (270 MHz, DMSO-$d_6$, δ): 7.15 (q, J=7.1 Hz, 1H), 7.48-7.77 (m, 6H), 7.86 (d, J=4.8 Hz, 2H), 8.25 (d, J=7.9 Hz, 1H), 8.65 (dd, J=1.5, 4.8 Hz, 1H), 9.03 (s, 1H).

EXAMPLE 149

1,2-dimethyl-N-{3-[2,2,2-trifluoro-1-(pyridin-3-yl)ethoxy]-quinoxalin-2-yl}-1H-imidazole-4-sulfonamide (Compound 154)

According to Example 132, by use of 2-chloro-3-[2,2,2-trifluoro-1-(pyridin-3-yl)ethoxy]-quinoxaline (Compound BJ) (80 mg, 0.24 mmol), dimethyl sulfoxide (2 mL), Compound FG (82 mg, 0.48 mmol) and potassium carbonate (66 mg, 0.48 mmol), the mixture was stirred and reacted at 150° C. for 3 hours. Then, purification by silica gel column chromatography (chloroform/methanol=10/1) was performed to give 1,2-dimethyl-N-{3-[2,2,2-trifluoro-1-(pyridin-3-yl)ethoxy]-quinoxalin-2-yl}-1H-imidazole-4-sulfonamide (Compound 154) (15 mg, 13%).

ESIMS m/z: 479 (M+H)$^+$; $^1$H-NMR (270 MHz, DMSO-$d_6$, δ): 2.27 (s, 3H), 3.62 (s, 3H), 7.15 (q, J=6.9 Hz, 1H), 7.46-7.69 (m, 4H), 7.82 (d, J=7.8 Hz, 1H), 8.12 (s, 1H), 8.31 (d, J=7.8 Hz, 1H), 8.64 (d, J=4.8 Hz, 1H), 9.06 (s, 1H).

EXAMPLE 150

3,5-dimethyl-N-{3-[2,2,2-trifluoro-1-(pyridin-3-yl)ethoxy]-quinoxalin-2-yl}isoxazole-4-sulfonamide (Compound 155)

According to Example 132, by use of 2-chloro-3-[2,2,2-trifluoro-1-(pyridin-3-yl)ethoxy]-quinoxaline (Compound BJ) (80 mg, 0.24 mmol), dimethyl sulfoxide (2 mL), Compound FC (42 mg, 0.24 mmol) and potassium carbonate (33 mg, 0.24 mmol), the mixture was stirred and reacted at 150° C. for 1.5 hours. Thus, 3,5-dimethyl-N-{3-[2,2,2-trifluoro-1-(pyridin-3-yl)ethoxy]-quinoxalin-2-yl}isoxazole-4-sulfonamide (Compound 155) (40 mg, yield: 36%) was obtained.

ESIMS m/z: 480 (M+H)$^+$; $^1$H-NMR (270 MHz, DMSO-$d_6$, δ): 2.49 (s, 3H), 2.84 (s, 3H), 7.18 (q, J=7.0 Hz, 1H), 7.49-7.75 (m, 5H), 8.31 (d, J=8.1 Hz, 1H), 8.65 (dd, J=1.5, 4.8 Hz, 1H), 9.07 (d, J=1.5 Hz, 1H).

EXAMPLE 151

2-methyl-N-{3-[2,2,2-trifluoro-1-(pyridin-3-yl)ethoxy]-quinoxalin-2-yl}benzenesulfonamide (Compound 156)

According to Example 140, by use of 2-chloro-3-[2,2,2-trifluoro-1-(pyridin-3-yl)ethoxy]-quinoxaline (Compound BJ) (85 mg, 0.25 mmol), dimethyl sulfoxide (2 mL), o-toluenesulfonamide (43 mg, 0.25 mmol) and potassium carbonate (35 mg, 0.25 mmol), the mixture was stirred and reacted at 150° C. for 1.5 hours. Thus, 2-methyl-N-{3-[2,2,2-trifluoro-1-(pyridin-3-yl)ethoxy]-quinoxalin-2-yl}benzenesulfonamide (Compound 156) (81 mg, yield: 69%) was obtained.

ESIMS m/z: 475 (M+H)$^+$; $^1$H-NMR (270 MHz, DMSO-$d_6$, δ): 2.69 (s, 3H), 7.17 (br s, 1H), 7.31-7.69 (m, 8H), 8.17-8.40 (m, 2H), 8.65 (dd, J=1.6, 4.9 Hz, 1H), 9.08 (s, 1H).

EXAMPLE 152

2-amino-N-{3-[2,2,2-trifluoro-1-(pyridin-3-yl)ethoxy]-quinoxalin-2-yl}benzenesulfonamide (Compound 157)

According to Example 132, by use of 2-chloro-3-[2,2,2-trifluoro-1-(pyridin-3-yl)ethoxy]-quinoxaline (Compound BJ) (85 mg, 0.25 mmol), dimethyl sulfoxide (2 mL), 2-aminobenzenesulfonamide (43 mg, 0.25 mmol) and potassium carbonate (35 mg, 0.25 mmol), the mixture was stirred and reacted at 150° C. for 1.5 hours. Thus, 2-amino-N-{3-[2,2,2-trifluoro-1-(pyridin-3-yl)ethoxy]-quinoxalin-2-yl}benzenesulfonamide (Compound 157) (70 mg, yield: 59%) was obtained.

ESIMS m/z: 476 (M+H)$^+$; $^1$H-NMR (270 MHz, DMSO-$d_6$, δ): 6.65 (t, J=7.7 Hz, 1H), 6.73 (d, J=7.7 Hz, 1H), 7.15-7.26 (m, 2H), 7.49-7.71 (m, 5H), 7.87 (dd, J=1.6, 7.7 Hz, 1H), 8.29 (d, J=7.7 Hz, 1H), 8.65 (dd, J=1.6, 4.9 Hz, 1H), 9.07 (d, J=1.6 Hz, 1H).

EXAMPLE 153

2-methoxy-N-{3-[2,2,2-trifluoro-1-(pyridin-3-yl)ethoxy]-quinoxalin-2-yl}benzenesulfonamide (Compound 158)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FH (39 mg, 0.21 mmol) and potassium carbonate (28 mg, 0.21 mmol), the mixture was stirred and reacted at 150° C. for 1.5 hours. Thus, 2-methoxy-N-{3-[2,2,2-trifluoro-1-(pyridin-3-yl)ethoxy]-quinoxalin-2-yl}benzenesulfonamide (Compound 158) (22 mg, yield: 22%) was obtained.

ESIMS m/z: 491 (M+H)$^+$; $^1$H-NMR (270 MHz, DMSO-$d_6$, δ): 3.78 (s, 3H), 7.05-7.27 (m, 3H), 7.34-7.68 (m, 6H), 8.11 (d, J=7.7 Hz, 1H), 8.40 (d, J=7.7 Hz, 1H), 8.65 (d, J=4.9 Hz, 1H), 9.12 (s, 1H).

EXAMPLE 154

2,3-dichloro-N-{3-[3-(pyridin-3-yl)propoxy]quinoxalin-2-yl}benzenesulfonamide (Compound 159)

Sixty percent sodium hydride (in oil) (25 mg, 0.62 mmol) was suspended in tetrahydrofuran (2 mL). To this, 3-pyridinepropanol (0.048 mL, 0.37 mmol) was added under a nitrogen atmosphere at room temperature and the mixture was stirred at the same temperature for 15 minutes. To this, 2,3-dichloro-N-(3-chloroquinoxalin-2-yl)benzenesulfonamide (Compound AA) (100 mg, 0.25 mmol) was added and the mixture was stirred at room temperature for 5 hours. Then, a saturated aqueous ammonium chloride solution and ethyl acetate were added to the reaction mixture and the precipitate was collected by filtration. The obtained solid was subjected to slurry purification using methanol, to give 2,3-dichloro-N-{3-[3-(pyridin-3-yl)propoxy]quinoxalin-2-yl}benzenesulfonamide (Compound 159) (77 mg, yield: 63%).

ESIMS m/z: 490 (M+H)$^+$; $^1$H-NMR (270 MHz, DMSO-d$_6$, δ): 2.13 (quin, J=6.8 Hz, 2H), 2.79 (t, J=6.8 Hz, 2H), 4.34 (t, J=6.8 Hz, 2H), 6.99-7.23 (m, 3H), 7.26-7.49 (m, 3H), 7.63 (dd, J=1.6, 7.7 Hz, 1H), 7.72 (dt, J=1.6, 7.7 Hz, 1H), 8.23 (dd, J=1.6, 7.7 Hz, 1H), 8.41 (dd, J=1.6, 4.8 Hz, 1H), 8.49 (d, J=1.6 Hz, 1H).

EXAMPLE 155

N-{3-[2,2,2-trifluoro-1-(pyridin-3-yl)ethoxy]quinoxalin-2-yl}pyridine-2-sulfonamide (Compound 160)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FI (33 mg, 0.21 mmol) and potassium carbonate (28 mg, 0.21 mmol), the mixture was stirred and reacted at 150° C. for 0.5 hour. Thus, N-{3-[2,2,2-trifluoro-1-(pyridin-3-yl)ethoxy]quinoxalin-2-yl}pyridine-2-sulfonamide (Compound 160) (61 mg, yield: 64%) was obtained.

ESIMS m/z: 462 (M+H)$^+$; $^1$H-NMR (270 MHz, DMSO-d$_6$, δ): 7.18 (q, J=7.0 Hz, 1H), 7.46-7.71 (m, 6H), 8.18 (td, J=1.6, 7.8 Hz, 1H), 8.30-8.39 (m, 2H), 8.64-8.68 (m, 2H), 9.09 (s, 1H).

EXAMPLE 156

N-{3-[2,2,2-trifluoro-1-(pyridin-3-yl)ethoxy]quinoxalin-2-yl}thiophene-3-sulfonamide (Compound 161)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FJ (34 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}thiophene-3-sulfonamide (Compound 161) (72 mg, yield: 75%) was obtained.

ESIMS m/z: 467 (M+H)$^+$; $^1$H-NMR (270 MHz, DMSO-d$_6$, δ): 7.16 (q, J=7.1 Hz, 1H), 7.47-7.75 (m, 6H), 7.84-7.90 (m, 1H), 8.30 (d, J=7.7 Hz, 1H), 8.60-8.70 (m, 2H), 9.07 (s, 1H).

EXAMPLE 157

2,5-dimethyl-N-{3-[2,2,2-trifluoro-1-(pyridin-3-yl)ethoxy]-quinoxalin-2-yl}thiophene-3-sulfonamide (Compound 162)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FK (43 mg, 0.21 mmol) and potassium carbonate (28 mg, 0.21 mmol), the mixture was stirred and reacted at 150° C. for 1.5 hours. Thus, 2,5-dimethyl-N-{3-[2,2,2-trifluoro-1-(pyridin-3-yl)ethoxy]-quinoxalin-2-yl}thiophene-3-sulfonamide (Compound 162) (67 mg, yield: 66%) was obtained.

ESIMS m/z: 495 (M+H)$^+$; $^1$H-NMR (270 MHz, DMSO-d$_6$, δ): 2.35 (s, 3H), 2.80 (s, 3H), 7.10-7.24 (m, 2H), 7.49-7.75 (m, 5H), 8.31 (d, J=4.8 Hz, 1H), 8.65 (d, J=4.8 Hz, 1H), 9.08 (s, 1H), 11.85 (br s, 1H).

EXAMPLE 158

2,4-dimethyl-N-{3-[2,2,2-trifluoro-1-(pyridin-3-yl)ethoxy]-quinoxalin-2-yl}thiazole-5-sulfonamide (Compound 163)

According to Example 144, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FL (40 mg, 0.21 mmol) and potassium carbonate (28 mg, 0.21 mmol), the mixture was stirred and reacted at 150° C. for 0.5 hour. After purification by silica gel column chromatography (chloroform/methanol=100/1 to 20/1), slurry purification was further performed using isopropyl ether, to give 2,4-dimethyl-N-{3-[2,2,2-trifluoro-1-(pyridin-3-yl)ethoxy]-quinoxalin-2-yl}thiazole-5-sulfonamide (Compound 163) (72 mg, 70%).

ESIMS m/z: 496 (M+H)$^+$; $^1$H-NMR (270 MHz, DMSO-d$_6$, δ): 2.63 (s, 3H), 2.71 (s, 3H), 7.18 (q, J=7.1 Hz, 1H), 7.49-7.80 (m, 5H), 8.30 (d, J=7.7 Hz, 1H), 8.65 (d, J=4.8 Hz, 1H), 9.07 (s, 1H).

EXAMPLE 159

N-{3-[2,2,2-trifluoro-1-(pyridin-3-yl)ethoxy]quinoxalin-2-yl}benzo[b]thiophene-2-sulfonamide (Compound 164)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FM (44 mg, 0.21 mmol) and potassium carbonate (28 mg, 0.21 mmol), the mixture was stirred and reacted at 150° C. for 0.5 hour. Thus, N-{3-[2,2,2-trifluoro-1-(pyridin-3-yl)ethoxy]quinoxalin-2-yl}benzo[b]thiophene-2-sulfonamide (Compound 164) (72 mg, yield: 68%) was obtained.

ESIMS m/z: 517 (M+H)$^+$; $^1$H-NMR (270 MHz, DMSO-d$_6$, δ): 7.18 (q, J=7.0 Hz, 1H), 7.45-7.71 (m, 6H), 7.90-7.97 (m, 1H), 8.06-8.14 (m, 2H), 8.30 (d, J=8.1 Hz, 1H), 8.47 (s, 1H), 8.65 (dd, J=1.5, 4.9 Hz, 1H), 9.08 (d, J=1.5 Hz, 1H).

EXAMPLE 160

4-methyl-N-{3-[2,2,2-trifluoro-1-(pyridin-3-yl)ethoxy]-quinoxalin-2-yl}-3,4-dihydro-2H-benzo[b][1,4]oxazine-7-sulfonamide (Compound 165)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FN (47 mg, 0.21 mmol) and potassium carbonate (28 mg, 0.21 mmol), the mixture was stirred and reacted at 150° C. for 0.5 hour. Thus, 4-methyl-N-{3-[2,2,2-trifluoro-1-(pyridin-3-yl)ethoxy]-quinoxalin-2-yl}-3,4-dihydro-2H-benzo[b][1,4]oxazine-7-sulfonamide (Compound 165) (40 mg, yield: 37%) was obtained.

ESIMS m/z: 532 (M+H)$^+$; $^1$H-NMR (270 MHz, DMSO-d$_6$, δ): 2.93 (s, 3H), 3.26 (t, J=4.2 Hz, 2H), 4.26 (t, J=4.2 Hz, 2H), 6.84 (d, J=8.1 Hz, 1H), 7.16 (q, J=7.0 Hz, 1H), 7.38-7.69 (m, 6H), 7.74 (d, J=8.1 Hz, 1H), 8.30 (d, J=7.0 Hz, 1H), 8.64 (dd, J=1.5, 4.8 Hz, 1H), 9.07 (s, 1H).

EXAMPLE 161

2,3-dichloro-N-{3-[2-(pyridin-2-yl)ethoxy]quinoxalin-2-yl}-benzenesulfonamide (Compound 166)

According to Example 154, by use of 60% sodium hydride (in oil) (31 mg, 0.77 mmol), tetrahydrofuran (2 mL), 2-pyridineethanol (47 mg, 0.38 mmol) and 2,3-dichloro-N-(3-chloroquinoxalin-2-yl)benzenesulfonamide (Compound AA) (100 mg, 0.25 mmol), the mixture was stirred and reacted at room temperature for 1 hour. Thus, 2,3-dichloro-N-{3-[2-(pyridin-2-yl)ethoxy]quinoxalin-2-yl}-benzenesulfonamide (Compound 166) (60 mg, yield: 51%) was obtained.

ESIMS m/z: 476 (M+H)$^+$; $^1$H-NMR (270 MHz, DMSO-d$_6$, δ): 3.29 (t, J=7.0 Hz, 2H), 4.68 (t, J=7.0 Hz, 2H), 6.98-7.48 (m, 7H), 7.62 (dd, J=1.5, 8.1 Hz, 1H), 7.73 (td, J=1.5, 8.1 Hz, 1H), 8.21 (dd, J=1.5, 8.1 Hz, 1H), 8.52 (d, J=5.1 Hz, 1H).

EXAMPLE 162

2-chloro-N-{3-[2-methyl-2-(pyridin-3-yl)propoxy]quinoxalin-2-yl}benzenesulfonamide (Compound 167)

According to Example 154, by use of 60% sodium hydride (in oil) (28 mg, 0.70 mmol), tetrahydrofuran (2 mL), Compound EK (64 mg, 0.42 mmol) and 2-chloro-N-(3-chloroquinoxalin-2-yl)benzenesulfonamide (Compound AD) (100 mg, 0.28 mmol), the mixture was stirred and reacted at room temperature for 1 hour. Thus, 2-chloro-N-{3-[2-methyl-2-(pyridin-3-yl)propoxy]quinoxalin-2-yl}benzenesulfonamide (Compound 167) (101 mg, yield: 77%) was obtained.

ESIMS m/z: 469 (M+H)$^+$; $^1$H-NMR (270 MHz, DMSO-d$_6$, δ): 1.51 (s, 6H), 4.50 (s, 2H), 7.24 (dd, J=4.8, 8.1 Hz, 1H), 7.40-7.49 (m, 2H), 7.54-7.66 (m, 5H), 7.91 (dt, J=1.8, 8.1 Hz, 1H), 8.28 (dd, J=1.8, 8.1 Hz, 1H), 8.40 (dd, J=1.8, 4.8 Hz, 1H), 8.74 (d, J=1.8 Hz, 1H).

EXAMPLE 163

N-{3-[2,2,2-trifluoro-1-(pyridin-3-yl)ethoxy]quinoxalin-2-yl}propane-2-sulfonamide (Compound 168)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FO (25 mg, 0.21 mmol) and potassium carbonate (28 mg, 0.21 mmol), the mixture was stirred and reacted at 150° C. for 0.5 hour. Thus, N-{3-[2,2,2-trifluoro-1-(pyridin-3-yl)ethoxy]quinoxalin-2-yl}propane-2-sulfonamide (Compound 168) (32 mg, yield: 37%) was obtained.

ESIMS m/z: 427 (M+H)$^+$; $^1$H-NMR (270 MHz, DMSO-d$_6$, δ): 1.30-1.47 (m, 6H), 4.24 (m, 1H), 7.19 (q, J=6.0 Hz, 1H), 7.47-7.88 (m, 5H), 8.23-7.42 (m, 1H), 8.65 (d, J=3.6 Hz, 1H), 9.09 (s, 1H).

EXAMPLE 164

N-{3-[2,2,2-trifluoro-1-(pyridin-3-yl)ethoxy]quinoxalin-2-yl}cyclopentanesulfonamide (Compound 169)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FP (31 mg, 0.21 mmol) and potassium carbonate (28 mg, 0.21 mmol), the mixture was stirred and reacted at 150° C. for 0.5 hour. Thus, N-{3-[2,2,2-trifluoro-1-(pyridin-3-yl)ethoxy]quinoxalin-2-yl}cyclopentanesulfonamide (Compound 169) (33 mg, yield: 36%) was obtained.

ESIMS m/z: 453 (M+H)$^+$; $^1$H-NMR (270 MHz, DMSO-d$_6$, δ): 1.49-2.22 (m, 8H), 4.55 (br s, 1H), 7.20 (q, J=6.9 Hz, 1H), 7.46-7.90 (m, 5H), 8.34 (d, J=5.6 Hz, 1H), 8.66 (dd, J=1.3, 4.6 Hz, 1H), 9.09 (s, 1H).

EXAMPLE 165

5-chloro-1,3-dimethyl-N-{3-[2,2,2-trifluoro-1-(1-methyl-1H-imidazol-5-yl)ethoxy]quinoxalin-2-yl}-1H-pyrazole-4-sulfonamide (Compound 170)

According to Example 132, by use of 2-chloro-3-[2,2,2-trifluoro-1-(1-methyl-1H-imidazol-2-yl)-ethoxy]quinoxaline (Compound BK) (70 mg, 0.20 mmol), dimethyl sulfoxide (2 mL), Compound FB (43 mg, 0.20 mmol) and potassium carbonate (28 mg, 0.20 mmol), the mixture was stirred and reacted at 150° C. for 1.5 hours. Thus, 5-chloro-1,3-dimethyl-N-{3-[2,2,2-trifluoro-1-(1-methyl-1H-imidazol-5-yl)ethoxy]quinoxalin-2-yl}-1H-pyrazole-4-sulfonamide (Compound 170) (21 mg, yield: 20%) was obtained.

ESIMS m/z: 516 (M+H)$^+$; $^1$H-NMR (270 MHz, DMSO-d$_6$, δ): 2.38 (s, 3H), 3.64 (s, 3H), 3.81 (s, 3H), 7.04 (q, J=6.9 Hz, 1H), 7.28 (s, 1H), 7.41-7.65 (m, 4H), 7.79 (s, 1H).

EXAMPLE 166

3,5-dimethyl-N-{3-[2,2,2-trifluoro-1-(1-methyl-1H-imidazol-5-yl)ethoxy]quinoxalin-2-yl}isoxazole-4-sulfonamide (Compound 171)

According to Example 132, by use of 2-chloro-3-[2,2,2-trifluoro-1-(1-methyl-1H-imidazol-2-yl)-ethoxy]quinoxaline (Compound BK) (70 mg, 0.20 mmol), dimethyl sulfoxide (2 mL), Compound FC (36 mg, 0.20 mmol) and potassium carbonate (28 mg, 0.20 mmol), the mixture was stirred and reacted at 150° C. for 0.5 hour. Thus, 3,5-dimethyl-N-{3-[2,2,2-trifluoro-1-(1-methyl-1H-imidazol-5-yl)ethoxy]quinoxalin-2-yl}isoxazole-4-sulfonamide (Compound 171) (16 mg, yield: 16%) was obtained.

ESIMS m/z: 483 (M+H)$^+$; $^1$H-NMR (270 MHz, DMSO-d$_6$, δ): 2.32 (s, 3H), 2.68 (s, 3H), 3.86 (s, 3H), 7.05 (q, J=6.9 Hz, 1H), 7.34-7.61 (m, 5H), 8.05 (s, 1H).

EXAMPLE 167

2-chloro-N-{3-[1,1,1-trifluoro-4-(pyridin-3-yl)butan-2-yloxy]quinoxalin-2-yl}benzenesulfonamide (Compound 172)

Sixty percent sodium hydride (in oil) (25 mg, 0.62 mmol) was suspended in tetrahydrofuran (2 mL). To this, Compound EL (0.048 mL, 0.37 mmol) was added under a nitrogen atmosphere at room temperature and the mixture was stirred at the same temperature for 15 minutes. To this, 2-chloro-N-(3-chloroquinoxalin-2-yl)benzenesulfonamide (Compound AD) (88 mg, 0.25 mmol) was added and the mixture was stirred at room temperature for 5 hours. After water was added to the reaction mixture, extraction with ethyl acetate was performed, followed by washing with brine and drying over anhydrous sodium sulfate. The solvent was evaporated off under reduced pressure, and the residue was purified by silica gel column chromatography (chloroform/methanol=1/0 to 1/33). Further, slurry purification was performed using isopropyl ether, to give 2-chloro-N-{3-[1,1,1-trifluoro-4-(pyridin-3-yl)butan-2-yloxy]quinoxalin-2-yl}benzenesulfonamide (Compound 172) (45 mg, yield: 35%).

ESIMS m/z: 523 (M+H)⁺; ¹H-NMR (270 MHz, DMSO-d₆, δ): 2.17-2.44 (m, 2H), 2.67-2.87 (m, 2H), 5.96-6.11 (m, 1H), 7.32 (dd, J=4.8, 7.7 Hz, 1H), 7.47-7.74 (m, 8H), 8.33-8.46 (m, 3H).

EXAMPLE 168

1-(2-chlorophenyl)-N-{3-[2,2,2-trifluoro-1-(pyridin-3-yl)-ethoxy]quinoxalin-2-yl}methanesulfonamide (Compound 173)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FQ (42 mg, 0.21 mmol) and potassium carbonate (28 mg, 0.21 mmol), the mixture was stirred and reacted at 150° C. for 1 hour. Thus, 1-(2-chlorophenyl)-N-{3-[2,2,2-trifluoro-1-(pyridin-3-yl)-ethoxy]quinoxalin-2-yl}methanesulfonamide (Compound 173) (53 mg, yield: 51%) was obtained.

ESIMS m/z: 509 (M+H)⁺; ¹H-NMR (270 MHz, DMSO-d₅, δ): 5.23 (s, 2H), 7.20 (q, J=6.8 Hz, 1H), 7.33-7.79 (m, 8H), 7.89 (d, J=7.3 Hz, 1H), 8.30 (d, J=4.8 Hz, 1H), 8.66 (dd, J=1.5, 4.8 Hz, 1H), 9.06 (s, 1H).

EXAMPLE 169

N-{3-[2,2,2-trifluoro-1-(pyridin-3-yl)ethoxy]quinoxalin-2-yl}-N',N'-dimethyl-sulfuric diamide (Compound 174)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FR (26 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}-N',N'-dimethyl-sulfuric diamide (Compound 174) (28 mg, yield: 32%) was obtained.

ESIMS m/z: 428 (M+H)⁺; ¹H-NMR (270 MHz, DMSO-d₆, δ): 2.99 (s, 6H), 7.21 (q, J=6.8 Hz, 1H), 7.47-7.86 (m, 5H), 8.37 (d, J=7.0 Hz, 1H), 8.66 (dd, J=1.5, 4.8 Hz, 1H), 9.11 (s, 1H), 11.17 (br s, 1H).

EXAMPLE 170

2-chloro-N-{3-[2,2,2-trifluoro-1-(1-methyl-1H-imidazol-5-yl)ethoxy]quinoxalin-2-yl}benzenesulfonamide (Compound 175)

According to Example 167, by use of 60% sodium hydride (in oil) (24 mg, 0.59 mmol), tetrahydrofuran (2 mL), Compound DK (53 mg, 0.30 mmol) and 2-chloro-N-(3-chloroquinoxalin-2-yl)benzenesulfonamide (Compound AD) (70 mg, 0.20 mmol), the mixture was stirred and reacted at 60° C. for 4 hours. Then, slurry purification was performed using methanol, to give 2-chloro-N-{3-[2,2,2-trifluoro-1-(1-methyl-1H-imidazol-5-yl) ethoxy]quinoxalin-2-yl}benzenesulfonamide (Compound 175) (54 mg, yield: 56%).

ESIMS m/z: 498 (M+H)⁺; ¹H-NMR (270 MHz, DMSO-d₆, δ): 3.92 (s, 3H), 7.15 (q, J=6.8 Hz, 1H), 7.39-7.68 (m, 8H), 8.03 (s, 1H), 8.26-8.35 (m, 1H).

EXAMPLE 171

2-chloro-N-{3-[2-methyl-3-(pyridin-3-yl)propoxy]quinoxalin-2-yl}benzenesulfonamide (Compound 176)

According to Example 167, by use of 60% sodium hydride (in oil) (26 mg, 0.66 mmol), tetrahydrofuran (2 mL), Compound EM (51 mg, 0.34 mmol) and 2-chloro-N-(3-chloroquinoxalin-2-yl)benzenesulfonamide (Compound AD) (80 mg, 0.22 mmol), the mixture was stirred and reacted at room temperature for 2 hours. After purification by silica gel column chromatography (hexane/ethyl acetate=1/0 to 1/1), slurry purification was further performed using isopropyl ether, to give 2-chloro-N-{3-[2-methyl-3-(pyridin-3-yl)propoxy]quinoxalin-2-yl}benzenesulfonamide (Compound 176) (22 mg, yield: 21%).

ESIMS m/z: 469 (M+H)⁺; ¹H-NMR (270 MHz, DMSO-d₆, δ): 0.98 (d, J=6.6 Hz, 3H), 2.24-2.68 (m, 2H), 2.87-3.02 (m, 1H), 4.28 (d, J=5.6 Hz, 2H), 7.27-7.73 (m, 9H), 8.29-8.51 (m, 3H).

EXAMPLE 172

2-chloro-N-{3-[3-(pyridin-3-yl)butoxy]quinoxalin-2-yl}-benzenesulfonamide (Compound 177)

According to Example 167, by use of 60% sodium hydride (in oil) (26 mg, 0.66 mmol), tetrahydrofuran (2 mL), Compound EN (51 mg, 0.34 mmol) and 2-chloro-N-(3-chloroquinoxalin-2-yl)benzenesulfonamide (Compound AD) (80 mg, 0.22 mmol), the mixture was stirred and reacted at room temperature for 2 hours. Then, purification by silica gel column chromatography (hexane/ethyl acetate=1/0 to 1/1) was performed to give 2-chloro-N-{3-[3-(pyridin-3-yl)butoxy]quinoxalin-2-yl}-benzenesulfonamide (Compound 177) (51 mg, yield: 49%).

ESIMS m/z: 469 (M+H)⁺; ¹H-NMR (270 MHz, DMSO-d₆, δ): 1.29 (d, J=6.9 Hz, 3H), 2.02-2.25 (m, 2H), 3.01-3.18 (m, 1H), 4.17-4.44 (m, 2H), 7.28-7.77 (m, 9H), 8.28-8.51 (m, 3H).

EXAMPLE 173

3,5-dimethyl-N-{3-[2,2,2-trifluoro-1-(thiazol-5-yl)ethoxy]-quinoxalin-2-yl}isoxazole-4-sulfonamide (Compound 178)

According to Example 167, by use of 60% sodium hydride (in oil) (24 mg, 0.60 mmol), tetrahydrofuran (2 mL), Compound DL (57 mg, 0.30 mmol) and N-(3-chloroquinoxalin-2-yl)-3,5-dimethylisoxazole-4-sulfonamide (Compound AG) (70 mg, 0.20 mmol), the mixture was stirred and reacted at 60° C. for 3 hours. Then, purification by silica gel column chromatography (chloroform/methanol=1/0 to 33/1) was performed to give 3,5-dimethyl-N-{3-[2,2,2-trifluoro-1-(thiazol-5-yl)ethoxy]-quinoxalin-2-yl}isoxazole-4-sulfonamide (Compound 178) (9.8 mg, yield: 10%).

ESIMS m/z: 486 (M+H)⁺; ¹H-NMR (270 MHz, CDCl₃, δ): 1.56 (s, 3H), 2.53 (s, 3H), 7.37-8.04 (m, 5H), 8.23 (s, 1H), 8.92 (s, 1H).

EXAMPLE 174

N-{3-[2,2,2-trifluoro-1-(pyridin-3-yl)ethoxy]quinoxalin-2-yl}propane-1-sulfonamide (Compound 179)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FS (25 mg, 0.21 mmol) and potassium carbonate (28 mg, 0.21 mmol), the mixture was stirred and reacted at 150° C. for 0.5 hour. Thus, N-{3-[2,2,2-trifluoro-1-(pyridin-3-yl)ethoxy]quinoxalin-2-yl}propane-1-sulfonamide (Compound 179) (28 mg, yield: 33%) was obtained.

ESIMS m/z: 427 (M+H)$^+$; $^1$H-NMR (270 MHz, DMSO-d$_6$, δ): 1.01 (t, J=7.5 Hz, 3H), 1.76-1.88 (m, 2H), 3.73 (br s, 2H), 7.20 (q, J=6.7 Hz, 1H), 7.53 (dd, J=4.8, 7.7 Hz, 1H), 7.56-7.77 (m, 3H), 7.78-7.88 (m, 1H), 8.33 (d, J=7.7 Hz, 1H), 8.65 (dd, J=1.5, 4.8 Hz, 1H), 9.09 (s, 1H), 11.38 (br s, 1H).

EXAMPLE 175

2-methyl-N-{3-[2,2,2-trifluoro-1-(pyridin-3-yl)ethoxy]-quinoxalin-2-yl}propane-1-sulfonamide (Compound 180)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FT (28 mg, 0.21 mmol) and potassium carbonate (28 mg, 0.21 mmol), the mixture was stirred and reacted at 150° C. for 0.5 hour. Thus, 2-methyl-N-{3-[2,2,2-trifluoro-1-(pyridin-3-yl)ethoxy]-quinoxalin-2-yl}propane-1-sulfonamide (Compound 180) (47 mg, yield: 52%) was obtained.

ESIMS m/z: 441 (M+H)$^+$; $^1$H-NMR (270 MHz, DMSO-d$_6$, δ): 1.08 (dd, J=6.8, 12.6 Hz, 6H), 2.19-2.37 (m, 1H), 3.56-3.79 (m, 2H), 7.20 (q, J=7.1 Hz, 1H), 7.53 (dd, J=4.8, 7.7 Hz, 1H), 7.56-7.88 (m, 4H), 8.34 (d, J=7.7 Hz, 1H), 8.66 (d, J=4.8 Hz, 1H), 9.09 (s, 1H), 11.41 (br s, 1H).

EXAMPLE 176

3-chloro-N-{3-[2,2,2-trifluoro-1-(pyridin-3-yl)ethoxy]-quinoxalin-2-yl}benzenesulfonamide (Compound 181)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FU (39 mg, 0.21 mmol) and potassium carbonate (28 mg, 0.21 mmol), the mixture was stirred and reacted at 150° C. for 1 hour. Thus, 3-chloro-N-{3-[2,2,2-trifluoro-1-(pyridin-3-yl)ethoxy]-quinoxalin-2-yl}benzenesulfonamide (Compound 181) (70 mg, yield: 70%) was obtained.

ESIMS m/z: 495 (M+H)$^+$; $^1$H-NMR (270 MHz, DMSO-d$_6$, δ): 7.16 (q, J=7.0 Hz, 1H), 7.48-7.80 (m, 7H), 8.15 (d, J=8.1 Hz, 1H), 8.24 (t, J=1.5 Hz, 1H), 8.28 (d, J=8.1 Hz, 1H), 8.65 (dd, J=1.5, 4.8 Hz, 1H), 9.06 (d, J=1.5 Hz, 1H).

EXAMPLE 177

4-chloro-N-{3-[2,2,2-trifluoro-1-(pyridin-3-yl)ethoxy]-quinoxalin-2-yl}benzenesulfonamide (Compound 182)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FV (39 mg, 0.21 mmol) and potassium carbonate (28 mg, 0.21 mmol), the mixture was stirred and reacted at 150° C. for 1 hour. Thus, 4-chloro-N-{3-[2,2,2-trifluoro-1-(pyridin-3-yl)ethoxy]-quinoxalin-2-yl}benzenesulfonamide (Compound 182) (59 mg, yield: 58%) was obtained.

ESIMS m/z: 495 (M+H)$^+$; $^1$H-NMR (270 MHz, DMSO-d$_6$, δ): 7.17 (q, J=7.0 Hz, 1H), 7.48-7.83 (m, 7H), 8.22 (d, J=8.8 Hz, 2H), 8.29 (d, J=7.7 Hz, 1H), 8.65 (dd, J=1.5, 4.8 Hz, 1H), 9.06 (d, J=1.5 Hz, 1H).

EXAMPLE 178

N-{3-[2,2,2-trifluoro-1-(pyridin-3-yl)ethoxy]quinoxalin-2-yl}cyclohexanesulfonamide (Compound 183)

According to Example 140, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FW (34 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}cyclohexanesulfonamide (Compound 183) (52 mg, yield: 54%) was obtained.

ESIMS m/z: 467 (M+H)$^+$; $^1$H-NMR (270 MHz, DMSO-d$_6$, δ): 1.13-1.41 (m, 3H), 1.47-1.69 (m, 3H), 1.76-1.93 (m, 2H), 2.06-2.27 (m, 2H), 7.19 (q, J=7.1 Hz, 1H), 7.53 (dd, J=4.8, 7.7 Hz, 1H), 7.56-7.75 (m, 3H), 7.80-7.89 (m, 1H), 8.34 (d, J=7.7 Hz, 1H), 8.65 (dd, J=1.5, 4.8 Hz, 1H), 9.09 (s, 1H), 11.31 (br s, 1H).

EXAMPLE 179

5-chloro-1,3-dimethyl-N-[3-(2,2,2-trifluoro-1-phenyl-ethoxy)quinoxalin-2-yl]-1H-pyrazole-4-sulfonamide (Compound 184)

According to Example 167, by use of 60% sodium hydride (in oil) (23 mg, 0.56 mmol), tetrahydrofuran (2 mL), α-(trifluoromethyl)benzyl alcohol (50 mg, 0.28 mmol) and 5-chloro-N-(3-chloroquinoxalin-2-yl)-1,3-dimethyl-1H-pyrazole-4-sulfonamide (Compound AF) (70 mg, 0.19 mmol), the mixture was stirred and reacted at 60° C. for 6 hours. After purification by silica gel column chromatography (hexane/ethyl acetate=1/0 to 1/1), slurry purification was further performed using methanol, to give 5-chloro-1,3-dimethyl-N-[3-(2,2,2-trifluoro-1-phenyl-ethoxy)quinoxalin-2-yl]-1H-pyrazole-4-sulfonamide (Compound 184) (16 mg, yield: 17%).

ESIMS m/z: 512 (M+H)$^+$; $^1$H-NMR (270 MHz, DMSO-d$_6$, δ): 2.50 (s, 3H), 3.73 (s, 3H), 7.04 (q, J=7.3 Hz, 1H), 7.39-7.73 (m, 7H), 7.82-7.95 (m, 2H), 12.24 (br s, 1H).

EXAMPLE 180

3,5-dimethyl-N-[3-(2,2,2-trifluoro-1-phenylethoxy)-quinoxalin-2-yl]isoxazole-4-sulfonamide (Compound 185)

According to Example 167, by use of 60% sodium hydride (in oil) (25 mg, 0.62 mmol), tetrahydrofuran (2 mL), α-(trifluoromethyl)benzyl alcohol (55 mg, 0.31 mmol) and N-(3-chloroquinoxalin-2-yl)-3,5-dimethylisoxazole-4-sulfonamide (Compound AG) (70 mg, 0.21 mmol), the mixture was stirred and reacted at 60° C. for 6 hours. After purification by silica gel column chromatography (hexane/ethyl acetate=1/0 to 1/1), slurry purification was further performed using methanol, to give 3,5-dimethyl-N-[3-(2,2,2-trifluoro-1-phenylethoxy)-quinoxalin-2-yl]isoxazole-4-sulfonamide (Compound 185) (21 mg, yield: 21%).

ESIMS m/z: 479 (M+H)⁺; ¹H-NMR (270 MHz, DMSO-d₆, δ): 2.49 (s, 3H), 2.84 (s, 3H), 7.03 (q, J=7.2 Hz, 1H), 7.39-7.73 (m, 7H), 7.80-7.90 (m, 2H).

EXAMPLE 181

5-chloro-1,3-dimethyl-N-{3-[2,2,2-trifluoro-1-(thiazol-5-yl)ethoxy]quinoxalin-2-yl}-1H-pyrazole-4-sulfonamide (Compound 186)

According to Example 167, by use of 60% sodium hydride (in oil) (30 mg, 0.75 mmol), tetrahydrofuran (2 mL), Compound DL (103 mg, 0.56 mmol) and 5-chloro-N-(3-chloroquinoxalin-2-yl)-1,3-dimethyl-1H-pyrazole-4-sulfonamide (Compound AF) (70 mg, 0.19 mmol), the mixture was stirred and reacted at 50° C. for 5 hours. After purification by silica gel column chromatography (chloroform/methanol=1/0 to 33/1), slurry purification was further performed using methanol, to give 5-chloro-1,3-dimethyl-N-{3-[2,2,2-trifluoro-1-(thiazol-5-yl)ethoxy]quinoxalin-2-yl}-1H-pyrazole-4-sulfonamide (Compound 186) (36 mg, yield: 37%).

ESIMS m/z: 519 (M+H)⁺; ¹H-NMR (270 MHz, DMSO-d₆, δ): 2.48 (s, 3H), 3.75 (s, 3H), 7.50-7.78 (m, 5H), 8.41 (s, 1H), 9.24 (s, 1H), 12.20 (br s, 1H).

EXAMPLE 182

N-{3-[2,2,2-trifluoro-1-(pyridin-3-yl)ethoxy]quinoxalin-2-yl}butane-2-sulfonamide (Compound 187)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FX (28 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}butane-2-sulfonamide (Compound 187) (18 mg, yield: 20%) was obtained.

ESIMS m/z: 441 (M+H)⁺; ¹H-NMR (270 MHz, DMSO-d₆, δ): 0.92-1.12 (m, 3H), 1.30-1.44 (m, 3H), 1.50-1.75 (m, 1H), 1.93-2.16 (m, 1H), 3.92-4.18 (m, 1H), 7.20 (q, J=7.1 Hz, 1H), 7.47-7.87 (m, 5H), 8.27-8.44 (m, 1H), 8.65 (d, J=3.3 Hz, 1H), 9.09 (s, 1H).

EXAMPLE 183

N-{3-[2,2,2-trifluoro-1-(pyridin-3-yl)ethoxy]quinoxalin-2-yl}morpholine-4-sulfonamide (Compound 188)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FY (34 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}morpholine-4-sulfonamide (Compound 188) (46 mg, yield: 48%) was obtained.

ESIMS m/z: 470 (M+H)⁺; ¹H-NMR (270 MHz, CDCl₃, δ): 3.21-3.36 (m, 2H), 3.56-3.69 (m, 2H), 3.76-3.89 (m, 4H), 6.82 (q, J=6.5 Hz, 1H), 7.32-7.84 (m, 5H), 7.91-8.03 (m, 1H), 8.68 (d, J=4.0 Hz, 1H), 8.89 (s, 1H), 11.22 (br s, 1H).

EXAMPLE 184

N-cyclopropyl-N'-{3-[2,2,2-trifluoro-1-(pyridin-3-yl)-ethoxy]quinoxalin-2-yl}sulfuric diamide (Compound 189)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound FZ (28 mg, 0.21 mmol) and potassium carbonate (28 mg, 0.21 mmol), the mixture was stirred and reacted at 150° C. for 1 hour. Thus, N-cyclopropyl-N'-{3-[2,2,2-trifluoro-1-(pyridin-3-yl)-ethoxy]quinoxalin-2-yl}sulfuric diamide (Compound 189) (32 mg, yield: 35%) was obtained.

ESIMS m/z: 440 (M+H)⁺; ¹H-NMR (270 MHz, CDCl₃, δ): 0.63-0.91 (m, 4H), 2.34-2.47 (m, 1H), 6.09 (s, 1H), 6.83 (q, J=6.8 Hz, 1H), 7.40 (dd, J=4.0, 7.7 Hz, 1H), 7.50-8.03 (m, 5H), 8.69 (d, J=4.0 Hz, 1H), 8.90 (s, 1H).

EXAMPLE 185

N-{3-[2,2,2-trifluoro-1-(pyridin-3-yl)ethoxy]quinoxalin-2-yl}ethanesulfonamide (Compound 190)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound GA (22 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}ethanesulfonamide (Compound 190) (32 mg, yield: 38%) was obtained.

ESIMS m/z: 413 (M+H)⁺; ¹H-NMR (270 MHz, DMSO-d₆, δ): 1.33 (t, J=7.3 Hz, 3H), 1.53 (br s, 2H), 7.20 (q, J=7.0 Hz, 1H), 7.53 (dd, J=4.8, 7.9 Hz, 1H), 7.57-7.77 (m, 3H), 7.79-7.87 (m, 1H), 8.34 (d, J=7.0 Hz, 1H), 8.66 (dd, J=1.5, 4.8 Hz, 1H), 9.10 (s, 1H), 11.38 (br s, 1H).

EXAMPLE 186

N-{3-[2,2,2-trifluoro-1-(pyridin-3-yl)ethoxy]quinoxalin-2-yl}butane-1-sulfonamide (Compound 191)

According to Example 132, by use of 2-chloro-3-[2,2,2-trifluoro-1-(pyridin-3-yl)ethoxy]-quinoxaline (Compound BJ) (70 mg, 0.21 mmol), dimethyl sulfoxide (2 mL), Compound GB (28 mg, 0.21 mmol) and potassium carbonate (28 mg, 0.21 mmol), the mixture was stirred and reacted at 150° C. for 1 hour. Thus, N-{3-[2,2,2-trifluoro-1-(pyridin-3-yl)ethoxy]quinoxalin-2-yl}butane-1-sulfonamide (Compound 191) (31 mg, yield: 34%) was obtained.

ESIMS m/z: 441 (M+H)⁺; ¹H-NMR (270 MHz, DMSO-d₆, δ): 0.87 (t, J=7.3 Hz, 3H), 1.36-1.52 (m, 2H), 1.70-1.86 (m, 2H), 3.76 (br s, 2H), 7.20 (q, J=6.8 Hz, 1H), 7.53 (dd, J=4.8, 8.1 Hz, 1H), 7.57-7.77 (m, 3H), 7.79-7.87 (m, 1H), 8.34 (d, J=7.3 Hz, 1H), 8.66 (dd, J=1.8, 4.8 Hz, 1H), 9.09 (s, 1H), 11.39 (br s, 1H).

EXAMPLE 187

N-{3-[2,2,2-trifluoro-1-(6-methylpyridin-3-yl)ethoxy]-quinoxalin-2-yl}propane-1-sulfonamide (Compound 192)

According to Example 132, by use of 2-chloro-3-[2,2,2-trifluoro-1-(6-methylpyridin-3-yl)-ethoxy]quinoxaline (Compound BM) (77 mg, 0.19 mmol), dimethyl sulfoxide (2 mL), Compound FS (37 mg, 0.19 mmol) and potassium carbonate (26 mg, 0.19 mmol), the mixture was stirred and reacted at 150° C. for 2 hours. After purification by silica gel column chromatography (hexane/ethyl acetate=1/0 to 1/1), slurry purification was further performed using methanol, to give N-{3-[2,2,2-trifluoro-1-(6-methylpyridin-3-yl)ethoxy]-quinoxalin-2-yl}propane-1-sulfonamide (Compound 192) (41 mg, 39%).

ESIMS m/z: 441 (M+H)$^+$; $^1$H-NMR (270 MHz, DMSO-d$_6$, δ): 1.03 (t, J=7.2 Hz, 3H), 1.76-1.90 (m, 2H), 3.73 (br s, 2H), 7.14 (q, J=6.8 Hz, 1H), 7.39 (d, J=7.9 Hz, 1H), 7.54-7.90 (m, 4H), 8.21 (d, J=7.9 Hz, 1H), 8.94 (s, 1H), 11.43 (br s, 1H).

EXAMPLE 188

2,2,2-trifluoro-N-{3-[2,2,2-trifluoro-1-(pyridin-3-yl)-ethoxy]quinoxalin-2-yl}ethanesulfonamide (Compound 193)

According to Example 132, by use of 2-chloro-3-[2,2,2-trifluoro-1-(pyridin-3-yl)ethoxy]-quinoxaline (Compound BJ) (34 mg, 0.21 mmol), dimethyl sulfoxide (2 mL), Compound GC (34 mg, 0.21 mmol) and potassium carbonate (28 mg, 0.21 mmol), the mixture was stirred and reacted at 150° C. for 1 hour. After purification by silica gel column chromatography (chloroform/methanol=1/0 to 10/1), slurry purification was further performed using methanol, to give 2,2,2-trifluoro-N-{3-[2,2,2-trifluoro-1-(pyridin-3-yl)-ethoxy]quinoxalin-2-yl}ethanesulfonamide (Compound 193) (7.2 mg, 8%).

ESIMS m/z: 467 (M+H)$^+$; $^1$H-NMR (270 MHz, CDCl$_3$, δ): 4.38 (br s, 2H), 6.76 (q, J=6.8 Hz, 1H), 7.40 (dd, J=4.8, 8.1 Hz, 1H), 7.48-8.04 (m, 5H), 8.68 (dd, J=1.8, 4.8 Hz, 1H), 8.88 (d, J=1.8 Hz, 1H).

EXAMPLE 189

N-propyl-N'-{3-[2,2,2-trifluoro-1-(pyridin-3-yl)ethoxy]-quinoxalin-2-yl}sulfuric diamide (Compound 194)

According to Example 132, by use of 2-chloro-3-[2,2,2-trifluoro-1-(pyridin-3-yl)ethoxy]-quinoxaline (Compound BJ) (73 mg, 0.21 mmol), dimethyl sulfoxide (2 mL), Compound GD (28 mg, 0.21 mmol) and potassium carbonate (28 mg, 0.21 mmol), the mixture was stirred and reacted at 150° C. for 1 hour. After purification by silica gel column chromatography (chloroform/methanol=1/0 to 15/1), slurry purification was further performed using methanol, to give N-propyl-N'-{3-[2,2,2-trifluoro-1-(pyridin-3-yl)ethoxy]-quinoxalin-2-yl}sulfuric diamide (Compound 194) (19 mg, 21%).

ESIMS m/z: 442 (M+H)$^+$; $^1$H-NMR (270 MHz, CDCl$_3$, δ): 0.93 (t, J=7.1 Hz, 3H), 1.53-1.69 (m, 2H), 3.09 (q, J=7.1 Hz, 2H), 5.69 (t, J=6.3 Hz, 1H), 6.82 (q, J=6.7 Hz, 1H), 7.40 (dd, J=4.8, 8.1 Hz, 1H), 7.47-7.93 (m, 4H), 7.96 (d, J=8.1 Hz, 1H), 8.69 (dd, J=1.5, 4.8 Hz, 1H), 8.89, (d, J=1.5 Hz, 1H).

EXAMPLE 190

N-ethyl-N'-{3-[2,2,2-trifluoro-1-(pyridin-3-yl)ethoxy]-quinoxalin-2-yl}sulfuric diamide (Compound 195)

According to Example 140, by use of 2-chloro-3-[2,2,2-trifluoro-1-(pyridin-3-yl)ethoxy]-quinoxaline (Compound BJ) (73 mg, 0.21 mmol), dimethyl sulfoxide (2 mL), Compound GE (26 mg, 0.21 mmol) and potassium carbonate (28 mg, 0.21 mmol), the mixture was stirred and reacted at 150° C. for 1 hour. After purification by silica gel column chromatography (chloroform/methanol=1/0 to 20/1), slurry purification was further performed using methanol, to give N-ethyl-N'-{3-[2,2,2-trifluoro-1-(pyridin-3-yl)ethoxy]-quinoxalin-2-yl}sulfuric diamide (Compound 195) (38 mg, 23%).

ESIMS m/z: 428 (M+H)$^+$; $^1$H-NMR (270 MHz, CDCl$_3$, δ): 1.21 (t, J=7.2 Hz, 3H), 3.19 (quin, J=7.1 Hz, 2H), 5.64 (t, J=5.9 Hz, 1H), 6.82 (q, J=6.6 Hz, 1H), 7.40 (dd, J=4.9, 7.9 Hz, 1H), 7.48-7.87 (m, 4H), 7.96 (d, J=7.9 Hz, 1H), 8.68 (dd, J=1.6, 4.9 Hz, 1H), 8.89 (d, J=1.6 Hz, 1H).

EXAMPLE 191

N-{3-[1-(2-chlorothiazol-5-yl)-2,2,2-trifluoroethoxy]-quinoxalin-2-yl}propane-1-sulfonamide (Compound 196)

According to Example 140, by use of 2-chloro-5-[1-(3-chloroquinoxalin-2-yloxy)-2,2,2-trifluoroethyl]thiazole (Compound BL) (70 mg, 0.18 mmol), dimethyl sulfoxide (2 mL), Compound FS (24 mg, 0.18 mmol) and potassium carbonate (26 mg, 0.18 mmol), the mixture was stirred and reacted at 150° C. for 2 hours. Then, purification by silica gel column chromatography (hexane/ethyl acetate=1/0 to 3/1) was performed to give N-{3-[1-(2-chlorothiazol-5-yl)-2,2,2-trifluoroethoxy]-quinoxalin-2-yl}propane-1-sulfonamide (Compound 196) (22 mg, 26%).

ESIMS m/z: 467 (M+H)$^+$; $^1$H-NMR (270 MHz, CDCl$_3$, δ): 1.12 (t, J=7.4 Hz, 3H), 1.90-2.08 (m, 2H), 3.72-3.83 (m, 2H), 7.10 (q, J=6.4 Hz, 1H), 7.50-7.97 (m, 5H), 11.56 (br s, 1H).

EXAMPLE 192

N-{3-[1-(4-((dimethylamino)methyl)phenyl)-2,2,2-trifluoroethoxy]quinoxalin-2-yl}propane-1-sulfonamide (Compound 197)

According to Example 140, by use of 1-{4-[1-(3-chloroquinoxalin-2-yloxy)-2,2,2-trifluoroethyl]-phenyl}-N,N-dimethylmethanamine (Compound BN) (90 mg, 0.23 mmol), dimethyl sulfoxide (2.6 mL), Compound FS (28 mg, 0.23 mmol) and potassium carbonate (31 mg, 0.23 mmol), the mixture was stirred and reacted at 150° C. for 4 hours. After purification by silica gel column chromatography (chloroform/methanol=1/0 to 1/1), purification by preparative HPLC (acetonitrile/water system) was further performed to give N-{3-[1-(4-((dimethylamino)methyl)phenyl)-2,2,2-trifluoroethoxy]quinoxalin-2-yl}propane-1-sulfonamide (Compound 197) (13 mg, 12%).

ESIMS m/z: 483 (M+H)$^+$; $^1$H-NMR (270 MHz, DMSO-d$_6$, δ): 1.03 (t, J=7.3 Hz, 3H), 1.75-1.90 (m, 2H), 2.69 (s, 6H), 4.29 (s, 2H), 7.14 (q, J=6.8 Hz, 1H), 7.55-8.06 (m, 8H), 10.39 (br s, 1H).

EXAMPLE 193

N-{3-[1-(2-chlorothiazol-5-yl)-2,2,2-trifluoroethoxy]-quinoxalin-2-yl}-3,5-dimethylisoxazole-4-sulfonamide (Compound 198)

According to Example 140, by use of 2-chloro-5-[1-(3-chloroquinoxalin-2-yloxy)-2,2,2-trifluoroethyl]thiazole (Compound BL) (70 mg, 0.18 mmol), dimethyl sulfoxide (2 mL), Compound FC (32 mg, 0.18 mmol) and potassium carbonate (26 mg, 0.18 mmol), the mixture was stirred and reacted at 150° C. for 2 hours. Then, purification by silica gel column chromatography (hexane/ethyl acetate=1/0 to 1/1) was performed to give N-{3-[1-(2-chlorothiazol-5-yl)-2,2,2-trifluoroethoxy]-quinoxalin-2-yl}-3,5-dimethylisoxazole-4-sulfonamide (Compound 198) (32 mg, 34%).

ESIMS m/z: 520 (M+H)$^+$; $^1$H-NMR (270 MHz, CDCl$_3$, δ): 1.61 (s, 3H), 2.93 (s, 3H), 7.10 (q, J=6.6 Hz, 1H), 7.51-7.10 (m, 5H), 11.52 (br s, 1H).

EXAMPLE 194

5-chloro-N-{3-[1-(2-chlorothiazol-5-yl)-2,2,2-trifluoroethoxy]quinoxalin-2-yl}-1,3-dimethyl-1H-pyrazole-4-sulfonamide (Compound 199)

According to Example 140, by use of 2-chloro-5-[1-(3-chloroquinoxalin-2-yloxy)-2,2,2-trifluoroethyl]thiazole (Compound BL) (120 mg, 0.31 mmol), dimethyl sulfoxide (3.4 mL), Compound FB (66 mg, 0.31 mmol) and potassium carbonate (43 mg, 0.31 mmol), the mixture was stirred and reacted at 150° C. for 2 hours. After purification by silica gel column chromatography (hexane/ethyl acetate=1/0 to 1/1), slurry purification was further performed using hexane, to give 5-chloro-N-{3-[1-(2-chlorothiazol-5-yl)-2,2,2-trifluoroethoxy]quinoxalin-2-yl}-1,3-dimethyl-1H-pyrazole-4-sulfonamide (Compound 199) (29 mg, 17%).

ESIMS m/z: 534 (M+H)$^+$; $^1$H-NMR (270 MHz, DMSO-d$_6$, δ): 2.49 (s, 3H), 3.74 (s, 3H), 7.50-7.84 (m, 5H), 8.23 (s, 1H), 12.15 (br s, 1H).

EXAMPLE 195

5-chloro-N-{3-[1-(4-cyanophenyl)-2,2,2-trifluoroethoxy]-quinoxalin-2-yl}-1,3-dimethyl-1H-pyrazole-4-sulfonamide (Compound 200)

According to Example 140, by use of 4-[1-(3-chloroquinoxalin-2-yloxy)-2,2,2-trifluoroethyl]-benzonitrile (Compound BO) (100 mg, 0.27 mmol), dimethyl sulfoxide (2.8 mL), Compound FB (58 mg, 0.27 mmol) and potassium carbonate (37 mg, 0.27 mmol), the mixture was stirred and reacted at 150° C. for 2 hours. After purification by silica gel column chromatography (hexane/ethyl acetate=1/0 to 3/1), slurry purification was further performed using methanol, to give 5-chloro-N-{3-[1-(4-cyanophenyl)-2,2,2-trifluoroethoxy]-quinoxalin-2-yl}-1,3-dimethyl-1H-pyrazole-4-sulfonamide (Compound 200) (32 mg, 22).

ESIMS m/z: 537 (M+H)$^+$; $^1$H-NMR (270 MHz, DMSO-d$_6$, δ): 2.52 (s, 3H), 3.75 (s, 3H), 7.23 (q, J=6.8 Hz, 1H), 7.49-7.77 (m, 4H), 7.95-8.23 (m, 4H), 12.24 (br s, 1H).

EXAMPLE 196

N-{3-[1-(4-cyanophenyl)-2,2,2-trifluoroethoxy]quinoxalin-2-yl}-3,5-dimethylisoxazole-4-sulfonamide (Compound 201)

According to Example 140, by use of 4-[1-(3-chloroquinoxalin-2-yloxy)-2,2,2-trifluoroethyl]-benzonitrile (Compound BO) (100 mg, 0.27 mmol), dimethyl sulfoxide (2.8 mL), Compound FC (48 mg, 0.27 mmol) and potassium carbonate (37 mg, 0.27 mmol), the mixture was stirred and reacted at 150° C. for 2 hours. After purification by silica gel column chromatography (hexane/ethyl acetate=1/0 to 4/1), slurry purification was further performed using methanol, to give N-{3-[1-(4-cyanophenyl)-2,2,2-trifluoroethoxy]quinoxalin-2-yl}-3,5-dimethylisoxazole-4-sulfonamide (Compound 201) (27 mg, 20%).

ESIMS m/z: 504 (M+H)$^+$; $^1$H-NMR (270 MHz, DMSO-d$_6$, δ): 2.52 (s, 3H), 2.85 (s, 3H), 7.21 (q, J=6.8 Hz, 1H), 7.52-7.74 (m, 4H), 7.95-8.15 (m, 4H).

EXAMPLE 197

N-{3-[1-(4-cyanophenyl)-2,2,2-trifluoroethoxy]quinoxalin-2-yl}propane-1-sulfonamide (Compound 202)

According to Example 140, by use of 4-[1-(3-chloroquinoxalin-2-yloxy)-2,2,2-trifluoroethyl]-benzonitrile (Compound BO) (100 mg, 0.27 mmol), dimethyl sulfoxide (2.8 mL), Compound FS (37 mg, 0.27 mmol) and potassium carbonate (37 mg, 0.27 mmol), the mixture was stirred and reacted at 150° C. for 2 hours. Then, purification by silica gel column chromatography (hexane/ethyl acetate=1/0 to 5/1) was performed to give N-{3-[1-(4-cyanophenyl)-2,2,2-trifluoroethoxy]quinoxalin-2-yl}propane-1-sulfonamide (Compound 202) (27 mg, 22%).

ESIMS m/z: 451 (M+H)$^+$; $^1$H-NMR (270 MHz, DMSO-d$_6$, δ): 1.02 (t, J=7.6 Hz, 3H), 1.73-1.93 (m, 2H), 3.64-3.84 (m, 2H), 7.23 (q, J=6.7 Hz, 1H), 7.52-7.74 (m, 3H), 7.80-7.88 (m, 1H), 7.94-8.04 (m, 2H), 8.07-8.19 (m, 2H), 11.45 (br s, 1H).

EXAMPLE 198

5-chloro-N-{3-[1-(4-((dimethylamino)methyl)phenyl)-2,2,2-trifluoroethoxy]quinoxalin-2-yl}-1,3-dimethyl-1H-pyrazole-4-sulfonamide (Compound 203)

According to Example 140, by use of 1-{4-[1-(3-chloroquinoxalin-2-yloxy)-2,2,2-trifluoroethyl]-phenyl}-N,N-dimethylmethanamine (Compound BN) (90 mg, 0.23 mmol), dimethyl sulfoxide (2.6 mL), Compound FB (48 mg, 0.23 mmol) and potassium carbonate (31 mg, 0.23 mmol), the mixture was stirred and reacted at 150° C. for 3.5 hours. Then, purification by preparative HPLC (acetonitrile/water system) was performed to give 5-chloro-N-{3-[1-(4-((dimethylamino)methyl)phenyl)-2,2,2-trifluoroethoxy]quinoxalin-2-yl}-1,3-dimethyl-1H-pyrazole-4-sulfonamide (Compound 203) (40 mg, 31%).

ESIMS m/z: 570 (M+H)$^+$; $^1$H-NMR (270 MHz, CDCl$_3$, δ): 2.64 (s, 3H), 2.75 (s, 6H), 3.78 (s, 3H), 4.17 (s, 2H), 6.79 (br s, 1H), 7.45-7.78 (m, 8H).

ESIMS m/z: 570 (M+H)$^+$; $^1$H-NMR (270 MHz, CDCl$_3$, δ): 2.64 (s, 3H), 2.75 (s, 6H), 3.78 (s, 3H), 4.17 (s, 2H), 6.79 (br s, 1H), 7.45-7.78 (m, 8H).

EXAMPLE 199

N-{3-[1-(4-((dimethylamino)methyl)phenyl)-2,2,2-trifluoroethoxy]quinoxalin-2-yl}-3,5-dimethylisoxazole-4-sulfonamide (Compound 204)

According to Example 140, by use of 1-{4-[1-(3-chloroquinoxalin-2-yloxy)-2,2,2-trifluoroethyl]-phenyl}-N,N-dimethylmethanamine (Compound BN) (90 mg, 0.23 mmol), dimethyl sulfoxide (2.6 mL), Compound FC (40 mg, 0.23 mmol) and potassium carbonate (31 mg, 0.23 mmol), the mixture was stirred and reacted at 150° C. for 3.5 hours. Then, purification by preparative HPLC (acetonitrile/water system) was performed to give N-{3-[1-(4-((dimethylamino)methyl)phenyl)-2,2,2-trifluoroethoxy]quinoxalin-2-yl}-3,5-dimethylisoxazole-4-sulfonamide (Compound 204) (23 mg, 19%).

ESIMS m/z: 536 (M+H)⁺; ¹H-NMR (270 MHz, DMSO-d₆, δ): 2.52 (s, 3H), 2.69 (s, 6H), 2.85 (s, 3H), 4.28 (d, J=5.0 Hz, 2H), 7.12 (q, J=7.2 Hz, 1H), 7.52-7.75 (m, 6H), 7.96 (d, J=7.6 Hz, 2H), 10.31 (br s, 1H).

EXAMPLE 200

N-{3-[1-(4-((dimethylamino)methyl)phenyl)-2,2,2-trifluoroethoxy]quinoxalin-2-yl}-3,5-dimethylisoxazole-4-sulfonamide (Compound 205)

According to Example 144, by use of 2-chloro-3-[2,2,2-trifluoro-1-(pyridin-3-yl)ethoxy]-quinoxaline (Compound BJ) (100 mg, 0.29 mmol), dimethyl sulfoxide (2.8 mL), Compound GF (45 mg, 0.29 mmol) and potassium carbonate (41 mg, 0.29 mmol), the mixture was stirred and reacted at 150° C. for 1 hour. After purification by silica gel column chromatography (hexane/ethyl acetate=1/0 to 1/1), slurry purification was further performed using a mixed solvent of isopropyl ether and hexane, to give N-{3-[1-(4-((dimethylamino)methyl)phenyl)-2,2,2-trifluoroethoxy]quinoxalin-2-yl}-3,5-dimethylisoxazole-4-sulfonamide (Compound 205) (40 mg, 30%).

ESIMS m/z: 458 (M+H)⁺; ¹H-NMR (270 MHz, CDCl₃, δ): 3.16 (s, 3H), 3.31 (t, J=5.0 Hz, 2H), 3.49 (t, J=5.0 Hz, 2H), 6.20 (s, 1H), 6.82 (q, J=6.3 Hz, 1H), 7.40 (dd, J=4.6, 7.9 Hz, 1H), 7.47-7.63 (m, 2H), 7.65-7.88 (m, 2H), 7.97 (d, J=7.9 Hz, 1H), 8.68 (dd, J=1.7, 4.6 Hz, 1H), 8.90 (d, J=1.7 Hz, 1H).

EXAMPLE 201

N-{3-[2,2,2-trifluoro-1-(pyridin-3-yl)ethoxy]quinoxalin-2-yl}-N'-(3-methoxypropyl)-sulfuric diamide (Compound 206)

According to Example 144, by use of 2-chloro-3-[2,2,2-trifluoro-1-(pyridin-3-yl)ethoxy]-quinoxaline (Compound BJ) (90 mg, 0.26 mmol), dimethyl sulfoxide (2.6 mL), Compound GG (45 mg, 0.26 mmol) and potassium carbonate (36 mg, 0.26 mmol), the mixture was stirred and reacted at 150° C. for 1 hour. After purification by silica gel column chromatography (hexane/ethyl acetate=1/0 to 1/1), slurry purification was further performed using a mixed solvent of isopropyl ether and hexane, to give N-{3-[2,2,2-trifluoro-1-(pyridin-3-yl)ethoxy]quinoxalin-2-yl}-N'-(3-methoxypropyl)-sulfuric diamide (Compound 206) (45 mg, 37%).

ESIMS m/z: 472 (M+H)⁺; ¹H-NMR (270 MHz, DMSO-d₆, δ): 1.66 (quin, J=6.1 Hz, 2H), 2.98-3.10 (m, 5H), 3.25 (t, J=6.1 Hz, 2H), 7.21 (q, J=6.3 Hz, 1H), 7.47-7.75 (m, 5H), 7.94 (d, J=7.3 Hz, 1H), 8.38 (d, J=8.3 Hz, 1H), 8.66 (dd, J=1.3, 4.6 Hz, 1H), 9.11 (s, 1H), 11.18 (br s, 1H).

EXAMPLE 202

N-{3-[2,2,2-trifluoro-1-(pyridin-3-yl)ethoxy]quinoxalin-2-yl}-N'-(2-ethoxyethyl)-sulfuric diamide (Compound 207)

According to Example 144, by use of 2-chloro-3-[2,2,2-trifluoro-1-(pyridin-3-yl)ethoxy]-quinoxaline (Compound BJ) (90 mg, 0.26 mmol), dimethyl sulfoxide (2.6 mL), Compound GH (45 mg, 0.26 mmol) and potassium carbonate (36 mg, 0.26 mmol), the mixture was stirred and reacted at 150° C. for 1 hour. After purification by silica gel column chromatography (hexane/ethyl acetate=1/0 to 1/1), slurry purification was further performed using a mixed solvent of isopropyl ether and hexane, to give N-{3-[2,2,2-trifluoro-1-(pyridin-3-yl)ethoxy]quinoxalin-2-yl}-N'-(2-ethoxyethyl)-sulfuric diamide (Compound 207) (48 mg, 39%).

ESIMS m/z: 472 (M+H)⁺; ¹H-NMR (270 MHz, DMSO-d₆, δ): 0.78 (t, J=6.9 Hz, 3H), 3.08-3.24 (m, 4H), 3.40 (t, J=5.6 Hz, 2H), 7.22 (q, J=7.0 Hz, 1H), 7.34-7.74 (m, 5H), 7.90 (d, J=7.6 Hz, 1H), 8.39 (d, J=7.6 Hz, 1H), 8.67 (d, J=4.6 Hz, 1H), 9.12 (s, 1H), 11.26 (br s, 1H).

EXAMPLE 203 tert-butyl 4-(N-{3-[2,2,2-trifluoro-1-(pyridin-3-yl)ethoxy]quinoxalin-2-yl}sulfamoyl)phenethylcarbamate (Compound 208)

According to Example 144, by use of 2-chloro-3-[2,2,2-trifluoro-1-(pyridin-3-yl)ethoxy]-quinoxaline (Compound BJ) (150 mg, 0.44 mmol), dimethyl sulfoxide (4.2 mL), Compound GI (132 mg, 0.44 mmol) and potassium carbonate (61 mg, 0.44 mmol), the mixture was stirred and reacted at 150° C. for 1.5 hours. After purification by silica gel column chromatography (hexane/ethyl acetate=1/0 to 1/1), slurry purification was further performed using methanol, to give tert-butyl 4-(N-{3-[2,2,2-trifluoro-1-(pyridin-3-yl)ethoxy]quinoxalin-2-yl}sulfamoyl)phenethylcarbamate (Compound 208) (176 mg, 67%).

ESIMS m/z: 604 (M+H)⁺; ¹H-NMR (270 MHz, DMSO-d₆, δ): 1.18 (s, 9H), 2.75 (t, J=6.6 Hz, 2H), 3.16 (q, J=6.6 Hz, 2H), 6.85 (s, 1H), 7.17 (q, J=6.8 Hz, 1H), 7.38-7.71 (m, 6H), 7.79 (d, J=7.2 Hz, 1H), 8.14 (d, J=7.9 Hz, 2H), 8.31 (d, J=7.2 Hz, 1H), 8.64 (d, J=4.6 Hz, 1H), 9.07 (s, 1H), 11.83 (br s, 1H).

EXAMPLE 204

4-(2-aminoethyl)-N-{3-[2,2,2-trifluoro-1-(pyridin-3-yl)-ethoxy]quinoxalin-2-yl}benzenesulfonamide (Compound 209)

tert-Butyl 4-(N-{3-[2,2,2-trifluoro-1-(pyridin-3-yl)ethoxy]quinoxalin-2-yl}sulfamoyl)phenethylcarbamate (Compound 208) was dissolved in dichloromethane (2 mL). To this, trifluoroacetic acid (2 mL) was added at room temperature and the mixture was stirred at room temperature for 24 hours. The solvent in the reaction mixture was evaporated off under reduced pressure, and purification by silica gel column chromatography (ethyl acetate/methanol=1/0 to 5/1) was performed to give 4-(2-aminoethyl)-N-{3-[2,2,2-trifluoro-1-(pyridin-3-yl)-ethoxy]quinoxalin-2-yl}benzenesulfonamide (Compound 209) (48 mg, 90%).

ESIMS m/z: 504 (M+H)⁺; ¹H-NMR (270 MHz, DMSO-d₆, δ): 2.87-2.98 (m, 2H), 3.00-3.14 (m, 2H), 7.16 (q, J=7.0 Hz, 1H), 7.46-7.89 (m, 9H), 8.18 (d, J=8.3 Hz, 2H), 8.29 (d, J=7.6 Hz, 1H), 8.64 (dd, J=1.7, 4.6 Hz, 1H), 9.06 (s, 1H).

EXAMPLE 205

N-{3-[2-methyl-1-(pyridin-3-yl)propoxy]quinoxalin-2-yl}-propane-1-sulfonamide (Compound 210)

According to Example 140, by use of 2-chloro-3-[2-methyl-1-(pyridin-3-yl)propoxy]quinoxaline (Compound BP) (160 mg, 0.51 mmol), dimethyl sulfoxide (4 mL), Compound FS (63 mg, 0.51 mmol) and potassium carbonate (70 mg, 0.51 mmol), the mixture was stirred and reacted at 150° C. for 2.5 hours. Then, purification by silica gel column chromatography (hexane/ethyl acetate=1/0 to 1/1) was performed to give N-{3-[2-methyl-1-(pyridin-3-yl)propoxy]quinoxalin-2-yl}-propane-1-sulfonamide (Compound 210) (104 mg, 51%).

ESIMS m/z: 401 (M+H)$^+$; $^1$H-NMR (270 MHz, DMSO-$d_6$, δ): 0.84 (d, J=6.9 Hz, 3H), 1.00 (t, J=7.4 Hz, 3H), 1.10 (d, J=6.9 Hz, 3H), 1.70-1.90 (m, 2H), 2.29-2.46 (m, 1H), 3.60-3.83 (m, 2H), 5.99 (d, J=7.9 Hz, 1H), 7.32-7.80 (m, 5H), 8.02 (d, J=7.6 Hz, 1H), 8.47 (d, J=3.3 Hz, 1H), 8.81 (s, 1H), 11.06 (br s, 1H).

EXAMPLE 206

3-{2-methyl-1-[3-(propylsulfonamide)quinoxalin-2-yloxy]-propyl}pyridine 1-oxide (Compound 211)

N-{3-[2-methyl-1-(pyridin-3-yl)propoxy]quinoxalin-2-yl}propane-1-sulfonamide (Compound 210) (67 mg, 0.17 mmol) obtained in Example 205 was dissolved in dichloromethane (3.3 mL). To this, meta-chloroperbenzoic acid (96 mg, 0.42 mmol) was added and the mixture was stirred at room temperature for 3 hours. After water was added to the reaction mixture, extraction with ethyl acetate was performed, followed by washing with brine and drying over anhydrous magnesium sulfate. The solvent was evaporated off under reduced pressure, and the residue was subjected to slurry purification using isopropyl ether, to give 3-{2-methyl-1-[3-(propylsulfonamide)quinoxalin-2-yloxy]-propyl}pyridine 1-oxide (Compound 211) (53 mg, yield: 77%).

ESIMS m/z: 417 (M+H)$^+$; $^1$H-NMR (270 MHz, DMSO-$d_6$, δ): 0.89 (d, J=6.6 Hz, 3H), 0.96-1.11 (m, 6H), 1.69-1.93 (m, 2H), 2.24-2.43 (m, 1H), 3.64-3.84 (m, 2H), 6.02 (d, J=7.2 Hz, 1H), 7.36-7.83 (m, 6H), 8.13 (d, J=5.9 Hz, 1H), 8.68 (s, 1H), 11.09 (br s, 1H).

EXAMPLE 207

N-{3-[2,2,2-trifluoro-1-(pyridin-3-yl)ethoxy]quinoxalin-2-yl}-N'-[2-(tert-butoxycarbonylamino)ethyl]-sulfuric diamide (Compound 212)

According to Example 144, by use of 2-chloro-3-[2,2,2-trifluoro-1-(pyridin-3-yl)ethoxy]-quinoxaline (Compound BJ) (160 mg, 0.47 mmol), dimethyl sulfoxide (4 mL), Compound GJ (113 mg, 0.47 mmol) and potassium carbonate (65 mg, 0.47 mmol), the mixture was stirred and reacted at 150° C. for 1 hour. Then, purification by silica gel column chromatography (chloroform/methanol=1/0 to 20/1) was performed to give N-{3-[2,2,2-trifluoro-1-(pyridin-3-yl)ethoxy]quinoxalin-2-yl}-N'-[2-(tert-butoxycarbonylamino)ethyl]-sulfuric diamide (Compound 212) (123 mg, 48%).

ESIMS m/z: 543 (M+H)$^+$; $^1$H-NMR (270 MHz, DMSO-$d_6$, δ): 1.19 (s, 9H), 2.94-3.18 (m, 4H), 6.74 (br s, 1H), 7.13-7.31 (m, 1H), 7.38-7.80 (m, 5H), 7.96 (d, J=5.9 Hz, 1H), 8.37 (d, J=5.9 Hz, 1H), 8.66 (d, J=3.0 Hz, 1H), 9.11 (s, 1H), 11.26 (br s, 1H).

EXAMPLE 208

N-{3-[2-methyl-1-(pyridin-3-yl)propoxy]quinoxalin-2-yl}-N'-propyl-sulfuric diamide (Compound 213)

According to Example 140, by use of 2-chloro-3-[2-methyl-1-(pyridin-3-yl)propoxy]quinoxaline (Compound BP) (160 mg, 0.51 mmol), dimethyl sulfoxide (4 mL), Compound GD (70 mg, 0.51 mmol) and potassium carbonate (70 mg, 0.51 mmol), the mixture was stirred and reacted at 150° C. for 4 hours. Then, purification by silica gel column chromatography (hexane/ethyl acetate=1/0 to 3/1) was performed to give N-{3-[2-methyl-1-(pyridin-3-yl)propoxy]quinoxalin-2-yl}-N'-propyl-sulfuric diamide (Compound 213) (55 mg, 26%).

ESIMS m/z: 416 (M+H)$^+$; $^1$H-NMR (270 MHz, DMSO-$d_6$, δ): 0.74 (t, J=7.3 Hz, 3H), 0.81 (d, J=6.6 Hz, 3H), 1.08 (d, J=6.6 Hz, 3H), 1.31-1.49 (m, 2H), 2.30-2.44 (m, 1H), 2.83-2.99 (m, 2H), 5.97 (d, J=7.9 Hz, 1H), 7.29-7.66 (m, 5H), 7.83 (d, J=6.6 Hz, 1H), 8.02 (d, J=7.3 Hz, 1H), 8.45 (d, J=4.0 Hz, 1H), 8.79 (s, 1H), 10.77 (br s, 1H).

EXAMPLE 209

3-{2-methyl-1-[3-(N-propylsulfamoylamino)quinoxalin-2-yloxy]propyl}pyridine 1-oxide (Compound 214)

According to Example 206, by use of N-{3-[2-methyl-1-(pyridin-3-yl)propoxy]quinoxalin-2-yl}-N'-propyl-sulfuric diamide (Compound 213) (41 mg, 0.098 mmol) obtained in Example 208, dichloromethane (2 mL) and meta-chloroperbenzoic acid (57 mg, 0.25 mmol), the mixture was stirred and reacted at room temperature for 3 hours. Then, purification by silica gel column chromatography (chloroform/methanol=1/0 to 20/1) was performed to give 3-{2-methyl-1-[3-(N-propylsulfamoylamino)quinoxalin-2-yloxy]propyl}pyridine 1-oxide (Compound 214) (45 mg, 99%).

ESIMS m/z: 431 (M+H)$^+$; $^1$H-NMR (270 MHz, DMSO-$d_6$, δ): 0.74 (t, J=7.3 Hz, 3H), 0.85 (d, J=6.6 Hz, 3H), 1.04 (d, J=6.6 Hz, 3H), 1.33-1.49 (m, 2H), 2.21-2.38 (m, 1H), 2.85-2.99 (m, 2H), 5.99 (d, J=7.6 Hz, 1H), 7.32-7.67 (m, 6H), 7.86 (d, J=7.6 Hz, 1H), 8.11 (d, J=7.6 Hz, 1H), 8.69 (s, 1H), 10.83 (br s, 1H).

EXAMPLE 210

N-{3-[2,2,2-trifluoro-1-(tetrahydro-2H-pyran-4-yl)ethoxy]-quinoxalin-2-yl}propane-1-sulfonamide (Compound 215)

According to Example 140, by use of 2-chloro-3-[2,2,2-trifluoro-1-(tetrahydro-2H-pyran-4-yl)-ethoxy]quinoxaline (Compound BQ) (100 mg, 0.29 mmol), dimethyl sulfoxide (2.8 mL), Compound FS (36 mg, 0.29 mmol) and potassium carbonate (40 mg, 0.29 mmol), the mixture was stirred and reacted at 150° C. for 2 hours. Then, purification by silica gel column chromatography (hexane/ethyl acetate=1/0 to 3/1) was performed to give N-{3-[2,2,2-trifluoro-1-(tetrahydro-2H-pyran-4-yl)ethoxy]-quinoxalin-2-yl}propane-1-sulfonamide (Compound 215) (64 mg, 51%).

ESIMS m/z: 434 (M+H)$^+$; $^1$H-NMR (270 MHz, DMSO-$d_6$, δ): 1.01 (t, J=7.4 Hz, 3H), 1.36-1.97 (m, 8H), 2.26-2.47 (m, 1H), 3.58-4.02 (m, 4H), 5.94-6.13 (m, 1H), 7.56-7.91 (m, 4H), 11.18 (br s, 1H).

EXAMPLE 211

N-propyl-N'-{3-[2,2,2-trifluoro-1-(tetrahydro-2H-pyran-4-yl)ethoxy]quinoxalin-2-yl}sulfuric diamide (Compound 216)

According to Example 140, by use of 2-chloro-3-[2,2,2-trifluoro-1-(tetrahydro-2H-pyran-4-yl)-ethoxy]quinoxaline (Compound BQ) (100 mg, 0.29 mmol), dimethyl sulfoxide (2.8 mL), Compound GD (40 mg, 0.29 mmol) and potassium carbonate (40 mg, 0.29 mmol), the mixture was stirred and reacted at 150° C. for 2 hours. Then, purification by silica gel column chromatography (hexane/ethyl acetate=1/0 to 3/1) was performed to give N-propyl-N'-{3-[2,2,2-trifluoro-1-(tetrahydro-2H-pyran-4-yl)ethoxy]quinoxalin-2-yl}sulfuric diamide (Compound 216) (21 mg, 16%).

ESIMS m/z: 449 (M+H)$^+$; $^1$H-NMR (270 MHz, DMSO-$d_6$, δ): 0.77 (t, J=7.4 Hz, 3H), 1.31-1.75 (m, 6H), 2.26-2.48 (m, 1H), 2.83-3.01 (m, 2H), 3.24-3.41 (m, 2H), 3.79-3.96 (m, 2H), 5.92-6.10 (m, 1H), 7.45-8.01 (m, 4H), 10.91 (br s, 1H).

EXAMPLE 212

3-{2,2,2-trifluoro-1-[3-(propylsulfonamide)quinoxalin-2-yloxy]ethyl}pyridine 1-oxide (Compound 217)

According to Example 206, by use of N-{3-[2,2,2-trifluoro-1-(pyridin-3-yl)ethoxy]quinoxalin-2-yl}propane-1-sulfonamide (Compound 179) (53 mg, 0.12 mmol) obtained in Example 174, dichloromethane (2.5 mL) and meta-chloroperbenzoic acid (53 mg, 0.31 mmol), the mixture was stirred and reacted at room temperature for 3 hours. Then, purification by silica gel column chromatography (chloroform/methanol=1/0 to 20/1) was performed to give 3-{2,2,2-trifluoro-1-[3-(propylsulfonamide)quinoxalin-2-yloxy]ethyl}pyridine 1-oxide (Compound 217) (51 mg, 94%).

ESIMS m/z: 443 (M+H)$^+$; $^1$H-NMR (270 MHz, DMSO-$d_6$, δ): 1.04 (t, J=7.4 Hz, 3H), 1.82-2.02 (m, 2H), 3.54-3.93 (m, 2H), 2.26-2.48 (m, 1H), 2.83-3.01 (m, 2H), 3.24-3.41 (m, 2H), 3.79-3.96 (m, 2H), 5.92-6.10 (m, 1H), 7.45-8.01 (m, 4H), 10.91 (br s, 1H).

EXAMPLE 213

2,3-dichloro-N-{3-[(pyridin-3-yl)methylamino]quinoxalin-2-yl}benzenesulfonamide (Compound 218)

2,3-Dichloro-N-(3-chloroquinoxalin-2-yl)benzenesulfonamide (Compound AA) (71.0 mg, 0.183 mmol) and 3-(aminomethyl)pyridine (20.5 µL, 0.201 mmol) were dissolved in toluene (1.0 mL) and the mixture was stirred under a nitrogen atmosphere at 125° C. for 10 hours. The solvent was evaporated off under reduced pressure, and the residue was purified by preparative thin-layer chromatography (hexane/ethyl acetate=1/1). Further, slurry purification was performed using methanol, to give 2,3-dichloro-N-{3-[(pyridin-3-yl)methylamino]quinoxalin-2-yl}benzenesulfonamide (Compound 218) (26.6 mg, yield: 32%).

ESIMS m/z: 460 (M+H)$^+$; $^1$H-NMR (300 MHz, DMSO-$d_6$, δ): 4.65 (d, J=6.2 Hz, 2H), 7.22-7.36 (m, 3H), 7.44 (dd, J=1.5, 7.7 Hz, 1H), 7.58 (dd, J=7.7, 8.0 Hz, 1H), 7.76-7.82 (m, 2H), 7.92 (dd, J=1.5, 8.0 Hz, 1H), 8.07 (brt, J=6.2 Hz, 1H), 8.18 (dd, J=0.7, 8.1 Hz, 1H), 8.43 (dd, J=1.5, 8.7 Hz, 1H), 8.60 (d, J=1.8 Hz, 1H).

EXAMPLE 214

2,3-dichloro-N-{3-[1-(pyridin-3-yl)ethylamino]quinoxalin-2-yl}benzenesulfonamide (Compound 219)

2,3-Dichloro-N-(3-chloroquinoxalin-2-yl)benzenesulfonamide (Compound AA) (100 mg, 0.25 mmol) was suspended in toluene (2 mL). To this, 1-pyridin-3-yl-ethylamine (34 mg, 0.28 mmol) was added at room temperature and the mixture was stirred at 125° C. for 24 hours. The reaction mixture was allowed to cool down to room temperature. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=1/0 to 1/1). Further, slurry purification was performed using methanol, to give 2,3-dichloro-N-{3-[1-(pyridin-3-yl)ethylamino]quinoxalin-2-yl}benzenesulfonamide (Compound 219) (33 mg, yield: 28%).

ESIMS m/z: 475 (M+H)$^+$; $^1$H-NMR (270 MHz, DMSO-$d_6$, δ): 1.57 (d, J=7.0 Hz, 3H), 5.37 (quin, J=7.0 Hz, 1H), 7.19-7.44 (m, 4H), 7.53-7.64 (m, 2H), 7.75 (d, J=7.3 Hz, 1H), 7.85 (dt, J=1.5, 8.1 Hz, 1H), 7.91 (dd, J=1.5, 8.1 Hz, 1H), 8.19 (dd, J=1.5, 8.1 Hz, 1H), 8.43 (d, J=3.7 Hz, 1H), 8.67 (s, 1H).

EXAMPLE 215

2,3-dichloro-N-{3-[methyl(pyridin-3-ylmethyl) amino]-quinoxalin-2-yl}benzenesulfonamide (Compound 220)

According to Example 214, by use of 2,3-dichloro-N-(3-chloroquinoxalin-2-yl)benzenesulfonamide (Compound AA) (100 mg, 0.25 mmol), toluene (2 mL) and N-methyl-N-(3-pyridylmethyl)amine (34 mg, 0.28 mmol), the mixture was stirred and reacted at 125° C. for 4 hours. After purification by silica gel column chromatography (hexane/ethyl acetate=1/0 to 1/2), slurry purification was further performed using methanol, to give 2,3-dichloro-N-{3-[methyl(pyridin-3-ylmethyl)amino]-quinoxalin-2-yl}benzenesulfonamide (Compound 220) (42 mg, yield: 36%).

ESIMS m/z: 475 (M+H)$^+$; $^1$H-NMR (270 MHz, DMSO-$d_6$, δ): 3.00 (s, 3H), 4.91 (s, 2H), 7.10 (dd, J=4.8, 7.7 Hz, 1H), 7.29-7.58 (m, 5H), 7.82 (d, J=8.1 Hz, 1H), 7.98 (d, J=7.7 Hz, 1H), 8.32 (d, J=4.8 Hz, 1H), 8.39 (s, 1H).

EXAMPLE 216

N-[3-(benzylthio)quinoxalin-2-yl]-2-chlorobenzenesulfonamide (Compound 221)

According to Example 90, by use of 60% sodium hydride (in oil) (18.0 mg, 0.452 mmol), tetrahydrofuran (4 mL), phenylmethanethiol (0.040 mL, 0.339 mmol) and 2-chloro-N-(3-chloroquinoxalin-2-yl)benzenesulfonamide (Compound AD) (80.0 mg, 0.226 mmol), the mixture was stirred and reacted at room temperature for 1.8 hours. Then, purification by preparative thin-layer chromatography (hexane/ethyl acetate=3/1) was performed to give N-[3-(benzylthio)quinoxalin-2-yl]-2-chlorobenzenesulfonamide (Compound 221) (76.9 mg, yield: 77%).

ESIMS m/z: 444, 442 (M+H)$^+$; $^1$H-NMR (270 MHz, CDCl$_3$, δ): 4.40 (s, 2H), 7.20-7.54 (m, 11H), 7.85 (dd, J=1.8, 7.8 Hz, 1H), 8.24 (d, J=7.3 Hz, 1H), 11.91 (s, 1H).

EXAMPLE 217

N-[3-(benzylsulfonyl)quinoxalin-2-yl]-2-chlorobenzenesulfonamide (Compound 222)

According to the step of Example 127, by use of N-[3-(benzylthio)quinoxalin-2-yl]-2-chlorobenzenesulfonamide (Compound 221) (25.0 mg, 0.0566 mmol) obtained in Example 216 and dissolved in dichloromethane (2 mL), and meta-chloroperbenzoic acid (49.0 mg, 0.283 mmol), the mixture was stirred and reacted under a nitrogen atmosphere at room temperature for 18.5 hours. Then, purification by preparative thin-layer chromatography (chloroform/acetone=1/

1, chloroform/acetonitrile=8/1) was performed to give N-[3-(benzylsulfonyl)quinoxalin-2-yl]-2-chlorobenzenesulfonamide (Compound 222) (22.7 mg, yield: 85%).

ESIMS m/z: 476, 474 (M+H)$^+$; $^1$H-NMR (270 MHz, CDCl$_3$+CD$_3$OD, δ): 4.94 (s, 2H), 7.31-7.59 (m, 11H), 7.98 (br s, 1H), 8.45 (m, 1H).

EXAMPLE 218

N-[3-(benzylsulfinyl)quinoxalin-2-yl]-2-chlorobenzenesulfonamide (Compound 223)

According to the step of Example 127, by use of N-[3-(benzylthio)quinoxalin-2-yl]-2-chlorobenzenesulfonamide (Compound 221) (38.0 mg, 0.0860 mmol) obtained in Example 216 and dissolved in dichloromethane (3.0 mL), and meta-chloroperbenzoic acid (16.3 mg, 0.0946 mmol), the mixture was stirred and reacted under a nitrogen atmosphere at room temperature for 1 hour. Then, purification by preparative thin-layer chromatography (chloroform/acetone=3/1) was performed to give N-[3-(benzylsulfinyl)quinoxalin-2-yl]-2-chlorobenzenesulfonamide (Compound 223) (17.8 mg, yield: 45%).

ESIMS m/z: 460, 458 (M+H)$^+$; $^1$H-NMR (270 MHz, CDCl$_3$+CD$_3$OD, δ): 4.35 (d, J=12.9 Hz, 1H), 4.54 (d, J=12.9 Hz, 1H), 7.10 (m, 2H), 7.25-7.73 (m, 8H), 7.97 (m, 2H), 8.35 (m, 1H).

EXAMPLE 219

2-chloro-N-[3-(1-phenylethylthio)quinoxalin-2-yl]benzenesulfonamide (Compound 224)

According to Example 90, by use of 60% sodium hydride (in oil) (23.0 mg, 0.564 mmol), tetrahydrofuran (4 mL), 1-phenylethanethiol (58.0 mg, 0.423 mmol) and 2-chloro-N-(3-chloroquinoxalin-2-yl)benzenesulfonamide (Compound AD) (100.0 mg, 0.282 mmol), the mixture was stirred and reacted at 50° C. for 1.3 hours. Then, purification by preparative thin-layer chromatography (hexane/ethyl acetate=3/1) was performed to give 2-chloro-N-[3-(1-phenylethylthio)quinoxalin-2-yl]benzenesulfonamide (Compound 224) (97.3 mg, yield: 76%).

ESIMS m/z: 458, 456 (M+H)$^+$; $^1$H-NMR (270 MHz, CDCl$_3$, δ): 1.75 (d, J=7.3 Hz, 3H), 5.07 (q, J=7.1 Hz, 1H), 7.18-7.48 (m, 11H), 7.82 (m, 1H), 8.23 (d, J=7.3 Hz, 1H), 11.89 (s, 1H).

EXAMPLE 220

2-chloro-N-[3-(1-phenylethylsulfonyl)quinoxalin-2-yl]-benzenesulfonamide (Compound 225)

According to the step of Example 127, by use of 2-chloro-N-[3-(1-phenylethylthio)quinoxalin-2-yl]benzenesulfonamide (Compound 224) (32.6 mg, 0.0715 mmol) obtained in Example 219 and dissolved in dichloromethane (3.3 mL), and meta-chloroperbenzoic acid (74.0 mg, 0.429 mmol), the mixture was stirred and reacted under a nitrogen atmosphere at room temperature for 6 hours. Then, purification by preparative thin-layer chromatography (chloroform/acetonitrile=8/1) was performed to give 2-chloro-N-[3-(1-phenylethylsulfonyl)quinoxalin-2-yl]-benzenesulfonamide (Compound 225) (26.2 mg, yield: 75%).

ESIMS m/z: 490, 488 (M+H)$^+$; $^1$H-NMR (300 MHz, CDCl$_3$, δ): 1.89 (d, J=6.6 Hz, 3H), 5.01 (br s, 1H), 7.28-7.45 (m, 8H), 7.62 (m, 2H), 7.73 (m, 1H), 8.03 (m, 1H), 8.41 (m, 1H), 9.85 (br s, 1H).

EXAMPLE 221

2,3-dichloro-N-[3-(2,4-dimethylpentan-3-yloxy)quinoxalin-2-yl]benzenesulfonamide (Compound 226)

According to Example 90, by use of 60% sodium hydride (in oil) (21.0 mg, 0.516 mmol), tetrahydrofuran (2.5 mL), 2,4-dimethylpentan-3-ol (0.054 mL, 0.39 mmol) and 2,3-dichloro-N-(3-chloroquinoxalin-2-yl)benzenesulfonamide (Compound AA) (50.0 mg, 0.129 mmol), the mixture was stirred and reacted at a temperature of room temperature to 50° C. for 13.3 hours. Then, purification by preparative thin-layer chromatography (chloroform) was performed to give 2,3-dichloro-N-[3-(2,4-dimethylpentan-3-yloxy)quinoxalin-2-yl]benzenesulfonamide (Compound 226) (47.3 mg, yield: 78%).

ESIMS m/z: 470, 468 (M+H)$^+$; $^1$H-NMR (270 MHz, CDCl$_3$, δ): 0.95 (d, J=6.3 Hz, 12H), 2.11 (m, 2H), 5.38 (m, 1H), 7.37-7.54 (m, 4H), 7.64 (m, 1H), 7.66 (dd, J=1.7, 7.9 Hz, 1H), 8.21 (br s, 1H), 8.48 (m, 1H).

EXAMPLE 222

2,3-dichloro-N-[3-(1,2,3,4-tetrahydronaphthalen-1-yloxy)-quinoxalin-2-yl]benzenesulfonamide (Compound 227)

According to Example 90, by use of 60% sodium hydride (in oil) (21.0 mg, 0.516 mmol), tetrahydrofuran (2.5 mL), 1,2,3,4-tetrahydronaphthalen-1-ol (57.0 mL, 0.387 mmol) and 2,3-dichloro-N-(3-chloroquinoxalin-2-yl)benzenesulfonamide (Compound AA) (50.0 mg, 0.129 mmol), the mixture was stirred and reacted at 50° C. for 1.8 hours. Then, purification by preparative thin-layer chromatography (chloroform/methanol=4/1) was performed to give 2,3-dichloro-N-[3-(1,2,3,4-tetrahydronaphthalen-1-yloxy)-quinoxalin-2-yl]benzenesulfonamide (Compound 227) (48.3 mg, yield: 75%).

ESIMS m/z: 500, 498 (M−H)$^-$; $^1$H-NMR (270 MHz, CDCl$_3$, δ): 1.89-2.20 (m, 4H), 2.72-2.93 (m, 2H), 6.53 (t, J=4.6 Hz, 1H), 7.18-7.29 (m, 4H), 7.41-7.63 (m, 4H), 7.65 (dd, J=1.3, 7.9 Hz, 1H), 7.73 (dd, J=2.0, 8.2 Hz, 1H), 8.26 (m, 1H), 8.45 (br s, 1H).

EXAMPLE 223

2,3-dichloro-N-[3-(thiochroman-4-yloxy)quinoxalin-2-yl]-benzenesulfonamide (Compound 228)

According to Example 90, by use of 60% sodium hydride (in oil) (23.0 mg, 0.564 mmol), tetrahydrofuran (2.5 mL), thiochroman-4-ol (70.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.2 hours. Then, purification by preparative thin-layer chromatography (hexane/ethyl acetate=2/1, chloroform) was performed to give 2,3-dichloro-N-[3-(thiochroman-4-yloxy)quinoxalin-2-yl]-benzenesulfonamide (Compound 228) (18.5 mg, yield: 27%).

ESIMS m/z: 484, 482 (M−H)$^-$; $^1$H-NMR (270 MHz, CDCl$_3$, δ): 2.29 (m, 1H), 2.74 (m, 1H), 2.93 (m, 1H), 3.31 (m,

1H), 6.56 (t, J=3.6 Hz, 1H), 7.06 (m, 1H), 7.14-7.47 (m, 8H), 7.58 (m, 1H), 7.73 (m, 1H), 8.15 (br s, 1H), 8.50 (br s, 1H).

EXAMPLE 224

2-chloro-N-[3-(tetrahydro-2H-pyran-4-yloxy)quinoxalin-2-yl]benzenesulfonamide (Compound 229)

According to Example 90, by use of 60% sodium hydride (in oil) (23.0 mg, 0.564 mmol), tetrahydrofuran (2.5 mL), cyclohexanal (0.040 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 2.3 hours. Then, purification by preparative thin-layer chromatography (hexane/ethyl acetate=2/1) was performed to give 2-chloro-N-[3-(tetrahydro-2H-pyran-4-yloxy) quinoxalin-2-yl]benzenesulfonamide (Compound 229) (29.7 mg, yield: 50%).

ESIMS m/z: 422, 420 (M+H)$^+$; $^1$H-NMR (270 MHz, CDCl$_3$, δ): 1.91 (m, 2H), 2.13 (m, 2H), 3.64 (m, 2H), 4.02 (m, 2H), 5.48 (m, 1H), 7.42-7.67 (m, 7H), 8.18 (m, 1H), 8.51 (m, 1H).

EXAMPLE 225

2-chloro-N-[3-(1-morpholinopropan-2-yloxy)quinoxalin-2-yl]-benzenesulfonamide (Compound 230)

According to Example 90, by use of 60% sodium hydride (in oil) (23.0 mg, 0.564 mmol), tetrahydrofuran (2.5 mL), 1-morpholinopropan-2-ol (61.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2.3 hours. Then, purification by preparative thin-layer chromatography (chloroform/methanol=20/1) was performed to give 2-chloro-N-[3-(1-morpholinopropan-2-yloxy)quinoxalin-2-yl]-benzenesulfonamide (Compound 230) (44.8 mg, yield: 69%).

ESIMS m/z: 465, 463 (M+H)$^+$; $^1$H-NMR (270 MHz, CDCl$_3$, δ): 1.45 (d, J=6.3 Hz, 3H), 2.51 (m, 5H), 2.75 (dd, J=7.9, 13.2 Hz, 1H), 3.53 (m, 4H), 5.64 (m, 1H), 7.40-7.50 (m, 6H), 7.62 (m, 1H), 8.45 (br s, 1H).

EXAMPLE 226

2-chloro-N-[3-(3,3-dimethylbutan-2-yloxy)quinoxalin-2-yl]-benzenesulfonamide (Compound 231)

According to Example 90, by use of 60% sodium hydride (in oil) (23.0 mg, 0.564 mmol), tetrahydrofuran (2.5 mL), 3,3-dimethylbutan-2-ol (0.053 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 1 hour. Then, purification by preparative thin-layer chromatography (chloroform/methanol=30/1) was performed to give 2-chloro-N-[3-(3,3-dimethylbutan-2-yloxy)quinoxalin-2-yl]-benzenesulfonamide (Compound 231) (41.2 mg, yield: 70%).

ESIMS m/z: 422, 420 (M+H)$^+$; $^1$H-NMR (270 MHz, CDCl$_3$, δ): 1.05 (s, 9H), 1.34 (d, J=6.6 Hz, 3H), 5.31 (m, 1H), 7.39-7.47 (m, 5H), 7.57 (d, J=7.9 Hz, 1H), 7.65 (d, J=7.9 Hz, 1H), 8.04 (s, 1H), 8.53 (m, 1H).

EXAMPLE 227

2-chloro-N-[3-(1-ethoxypropan-2-yloxy)quinoxalin-2-yl]-benzenesulfonamide (Compound 232)

According to Example 90, by use of 60% sodium hydride (in oil) (23.0 mg, 0.564 mmol), tetrahydrofuran (2.5 mL), 1-ethoxypropan-2-ol (0.049 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 1.8 hours. Then, purification by preparative thin-layer chromatography (chloroform/methanol=40/1, hexane/ethyl acetate=4/1) was performed to give 2-chloro-N-[3-(1-ethoxypropan-2-yloxy)quinoxalin-2-yl]-benzenesulfonamide (Compound 232) (44.7 mg, yield: 75%).

ESIMS m/z: 424, 422 (M+H)$^+$; $^1$H-NMR (270 MHz, CDCl$_3$, δ): 1.91 (m, 3H), 1.43 (d, J=6.3 Hz, 3H), 3.55 (m, 2H), 3.67 (m, 2H), 5.62 (br s, 1H), 7.37-7.54 (m, 6H), 7.65 (m, 1H), 8.37 (br s, 1H), 8.52 (br s, 1H).

EXAMPLE 228

2-chloro-N-{3-[1,3-bis(dimethylamino)propan-2-yloxy]-quinoxalin-2-yl}benzenesulfonamide (Compound 233)

According to Example 90, by use of 60% sodium hydride (in oil) (23.0 mg, 0.564 mmol), tetrahydrofuran (2.5 mL), 1,3-bis(dimethylamino)propan-2-ol (0.069 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 2 hours. Then, purification by preparative thin-layer chromatography (chloroform/methanol=5/1) was performed to give 2-chloro-N-{3-[1,3-bis(dimethylamino)propan-2-yloxy]-quinoxalin-2-yl}benzenesulfonamide (Compound 233) (28.7 mg, yield: 44%).

ESIMS m/z: 466, 464 (M+H)$^+$; $^1$H-NMR (270 MHz, CDCl$_3$+CD$_3$OD, δ): 2.51 (s, 12H), 2.87 (dd, J=5.3, 12.9 Hz, 2H), 3.06 (dd, J=6.8, 12.7 Hz, 2H), 5.32 (m, 1H), 7.35-7.50 (m, 7H), 7.57 (m, 1H), 8.48 (m, 1H).

EXAMPLE 229

2-chloro-N-[3-(tetrahydrofuran-3-yloxy)quinoxalin-2-yl]-benzenesulfonamide (Compound 234)

According to Example 90, by use of 60% sodium hydride (in oil) (23.0 mg, 0.564 mmol), tetrahydrofuran (2.5 mL), tetrahydrofuran-3-ol (0.034 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 2 hours. Then, purification by preparative thin-layer chromatography (hexane/ethyl acetate=2/1, chloroform/methanol=100/1) was performed to give 2-chloro-N-[3-(tetrahydrofuran-3-yloxy)quinoxalin-2-yl]-benzenesulfonamide (Compound 234) (21.0 mg, yield: 37%).

ESIMS m/z: 408, 406 (M+H)$^+$; $^1$H-NMR (270 MHz, CDCl$_3$, δ): 2.19-2.36 (m, 2H), 3.99-4.16 (m, 4H), 5.79 (br s, 1H), 7.43-7.65 (m, 6H), 7.89 (m, 1H), 8.18 (br s, 1H), 8.51 (br s, 1H).

EXAMPLE 230

2-chloro-N-[3-(1-methylpiperidin-4-yloxy)quinoxalin-2-yl]-benzenesulfonamide (Compound 235)

According to Example 90, by use of 60% sodium hydride (in oil) (23.0 mg, 0.564 mmol), tetrahydrofuran (2.5 mL), 1-methylpiperidin-4-ol (49.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2 hours. Then, purification by preparative thin-layer chromatography (chloroform/methanol=12/1 to 8/1) was performed to give 2-chloro-N-[3-(1-methylpiperidin-4-yloxy)quinoxalin-2-yl]-benzenesulfonamide (Compound 235) (18.0 mg, yield: 29%).

ESIMS m/z: 435, 433 (M+H)$^+$; $^1$H-NMR (270 MHz, DMSO-d$_6$, δ): 1.98-2.23 (m, 4H), 2.76 (s, 3H), 3.15-3.32 (m, 4H), 5.30 (m, 1H), 7.07-7.19 (m, 3H), 7.33-7.41 (m, 4H), 8.22 (m, 1H), 9.50 (br s, 1H).

EXAMPLE 231

2-chloro-N-[3-(quinuclidin-3-yloxy)quinoxalin-2-yl] benzenesulfonamide (Compound 236)

According to Example 90, by use of 60% sodium hydride (in oil) (23.0 mg, 0.564 mmol), tetrahydrofuran (2.5 mL), 3-quinuclidinol (54.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.7 hours. Then, purification by preparative thin-layer chromatography (chloroform/methanol=12/1 to 8/1) was performed to give 2-chloro-N-[3-(quinuclidin-3-yloxy)quinoxalin-2-yl]benzenesulfonamide (Compound 236) (16.7 mg, yield: 27%).

ESIMS m/z: 447, 445 (M+H)$^+$; $^1$H-NMR (270 MHz, DMSO-d$_6$, δ): 1.79 (m, 1H), 1.95 (m, 2H), 2.21 (m, 1H), 3.23 (m, 6H), 3.83 (m, 1H), 5.30 (m, 1H), 7.04-7.29 (m, 3H), 7.32-7.40 (m, 4H), 8.22 (m, 1H), 9.55 (br s, 1H).

EXAMPLE 232

2-chloro-N-[3-(4-oxohexan-3-yloxy)quinoxalin-2-yl] benzenesulfonamide (Compound 237)

According to Example 90, by use of 60% sodium hydride (in oil) (23.0 mg, 0.564 mmol), tetrahydrofuran (2.5 mL), 4-hydroxyhexan-3-one (0.052 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 1.5 hours. Then, purification by preparative thin-layer chromatography (hexane/ethyl acetate=2/1, chloroform/acetonitrile=40/1) was performed to give 2-chloro-N-[3-(4-oxohexan-3-yloxy)quinoxalin-2-yl]benzenesulfonamide (Compound 237) (14.9 mg, yield: 24%).

ESIMS m/z: 436, 434 (M+H)$^+$; $^1$H-NMR (270 MHz, CDCl$_3$, δ): 1.08 (m, 6H), 1.99 (m, 2H), 2.44 (m, 1H), 2.63 (m, 1H), 5.42 (br s, 1H), 7.43-7.65 (m, 7H), 8.28 (br s, 1H), 8.53 (br s, 1H).

EXAMPLE 233

Ethyl 2-[3-(2-chlorophenylsulfonamide)quinoxalin-2-yloxy]-propanoate (Compound 238)

According to Example 90, by use of 60% sodium hydride (in oil) (23.0 mg, 0.564 mmol), tetrahydrofuran (2.5 mL), ethyl 2-hydroxypropanoate (0.048 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 3 hours. Then, purification by preparative thin-layer chromatography (hexane/ethyl acetate=2/1) was performed to give ethyl 2-[3-(2-chlorophenylsulfonamide)quinoxalin-2-yloxy]-propanoate (Compound 238) (21.7 mg, yield: 35%).

ESIMS m/z: 438, 436 (M+H)$^+$; $^1$H-NMR (270 MHz, CDCl$_3$, δ): 1.23 (t, J=6.9 Hz, 3H), 1.71 (d, J=6.6 Hz, 3H), 4.21 (m, 2H), 5.55 (m, 1H), 7.44-7.62 (m, 7H), 8.30 (br s, 1H), 8.51 (br s, 1H).

EXAMPLE 234

2-chloro-N-[3-(3-methyl-1-morpholino-1-oxobutan-2-yloxy)-quinoxalin-2-yl]benzenesulfonamide (Compound 239)

According to Example 90, by use of 60% sodium hydride (in oil) (23.0 mg, 0.564 mmol), tetrahydrofuran (2.5 mL), Compound EO (79.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.8 hours. Then, purification by preparative thin-layer chromatography (chloroform/methanol=15/1) was performed to give 2-chloro-N-[3-(3-methyl-1-morpholino-1-oxobutan-2-yloxy)-quinoxalin-2-yl]benzenesulfonamide (Compound 239) (46.7 mg, yield: 66%).

ESIMS m/z: 507, 505 (M+H)$^+$; $^1$H-NMR (270 MHz, CDCl$_3$, δ): 0.82 (d, J=6.9 Hz, 3H), 1.07 (d, J=6.9 Hz, 3H), 1.82 (m, 1H), 3.43-3.73 (m, 8H), 5.51 (br s, 1H), 7.44-7.56 (m, 7H), 8.30 (br s, 1H), 8.52 (br s, 1H).

EXAMPLE 235

2-chloro-N-{3-[(tetrahydro-2H-pyran-4-yl)methoxy]-quinoxalin-2-yl}benzenesulfonamide (Compound 240)

According to Example 90, by use of 60% sodium hydride (in oil) (23.0 mg, 0.564 mmol), tetrahydrofuran (2.5 mL), cyclohexylmethanol (49.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.7 hours. Then, purification by preparative thin-layer chromatography (hexane/ethyl acetate=2/1) was performed to give 2-chloro-N-{3-[(tetrahydro-2H-pyran-4-yl)methoxy]-quinoxalin-2-yl}benzenesulfonamide (Compound 240) (14.1 mg, yield: 23%).

ESIMS m/z: 436, 434 (M+H)$^+$; $^1$H-NMR (270 MHz, CDCl$_3$, δ): 1.45 (m, 2H), 1.75 (m, 2H), 2.19 (m, 1H), 3.44 (m, 2H), 4.01 (m, 2H), 4.38 (d, J=6.9 Hz, 2H), 7.42-7.49 (m, 6H), 7.67 (m, 1H), 8.17 (br s, 1H), 8.48 (br s, 1H).

EXAMPLE 236

2-chloro-N-[3-(3,3-dimethyl-5-oxotetrahydrofuran-2-yloxy)-quinoxalin-2-yl]benzenesulfonamide (Compound 241)

According to Example 90, by use of 60% sodium hydride (in oil) (23.0 mg, 0.564 mmol), tetrahydrofuran (2.5 mL), pantolactone (55.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 2 hours. Then, purification by preparative thin-layer chromatography (hexane/ethyl acetate=2/1) was performed to give 2-chloro-N-[3-(3,3-dimethyl-5-oxotetrahydrofuran-2-yloxy)-quinoxalin-2-yl]benzenesulfonamide (Compound 241) (17.8 mg, yield: 28%).

ESIMS m/z: 450, 448 (M+H)$^+$; $^1$H-NMR (300 MHz, CDCl$_3$, δ): 1.24 (s, 6H), 4.16 (s, 2H), 6.01 (br s, 1H), 7.46-7.49 (m, 7H), 7.64 (m, 1H), 8.46 (br s, 1H).

EXAMPLE 237

2-chloro-N-[3-(dipyridin-3-ylmethoxy)quinoxalin-2-yl]-benzenesulfonamide (Compound 242)

According to Example 90, by use of 60% sodium hydride (in oil) (23.0 mg, 0.564 mmol), tetrahydrofuran (2.5 mL), Compound EP (79.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.5 hours. Then, purification by preparative thin-layer chromatography (chloroform/methanol=15/1, hexane/ethyl acetate=1/3, ethyl acetate/methanol=40/1) was performed to give 2-chloro-N-[3-(dipyridin-3-ylmethoxy)quinoxalin-2-yl]-benzenesulfonamide (Compound 242) (29.0 mg, yield: 41%).

ESIMS m/z: 506, 504 (M+H)$^+$; $^1$H-NMR (270 MHz, CDCl$_3$, δ): 7.29 (dd, 3=4.6, 7.6 Hz, 2H), 7.44-7.49 (m, 8H), 7.64 (m, 1H), 7.76 (d, J=7.7 Hz, 2H), 8.41 (m, 1H), 8.57 (d, J=3.6 Hz, 2H), 8.75 (d, J=1.7 Hz, 2H).

EXAMPLE 238

2-chloro-N-{3-[pyridin-3-yl(thiazol-5-yl)methoxy]-quinoxalin-2-yl}benzenesulfonamide (Compound 243)

According to Example 90, by use of 60% sodium hydride (in oil) (23.0 mg, 0.564 mmol), tetrahydrofuran (2.5 mL), Compound EQ (81.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.7 hours. Then, purification by preparative thin-layer chromatography (chloroform/methanol=15/1) was performed to give 2-chloro-N-{3-[pyridin-3-yl(thiazol-5-yl)methoxy]-quinoxalin-2-yl}benzenesulfonamide (Compound 243) (52.8 mg, yield: 73%).

ESIMS m/z: 512, 510 (M+H)$^+$; $^1$H-NMR (270 MHz, CDCl$_3$, δ): 7.33 (dd, J=5.0, 7.9 Hz, 1H), 7.43-7.50 (m, 7H), 7.68 (m, 1H), 7.71 (br s, 1H), 7.80 (s, 1H), 7.89 (ddd, J=1.7, 2.0, 7.9 Hz, 1H), 8.39 (br s, 1H), 8.61 (dd, J=1.5, 4.8 Hz, 1H), 8.81 (s, 1H), 8.82 (s, 1H).

EXAMPLE 239

2-chloro-N-{3-[2-(2-oxypyrrolidin-1-yl)ethoxy]quinoxalin-2-yl}benzenesulfonamide (Compound 244)

According to Example 90, by use of 60% sodium hydride (in oil) (23.0 mg, 0.564 mmol), tetrahydrofuran (3.5 mL), 1-(2-hydroxyethyl)-2-pyrrolidone (0.056 mL, 0.42 mmol) and 2-chloro-N-(3-chloroquinoxalin-2-yl)benzenesulfonamide (Compound AD) (50.0 mg, 0.141 mmol), the mixture was stirred and reacted at 50° C. for 1.2 hours. Then, purification by preparative thin-layer chromatography (chloroform/methanol=40/1) was performed to give 2-chloro-N-{3-[2-(2-oxypyrrolidin-1-yl)ethoxy]quinoxalin-2-yl}benzenesulfonamide (Compound 244) (32.0 mg, yield: 51%).

ESIMS m/z: 449, 447 (M+H)$^+$; $^1$H-NMR (270 MHz, CDCl$_3$, δ): 1.78 (m, 2H), 2.33 (m, 2H), 3.50 (m, 2H), 3.74 (m, 2H), 4.63 (t, J=5.1 Hz, 2H), 7.44-7.49 (m, 6H), 7.67 (m, 1H), 8.30 (br s, 1H), 8.50 (br s, 1H).

EXAMPLE 240

2-chloro-N-{3-[(4-ethyltetrahydro-2H-pyran-4-yl)methoxy]-quinoxalin-2-yl}benzenesulfonamide (Compound 245)

According to Example 90, by use of 60% sodium hydride (in oil) (23.0 mg, 0.564 mmol), tetrahydrofuran (2.5 mL), (4-ethyltetrahydro-2H-pyran-4-yl)methanol (61.0 mg, 0.423 mmol) synthesized according to the method described in WO 08/029,825 and 2-chloro-N-(3-chloroquinoxalin-2-yl)benzenesulfonamide (Compound AD) (50.0 mg, 0.141 mmol), the mixture was stirred and reacted at 50° C. for 1.2 hours. Then, purification by preparative thin-layer chromatography (hexane/ethyl acetate=2/1) was performed to give 2-chloro-N-{3-[(4-ethyltetrahydro-2H-pyran-4-yl)methoxy]-quinoxalin-2-yl}benzenesulfonamide (Compound 245) (49.8 mg, yield: 76%).

ESIMS m/z: 464, 462 (M+H)$^+$; $^1$H-NMR (270 MHz, CDCl$_3$, δ): 0.90 (m, 3H), 1.63 (m, 6H), 3.72 (m, 4H), 4.45 (m, 2H), 7.42-7.57 (m, 6H), 7.68 (m, 1H), 8.04-8.52 (m, 2H).

EXAMPLE 241

2-chloro-N-{3-[(4-methyltetrahydro-2H-pyran-4-yl)methoxy]-quinoxalin-2-yl}benzenesulfonamide (Compound 246)

According to Example 90, by use of 60% sodium hydride (in oil) (23.0 mg, 0.564 mmol), tetrahydrofuran (2.5 mL), (4-methyltetrahydro-2H-pyran-4-yl)methanol (55.0 mg, 0.423 mmol) synthesized according to the method described in WO 08/029,825 and 2-chloro-N-(3-chloroquinoxalin-2-yl)benzenesulfonamide (Compound AD) (50.0 mg, 0.141 mmol), the mixture was stirred and reacted at 50° C. for 1.3 hours. Then, purification by preparative thin-layer chromatography (hexane/ethyl acetate=2/1) was performed to give 2-chloro-N-{3-[(4-methyltetrahydro-2H-pyran-4-yl)methoxy]-quinoxalin-2-yl}benzenesulfonamide (Compound 246) (14.8 mg, yield: 23%).

ESIMS m/z: 450, 448 (M+H)$^+$; $^1$H-NMR (270 MHz, CDCl$_3$, δ): 1.19 (m, 3H), 1.46 (m, 2H), 1.69 (m, 2H), 3.68-3.78 (m, 4H), 4.34 (br s, 2H), 7.42-7.49 (m, 6H), 7.67 (m, 1H), 8.08 (br s, 1H), 8.51 (m, 2H).

EXAMPLE 242

2-chloro-N-{3-[(4-methoxytetrahydro-2H-pyran-4-yl)methoxy]-quinoxalin-2-yl}benzenesulfonamide (Compound 247)

According to Example 90, by use of 60% sodium hydride (in oil) (23.0 mg, 0.564 mmol), tetrahydrofuran (2.5 mL), (4-methoxytetrahydro-2H-pyran-4-yl)methanol (62.0 mg, 0.423 mmol) synthesized according to the method described in WO 08/029825 and 2-chloro-N-(3-chloroquinoxalin-2-yl)benzenesulfonamide (Compound AD) (50.0 mg, 0.141 mmol), the mixture was stirred and reacted at 50° C. for 1.3 hours. Then, purification by preparative thin-layer chromatography (chloroform/methanol=30/1) was performed to give 2-chloro-N-{3-[(4-methoxytetrahydro-2H-pyran-4-yl)methoxy]-quinoxalin-2-yl}benzenesulfonamide (Compound 247) (49.8 mg, yield: 76%).

ESIMS m/z: 466, 464 (M+H)$^+$; $^1$H-NMR (270 MHz, CDCl$_3$, δ): 1.74-2.04 (m, 4H), 3.31 (s, 3H), 3.77 (br s, 4H), 4.50 (s, 2H), 7.43-7.56 (m, 6H), 7.67 (m, 1H), 8.27-8.84 (m, 2H).

EXAMPLE 243

2-chloro-N-{3-[(5-oxymorpholin-3-yl)methoxy]quinoxalin-2-yl}benzenesulfonamide (Compound 248)

According to Example 90, by use of 60% sodium hydride (in oil) (23.0 mg, 0.564 mmol), tetrahydrofuran (2.5 mL), Compound EE (55.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.5 hours. Then, purification by preparative thin-layer chromatography (chloroform/methanol=15/1) was performed to give 2-chloro-N-{3-[(5-oxymorpholin-3-yl)methoxy]quinoxalin-2-yl}benzenesulfonamide (Compound 248) (25.4 mg, yield: 40%).

ESIMS m/z: 451, 449 (M+H)$^+$; $^1$H-NMR (270 MHz, DMSO-d$_6$, δ): 3.87 (m, 3H), 4.03 (s, 2H), 4.25 (m, 1H), 4.58 (m, 1H), 7.43-7.67 (m, 7H), 8.40 (br s, 1H), 8.69 (s, 1H), 11.72 (s, 1H).

EXAMPLE 244

2-chloro-N-{3-[(5-oxymorpholin-2-yl)methoxy]quinoxalin-2-yl}benzenesulfonamide (Compound 249)

According to Example 90, by use of 60% sodium hydride (in oil) (29.0 mg, 0.725 mmol), tetrahydrofuran (2.5 mL), 6-(hydroxymethyl)morpholin-3-one (55.0 mg, 0.423 mmol) synthesized according to the method described in Organic Letters, vol. 7, p. 937, 2005, and 2-chloro-N-(3-chloroquinoxalin-2-yl)benzenesulfonamide (Compound AD) (50.0 mg, 0.141 mmol), the mixture was stirred and reacted from 50° C. to reflux temperature for 6.8 hours. Then, purification by preparative thin-layer chromatography (chloroform/methanol=15/1) was performed to give 2-chloro-N-{3-[(5-oxymorpholin-2-yl)methoxy]quinoxalin-2-yl}benzenesulfonamide (Compound 249) (12.4 mg, yield: 20%).

ESIMS m/z: 451, 449 (M+H)$^+$; $^1$H-NMR (270 MHz, CDCl$_3$, δ): 3.49 (d, J=7.3 Hz, 2H), 4.21-4.37 (m, 3H), 4.68 (m, 2H), 6.75 (br s, 1H), 7.47-7.49 (m, 6H), 7.67 (m, 1H), 8.45 (m, 2H).

EXAMPLE 245

2-chloro-N-{3-[(4-cyanotetrahydro-2H-pyran-4-yl)methoxy]-quinoxalin-2-yl}benzenesulfonamide (Compound 250)

According to Example 90, by use of 60% sodium hydride (in oil) (29.0 mg, 0.725 mmol), tetrahydrofuran (2.5 mL), 4-(hydroxymethyl)tetrahydro-2H-pyran-4-carbonitrile (60.0 mg, 0.423 mmol) synthesized according to the method described in WO 08/029,825 and 2-chloro-N-(3-chloroquinoxalin-2-yl)benzenesulfonamide (Compound AD) (50.0 mg, 0.141 mmol), the mixture was stirred and reacted at 50° C. for 1.2 hours. Then, purification by preparative thin-layer chromatography (chloroform/methanol=30/1) was performed to give 2-chloro-N-{3-[(4-cyanotetrahydro-2H-pyran-4-yl)methoxy]-quinoxalin-2-yl}benzenesulfonamide (Compound 250) (48.3 mg, yield: 75%).

ESIMS m/z: 461, 459 (M+H)$^+$; $^1$H-NMR (270 MHz, CDCl$_3$, δ): 1.85 (m, 2H), 2.04 (m, 2H), 3.77 (m, 2H), 4.03 (m, 2H), 4.58 (s, 2H), 7.47 (m, 6H), 7.68 (m, 1H), 8.28 (br s, 1H), 8.51 (br s, 1H).

EXAMPLE 246

2-chloro-N-{3-[(5-methyl-1,3-dioxan-5-yl)methoxy]-quinoxalin-2-yl}benzenesulfonamide (Compound 251)

According to Example 90, by use of 60% sodium hydride (in oil) (29.0 mg, 0.725 mmol), tetrahydrofuran (2.5 mL), (5-methyl-1,3-dioxan-5-yl)methanol (56.0 mg, 0.423 mmol) and 2-chloro-N-(3-chloroquinoxalin-2-yl)benzenesulfonamide (Compound AD) (50.0 mg, 0.141 mmol), the mixture was stirred and reacted at 50° C. for 1.2 hours. Then, purification by preparative thin-layer chromatography (hexane/ethyl acetate=2/1) was performed to give 2-chloro-N-{3-[(5-methyl-1,3-dioxan-5-yl)methoxy]-quinoxalin-2-yl}benzenesulfonamide (Compound 251) (47.0 mg, yield: 74%).

ESIMS m/z: 452, 450 (M+H)$^+$; $^1$H-NMR (270 MHz, CDCl$_3$, δ): 0.96 (s, 3H), 3.53 (br d, J=9.6 Hz, 2H), 4.00 (d, J=11.6 Hz, 2H), 4.64 (br s, 1H), 4.69 (d, J=5.9 Hz, 2H), 5.00 (br s, 1H), 7.46 (m, 6H), 7.68 (m, 1H), 8.05-8.49 (m, 2H).

EXAMPLE 247

2-chloro-N-methyl-N-{3-[2,2,2-trifluoro-1-(pyridin-3-yl)-ethoxy]quinoxalin-2-yl}benzenesulfonamide (Compound 252)

2-Chloro-N-{3-[2,2,2-trifluoro-1-(pyridin-3-yl)ethoxy]-quinoxalin-2-yl}benzenesulfonamide (Compound 138) (50 mg, 0.10 mmol) obtained in Example 133 was dissolved in a mixed solvent of acetonitrile (1.5 mL) and methanol (1 mL). To this, trimethylsilyl diazomethane (0.15 mL, 0.30 mmol) was added at room temperature and the mixture was stirred at the same temperature for 1 hour. The solvent was evaporated off under reduced pressure, and the residue was purified by silica gel column chromatography (hexane/ethyl acetate=1/0 to 1/1). Further, purification by preparative HPLC (acetonitrile/water system) was performed to give 2-chloro-N-methyl-N-{3-[2,2,2-trifluoro-1-(pyridin-3-yl)-ethoxy]quinoxalin-2-yl}benzenesulfonamide (Compound 252) (20 mg, yield: 40%).

ESIMS m/z: 509 (M+H)$^+$; $^1$H-NMR (270 MHz, DMSO-d$_6$, δ): 3.48 (s, 3H), 7.08 (q, J=6.7 Hz, 1H), 7.50 (dd, J=4.8, 7.7 Hz, 1H), 7.59-7.84 (m, 7H), 8.06 (d, J=7.7 Hz, 1H), 8.22 (d, J=7.7 Hz, 1H), 8.64 (d, J=4.8 Hz, 1H), 8.92 (s, 1H).

EXAMPLE 248

2-chloro-N-methyl-N-{3-[2,2,2-trifluoro-1-(tert-butoxy-carbonylaminomethylphenyl)ethoxy]quinoxalin-2-yl}benzenesulfonamide (Compound 253)

2-Chloro-N-{3-[2,2,2-trifluoro-1-(tert-butoxycarbonylaminomethylphenyl)ethoxy]quinoxalin-2-yl}benzenesulfonamide (Compound 92) (52.8 mg, 0.085 mmol) was dissolved in acetonitrile (0.5 mL) and methanol (0.5 mL). To this, trimethylsilyl diazomethane (a 2.0 mol/L solution in hexane, 127 µL, 0.254 mmol) was added under a nitrogen atmosphere at room temperature and the mixture was stirred at the same temperature for 30 minutes. The solvent was evaporated off under reduced pressure, and the residue was purified by preparative thin-layer chromatography (hexane/ethyl acetate=1/1) to give 2-chloro-N-methyl-N-{3-[2,2,2-trifluoro-1-(tert-butoxy-carbonylaminomethylphenyl)ethoxy]quinoxalin-2-yl}benzenesulfonamide (Compound 253) (50.1 mg, yield: 93%).

ESIMS m/z: 637 (M+H)+; 1H-NMR (270 MHz, DMSO-d6, δ): 1.44 (s, 9H), 3.57 (s, 3H), 4.31 (d, J=5.5 Hz, 2H), 4.84 (br s, 1H), 6.76 (q, J=6.6 Hz, 1H), 7.30-7.76 (m, 11H), 8.18 (d, J=7.0 Hz, 1H).

EXAMPLE 249

2,3-dichloro-N-{5-chloro-3-[2,2,2-trifluoro-1-(pyridin-3-yl)ethoxy]pyrazin-2-yl}benzenesulfonamide (Compound 254)

According to Example 90, by use of 60% sodium hydride (in oil) (65.0 mg, 1.63 mmol), dimethoxyethane (5.5 mL), Compound CB (118 mg, 0.666 mmol) and 2,3-dichloro-N-(3,5-dichloropyrazin-2-yl)benzenesulfonamide (100 mg, 0.269 mmol) synthesized according to the method described in JP-A 2006-137723, the mixture was stirred and reacted at room temperature for 5 hours. Then, purification by preparative thin-layer chromatography (chloroform/methanol=15/1) was performed to give 2,3-dichloro-N-{5-chloro-3-[2,2,2-trifluoro-1-(pyridin-3-yl)ethoxy]pyrazin-2-yl}benzenesulfonamide (Compound 254) (57.3 mg, yield: 41%).

ESIMS m/z: 517, 515, 513 (M+H)+; 1H-NMR (270 MHz, CDCl3, δ): 6.46 (q, J=6.6 Hz, 1H), 7.27 (m, 1H), 7.35 (dd, J=5.0, 7.6 Hz, 2H), 7.62 (m, 2H), 7.88 (d, J=7.6 Hz, 1H), 8.16 (m, 1H), 8.66 (d, J=4.0 Hz, 1H), 8.79 (br s, 1H).

EXAMPLE 250

2,3-dichloro-N-{6-methoxy-2-[2,2,2-trifluoro-1-(pyridin-3-yl)ethoxy]pyrazin-3-yl}benzenesulfonamide (Compound 255)

According to Example 2, by use of 6-methoxy-2-[2,2,2-trifluoro-1-(pyridin-3-yl)ethoxy]-pyridin-3-amine (Compound HA) (88.7 mg, 0.296 mmol) dissolved in pyridine (3.5 mL), 2,3-dichlorobenzene-1-sulfonyl chloride (145 mg, 0.592 mmol) and DMAP (36.0 mg, 0.296 mmol), the mixture was stirred and reacted at room temperature for 3.5 hours. Then, purification by preparative thin-layer chromatography (chloroform/methanol=40/1) was performed to give 2,3-dichloro-N-{6-methoxy-2-[2,2,2-trifluoro-1-(pyridin-3-yl)ethoxy]pyrazin-3-yl}benzenesulfonamide (Compound 255) (108 mg, yield: 74%).

ESIMS m/z: 510, 508 (M+H)+; 1H-NMR (270 MHz, CDCl3, δ): 3.67 (s, 3H), 6.28 (q, J=6.7 Hz, 1H), 6.35 (d, J=8.6 Hz, 1H), 7.25-7.30 (m, 2H), 7.57 (br s, 1H), 7.59 (s, 1H), 7.69 (dd, J=1.5, 8.1 Hz, 1H), 7.78 (d, J=8.6 Hz, 1H), 7.87 (dd, J=1.7, 7.9 Hz, 1H), 8.56 (d, J=2.0 Hz, 1H), 8.61 (dd, J=1.7, 5.0 Hz, 1H).

EXAMPLE 251

2,3-dichloro-N-{6-chloro-2-[1-(pyridin-3-yl)propoxy]-pyrazin-3-yl}benzenesulfonamide (Compound 256)

According to Example 90, by use of 60% sodium hydride (in oil) (21.0 mg, 0.536 mmol), dimethoxyethane (2.5 mL), Compound CC (33.0 mg, 0.241 mmol) and 2,3-dichloro-N-(3,5-dichloropyrazin-2-yl)benzenesulfonamide (50.0 mg, 0.134 mmol) synthesized according to the method described in JP-A 2006-137723, the mixture was stirred and reacted at room temperature for 1.8 hours. Then, purification by preparative thin-layer chromatography (chloroform/methanol 15/1) was performed to give 2,3-dichloro-N-{6-chloro-2-[1-(pyridin-3-yl)propoxy]-pyrazin-3-yl}benzenesulfonamide (Compound 256) (50.9 mg, yield: 80%).

ESIMS m/z: 477, 475 (M+H)+; 1H-NMR (270 MHz, CDCl3, δ): 0.97 (t, J=7.4 Hz, 3H), 1.90-2.00 (m, 1H), 2.05-2.18 (m, 1H), 5.95 (t, J=7.1 Hz, 1H), 7.31 (dd, J=4.9, 7.9 Hz, 1H), 7.40 (dd, J=7.9, 8.2 Hz, 1H), 7.57 (s, 1H), 7.67 (dd, J=1.3, 8.2 Hz, 1H), 7.73 (m, 1H), 8.26 (dd, J=1.3, 7.9 Hz, 1H), 8.57 (dd, J=1.3, 4.9 Hz, 1H), 8.67 (d, J=2.3 Hz, 1H).

EXAMPLE 252

2,3-dichloro-N-{2-[2,2,2-trifluoro-1-(pyridin-3-yl)ethoxy]-pyrido[3,2-b]pyrazin-3-yl}benzenesulfonamide (Compound 257)

According to Example 90, by use of 60% sodium hydride (in oil) (17.4 mg, 0.435 mmol), tetrahydrofuran (3.3 mL), Compound CB (39.0 mg, 0.218 mmol) and 2,3-dichloro-N-(2-chloropyrido[3,2-b]pyrazin-3-yl)benzenesulfonamide (56.6 mg, 0.145 mmol) synthesized according to the method described in JP-A 2006-137723, the mixture was stirred and reacted at room temperature for 50 minutes. Then, purification by preparative thin-layer chromatography (chloroform/methanol=15/1) was performed to give 2,3-dichloro-N-{2-[2,2,2-trifluoro-1-(pyridin-3-yl)ethoxy]-pyrido[3,2-b]pyrazin-3-yl}benzenesulfonamide (Compound 257) (20.4 mg, yield: 27%).

ESIMS m/z: 532, 530 (M+H)+; 1H-NMR (270 MHz, CDCl3, δ): 6.65 (q, J=6.6 Hz, 1H), 7.05-7.15 (m, 2H), 7.26-7.35 (m, 2H), 7.79 (d, J=7.6 Hz, 1H), 7.90 (d, J=7.3 Hz, 1H), 8.20 (br s, 1H), 8.32 (br s, 1H), 8.59 (d, J=4.3 Hz, 1H), 8.79 (s, 1H).

EXAMPLE 253

2,3-dichloro-N-{3-[2,2,2-trifluoro-1-(pyridin-3-yl)ethoxy]-pyrido[2,3-b]pyrazin-2-yl}benzenesulfonamide (Compound 258)

According to Example 37, by use of 2-chloro-3-[2,2,2-trifluoro-1-(pyridin-3-yl)ethoxy]-pyrido[3,2-b]pyrazine (Compound HB) (40.0 mg, 0.117 mmol) dissolved in dimethyl sulfoxide (1.6 mL), 2,3-dichlorobenzene-1-sulfonamide (18.5 mg, 0.0819 mmol) and potassium carbonate (16.2 mg, 0.117 mmol), the mixture was stirred and reacted at 150° C. for 1 hour. Then, purification by preparative thin-layer chromatography (chloroform/methanol=8/1) was performed to give 2,3-dichloro-N-{3-[2,2,2-trifluoro-1-(pyridin-3-yl)ethoxy]-pyrido[2,3-b]pyrazin-2-yl}benzenesulfonamide (Compound 258) (14.2 mg, yield: 33%).

(m, 3H), 7.56 (m, 1H), 7.86 (d, J=7.4 Hz, 1H), 7.93 (d, J=7.8 Hz, 1H), 8.35 (d, J=7.1 Hz, 1H), 8.59 (br s, 1H), 8.69 (s, 1H), 8.88 (s, 1H).

EXAMPLE 254

2,3-dichloro-N-{5-chloro-3-[2,2,2-trifluoro-1-(4-methoxy-phenyl)ethoxy]pyrazin-2-yl}benzenesulfonamide (Compound 259)

According to Example 90, by use of 60% sodium hydride (in oil) (29.0 mg, 0.725 mmol), dimethoxyethane (3.5 mL), Compound CJ (83.0 mg, 0.403 mmol) and 2,3-dichloro-N-(3,5-dichloropyrazin-2-yl)benzenesulfonamide (50.0 mg, 0.134 mmol) synthesized according to the method described in JP-A 2006-137723, the mixture was stirred and reacted at room temperature for 3.7 hours. Then, purification by preparative thin-layer chromatography (chloroform/methanol=15/1, hexane/ethyl acetate=2/1) was performed to give 2,3-dichloro-N-{5-chloro-3-[2,2,2-trifluoro-1-(4-methoxyphenyl)ethoxy]pyrazin-2-yl}benzenesulfonamide (Compound 259) (35.0 mg, yield: 48%).

ESIMS m/z: 542 (M−H)⁻; ¹H-NMR (270 MHz, CDCl$_3$, δ): 3.82 (s, 3H), 6.40 (q, J=6.7 Hz, 1H), 6.93 (d, J=8.9 Hz, 2H), 7.39 (dd, J=7.9, 8.1 Hz, 1H), 7.47 (d, J=8.8 Hz, 2H), 7.67 (s, 1H), 7.69 (m, 1H), 8.26 (dd, J=1.6, 8.0 Hz, 1H).

EXAMPLE 255

2-chloro-N-{6,7-dimethyl-3-[2,2,2-trifluoro-1-(pyridin-3-yl)ethoxy]quinoxalin-2-yl}benzenesulfonamide (Compound 260)

Step 1

According to Example 132, by use of 2,3-dichloro-6,7-dimethylquinoxaline (Compound HC) (300 mg, 1.32 mmol), dimethyl sulfoxide (5 mL), 2-chlorobenzenesulfonamide (253 mg, 1.32 mmol) and potassium carbonate (182 mg, 1.32 mmol), the mixture was stirred and reacted at 150° C. for 2 hours. Then, slurry purification was performed using diisopropyl ether, to give 2-chloro-N-(3-chloro-6,7-dimethylquinoxalin-2-yl)benzenesulfonamide (360 mg, yield: 71%).

ESIMS m/z: 383 (M+H)⁺; ¹H-NMR (270 MHz, CDCl$_3$, δ): 2.40 (s, 6H), 7.32-7.75 (m, 4H), 8.08-8.64 (m, 2H).

Step 2

According to Example 167, by use of 60% sodium hydride (in oil) (31 mg, 0.78 mmol), tetrahydrofuran (3 mL), Compound CB (70 mg, 0.39 mmol) and 2-chloro-N-(3-chloro-6,7-dimethylquinoxalin-2-yl)benzenesulfonamide (100 mg, 0.26 mmol) obtained in Step 1 of Example 255, the mixture was stirred and reacted at 80° C. for 10 hours. After purification by silica gel column chromatography (hexane/methyl acetate=1/0 to 1/3), slurry purification was further performed using methanol, to give 2-chloro-N-{6,7-dimethyl-3-[2,2,2-trifluoro-1-(pyridin-3-yl)ethoxy]quinoxalin-2-yl}benzenesulfonamide (Compound 260) (71 mg, yield: 52%).

ESIMS m/z: 523 (M+H)⁺; ¹H-NMR (270 MHz, CDCl$_3$, δ): 2.34 (s, 6H), 2.34-2.47 (m, 1H), 6.72 (br s, 1H), 7.31-7.56 (m, 3H), 7.94 (d, J=7.9 Hz, 1H), 8.66 (d, J=4.3 Hz, 1H), 8.84 (s, 1H), 12.00 (br s, 1H).

EXAMPLE 256

2-chloro-N-{6,7-dimethoxy-3-[2,2,2-trifluoro-1-(pyridin-3-yl)ethoxy]quinoxalin-2-yl}benzenesulfonamide (Compound 261)

Step 1

According to Example 167, by use of 60% sodium hydride (in oil) (31 mg, 0.77 mmol), tetrahydrofuran (3 mL), Compound CB (75 mg, 0.42 mmol) and 2,3-dichloro-6,7-dimethoxyquinoxaline (100 mg, 0.38 mmol), the mixture was stirred and reacted at 60° C. for 8 hours. Then, purification by silica gel column chromatography (chloroform/methanol=10/1) was performed to give 2-chloro-6,7-dimethoxy-3-[2,2,2-trifluoro-1-(pyridin-3-yl)-ethoxy]quinoxaline (75 mg, yield: 50%).

ESIMS m/z: 400 (M+H)⁺; ¹H-NMR (270 MHz, CDCl$_3$, δ): 3.99 (s, 3H), 4.03 (s, 3H), 6.76 (q, J=6.6 Hz, 1H), 7.09 (s, 1H), 7.26 (s, 1H), 7.39 (dd, J=4.8, 8.1 Hz, 1H), 8.01 (d, J=8.1 Hz, 1H), 8.67 (dd, J=1.6, 4.8 Hz, 1H), 8.91 (d, J=1.6 Hz, 1H).

Step 2

According to Example 140, by use of 2-chloro-6,7-dimethoxy-3-[2,2,2-trifluoro-1-(pyridin-3-yl)-ethoxy]quinoxaline (77 mg, 0.19 mmol) obtained in Step 1 of Example 256, dimethyl sulfoxide (2 mL), 2-chlorobenzenesulfonamide (37 mg, 0.19 mmol) and potassium carbonate (26 mg, 0.19 mmol), the mixture was stirred and reacted at 150° C. for 2 hours. After purification by silica gel column chromatography (hexane/ethyl acetate=1/0 to 1/1), slurry purification was further performed using methanol, to give 2-chloro-N-{6,7-dimethoxy-3-[2,2,2-trifluoro-1-(pyridin-3-yl)ethoxy]quinoxalin-2-yl}benzenesulfonamide (Compound 261) (71 mg, yield: 52%).

ESIMS m/z: 555 (M+H)⁺; ¹H-NMR (270 MHz, DMSO-d$_6$, δ): 3.82 (s, 3H), 3.85 (s, 3H), 6.89 (s, 1H), 7.07 (s, 1H), 7.16 (q, J=7.0 Hz, 1H), 7.49-7.70 (m, 4H), 8.29-8.42 (m, 2H), 8.67 (dd, J=1.5, 4.8 Hz, 1H), 9.08 (s, 1H), 12.06 (br s, 1H).

EXAMPLE 257

2-chloro-N-{6-methyl-3-[2,2,2-trifluoro-1-(pyridin-3-yl)-ethoxy]quinoxalin-2-yl}benzenesulfonamide (Compound 262)

Step 1

According to Example 167, by use of 60% sodium hydride (in oil) (84 mg, 2.1 mmol), tetrahydrofuran (2 mL), Compound CB (187 mg, 1.1 mmol) and 2,3-dichloro-6-methylquinoxaline (150 mg, 0.70 mmol), the mixture was stirred and reacted at room temperature for 1 hour. Then, purification by silica gel column chromatography (hexane/ethyl acetate=1/0 to 3/1) was performed to give 2-chloro-6-methyl-3-[2,2,2-trifluoro-1-(pyridin-3-yl)-ethoxy]quinoxaline (85 mg, yield: 34%).

ESIMS m/z: 354 (M+H)⁺; ¹H-NMR (270 MHz, CDCl$_3$, δ): 2.54 (s, 3H), 6.78 (q, J=6.6 Hz, 1H), 7.38 (dd, J=4.8, 8.1 Hz, 1H), 7.46 (dd, J=2.0, 8.6 Hz, 1H), 7.59 (s, 1H), 7.83 (d, J=8.6 Hz, 1H), 8.00 (d, J=8.1 Hz, 1H), 8.67 (dd, J=1.7, 4.8 Hz, 1H), 8.91 (d, J=1.7 Hz, 1H).

Step 2

According to Example 140, by use of 2-chloro-6-methyl-3-[2,2,2-trifluoro-1-(pyridin-3-yl)-ethoxy]quinoxaline (81 mg, 0.23 mmol) obtained in Step 1 of Example 257, dimethyl sulfoxide (2 mL), 2-chlorobenzenesulfonamide (44 mg, 0.23 mmol) and potassium carbonate (32 mg, 0.23 mmol), the mixture was stirred and reacted at 150° C. for 1 hour. Then, slurry purification was performed using methanol, to give 2-chloro-N-{6-methyl-3-[2,2,2-trifluoro-1-(pyridin-3-yl)-ethoxy]quinoxalin-2-yl}benzenesulfonamide (Compound 262) (92 mg, yield: 80%).

ESIMS m/z: 509 (M+H)⁺; ¹H-NMR (270 MHz, DMSO-d$_6$, δ): 2.40 (s, 3H), 7.18 (q, J=7.0 Hz, 1H), 7.30-7.45 (m, 3H), 7.52-7.69 (m, 4H), 8.29-8.42 (m, 2H), 8.68 (dd, J=1.6, 4.9 Hz, 1H), 9.09 (d, J=1.6 Hz, 1H).

EXAMPLE 258

2-chloro-N-{3-[2,2,2-trifluoro-1-(pyridin-3-yl)ethoxy]-benzo[g]quinoxalin-2-yl}benzenesulfonamide (Compound 263)

Step 1

According to Example 167, by use of 60% sodium hydride (in oil) (48 mg, 1.2 mmol), a mixed solvent of tetrahydrofuran (8 mL) and dimethylformamide (8 mL), Compound CB (117 mg, 0.66 mmol) and 2,3-dichlorobenzo[g]quinoxaline (Compound HD) (150 mg, 0.60 mmol), the mixture was stirred and reacted at room temperature for 1 hour. Then, purification by silica gel column chromatography (hexane/ethyl acetate=1/0 to 1/1) was performed to give 2-chloro-3-[2,2,2-trifluoro-1-(pyridin-3-yl)ethoxy]-benzo[g]quinoxaline (38 mg, yield: 16%).

ESIMS m/z: 390 (M+H)$^+$; $^1$H-NMR (270 MHz, CDCl$_3$, δ): 6.85 (q, J=6.3 Hz, 1H), 7.33-7.73 (m, 3H), 7.90-8.19 (m, 3H), 8.28 (s, 1H), 8.46 (s, 1H), 8.69 (d, J=4.9 Hz, 1H), 8.97 (s, 1H).

Step 2

According to Example 140, by use of 2-chloro-3-[2,2,2-trifluoro-1-(pyridin-3-yl)ethoxy]-benzo[g]quinoxaline (71 mg, 0.18 mmol) obtained in Step 1 of Example 258, dimethyl sulfoxide (2 mL), 2-chlorobenzenesulfonamide (35 mg, 0.18 mmol) and potassium carbonate (25 mg, 0.18 mmol), the mixture was stirred and reacted at 150° C. for 3 hours. After purification by silica gel column chromatography (hexane/ethyl acetate=1/0 to 3/1), slurry purification was further performed using methanol, to give 2-chloro-N-{3-[2,2,2-trifluoro-1-(pyridin-3-yl)ethoxy]-benzo[g]quinoxalin-2-yl}benzenesulfonamide (Compound 263) (62 mg, yield: 61%).

ESIMS m/z: 545 (M+H)$^+$; $^1$H-NMR (270 MHz, DMSO-d$_6$, δ): 7.18 (q, J=6.8 Hz, 1H), 7.47-7.73 (m, 6H), 7.95-8.43 (m, 6H), 8.67 (dd. J=1.5, 4.8 Hz, 1H), 9.02 (d, J=1.5 Hz, 1H).

EXAMPLE 259

2-chloro-N-{6,7-dichloro-3-[2,2,2-trifluoro-1-(pyridin-3-yl)ethoxy]quinoxalin-2-yl}benzenesulfonamide (Compound 264)

Step 1

According to Example 140, by use of 2,3,6,7-tetrachloroquinoxaline (100 mg, 0.37 mmol), dimethyl sulfoxide (2.8 mL), 2-chlorobenzenesulfonamide (72 mg, 0.37 mmol) and potassium carbonate (52 mg, 0.37 mmol), the mixture was stirred and reacted at 150° C. for 1 hour. Then, slurry purification was performed using methanol, to give 2,6,7-trichloro-3-[2,2,2-trifluoro-1-(pyridin-3-yl)ethoxy]-quinoxaline (136 mg, yield: 87%).

ESIMS m/z: 424 (M+H)$^+$; $^1$H-NMR (270 MHz, CDCl$_3$, δ): 7.43-7.63 (m, 3H), 7.75 (m, 1H), 7.98 (s, 1H), 8.48 (m, 1H).

Step 2

According to Example 167, by use of 60% sodium hydride (in oil) (25 mg, 0.63 mmol), tetrahydrofuran (5.5 mL), Compound CB (67 mg, 0.38 mmol) and 2,6,7-trichloro-3-[2,2,2-trifluoro-1-(pyridin-3-yl)ethoxy]-quinoxaline (134 mg, 0.32 mmol) obtained in Step 1 of Example 259, the mixture was stirred and reacted at room temperature for 2 hours. After purification by silica gel column chromatography (hexane/methyl acetate=1/0 to 1/1), slurry purification was further performed using methanol, to give 2-chloro-N-{6,7-dichloro-3-[2,2,2-trifluoro-1-(pyridin-3-yl)ethoxy]quinoxalin-2-yl}benzenesulfonamide (Compound 264) (61 mg, yield: 34%).

ESIMS m/z: 564 (M+H)$^+$; $^1$H-NMR (270 MHz, DMSO-d$_6$, δ): 7.16 (q, J=6.9 Hz, 1H), 7.51-7.91 (m, 6H), 8.28-8.47 (m, 2H), 8.69 (dd, J=1.6, 4.6 Hz, 1H), 9.08 (d, J=1.6 Hz, 1H).

EXAMPLE 260

2-chloro-N-{8-methyl-3-[2,2,2-trifluoro-1-(pyridin-3-yl)-ethoxy]quinoxalin-2-yl}benzenesulfonamide (Compound 265)

Step 1

According to Example 167, by use of 60% sodium hydride (in oil) (112 mg, 2.8 mmol), tetrahydrofuran (12 mL), Compound CB (274 mg, 1.6 mmol) and 2,3-dichloro-5-methylquinoxaline (Compound HE) (300 mg, 1.4 mmol), the mixture was stirred and reacted at room temperature for 3 hours. After purification by silica gel column chromatography (hexane/ethyl acetate=1/0 to 4/1), purification by preparative HPLC (acetonitrile/water system) was further performed to give both of 3-chloro-5-methyl-2-[2,2,2-trifluoro-1-(pyridin-3-yl)-ethoxy]quinoxaline (71 mg, yield: 14%) and 2-chloro-5-methyl-3-[2,2,2-trifluoro-1-(pyridin-3-yl)-ethoxy]quinoxaline (104 mg, yield: 21%). 3-chloro-5-methyl-2-[2,2,2-trifluoro-1-(pyridin-3-yl)-ethoxy]quinoxaline ESIMS m/z: 354 (M+H)$^+$; $^1$H-NMR (270 MHz, CDCl$_3$, δ): 2.59 (s, 3H), 6.67 (q, J=6.6 Hz, 1H), 7.40-7.59 (m, 3H), 7.74-7.85 (m, 1H), 8.07 (d, J=8.3 Hz, 1H), 8.69 (dd, J=1.7, 5.0 Hz, 1H), 8.94 (d, J=1.7 Hz, 1H).

2-chloro-5-methyl-3-[2,2,2-trifluoro-1-(pyridin-3-yl)-ethoxy]quinoxaline

ESIMS m/z: 354 (M+H)$^+$; $^1$H-NMR (270 MHz, CDCl$_3$, δ): 2.71 (s, 3H), 6.81 (q, J=6.4 Hz, 1H), 7.37-7.68 (m, 4H), 8.05 (d, J=7.6 Hz, 1H), 8.68 (d, J=5.0 Hz, 1H), 8.92 (s, 1H).

Step 2

According to Example 140, by use of 3-chloro-5-methyl-2-[2,2,2-trifluoro-1-(pyridin-3-yl)-ethoxy]quinoxaline (70 mg, 0.20 mmol) obtained in Step 1 of Example 260, dimethyl sulfoxide (2 mL), 2-chlorobenzenesulfonamide (38 mg, 0.20 mmol) and potassium carbonate (27 mg, 0.20 mmol), the mixture was stirred and reacted at 150° C. for 1 hour. Then, purification by silica gel column chromatography (hexane/ethyl acetate=1/0 to 1/1) was performed to give 2-chloro-N-{8-methyl-3-[2,2,2-trifluoro-1-(pyridin-3-yl)-ethoxy]quinoxalin-2-yl}benzenesulfonamide (Compound 265) (52 mg, yield: 52%).

ESIMS m/z: 509 (M+$^1$H-NMR (270 MHz, DMSO-d$_6$, δ): 2.45 (s, 3H), 7.09 (q, J=6.9 Hz, 1H), 7.28-7.42 (m, 2H), 7.48-7.69 (m, 2H), 8.15-8.43 (m, 2H), 8.64 (dd, J=1.7, 5.0 Hz, 1H), 9.03 (s, 1H).

EXAMPLE 261

2-chloro-N-{5-methyl-3-[2,2,2-trifluoro-1-(pyridin-3-yl)-ethoxy]quinoxalin-2-yl}benzenesulfonamide (Compound 266)

According to Example 140, by use of 2-chloro-5-methyl-3-[2,2,2-trifluoro-1-(pyridin-3-yl)-ethoxy]quinoxaline (104 mg, 0.29 mmol) obtained in Step 1 of Example 260, dimethyl sulfoxide (3 mL), 2-chlorobenzenesulfonamide (56 mg, 0.29 mmol) and potassium carbonate (41 mg, 0.29 mmol), the mixture was stirred and reacted at 150° C. for 1 hour. Then, purification by silica gel column chromatography (hexane/ethyl acetate=1/0 to 1/1) was performed to give 2-chloro-N-{5-methyl-3-[2,2,2-trifluoro-1-(pyridin-3-yl)-ethoxy]quinoxalin-2-yl}benzenesulfonamide (Compound 266) (101 mg, yield: 68%).

ESIMS m/z: 509 (M+H)$^+$; $^1$H-NMR (270 MHz, DMSO-d$_6$, δ): 2.18 (s, 3H), 7.23 (q, J=7.0 Hz, 1H), 7.31-7.70 (m, 7H), 8.32-8.44 (m, 2H), 8.67 (dd, J=1.7, 5.0 Hz, 1H), 9.12 (d, J=1.7 Hz, 1H).

EXAMPLE 262

2-chloro-N-{3-[2,2,2-trifluoro-1-(tetrahydro-2H-thiopyran-4-yl)ethoxy]quinoxalin-2-yl}benzenesulfonamide (Compound 267)

According to Example 90, by use of 60% sodium hydride (in oil) (36.0 mg, 0.904 mmol), tetrahydrofuran (3.5 mL), Compound EH (136 mg, 0.678 mmol) and 2-chloro-N-(3-chloroquinoxalin-2-yl)benzenesulfonamide (Compound AD) (80.0 mg, 0.226 mmol), the mixture was stirred and reacted at a temperature of room temperature to 50° C. for 5.2 hours. Then, purification by preparative thin-layer chromatography (hexane/ethyl acetate=4/1) was performed to give 2 chloro-N-{3-[2,2,2-trifluoro-1-(tetrahydro-2H-thiopyran-4-yl)ethoxy]quinoxalin-2-yl}benzenesulfonamide (Compound 267) (80.7 mg, yield: 70%).

ESIMS m/z: 520, 518 (M+H)$^+$; $^1$H-NMR (270 MHz, CDCl$_3$, δ): 1.67 (m, 2H), 2.19 (m, 3H), 2.66 (m, 4H), 5.92 (br s, 1H), 7.43-7.52 (m, 6H), 7.68 (m, 1H), 8.15-8.50 (m, 2H).

EXAMPLE 263

2-chloro-N-{3-[2,2,2-trifluoro-1-(tetrahydro-2H-thiopyran-1,1-dioxide-4-yl)ethoxy]quinoxalin-2-yl}benzenesulfonamide (Compound 268)

According to the step of Example 127, by use of 2-chloro-N-{3-[2,2,2-trifluoro-1-(tetrahydro-2H-thiopyran-4-yl)ethoxy]quinoxalin-2-yl}benzenesulfonamide (Compound 267) (25.0 mg, 0.0483 mmol) obtained in Example 262 and dissolved in dichloromethane (2 mL), and meta-chloroperbenzoic acid (25.0 mg, 0.145 mmol), the mixture was stirred and reacted at room temperature for 2.2 hours. Then, purification by preparative thin-layer chromatography (chloroform/methanol=30/1) was performed to give 2-chloro-N-{3-[2,2,2-trifluoro-1-(tetrahydro-2H-thiopyran-1,1-dioxide-4-yl)ethoxy]quinoxalin-2-yl}benzenesulfonamide (Compound 268) (20.8 mg, yield: 78%).

ESIMS m/z: 552, 550 (M+H)$^+$; $^1$H-NMR (270 MHz, CDCl$_3$, δ): 2.20 (m, 1H), 2.33 (m, 4H), 3.09 (m, 4H), 6.03 (br s, 1H), 7.50-7.52 (m, 6H), 7.68 (m, 1H), 8.34 (br s, 1H), 8.52 (br s, 1H).

EXAMPLE 264

2 chloro-N-{3-[2,2,2-trifluoro-1-(tetrahydro-2H-thiopyran-1-oxide-4-yl)ethoxy]quinoxalin-2-yl}benzenesulfonamide (Compound 269) (Compound 270)

According to the step of Example 127, by use of 2-chloro-N-{3-[2,2,2-trifluoro-1-(tetrahydro-2H-thiopyran-4-yl)ethoxy]quinoxalin-2-yl}benzenesulfonamide (Compound 267) (31.4 mg, 0.0606 mmol) obtained in Example 262 and dissolved in dichloromethane (2.5 mL), and meta-chloroperbenzoic acid (11.5 mg, 0.0667 mmol), the mixture was stirred and reacted at room temperature for 4.2 hours. Then, purification by preparative thin-layer chromatography (chloroform/acetonitrile=4/1) was performed to give 2-chloro-N-{3-[2,2,2-trifluoro-1-(tetrahydro-2H-thiopyran-1-oxide-4-yl)ethoxy]quinoxalin-2-yl}benzenesulfonamide (Rf=0.52: Compound 269) (13.6 mg, yield: 42%) (Rf=0.42: Compound 270) (18.8 mg, yield: 58%).
Compound 269
ESIMS m/z: 536, 534 (M+H)$^+$; $^1$H-NMR (270 MHz, CDCl$_3$, δ): 1.97 (m, 2H), 2.31-2.58 (m, 5H), 3.11 (m, 2H), 5.98 (m, 1H), 7.35-7.56 (m, 6H), 7.68 (m, 1H), 7.93-8.47 (m, 2H).
Compound 270
ESIMS m/z: 536, 534 (M+H)$^+$; $^1$H-NMR (270 MHz, CDCl$_3$, δ): 1.75 (m, 2H), 2.35 (m, 3H), 2.77 (m, 2H), 3.35 (m, 2H), 5.97 (m, 1H), 7.37-7.53 (m, 6H), 7.62 (m, 1H), 7.95-8.45 (m, 2H).

EXAMPLE 265

N-{3-[2,2,2-trifluoro-1-(1-methyl-2(1H)pyridon-5-yl)-ethoxy]quinoxalin-2-yl}propane-1-sulfonamide (Compound 271)

According to Example 37, by use of 2-chloro-3-[2,2,2-trifluoro-1-(1-methyl-2(1H)pyridon-5-yl)-ethoxy]quinoxaline (Compound BT) (70.0 mg, 0.190 mmol), dimethyl sulfoxide (2.0 mL), Compound FS (25.6 mg, 0.208 mmol) and potassium carbonate (28.7 mg, 0.208 mmol), the mixture was stirred and reacted at 150° C. for 2 hours. Then, purification by preparative thin-layer chromatography (hexane/ethyl acetate=1/1) was performed to give N-{3-[2,2,2-trifluoro-1-(1-methyl-2(1H)pyridon-5-yl)-ethoxy]quinoxalin-2-yl}propane-1-sulfonamide (Compound 271) (34.0 mg, yield: 39%).

ESIMS m/z: 457 (M+H)$^+$; $^1$H-NMR (300 MHz, CDCl$_3$, δ): 1.12 (t, J=7.3 Hz, 3H), 1.96-2.04 (m, 2H), 3.58 (s, 3H), 3.78-3.82 (m, 2H), 6.55-6.64 (m, 2H), 7.56-7.76 (m, 5H), 7.89-7.92 (m, 1H).

EXAMPLE 266

N-{3-[2,2,2-trifluoro-1-(pyridin-3-yl)ethoxy]quinoxalin-2-yl}-N'-(3,3-diethoxypropyl)-sulfuric diamide (Compound 272)

According to Example 132, by use of 2-chloro-3-[2,2,2-trifluoro-1-(pyridin-3-yl)ethoxy]-quinoxaline (Compound BJ) (400 mg, 1.18 mmol) and Compound GK (266 mg, 1.18 mmol), Compound 272 (160 mg, yield: 26%) was obtained.

ESIMS m/z: 530 (M+H)$^+$.

EXAMPLE 267

N-{3-[2,2,2-trifluoro-1-(pyridin-3-yl)ethoxy]quinoxalin-2-yl}-N'-(3-oxopropyl)-sulfuric diamide (Compound 273)

Compound 272 (72.0 mg, 0.136 mmol) obtained in Example 266 was dissolved in THF (1.50 mL). To this, a 1.00 mol/L aqueous hydrochloric acid solution (1.50 mL) was added and the mixture was stirred at room temperature for 1.5 hours. The reaction was stopped by addition of a saturated aqueous sodium bicarbonate solution to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=1/0 to 1/1) to give Compound 273 (41.6 mg, yield: 67%).

ESIMS m/z: 456 (M+H)$^+$.

EXAMPLE 268

N-{3-[2,2,2-trifluoro-1-(pyridin-3-yl)ethoxy]quinoxalin-2-yl}-N'-(2-propynyl)-sulfuric diamide (Compound 274)

According to Example 132, by use of Compound BJ (70.0 mg, 0.206 mmol) and Compound GL (28.0 mg, 0.206 mmol), Compound 274 (31.0 mg, yield: 26%) was obtained.

ESIMS m/z: 438 (M+H)$^+$.

EXAMPLE 269

N-{3-[2,2,2-trifluoro-1-(tetrahydro-2H-thiopyran-1,1-dioxide-4-yl)ethoxy]quinoxalin-2-yl}propane-1-sulfonamide (Compound 275)

Step 1

According to Example 90, by use of Compound EH (168 mg, 0.840 mmol) and Compound AH (120 mg, 0.420 mmol), N-{3-[2,2,2-trifluoro-1-(tetrahydro-2H-thiopyran-4-yl)-ethoxy]quinoxalin-2-yl}propane-1-sulfonamide (120 mg, yield: 63%) was obtained.
ESIMS m/z: 450 (M+H)$^+$.

Step 2

According to Example 127, by use of N-{3-[2,2,2-trifluoro-1-(tetrahydro-2H-thiopyran-4-yl)-ethoxy]quinoxalin-2-yl}propane-1-sulfonamide (120 mg, 0.267 mmol) obtained in the above Step 1, Compound 275 (34.0 mg, yield: 27%) was obtained.
ESIMS m/z: 482 (M+H)$^+$.

EXAMPLE 270

N-{3-[2,2,2-trifluoro-1-(thiazol-5-yl)ethoxy]quinoxalin-2-yl}propane-1-sulfonamide (Compound 276)

According to Example 132, by use of Compound BU (100 mg, 0.290 mmol) and Compound FS (36.0 mg, 0.290 mmol), Compound 276 (58.0 mg, yield: 46%) was obtained.
ESIMS m/z: 434 (M+H)$^+$.

EXAMPLE 271

N-{3-[2,2,2-trifluoro-1-(1-methyl-1H-imidazol-5-yl)ethoxy]-quinoxalin-2-yl}propane-1-sulfonamide (Compound 277)

According to Example 132, by use of Compound BV (100 mg, 0.290 mmol) and Compound FS (36.0 mg, 0.290 mmol), Compound 277 (40.0 mg, yield: 32%) was obtained.
ESIMS m/z: 430 (M+H)$^+$.

EXAMPLE 272

N-{3-[1-(6-chloropyridin-3-yl)-2,2,2-trifluoroethoxy]-quinoxalin-2-yl}propane-1-sulfonamide (Compound 278)

According to Example 132, by use of Compound BW (100 mg, 0.270 mmol) and Compound FS (33.0 mg, 0.270 mmol), Compound 278 (54.0 mg, yield: 44%) was obtained.
ESIMS m/z: 461 (M+H)$^+$.

EXAMPLE 273

2-methyl-5-{2,2,2-trifluoro-1-[3-(propylsulfonamide)-quinoxalin-2-yloxy]ethyl}pyridine 1-oxide (Compound 279)

According to Example 206, by use of Compound 192 (100 mg, 0.227 mmol) obtained in Example 187, Compound 279 (91.0 mg, 88%) was obtained.
ESIMS m/z: 456 (M+H)$^+$.

EXAMPLE 274

N-{3-[2,2,2-trifluoro-1-(6-methylpyridin-3-yl)ethoxy]-quinoxalin-2-yl}-N'-propyl-sulfuric diamide (Compound 280)

According to Example 132, by use of Compound BM (200 mg, 0.560 mmol) and Compound GD (78.0 mg, 0.560 mmol), Compound 280 (137 mg, yield: 54%) was obtained.
ESIMS m/z: 456 (M+H)$^+$.

EXAMPLE 275

N-{3-[2,2,2-trifluoro-1-(thiazol-5-yl)ethoxy]quinoxalin-2-yl}-N'-propyl-sulfuric diamide (Compound 281)

According to Example 132, by use of Compound BU (100 mg, 0.290=01) and Compound GD (40.0 mg, 0.290 mmol), Compound 281 (47.0 mg, yield: 36%) was obtained.
ESIMS m/z: 448 (M+H)$^+$.

EXAMPLE 276

N-{3-[2,2,2-trifluoro-1-(1-methyl-1H-imidazol-5-yl)ethoxy]-quinoxalin-2-yl}-N'-propyl-sulfuric diamide (Compound 282)

According to Example 132, by use of Compound BV (100 mg, 0.290 mmol) and Compound GD (40.0 mg, 0.290 mmol), Compound 282 (46.0 mg, yield: 36%) was obtained.
ESIMS m/z: 445 (M+H)$^+$.

EXAMPLE 277

N-{3-[1-(6-chloropyridin-3-yl)-2,2,2-trifluoroethoxy]-quinoxalin-2-yl}-N'-propyl-sulfuric diamide (Compound 283)

According to Example 132, by use of Compound BW (100 mg, 0.270 mmol) and Compound GD (37.0 mg, 0.270 mmol), Compound 283 (39.0 mg, yield: 31%) was obtained.
ESIMS m/z: 476 (M+H)$^+$.

EXAMPLE 278

2-methyl-5-{2,2,2-trifluoro-1-[3-(N-propylsulfamoylamino)-quinoxalin-2-yloxy]ethyl}pyridine 1-oxide (Compound 284)

According to Example 206, by use of Compound 280 (93.0 mg, 0.200 mmol) obtained in Example 274, Compound 284 (61.0 mg, 65%) was obtained.
ESIMS m/z: 472 (M+H)$^+$.

EXAMPLE 279

N-{3-[2,2,2-trifluoro-1-(6-methylpyridin-3-yl)ethoxy]-quinoxalin-2-yl}-N'-cyclopropyl-sulfuric diamide (Compound 285)

According to Example 132, by use of Compound BM (200 mg, 0.560 mmol) and Compound FZ (78.0 mg, 0.560 mmol), Compound 285 (109 mg, yield: 43%) was obtained.
ESIMS m/z: 454 (M+H)$^+$.

EXAMPLE 280

N-{3-[2,2,2-trifluoro-1-(thiazol-5-yl)ethoxy]quinoxalin-2-yl}-N'-cyclopropyl-sulfuric diamide (Compound 286)

According to Example 132, by use of Compound BU (100 mg, 0.290 mmol) and Compound FZ (39.0 mg, 0.290 mmol), Compound 286 (51.0 mg, yield: 40%) was obtained.
ESIMS m/z: 446 (M+H)$^+$.

EXAMPLE 281

N-{3-[2,2,2-trifluoro-1-(1-methyl-1H-imidazol-5-yl)ethoxy]-quinoxalin-2-yl}-N'-cyclopropyl-sulfuric diamide (Compound 287)

According to Example 132, by use of Compound BV (100 mg, 0.290 mmol) and Compound FZ (40.0 mg, 0.290 mmol), Compound 287 (51.0 mg, yield: 40%) was obtained.
ESIMS m/z: 443 (M+H)$^+$.

EXAMPLE 282

N-{3-[1-(6-chloropyridin-3-yl)-2,2,2-trifluoroethoxy]-quinoxalin-2-yl}-N'-cyclopropyl-sulfuric diamide (Compound 288)

According to Example 132, by use of Compound BW (100 mg, 0.270 mmol) and Compound FZ (36.0 mg, 0.270 mmol), Compound 288 (48.0 mg, yield: 38%) was obtained.
ESIMS m/z: 474 (M+H)$^+$.

EXAMPLE 283

5-{1-[3-(N-cyclopropylsulfamoylamino) quinoxalin-2-yloxy]-2,2,2-trifluoroethyl}-2-methylpyridine 1-oxide (Compound 289)

According to Example 206, by use of Compound 285 (73.0 mg, 0.160 mmol) obtained in Example 279, Compound 289 (41.0 mg, 55%) was obtained.
ESIMS m/z: 470 (M+H)$^+$.

EXAMPLE 284

N-{3-[1-(3-cyanophenyl)-2,2,2-trifluoroethoxy]quinoxalin-2-yl}propane-1-sulfonamide (Compound 290)

According to Example 132, by use of Compound BX (100 mg, 0.280 mmol) and Compound FS (34.0 mg, 0.280 mmol), Compound 290 (53.0 mg, yield: 43%) was obtained.
ESIMS m/z: 451 (M+H)$^+$.

EXAMPLE 285

N-{3-[1-(3-cyanophenyl)-2,2,2-trifluoroethoxy]quinoxalin-2-yl}-N'-propyl-sulfuric diamide (Compound 291)

According to Example 132, by use of Compound BX (100 mg, 0.280 mmol) and Compound GD (38.0 mg, 0.280 mmol), Compound 291 (39.0 mg, yield: 31%) was obtained.
ESIMS m/z: 466 (M+H)$^+$.

EXAMPLE 286

N-{3-[1-(4-cyanophenyl)-2,2,2-trifluoroethoxy]quinoxalin-2-yl}-N'-propyl-sulfuric diamide (Compound 292)

According to Example 132, by use of Compound BO (85.0 mg, 0.230 mmol) and Compound GD (32.0 mg, 0.230 mmol), Compound 292 (31.0 mg, yield: 24%) was obtained.
ESIMS m/z: 466 (M+H)$^+$.

EXAMPLE 287

N-{3-[1-(3-cyanophenyl)-2,2,2-trifluoroethoxy]quinoxalin-2-yl}-N'-cyclopropyl-sulfuric diamide (Compound 293)

According to Example 132, by use of Compound BX (100 mg, 0.270 mmol) and Compound FZ (37.0 mg, 0.270 mmol), Compound 293 (57.0 mg, yield: 46%) was obtained.
ESIMS m/z: 464 (M+H)$^+$.

EXAMPLE 288

N-{3-[1-(4-cyanophenyl)-2,2,2-trifluoroethoxy]quinoxalin-2-yl}-N'-propyl-sulfuric diamide (Compound 294)

According to Example 132, by use of Compound BO (90.0 mg, 0.250 mmol) and Compound FZ (34.0 mg, 0.250 mmol), Compound 294 (47.0 mg, yield: 41%) was obtained.
ESIMS m/z: 464 (M+H)$^+$.

EXAMPLE 289

Benzyl 3-{N-[2,2,2-trifluoro-1-(pyridin-3-yl)ethoxy]quinoxalin-2-yl}sulfamoylpropanoate (Compound 295)

According to Example 132, by use of Compound BJ (500 mg, 1.47 mmol) and Compound GM (379 mg, 1.47 mmol), Compound 295 (420 mg, yield: 51%) was obtained.
ESIMS m/z: 561 (M+H)$^+$.

EXAMPLE 290

3-{N-[2,2,2-trifluoro-1-(pyridin-3-yl)ethoxy]quinoxalin-2-yl}sulfamoylpropanoic acid (Compound 296)

Compound 295 (380 mg, 0.680 mmol) obtained in Example 289 was dissolved in methanol (3.00 mL). To this, a 2.00 mol/L aqueous sodium hydroxide solution (3.00 mL) was added and the mixture was stirred at room temperature for 1 hour. By addition of a 2.00 mol/L aqueous hydrochloric acid solution to neutralize the reaction mixture, the reaction was stopped. Then, extraction with ethyl acetate was performed, followed by washing with brine and drying over anhydrous sodium sulfate. The solvent was evaporated off under reduced pressure, and the residue was purified by silica gel column chromatography (ethyl acetate/methanol=1/0 to 14/1) to give Compound 296 (308 mg, yield: 37%).
ESIMS m/z: 471 (M+H)$^+$.

EXAMPLE 291

N-ethyl-N-methyl-N'-{3-[2,2,2-trifluoro-1-(pyridin-3-yl)-ethoxy]quinoxalin-2-yl}-sulfuric diamide (Compound 297)

According to Example 132, by use of Compound BJ (100 mg, 0.290 mmol) and Compound GN (45.0 mg, 0.290 mmol), Compound 297 (54.0 mg, yield: 41%) was obtained. ESIMS m/z: 456 (M+H)$^+$.

EXAMPLE 292

N-diethyl-N'-{3-[2,2,2-trifluoro-1-(pyridin-3-yl)ethoxy]-quinoxalin-2-yl}-sulfuric diamide (Compound 298)

According to Example 132, by use of Compound BJ (100 mg, 0.290 mmol) and Compound GO (53.0 mg, 0.290 mmol), Compound 298 (61.0 mg, yield: 44%) was obtained. ESIMS m/z: 484 (M+H)$^+$.

EXAMPLE 293

N-{3-[2,2,2-trifluoro-1-(tetrahydro-2H-pyran-4-yl)ethoxy]-quinoxalin-2-yl}-N'-cyclopropyl-sulfuric diamide (Compound 299)

According to Example 132, by use of Compound BQ (150 mg, 0.430 mmol) and Compound FZ (59.0 mg, 0.430 mmol), Compound 299 (45.8 mg, yield: 24%) was obtained. ESIMS m/z: 447 (M+H)$^+$.

EXAMPLE 294

2-methoxy-N-{3-[2,2,2-trifluoro-1-(pyridin-3-yl)ethoxy]-quinoxalin-2-yl}ethanesulfonamide (Compound 300)

According to Example 132, by use of Compound BJ (100 mg, 0.290 mmol) and Compound GP (41.0 mg, 0.290 mmol), Compound 300 (34.0 mg, yield: 26%) was obtained. ESIMS m/z: 443 (M+H)$^+$.

EXAMPLE 295

3-methoxy-N-{3-[2,2,2-trifluoro-1-(pyridin-3-yl)ethoxy]-quinoxalin-2-yl}propane-1-sulfonamide (Compound 301)

According to Example 132, by use of Compound BJ (100 mg, 0.290 mmol) and Compound GQ (45.0 mg, 0.290 mmol), Compound 301 (42.8 mg, yield: 31%) was obtained. ESIMS m/z: 457 (M+H)$^+$.

EXAMPLE 296

N-{3-[1-(4-chlorophenyl)-2,2,2-trifluoroethoxy]quinoxalin-2-yl}propane-1-sulfonamide (Compound 302)

According to Example 90, by use of Compound CP (147 mg, 0.700 mmol) and Compound AH (100 mg, 0.350 mmol), Compound 302 (106 mg, yield: 66%) was obtained. ESIMS m/z: 460 (M+H)$^+$.

EXAMPLE 297

1-cyclopropyl-N-{3-[2,2,2-trifluoro-1-(pyridin-3-yl)-ethoxy]quinoxalin-2-yl}methanesulfonamide (Compound 303)

According to Example 132, by use of Compound BJ (150 mg, 0.440 mmol) and Compound GS (60.0 mg, 0.440 mmol), Compound 303 (116 mg, yield: 60%) was obtained. ESIMS m/z: 439 (M+H)$^+$.

EXAMPLE 298

N-{3-[2,2,2-trifluoro-1-(pyridin-3-yl)ethoxy]quinoxalin-2-yl}-2-propene-1-sulfonamide (Compound 304)

According to Example 132, by use of Compound BJ (123 mg, 0.360 mmol) and Compound GT (44.0 mg, 0.360 mmol), Compound 304 (92.2 mg, yield: 61%) was obtained. ESIMS m/z: 425 (M+H)$^+$.

EXAMPLE 299

1-cyclopropyl-N-{3-[2,2,2-trifluoro-1-(6-methylpyridin-3-yl)ethoxy]quinoxalin-2-yl}methanesulfonamide (Compound 305)

According to Example 132, by use of Compound BM (90.0 mg, 0.250 mmol) and Compound GS (35.0 mg, 0.250 mmol), Compound 305 (68.0 mg, yield: 60%) was obtained. ESIMS m/z: 453 (M+H)$^+$.

EXAMPLE 300

1-cyclopropyl-N-{3-[2,2,2-trifluoro-1-(2-methylthiazol-5-yl)ethoxy]quinoxalin-2-yl}methanesulfonamide (Compound 306)

According to Example 132, by use of Compound BY (90.0 mg, 0.250 mmol) and Compound GS (34.0 mg, 0.250 mmol), Compound 306 (68.0 mg, yield: 60%) was obtained. ESIMS m/z: 459 (M+H)$^+$.

EXAMPLE 301

(R)-1-cyclopropyl-N-{3-[2,2,2-trifluoro-1-(pyridin-3-yl)-ethoxy]quinoxalin-2-yl}methanesulfonamide (Compound 307)

According to Example 132, by use of Compound BZ (177 mg, 0.520=01) and Compound GS (70.0 rag, 0.520 mmol), Compound 307 (90.0 mg, yield: 40%) was obtained. ESIMS m/z: 439 (M+H)$^+$.

EXAMPLE 302

1-cyclopropyl-N-{3-[1-(6-chloropyridin-3-yl)-2,2,2-trifluoroethoxy]quinoxalin-2-yl}methanesulfonamide (Compound 308)

According to Example 132, by use of Compound BW (90.0 mg, 0.240 mmol) and Compound GS (33.0 mg, 0.240 mmol), Compound 308 (35.0 mg, yield: 31%) was obtained. ESIMS m/z: 473 (M+H)$^+$.

EXAMPLE 303

1-cyclopropyl-N-{3-[1-(3-cyanophenyl)-2,2,2-trifluoroethoxy]quinoxalin-2-yl}methanesulfonamide (Compound 309)

According to Example 132, by use of Compound BX (90.0 mg, 0.240 mmol) and Compound GS (33.0 mg, 0.240 mmol), Compound 309 (45.0 mg, yield: 39%) was obtained.
ESIMS m/z: 463 (M+H)$^+$.

EXAMPLE 304

(S)-2-chloro-N-3-{(2,2,2-trifluoro-1-phenylethoxy)-quinoxalin-2-yl}benzenesulfonamide (Compound 310)

According to Example 8, by use of Compound AD (70.0 mg, 0.198 mmol), Compound 310 (59.7 mg, yield: 61%) was obtained.
ESIMS m/z: 493 (M+H)$^+$.

EXAMPLE 305

(R)-2-chloro-N-3-{(2,2,2-trifluoro-1-phenylethoxy)-quinoxalin-2-yl}benzenesulfonamide (Compound 311)

According to Example 8, by use of Compound AD (70.0 mg, 0.198 mmol), Compound 311 (72.5 mg, yield: 74%) was obtained.
ESIMS m/z: 493 (M+H)$^+$.

EXAMPLE 306

(R)—N-{3-[2,2,2-trifluoro-1-(pyridin-3-yl)ethoxy]-quinoxalin-2-yl}propane-1-sulfonamide (Compound 312)

According to Example 8, by use of Compound AH (80.5 mg, 0.282 mmol) and Compound EU (59.8 mg, 0.338 mmol), Compound 312 (42.6 mg, yield: 38%) was obtained.
$[\alpha]_D^{20}=-118$ (CHCl$_3$, c=1.00);
ESIMS m/z: 427 (M+H)$^+$.

EXAMPLE 307

(S)—N-{3-[2,2,2-trifluoro-1-(pyridin-3-yl)ethoxy]-quinoxalin-2-yl}propane-1-sulfonamide (Compound 313)

According to Example 8, by use of Compound AH (88.1 mg, 0.308 mmol) and Compound EV (65.6 mg, 0.370 mmol), Compound 313 (49.5 mg, yield: 38%) was obtained.
$[\alpha]_D^{20}=+122$ (CHCl$_3$, c=1.00);
ESIMS m/z: 427 (M+H)$^+$.

EXAMPLE 308

(R)—N-propyl-N'-{3-[2,2,2-trifluoro-1-(pyridin-3-yl)-ethoxy]quinoxalin-2-yl}sulfuric diamide (Compound 314)

According to Example 37, by use of Compound BZ (251 mg, 0.739 mmol) and Compound GD (102 mg, 0.739 mmol), Compound 314 (131 mg, 40%) was obtained.
ESIMS m/z: 442 (M+H)$^+$.

EXAMPLE 309

N-{3-[2,2,2-trifluoro-1-(2-methylthiazol-5-yl)ethoxy]-quinoxalin-2-yl}propane-1-sulfonamide (Compound 315)

According to Example 8, by use of Compound AH (57.0 mg, 0.200 mmol) and Compound EX (59.0 mg, 0.300 mmol), Compound 315 (30.0 mg, yield: 34%) was obtained.
ESIMS m/z: 447 (M+H)$^+$.

EXAMPLE 310

2-chloro-N-3-{[2,2,2-trifluoro-1-(2-methylthiazol-5-yl)-ethoxy]quinoxalin-2-yl}benzenesulfonamide (Compound 316)

According to Example 8, by use of Compound AD (106 mg, 0.300 mmol) and Compound EX (89.0 mg, 0.450 mmol), Compound 316 (70.0 mg, yield: 45%) was obtained.
ESIMS m/z: 515 (M+H)$^+$.

EXAMPLE 311

(R)—N-cyclopropyl-N'-{3-[2,2,2-trifluoro-1-(pyridin-3-yl)-ethoxy]quinoxalin-2-yl}sulfuric diamide (Compound 317)

According to Example 37, by use of Compound BZ (223 mg, 0.656 mmol) and Compound FZ (89.4 mg, 0.656 mmol), Compound 317 (172 mg, yield: 60%) was obtained.
ESIMS m/z: 440 (M+H)$^+$.

EXAMPLE 312

2-chloro-N-{3-[2,2,2-trifluoro-1-(1-methyl-2(1H)pyridon-4-yl)ethoxy]quinoxalin-2-yl}benzenesulfonamide (Compound 318)

According to Example 37, by use of Compound BAA (71.0 mg, 0.190 mmol), Compound 318 (15.0 mg, yield: 15%) was obtained.
ESIMS m/z: 524 (M+H)$^+$.

EXAMPLE 313

(R)—N-{3-[2,2,2-trifluoro-1-(6-methylpyridin-3-yl)ethoxy]-quinoxalin-2-yl}propane-1-sulfonamide (Compound 319)

According to Example 8, by use of Compound AH (429 mg, 1.50 mmol) and Compound EZ (344 mg, 1.80 mmol), Compound 319 (420 mg, yield: 63%) was obtained.
ESIMS m/z: 441 (M+H)$^+$.

EXAMPLE 314

(S)—N-{3-[2,2,2-trifluoro-1-(6-methylpyridin-3-yl)ethoxy]-quinoxalin-2-yl}propane-1-sulfonamide (Compound 320)

According to Example 8, by use of Compound AH (429 mg, 1.50 mmol) and Compound EAA (344 mg, 1.80 mmol), Compound 320 (395 mg, yield: 60%) was obtained.
ESIMS m/z: 441 (M+H)$^+$.

EXAMPLE 315

2-chloro-N-{3-[(1,1,1,3,3,3-hexafluoropropan-2-yl)oxy]-quinoxalin-2-yl}benzenesulfonamide (Compound 321)

According to Example 37, by use of Compound BAB (102 mg, 0.221 mmol), Compound 321 (15.7 mg, yield: 15%) was obtained.
ESIMS m/z: 486 (M+H)$^+$.

EXAMPLE 316

N-{3-[(1,1,1,3,3,3-hexafluoropropan-2-yl)oxy]quinoxalin-2-yl}propane-1-sulfonamide (Compound 322)

According to Example 37, by use of Compound BAB (307 mg, 0.664 mmol) and Compound FS (81.8 mg, 0.664 mmol), Compound 322 (44.9 mg, yield: 15%) was obtained.
ESIMS m/z: 418 (M+H)$^+$.

EXAMPLE 317

N-propyl-N'-{3-[2,2,2-trifluoro-1-(2-methylthiazol-5-yl)-ethoxy]quinoxalin-2-yl}sulfuric diamide (Compound 323)

According to Example 37, by use of Compound BY (108 mg, 0.300 mmol) and Compound GD (62.0 mg, 0.450 mmol), Compound 323 (55.0 mg, yield: 40%) was obtained.
ESIMS m/z: 462 (M+H)$^+$.

EXAMPLE 318

N-cyclopropyl-N'-{3-[2,2,2-trifluoro-1-(2-methylthiazol-5-yl) ethoxy]quinoxalin-2-yl}sulfuric diamide (Compound 324)

According to Example 37, by use of Compound BY (108 mg, 0.300 mmol) and Compound FZ (61.0 mg, 0.450 mmol), Compound 324 (42.0 mg, yield: 30%) was obtained.
ESIMS m/z: 460 (M+H)$^+$.

EXAMPLE 319

2-chloro-N-3-{[2,2,2-trifluoro-1-(1-methylpiperidin-4-yl)-ethoxy]quinoxalin-2-yl}benzenesulfonamide (Compound 325)

According to Example 8, by use of Compound AD (70.0 mg, 0.198 mmol) and Compound EAC (58.6 mg, 0.297 mmol), Compound 325 (91.2 mg, yield: 89%) was obtained.
ESIMS m/z: 515 (M+H)$^+$.

EXAMPLE 320

N-{3-[2,2,2-trifluoro-1-(1-methylpiperidin-4-yl)ethoxy]-quinoxalin-2-yl}propane-1-sulfonamide (Compound 326)

According to Example 8, by use of Compound AH (70.0 mg, 0.245 mmol) and Compound EAC (72.5 mg, 0.367 mmol), Compound 326 (85.4 mg, yield: 78%) was obtained.
ESIMS m/z: 447 (M+H)$^+$.

EXAMPLE 321

N-{3-[2,2,2-trifluoro-1-(piperidin-4-yl)ethoxy]quinoxalin-2-yl}propane-1-sulfonamide (Compound 327)

Step 1
According to Example 8, by use of Compound AH (1.00 g, 3.50 mmol) and Compound EAB (1.33 mg, 4.20 mmol), N-{3-[2,2,2-trifluoro-1-(1-benzyloxycarbonylpiperidin-4-yl)ethoxy]quinoxalin-2-yl}propane-1-sulfonamide (1.88 g, yield: 95%) was obtained.
Step 2
Ten percent palladium/carbon (15.0 mg) was suspended in tetrahydrofuran (1.0 mL). To this, a tetrahydrofuran solution (2.0 mL) of N-{3-[2,2,2-trifluoro-1-(1-benzyloxycarbonylpiperidin-4-yl)ethoxy]quinoxalin-2-yl}propane-1-sulfonamide (150 mg, 0.245 mmol) was added and the mixture was stirred under hydrogen stream at room temperature for 3 days. To the reaction mixture, 10% palladium/carbon (15.0 mg) and ethanol (2.0 mL) were added and the mixture was stirred under hydrogen stream at room temperature for 8 hours. The reaction mixture was filtered through Celite and the solvent was evaporated off under reduced pressure. The residue was purified by preparative thin-layer chromatography (chloroform/methanol=9/1) to give Compound 327 (38.7 mg, yield: 37%).
ESIMS m/z: 433 (M+H)$^+$.

EXAMPLE 322

N-propyl-N'-{3-[2,2,2-trifluoro-1-(1-methylpiperidin-4-yl)ethoxy]quinoxalin-2-yl}sulfuric diamide (Compound 328)

According to Example 37, by use of Compound BAC (78.4 mg, 0.218 mmol) and Compound GD (30.1 mg, 0.218 mmol), Compound 328 (42.1 mg, yield: 42%) was obtained.
ESIMS m/z: 462 (M+H)$^+$.

EXAMPLE 323

N-cyclopropyl-N'-{3-[2,2,2-trifluoro-1-(1-methylpiperidin-4-yl)ethoxy]quinoxalin-2-yl}sulfuric diamide (Compound 329)

According to Example 37, by use of Compound BAC (82.1 mg, 0.228 mmol) and Compound FZ (31.1 mg, 0.228 mmol), Compound 329 (38.1 mg, yield: 36%) was obtained.
ESIMS m/z: 460 (M+H)$^+$.

EXAMPLE 324

N-{3-[2,2,2-trifluoro-1-(1-acetylpiperidin-4-yl)ethoxy]-quinoxalin-2-yl}propane-1-sulfonamide (Compound 330)

Compound 327 (59.0 mg, 0.136 mmol) was dissolved in pyridine (0.5 mL). To this, acetic anhydride (0.5 mL) was added and the mixture was stirred at room temperature for 1.5 hours. The reaction was stopped by addition of water, and extraction with ethyl acetate was performed, followed by washing with brine and drying over anhydrous sodium sulfate. The solvent was evaporated off under reduced pressure, and the residue was purified by preparative thin-layer column chromatography (hexane/ethyl acetate=19/1) to give N-acetyl-{3-[2,2,2-trifluoro-1-(1-acetylpiperidin-4-yl)- ethoxy]quinoxalin-2-yl}propane-1-sulfonamide (55.8 mg). The obtained compound (55.8 mg) was dissolved in methanol (1.0 mL). To this, potassium carbonate (56.4 mg, 0.408 mmol) was added and the mixture was stirred at room temperature for 4 hours. The reaction was stopped by addition of water, and extraction with ethyl acetate was performed, followed by washing with brine and drying over anhydrous sodium sulfate. The solvent was evaporated off under reduced pressure, and the residue was purified by preparative thin-layer column chromatography (chloroform/methanol=19/1) to give Compound 330 (50.8 mg, yield: 79%).
ESIMS m/z: 475 (M+H)$^+$.

EXAMPLE 325

N-{3-[2,2,2-trifluoro-1-(5-methylpyridin-3-yl)ethoxy]-quinoxalin-2-yl}propane-1-sulfonamide (Compound 331)

According to Example 8, by use of Compound AH (100 mg, 0.350 mmol) and Compound EAD (201 mg, 1.05 mmol), Compound 331 (30.0 mg, yield: 19%) was obtained.
ESIMS m/z: 441 (M+H)$^+$.

EXAMPLE 326

N-{3-[2,2,2-trifluoro-1-(5-fluoropyridin-3-yl)ethoxy]-quinoxalin-2-yl}propane-1-sulfonamide (Compound 332)

According to Example 37, by use of Compound BAD (100 mg, 0.280 mmol) and Compound FS (34.4 rag, 0.280 mmol), Compound 332 (52.8 mg, yield: 42%) was obtained.
ESIMS m/z: 445 (M+H)$^+$.

EXAMPLE 327

N-{3-[2,2,2-trifluoro-1-(1-methyl-2(1H)pyridon-4-yl)-ethoxy]quinoxalin-2-yl}propane-1-sulfonamide (Compound 333)

According to Example 37, by use of Compound BAA (384 mg, 1.04 mmol) and Compound FS (192 mg, 1.56 mmol), Compound 333 (15.0 mg, yield: 3%) was obtained.
ESIMS m/z: 457 (M+H)$^+$.

EXAMPLE 328

N-{3-[2,2,2-trifluoro-1-(5-methoxypyridin-3-yl)ethoxy]-quinoxalin-2-yl}propane-1-sulfonamide (Compound 334)

According to Example 8, by use of Compound AH (86.0 mg, 0.300 mmol) and Compound CV (93.0 mg, 0.450 mmol), Compound 334 (34.0 mg, yield: 25%) was obtained.
ESIMS m/z: 457 (M+H)$^+$.

EXAMPLE 329

N-{3-[2,2,2-trifluoro-1-(5-chloropyridin-3-yl)ethoxy]-quinoxalin-2-yl}propane-1-sulfonamide (Compound 335)

According to Example 8, by use of Compound AH (129 mg, 0.450 mmol) and Compound EAF (64.0 mg, 0.300 mmol), Compound 335 (40.0 mg, yield: 29%) was obtained.
ESIMS m/z: 461 (M+H)$^+$.

EXAMPLE 330

N-{3-[2,2,2-trifluoro-1-(1-methanesulfonylpiperidin-4-yl)-ethoxy]quinoxalin-2-yl}propane-1-sulfonamide (Compound 336)

According to Example 8, by use of Compound AH (51.3 mg, 0.180 mmol) and Compound EAG (70.3 mg, 0.269 mmol), Compound 336 (57.0 mg, yield: 62%) was obtained.
ESIMS m/z: 511 (M+H)$^+$.

EXAMPLE 331

N-{3-[2,2,2-trifluoro-1-(1-methoxycarbonylpiperidin-4-yl)-ethoxy]quinoxalin-2-yl}propane-1-sulfonamide (Compound 337)

According to Example 8, by use of Compound AH (35.1 mg, 0.122 mmol) and Compound EAH (44.4 mg, 0.184 mmol), Compound 337 (58.9 mg, yield: 98%) was obtained.
ESIMS m/z: 491 (M+H)$^+$.

EXAMPLE 332

2-chloro-N-3-{[2,2,2-trifluoro-1-(5-chloropyridin-3-yl)-ethoxy]quinoxalin-2-yl}benzenesulfonamide (Compound 338)

According to Example 8, by use of Compound AD (159 mg, 0.450 mmol) and Compound EAF (64.0 mg, 0.300 mmol), Compound 338 (37.0 mg, yield: 23%) was obtained.
ESIMS m/z: 528 (M+H)$^+$.

EXAMPLE 333

2-chloro-N-3-{[2,2,2-trifluoro-1-(5-fluoropyridin-3-yl)-ethoxy]quinoxalin-2-yl}benzenesulfonamide (Compound 339)

According to Example 37, by use of Compound BAD (107 mg, 0.300 mmol), Compound 339 (69.0 mg, yield: 49%) was obtained.
ESIMS m/z: 513 (M+H)$^+$.

EXAMPLE 334

N-{3-[2,2,2-trifluoro-1-(1-propionylpiperidin-4-yl)ethoxy]-quinoxalin-2-yl}propane-1-sulfonamide (Compound 340)

According to Example 8, by use of Compound AH (106 mg, 0.370 mmol) and Compound EAI (133 mg, 0.555 mmol), Compound 340 (159 mg, yield: 88%) was obtained.
ESIMS m/z: 489 (M+H)$^+$.

EXAMPLE 335

N-{3-[2,2,2-trifluoro-1-(1-cyclopropanecarbonylpiperidin-4-yl)ethoxy]quinoxalin-2-yl}propane-1-sulfonamide (Compound 341)

According to Example 8, by use of Compound AH (122 mg, 0.427 mmol) and Compound EAJ (161 mg, 0.640 mmol), Compound 341 (182 mg, yield: 85%) was obtained.
ESIMS m/z: 501 (M+H)$^+$.

EXAMPLE 336

(S)—N-{3-[2,2,2-trifluoro-1-(2-methylthiazol-5-yl)
ethoxy]-quinoxalin-2-yl}propane-1-sulfonamide
(Compound 342)

According to Example 8, by use of Compound MI (486 mg, 1.70 mmol) and Compound EAK (402 mg, 2.04 mmol), Compound 342 (355 mg, yield: 47%) was obtained.
ESIMS m/z: 447 (M+H)$^+$.

EXAMPLE 337

(R)—N-{3-[2,2,2-trifluoro-1-(2-methylthiazol-5-yl)
ethoxy]-quinoxalin-2-yl}propane-1-sulfonamide
(Compound 343)

According to Example 8, by use of Compound AH (486 mg, 1.70 mmol) and Compound EAL (402 mg, 2.04 mmol), Compound 343 (450 mg, yield: 59%) was obtained.
ESIMS m/z: 447 (M+H)$^+$.

EXAMPLE 338

N-{3-[2,2,2-trifluoro-1-(2-methylthiazol-4-yl)
ethoxy]-quinoxalin-2-yl}propane-1-sulfonamide
(Compound 344)

According to Example 37, by use of Compound BAE (70.0 mg, 0.195 mmol) and Compound FS (28.7 mg, 0.233 mmol), Compound 344 (70.3 mg, yield: 81%) was obtained.
ESIMS m/z: 447 (M+H)$^+$.

EXAMPLE 339

N-{3-[(2-methylthiazol-5-yl)methoxy]quinoxalin-2-
yl}-propane-1-sulfonamide (Compound 345)

According to Example 8, by use of Compound AH (486 mg, 1.70 mmol) and Compound EAM (402 mg, 2.04 mmol), Compound 345 (71.9 mg, yield: 76%) was obtained.
ESIMS m/z: 379 (M+H)$^+$.

EXAMPLE 340

(S)—N-{3-[2,2,2-trifluoro-1-(tetrahydro-2H-pyran-
4-yl)-ethoxy]quinoxalin-2-yl}propane-1-sulfona-
mide (Compound 346) and (R)—N-{3-[2,2,2-trif-
luoro-1-(tetrahydro-2H-pyran-4-yl)-ethoxy]
quinoxalin-2-yl}propane-1-sulfonamide
(Compound 347)

Separation of Compound 215 by preparative high performance liquid chromatography (CHIRALPAK (registered trademark) IC, hexane/ethyl acetate=9/1) gave Compound 346 and Compound 347.
Compound 346
ESIMS m/z: 434 (M+H)$^+$.
Compound 347
ESIMS m/z: 434 (M+H)$^+$.

EXAMPLE 341

(R)—N-{3-[2,2,2-trifluoro-1-(6-chloropyridin-3-yl)
ethoxy]-quinoxalin-2-yl}propane-1-sulfonamide
(Compound 348)

Separation of Compound 278 by preparative high performance liquid chromatography (CHIRALPAK (registered trademark) IC, hexane/ethyl acetate=9/1) gave Compound 348.

EXAMPLE 342

(R)—N-{3-[2,2,2-trifluoro-1-(3-cyanophenyl)
ethoxy]-quinoxalin-2-yl}propane-1-sulfonamide
(Compound 349)

Separation of Compound 290 by preparative high performance liquid chromatography (CHIRALPAK (registered trademark) IC, hexane/ethyl acetate=9/1) gave Compound 349.

EXAMPLE 343

N-{3-[2,2,2-trifluoro-1-(4-fluorotetrahydro-2H-py-
ran-4-yl)-ethoxy]quinoxalin-2-yl}propane-1-sulfona-
mide (Compound 350)

According to Example 37, by use of Compound BAF (70.0 mg, 0.192 mmol) and Compound FS (28.4 mg, 0.230 mmol), Compound 350 (55.4 mg, yield: 64%) was obtained.
ESIMS m/z: 452 (M+H)$^+$.

EXAMPLE 344

N-{3-[2,2,2-trifluoro-1-(4-cyanotetrahydro-2H-py-
ran-4-yl)-ethoxy]quinoxalin-2-yl}propane-1-sulfona-
mide (Compound 351)

According to Example 37, by use of Compound BAG (70.0 mg, 0.188 mmol) and Compound FS (27.8 mg, 0.226 mmol), Compound 351 (76.9 mg, yield: 89%) was obtained.
ESIMS m/z: 459 (M+H)$^+$.

EXAMPLE 345

N-{3-[2,2,2-trifluoro-1-(4-hydroxytetrahydro-2H-
pyran-4-yl)ethoxy]quinoxalin-2-yl}propane-1-sul-
fonamide (Compound 352)

According to Example 8, by use of Compound AH (70.0 mg, 0.245 mmol) and Compound EAP (73.5 mg, 0.367 mmol), Compound 352 (14.9 mg, yield: 14%) was obtained.
ESIMS m/z: 450 (M+H)$^+$.

EXAMPLE 346

N-{3-[2,2,2-trifluoro-1-(4-methoxytetrahydro-2H-
pyran-4-yl)ethoxy]quinoxalin-2-yl}propane-1-sul-
fonamide (Compound 353)

According to Example 8, by use of Compound AH (70.0 mg, 0.245 mmol) and Compound EAQ (78.6 mg, 0.367 mmol), Compound 353 (83.1 mg, yield: 73%) was obtained.
ESIMS m/z: 464 (M+H)$^+$.

EXAMPLE 347

N-{3-[2,2,2-trifluoro-1-(1-acetyl-4-fluoropiperidin-4-yl)-ethoxy]quinoxalin-2-yl}propane-1-sulfonamide (Compound 354)

According to Example 8, by use of Compound AH (70.0 mg, 0.245 mmol) and Compound EAR (89.4 mg, 0.367 mmol), Compound 354 (43.0 mg, yield: 36%) was obtained.
ESIMS m/z: 493 (M+H)$^+$.

EXAMPLE 348

N-{3-[2,2,2-trifluoro-1-(4-fluoro-1-methanesulfonylpiperidin-4-yl)ethoxy]quinoxalin-2-yl}propane-1-sulfonamide (Compound 355)

According to Example 37, by use of Compound BAH (74.6 mg, 0.169 mmol) and Compound FS (22.9 mg, 0.186 mmol), Compound 355 (58.1 mg, yield: 65%) was obtained.
ESIMS m/z: 529 (M+H)$^+$.

EXAMPLE 349

N-{3-[2,2,2-trifluoro-1-(1-acetyl-4-methylpiperidin-4-yl)-ethoxy]quinoxalin-2-yl}propane-1-sulfonamide (Compound 356)

According to Example 8, by use of Compound AH (67.0 mg, 0.245 mmol) and Compound EAT (84.1 mg, 0.352 mmol), Compound 356 (66.7 mg, yield: 58%) was obtained.
ESIMS m/z: 489 (M+H)$^+$.

EXAMPLE 350

N-{3-[2,2,2-trifluoro-1-(1-methanesulfonyl-4-methylpiperidin-4-yl)ethoxy]quinoxalin-2-yl}propane-1-sulfonamide (Compound 357)

According to Example 37, by use of Compound BAI (140 mg, 0.320 mmol) and Compound FS (39.4 mg, 0.320 mmol), Compound 357 (64.8 mg, yield: 39%) was obtained.
ESIMS m/z: 525 (M+H)$^+$.

EXAMPLE 351

N-{2-[2,2,2-trifluoro-1-(pyridin-3-yl)ethoxy]quinolin-3-yl}propane-1-sulfonamide (Compound 358)

Compound HF (105 mg, 0.330 mmol) was dissolved in pyridine (1.05 mL). To this, propane-1-sulfonyl chloride (0.111 mL, 0.990 mmol) was added and the mixture was stirred at room temperature for 17 hours. The reaction was stopped by addition of an aqueous ammonium chloride solution, and the organic layer was extracted with ethyl acetate, washed with brine and dried over anhydrous magnesium sulfate. The solvent was evaporated off under reduced pressure, and the residue was purified by silica gel column chromatography (hexane/ethyl acetate=1/0 to 3/1) to give Compound 358 (80.0 mg, yield: 57%).
ESIMS m/z: 426 (M+H)$^+$.

EXAMPLE 352

2-(1,1-dioxoisothiazolidin-2-yl)-3-[2,2,2-trifluoro-1-(pyridin-3-yl)ethoxy]quinoxaline (Compound 359)

According to Example 132, by use of Compound BJ (55.0 mg, 0.163 mmol) and Compound GR (25.7 mg, 0.163 mmol), Compound 359 (42.0 mg, yield: 61%) was obtained.
ESIMS m/z: 425 (M+H)$^+$.

EXAMPLE 353

2-chloro-N-{2-[2,2,2-trifluoro-1-(pyridin-3-yl)ethoxy]-quinolin-3-yl}benzenesulfonamide (Compound 360)

According to Example 351, by use of Compound HF (105 mg, 0.330 mmol), Compound 360 (110 mg, yield: 68%) was obtained.
ESIMS m/z: 494 (M+H)$^+$.

EXAMPLE 354

N-{3-[2,2,2-trifluoro-1-(pyridin-3-yl)ethoxy]-pyrido[3,4-b]pyrazin-2-yl}propane-1-sulfonamide (Compound 361)

Step 1

Compound HG (830 mg, 4.15 mmol) was dissolved in DMF (30.0 mL). To this, ammonium carbonate (2.39 g, 24.9 mmol) was added and the mixture was stirred with heat at 60° C. for 10 minutes. Then, a saturated aqueous sodium bicarbonate solution was added to the reaction mixture, and extraction with ethyl acetate was performed, followed by washing with brine and drying over anhydrous magnesium sulfate. The solvent was evaporated off under reduced pressure, and the residue was subjected to slurry purification using diisopropyl ether, to give 3-chloropyrido[3,4-b]pyrazin-2-amine (479 mg, yield: 64%).
ESIMS m/z: 181 (M+H)$^+$.

Step 2

According to Example 90, by use of Compound CB (441 mg, 2.49 mmol) and 3-chloropyrido[3,4-b]pyrazin-2-amine (150 mg, 0.830 mmol) obtained in Step 1, 3-[2,2,2-trifluoro-1-(pyridin-3-yl)ethoxy]-pyrido[3,4-b]pyrazin-2-amine (106 mg, yield: 40%) was obtained.
ESIMS m/z: 322 (M+H)$^+$.

Step 3

3-[2,2,2-Trifluoro-1-(pyridin-3-yl)ethoxy]-pyrido[3,4-b]pyrazin-2-amine (100 mg, 0.310 mmol) obtained in Step 2 was dissolved in THF (2.50 mL). To this, propane-1-sulfonyl chloride (0.094 mL, 0.840 mmol) and 60% sodium hydride (in oil) (23.0 mg, 0.560 mmol) were added, and the mixture was stirred with heat at 80° C. for 4 hours. The reaction was stopped by addition of water to the reaction mixture, and extraction with ethyl acetate was performed, followed by washing with brine and drying over anhydrous magnesium sulfate. The solvent was evaporated off under reduced pressure, and purification by silica gel column chromatography (chloroform/methanol=1/0 to 16/1) was performed to give Compound 361 (40.0 mg, yield: 30%).
ESIMS m/z: 428 (M+H)$^+$.

EXAMPLE 355

2-chloro-N-{2-[2,2,2-trifluoro-1-(pyridin-3-yl)ethoxy]-pyrido[3,4-b]pyrazin-2-yl}benzenesulfonamide (Compound 362)

According to Step 3 of Example 354, by use of 3-[2,2,2-trifluoro-1-(pyridin-3-yl)ethoxy]-pyrido[3,4-b]pyrazin-2-amine (90 mg, 0.280 mmol) obtained in Step 2 of Example 354, Compound 362 (59.0 mg, 0.280 mmol) was obtained.
ESIMS m/z: 496 (M+H)$^+$.

REFERENCE EXAMPLE 6-1

2,3-dichloro-N-(3-chloroquinoxalin-2-yl)benzenesulfonamide (Compound AA)

2,3-Dichloroquinoxaline (1.00 g, 5.02 mmol), 2,3-dichlorobenzenesulfonamide (1.41 g, 5.02 mmol) and potassium carbonate (694 mg, 5.02 mmol) were suspended in dimethyl sulfoxide (30 mL) and the mixture was stirred at 150° C. for 3 hours. The reaction mixture was slowly added to a mixture (300 ml) of a 1% aqueous acetic acid solution and ice, and the mixture was stirred for 3 hours. The resulting solid was collected by filtration and washed with water. Then, slurry purification was performed using diisopropyl ether, to give 2,3-dichloro-N-{3-chloroquinoxalin-2-yl}benzenesulfonamide (Compound AA) (1.53 g, yield: 78%).
ESIMS m/z: 389 (M+H)$^+$; $^1$H-NMR (300 MHz, CDCl$_3$, δ): 7.39-7.72 (m, 2H), 7.90 (d, J=7.7 Hz, 1H), 8.21-8.50 (m, 1.5H), 12.18 (br s, 0.5H).

REFERENCE EXAMPLE 6-2

N-(3-chloroquinoxalin-2-yl)-4-methylbenzenesulfonamide (Compound AB)

According to the step of Example 6-1, by use of 2,3-dichloroquinoxaline (1.00 g, 5.02 mmol) dissolved in dimethyl sulfoxide (30 mL), 4-methylbenzene-1-sulfonamide (860 mg, 5.02 mmol) and potassium carbonate (694 mg, 5.02 mmol), the mixture was stirred and reacted at 150° C. for 4.2 hours. Then, slurry purification was performed using diisopropyl ether, to give N-(3-chloroquinoxalin-2-yl)-4-methylbenzenesulfonamide (Compound AB) (1.24 g, yield: 74%).
ESIMS m/z: 336, 334 (M+H)$^+$; $^1$H-NMR (300 MHz, CDCl$_3$, δ): 2.42 (s, 3H), 7.34 (d, J=8.1 Hz, 2H), 7.61-7.70 (m, 2H), 7.87 (d, J=7.3 Hz, 2H), 8.03 (br s, 1H), 8.19 (d, J=7.7 Hz, 2H).

REFERENCE EXAMPLE 6-3

2-(trifluoromethyl)-N-(3-chloroquinoxalin-2-yl)benzenesulfonamide (Compound AC)

To a 7 mol/L solution of ammonia in methanol (4.0 mL), 2-(trifluoromethyl)benzenesulfonyl chloride (200 mg, 0.818 mmol) was added and the mixture was stirred at room temperature for 1 hour. After the reaction mixture was concentrated, 2,3-dichloroquinoxaline (162 mg, 0.818 mmol), potassium carbonate (113 mg, 0.818 mmol) and dimethyl sulfoxide (5.0 mL) were added to the residue, and the mixture was stirred at 150° C. for 1 hour. The reaction mixture was slowly added to a mixture (50 ml) of a 1% aqueous acetic acid solution and ice, and the mixture was stirred for 3 hours. The resulting solid was collected by filtration and purified by preparative thin-layer chromatography (chloroform/methanol=19/1). Further, slurry purification was performed using hexane, to give 2-(trifluoromethyl)-N-{3-chloroquinoxalin-2-yl}benzenesulfonamide (Compound AC) (97.0 mg, yield: 31%).
ESIMS m/z: 388 (M+H)$^+$; $^1$H-NMR (300 MHz, CDCl$_3$, δ): 7.30-7.89 (m, 8H), 8.69 (s, 1H).

REFERENCE EXAMPLE 6-4

2-chloro-N-(3-chloroquinoxalin-2-yl)benzenesulfonamide (Compound AD)

According to the step of Example 6-1, by use of 2,3-dichloroquinoxaline (5.00 g, 25.1 mmol) dissolved in dimethyl sulfoxide (100 mL), 2-chlorobenzene-1-sulfonamide (4.81 g, 25.1 mmol) and potassium carbonate (3.47 g, 25.1 mmol), the mixture was stirred and reacted at 150° C. for 3 hours. Then, slurry purification was performed using diisopropyl ether, to give 2-chloro-N-(3-chloroquinoxalin-2-yl)benzenesulfonamide (Compound AD) (8.30 g, yield: 93%).
ESIMS m/z: 354, 352 (M–H)$^-$; $^1$H-NMR (300 MHz, CDCl$_3$, δ): 7.51-7.64 (m, 6H), 7.87 (dd, J=1.1, 7.7 Hz, 1H), 8.29 (br s, 1H), 8.53 (br s, 1H).

REFERENCE EXAMPLE 6-5

N-(3-chloroquinoxalin-2-yl)-2-fluorobenzenesulfonamide (Compound AE)

According to Reference Example 6-1, by use of 2,3-dichloroquinoxaline (80 mg, 0.40 mmol), dimethyl sulfoxide (2 mL), 2-fluorobenzenesulfonamide (70 mg, 0.40 mmol) and potassium carbonate (56 mg, 0.40 mmol), the mixture was stirred and reacted at 150° C. for 1.5 hours. Thus, N-(3-chloroquinoxalin-2-yl)-2-fluorobenzenesulfonamide (Compound AE) (101 mg, yield: 75%) was obtained.
ESIMS m/z: 338 (M+H)$^+$.

REFERENCE EXAMPLE 6-6

5-chloro-N-(3-chloroquinoxalin-2-yl)-1,3-dimethyl-1H-pyrazole-4-sulfonamide (Compound AF)

According to Reference Example 6-1, by use of 2,3-dichloroquinoxaline (600 mg, 3.0 mmol), dimethyl sulfoxide (6 mL), Compound FB (632 mg, 3.0 mmol) and potassium carbonate (416 mg, 3.0 mmol), the mixture was stirred and reacted at 150° C. for 1 hour. Thus, 5-chloro-N-(3-chloroquinoxalin-2-yl)-1,3-dimethyl-1H-pyrazole-4-sulfonamide (Compound AF) (958 mg, yield: 86%) was obtained.
ESIMS m/z: 373 (M+H)$^+$; $^1$H-NMR (270 MHz, CDCl$_3$, δ): 2.60 (s, 3H), 3.79 (s, 3H), 7.52-8.30 (m, 4H).

REFERENCE EXAMPLE 6-7

N-(3-chloroquinoxalin-2-yl)-3,5-dimethylisoxazole-4-sulfonamide (Compound AG)

According to Reference Example 6-1, by use of 2,3-dichloroquinoxaline (600 mg, 3.0 mmol), dimethyl sulfoxide (6 mL), Compound FC (531 mg, 3.0 mmol) and potassium carbonate (416 mg, 3.0 mmol), the mixture was stirred and reacted at 150° C. for 1 hour. Thus, N-(3-chloroquinoxalin-2-yl)-3,5-dimethylisoxazole-4-sulfonamide (Compound AG) (873 mg, yield: 86%) was obtained.
ESIMS m/z: 339 (M+H)$^+$; $^1$H-NMR (270 MHz, CDCl$_3$, δ): 2.56 (s, 3H), 2.95 (s, 3H), 7.59-8.01 (m, 4H).

REFERENCE EXAMPLE 6-8

N-(3-chloroquinoxalin-2-yl)propane-1-sulfonamide (Compound AH)

According to Reference Example 6-1, by use of 2,3-dichloroquinoxaline (836 mg, 4.2 mmol), dimethyl sulfoxide (8 mL), Compound FS (517 mg, 4.2=01) and potassium carbonate (580 mg, 4.2 mmol), the mixture was stirred and reacted at 150° C. for 1 hour. Thus, N-(3-chloroquinoxalin-2-yl)propane-1-sulfonamide (Compound AH) (1.1 g, yield: 92%) was obtained.

ESIMS m/z: 286 (M+H)⁺; ¹H-NMR (270 MHz, CDCl₃, δ): 1.12 (t, J=7.4 Hz, 3H), 1.92-2.06 (m, 2H), 3.77 (br s, 2H), 7.39-8.09 (m, 4H).

REFERENCE EXAMPLE 7-1

2-amino-3-[(pyridin-3-yl)methoxy]quinoxaline (Compound BA)

Step 1

2,3-Dichloroquinoxaline (9.90 g, 50.0 mmol) and ammonium carbonate (24.3 g, 300 mmol) were suspended in N,N-dimethylformamide (50 mL) in a stainless steel sealed tube and the mixture was stirred at 60° C. for 72 hours. After water was added to the reaction mixture, extraction with ethyl acetate was performed, followed by washing with brine and drying over anhydrous sodium sulfate. The solvent was evaporated off under reduced pressure, and the residue was purified by silica gel column chromatography (hexane/ethyl acetate=7/3). Further, slurry purification was performed using diisopropyl ether, to give 2-amino-3-chloroquinoxaline (2.41 g, yield: 27%).

ESIMS m/z: 180 (M+H)⁺; ¹H-NMR (270 MHz, CDCl₃, δ): 5.37 (br s, 2H), 7.43-7.50 (m, 1H), 7.59-7.70 (m, 2H), 7.84-7.87 (m, 1H).

Step 2

3-Pyridinemethanol (487 μL, 5.01 mmol) was dissolved in tetrahydrofuran (6.0 mL). To this, 60% sodium hydride (in oil) (200 mg, 5.01 mmol) was added under a nitrogen atmosphere at 0° C. and the mixture was stirred at the same temperature for 15 minutes. To this, 2-amino-3-chloroquinoxaline (300 mg, 1.67 mmol) was added and the mixture was stirred at room temperature for 14 hours. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol=9/1). Further, slurry purification was performed using diisopropyl ether, to give 2-amino-3-[(pyridin-3-yl)methoxy]quinoxaline (Compound BA) (383 mg, yield: 91%).

ESIMS m/z: 443 (M+H)⁺; ¹H-NMR (300 MHz, CDCl₃, δ): 5.20 (br s, 2H), 5.61 (s, 2H), 7.32-7.48 (m, 3H), 7.62 (dd, J=1.5, 8.1 Hz, 1H), 7.72 (dd, J=1.5, 8.1 Hz, 1H), 7.84-7.87 (m, 1H), 8.62 (dd, J=1.5, 4.8 Hz, 1H), 8.80 (d, J=2.2 Hz, 1H), 8.35 (s, 1H).

REFERENCE EXAMPLE 7-2

2-amino-3-[(4-methoxyphenyl)methoxy]quinoxaline (Compound BB)

According to Step 2 of Reference Example 7-1, by use of 4-methoxybenzyl alcohol (625 μL, 5.01 mmol), 60% sodium hydride (in oil) (200 mg, 5.01 mmol), tetrahydrofuran (6.0 mL) and 2-amino-3-chloroquinoxaline (300 mg, 1.67 mmol), the mixture was stirred and reacted at room temperature for 17 hours. Then, slurry purification was performed using diisopropyl ether, to give 2-amino-3-[(4-methoxyphenyl)methoxy]quinoxaline (Compound BB) (357 mg, yield: 76%).

ESIMS m/z: 282 (M+H)⁺; ¹H-NMR (300 MHz, CDCl₃, δ): 3.83 (s, 3H), 5.23 (br s, 2H), 5.50 (s, 2H), 6.91-6.90 (m, 2H), 7.34-7.37 (m, 4H), 7.60 (dd, J=1.5, 8.1 Hz, 1H), 7.72 (dd, J=1.8, 7.7 Hz, 1H).

REFERENCE EXAMPLE 7-3

2-amino-3-[(2-naphthyl)methoxy]quinoxaline (Compound BC)

According to Step 2 of Reference Example 7-1, by use of 2-naphthalenemethanol (792 mg, 5.01 mmol), 60% sodium hydride (in oil) (200 mg, 5.01 mmol), tetrahydrofuran (6.0 mL) and 2-amino-3-chloroquinoxaline (300 mg, 1.67 mmol), the mixture was stirred and reacted at room temperature for 17 hours. Then, slurry purification was performed using diisopropyl ether, to give 2-amino-3-[(naphthalen-2-yl)methoxy]quinoxaline (Compound BC) (413 mg, yield: 82%).

ESIMS m/z: 302 (M+H)⁺; ¹H-NMR (300 MHz, CDCl₃, δ): 5.23 (br s, 2H), 5.74 (s, 2H), 7.26-7.97 (m, 11H).

REFERENCE EXAMPLE 7-4

2-chloro-3-[2,2,2-trifluoro-1-(pyridin-4-yl)ethoxy]-quinoxaline (Compound BD)

Compound CO (500 mg, 2.82 mmol) was dissolved in tetrahydrofuran (10 mL). To this, 60% sodium hydride (in oil) (124 mg, 3.11 mmol) was added under a nitrogen atmosphere at 0° C. and the mixture was stirred at the same temperature for 30 minutes. To this, 2,3-dichloroquinoxaline (618 mg, 3.11 mmol) was added and the mixture was stirred at room temperature for 30 minutes. Then, saturated ammonium chloride was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol=19/1) to give 2-chloro-3-[2,2,2-trifluoro-1-(pyridin-4-yl)ethoxy]-quinoxaline (Compound BD) (557 mg, yield: 58%).

¹H-NMR (300 MHz, CDCl₃, δ): 6.76 (q, J=6.6 Hz, 1H), 7.57 (d, J=5.5 Hz, 2H), 7.62-7.73 (m, 2H), 7.77-7.80 (m, 1H), 7.96-7.99 (m, 1H), 8.70-8.72 (m, 2H).

REFERENCE EXAMPLE 7-5

2-chloro-3-[tetrahydropyran-4-yl(pyridin-3-yl)methoxy]-quinoxaline (Compound BE)

According to Reference Example 7-4, by use of Compound CW (148 mg, 0.766 mmol), tetrahydrofuran (3.0 mL), 60% sodium hydride (in oil) (36.8 mg, 0.919 mmol) and 2,3-dichloroquinoxaline (183 mg, 0.919 mmol), the mixture was stirred and reacted at room temperature for 1 hour. Then, purification by silica gel column chromatography (chloroform/methanol=19/1) was performed to give 2-chloro-3-[tetrahydropyran-4-yl(pyridin-3-yl)methoxy]-quinoxaline (Compound BE) (176 mg, yield: 65%).

¹H-NMR (300 MHz, CDCl₃, δ): 1.34-1.63 (m, 3H), 1.99-2.03 (m, 1H), 2.30-2.35 (m, 1H), 3.35-3.50 (m, 2H), 4.03 (ddd, J=3.3, 11.0, 22.4 Hz, 2H), 6.02 (d, J=8.1 Hz, 1H), 7.30 (dd, J=5.1, 8.1 Hz, 1H), 7.53-7.66 (m, 2H), 7.72-7.82 (m, 2H), 7.90 (dd, J=1.5, 8.1 Hz, 1H), 8.53 (dd, J=1.5, 4.8 Hz, 1H), 8.77 (d, J=2.2 Hz, 1H).

REFERENCE EXAMPLE 7-6

2-chloro-3-[4-fluorotetrahydropyran-4-yl(pyridin-3-yl)-methoxy]quinoxaline (Compound BF)

According to Reference Example 7-4, by use of Compound CX (417 mg, 1.97 mmol), tetrahydrofuran (8.0 mL), 60% sodium hydride (in oil) (94.8 mg, 2.37 mmol) and 2,3-dichloroquinoxaline (472 mg, 2.37 mmol), the mixture was stirred and reacted at room temperature for 2 hours. Then, purification by silica gel column chromatography (chloroform/methanol=19/1) was performed to give 2-chloro-3-[4-fluorotetrahydropyran-4-yl(pyridin-3-yl)-methoxy]quinoxaline (Compound BF) (651 mg, yield: 65%).

ESIMS m/z: 373 (M+H)$^+$; $^1$H-NMR (300 MHz, CDCl$_3$, δ): 1.66-1.74 (m, 1H), 1.82-2.12 (m, 3H), 3.68-3.79 (m, 2H), 3.87-3.95 (m, 2H), 6.26 (d, J=17.6 Hz, 1H), 7.31 (ddd, J=0.7, 4.8, 7.7 Hz, 1H), 7.55-7.67 (m, 2H), 7.74 (dd, J=1.8, 8.1 Hz, 1H), 7.87-7.93 (m, 1H), 8.57 (dd, J=1.8, 4.8 Hz, 1H), 8.79 (d, J=1.8 Hz, 1H).

REFERENCE EXAMPLE 7-7

2-chloro-3-[2,2,2-trifluoro-1-(4-cyanophenyl) ethoxy]-quinoxaline (Compound BG)

According to Reference Example 7-4, by use of Compound CL (70.7 mg, 0.352 mmol), tetrahydrofuran (1.5 mL), 60% sodium hydride (in oil) (14.1 mg, 0.352 mmol) and 2,3-dichloroquinoxaline (70.0 mg, 0.352 mmol) the mixture was stirred and reacted at room temperature for 1 hour. Then, purification by preparative thin-layer chromatography (hexane/ethyl acetate=19/1) was performed to give 2-chloro-3-[2,2,2-trifluoro-1-(4-cyanophenyl)ethoxy]-quinoxaline (Compound BG) (41.8 mg, yield: 33%).

$^1$H-NMR (300 MHz, CDCl$_3$, δ): 6.80 (q, J=6.6 Hz, 1H), 7.62-7.81 (m, 7H), 7.97 (dd, J=1.8, 7.7 Hz, 1H).

REFERENCE EXAMPLE 7-8

2-chloro-3-{[4-(pyridin-3-yl)tetrahydropyran-4-yl] oxy}-quinoxaline (Compound BH)

Compound DF (70.0 mg, 0.391 mmol) and 2,3-dichloroquinoxaline (155 mg, 0.781 mmol) were dissolved in 1,2-dimethoxyethane (10 mL). To this, 60% sodium hydride (in oil) (23.5 mg, 0.587 mmol) was added under a nitrogen atmosphere at 0° C. and the mixture was stirred at 100° C. for 15 hours. Then, saturated ammonium chloride was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol=19/1) to give 2-chloro-3-{[4-(pyridin-3-yl)tetrahydropyran-4-yl] oxy}-quinoxaline (Compound BH) (28.0 mg, yield: 21%).

ESIMS m/z: 342 (M+H)$^+$; $^1$H-NMR (300 MHz, CDCl$_3$, δ): 2.29-2.39 (m, 2H), 2.83-2.87 (m, 2H), 3.96-4.00 (m, 4H), 7.25 (ddd, J=0.7, 4.8, 8.1 Hz, 1H), 7.40-7.47 (m, 1H), 7.48-7.57 (m, 2H), 7.78 (ddd, J=1.8, 2.2, 8.1 Hz, 1H), 7.83-7.89 (m, 1H), 8.50 (dd, J=1.8, 4.8 Hz, 1H), 8.80 (dd, J=0.7, 2.2 Hz, 1H).

REFERENCE EXAMPLE 7-9

2-chloro-3-[1-methyl-1-(pyridin-3-yl)ethoxy]quinoxaline (Compound BI)

According to Reference Example 7-8, by use of Compound DG (137 mg, 0.999 mmol), 2,3-dichloroquinoxaline (398 mg, 2.00 mmol), 1,2-dimethoxyethane (5.0 mL) and 60% sodium hydride (in oil) (60.0 mg, 1.50 mmol), the mixture was stirred and reacted at 100° C. for 15 hours. Then, purification by silica gel column chromatography (chloroform/methanol=19/1) was performed to give 2-chloro-3-[1-methyl-1-(pyridin-3-yl)ethoxy]quinoxaline (Compound BI) (102 mg, yield: 34%).

ESIMS m/z: 300 (M+H)$^+$; $^1$H-NMR (300 MHz, CDCl$_3$, δ): 2.09 (s, 6H), 7.24 (ddd, J=0.7, 4.8, 8.1 Hz, 1H), 7.48-7.60 (m, 3H), 7.81 (ddd, J=1.8, 2.2, 8.1 Hz, 1H), 7.85-7.88 (m, 1H), 8.48 (dd, J=1.8, 4.8 Hz, 1H), 8.80 (dd, J=0.7, 2.2 Hz, 1H).

REFERENCE EXAMPLE 7-10

2-chloro-3-[2,2,2-trifluoro-1-(pyridin-3-yl)ethoxy]-quinoxaline (Compound BJ)

According to Reference Example 7-4, by use of Compound CB (78 mg, 0.44 mmol), tetrahydrofuran (3 mL), 60% sodium hydride (in oil) (32 mg, 0.80 mmol) and 2,3-dichloroquinoxaline (80 mg, 0.40 mmol), the mixture was stirred and reacted at room temperature for 3 hours. Then, purification by silica gel column chromatography (hexane/ethyl acetate=1/0 to 3/1) was performed to give 2-chloro-3-[2,2,2-trifluoro-1-(pyridin-3-yl)ethoxy]-quinoxaline (Compound BJ) (78 mg, yield: 57%).

ESIMS m/z: 340 (M+H)$^+$; $^1$H-NMR (270 MHz, CDCl$_3$, δ): 6.81 (q, J=6.6 Hz, 1H), 7.39 (dd, J=5.0, 7.9 Hz, 1H), 7.61-7.73 (m, 2H), 7.80-7.83 (m, 1H), 7.95-8.03 (m, 2H), 8.67 (dd, J=1.7, 5.0 Hz, 1H), 8.92 (d, J=2.3 Hz, 1H).

REFERENCE EXAMPLE 7-11

2-chloro-3-[2,2,2-trifluoro-1-(1-methyl-1H-imidazol-2-yl)-ethoxy]quinoxaline (Compound BK)

According to Reference Example 7-4, by use of Compound DK (199 mg, 1.1 mmol), tetrahydrofuran (8 mL), 60% sodium hydride (in oil) (80 mg, 2.0 mmol) and 2,3-dichloroquinoxaline (200 mg, 1.0 mmol), the mixture was stirred and reacted at room temperature for 2 hours. Then, purification by silica gel column chromatography (chloroform/methanol=1/0 to 20/1) was performed to give 2-chloro-3-[2,2,2-trifluoro-1-(1-methyl-1H-imidazol-2-yl)-ethoxy]quinoxaline (Compound BK) (210 mg, yield: 61%).

ESIMS m/z: 343 (M+H)$^+$; $^1$H-NMR (270 MHz, CDCl$_3$, δ): 3.95 (s, 3H), 6.92 (q, J=6.8 Hz, 1H), 7.39 (s, 1H), 7.50 (s, 1H), 7.63-7.77 (m, 2H), 7.79-7.87 (m, 1H), 7.99 (d, J=8.1 Hz, 1H).

REFERENCE EXAMPLE 7-12

2-chloro-5-[1-(3-chloroquinoxalin-2-yloxy)-2,2,2-trifluoroethyl]thiazole (Compound BL)

According to Reference Example 7-4, by use of Compound DV (360 mg, 1.7 mmol), tetrahydrofuran (12 mL), 60% sodium hydride (in oil) (120 mg, 3=01) and 2,3-dichloroquinoxaline (300 mg, 1.5 mmol), the mixture was stirred and reacted at 60° C. for 6 hours. Then, purification by silica gel column chromatography (hexane/ethyl acetate=1/0 to 5/1) was performed to give 2-chloro-5-[1-(3-chloroquinoxalin-2-yloxy)-2,2,2-trifluoroethyl]thiazole (Compound BL) (167 mg, yield: 29%).

ESIMS m/z: 381 (M+H)$^+$; $^1$H-NMR (270 MHz, CDCl$_3$, δ): 7.05 (q, J=6.3 Hz, 1H), 7.62-8.01 (m, 5H).

REFERENCE EXAMPLE 7-13

2-chloro-3-[2,2,2-trifluoro-1-(6-methylpyridin-3-yl)-ethoxy]quinoxaline (Compound BM)

According to Reference Example 7-4, by use of Compound CK (58 mg, 0.30 mmol), tetrahydrofuran (3 mL), 60% sodium hydride (in oil) (22 mg, 0.55 mmol) and 2,3-dichloroquinoxaline (108 mg, 0.28 mmol), the mixture was stirred and reacted at room temperature for 3 hours. Then, purification by silica gel column chromatography (hexane/ethyl acetate=1/0 to 3/1) was performed to give 2-chloro-3-[2,2,2-trifluoro-1-(6-methylpyridin-3-yl)-ethoxy]quinoxaline (Compound BM) (80 mg, yield: 82%).

ESIMS m/z: 356 (M+H)$^+$; $^1$H-NMR (270 MHz, CDCl$_3$, δ): 2.57 (s, 3H), 6.76 (q, J=6.6 Hz, 1H), 7.20-7.26 (m, 1H), 7.58-8.00 (m, 5H), 8.78 (d, J=2.0 Hz, 1H).

REFERENCE EXAMPLE 7-14

1-{4-[1-(3-chloroquinoxalin-2-yloxy)-2,2,2-trifluoroethyl]-phenyl}-N,N-dimethylmethanamine (Compound BN)

According to Reference Example 7-4, by use of Compound ER (280 mg, 1.2 mmol), tetrahydrofuran (8.7 mL), 60% sodium hydride (in oil) (87 mg, 2.2 mmol) and 2,3-dichloroquinoxaline (217 mg, 1.1 mmol), the mixture was stirred and reacted at room temperature for 2 hours. Then, purification by silica gel column chromatography (hexane/ethyl acetate=1/0 to 1/1) was performed to give 1-{4-[1-(3-chloroquinoxalin-2-yloxy)-2,2,2-trifluoroethyl]-phenyl}-N,N-dimethylmethanamine (Compound BN) (280 mg, yield: 65%).

ESIMS m/z: 396 (M+H)$^+$; $^1$H-NMR (270 MHz, CDCl$_3$, δ): 2.22 (s, 6H), 3.41 (s, 2H), 6.78 (q, J=6.7 Hz, 1H), 7.37 (d, J=8.4 Hz, 2H), 7.57-7.72 (m, 4H), 7.80 (dd, J=1.3, 7.9 Hz, 1H), 7.95 (dd, J=1.3, 7.9 Hz, 1H).

REFERENCE EXAMPLE 7-15

2-chloro-3-[2,2,2-trifluoro-1-(4-cyanophenyl)ethoxy]-quinoxaline (Compound BO)

According to Reference Example 7-4, by use of Compound CL (70.7 mg, 0.352 mmol), tetrahydrofuran (1.5 mL), 60% sodium hydride (in oil) (14.1 mg, 0.352 mmol) and 2,3-dichloroquinoxaline (70.0 mg, 0.352 mmol), the mixture was stirred and reacted at room temperature for 1 hour. Then, purification by preparative thin-layer chromatography (hexane/ethyl acetate=19/1) was performed to give 2-chloro-3-[2,2,2-trifluoro-1-(4-cyanophenyl)ethoxy]-quinoxaline (Compound BO) (41.8 mg, yield: 33%).

$^1$H-NMR (300 MHz, CDCl$_3$, δ): 6.80 (q, J=6.6 Hz, 1H), 7.62-7.81 (m, 7H), 7.97 (dd, J=1.8, 7.7 Hz, 1H).

REFERENCE EXAMPLE 7-16

2-chloro-3-[2-methyl-1-(pyridin-3-yl)propoxy]quinoxaline (Compound BP)

According to Reference Example 7-4, by use of Compound CE (360 mg, 2.4 mmol), tetrahydrofuran (17 mL), 60% sodium hydride (in oil) (168 mg, 4.2 mmol) and 2,3-dichloroquinoxaline (418 mg, 2.1 mmol), the mixture was stirred and reacted at room temperature for 1 hour. Then, purification by silica gel column chromatography (hexane/ethyl acetate=1/0 to 2/1) was performed to give 2-chloro-3-[2-methyl-1-(pyridin-3-yl)propoxy]quinoxaline (Compound BP) (620 mg, yield: 94%).

ESIMS m/z: 314 (M+H)$^+$; $^1$H-NMR (270 MHz, CDCl$_3$, δ): 0.96 (d, J=6.6 Hz, 3H), 1.15 (d, J=6.6 Hz, 3H), 2.33-2.47 (m, 1H), 6.00 (d, J=7.0 Hz, 1H), 7.23-7.31 (m, 1H), 7.48-7.67 (m, 2H), 7.69-7.82 (m, 2H), 7.84-7.93 (m, 1H), 8.51 (dd, J=1.5, 4.8 Hz, 1H), 8.75 (d, J=1.5 Hz, 1H).

REFERENCE EXAMPLE 7-17

2-chloro-3-[2,2,2-trifluoro-1-(tetrahydro-2H-pyran-4-yl)-ethoxy]quinoxaline (Compound BQ)

According to Reference Example 7-4, by use of Compound EA (325 mg, 1.8 mmol), tetrahydrofuran (12 mL), 60% sodium hydride (in oil) (118 mg, 2.9 mmol) and 2,3-dichloroquinoxaline (292 mg, 1.5 mmol), the mixture was stirred and reacted at room temperature for 2 hours. Then, purification by silica gel column chromatography (hexane/ethyl acetate=1/0 to 4/1) was performed to give 2-chloro-3-[2,2,2-trifluoro-1-(tetrahydro-2H-pyran-4-yl)-ethoxy]quinoxaline (Compound BQ) (356 mg, yield: 70%).

ESIMS m/z: 347 (M+H)$^+$; $^1$H-NMR (270 MHz, CDCl$_3$, δ): 1.57-1.87 (m, 4H), 2.28-2.48 (m, 1H), 3.45 (td, J=2.2, 11.6 Hz, 2H), 4.02 (td, J=2.2, 11.6 Hz, 2H), 5.87-6.00 (m, 1H), 7.61-7.77 (m, 2H), 7.85 (dd, J=1.6, 8.1 Hz, 1H), 7.99 (dd, J=1.6, 8.1 Hz, 1H).

REFERENCE EXAMPLE 7-18

2-chloro-3-{methoxycarbonyl[4-(trifluoromethyl)phenyl]-methoxy}quinoxaline (Compound BR)

According to Reference Example 7-4, by use of Compound CH (71.6 mg, 0.306 mmol), tetrahydrofuran (1.5 mL), 60% sodium hydride (in oil) (12.2 mg, 0.306 mmol) and 2,3-dichloroquinoxaline (60.9 mg, 0.306 mmol), the mixture was stirred and reacted at room temperature for 3 hours. Then, purification by preparative thin-layer chromatography (hexane/ethyl acetate=19/1) was performed to give 2-chloro-3-{methoxycarbonyl[4-(trifluoromethyl)phenyl]-methoxy}quinoxaline (Compound BR) (50.1 mg, yield: 41%).

$^1$H-NMR (300 MHz, CDCl$_3$, δ): 3.76 (s, 3H), 6.44 (s, 1H), 7.61-7.74 (m, 4H), 7.82-7.87 (m, 3H), 7.98 (dd, J=1.5, 7.7 Hz, 1H).

REFERENCE EXAMPLE 7-19

2-chloro-3-[2,2,2-trifluoro-1-(6-cyanopyridin-3-yl)ethoxy]-quinoxaline (Compound BS)

According to Reference Example 7-4, by use of Compound ES (424 mg, 2.10 mmol), tetrahydrofuran (8.0 mL), 60% sodium hydride (in oil) (101 mg, 2.52 mmol) and 2,3-dichloroquinoxaline (501 mg, 2.52 mmol), the mixture was stirred and reacted at room temperature for 1 hour. Then, purification by silica gel column chromatography (hexane/ethyl acetate=4/1) was performed to give 2-chloro-3-[2,2,2-trifluoro-1-(6-cyanopyridin-3-yl)ethoxy]-quinoxaline (Compound BS) (292 mg, yield: 38%).

$^1$H-NMR (300 MHz, CDCl$_3$, δ): 6.85 (q, J=6.2 Hz, 1H), 7.64-7.81 (m, 4H), 7.99 (dd, J=1.5, 7.7 Hz, 1H), 8.16 (dd, J=2.2, 7.7 Hz, 1H), 9.02 (d, J=2.2 Hz, 1H).

REFERENCE EXAMPLE 7-20

2-chloro-3-[2,2,2-trifluoro-1-(1-methyl-2(1H)pyridon-5-yl)-ethoxy]quinoxaline (Compound BT)

According to Reference Example 7-4, by use of Compound ET (214 mg, 1.03 mmol), tetrahydrofuran (5.0 mL), 60% sodium hydride (in oil) (49.6 mg, 1.24 mmol) and 2,3-dichloroquinoxaline (247 mg, 1.24 mmol), the mixture was stirred and reacted at room temperature for 3 hours. Then, purification by silica gel column chromatography (hexane/ethyl acetate=1/1) was performed to give 2-chloro-3-[2,2,2-trifluoro-1-(1-methyl-2(1H)pyridon-5-yl)-ethoxy]quinoxaline (Compound BT) (250 mg, yield: 66%).

$^1$H-NMR (300 MHz, CDCl$_3$, δ): 3.57 (s, 3H), 6.54 (q, J=6.6 Hz, 1H), 6.62 (d, J=9.5 Hz, 1H), 7.59-7.76 (m, 4H), 7.83 (dd, J=1.5, 8.1 Hz, 1H), 7.99 (dd, J=1.5, 8.1 Hz, 1H).

REFERENCE EXAMPLE 7-21

2-chloro-3-[2,2,2-trifluoro-1-(thiazol-5-yl)ethoxy]-quinoxaline (Compound BU)

According to Reference Example 7-4, by use of Compound DL (446 mg, 2.46 mmol) and 2,3-dichloroquinoxaline (446 mg, 2.24 mmol), Compound BU (495 mg, yield: 64%) was obtained.

ESIMS m/z: 346 (M+H)$^+$.

REFERENCE EXAMPLE 7-22

2-chloro-3-[2,2,2-trifluoro-1-(1-methyl-1H-imidazol-5-yl)-ethoxy]quinoxaline (Compound BV)

According to Reference Example 7-4, by use of Compound DK (420 mg, 2.11 mmol) and 2,3-dichloroquinoxaline (420 mg, 2.11 mmol), Compound BV (435 mg, yield: 60%) was obtained.

ESIMS m/z: 343 (M+H)$^+$.

REFERENCE EXAMPLE 7-23

2-chloro-3-[1-(6-chloropyridin-3-yl)-2,2,2-trifluoro-ethoxy]quinoxaline (Compound BW)

According to Reference Example 7-4, by use of Compound DC (587 mg, 2.80=01) and 2,3-dichloroquinoxaline (500 mg, 2.50 mmol), Compound BW (580 mg, yield: 62%) was obtained.

ESIMS m/z: 375 (M+H)$^+$.

REFERENCE EXAMPLE 7-24

2-chloro-3-[1-(3-cyanophenyl)-2,2,2-trifluoroethoxy]-quinoxaline (Compound BX)

According to Reference Example 7-4, by use of Compound CZ (582 mg, 2.89 mmol) and 2,3-dichloroquinoxaline (523 mg, 2.63 mmol), Compound BX (640 mg, yield: 67%) was obtained.

ESIMS m/z: 364 (M+H)$^+$.

REFERENCE EXAMPLE 7-25

2-chloro-3-[2,2,2-trifluoro-1-(2-methylthiazol-5-yl)-ethoxy]quinoxaline (Compound BY)

According to Reference Example 7-8, by use of Compound EX (299 mg, 1.50 mmol) and 2,3-dichloroquinoxaline (296 mg, 1.50 mmol), Compound BY (380 mg, yield: 70%) was obtained.

REFERENCE EXAMPLE 7-26

(R)-2-chloro-3-[2,2,2-trifluoro-1-(pyridin-3-yl)ethoxy]-quinoxaline (Compound BZ)

According to Reference Example 7-8, by use of Compound EU (759 mg, 3.34 mmol) and 2,3-dichloroquinoxaline (797 mg, 4.00 mmol), Compound BZ (977 mg, yield: 88%) was obtained.

REFERENCE EXAMPLE 7-27

2-chloro-3-[2,2,2-trifluoro-1-(1-methyl-2(1H)pyridon-4-yl)-ethoxy]quinoxaline (Compound BAA)

According to Reference Example 7-8, by use of Compound EY (300 mg, 1.54 mmol) and 2,3-dichloroquinoxaline (346 mg, 1.74 mmol), Compound BAA (248 mg, yield: 46%) was obtained.

REFERENCE EXAMPLE 7-28

2,3-bis(1,1,1,3,3,3-hexafluoro-2-ethoxy)quinoxaline (Compound BAB)

According to Reference Example 7-8, by use of 1,1,1,3,3,3-hexafluoro-2-ethanol (0.792 mL, 7.53 mmol) and 2,3-dichloroquinoxaline (500 mg, 2.51 mmol), Compound BAB (307 mg, yield: 26%) was obtained.

REFERENCE EXAMPLE 7-29

2-chloro-3-[2,2,2-trifluoro-1-(1-methylpiperidin-4-yl)ethoxy]quinoxaline (Compound BAC)

According to Reference Example 7-8, by use of Compound EAC (252 mg, 1.28 mmol) and 2,3-dichloroquinoxaline (305 mg, 1.53 mmol), Compound BAC (444 mg, yield: 96%) was obtained.

REFERENCE EXAMPLE 7-30

2-chloro-3-[2,2,2-trifluoro-1-(5-fluoropyridin-3-yl)-ethoxy]quinoxaline (Compound BAD)

According to Reference Example 7-8, by use of Compound EAE (379 mg, 1.91 mmol) and 2,3-dichloroquinoxaline (310 mg, 1.59 mmol), Compound BAD (441 mg, yield: 78%) was obtained.

REFERENCE EXAMPLE 7-31

2-chloro-3-[2,2,2-trifluoro-1-(2-methylthiazol-4-yl)-ethoxy]quinoxaline (Compound BAE)

According to Reference Example 7-8, by use of Compound EAM (155 mg, 0.786 mmol) and 2,3-dichloroquinoxaline (188 mg, 0.943 mmol), Compound BAE (230 mg, yield: 81%) was obtained.

REFERENCE EXAMPLE 7-32

2-chloro-3-[2,2,2-trifluoro-1-(4-fluorotetrahydro-2H-pyran-4-yl)ethoxy]quinoxaline (Compound BAF)

According to Reference Example 7-8, by use of Compound EAN (147 mg, 0.727 mmol) and 2,3-dichloroquinoxaline (217 mg, 1.09 mmol), Compound BAF (226 mg, yield: 85%) was obtained.

REFERENCE EXAMPLE 7-33

2-chloro-3-[2,2,2-trifluoro-1-(4-cyanotetrahydro-2H-pyran-4-yl)ethoxy]quinoxaline (Compound BAG)

According to Reference Example 7-8, by use of Compound EAO (147 mg, 703 mmol) and 2,3-dichloroquinoxaline (210 mg, 1.05 mmol), Compound BAG (156 mg, yield: 60%) was obtained.

REFERENCE EXAMPLE 7-34

2-chloro-3-[2,2,2-trifluoro-1-(4-fluoro-1-methanesulfonylpiperidin-4-yl)ethoxy]quinoxaline (Compound BAH)

According to Reference Example 7-8, by use of Compound EAS (167 mg, 0.598 mmol) and 2,3-dichloroquinoxaline (143 mg, 0.718 mmol), Compound BAH (161 mg, yield: 61%) was obtained.
ESIMS m/z: 442 (M+H)$^+$.

REFERENCE EXAMPLE 7-35

2-chloro-3-[2,2,2-trifluoro-1-(1-methanesulfonyl-4-methylpiperidin-4-yl)ethoxy]quinoxaline (Compound BAI)

Step 1
According to Reference Example 7-8, by use of Compound EAT (250 mg, 0.841 mmol) and 2,3-dichloroquinoxaline (201 mg, 0.101 mmol), 2-chloro-3-[2,2,2-trifluoro-1-(1-tert-butoxycarbonyl-4-fluoropiperidin-4-yl)ethoxy]quinoxaline (387 mg, yield: 100%) was obtained.

Step 2
2-Chloro-3-[2,2,2-trifluoro-1-(1-tert-butoxycarbonyl-4-fluoropiperidin-4-yl)ethoxy]quinoxaline (367 mg, 0.797 mmol) was dissolved in methanol (4.0 mL). To this, a 10% solution of hydrogen chloride in methanol (4.0 mL) was added and the mixture was stirred at room temperature for 1 hour. The mixture was further stirred at 50° C. for 1 hour and the solvent was evaporated off under reduced pressure. Thus, 2-chloro-3-[2,2,2-trifluoro-1-(4-fluoropiperidin-4-yl)-ethoxy]quinoxaline hydrochloride (334 mg, yield: 100%) was obtained.

Step 3
2-Chloro-3-[2,2,2-trifluoro-1-(4-fluoropiperidin-4-yl)-ethoxy]quinoxaline hydrochloride (157 mg, 0.396 mmol) was dissolved in dichloromethane (3.0 mL). To this, triethylamine (0.197 mL, 1.19 mmol) and methanesulfonyl chloride (0.0459 mL, 0.594 mmol) were successively added and the mixture was stirred at room temperature for 1 hour. The reaction was stopped by addition of a saturated aqueous sodium bicarbonate solution to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=7/3) to give Compound BAI (146 mg, yield: 84%).

REFERENCE EXAMPLE 8-1

3-(1-hydroxyethyl)pyridine (Compound CA)

To methylmagnesium bromide (a 0.96 mol/L solution in tetrahydrofuran, 16.6 mL, 15.9 mmol), a solution of 3-pyridinecarboxaldehyde (500 μL, 5.30 mmol) in tetrahydrofuran (5.0 mL) was slowly added under a nitrogen atmosphere at 0° C., and the mixture was stirred at the same temperature for 1. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol 9/1) to give 3-(1-hydroxyethyl)pyridine (Compound CA) (498 mg, yield: 76%).
ESIMS m/z: 124 (M+H)$^+$; $^1$H-NMR (300 MHz, CDCl$_3$, δ): 1.53 (d, J=6.2 Hz, 3H), 2.62 (br s, 1H), 4.96 (q, J=6.2 Hz, 1H), 7.26-7.30 (m, 1H), 7.74 (ddd, J=1.8, 2.1, 7.7 Hz, 1H), 8.49 (dd, J=1.5, 4.8 Hz, 1H), 8.57 (d, J=1.8 Hz, 1H).

REFERENCE EXAMPLE 8-2

3-(2,2,2-trifluoro-1-hydroxyethyl)pyridine (Compound CB)

3-Pyridinecarboxaldehyde (200 μL, 2.12 mmol) and potassium carbonate (58.6 mg, 0.424 mmol) were suspended in N,N-dimethylformamide (4.0 mL). To this, (trifluoromethyl)trimethylsilane (940 μL, 3.63 mmol) was added dropwise under a nitrogen atmosphere at room temperature and the mixture was stirred at the same temperature for 1.5. After water was added to the reaction mixture, extraction with ethyl acetate was performed, followed by washing with brine and drying over anhydrous sodium sulfate. The solvent was evaporated off under reduced pressure and the residue was dissolved in tetrahydrofuran (4.0 mL). To this, a 1 mol/L aqueous hydrogen chloride solution (5.0 mL) was added at room temperature and the mixture was stirred at the same temperature for 10 minutes. Then, the reaction mixture was neutralized with a saturated aqueous sodium bicarbonate solution, and extraction with ethyl acetate was performed, followed by washing with brine and drying over anhydrous sodium sulfate. The solvent was evaporated off under reduced pressure, and the residue was purified by silica gel column chromatography (chloroform/methanol=9/1) to give 3-(2,2,2-trifluoro-1-hydroxyethyl) pyridine (Compound CB) (341 mg, yield: 91%).
ESIMS m/z: 178 (M+H)$^+$; $^1$H-NMR (270 MHz, CDCl$_3$, δ): 4.77 (br s, 1H), 5.10 (q, J=6.6 Hz, 1H), 7.39 (dd, J=5.0, 7.9 Hz, 1H), 7.91 (d, J=7.9 Hz, 1H), 8.59-8.63 (m, 2H).

REFERENCE EXAMPLE 8-3

3-(1-hydroxypropyl)pyridine (Compound CC)

According to Reference Example 8-1, by use of ethylmagnesium bromide (a 1.0 mol/L solution in tetrahydrofuran, 3.18 mL, 3.18 mmol), 3-pyridinecarboxaldehyde (200 μL, 2.12 mmol) and tetrahydrofuran (2.0 mL), the mixture was stirred and reacted at 0° C. for 1 hour. Then, purification by silica gel column chromatography (chloroform/methanol=9/1) was performed to give 3-(1-hydroxypropyl)pyridine (Compound CC) (194 mg, yield: 67%).
$^1$H-NMR (300 MHz, CDCl$_3$, δ): 0.94 (t, J=7.3 Hz, 1H), 1.68-1.92 (m, 2H), 2.53 (br s, 1H), 4.66 (t, J=7.0 Hz, 1H), 7.26-7.30 (m, 1H), 7.71 (ddd, J=1.5, 2.2, 8.1 Hz, 1H), 8.49-8.54 (m, 2H).

REFERENCE EXAMPLE 8-4

2-pyrazinemethanol (Compound CD)

Step 1
To methanol (8.0 mL), thionyl chloride (2.08 mL) was added dropwise under a nitrogen atmosphere at −10° C. and the mixture was stirred at the same temperature for 30 minutes. To this, 2-pyrazinecarboxylic acid (1.00 g, 8.06 mmol) was added at the same temperature and the mixture was stirred at room temperature for 72 hours. The reaction mixture was concentrated, a saturated aqueous sodium bicarbonate solution was added to the residue, and extraction with ethyl acetate was performed, followed by washing with brine and drying over anhydrous sodium sulfate. The solvent was evaporated off under reduced pressure, and the residue was purified by silica gel column chromatography (chloroform/methanol 19/1) to give methyl 2-pyrazinecarboxylate (969 mg, yield: 87%).

$^1$H-NMR (270 MHz, CDCl$_3$, δ); 4.06 (s, 3H), 8.74 (dd, J=1.3, 2.3 Hz, 1H), 8.79 (d, J=1.3 Hz, 1H), 9.34 (d, J=2.3 Hz, 1H).

Step 2

Lithium aluminum hydride (40.0 mg, 1.06 mmol) was suspended in tetrahydrofuran (1.0 mL). To this, a solution of methyl 2-pyrazinecarboxylate (66.0 mg, 0.478 mmol) in tetrahydrofuran (0.5 mL) was added dropwise under a nitrogen atmosphere at 0° C. and the mixture was stirred at the same temperature for 15 minutes. Then, water (40 μL), a 15% aqueous sodium hydroxide solution (40 μL) and water (120 μL) were successively added to the reaction mixture and the mixture was stirred at room temperature for 1 hour. The mixture was filtered through Celite and the mother liquid was concentrated. The residue was purified by silica gel column chromatography (chloroform/methanol=9/1) to give 2-pyrazinemethanol (Compound CD) (19.0 yield: 36%).

$^1$H-NMR (270 MHz, CDCl$_3$, δ): 3.11 (brd, J=5.6 Hz, 1H), 4.85 (d, J=5.6 Hz, 1H), 8.52-8.55 (m, 2H), 8.64 (s, 1H).

REFERENCE EXAMPLE 8-5

3-(1-hydroxy-2-methylpropyl)pyridine (Compound CE)

According to Reference Example 8-1, by use of isopropylmagnesium bromide (a 0.76 mol/L solution in tetrahydrofuran, 4.18 mL, 3.18 mmol), 3-pyridinecarboxaldehyde (200 μL, 2.12 mmol) and tetrahydrofuran (2.0 mL), the mixture was stirred and reacted at 0° C. for 1 hour. Then, purification by silica gel column chromatography (chloroform/methanol=9/1) was performed to give 3-(1-hydroxy-2-methylpropyl)pyridine (Compound CE) (69.0 mg, yield: 22%).

$^1$H-NMR (270 MHz, CDCl$_3$, δ): 0.84 (d, J=6.9 Hz, 3H), 1.00 (d, J=6.6 Hz, 3H), 1.92-2.07 (m, 2H), 4.45 (d, J=6.6 Hz, 1H), 7.21-7.30 (m, 1H), 7.68 (ddd, J=1.7, 2.3, 7.9 Hz, 1H), 8.50-8.54 (m, 2H).

REFERENCE EXAMPLE 8-6

1-(trifluoromethyl)-4-(2,2,2-trifluoro-1-hydroxyethyl)-benzene (Compound CF)

According to Reference Example 8-2, by use of 4-(trifluoromethyl)benzaldehyde (100 μL, 0.732 mmol), potassium carbonate (20.2 mg, 0.146 mmol), (trifluoromethyl)trimethylsilane (162 μL, 1.10 mmol) and N,N-dimethylformamide (2.0 mL), the mixture was stirred and reacted at room temperature for 1 hour. Then, purification by silica gel column chromatography (chloroform/methanol=9/1) was performed to give 1-(trifluoromethyl)-4-(2,2,2-trifluoro-1-hydroxyethyl)-benzene (Compound CF) (102 mg, yield: 57%).

$^1$H-NMR (300 MHz, CDCl$_3$, δ): 2.78 (d, J=4.8 Hz, 1H), 5.08-5.16 (m, 1H), 7.26-7.70 (m, 4H).

REFERENCE EXAMPLE 8-7

3-(2,2-dimethyl-1-hydroxypropyl)pyridine (Compound CG)

3-Pyridinecarboxaldehyde (200 μL, 2.12 mmol) was dissolved in tetrahydrofuran (5.0 mL). To this, tert-butyllithium (a 1.46 mol/L solution in pentane, 4.37 mL, 6.36 mmol) was added dropwise under a nitrogen atmosphere at 0° C. and the mixture was stirred at the same temperature for 1. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol=9/1, hexane/ethyl acetate=1/1) to give 3-(2,2-dimethyl-1-hydroxypropyl)pyridine (Compound CG) (64.0 mg, yield: 18%).

ESIMS m/z: 166 (M+H)$^+$; $^1$H-NMR (270 MHz, CDCl$_3$, δ): 0.94 (s, 9H), 4.44 (s, 1H), 7.24-7.28 (m, 1H), 7.68 (ddd, J=2.0, 2.0, 7.6 Hz, 1H), 8.49-8.53 (m, 2H).

REFERENCE EXAMPLE 8-8

Methyl hydroxy-4-(trifluoromethyl)phenylacetate (Compound CH)

To a mixture of 4-(trifluoromethyl)benzaldehyde (500 μL, 3.66 mmol) and trimethylsilyl cyanate (537 μL, 4.03 mmol), lithium chloride (a 0.307 mol/L solution in tetrahydrofuran, 1.2 μL, 0.366 μmol) was added and the mixture was stirred under a nitrogen atmosphere at room temperature for 2 hours. The reaction mixture was diluted with diethyl ether (10 mL). To this, a 10% solution of hydrogen chloride in methanol (10 mL) was added at 0° C. and the mixture was stirred at room temperature for 24 hours. The reaction mixture was concentrated, water was added thereto, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=7/3) to give methyl hydroxy-4-(trifluoromethyl)phenylacetate (Compound CH) (587 mg, yield: 68%).

$^1$H-NMR (270 MHz, CDCl$_3$, δ): 3.51 (d, J=5.1 Hz, 1H), 3.79 (s, 3H), 5.25 (d, J=5.1 Hz, 1H), 7.55-7.56 (m, 4H).

REFERENCE EXAMPLE 8-9

3-(2-fluoro-2-methyl-1-hydroxypropyl)pyridine (Compound CI)

Step 1

Compound CE (410 mg, 2.71 mmol) was dissolved in dichloromethane (10 mL). To this, manganese dioxide (3.08 g) was added at room temperature and the mixture was stirred at the same temperature for 72 hours. The reaction mixture was filtered through Celite and the mother liquid was concentrated. The residue was purified by silica gel column chromatography (hexane/ethyl acetate=1/1) to give isopropyl(pyridin-3-yl)ketone (330 mg, yield: 82%).

$^1$H-NMR (300 MHz, CDCl$_3$, δ): 1.24 (s, 3H), 1.26 (s, 3H), 3.53 (sept, J=6.9 Hz, 1H), 7.43 (ddd, J=0.7, 4.8, 8.1 Hz, 1H), 8.23 (ddd, J=1.8, 2.2, 8.1 Hz, 1H), 8.78 (dd, J=1.8, 4.8 Hz, 1H), 9.17 (dd, J=0.7, 2.2 Hz, 1H).

Step 2

To lithium bis(trimethylsilyl) amide (a 1.0 mol/L solution in tetrahydrofuran, 2.35 mL, 2.35 mmol), a solution of isopropyl(pyridin-3-yl)ketone (292 mg, 1.96 mmol) in tetrahydrofuran (3.5 mL) was added dropwise under a nitrogen atmosphere at −78° C. and the mixture was stirred at the same temperature for 30 minutes. To this, N-fluorobenzenesulfonimide (865 mg, 2.74 mmol) was added and the mixture was stirred at the same temperature for 1 hour. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=4/1) to give 1-fluoro-1-methylethyl(pyridin-3-yl)ketone (214 mg, yield: 65%).

$^1$H-NMR (270 MHz, CDCl$_3$, δ): 1.66 (s, 3H), 1.74 (s, 3H), 7.41 (ddd, J=0.7, 5.0, 8.3 Hz, 1H), 8.31-8.36 (m, 1H), 8.78 (dd, J=1.7, 5.0 Hz, 1H), 9.27-9.29 (m, 1H).

Step 3

1-Fluoro-1-methylethyl(pyridin-3-yl)ketone (210 mg, 1.25 mmol) was dissolved in methanol (4.0 mL). To this, sodium borohydride (70.9 mg, 1.88 mmol) was added under a nitrogen atmosphere at 0° C. and the mixture was stirred at room temperature for 20 minutes. The reaction mixture was concentrated, water was added thereto, and extraction with ethyl acetate was performed, followed by drying over anhydrous sodium sulfate. The solvent was evaporated off under reduced pressure, and the residue was purified by silica gel column chromatography (hexane/ethyl acetate=3/7) to give 3-(2-fluoro-2-methyl-1-hydroxypropyl)pyridine (Compound CI) (200 mg, yield: 95%).

$^1$H-NMR (270 MHz, CDCl$_3$, δ): 1.30 (d, J=6.3 Hz, 3H), 1.38 (d, J=6.3 Hz, 3H), 2.92 (br s, 1H), 4.75 (d, J=11.6 Hz, 1H), 7.30 (ddd, J=1.0, 4.6, 7.9 Hz, 1H), 7.75-7.80 (m, 1H), 8.55 (dd, J=1.7, 4.6 Hz, 1H), 8.59 (d, J=1.7 Hz, 1H).

REFERENCE EXAMPLE 8-10

2,2,2-trifluoro-1-(4-methoxyphenyl)ethanol
(Compound CJ)

According to Reference Example 8-2, by use of 4-methoxybenzaldehyde (500 mg, 3.67 mmol) dissolved in N,N-dimethylformamide (7.5 mL), potassium carbonate (101 mg, 0.734 mmol) and (trifluoromethyl)trimethylsilane (1.09 mL, 7.34 mmol), the mixture was stirred and reacted at room temperature, at 80° C. for 7 hours. Then, purification by preparative thin-layer chromatography (chloroform/methanol=100/1) was performed to give 2,2,2-trifluoro-1-(4-methoxyphenyl)ethanol (Compound CJ) (636 mg, yield: 84%).

$^1$H-NMR (270 MHz, CDCl$_3$, δ): 2.73 (d, J=4.1 Hz, 1H), 3.82 (s, 3H), 4.96 (m, 1H), 6.93 (d, J=8.9 Hz, 2H), 7.40 (d, J=8.9 Hz, 2H).

REFERENCE EXAMPLE 8-11

2-methyl-5-(2,2,2-trifluoro-1-hydroxyethyl)pyridine
(Compound CK)

Step 1

N,O-dimethylhydroxylamine hydrochloride (710 mg, 7.28 mmol) was suspended in dichloromethane (50 mL). To this, dimethylaluminum chloride (a 1.04 mol/L solution in hexane, 7.00 mL, 7.28 mmol) was slowly added under a nitrogen atmosphere at 0° C. and the mixture was stirred at the same temperature for 1 hour. To this, methyl 6-methylnicotinate (1.00 g, 6.62 mmol) was added, and (7.00 mg, 1.88 mmol) was added at room temperature. Then, water was added to the reaction mixture, and extraction with dichloromethane was performed, followed by drying over anhydrous sodium sulfate. The solvent was evaporated off under reduced pressure, and the residue was purified by silica gel column chromatography (chloroform/methanol=19/1) to give 6-methylnicotinic acid N,O-dimethylhydroxylamide (737 mg, yield: 62%).

$^1$H-NMR (300 MHz, CDCl$_3$, δ): 2.61 (s, 3H), 3.38 (s, 3H), 3.56 (s, 3H), 7.21 (d, J=8.1 Hz, 1H), 7.94 (dd, J=2.2, 8.1 Hz, 1H), 8.87 (d, J=2.2 Hz, 1H).

Step 2

6-Methylnicotinic acid N,O-dimethylhydroxylamide (737 mg, 4.09 mmol) was dissolved in dichloromethane. To this, diisobutylaluminum hydride (a 0.98 mol/L solution in hexane, 4.60 mL, 4.50 mmol) was added dropwise under a nitrogen atmosphere at −10° C. and the mixture was stirred at the same temperature for 10 minutes. To this, water (4.60 mL) was added and the mixture was stirred at room temperature for 1 hour. The reaction mixture was filtered through Celite and the filtrate was concentrated. The residue was purified by silica gel column chromatography (chloroform/methanol=19/1) to give a 3:1 mixture (405 mg) of 2-methyl-5-formylpyridine and 6-methylnicotinic acid N,O-dimethylhydroxylamide. The mixture was dissolved in tetrahydrofuran (8.0 mL). To this, (trifluoromethyl)trimethylsilane (593 μL, 4.01 mmol) and tetrabutylammonium fluoride (a 1.0 mol/L solution in tetrahydrofuran, 340 μL, 0.340 mmol) were added under a nitrogen atmosphere at room temperature and the mixture was stirred at the same temperature for 1 hour. To the reaction mixture, a 1N aqueous hydrogen chloride solution (6.0 mL) was added and the mixture was further stirred for 10 minutes. Then, the reaction mixture was neutralized with a saturated sodium bicarbonate solution, and extraction with ethyl acetate was performed, followed by washing with brine and drying over anhydrous sodium sulfate. The solvent was evaporated off under reduced pressure, and the residue was purified by silica gel column chromatography (chloroform/methanol=19/1) to give 2-methyl-5-(2,2,2-trifluoro-1-hydroxyethyl)pyridine (Compound CK) (387 mg, yield: 50%).

$^1$H-NMR (270 MHz, CDCl$_3$, δ): 2.55 (s, 3H), 5.00-5.07 (m, 2H), 7.23 (d, J=7.9 Hz, 1H), 7.79 (dd, J=2.0, 7.9 Hz, 1H), 8.44 (d, J=2.0 Hz, 1H).

REFERENCE EXAMPLE 8-12

4-(2,2,2-trifluoro-1-hydroxyethyl)benzonitrile
(Compound CL)

4-Formylbenzonitrile (200 mg, 1.53 mmol) was dissolved in tetrahydrofuran (4.0 mL). To this, (trifluoromethyl)trimethylsilane (271 μL, 1.83 mmol) and tetrabutylammonium fluoride (a 1.0 mol/L solution in tetrahydrofuran, 153 μL, 0.153 mmol) were added under a nitrogen atmosphere at room temperature and the mixture was stirred at the same temperature for 1 hour. To the reaction mixture, a 1 mol/L aqueous hydrogen chloride solution (3.0 mL) was added and the mixture was further stirred for 0.5 minute. Then, the reaction mixture was neutralized with a saturated sodium bicarbonate solution, and extraction with ethyl acetate was performed, followed by washing with brine and drying over anhydrous sodium sulfate. The solvent was evaporated off under reduced pressure, and the residue was subjected to slurry purification using hexane, to give 4-(2,2,2-trifluoro-1-hydroxyethyl)benzonitrile (Compound CL) (276 mg, yield: 90%).

¹H-NMR (300 MHz, CDCl₃, δ): 2.85 (br s, 1H), 5.12 (q, J=6.2 Hz, 1H), 7.63 (d, J=8.1 Hz, 2H), 7.72 (d, J=8.1 Hz, 2H).

REFERENCE EXAMPLE 8-13

1-(1-hydroxy-2-triisopropylsiloxyethyl)-4-(trifluoromethyl)benzene (Compound CM)

Step 1
Compound CH (240 mg, 1.02 mmol) was dissolved in methanol (5.0 mL). To this, sodium borohydride (96.8 mg, 2.56 mmol) was added under a nitrogen atmosphere at 0° C. and the mixture was stirred at room temperature for 1 hour. The reaction mixture was concentrated, water was added thereto, and extraction with chloroform was performed, followed by drying over anhydrous sodium sulfate. The solvent was evaporated off under reduced pressure, and the residue was purified by silica gel column chromatography (chloroform/methanol=9/1) to give 1-(1,2-dihydroxyethyl)-4-(trifluoromethyl)benzene (183 mg, yield: 87%).
¹H-NMR (300 MHz, CDCl₃, δ): 1.98 (dd, J=5.1, 7.0 Hz, 1H), 2.61 (d, J=3.3 Hz, 1H), 3.65 (ddd, J=5.1, 8.1, 11.4 Hz, 1H), 3.82 (ddd, J=3.3, 7.0, 11.4 Hz, 1H), 4.91 (ddd, J=3.3, 3.3, 8.1 Hz, 1H), 7.51 (d, J=8.8 Hz, 2H), 7.63 (d, J=8.8 Hz, 1H).
Step 2
1-(1,2-Dihydroxyethyl)-4-(trifluoromethyl)benzene (81.0 mg, 0.393 mmol) and triethylamine (57.6 μL, 0.413 mmol) were dissolved in N,N-dimethylformamide (1.6 mL). To this, triisopropylsilyl chloride (87.2 μL, 0.413 mmol) was added under a nitrogen atmosphere at 0° C. and the mixture was stirred at room temperature for 2 hours. After water was added to the reaction mixture, extraction with ethyl acetate was performed, followed by washing with brine and drying over anhydrous sodium sulfate. The solvent was evaporated off under reduced pressure, and the residue was purified by silica gel column chromatography (hexane/ethyl acetate=9/1) to give 1-(1-hydroxy-2-triisopropylsiloxyethyl)-4-(trifluoromethyl)benzene (Compound CM) (117 mg, yield: 82%).
¹H-NMR (270 MHz, CDCl₃, δ): 1.01-1.19 (m, 21H), 3.13 (d, J=2.3 Hz, 1H), 3.61 (dd, J=8.6, 9.9 Hz, 1H), 3.88 (dd, J=3.6, 9.9 Hz, 1H), 4.84 (ddd, J=2.3, 3.6, 8.6 Hz, 1H), 7.50 (d, J=8.9 Hz, 2H), 7.61 (d, J=8.9 Hz, 2H).

REFERENCE EXAMPLE 8-14

2-(2,2,2-trifluoro-1-hydroxyethyl)pyridine (Compound CN)

According to Reference Example 8-12, by use of 2-pyridinecarboxaldehyde (500 μL, 5.26 mmol), (trifluoromethyl)trimethylsilane (932 μL, 6.31 mmol), tetrabutylammonium fluoride (a 1.0 mol/L solution in tetrahydrofuran, 526 μL, 0.526 mmol) and tetrahydrofuran (10 mL), the mixture was stirred and reacted at room temperature for 10 minutes. Then, purification by silica gel column chromatography (chloroform/methanol=9/1) was performed to give 2-(2,2,2-trifluoro-1-hydroxyethyl)pyridine (Compound CN) (1.18 g, yield: quantitative).
¹H-NMR (300 MHz, CDCl₃, δ): 4.99-5.08 (m, 1H), 5.49 (d, J=7.0 Hz, 1H), 7.36-7.45 (m, 2H), 7.80 (ddd, J=1.8, 7.7, 7.7 Hz, 1H), 8.62-8.65 (m, 1H).

REFERENCE EXAMPLE 8-15

4-(2,2,2-trifluoro-1-hydroxyethyl)pyridine (Compound CO)

According to Reference Example 8-12, by use of 2-pyridinecarboxaldehyde (500 μL, 5.24 mmol), (trifluoromethyl) trimethylsilane (928 μL, 6.28 mmol), tetrabutylammonium fluoride (a 1.0 mol/L solution in tetrahydrofuran, 524 μL, 0.524 mmol) and tetrahydrofuran (10 mL), the mixture was stirred and reacted at room temperature for 2 hours. Then, purification by silica gel column chromatography (chloroform/methanol=9/1) was performed to give 4-(2,2,2-trifluoro-1-hydroxyethyl)pyridine (Compound CO) (1.04 g, yield: quantitative).
¹H-NMR (300 MHz, CDCl₃, δ): 5.04-5.10 (m, 2H), 7.48 (d, J=5.9 Hz, 2H), 8.59-8.61 (m, 2H).

REFERENCE EXAMPLE 8-16

1-chloro-4-(2,2,2-trifluoro-1-hydroxyethyl)benzene (Compound CP)

According to Reference Example 8-12, by use of 4-chlorobenzaldehyde (500 mg, 3.56 mmol), (trifluoromethyl)trimethylsilane (631 μL, 4.27 mmol), tetrabutylammonium fluoride (a 1.0 mol/L solution in tetrahydrofuran, 360 μL, 0.360 mmol) and tetrahydrofuran (10 mL), the mixture was stirred and reacted at room temperature for 30 minutes. Thus, 1-chloro-4-(2,2,2-trifluoro-1-hydroxyethyl)benzene (Compound CP) (922 mg, yield: quantitative) was obtained.
¹H-NMR (270 MHz, CDCl₃, δ): 4.88 (q, J=6.3 Hz, 1H), 7.37-7.42 (m, 2H).

REFERENCE EXAMPLE 8-17

1-methoxymethoxy-4-(2,2,2-trifluoro-1-hydroxyethyl)benzene (Compound CQ)

Step 1
4-Hydroxybenzaldehyde (500 mg, 4.09 mmol) and diisopropylethylamine (2.85 mL, 16.4 mmol) were dissolved in dichloromethane (10 mL). To this, chloromethyl methyl ether (614 μL, 8.09 mmol) was added under a nitrogen atmosphere at 0° C. and the mixture was stirred at room temperature for 8 hours. Then, water was added to the reaction mixture, and extraction with chloroform was performed, followed by drying over anhydrous sodium sulfate. The solvent was evaporated off under reduced pressure, and the residue was purified by silica gel column chromatography (hexane/ethyl acetate=7/3) to give 4-methoxymethoxybenzaldehyde (658 mg, yield: 97%).
¹H-NMR (270 MHz, CDCl₃, δ): 3.50 (s, 3H), 5.26 (s, 2H), 7.12-7.18 (m, 2H), 7.82-7.87 (m, 2H), 9.19 (s, 1H).
Step 2
4-Methoxymethoxybenzaldehyde (658 mg, 3.96 mmol) was dissolved in tetrahydrofuran (4.0 mL). To this, (trifluoromethyl)trimethylsilane (702 μL, 475 mmol) and tetrabutylammonium fluoride (a 1.0 mol/L solution in tetrahydrofuran, 396 μL, 0.396 mmol) were added under a nitrogen atmosphere at 0° C. and the mixture was stirred at room temperature for 1 hour. To the reaction mixture, tetrabutylammonium fluoride (a 1.0 mol/L solution in tetrahydrofuran, 4.00 mL, 4.00 mmol) was added and the mixture was further stirred for 10 minutes. After water was added to the reaction mixture, extraction with ethyl acetate was performed, followed by washing with brine and drying over anhydrous sodium sulfate. The solvent was evaporated off under reduced pressure, and the residue was purified by silica gel column chromatography (hexane/ethyl acetate=7/3) to give 1-methoxymethoxy-4-(2,2,2-trifluoro-1-hydroxyethyl)benzene (Compound CQ) (895 mg, yield: 96%).

¹H-NMR (270 MHz, CDCl₃, δ): 2.48 (d, J=4.3 Hz, 1H), 3.48 (s, 3H), 4.93-5.02 (m, 1H), 5.19 (s, 2H), 7.05-7.10 (m, 2H), 7.39-7.42 (m, 2H).

REFERENCE EXAMPLE 8-18

1-diethoxymethyl-4-(2,2,2-trifluoro-1-hydroxyethyl) benzene (Compound CR)

According to Step 2 of Reference Example 8-17, by use of terephthalaldehyde mono(diethyl acetal) (796 μL, 4.00 mol), (trifluoromethyl)trimethylsilane (709 μL, 4.80 mmol), tetrabutylammonium fluoride (a 1.0 mol/L solution in tetrahydrofuran, 4.40 mL, 4.40 mmol) and tetrahydrofuran (10 mL), the mixture was stirred and reacted at room temperature for 2.5 hours. Then, purification by silica gel column chromatography (hexane/ethyl acetate=4/1) was performed to give 1-diethoxymethyl-4-(2,2,2-trifluoro-1-hydroxyethyl)benzene (Compound CR) (1.04 g, yield: 93%).
¹H-NMR (300 MHz, CDCl₃, δ): 1.24 (t, J=7.3 Hz, 6H), 2.56 (br s, 1H), 3.49-3.67 (m, 4H), 4.99-5.07 (m, 1H), 5.51 (s, 1H), 7.46-7.54 (m, 4H).

REFERENCE EXAMPLE 8-19

1-fluoro-4-(2,2,2-trifluoro-1-hydroxyethyl)benzene (Compound CS)

According to Reference Example 8-12, by use of 4-fluorobenzaldehyde (500 mg, 4.03 mmol), (trifluoromethyl)trimethylsilane (715 μL, 4.83 mmol), tetrabutylammonium fluoride (a 1.0 mol/L solution in tetrahydrofuran, 403 μL, 0.403 mmol) and tetrahydrofuran (10 mL), the mixture was stirred and reacted at room temperature for 30 minutes. Thus, 1-fluoro-4-(2,2,2-trifluoro-1-hydroxyethyl)benzene (Compound CS) (948 mg, yield: quantitative) was obtained.
¹H-NMR (300 MHz, CDCl₃, δ): 2.75 (d, J=14.3 Hz, 1H), 4.99-5.05 (m, 1H), 7.06-5.14 (m, 2H), 7.45-7.49 (m, 2H).

REFERENCE EXAMPLE 8-20

2-methoxy-5-(2,2,2-trifluoro-1-hydroxyethyl)pyridine (Compound CT)

According to Reference Example 8-12, by use of 6-methoxy-3-pyridinecarboxaldehyde (300 mg, 2.19 mmol), (trifluoromethyl)trimethylsilane (388 μL, 2.63 mmol), tetrabutylammonium fluoride (a 1.0 mol/L solution in tetrahydrofuran, 220 μL, 0.220 mmol) and tetrahydrofuran (6.0 mL), the mixture was stirred and reacted at room temperature for 3 hours. Then, purification by silica gel column chromatography (hexane/ethyl acetate=4/1) was performed to give 2-methoxy-5-(2,2,2-trifluoro-1-hydroxyethyl)pyridine (Compound CT) (424 mg, yield: 93%).
¹H-NMR (270 MHz, CDCl₃, δ): 2.78 (d, J=4.6 Hz, 1H), 3.95 (s, 3H), 4.96-5.05 (m, 1H), 6.80 (d, J=8.6 Hz, 1H), 7.73 (dd, J=2.0, 8.6 Hz, 1H), 8.21 (d, J=2.0 Hz, 1H).

REFERENCE EXAMPLE 8-21

3-(2-cyano-2-methyl-1-hydroxypropyl)pyridine (Compound CU)

3-Pyridinecarboxaldehyde (300 μL, 3.18 mmol) and isobutyronitrile (428 μL, 4.77 mmol) were dissolved in tetrahydrofuran (6.0 mL). To this, lithium diisopropylamide (a 2.0 mmol solution, 2.38 mL, 4.77 mmol) was slowly added dropwise under a nitrogen atmosphere at −78° C. and the mixture was stirred at room temperature for 1 hour. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol 19/1) to give 3-(2-cyano-2-methyl-1-hydroxypropyl)pyridine (Compound CU) (166 mg, yield: 30%).
¹H-NMR (300 MHz, CDCl₃, δ): 1.25 (s, 3H), 1.44 (s, 3H), 4.18 (br s, 1H), 4.60 (s, 1H), 7.34 (dd, J=4.8, 7.3 Hz, 1H), 7.91 (ddd, J=1.8, 1.8, 8.1 Hz, 1H), 8.48-8.50 (m, 2H).

REFERENCE EXAMPLE 8-22

3-methoxy-5-(2,2,2-trifluoro-1-hydroxyethyl)pyridine (Compound CV)

According to Reference Example 8-12, by use of 5-methoxy-3-pyridinecarboxaldehyde (300 mg, 2.19 mmol), (trifluoromethyl)trimethylsilane (388 μL, 2.63 mmol), tetrabutylammonium fluoride (a 1.0 mol/L solution in tetrahydrofuran, 220 μL, 0.220 mmol) and tetrahydrofuran (6.0 mL), the mixture was stirred and reacted at room temperature for 30 minutes. Then, purification by silica gel column chromatography (chloroform/methanol=9/1) was performed to give 3-methoxy-5-(2,2,2-trifluoro-1-hydroxyethyl)pyridine (Compound CV) (456 mg, yield: quantitative).
¹H-NMR (300 MHz, CDCl₃, δ): 3.88 (s, 3H), 4.39-4.64 (m, 1H), 5.04-5.11 (m, 1H), 7.41 (s, 1H), 8.20 (s, 1H), 8.28 (d, J=2.6 Hz, 1H).

REFERENCE EXAMPLE 8-23

3-[hydroxy(tetrahydropyran-4-yl)methyl]pyridine (Compound CW)

To toluene (2.2 mL), n-butyllithium (a 2.77 mol/L solution in hexane, 0.82 mL, 2.28 mmol) was added under a nitrogen atmosphere at −60° C. To this, a solution of 3-bromopyridine (200 μL, 2.08 mmol) in toluene (0.73 mL) was slowly added dropwise at the same temperature and the mixture was stirred at −78° C. for 15 minutes. To this suspension, tetrahydrofuran (0.73 mL) was slowly added dropwise and the mixture was stirred at the same temperature for 15 minutes. Then, 4-formyltetrahydropyran (285 mg, 2.50 mmol) was added thereto. Over 1 hour, the reaction mixture was heated to −15° C. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and the residue was purified by silica gel column chromatography (chloroform/methanol=19/1) to give 3-[hydroxy(tetrahydropyran-4-yl) methyl]pyridine (Compound CW) (353 mg, yield: 88%).
¹H-NMR (300 MHz, CDCl₃, δ): 1.16-1.61 (m, 3H), 1.80-1.92 (m, 2H), 2.17 (br s, 1H), 3.25-3.41 (m, 2H), 3.97 (ddd, J=3.7, 11.4, 30.8 Hz, 2H), 4.45 (d, J=7.0 Hz, 1H), 7.30 (ddd, J=0.7, 4.8, 8.1 Hz, 1H), 7.68 (ddd, J=1.8, 1.8, 8.1 Hz, 1H), 8.53-8.54 (m, 2H).

REFERENCE EXAMPLE 8-24

3-[hydroxy(4-fluorotetrahydropyran-4-yl)methyl] pyridine (Compound CX)

Step 1
According to Step 1 of Reference Example 8-9, manganese dioxide (6.38 g) was added to Compound CW (850 mg, 4.40 mmol) and dichloromethane (26 mL), and the mixture was stirred. Then, purification by silica gel column chromatography (chloroform/methanol=19/1) was performed to give tetrahydropyran-4-yl(pyridin-3-yl)ketone (480 mg, yield: 57%).

$^1$H-NMR (300 MHz, CDCl$_3$, δ): 1.34-1.63 (m, 3H), 1.79-1.97 (m, 4H), 3.43-3.62 (m, 3H), 4.04-4.10 (m, 2H), 7.45 (ddd, J=0.7, 5.1, 8.1 Hz, 1H), 8.23 (ddd, J=1.8, 2.2, 8.1 Hz, 1H), 8.80 (dd, J=1.8, 5.1 Hz, 1H), 9.17 (dd, J=0.7, 2.2 Hz, 1H).

Step 2

According to Step 2 of Reference Example 8-9, by use of lithium bis(trimethylsilyl)amide (a 1.0 mol/L solution in tetrahydrofuran, 3.71 mL, 3.71 mmol), tetrahydropyran-4-yl (pyridin-3-yl)ketone (473 mg, 2.47 mmol), tetrahydrofuran (6.29 mL) and N-fluorobenzenesulfonimide (1.17 g, 3.71 mmol), the mixture was stirred and reacted at room temperature for 1 hour. Then, purification by silica gel column chromatography (hexane/ethyl acetate=1/1) was performed to give 4-fluorotetrahydrofuran-4-yl(pyridin-3-yl)ketone (413 mg, yield: 80%).

$^1$H-NMR (300 MHz, CDCl$_3$, δ): 1.93-2.02 (m, 2H), 2.19-2.41 (m, 2H), 3.82-3.99 (m, 4H), 7.43 (ddd, J=0.7, 4.8, 8.1 Hz, 1H), 8.31-8.35 (m, 1H), 8.80 (dd, J=1.8, 4.8 Hz, 1H), 9.28-9.29 (m, 1H).

Step 3

4-Fluorotetrahydrofuran-4-yl(pyridin-3-yl)ketone (396 mg, 1.89 mmol) was dissolved in methanol (8.0 mL). To this, sodium borohydride (107 mg, 2.84 mmol) was added under a nitrogen atmosphere at 0° C. and the mixture was stirred at room temperature for 30 minutes. The reaction mixture was concentrated, water was added thereto, and extraction with ethyl acetate was performed, followed by drying over anhydrous sodium sulfate. The solvent was evaporated off under reduced pressure, and the residue was purified by silica gel column chromatography (chloroform/methanol 19/1) to give 3-[hydroxy(4-fluorotetrahydropyran-4-yl)methyl]pyridine (Compound CX) (417 mg, yield: quantitative).

$^1$H-NMR (300 MHz, CDCl$_3$, δ): 1.59-1.89 (m, 4H), 3.02 (br s, 1H), 3.61-3.72 (m, 2H), 3.81-3.89 (m, 2H), 4.67 (d, J=14.7 Hz, 1H), 7.32 (ddd, J=0.7, 4.8, 8.1 Hz, 1H), 7.75-7.77 (m, 1H), 8.54-8.55 (m, 2H).

REFERENCE EXAMPLE 8-25

3-(2-methanesulfonyl-2-methyl-1-hydroxypropyl) pyridine (Compound CY)

Step 1

3-(Methanesulfonylacetyl)pyridine (300 mg, 1.51 mmol) and potassium carbonate (4.17 mg, 3.02 mmol) were suspended in N,N-dimethylformamide (5.0 mL). To this, iodomethane (188 μL, 3.02 mmol) was added under a nitrogen atmosphere at room temperature and the mixture was stirred at room temperature for 13 hours. After water was added to the reaction mixture, extraction with ethyl acetate was performed, followed by washing with brine and drying over anhydrous sodium sulfate. The solvent was evaporated off under reduced pressure, and the residue was purified by silica gel column chromatography (chloroform/methanol 19/1) to give 3-[dimethyl(methanesulfonyl)acetyl]pyridine (81.0 mg, yield: 24%).

$^1$H-NMR (300 MHz, CDCl$_3$, δ): 1.78 (s, 6H), 3.02 (s, 3H), 7.39 (ddd, J=1.1, 4.8, 8.1 Hz, 1H), 8.25 (ddd, J=1.8, 2.2, 8.1 Hz, 1H), 8.76 (dd, J=1.8, 4.8 Hz, 1H), 8.94 (dd, J=1.1, 2.2 Hz, 1H).

Step 2

3-[Dimethyl(methanesulfonyl)acetyl]pyridine (81.0 mg, 0.356 mmol) was dissolved in methanol (2.0 mL). To this, sodium borohydride (20.2 mg, 0.535 mmol) was added under a nitrogen atmosphere at 0° C. and the mixture was stirred at room temperature for 30 minutes. The reaction mixture was concentrated, water was added thereto, and extraction with ethyl acetate was performed, followed by drying over anhydrous sodium sulfate. The solvent was evaporated off under reduced pressure, and the residue was purified by preparative thin-layer chromatography (chloroform/methanol 9/1) to give 3-(2-methanesulfonyl-2-methyl-1-hydroxypropyl)pyridine (Compound CY) (86.7 mg, yield: quantitative).

$^1$H-NMR (300 MHz, CDCl$_3$, δ): 1.13 (s, 3H), 1.42 (s, 3H), 3.09 (s, 3H), 3.82 (br s, 1H), 5.27 (d, J=1.8 Hz, 1H), 7.33 (ddd, J=0.7, 4.8, 7.7 Hz, 1H), 7.75 (ddd, J=1.8, 1.8, 7.7 Hz, 1H), 8.54-8.55 (m, 2H).

REFERENCE EXAMPLE 8-26

3-(2,2,2-trifluoro-1-hydroxyethyl)benzonitrile (Compound CZ)

According to Reference Example 8-12, by use of 3-formylbenzonitrile (500 mg, 3.81 mmol), (trifluoromethyl)trimethylsilane (678 μL, 4.58 mmol), tetrabutylammonium fluoride (a 1.0 mol/L solution in tetrahydrofuran, 381 μL, 0.381 mmol) and tetrahydrofuran (10 mL), the mixture was stirred and reacted at room temperature for 3 hours. Then, purification by silica gel column chromatography (hexane/ethyl acetate=7/3) was performed to give 3-(2,2,2-trifluoro-1-hydroxyethyl)benzonitrile (Compound CZ) (705 mg, yield: 92%).

$^1$H-NMR (270 MHz, CDCl$_3$, δ): 2.93 (br s, 1H), 5.06-5.14 (m, 1H), 7.55 (dd, J=7.5, 7.9 Hz, 1H), 7.70-7.76 (m, 2H), 7.82 (s, 1H).

REFERENCE EXAMPLE 8-27

1-fluoro-3-(2,2,2-trifluoro-1-hydroxyethyl)benzene (Compound DA)

According to Reference Example 8-12, by use of 3-fluorobenzaldehyde (500 mg, 4.03 mmol), (trifluoromethyl)trimethylsilane (715 μL, 4.83 mmol), tetrabutylammonium fluoride (a 1.0 mol/L solution in tetrahydrofuran, 403 μL, 0.403 mmol) and tetrahydrofuran (10 mL), the mixture was stirred and reacted at room temperature for 3 hours. Thus, 1-fluoro-3-(2,2,2-trifluoro-1-hydroxyethyl)benzene (Compound DA) (942 mg, yield: quantitative) was obtained.

$^1$H-NMR (300 MHz, CDCl$_3$, δ): 2.64-2.67 (m, 1H), 5.00-5.08 (m, 1H), 7.11 (dddd, J=1.1, 2.6, 8.1, 8.1 Hz, 1H), 7.22-7.26 (m, 2H), 7.90 (ddd, J=5.6, 8.1, 8.1 Hz, 1H).

REFERENCE EXAMPLE 8-28

1-chloro-3-(2,2,2-trifluoro-1-hydroxyethyl)benzene (Compound DD)

According to Reference Example 8-12, by use of 3-chlorobenzaldehyde (500 mg, 3.56 mmol), (trifluoromethyl)trimethylsilane (631 μL, 4.27 mmol), tetrabutylammonium fluoride (a 1.0 mol/L solution in tetrahydrofuran, 360 μL, 0.360 mmol) and tetrahydrofuran (10 mL), the mixture was stirred and reacted at room temperature for 3 hours. Thus, 1-chloro-3-(2,2,2-trifluoro-1-hydroxyethyl)benzene (Compound DB) (1.02 g, yield: quantitative) was obtained.

REFERENCE EXAMPLE 8-29

2-chloro-5-(2,2,2-trifluoro-1-hydroxyethyl)pyridine (Compound DC)

According to Reference Example 8-12, by use of 6-chloro-3-pyridinecarboxaldehyde (1.00 g, 7.06 mmol), (trifluoromethyl)trimethylsilane (1.25 mL, 8.48 mmol), tetrabutylammonium fluoride (a 1.0 mol/L solution in tetrahydrofuran, 706 μL, 0.706 mmol) and tetrahydrofuran (20 mL), the mixture was stirred and reacted at room temperature for 1 hour. Then, purification by silica gel column chromatography (chloroform/methanol=9/1) was performed to give 2-chloro-5-(2,2,2-trifluoro-1-hydroxyethyl)pyridine (Compound DC) (1.48 g, yield: 99%).

$^1$H-NMR (300 MHz, CDCl$_3$, δ): 3.43 (d, J=4.4 Hz, 1H), 5.08-5.16 (m, 1H), 7.41 (d, J=8.1 Hz, 1H), 7.83-7.87 (m, 1H), 8.46 (d, J=2.6 Hz, 1H).

REFERENCE EXAMPLE 8-30

2-bromo-5-(2,2,2-trifluoro-1-hydroxyethyl)pyridine (Compound DD)

According to Reference Example 8-12, by use of 6-bromo-3-pyridinecarboxaldehyde (1.00 g, 5.37 mmol), (trifluoromethyl)trimethylsilane (935 μL, 6.45 mmol), tetrabutylammonium fluoride (a 1.0 mol/L solution in tetrahydrofuran, 537 μL, 0.537 mmol) and tetrahydrofuran (20 mL), the mixture was stirred and reacted at room temperature for 1 hour. Then, purification by silica gel column chromatography (chloroform/methanol=19/1) was performed to give 2-bromo-5-(2,2,2-trifluoro-1-hydroxyethyl)pyridine (Compound DD) (1.12 g, yield: 81%).

$^1$H-NMR (300 MHz, CDCl$_3$, δ): 3.64 (br s, 1H), 5.06-5.14 (m, 1H), 7.57 (d, J=8.4 Hz, 1H), 7.73-7.76 (m, 1H), 8.44 (d, J=2.6 Hz, 1H).

REFERENCE EXAMPLE 8-31

4-(2,2,2-trifluoro-1-hydroxyethyl)toluene (Compound DE)

According to Reference Example 8-12, by use of p-tolualdehyde (500 μL, 4.24 mmol), (trifluoromethyl)trimethylsilane (752 μL, 5.09 mmol), tetrabutylammonium fluoride (a 1.0 mol/L solution in tetrahydrofuran, 424 μL, 0.424 mmol) and tetrahydrofuran (10 mL), the mixture was stirred and reacted at room temperature for 30 minutes. Thus, 4-(2,2,2-trifluoro-1-hydroxyethyl)toluene (Compound DE) (1.01 g, yield: quantitative) was obtained.

$^1$H-NMR (270 MHz, CDCl$_3$, δ): 2.36 (s, 3H), 4.87 (q, J=6.6 Hz, 1H), 7.18 (d, J=7.9 Hz, 2H), 7.33 (d, J=7.9 Hz, 2H).

REFERENCE EXAMPLE 8-32

4-hydroxy-4-(pyridin-3-yl)tetrahydropyran (Compound DF)

According to Reference Example 8-23, by use of toluene (3.3+1.1 mL), n-butyllithium (a 2.77 mol/L solution in hexane, 1.24 mL, 2.28 mmol), 3-bromopyridine (300 μL, 3.12 mmol), tetrahydrofuran (1.1 mL) and tetrahydropyran-4-one (345 μL, 3.74 mmol), the mixture was stirred and reacted at 0° C. for 2 hours. Then, purification by silica gel column chromatography (chloroform/methanol=19/1) was performed to give 4-hydroxy-4-(pyridin-3-yl)tetrahydropyran (Compound DF) (167 mg, yield: 30%).

$^1$H-NMR (300 MHz, CDCl$_3$, δ): 1.68-1.74 (m, 2H), 2.17 (ddd, J=5.8, 11.7, 13.6 Hz, 2H), 2.57 (br s, 1H), 3.86-4.00 (m, 4H), 7.31 (dd, J=5.1, 8.1 Hz, 1H), 7.82 (ddd, J=1.8, 2.2, 8.1 Hz, 1H), 8.49 (dd, J=1.8, 5.1 Hz, 1H), 8.74 (d, J=2.2 Hz, 1H).

REFERENCE EXAMPLE 8-33

3-(1-hydroxy-1-methylethyl)pyridine (Compound DG)

To methylmagnesium bromide (a 0.96 mol/L solution in tetrahydrofuran, 6.26 mL, 5.97 mmol), a solution of 3-acetylpyridine (362 mg, 2.99 mmol) in tetrahydrofuran (3.6 mL) was slowly added under a nitrogen atmosphere at 0° C., and the mixture was stirred at the same temperature for 1. Then, a saturated aqueous ammonium chloride solution was added to the reaction mixture, and extraction with ethyl acetate was performed, followed by washing with brine and drying over anhydrous sodium sulfate. The solvent was evaporated off under reduced pressure, and thereby 3-(1-hydroxy-1-methylethyl)pyridine (Compound DG) (415 mg, yield: quantitative) was obtained.

1.62 (s, 6H), 7.24-7.28 (m, 1H), 7.83 (ddd, J=1.8, 2.2, 8.1 Hz, 1H), 8.48 (dd, J=1.8, 4.8 Hz, 1H), 8.73 (dd, J=0.7, 2.2 Hz, 1H).

REFERENCE EXAMPLE 8-34

2-(pyrrolidin-1-yl)-5-(2,2,2-trifluoro-1-hydroxyethyl)-pyridine (Compound DH)

Step 1

6-Fluoro-3-pyridinecarboxaldehyde (152 mg, 1.22=01) was dissolved in tetrahydrofuran (3.0 mL). To this, pyrrolidine (507 μL, 6.08 mmol) was added under a nitrogen atmosphere at room temperature and the mixture was stirred at the same temperature for 2 hours and successively at 60° C. for 5 hours. The reaction mixture was concentrated, and the residue was purified by silica gel column chromatography (hexane/ethyl acetate=1/1) to give 6-(pyrrolidin-1-yl)-3-pyridinecarboxaldehyde (181 mg, yield: 84%).

$^1$H-NMR (300 MHz, CDCl$_3$, δ): 2.04-2.08 (m, 4H), 3.57 (br s, 4H), 6.42 (d, J=8.8 Hz, 1H), 7.90 (dd, J=2.6, 8.8 Hz, 1H), 8.55 (d, J=2.6 Hz, 1H), 9.76 (s, 1H).

Step 2

According to Reference Example 8-12, by use of 6-(pyrrolidin-1-yl)-3-pyridinecarboxaldehyde (173 mg, 0.982 mmol), (trifluoromethyl)trimethylsilane (174 μL, 1.18 mmol), tetrabutylammonium fluoride (a 1.0 mol/L solution in tetrahydrofuran, 98.0 μL, 0.098 mmol) and tetrahydrofuran (5.0 mL), the mixture was stirred and reacted at room temperature for 30 minutes. Then, slurry purification was performed using hexane, to give 2-(pyrrolidin-1-yl)-5-(2,2,2-trifluoro-1-hydroxyethyl)-pyridine (Compound DH) (227 mg, yield: 94%).

$^1$H-NMR (270 MHz, CDCl$_3$, δ): 1.99-2.04 (m, 4H), 2.70 (br s, 1H), 3.44-3.49 (m, 4H), 4.89 (q, J=6.6 Hz, 1H), 6.39 (d, J=8.9 Hz, 1H), 7.57 (dd, J=2.0, 8.9 Hz, 1H), 8.13 (d, J=2.0 Hz, 1H).

---

$^1$H-NMR (300 MHz, CDCl$_3$, δ): 2.60-2.64 (m, 1H), 4.98-5.06 (m, 1H), 7.34-7.42 (m, 3H), 7.50 (s, 1H).

REFERENCE EXAMPLE 8-35

1-methyl-2-(2,2,2-trifluoro-1-hydroxyethyl)imidazole (Compound DI)

According to Reference Example 8-2, by use of 1-methyl-2-imidazolecarboxaldehyde (100 mg, 0.908 mmol), potassium carbonate (25.1 mg, 0.182 mmol), (trifluoromethyl)trimethylsilane (201 μL, 1.36 mmol) and N,N-dimethylformamide (2.0 mL), the mixture was stirred and reacted at room temperature for 2 hours. Then, slurry purification was performed using diisopropyl ether, to give 1-methyl-2-(2,2,2-trifluoro-1-hydroxyethyl)imidazole (Compound DI) (142 mg, yield: 87%).

ESIMS m/z: 181 $(M+H)^+$; $^1$H-NMR (270 MHz, $CDCl_3$, δ): 3.75 (s, 3H), 5.03 (q, J=6.6 Hz, 1H), 6.29 (br s, 1H), 6.91 (d, J=1.0 Hz, 1H), 6.96 (d, J=1.0 Hz, 1H).

REFERENCE EXAMPLE 8-36

2,2,2-trifluoro-1-(1-methyl-1H-pyrazol-4-yl)ethanol (Compound DJ)

According to Reference Example 8-2, by use of 1-methyl-1H-pyrazole-4-carbaldehyde (300 mg, 2.72 mmol) dissolved in N,N-dimethylformamide (4.5 mL), potassium carbonate (75 mg, 0.54 mmol) and (trifluoromethyl)trimethylsilane (0.442 mL, 2.99 mmol), the mixture was stirred and reacted at room temperature for 3 hours. Then, purification by preparative thin-layer chromatography (chloroform/methanol=10/1) was performed to give 2,2,2-trifluoro-1-(1-methyl-1H-pyrazol-4-yl)ethanol (Compound DJ) (231 mg, yield: 47%).

ESIMS m/z: 181 $(M+H)^+$; $^1$H-NMR (270 MHz, $CDCl_3$+$CD_3OD$, δ): 3.74 (s, 3H), 5.07 (q, J=7.0 Hz, 1H), 7.07 (s, 1H), 7.47 (s, 1H).

REFERENCE EXAMPLE 8-37

2,2,2-trifluoro-1-(1-methyl-1H-imidazol-5-yl)ethanol (Compound DK)

According to Reference Example 8-2, by use of 1-methyl-1H-imidazole-5-carbaldehyde (300 mg, 2.72 mmol) dissolved in N,N-dimethylformamide (4.5 mL), potassium carbonate (75 mg, 0.54 mmol) and (trifluoromethyl)trimethylsilane (0.442 mL, 2.99 mmol), the mixture was stirred and reacted at room temperature for 3 hours. Then, purification by preparative thin-layer chromatography (chloroform/methanol=10/1) was performed to give 2,2,2-trifluoro-1-(1-methyl-1H-imidazol-5-yl)ethanol (Compound DK) (358 mg, yield: 73%).

ESIMS m/z: 181 $(M+H)^+$; $^1$H-NMR (270 MHz, $CDCl_3$, δ): 3.88 (s, 3H), 5.02 (q, J=6.7 Hz, 1H), 7.48 (s, 1H), 7.50 (s, 1H).

REFERENCE EXAMPLE 8-38

2,2,2-trifluoro-1-(thiazol-5-yl)ethanol (Compound DL)

According to Reference Example 8-2, by use of thiazole-5-carbaldehyde (300 mg, 2.65 mmol) dissolved in N,N-dimethylformamide (4.5 mL), potassium carbonate (73 mg, 0.53 mmol) and (trifluoromethyl)trimethylsilane (0.470 mL, 3.18 mmol), the mixture was stirred and reacted at room temperature for 1 hour. Then, purification by preparative thin-layer chromatography (chloroform/methanol=15/1) was performed to give 2,2,2-trifluoro-1-(thiazol-5-yl)ethanol (Compound DL) (353 mg, yield: 73%).

ESIMS m/z: 184 $(M+H)^+$; $^1$H-NMR (270 MHz, $CDCl_3$, δ): 4.92 (m, 1H), 5.40 (m, 1H), 7.92 (s, 1H), 8.85 (s, 1H).

REFERENCE EXAMPLE 8-39

2,2,2-trifluoro-1-(thiazol-2-yl)ethanol (Compound DM)

According to Reference Example 8-2, by use of thiazole-2-carbaldehyde (300 mg, 2.65 mmol) dissolved in N,N-dimethylformamide (4.5 mL), potassium carbonate (73 mg, 0.53 mmol) and (trifluoromethyl)trimethylsilane (0.470 mL, 3.18 mmol), the mixture was stirred and reacted at room temperature for 1.2 hours. Then, purification by preparative thin-layer chromatography (chloroform/methanol=15/1) was performed to give 2,2,2-trifluoro-1-(thiazol-2-yl)ethanol (Compound DM) (357 mg, yield: 74%).

ESIMS m/z: 182 $(M-H)^-$; $^1$H-NMR (270 MHz, $CDCl_3$, δ): 5.10 (br s, 1H), 5.36 (q, J=6.2 Hz, 1H), 7.49 (d, J=3.3 Hz, 1H), 7.85 (d, J=3.3 Hz, 1H).

REFERENCE EXAMPLE 8-40

2,2,2-trifluoro-1-(thiophen-2-yl)ethanol (Compound DN)

According to Reference Example 8-2, by use of thiophene-2-carbaldehyde (300 mg, 2.67 mmol) dissolved in tetrahydrofuran (4.5 mL) and N,N-dimethylformamide (1.5 mL), potassium carbonate (74 mg, 0.53 mmol) and (trifluoromethyl)trimethylsilane (0.772 mL, 5.34 mmol), the mixture was stirred and reacted at room temperature for 16 hours. Then, purification by extraction gave 2,2,2-trifluoro-1-(thiophen-2-yl)ethanol (Compound DN) (378 mg, yield: 78%).

ESIMS m/z: 181 $(M-H)^-$; $^1$H-NMR (270 MHz, $CDCl_3$, δ): 5.29 (q, J=6.4 Hz, 1H), 7.04 (dd, J=3.5, 5.1 Hz, 1H), 7.20 (d, J=3.6 Hz, 1H), 7.39 (dd, J=1.2, 5.1 Hz, 1H).

REFERENCE EXAMPLE 8-41

2,2,2-trifluoro-1-(thiophen-3-yl)ethanol (Compound DO)

According to Reference Example 8-2, by use of thiophene-3-carbaldehyde (300 mg, 2.67 mmol) dissolved in tetrahydrofuran (4.5 mL) and N,N-dimethylformamide (1.5 mL), potassium carbonate (74 mg, 0.53 mmol) and (trifluoromethyl)trimethylsilane (0.772 mL, 5.34 mmol), the mixture was stirred and reacted at room temperature for 16 hours. Then, purification by preparative thin-layer chromatography (chloroform/methanol=100/1) was performed to give 2,2,2-trifluoro-1-(thiophen-3-yl)ethanol (Compound DO) (258 mg, yield: 53%).

ESIMS m/z: 181 $(M-H)^-$; $^1$H-NMR (270 MHz, $CDCl_3$, δ): 3.09 (q, J=5.3 Hz, 1H), 5.13 (m, 1H), 7.19 (d, J=5.3 Hz, 1H), 7.37 (dd, J=3.1, 5.1 Hz, 1H), 7.46 (d, J=3.0 Hz, 1H).

REFERENCE EXAMPLE 8-42

1-cyclohexyl-2,2,2-trifluoroethanol (Compound DP)

According to Reference Example 8-12, by use of cyclohexylcarbaldehyde (300 mg, 2.67 mmol) dissolved in tetrahydrofuran (6 mL), a 1 mol/L solution of tetrabutylammonium fluoride in tetrahydrofuran (0.534 mL, 0.534 mmol) and (trifluoromethyl)trimethylsilane (0.474 mL, 3.20 mmol), the mixture was stirred and reacted at room temperature for 1.5 hours. Then, purification by preparative thin-layer chromatography (hexane/ethyl acetate=10/1) was performed to give 1-cyclohexyl-2,2,2-trifluoroethanol (Compound DP) (181 mg, yield: 37%).

$^1$H-NMR (270 MHz, CDCl$_3$, δ): 1.13-1.35 (m, 4H), 1.70-1.77 (m, 6H), 1.90 (m, 1H), 2.11 (br s, 1H), 3.72 (m, 1H).

REFERENCE EXAMPLE 8-43

2,2,2-trifluoro-1-(1-methyl-1H-indol-2-yl)ethanol
(Compound DQ)

According to Reference Example 8-2, by use of 1-methyl-1H-indole-2-carbaldehyde (300 mg, 1.88 mmol) dissolved in N,N-dimethylformamide (4.5 mL), potassium carbonate (52 mg, 0.38 mmol) and (trifluoromethyl)trimethylsilane (0.416 mL, 2.82 mmol), the mixture was stirred and reacted at room temperature for 4 hours. Then, purification by preparative thin-layer chromatography (chloroform/methanol=100/1) was performed to give 2,2,2-trifluoro-1-(1-methyl-1H-indol-2-yl)ethanol (Compound DQ) (339 mg, yield: 79%).

ESIMS m/z: 228 (M+H)$^+$; $^1$H-NMR (300 MHz, CDCl$_3$, δ): 2.44 (d, J=7.3 Hz, 1H), 3.83 (s, 3H), 5.27 (m, 1H), 6.72 (s, 1H), 7.15 (ddd, J=1.1, 6.8, 7.9 Hz, 1H), 7.28 (m, 1H), 7.35 (dd, J=7.3, 8.4 Hz, 1H), 7.51 (d, J=8.1 Hz, 1H).

REFERENCE EXAMPLE 8-44

1-(benzofuran-2-yl)-2,2,2-trifluoroethanol
(Compound DR)

According to Reference Example 8-12, by use of benzofuran-2-carbaldehyde (300 mg, 2.05 mmol) dissolved in tetrahydrofuran (6 mL), a 1 mol/L solution of tetrabutylammonium fluoride in tetrahydrofuran (1.03 mL, 1.03 mmol) and (trifluoromethyl)trimethylsilane (0.516 mL, 3.49 mmol), the mixture was stirred and reacted at room temperature for 5 hours. Then, purification by preparative thin-layer chromatography (chloroform/methanol=100/1) was performed to give 1-(benzofuran-2-yl)-2,2,2-trifluoroethanol (Compound DR) (194 mg, yield: 44%).

ESIMS m/z: $^1$H-NMR (300 MHz, CDCl$_3$, δ): 2.92 (t, J=7.0 Hz, 1H), 5.21 (m, 1H), 6.92 (s, 1H), 7.28 (ddd, J=1.1, 7.3, 7.3 Hz, 1H), 7.36 (ddd, J=1.5, 7.3, 8.1 Hz, 1H), 7.52 (dd, J=0.7, 8.1 Hz, 1H), 7.61 (dd, J=0.7, 7.7 Hz, 1H).

REFERENCE EXAMPLE 8-45

1-(2,4-dimethylthiazol-5-yl)-2,2,2-trifluoroethanol
(Compound DS)

According to Reference Example 8-2, by use of 2,4-dimethylthiazole-5-carbaldehyde (300 mg, 2.12 mmol) dissolved in N,N-dimethylformamide (4 mL), potassium carbonate (59 mg, 0.42 mmol) and (trifluoromethyl)trimethylsilane (0.376 mL, 2.54 mmol), the mixture was stirred and reacted at room temperature for 1.5 hours. Then, purification by preparative thin-layer chromatography (chloroform/methanol=15/1) was performed to give 1-(2,4-dimethylthiazol-5-yl)-2,2,2-trifluoroethanol (Compound DS) (335 mg, yield: 75%).

ESIMS m/z: 212 (M+H)$^+$; $^1$H-NMR (270 MHz, CDCl$_3$, δ): 2.35 (s, 3H), 2.64 (s, 3H), 4.90 (m, 1H), 5.27 (m, 1H).

REFERENCE EXAMPLE 8-46

2,2,2-trifluoro-1-(4-methylthiazol-5-yl)ethanol
(Compound DT)

According to Reference Example 8-2, by use of 4-methylthiazole-5-carbaldehyde (300 mg, 2.36 mmol) dissolved in N,N-dimethylformamide (4 mL), potassium carbonate (65 mg, 0.47 mmol) and (trifluoromethyl)trimethylsilane (0.419 mL, 2.83 mmol), the mixture was stirred and reacted at room temperature for 2.2 hours. Then, purification by preparative thin-layer chromatography (chloroform/methanol=15/1) was performed to give 2,2,2-trifluoro-1-(4-methylthiazol-5-yl)ethanol (Compound DT) (393 mg, yield: 84%).

ESIMS m/z: 198 (M+H)$^+$; $^1$H-NMR (300 MHz, CDCl$_3$, δ): 2.44 (s, 3H), 5.28 (br s, 1H), 5.35 (m, 1H), 8.73 (s, 1H).

REFERENCE EXAMPLE 8-47

1-(1-ethyl-1H-imidazol-5-yl)-2,2,2-trifluoroethanol
(Compound DU)

Step 1

1H-Imidazole-5-carbaldehyde (300 mg, 3.12 mmol) was dissolved in N,N-dimethylformamide (4 mL). To this, potassium carbonate (862 mg, 6.24 mmol) and ethyl iodide (0.275 mL, 3.43 mmol) were added at room temperature and the mixture was stirred at the same temperature for 1.5 hours. After water was added to the reaction mixture, extraction with ethyl acetate was performed, followed by washing with brine and drying over anhydrous sodium sulfate. The solvent was evaporated off under reduced pressure, and the residue was purified by preparative thin-layer chromatography (chloroform/methanol=20/1) to give 1-ethyl-1H-imidazole-5-carbaldehyde (115 mg, yield: 30%) and 1-ethyl-1H-imidazole-4-carbaldehyde (36 mg, yield: 9%). 1-ethyl-1H-imidazole-5-carbaldehyde ESIMS m/z: 125 (M+H)$^-$; $^1$H-NMR (270 MHz, CDCl$_3$, δ): 1.45 (t, J=7.3 Hz, 3H), 4.36 (q, J=7.3 Hz, 2H), 7.70 (s, 1H), 7.81 (d, J=0.7 Hz, 1H), 9.76 (d, J=1.0 Hz, 1H).

1-ethyl-1H-imidazole-4-carbaldehyde

ESIMS m/z: 125 (M+H)$^+$; $^1$H-NMR (270 MHz, CDCl$_3$, δ): 1.52 (t, J=7.3 Hz, 3H), 4.07 (q, J=7.3 Hz, 2H), 7.58 (s, 1H), 7.66 (s, 1H), 9.87 (s, 1H).

Step 2

According to Reference Example 8-2, by use of 1-ethyl-1H-imidazole-5-carbaldehyde (115 mg, 0.926 mmol) dissolved in N,N-dimethylformamide (2.3 mL), potassium carbonate (26 mg, 0.19 mmol) and (trifluoromethyl)trimethylsilane (0.300 mL, 2.04 mmol), the mixture was stirred and reacted at a temperature of room temperature to 50° C. for 6.8 hours. Then, purification by preparative thin-layer chromatography (chloroform/methanol=10/1) was performed to give 1-(1-ethyl-1H-imidazol-5-yl)-2,2,2-trifluoroethanol (Compound DU) (84.7 mg, yield: 47%).

ESIMS m/z: 195 (M+H)$^+$; $^1$H-NMR (270 MHz, CDCl$_3$, δ): 1.46 (t, J=7.3 Hz, 3H), 4.08 (m, 2H), 5.02 (q, J=6.9 Hz, 1H), 6.84 (s, 1H), 7.44 (s, 1H).

REFERENCE EXAMPLE 8-48

1-(2-chlorothiazol-5-yl)-2,2,2-trifluoroethanol (Compound DV)

According to Reference Example 8-2, by use of 2-chlorothiazole-5-carbaldehyde (300 mg, 2.03 mmol) dissolved in N,N-dimethylformamide (4 mL), potassium carbonate (56 mg, 0.41 mmol) and (trifluoromethyl)trimethylsilane (0.360 mL, 2.44 mmol), the mixture was stirred and reacted at room temperature for 1.3 hours. Then, purification by preparative thin-layer chromatography (chloroform/methanol=15/1) was performed to give 1-(2-chlorothiazol-5-yl)-2,2,2-trifluoroethanol (Compound DV) (382 mg, yield: 86%).

ESIMS m/z: 218, 216 (M−H)$^-$; $^1$H-NMR (300 MHz, CDCl$_3$, δ): 5.00 (m, 1H), 5.28 (m, 1H), 7.59 (s, 1H).

REFERENCE EXAMPLE 8-49

1-[1-(cyclopropylmethyl)-1H-imidazol-5-yl]-2,2,2-trifluoroethanol (Compound DW)

Step 1

According to Step 1 of Reference Example 8-47, by use of 1H-imidazole-5-carbaldehyde (400 mg, 4.16 mmol) dissolved in N,N-dimethylformamide (6 mL), potassium carbonate (1.15 g, 8.32 mmol) and (bromomethyl)cyclopropane (0.444 mL, 4.58 mmol), the mixture was stirred and reacted at room temperature for 2 hours. Then, purification by preparative thin-layer chromatography (chloroform/methanol=30/1, 50/1) was performed to give 1-(cyclopropylmethyl)-1H-imidazole-5-carbaldehyde (212 mg, yield: 34%) and 1-(cyclopropylmethyl)-1H-imidazole-4-carbaldehyde (209 mg, yield: 33%). 1-(cyclopropylmethyl)-1H-imidazole-5-carbaldehyde ESIMS m/z: 151 (M+H)$^+$; $^1$H-NMR (270 MHz, CDCl$_3$, δ): 0.38 (m, 2H), 0.65 (m, 2H), 1.28 (m, 1H), 4.17 (d, J=7.3 Hz, 2H), 7.80 (s, 1H), 7.81 (s, 1H), 9.77 (s, 1H).

1-(cyclopropylmethyl)-1H-imidazole-4-carbaldehyde

ESIMS m/z: 151 (M+H)$^+$; $^1$H-NMR (270 MHz, CDCl$_3$, δ): 0.41 (m, 2H), 0.75 (m, 2H), 1.22 (m, 1H), 3.87 (d, J=7.3 Hz, 2H), 7.63 (s, 1H), 7.75 (s, 1H), 9.88 (s, 1H).

Step 2

According to Reference Example 8-2, by use of 1-(cyclopropylmethyl)-1H-imidazole-5-carbaldehyde (212 mg, 1.41 mmol) dissolved in N,N-dimethylformamide (4.2 mL), potassium carbonate (39 mg, 0.28 mmol) and (trifluoromethyl)trimethylsilane (0.626 mL, 4.23 mmol), the mixture was stirred and reacted at room temperature for 2 hours. Then, purification by preparative thin-layer chromatography (chloroform/methanol=12/1) was performed to give 1-[1-(cyclopropylmethyl)-1H-imidazol-5-yl]-2,2,2-trifluoroethanol (Compound DW) (206 mg, yield: 66%).

ESIMS m/z: 221 (M+H)$^+$; $^1$H-NMR (270 MHz, CDCl$_3$, δ): 0.36 (m, 2H), 0.70 (m, 2H), 1.23 (m, 1H), 3.84 (dd, J=7.1, 14.4 Hz, 1H), 3.91 (dd, J=7.1, 14.4 Hz, 1H), 5.05 (q, J=6.9 Hz, 1H), 6.83 (s, 1H), 7.57 (s, 1H).

REFERENCE EXAMPLE 8-50

1-(1-(cyclopropylmethyl)-1H-imidazol-4-yl)-2,2,2-trifluoroethanol (Compound DX)

According to Reference Example 8-2, by use of 1-(cyclopropylmethyl)-1H-imidazole-4-carbaldehyde (133 mg, 0.886 mmol) obtained in Step 1 of Reference Example 8-49 and dissolved in N,N-dimethylformamide (2.7 mL), potassium carbonate (24 mg, 0.18 mmol) and (trifluoromethyl)trimethylsilane (0.196 mL, 1.33 mmol), the mixture was stirred and reacted at room temperature for 2 hours. Then, purification by preparative thin-layer chromatography (chloroform/methanol=15/1) was performed to give 1-(1-(cyclopropylmethyl)-1H-imidazol-4-yl)-2,2,2-trifluoroethanol (Compound DX) (85.2 mg, yield: 44%).

ESIMS m/z: 221 (M+H)$^+$; $^1$H-NMR (270 MHz, CDCl$_3$, δ): 0.37 (m, 2H), 0.71 (m, 2H), 1.20 (m, 1H), 3.79 (d, J=6.9 Hz, 2H), 5.03 (q, J=6.9 Hz, 1H), 5.27 (br s, 1H), 7.07 (s, 1H), 7.54 (s, 1H).

REFERENCE EXAMPLE 8-51

2,2,2-trifluoro-1-(2-morpholinothiazol-5-yl)ethanol (Compound DY)

Step 1

2-Chlorothiazole-5-carbaldehyde (200 mg, 1.36 mmol) was dissolved in acetonitrile (4 mL). To this, potassium carbonate (376 mg, 2.72 mmol) and morpholine (0.237 mL, 2.72 mmol) were added at room temperature and the mixture was stirred at the same temperature for 23.5 hours. After water was added to the reaction mixture, extraction with ethyl acetate was performed, followed by washing with brine and drying over anhydrous sodium sulfate. The solvent was evaporated off under reduced pressure, and the residue was purified by preparative thin-layer chromatography (chloroform/methanol=15/1) to give 2-morpholinothiazole-5-carbaldehyde (179 mg, yield: 66%).

ESIMS m/z: 199 (M+H)$^+$; $^1$H-NMR (270 MHz, CDCl$_3$, δ): 3.64 (m, 4H), 3.83 (m, 4H), 7.87 (s, 1H), 9.72 (s, 1H).

Step 2

According to Reference Example 8-2, by use of 2-morpholinothiazole-5-carbaldehyde (177 mg, 0.893 mmol) dissolved in N,N-dimethylformamide (5.3 mL), potassium carbonate (25 mg, 0.18 mmol) and (trifluoromethyl)trimethylsilane (0.198 mL, 1.34 mmol), the mixture was stirred and reacted at room temperature for 2.3 hours. Then, purification by preparative thin-layer chromatography (chloroform/methanol=15/1) was performed to give 2,2,2-trifluoro-1-(2-morpholinothiazol-5-yl)ethanol (Compound DY) (156 mg, yield: 65%).

ESIMS m/z: 269 (M+$^1$H-NMR (270 MHz, CDCl$_3$, δ): 3.46 (m, 4H), 3.80 (m, 4H), 4.90 (m, 1H), 5.15 (m, 1H), 7.19 (s, 1H).

REFERENCE EXAMPLE 8-52

1-(1,2-dimethyl-1H-imidazol-5-yl)-2,2,2-trifluoroethanol (Compound DZ)

Step 1

According to Step 1 of Reference Example 8-47, by use of 2-methyl-1H-imidazole-5-carbaldehyde (500 mg, 4.54 mmol) dissolved in N,N-dimethylformamide (7.5 mL), potassium carbonate (1.25 g, 9.08 mmol) and methyl iodide (0.311 mL, 4.99 mmol), the mixture was stirred and reacted at room temperature for 3 hours. Then, purification by preparative thin-layer chromatography (chloroform/methanol=20/1) was performed to give 1,2-dimethyl-1H-imidazole-5-carbaldehyde (125 mg, yield: 22%) and 1,2-dimethyl-1H-imidazole-4-carbaldehyde (12.7 mg, yield: 2%).

1,2-dimethyl-1H-imidazole-4-carbaldehyde

ESIMS m/z: 125 (M+H)$^+$; $^1$H-NMR (270 MHz, CDCl$_3$, δ): 2.45 (s, 3H), 3.67 (s, 3H), 7.54 (s, 1H), 9.79 (s, 1H).

1,2-dimethyl-1H-imidazole-5-carbaldehyde

ESIMS m/z: 125 (M+H)$^+$; $^1$H-NMR (270 MHz, CDCl$_3$, δ): 2.45 (s, 3H), 3.88 (s, 3H), 7.67 (s, 1H), 9.65 (s, 1H).

Step 2

According to Reference Example 8-2, by use of 1,2-dimethyl-1H-imidazole-5-carbaldehyde (125 mg, 1.01 mmol) dissolved in N,N-dimethylformamide (2.5 mL), potassium carbonate (28 mg, 0.20 mmol) and (trifluoromethyl)trimethylsilane (0.358 mL, 2.42 mmol), the mixture was stirred and reacted at a temperature of room temperature to 50° C. for 2.8 hours. Then, purification by preparative thin-layer chromatography (chloroform/methanol=15/1) was performed to give 1-(1,2-dimethyl-1H-imidazol-5-yl)-2,2,2-trifluoroethanol (Compound DZ) (115 mg, yield: 59%).

ESIMS m/z: 195 (M+H)$^+$; $^1$H-NMR (270 MHz, CDCl$_3$, δ): 2.36 (s, 3H), 3.61 (s, 3H), 5.00 (q, J=7.0 Hz, 1H), 6.93 (s, 1H).

REFERENCE EXAMPLE 8-53

2,2,2-trifluoro-1-(tetrahydro-2H-pyran-4-yl)ethanol (Compound EA)

According to Reference Example 8-12, by use of tetrahydro-2H-pyran-4-carbaldehyde (300 mg, 2.63 mmol) dissolved in tetrahydrofuran (6 mL), a 1 mol/L solution of tetrabutylammonium fluoride in tetrahydrofuran (0.526 mL, 0.526 mmol) and (trifluoromethyl)trimethylsilane (0.466 mL, 3.16 mmol), the mixture was stirred and reacted at room temperature for 1.7 hours. Then, purification by preparative thin-layer chromatography (hexane/ethyl acetate=4/1) was performed to give 2,2,2-trifluoro-1-(tetrahydro-2H-pyran-4-yl)ethanol (Compound EA) (228 mg, yield: 47%).

$^1$H-NMR (270 MHz, CDCl$_3$, δ): 1.58-1.87 (m, 4H), 2.51-2.59 (m, 1H), 3.41-3.50 (m, 2H), 3.74 (d, J=7.3 Hz, 1H), 3.96-4.02 (m, 2H).

REFERENCE EXAMPLE 8-54

1-cyclopropyl-2,2,2-trifluoroethanol (Compound EB)

According to Reference Example 8-12, by use of cyclopropanecarbaldehyde (300 mg, 4.28 mmol) dissolved in tetrahydrofuran (6 mL), a 1 mol/L solution of tetrabutylammonium fluoride in tetrahydrofuran (0.856 mL, 0.856 mmol) and (trifluoromethyl)trimethylsilane (0.759 mL, 5.14 mmol), the mixture was stirred and reacted at room temperature for 1.7 hours. Then, purification by extraction gave 1-cyclopropyl-2,2,2-trifluoroethanol (Compound EB) (161 mg, yield: 27%).

$^1$H-NMR (270 MHz, CDCl$_3$, δ): 0.48 (m, 2H), 0.67 (m, 2H), 1.11 (m, 1H), 2.36 (br s, 1H), 3.30 (m, 1H).

REFERENCE EXAMPLE 8-55

2,2,2-trifluoro-1-(4-methyltetrahydro-2H-pyran-4-yl)ethanol (Compound EC)

Step 1

Oxalyl chloride (0.419 mL, 4.80 mmol) was dissolved in dichloromethane (7.5 mL). To this, dimethyl sulfoxide (0.409 mL, 5.76 mmol) was added dropwise under a nitrogen atmosphere at −78° C. and the mixture was stirred for 15 minutes. To this, a dichloromethane solution (2.5 mL) of (4-methyltetrahydro-2H-pyran-4-yl)methanol (250 mg, 1.92 mmol) synthesized according to the method described in WO 08/029,825 was added at the same temperature and the mixture was stirred for 1 hour. To this, triethylamine (1.34 mL, 9.60 mmol) was added and the mixture was stirred at a temperature of −78° C. to room temperature for 1.2 hours. After water was added to the reaction mixture, extraction with ethyl acetate was performed, followed by washing with brine and drying over anhydrous sodium sulfate. The solvent was evaporated off under reduced pressure, and the residue was purified by preparative thin-layer chromatography (hexane/ethyl acetate=1/1) to give 4-methyltetrahydro-2H-pyran-4-carbaldehyde (173 mg, yield: 70%).

$^1$H-NMR (270 MHz, CDCl$_3$, δ): 1.11 (s, 3H), 1.46-1.56 (m, 2H), 1.90-2.04 (m, 2H), 3.51 (ddd, J=3.0, 9.3, 12.1 Hz, 2H), 3.78 (ddd, J=4.6, 4.6, 11.9 Hz, 2H), 9.48 (s, 1H).

Step 2

According to Reference Example 8-12, by use of 4-methyltetrahydro-2H-pyran-4-carbaldehyde (165 mg, 1.29 mmol) dissolved in tetrahydrofuran (5 mL), a 1 mol/L solution of tetrabutylammonium fluoride in tetrahydrofuran (0.258 mL, 0.258 mmol) and (trifluoromethyl)trimethylsilane (0.229 mL, 1.55 mmol), the mixture was stirred and reacted at room temperature for 1.7 hours. Then, purification by extraction gave 2,2,2-trifluoro-1-(4-methyltetrahydro-2H-pyran-4-yl)ethanol (Compound EC) (119 mg, yield: 47%).

$^1$H-NMR (270 MHz, CDCl$_3$, δ): 1.30 (s, 3H), 1.53 (ddd, J=4.2, 10.3, 14.1 Hz, 2H), 2.08 (br d, J=13.9 Hz, 2H), 3.55 (ddd, J=2.4, 9.9, 12.1 Hz, 2H), 3.68-3.85 (m, 3H).

REFERENCE EXAMPLE 8-56

N,N-diethyl-2-hydroxy-2-phenylacetamide (Compound ED)

2-Hydroxy-2-phenylacetic acid (500 mg, 3.29 mmol) was dissolved in dichloromethane (7.5 mL). To this, pyridine (0.532 mL, 6.58 mmol), DMAP (40 mg, 0.33 mmol) and trimethylsilyl chloride (0.835 mL, 6.58 mmol) were added at room temperature and the mixture was stirred for 7.8 hours. After the reaction mixture was cooled to 0° C., N,N-dimethylformamide (0.050 mL) and oxalyl chloride (0.301 mL, 3.45 mmol) were added thereto, and the mixture was stirred at a temperature of 0° C. to room temperature for 1 hour. After the reaction mixture was cooled to 0° C. again, a pyridine solution (0.878 mL) of diethylamine (0.374 mL, 3.62 mmol) was added thereto, and the mixture was stirred at a temperature of 0° C. to room temperature for 2 hours. Then, a methanol solution (5 mL) of citric acid (695 mg, 3.62 mmol) was added to the reaction mixture, and the mixture was stirred at room temperature for 12 hours. After addition of ethyl acetate, the reaction mixture was filtered. One mol/L hydrochloric acid was added to the filtrate, and extraction with ethyl acetate was performed, followed by washing with saturated sodium carbonate and brine and drying over anhydrous sodium sulfate. The solvent was evaporated off under reduced pressure, and thereby N,N-diethyl-2-hydroxy-2-phenylacetamide (Compound ED) (606 mg, yield: 89%) was obtained.

ESIMS m/z: 208 (M+H)$^+$; $^1$H-NMR (270 MHz, CDCl$_3$, δ): 0.80 (t, J=7.1 Hz, 3H), 1.14 (t, J=7.1 Hz, 3H), 3.02-3.21 (m, 2H), 3.29-3.55 (m, 2H), 4.86 (br s, 1H), 5.15 (s, 1H), 7.28-7.39 (m, 5H).

REFERENCE EXAMPLE 8-57

5-(hydroxymethyl)morpholin-3-one (Compound EE)

Step 1

2-Amino-1,3-propanediol (5.24 g, 57.5 mmol) was dissolved in a mixed solvent (220 mL) of acetonitrile/methanol (6/1). To this, triethylamine (9.60 mL, 69.6 mmol) and chloroacetyl chloride (5.10 mL, 63.3 mmol) were successively added under ice-cooling, and the mixture was stirred at room temperature overnight. After completion of the reaction, the solvent was evaporated off under reduced pressure. The residue was purified by silica gel column chromatography (ethyl acetate/methanol=90/10) to give 2-chloro-N-(2-hydroxy-1-hydroxymethylethyl)acetamide (8.30 g, yield: 86%).

$^1$H-NMR (270 MHz, DMSO-$d_6$, δ): 7.87 (d, J=7.9 Hz, 1H), 4.68 (t, J=5.4 Hz, 2H), 4.07 (s, 2H), 3.79-3.65 (m, 1H), 3.42 (dd, J=6.1, 5.4 Hz, 4H).

Step 2

Sodium tert-butoxide (6.70 g, 59.7 mmol) was dissolved in tert-amyl alcohol (40 mL). To this, a tert-amyl alcohol solution (90 mL) of 2-chloro-N-(2-hydroxy-1-hydroxymethylethyl)acetamide (4.00 g, 23.9 mmol) was added dropwise at room temperature over 30 minutes, and the mixture was stirred at room temperature for 2 hours. To this, methanol (25 mL) and water (1.5 mL) were successively added and the mixture was further stirred at room temperature for 30 minutes. The solvent was evaporated off under reduced pressure, and the residue was purified by silica gel column chromatography (ethyl acetate/methanol=80/20) to give 5-(hydroxymethyl)morpholin-3-one (Compound EE) (2.00 g, yield: 64%).

$^1$H-NMR (270 MHz, DMSO-$d_6$, δ): 7.06 (br s, 1H), 3.98-3.97 (m, 2H), 3.88-3.72 (m, 2H), 3.65-3.57 (m, 2H), 3.54-3.47 (m, 1H).

REFERENCE EXAMPLE 8-58

N-ethyl-2-hydroxy-2-phenylacetamide (Compound EF)

According to Reference Example 8-56, 2-hydroxy-2-phenylacetic acid (500 mg, 3.29 mmol) was dissolved in dichloromethane (7.5 mL), and the solution was stirred with pyridine (0.532 mL, 6.58 mmol), DMAP (40 mg, 0.33 mmol), trimethylsilyl chloride (0.835 mL, 6.58 mmol), N,N-dimethylformamide (0.050 mL), oxalyl chloride (0.301 mL, 3.45 mmol), a solution containing a 2 mol/L tetrahydrofuran solution of ethylamine (1.81 mL, 3.62 mmol) and pyridine (0.878 mL), and a solution containing a methanol (5 mL) and citric acid (695 mg, 3.62 mmol). Thus, N-ethyl-2-hydroxy-2-phenylacetamide (Compound EF) (489 mg, yield: 83%) was obtained.

ESIMS m/z: 178 (M−H)$^−$; $^1$H-NMR (270 MHz, CDCl$_3$, δ): 1.11 (t, J=7.3 Hz, 3H), 3.24-3.36 (m, 2H), 3.72 (br s, 1H), 5.35 (s, 1H), 6.09 (br s, 1H), 7.35-7.40 (m, 5H).

REFERENCE EXAMPLE 8-59

1-(2-bromothiazol-5-yl)-2,2,2-trifluoroethanol (Compound EG)

According to Reference Example 8-2, by use of 2-bromothiazole-5-carbaldehyde (500 mg, 2.60 mmol) dissolved in N,N-dimethylformamide (7.5 mL), potassium carbonate (72 mg, 0.52 mmol) and (trifluoromethyl)trimethylsilane (0.461 mL, 3.12 mmol), the mixture was stirred and reacted at room temperature for 1.7 hours. Then, purification by preparative thin-layer chromatography (chloroform/methanol=40/1) was performed to give 1-(2-bromothiazol-5-yl)-2,2,2-trifluoroethanol (Compound EG) (265 mg, yield: 39%).

ESIMS m/z: 262, 260 (M−H)$^−$; $^1$H-NMR (270 MHz, CDCl$_3$, δ): 3.97 (br s, 1H), 5.31 (m, 1H), 7.62 (s, 1H).

REFERENCE EXAMPLE 8-60

2,2,2-trifluoro-1-(tetrahydro-2H-thiopyran-4-yl)ethanol (Compound EH)

According to Reference Example 8-12, by use of tetrahydro-2H-thiopyran-4-carbaldehyde (300 mg, 2.30 mmol) dissolved in tetrahydrofuran (6 mL), a 1 mol/L solution of tetrabutylammonium fluoride in tetrahydrofuran (0.460 mL, 0.460 mmol) and (trifluoromethyl)trimethylsilane (0.408 mL, 2.76 mmol), the mixture was stirred and reacted at room temperature for 2 hours. Then, purification by extraction gave 2,2,2-trifluoro-1-(tetrahydro-2H-thiopyran-4-yl)ethanol (Compound EH) (413 mg, yield: 90%).

$^1$H-NMR (270 MHz, CDCl$_3$, δ): 1.75-1.80 (m, 3H), 2.23-2.32 (m, 2H), 2.63-2.71 (m, 4H), 3.76 (m, 1H).

REFERENCE EXAMPLE 8-61

2,2,2-trifluoro-1-(2-phenylthiazol-5-yl)ethanol (Compound EI)

1-(2-Bromothiazol-5-yl)-2,2,2-trifluoroethanol (Compound EG) (93.1 mg, 0.355 mmol) obtained in Reference Example 8-59 was dissolved in acetonitrile (2.8 mL). To this, palladium acetate (8.0 mg, 0.036 mmol), tri(o-tolyl)phosphine (22 mg, 0.071 mmol), phenylboronic acid (130 mg, 1.07 mmol) and triethylamine (0.495 mL, 3.55 mmol) were added, and the mixture was stirred by use of a microwave reactor at 250 W at 100° C. for 15 minutes. To this, palladium acetate (4.0 mg, 0.018 mmol), tri(o-tolyl)phosphine (11 mg, 0.036 mmol), phenylboronic acid (52.0 mg, 0.426 mmol) and triethylamine (0.247 mL, 1.78 mmol) were further added, and the mixture was stirred by use of the microwave reactor at 250 W at 100° C. for 15 minutes. After water was added to the reaction mixture, extraction with ethyl acetate was performed, followed by washing with brine and drying over anhydrous sodium sulfate. The solvent was evaporated off under reduced pressure, and the residue was purified by preparative thin-layer chromatography (hexane/ethyl acetate=3/1) to give 2,2,2-trifluoro-1-(2-phenylthiazol-5-yl)ethanol (Compound EI) (43.2 mg, yield: 47%).

ESIMS m/z: 260 (M+H)$^+$; $^1$H-NMR (300 MHz, CDCl$_3$, δ): 4.70 (br s, 1H), 5.33 (m, 1H), 7.43-7.47 (m, 3H), 7.79 (s, 1H), 7.88-7.91 (m, 2H).

REFERENCE EXAMPLE 8-62

2,2,2-trifluoro-1-(tetrahydrofuran-3-yl)ethanol (Compound EJ)

According to Reference Example 8-12, by use of a 50 wt % aqueous tetrahydrofuran-3-carbaldehyde solution (1.00 g, 5.00 mmol) dissolved in tetrahydrofuran (15 mL), a 1 mol/L solution of tetrabutylammonium fluoride in tetrahydrofuran (1.00 mL, 1.00 mmol) and (trifluoromethyl)trimethylsilane (0.887 mL, 6.00 mmol), the mixture was stirred and reacted at room temperature for 1.8 hours. Then, purification by extraction gave 2,2,2-trifluoro-1-(tetrahydrofuran-3-yl) ethanol (Compound EJ) (266 mg, yield: 31%).

ESIMS m/z: 171 (M+H)⁺; ¹H-NMR (270 MHz, CDCl₃, δ): 2.08-2.23 (m, 2H), 3.06 (m, 1H), 3.73-3.94 (m, 4H), 4.11 (dd, J=4.6, 9.3 Hz, 1H).

REFERENCE EXAMPLE 8-63

2-methyl-2-(pyridin-3-yl)propan-1-ol (Compound EK)

Step 1

Ethyl 3-pyridylacetate (300 mg, 1.8 mmol) was dissolved in dimethylformamide (3 mL). To this, potassium tert-butoxide (610 mg, 5.4 mmol) and iodomethane (0.34 mL, 5.4 mmol) were added with cooling in an ice bath, and the mixture was stirred at the same temperature for 1 hour. After water was added to the reaction mixture, extraction with ethyl acetate was performed, followed by washing with brine and drying over anhydrous magnesium sulfate. The solvent was evaporated off under reduced pressure, and the residue was purified by silica gel column chromatography (hexane/ethyl acetate=1/0 to 1/1) to give ethyl 2-methyl-2-(pyridin-3-yl)propanoate (201 mg, yield: 58%).

ESIMS m/z: 194 (M+H)⁺; ¹H-NMR (270 MHz, CDCl₃, δ): 1.19 (t, J=7.2 Hz, 3H), 1.59 (s, 6H), 4.13 (q, J=7.2 Hz, 2H), 7.24-7.26 (m, 1H), 7.66 (dt, J=2.0, 7.9 Hz, 1H), 8.50 (dd, J=2.0, 4.8 Hz, 1H), 8.63 (d, J=2.0 Hz, 1H).

Step 2

Tetrahydrofuran (10 mL) was added to lithium aluminum hydride (75 mg, 2.0 mmol). To this, a solution prepared by dissolving, in tetrahydrofuran (5 mL), ethyl 2-methyl-2-(pyridin-3-yl)propanoate (200 mg, 1.0 mmol) obtained in Step 1 of Reference Example 8-63 was slowly added with cooling in an ice bath, and the mixture was stirred at the same temperature for 1 hour. To this, sodium sulfate decahydrate was added and the mixture was stirred at room temperature for 1 hour. After Celite-filtration, the solvent in the filtrate was evaporated off under reduced pressure. Thus, 2-methyl-2-(pyridin-3-yl)propan-1-ol (Compound EK) (154 mg, yield: 99%) was obtained.

ESIMS m/z: 152 (M+H)⁺; ¹H-NMR (270 MHz, CDCl₃, δ): 1.37 (s, 6H), 3.66 (s, 2H), 7.20-7.30 (m, 1H), 7.70 (dq, J=1.4, 8.1 Hz, 1H), 8.44 (dd, J=1.4, 4.8 Hz, 1H), 8.65 (d, J=1.4 Hz, 1H).

REFERENCE EXAMPLE 8-64

1,1,1-trifluoro-4-(pyridin-3-yl)butan-2-ol (Compound EL)

Step 1

3-Pyridinepropanol (300 mg, 2.2 mmol) was dissolved in dichloromethane (5 mL). To this, the Dess-Martin reagent (1.0 g) was added with cooling in an ice bath and the mixture was stirred at the same temperature for 2 hours and successively at room temperature for 3 hours. The solvent in the reaction mixture was evaporated off under reduced pressure, and the residue was purified by silica gel column chromatography (chloroform/methanol=1/0 to 10/1) to give 3-(pyridin-3-yl)propanal (180 mg, yield: 61%).

ESIMS m/z: 136 (M+H)⁺; ¹H-NMR (270 MHz, CDCl₃, δ): 2.83 (t, J=7.0 Hz, 2H), 2.98 (t, J=7.0 Hz, 2H), 7.21-7.33 (m, 1H), 7.58 (d, J=7.7 Hz, 1H), 8.43-8.55 (m, 2H), 9.83 (s, 1H).

Step 2

According to Reference Example 8-12, by use of 3-(pyridin-3-yl)propanal (180 mg, 1.3 mmol) obtained in Step 1 of Reference Example 8-64, (trifluoromethyl)trimethylsilane (0.24 mL, 1.6 mmol), tetrabutylammonium fluoride (a 1.0 mol/L solution in tetrahydrofuran, 0.27 mL, 0.27 mmol) and tetrahydrofuran (3.6 mL), the mixture was stirred and reacted at room temperature for 30 minutes. Then, purification by silica gel column chromatography (chloroform/methanol=1/0 to 10/1) was performed to give 1,1,1-trifluoro-4-(pyridin-3-yl)butan-2-ol (Compound EL) (83 mg, yield: 31%).

ESIMS m/z: 206 (M+H)⁺; ¹H-NMR (270 MHz, CDCl₃, ε): 1.85-2.14 (m, 2H), 2.91 (dd, J=6.1, 8.1 Hz, 2H), 3.66-3.82 (m, 1H), 5.32 (s, 1H), 7.26-7.33 (m, 1H), 7.60 (dt, J=1.8, 7.9 Hz, 1H), 8.41 (dd, J=1.8, 4.9 Hz, 1H), 8.48 (d, J=1.8 Hz, 1H).

REFERENCE EXAMPLE 8-65

2-methyl-3-(pyridin-3-yl)propan-1-ol (Compound EM)

Step 1

Sixty percent sodium hydride (in oil) (224 mg, 5.6 mmol) was suspended in tetrahydrofuran (5 mL). To this, triethyl 2-phosphonopropionate (1.2 mL, 5.6 mmol) was added under a nitrogen atmosphere with cooling in an ice bath and the mixture was stirred at the same temperature for 30 minutes. To this, 3-pyridinecarboxaldehyde (300 mg, 2.8 mmol) was added and the mixture was stirred at the same temperature for 1.5 hours. After water was added to the reaction mixture, extraction with ethyl acetate was performed, followed by washing with brine and drying over anhydrous magnesium sulfate. The solvent was evaporated off under reduced pressure, and the residue was purified by silica gel column chromatography (hexane/ethyl acetate=1/0 to 2/1) to give ethyl 2-methyl-3-(pyridin-3-yl)acrylate (480 mg, yield: 90%).

ESIMS m/z: 192 (M+H)⁺; ¹H-NMR (270 MHz, CDCl₃, δ): 1.36 (t, J=7.1 Hz, 3H), 2.12 (d, J=1.5 Hz, 3H), 4.29 (q, J=7.1 Hz, 2H), 7.33 (dd, J=4.9, 8.1 Hz, 1H), 7.63 (s, 1H), 7.71 (dt, J=1.9, 8.1 Hz, 1H), 8.55 (dd, J=1.9, 4.9 Hz, 1H), 8.65 (d, J=1.9 Hz, 1H).

Step 2

Ethyl 2-methyl-3-(pyridin-3-yl)acrylate (480 mg, 2.4 mmol) obtained in Step 1 of Reference Example 8-65 was dissolved in ethanol (5 mL). To this, 10% palladium carbon (92 mg) was added under an argon atmosphere, and the mixture was stirred under a hydrogen atmosphere at room temperature for 3 hours. The reaction mixture was filtered through Celite and the solvent in the filtrate was evaporated off under reduced pressure. Thus, ethyl 2-methyl-3-(pyridin-3-yl)propanoate (453 mg, yield: 98%) was obtained.

ESIMS m/z: 194 (M+H)⁺; ¹H-NMR (270 MHz, CDCl₃, δ): 1.12-1.24 (m, 6H), 2.64-2.79 (m, 2H), 2.93-3.06 (m, 1H), 4.09 (q, J=7.2 Hz, 2H), 7.15-7.26 (m, 1H), 7.45-7.53 (m, 1H), 8.40-8.50 (m, 2H).

Step 3

According to Step 2 of Reference Example 8-63, tetrahydrofuran (10 mL) and a solution prepared by dissolving, in tetrahydrofuran (5 mL), ethyl 2-methyl-3-(pyridin-3-yl)propanoate (200 mg, 1.0 mmol) obtained in Step 2 of Reference Example 8-65 were added to lithium aluminum hydride (75 mg, 2.0 mmol), and the mixture was stirred with cooling in an ice bath for 1 hour. Thus, 2-methyl-3-(pyridin-3-yl)propan-1-ol (Compound EM) (154 mg, yield: 99%) was obtained.

ESIMS m/z: 152 (M+H)⁺; ¹H-NMR (270 MHz, CDCl₃, δ): 0.92 (d, J=6.9 Hz, 3H), 1.86-2.02 (m, 1H), 2.42 (dd, J=8.2, 13.8 Hz, 1H), 2.81 (dd, J=5.9, 13.5 Hz, 1H), 3.52 (d, J=5.9 Hz, 2H), 7.22 (dd, J=5.1, 7.4 Hz, 1H), 7.50 (dt, J=1.6, 7.4 Hz, 1H), 8.45 (dd, J=1.6, 5.1 Hz, 2H).

REFERENCE EXAMPLE 8-66

3-(pyridin-3-yl)butan-1-ol (Compound EN)

Step 1
According to Step 1 of Reference Example 8-65, by use of 60% sodium hydride (in oil) (300 mg, 7.4 mmol), tetrahydrofuran (5 mL), triethyl phosphonoacetate (1.5 mL, 7.5 mmol) and 3-acetylpyridine (300 mg, 2.5 mmol), the mixture was stirred and reacted at room temperature for 30 minutes. Then, purification by silica gel column chromatography (hexane/ethyl acetate=1/0 to 1/1) was performed to give ethyl 3-(pyridin-3-yl)-2-butenoate (350 mg, yield: 74%).

ESIMS m/z: 192 (M+H)$^+$; $^1$H-NMR (270 MHz, CDCl$_3$, δ): 1.33 (t, J=7.1 Hz, 3H), 2.58 (d, J=1.2 Hz, 3H), 4.23 (q, J=7.1 Hz, 2H), 6.15 (q, J=1.2 Hz, 1H), 7.29-7.34 (m, 1H), 7.76 (dt, J=2.0, 8.1 Hz, 1H), 8.60 (dd, J=2.0, 4.9 Hz, 1H), 8.73 (d, J=2.0 Hz, 1H).

Step 2
According to Step 2 of Reference Example 8-65, by use of ethyl 3-(pyridin-3-yl)-2-butenoate (350 mg, 1.8 mmol) obtained in Step 1 of Reference Example 8-66, ethanol (4 mL) and 10% palladium carbon (70 mg), the mixture was stirred and reacted under a hydrogen atmosphere at room temperature for 2 hours. Thus, ethyl 3-(pyridin-3-yl)butanoate (339 mg, yield: 96%) was obtained.

ESIMS m/z: 194 (M+H)$^+$; $^1$H-NMR (270 MHz, CDCl$_3$, δ): 1.18 (t, J=7.2 Hz, 3H), 1.33 (d, J=6.9 Hz, 3H), 2.60 (d, J=6.9 Hz, 2H), 3.31 (td, J=7.2, 14.5 Hz, 1H), 4.08 (q, J=7.2 Hz, 2H), 7.19-7.26 (m, 1H), 7.54 (td, J=2.6, 5.1 Hz, 1H), 8.47 (dd, J=1.6, 5.1 Hz, 1H), 8.51 (d, J=1.6 Hz, 1H).

Step 3
According to Step 3 of Reference Example 8-65, by use of lithium aluminum hydride (75 mg, 2.0 mmol), tetrahydrofuran (10 mL) and a solution prepared by dissolving, in tetrahydrofuran (5 mL), ethyl 3-(pyridin-3-yl)butanoate (339 mg, 2.0 mmol) obtained in Step 2 of Reference Example 8-66, the mixture was stirred and reacted under cooling in an ice bath for 1 hour. Thus, 3-(pyridin-3-yl)butan-1-ol (Compound EN) (153 mg, yield: 99%) was obtained.

ESIMS m/z: 152 (M+H)$^+$; $^1$H-NMR (270 MHz, CDCl$_3$, δ): 1.31 (d, J=7.0 Hz, 3H), 1.78-1.98 (m, 2H), 2.96 (td, J=7.0, 14.3 Hz, 1H), 3.45-3.67 (m, 2H), 7.19-7.28 (m, 1H), 7.53 (d, J=8.1 Hz, 1H), 8.41-8.54 (m, 2H).

REFERENCE EXAMPLE 8-67

2-hydroxy-3-methyl-1-morpholinobutan-1-one (Compound EO)

According to Reference Example 8-56, 2-hydroxy-3-methylbutyric acid (1.00 g, 8.47 mmol) was dissolved in dichloromethane (15 mL), and the solution was stirred with pyridine (1.37 mL, 16.9 mmol) DMAP (103 mg, 0.847 mmol), trimethylsilyl chloride (2.15 mL, 16.9 mmol), N,N-dimethylformamide (0.100 mL), oxalyl chloride (0.776 mL, 8.89 mmol), a pyridine solution (2.26 mL) of morpholine (0.813 mL, 9.32 mmol) and a methanol solution (10 mL) of citric acid (1.79 g, 9.32 mmol). Thus, 2-hydroxy-3-methyl-1-morpholinobutan-1-one (Compound EO) (933 mg, yield: 59%) was obtained.

ESIMS m/z: 188 (M+H)$^+$; $^1$H-NMR (270 MHz, CDCl$_3$, δ): 0.82 (d, J=6.6 Hz, 3H), 1.07 (d, J=6.6 Hz, 3H), 1.82 (m, 1H), 3.43-3.69 (m, 9H), 4.22 (br s, 1H).

REFERENCE EXAMPLE 8-68

Dipyridin-3-ylmethanol (Compound EP)

A 1.55 mol/L solution of n-butyllithium in hexane (2.24 mL, 3.48 mmol) was added to toluene (6 mL) and the mixture was cooled to −60° C. under a nitrogen atmosphere. To this, a toluene solution (2 mL) of 3-bromopyridine (500 mg, 3.16 mmol) was added dropwise and the mixture was stirred for 30 minutes. Tetrahydrofuran (2 mL) and nicotinaldehyde (0.358 mL, 3.79 mmol) were added to the reaction mixture and the mixture was stirred at a temperature of −60° C. to −15° C. for 30 minutes. After 4 mol/L hydrochloric acid (2.37 mL, 9.48 mmol) was added to the reaction mixture, extraction with ethyl acetate was performed, followed by washing with saturated sodium bicarbonate and brine, and drying over anhydrous sodium sulfate. The solvent was evaporated off under reduced pressure, and the residue was purified by preparative thin-layer chromatography (chloroform/methanol=12/1) to give dipyridin-3-ylmethanol (Compound EP) (235 mg, yield: 40%).

ESIMS m/z: 187 (M+H)$^+$; $^1$H-NMR (270 MHz, CDCl$_3$, δ): 5.10 (br s, 1H), 5.89 (s, 1H), 7.27 (dd, J=5.0, 7.6 Hz, 2H), 7.69 (ddd, J=1.7, 2.0, 7.9 Hz, 2H), 8.45 (dd, J=1.7, 5.0 Hz, 2H), 8.54 (d, J=2.0 Hz, 2H).

REFERENCE EXAMPLE 8-69

Pyridin-3-yl(thiazol-5-yl)methanol (Compound EQ)

According to Reference Example 8-68, a 1.55 mol/L solution of n-butyllithium in hexane (2.24 mL, 3.48 mmol) was added to toluene (6 mL), and the mixture was stirred with a toluene solution (2 mL) of 3-bromopyridine (500 mg, 3.16 mmol), tetrahydrofuran (2 mL), thiazole-5-carbaldehyde (0.329 mL, 3.79 mmol) and 4 mol/L hydrochloric acid (2.37 mL, 9.48 mmol). Then, purification by preparative thin-layer chromatography (chloroform/methanol=12/1) was performed to give pyridin-3-yl(thiazol-5-yl)methanol (Compound EQ) (271 mg, yield: 45%).

ESIMS m/z: 193 (M+H)$^+$; $^1$H-NMR (300 MHz, CDCl$_3$, δ): 5.05 (br s, 1H), 6.16 (s, 1H), 7.31 (dd, J=4.8, 7.9 Hz, 1H), 7.64 (s, 1H), 7.78 (ddd, J=1.8, 1.8, 7.7 Hz, 1H), 8.47 (dd, J=1.7, 4.9 Hz, 1H), 8.56 (d, J=2.2 Hz, 1H), 8.74 (s, 1H).

REFERENCE EXAMPLE 8-70

1-{4-[(dimethylamino)methyl]phenyl}-2,2,2-trifluoroethanol (Compound ER)

Step 1
According to Reference Example 8-12, by use of 4-(diethoxymethyl)benzaldehyde (400 mg, 1.92 mmol), (trifluoromethyl)trimethylsilane (0.34 mL, 2.3 mmol), tetrabutylammonium fluoride (a 1.0 mol/L solution in tetrahydrofuran, 0.19 mL, 0.19 mmol) and tetrahydrofuran (8 mL), the mixture was stirred and reacted at room temperature for 30 minutes. Then, purification by silica gel column chromatography (chloroform/methanol=1/0 to 3/1) was performed to give 4-(2,2,2-trifluoro-1-hydroxyethyl)benzaldehyde (300 mg, yield: 77%).

ESIMS m/z: 205 (M+H)$^+$; $^1$H-NMR (270 MHz, CDCl$_3$, δ): 5.06-5.22 (m, 1H), 7.68 (d, J=7.9 Hz, 2H), 7.94 (d, J=7.9 Hz, 2H), 10.06 (s, 1H).

Step 2
4-(2,2,2-Trifluoro-1-hydroxyethyl)benzaldehyde (295 mg, 1.4 mmol) obtained in Step 1 of Reference Example 8-70 was dissolved in acetonitrile (15 mL). To this, dimethylamine (a 1.0 mol/L solution in tetrahydrofuran, 7.2 mL, 14 mmol) and acetic acid (0.83 mL) were added and the mixture was stirred at room temperature for 30 minutes. To this, sodium triacetoxyborohydride (918 mg, 4.3 mmol) was added and the mixture was stirred at room temperature for 4 hours. Then, an aqueous sodium bicarbonate solution was added to the reaction mixture, and extraction with ethyl acetate was performed, followed by washing with brine and drying over anhydrous magnesium sulfate. The solvent was evaporated off under reduced pressure, and the residue was subjected to slurry purification using a mixed solvent of diisopropyl ether and hexane. Further, purification by silica gel column chromatography (hexane/ethyl acetate=1/0 to 2/1) was performed to give 1-{4-[(dimethylamino)methyl]phenyl}-2,2,2-trifluoroethanol (Compound ER) (284 mg, yield: 85%).

ESIMS m/z: 234 (M+H)$^+$; $^1$H-NMR (270 MHz, CDCl$_3$, δ): 2.21 (s, 6H), 3.42 (d, J=2.6 Hz, 2H), 4.96 (q, J=6.7 Hz, 1H), 7.27-7.43 (m, 4H).

REFERENCE EXAMPLE 8-71

2-cyano-5-(2,2,2-trifluoro-1-hydroxyethyl)pyridine (Compound ES)

Step 1

6 Bromo-3-pyridinecarboxaldehyde (1.03 g, 5.54 mmol), ethylene glycol (370 μL, 6.65 mol) and Amberlyst 15 (200 mg) were suspended in toluene (100 mL). The mixture was heated to reflux under a nitrogen atmosphere for 12 hours, during which produced water was removed by use of a Dean-Stark trap. The reaction mixture was filtered and the mother liquid was concentrated. The residue was purified by column chromatography (hexane/ethyl acetate=7/3) to give 2-bromo-5-(1,3-dioxolan-2-yl)pyridine (895 mg, yield: 70%).

$^1$H-NMR (300 MHZ, CDCl$_3$, δ): 4.02-4.14 (m, 4H), 5.82 (s, 1H), 7.51 (d, J=8.1 Hz, 1H), 7.65 (dd, J=2.6, 8.1 Hz, 1H), 8.47 (s, d, J=2.6 Hz, 1H).

Step 2

2-Bromo-5-(1,3-dioxolan-2-yl)pyridine (895 mg, 3.89 mmol), zinc cyanide (1.14 g, 5.83 mmol) and tetrakis(triphenylphosphine)palladium (899 mg, 0.778 mmol) were dissolved in N,N-dimethylformaldehyde (30 ml) and the mixture was heated to reflux at 80° C. under a nitrogen atmosphere for 12 hours. The reaction mixture was concentrated, water was added thereto, and extraction with ethyl acetate was performed, followed by washing with brine and drying over anhydrous sodium sulfate. The solvent was evaporated off under reduced pressure, and the residue was purified by column chromatography (hexane/ethyl acetate=7/3) to give 2-cyano-5-(1,3-dioxolan-2-yl)pyridine (506 mg, yield: 74%).

$^1$H-NMR (300 MHZ, CDCl$_3$, δ): 4.05-4.15 (m, 4H), 5.91 (s, 1H), 7.72 (d, J=8.0 Hz, 1H), 7.94 (dd, J=2.0, 8.0 Hz, 1H), 8.82 (d, J=2.0 Hz, 1H).

Step 3

2-Cyano-5-(1,3-dioxolan-2-yl)pyridine (478 mg, 2.71 mmol) was dissolved in tetrahydrofuran (5.0 mL). To this, 1N hydrochloric acid (5.0 mL) was added under a nitrogen atmosphere at room temperature and the mixture was stirred at the same temperature for 16 hours and successively at 50° C. for 13 hours. Then, the reaction mixture was neutralized with a saturated aqueous sodium bicarbonate solution, and extraction with ethyl acetate was performed, followed by washing with brine and drying over anhydrous sodium sulfate. The solvent was evaporated off under reduced pressure, and thereby 6-cyano-3-pyridinecarboxaldehyde (364 mg, yield: 100%) was obtained.

$^1$H-NMR (300 MHZ, CDCl$_3$, δ): 7.90 (d, J=8.1 Hz, 1H), 8.33 (dd, J=1.8, 8.1 Hz, 1H), 9.19 (d, J=1.8 Hz, 1H), 10.21 (s, 1H).

Step 4

According to Reference Example 8-12, by use of 6-cyano-3-pyridinecarboxaldehyde (364 mg, 2.76 mmol), (trifluoromethyl)trimethylsilane (490 μL, 3.31 mmol), tetrabutylammonium fluoride (a 1.0 mol/L solution in tetrahydrofuran, 276 μL, 0.276 mmol) and tetrahydrofuran (7.0 mL), the mixture was stirred and reacted at room temperature for 5 hours. Then, purification by column chromatography (hexane/ethyl acetate=7/3) was performed to give 2-cyano-5-(2,2,2-trifluoro-1-hydroxyethyl)pyridine (Compound ES) (455 mg, yield: 82%).

$^1$H-NMR (270 MHZ, DMSO-d$_6$, δ): 5.46-5.56 (m, 1H), 8.09-8.19 (m, 2H), 8.86 (s, 1H).

REFERENCE EXAMPLE 8-72

1-methyl-5-(2,2,2-trifluoro-1-hydroxyethyl)-2(1H)-pyridone (Compound ET)

Step 1

3-Pyridinecarboxaldehyde (3.00 mL, 31.8 mmol), ethylene glycol (2.66 mL, 47.7 mmol) and p-toluenesulfonic acid (302 mg, 1.59 mmol) were suspended in toluene (100 mL). The mixture was heated to reflux under a nitrogen atmosphere for 2 hours, during which produced water was removed by use of a Dean-Stark trap. Then, a saturated aqueous potassium carbonate solution was added to the reaction mixture, and extraction with ethyl acetate was performed, followed by washing with brine and drying over anhydrous sodium sulfate. The solvent was evaporated off under reduced pressure, and the residue was purified by column chromatography (hexane/ethyl acetate=1/1) to give 3-(1,3-dioxolan-2-yl)pyridine (4.27 g, yield: 89%).

$^1$H-NMR (300 MHZ, CDCl$_3$, δ): 4.02-4.18 (m, 4H), 5.86 (s, 1H), 7.32 (ddd, J=0.7, 4.8, 8.1 Hz, 1H), 7.80 (ddd, J=0.7, 1.8, 8.1 Hz, 1H), 8.63 (dd, J=1.8, 4.8 Hz, 1H), 8.72 (d, J=1.8 Hz, 1H).

Step 2

3-(1,3-Dioxolan-2-yl)pyridine (1.00 g, 6.62 mmol) was dissolved in dichloromethane (20.0 mL). To this, iodomethane (494 μL, 7.94 mmol) was added under a nitrogen atmosphere at room temperature and the mixture was stirred at room temperature for 72 hours. The reaction mixture was concentrated, and the residue was subjected to slurry purification using diisopropyl ether, to give 3-(1,3-dioxolan-2-yl)-1-pyridinium iodide (1.85 g, yield: 96%).

$^1$H-NMR (300 MHZ, DMSO-d$_6$, δ): 4.02-4.13 (m, 4H), 4.38 (s, 3H), 6.07 (s, 1H), 8.14 (dd, J=6.6, 7.7 Hz, 1H), 8.61 (d, J=7.7 Hz, 1H), 9.01 (d, J=6.6 Hz, 1H), 9.10 (s, 1H).

Step 3

3-(1,3-Dioxolan-2-yl)-1-pyridinium iodide (1.85 g, 6.31 mmol) was dissolved in water (40 mL). To this, a solution of potassium ferricyanide (22.9 g, 69.4 mmol) in water (50 mL) was added dropwise under a nitrogen atmosphere at 0° C. over 1 hour. To this, a solution of potassium hydroxide (55.9 g, 100 mmol) in water (9.5 mL) was added dropwise at the same temperature over 30 minutes. To this, toluene (65 mL) was added and the mixture was stirred at 40° C. for 30 minutes. Then, extraction with dichloromethane was performed, followed by drying over anhydrous sodium sulfate. The solvent was evaporated off under reduced pressure, and the residue was purified by column chromatography (hexane/ethyl acetate=1/1) to give a 73:27 mixture (933 mg, yield: 82%) of 1-methyl-5-(1,3-dioxolan-2-yl)-2(1H)-pyridone and 1-methyl-3-(1,3-dioxolan-2-yl)-2(1H)-pyridone.

$^1$H-NMR (300 MHZ, CDCl$_3$, δ): 3.54 (s, 2.19H), 3.56 (s, 0.81H), 3.95-4.15 (m, 4H), 5.57 (s, 0.73H), 6.00 (s, 0.27H), 6.18 (dd, J=6.6, 7.0 Hz, 0.27H), 6.19 (d, J=9.9 Hz, 0.73H), 7.31 (dd, J=2.2, 6.6 Hz, 0.27H), 7.40-7.44 (m, 1.46H), 7.60 (dd, J=2.2, 7.0 Hz, 0.27H).

Step 4

The 73:27 mixture (933 mg, 5.15 mmol) of 1-methyl-5-(1,3-dioxolan-2-yl)-2(1H)-pyridone and 1-methyl-3-(1,3-dioxolan-2-yl)-2(1H)-pyridone was dissolved in tetrahydrofuran (10.0 mL). To this, 1N hydrochloric acid (10.0 mL) was added under a nitrogen atmosphere at room temperature and the mixture was stirred at the same temperature for 12 hours. Then, the reaction mixture was neutralized with a saturated aqueous sodium bicarbonate solution, and extraction with ethyl acetate was performed, followed by washing with brine and drying over anhydrous sodium sulfate. The solvent was evaporated off under reduced pressure, and thereby 6-cyano-3-pyridinecarboxaldehyde (364 mg, yield: 100%) was obtained. The residue was purified by preparative thin-layer chromatography (ethyl acetate) to give 1-methyl-5-formyl-2 (1H)-pyridone (309 mg, yield: 45%).

$^1$H-NMR (270 MHZ, CDCl$_3$, δ): 3.65 (s, 3H), 6.62 (d, J=9.6 Hz, 1H), 7.83 (dd, J=2.6, 9.6 Hz, 1H), 7.94 (d, J=2.6 Hz, 1H), 9.63 (s, 1H)

Step 5

According to Reference Example 8-12, by use of 1-methyl-5-formyl-2-(1H)-pyridone (309 mg, 2.25 mmol), (trifluoromethyl)trimethylsilane (666 μL, 45.1 mmol), tetrabutylammonium fluoride (a 1.0 mol/L solution in tetrahydrofuran, 225 μL, 0.225 mmol) and tetrahydrofuran (10.0 mL), the mixture was stirred and reacted at room temperature fort hour. Then, purification by column chromatography (ethyl acetate) was performed to give 1-methyl-5-(2,2,2-trifluoro-1-hydroxyethyl)-2(1H)-pyridone (Compound ET) (214 mg, yield: 46%).

$^1$H-NMR (300 MHZ, CDCl$_3$, δ): 3.55 (s, 3H), 4.53 (br s, 1H), 4.79-4.87 (m, 1H), 6.56 (d, J=9.5 Hz, 1H), 7.43-7.48 (m, 2H)

REFERENCE EXAMPLE 8-73

(R)-3-(2,2,2-trifluoro-1-hydroxyethyl)pyridine (Compound EU)

Step 1

Compound CB (723 mg, 4.08 mmol) was dissolved in toluene (20 mL). To this, (R)-1-(naphthalen-1-yl)ethyl isocyanate (885 mg, 4.49 mmol) and bis(dibutylchlorotin)oxide (113 mg, 0.204 mmol) were successively added and the mixture was stirred at 50° C. for 6 hours. The solvent was evaporated off under reduced pressure, and the residue was purified by silica gel column chromatography (hexane/ethyl acetate=7/3) to give (R)-2,2,2-trifluoro-1-(pyridin-3-yl)ethyl (R)-1-(naphthalen-1-yl)ethylcarbamate (614 mg, yield: 40%) and (S)-2,2,2-trifluoro-1-(pyridin-3-yl)ethyl(R)-1-(naphthalen-1-yl)ethylcarbamate (578 mg, yield: 38%).

Step 2

Sodium (288 mg, 12.0 mmol) was suspended in ethanol (9.0 mL) and the mixture was stirred until sodium was completely dissolved. To this, (R)-2,2,2-trifluoro-1-(pyridin-3-yl)ethyl(R)-1-(naphthalen-1-yl)ethylcarbamate (452 mg, 1.20 mmol) was added and the mixture was heated to reflux for 30 minutes. The reaction mixture was concentrated and the reaction was stopped by addition of a 5% aqueous acetic acid solution. Then, extraction with ethyl acetate was performed, followed by washing with a saturated aqueous sodium bicarbonate solution and brine and drying over anhydrous sodium sulfate. The solvent was evaporated off under reduced pressure, and the residue was purified by silica gel column chromatography (hexane/ethyl acetate=1/1) to give Compound EU (203 mg, yield: 96%).

[α]$_D$$^{20}$=−44.4 (CHCl$_3$, c=1.03).

REFERENCE EXAMPLE 8-74

(S)-3-(2,2,2-trifluoro-1-hydroxyethyl)pyridine (Compound EV)

According to Step 2 of Reference Example 8-73, Compound EV (204 mg, yield: 97%) was obtained from (S)-2,2,2-trifluoro-1-(pyridin-3-yl)ethyl(R)-1-(naphthalen-1-yl)ethylcarbamate (421 mg, 1.19 mmol).

[α]$_D$$^{20}$=+44.6 (CHCl$_3$, c=1.00).

REFERENCE EXAMPLE 8-75

5-hydroxymethyl-2-methylthiazole (Compound EW)

Lithium aluminum hydride (146 mg, 3.85 mmol) was suspended in tetrahydrofuran (2.0 mL). To this, a tetrahydrofuran solution (2.0 mL) of ethyl 2-methylthiazol-5-carboxylate (300 mg, 1.75 mmol) was slowly added at 0° C. and the mixture was stirred at the same temperature for 30 minutes. The reaction was stopped by successive addition of water (0.146 mL), a 15% aqueous sodium hydroxide solution (0.146 mL) and water (0.438 mL) to the reaction mixture. The mixture was stirred at room temperature for 30 minutes and then filtered through Celite. The solvent was evaporated off under reduced pressure, and the residue was purified by silica gel column chromatography (chloroform/methanol=9/1) to give Compound EW (208 mg, yield: 92%).

REFERENCE EXAMPLE 8-76

2-methyl-5-(2,2,2-trifluoro-1-hydroxyethyl)thiazole (Compound EX)

Compound EW (3.86 g, 29.9 mmol) was dissolved in dichloromethane (115 mL). To this, manganese dioxide (29.0 g) was added and the mixture was stirred at room temperature for 8 hours. The reaction mixture was filtered through Celite and the solvent was evaporated off under reduced pressure. Thus, the crude product (4.01 g) of 5-formyl-2-methylthiazole was obtained. According to Reference Example 8-12, to the crude product dissolved in tetrahydrofuran (100 mL), a 1 mol/L solution of tetrabutylammonium fluoride in tetrahydrofuran (1.50 mL, 1.50 mmol) and (trifluoromethyl)trimethylsilane (6.87 mL, 44.8 mmol) were added and the mixture was stirred and reacted at room temperature for 10 minutes. Then, purification by silica gel column chromatography (hexane/ethyl acetate=1/1) was performed to give Compound EX (3.66 g, yield: 62%).

REFERENCE EXAMPLE 8-77

1-methyl-4-(2,2,2-trifluoro-1-hydroxyethyl)-2(1H)-pyridone (Compound EY)

Step 1

4-Pyridinecarboxaldehyde (3.00 mL, 31.4 mmol), ethyl orthoformate (15.7 mL, 94.2 mmol) and p-toluenesulfonic acid (229 mg, 1.57 mmol) were dissolved in ethanol (60.0 mL), and the mixture was heated to reflux under a nitrogen atmosphere for 10 hours. The reaction was stopped by addition of a saturated aqueous sodium bicarbonate solution to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=1/1) to give 4-(diethoxymethyl)pyridine (4.41 g, yield: 78%).

Step 2

4-(Diethoxymethyl)pyridine (4.41 g, 24.3 mmol) was dissolved in dichloromethane (90.0 mL). To this, iodomethane (1.82 mL, 29.2 mmol) was added under a nitrogen atmosphere at room temperature and the mixture was stirred at room temperature for 48 hours. The reaction mixture was concentrated, the residue was washed with diisopropyl ether, and thereby 4-(diethoxymethyl)-1-methylpyridinium iodide (7.47 g, yield: 95%) was obtained.

Step 3

4-(Diethoxymethyl)-1-methylpyridinium iodide (3.43 g, 10.6 mmol) was dissolved in water (70 mL). To this, a solution of potassium ferricyanide (38.4 g, 117 mmol) in water (85 mL) was added dropwise under a nitrogen atmosphere at 0° C. over 1 hour. To this, an aqueous solution (16 mL) of potassium hydroxide (9.40 g, 167 mmol) was added dropwise at the same temperature over 30 minutes. To this, toluene (100 mL) was added and the mixture was stirred at 40° C. for 30 minutes. Then, extraction with dichloromethane was performed, followed by drying over anhydrous sodium sulfate. The solvent was evaporated off under reduced pressure, and the residue was purified by silica gel column chromatography (ethyl acetate) to give 1-methyl-4-(diethoxymethyl)-2(1H)-pyridone (1.20 g, yield: 53%).

Step 4

1-Methyl-4-(diethoxymethyl)-2(1H)-pyridone (1.20 g, 5.58 mmol) was dissolved in tetrahydrofuran (10.0 mL). To this, 1 mol/L hydrochloric acid (10.0 mL) was added under a nitrogen atmosphere at room temperature and the mixture was stirred at 50° C. for 6 hours. By addition of a saturated aqueous sodium bicarbonate solution to neutralize the reaction mixture, the reaction was stopped. Then, extraction with ethyl acetate was performed, followed by washing with brine and drying over anhydrous sodium sulfate. The solvent was evaporated off under reduced pressure, and the residue was purified by preparative thin-layer chromatography (chloroform/methanol=9/1) to give 1-methyl-4-formyl-2(1H)-pyridone (717 mg, yield: 95%).

Step 5

According to Reference Example 8-12, Compound EY (1.01 g, yield: 94%) was obtained from 1-methyl-4-formyl-2(1H)-pyridone (717 mg, 5.23 mmol).

REFERENCE EXAMPLE 8-78

(R)-2-methyl-5-(2,2,2-trifluoro-1-hydroxyethyl)pyridine (Compound EZ)

According to Step 1 of Reference Example 8-73, (R)-2,2,2-trifluoro-1-(6-methylpyridin-3-yl)ethyl(R)-1-phenylethylcarbamate (975 mg, yield: 48%) and (S)-2,2,2-trifluoro-1-(6-methylpyridin-3-yl)ethyl(R)-1-phenylethylcarbamate (578 mg, yield: 45%) were obtained from Compound CK (1.15 g, 6.00 mmol).

Step 2

According to Step 2 of Reference Example 8-73, Compound EZ (163 mg, yield: 85%) was obtained from (R)-2,2,2-trifluoro-1-(6-methylpyridin-3-yl)ethyl(R)-1-phenylethylcarbamate (338 mg, 1.00 mmol).

REFERENCE EXAMPLE 8-79

(S)-2-methyl-5-(2,2,2-trifluoro-1-hydroxyethyl)pyridine (Compound EAA)

(S)-2,2,2-Trifluoro-1-(6-methylpyridin-3-yl)ethyl(R)-1-phenylethylcarbamate (946 mg, 2.80 mmol) was dissolved in ethanol (14 mL). To this, sodium ethoxide (1.90 g, 28.0 mmol) was added and the mixture was heated to reflux for 2 hours. The reaction mixture was concentrated, a 5% aqueous acetic acid solution was added thereto, and extraction with ethyl acetate was performed, followed by washing with a saturated aqueous sodium bicarbonate solution and brine and drying over anhydrous sodium sulfate. The solvent was evaporated off under reduced pressure, and the residue was purified by silica gel column chromatography (hexane/ethyl acetate=3/7) to give Compound EAA (493 mg, yield: 92%).

REFERENCE EXAMPLE 8-80

1-benzyloxycarbonyl-4-(2,2,2-trifluoro-1-hydroxyethyl)-piperidine (Compound EAB)

According to Reference Example 8-12, Compound EAB (1.02 g, yield: 80%) was obtained from 1-benzyloxycarbonyl-4-formylpiperidine (1.00 g, 4.04 mmol).

REFERENCE EXAMPLE 8-81

1-methyl-4-(2,2,2-trifluoro-1-hydroxyethyl)piperidine (Compound EAC)

Lithium aluminum hydride (366 mg, 9.64 mmol) was suspended in tetrahydrofuran (10 mL). To this, a tetrahydrofuran solution (10 mL) of Compound EAB (1.02 mg, 3.21 mmol) was slowly added at 0° C. and the mixture was stirred at room temperature for 30 minutes. After the reaction mixture was cooled to 0° C., the reaction was stopped by successive addition of water (0.366 mL), a 15% aqueous sodium hydroxide solution (0.366 mL) and water (1.10 mL) to the reaction mixture. The mixture was stirred at room temperature for 30 minutes and then filtered through Celite. The solvent was evaporated off under reduced pressure, the residue was dissolved in diisopropyl ether, and extraction with 1 mol/L hydrochloric acid was performed. After the pH of the aqueous layer was adjusted to 10 with 1 mol/L sodium hydroxide, extraction with dichloromethane was performed, followed by drying over anhydrous sodium sulfate. The solvent was evaporated off under reduced pressure, and the residue was subjected to slurry purification using diisopropyl ether, to give Compound EAC (386 mg, yield: 61%).

REFERENCE EXAMPLE 8-82

3-methyl-5-(2,2,2-trifluoro-1-hydroxyethyl)pyridine (Compound EAD)

Step 1

Lithium aluminum hydride (552 mg, 14.5 mmol) was suspended in tetrahydrofuran (10 mL). To this, a tetrahydrofuran solution (10 mL) of methyl 5-methyl nicotinate (1.00 g, 14.5 mmol) was slowly added at 0° C. and the mixture was stirred at the same temperature for 30 minutes. The reaction was stopped by successive addition of water (0.552 mL), a 15% aqueous sodium hydroxide solution (0.552 mL) and water (1.66 mL) to the reaction mixture. The mixture was stirred at room temperature for 30 minutes and then filtered through Celite. The solvent was evaporated off under reduced pressure, and the residue was purified by silica gel column chromatography (chloroform/methanol=9/1) to give 3-hydroxymethyl-5-methylpyridine (972 mg, yield: 100%).

Step 2

3-Hydroxymethyl-5-methylpyridine (972 mg, 7.89 mmol) was dissolved in dichloromethane (30 mL). To this, manganese dioxide (7.5 g) was added and the mixture was stirred at room temperature for 1 hour. The reaction mixture was filtered through Celite and the solvent was evaporated off under reduced pressure. The residue was purified by silica gel column chromatography (chloroform/methanol=19/1) to give 3-formyl-5-methylpyridine (936 mg, yield: 98%).

Step 3

According to Reference Example 8-12, Compound EAD (907 mg, yield: 61%) was obtained from 3-formyl-5-methylpyridine (936 mg, 7.73 mmol).

REFERENCE EXAMPLE 8-83

3-fluoro-5-(2,2,2-trifluoro-1-hydroxyethyl)pyridine (Compound EAE)

According to Reference Example 8-12, Compound EAE (1.53 g, yield: 98%) was obtained from 3-fluoro-5-formylpyridine (1.00 g, 7.99 mmol).

REFERENCE EXAMPLE 8-84

3-chloro-5-(2,2,2-trifluoro-1-hydroxyethyl)pyridine (Compound EAF)

According to Reference Example 8-12, Compound EAF (382 mg, yield: 51%) was obtained from 3-chloro-5-formylpyridine (479 mg, 3.50 mmol).

REFERENCE EXAMPLE 8-85

1-methanesulfonyl-4-(2,2,2-trifluoro-1-hydroxyethyl)-piperidine (Compound EAG)

Step 1

Compound EAB (1.00 g, 3.15 mmol) was dissolved in dichloromethane (20 mL). To this, triethylamine (0.527 mL, 3.78 mmol) and triethylsilyl trifluoromethanesulfonate (1.00 mL, 3.78 mmol) were added at 0° C. and the mixture was stirred at the same temperature for 30 minutes. The reaction was stopped by addition of water to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=4/1) to give 1-benzyloxycarbonyl-4-[2,2,2-trifluoro-1-(triethylsiloxy)-ethyl]piperidine (1.69 g, yield: 100%).

Step 2

Ten percent palladium/carbon (170 mg) was suspended in ethanol (5.0 mL). To this, an ethanol solution (25 mL) of 1-benzyloxycarbonyl-4-[2,2,2-trifluoro-1-(triethylsiloxy)-ethyl]piperidine (1.69 g, 3.92 mmol) was added and the mixture was stirred under a hydrogen atmosphere at room temperature for 2.5 hours. The reaction mixture was filtered through Celite and the solvent was evaporated off under reduced pressure. The residue was purified by silica gel column chromatography (chloroform) to give 4-[2,2,2-trifluoro-1-(triethylsiloxy)ethyl]piperidine (1.15 g, yield: 99%).

Step 3

4-[2,2,2-Trifluoro-1-(triethylsiloxy)ethyl]piperidine (303 mg, 1.02 mmol) was dissolved in dichloromethane (6 mL). To this, triethylamine (0.213 mL, 1.53 mmol) and methanesulfonyl chloride (0.118 mL, 1.53 mmol) were added at 0° C. and the mixture was stirred at room temperature for 30 minutes. The reaction was stopped by addition of water to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=4/1) to give 1-methanesulfonyl-4-[2,2,2-trifluoro-1-(triethylsiloxy)-ethyl]piperidine (302 mg, yield: 79%).

Step 4

1-Methanesulfonyl-4-[2,2,2-trifluoro-1-(triethyl-siloxy) ethyl]piperidine (300 mg, 0.999 mmol) was dissolved in tetrahydrofuran (2.4 mL). To this, a 1 mol/L aqueous hydrogen chloride solution (2.4 mL) was added and the mixture was stirred at room temperature for 2 hours. The reaction was stopped by addition of a saturated aqueous sodium bicarbonate solution to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=1/1) to give Compound EAG (198 mg, yield: 95%).

REFERENCE EXAMPLE 8-86

1-methoxycarbonyl-4-(2,2,2-trifluoro-1-hydroxyethyl)-piperidine (Compound EAH)

Step 1

4-[2,2,2-Trifluoro-1-(triethylsiloxy)ethyl]piperidine (303 mg, 1.02 mmol) was dissolved in dichloromethane (6 mL). To this, triethylamine (0.213 mL, 1.53 mmol) and methyl chloroformate (0.213 mL, 1.53 mmol) were added at 0° C. and the mixture was stirred at room temperature for 1 hour. The reaction was stopped by addition of water to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=17/3) to give 1-methoxycarbonyl-4-[2, 2,2-trifluoro-1-(triethylsiloxy)-ethyl]piperidine (287 mg, yield: 79%).

Step 2

According to Step 4 of Reference Example 8-85, Compound EAH (182 mg, yield: 95%) was obtained from 1-methoxycarbonyl-4-[2,2,2-trifluoro-1-(triethylsiloxy)-ethyl]piperidine (281 mg, 0.791 mmol).

REFERENCE EXAMPLE 8-87

1-propionyl-4-(2,2,2-trifluoro-1-hydroxyethyl)piperidine (Compound EAI)

Step 1

4-[2,2,2-Trifluoro-1-(triethylsiloxy)ethyl]piperidine (250 mg, 0.841 mmol) was dissolved in dichloromethane (5.0 mL). To this, triethylamine (0.176 mL, 1.26 mmol) and propionyl chloride (0.110 mL, 1.26 mmol) were added at 0° C. and the mixture was stirred at room temperature for 2 hours. The reaction was stopped by addition of a saturated aqueous sodium bicarbonate solution to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=7/3) to give 1-propionyl-4-[2,2,2-trifluoro-1-(triethylsiloxy)ethyl]-piperidine (231 mg, yield: 78%).
Step 2
According to Step 4 of Reference Example 8-85, Compound EAH (182 mg, yield: 95%) was obtained from 1-propionyl-4-[2,2,2-trifluoro-1-(triethylsiloxy)ethyl]-piperidine (226 mg, 0.639 mmol).

REFERENCE EXAMPLE 8-88

1-cyclopropanecarbonyl-4-(2,2,2-trifluoro-1-hydroxyethyl)-piperidine (Compound EAJ)

Step 1
4-[2,2,2-Trifluoro-1-(triethylsiloxy)ethyl]piperidine (250 mg, 0.841 mmol) was dissolved in dichloromethane (5.0 mL). To this, triethylamine (0.176 mL, 1.26 mmol) and cyclopropanecarbonyl chloride (0.114 mL, 1.26 mmol) were added at 0° C. and the mixture was stirred at room temperature for 2 hours. The reaction was stopped by addition of a saturated aqueous sodium bicarbonate solution to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=7/3) to give 1-cyclopropanecarbonyl-4-[2,2,2-trifluoro-1-(triethyl-siloxy)ethyl]piperidine (259 mg, yield: 84%).
Step 2
According to Step 4 of Reference Example 8-85, Compound EAJ (161 mg, yield: 92%) was obtained from 1-cyclopropanecarbonyl-4-[2,2,2-trifluoro-1-(triethyl-siloxy)ethyl] piperidine (226 mg, 0.639 mmol).

REFERENCE EXAMPLE 8-89

(R)-2-methyl-5-(2,2,2-trifluoro-1-hydroxyethyl)thiazole (Compound EAK)

Step 1
According to Step 1 of Reference Example 8-73, from 2-methyl-5-(2,2,2-trifluoro-1-hydroxyethyl)thiazole (Compound EX) (985 mg, 5.00 mmol), (R)-2,2,2-trifluoro-1-(2-methylthiazol-5-yl)ethyl(R)-1-phenylethylcarbamate (760 mg, yield: 44%) and (S)-2,2,2-trifluoro-1-(2-methylthiazol-5-yl)ethyl(R)-1-phenylethylcarbamate (785 mg, yield: 46%) were obtained.
Step 2
According to Step 2 of Reference Example 8-73, Compound EAK (1.81 g, yield: 95%) was obtained from (R)-2,2,2-trifluoro-1-(2-methylthiazol-5-yl)ethyl(R)-1-phenylethylcarbamate (3.30 g, 9.58 mmol).

REFERENCE EXAMPLE 8-90

(S)-2-methyl-5-(2,2,2-trifluoro-1-hydroxyethyl)thiazole (Compound EAL)

According to Reference Example 8-79, Compound EAL (425 mg, yield: 89%) was obtained from (S)-2,2,2-trifluoro-1-(2-methylthiazol-5-yl)ethyl(R)-1-phenylethylcarbamate (836 mg, 2.43 mmol).

REFERENCE EXAMPLE 8-91

2-methyl-4-(2,2,2-trifluoro-1-hydroxyethyl)thiazole (Compound EAM)

According to Reference Example 8-12, Compound EAM (157 mg, yield: 68%) was obtained from 4-formyl-2-methylthiazole (150 mg, 1.18 mmol).

REFERENCE EXAMPLE 8-92

2,2,2-trifluoro-1-(4-fluorotetrahydro-2H-pyran-4-yl) ethanol (Compound EAN)

Step 1
Tetrahydro-4H-pyran-4-one (2.50 g, 25.0 mmol) and chloroacetonitrile (1.58 mL, 25.0 mmol) were dissolved in tert-butanol (5.0 mL). To this, a tert-butanol solution (25 mL) of potassium tert-butoxide (2.81 g, 25.0 mmol) was added dropwise and the mixture was stirred at room temperature for 1 hour. The reaction was stopped by successive addition of ice and a 1 mol/L aqueous hydrogen chloride solution (30 mL) to the reaction mixture, and extraction with ether was performed, followed by washing with brine and drying over anhydrous magnesium sulfate. The solvent was evaporated off under reduced pressure, and the residue was purified by silica gel column chromatography (hexane/ethyl acetate=7/3) to give 1,6-dioxaspiro[2.5]octane-2-carbonitrile (3.14 g, yield: 90%).
Step 2
1,6-Dioxaspiro[2.5]octane-2-carbonitrile (3.14 g, 22.6 mmol) was dissolved in dichloromethane (9.0 mmol). To this, a hydrogen fluoride-pyridine complex (3.0 mL) was added and the mixture was stirred at room temperature for 3 hours. The reaction was stopped by slow addition of sodium bicarbonate to the reaction mixture. After filtration, ethyl acetate was added to the mother liquid, and washing with brine and drying over anhydrous sodium sulfate were performed. The solvent was evaporated off under reduced pressure, and the residue was purified by silica gel column chromatography (hexane/ethyl acetate=7/3) to give 2-(4-fluorotetrahydro-2H-pyran-4-yl)-2-hydroxyacetonitrile (2.66 g, yield: 74%).
Step 3
2-(4-Fluorotetrahydro-2H-pyran-4-yl)-2-hydroxyacetonitrile (2.06 g, 12.9 mmol) was dissolved in tert-butanol (20 mL) and water (5.0 mL). To this, sodium borohydride (537 mg, 14.2 mmol) was added and the mixture was stirred at room temperature for 1 hour. To the reaction mixture, ice and acetone were added and the mixture was stirred at room temperature for 1 hour. The solvent was evaporated off under reduced pressure, brine was added to the residue, and extraction with chloroform was performed, followed by drying over anhydrous sodium sulfate. The solvent was evaporated off under reduced pressure, and the residue was purified by silica gel column chromatography (hexane/ethyl acetate=3/7) to give 4-fluorotetrahydro-2H-pyran-4-ylmethanol (1.59 g, yield: 92%).
Step 4
4-Fluorotetrahydro-2H-pyran-4-ylmethanol (500 mg, 3.73 mmol) was dissolved in dichloromethane (15 mL). To this, Dess-Martin periodinane (1.96 g, 4.47 mmol) was added at 0° C. and the mixture was stirred at room temperature for 1 hour. The reaction was stopped by addition of a saturated aqueous sodium bicarbonate solution and a saturated aqueous sodium thiosulfate solution to the reaction mixture, and extraction with dichloromethane was performed, followed by drying over anhydrous sodium sulfate. The solvent was evaporated off under reduced pressure, and thereby the crude product (475 mg) of 4-fluorotetrahydro-2H-pyran-4-ylcarbaldehyde was obtained.

According to Reference Example 8-12, by use of the crude product dissolved in tetrahydrofuran (10 mL), a 1 mol/L solution of tetrabutylammonium fluoride in tetrahydrofuran (0.373 mL, 0.373 mmol) and (trifluoromethyl)trimethylsilane (0.827 mL, 5.60 mmol), the mixture was stirred and reacted at room temperature for 2 hours. Then, purification by silica gel column chromatography (hexane/ethyl acetate=4/1) was performed to give Compound FAN (147 mg, yield: 19%).

REFERENCE EXAMPLE 8-93

2,2,2-trifluoro-1-(4-cyanotetrahydro-2H-pyran-4-yl) ethanol (Compound EAO)

Step 1

Methyl cyanoacetate (2.50 mL, 28.3 mmol) and 2-bromoethyl ether (4.63 mL, 36.8 mol) were dissolved in acetone (50 ml). To this, potassium carbonate (9.78 g, 70.8 mmol) was added and the mixture was heated to reflux for 8 hours. The reaction mixture was filtered and the mother liquid was concentrated. The residue was purified by silica gel column chromatography (hexane/ethyl acetate=7/3) to give methyl 4-cyanotetrahydro-2H-pyran-4-carboxylate (2.93 g, yield: 61%).

Step 2

Methyl 4-cyanotetrahydro-2H-pyran-4-carboxylate (2.93 g, 17.3 mmol) was dissolved in tetrahydrofuran (50 mL), methanol (10 mL) and water (5.0 mL). To this, sodium borohydride (1.31 g, 34.6 mmol) was added and the mixture was stirred at room temperature for 30 minutes. The reaction was stopped by addition of water to the reaction mixture, and extraction with ethyl acetate was performed, followed by washing with brine and drying over anhydrous sodium sulfate. The solvent was evaporated off under reduced pressure, and the residue was purified by silica gel column chromatography (ethyl acetate) to give 4-cyanotetrahydro-2H-pyran-4-ylmethanol (1.59 g, yield: 92%).

Step 3

Oxalyl dichloride (0.625 mL, 7.16 mmol) was dissolved in dichloromethane (10 mL). To this, dimethyl sulfoxide (1.01 mL, 14.3 mmol) was added at −78° C. and the mixture was stirred at the same temperature for 2 minutes. To this, a dichloromethane solution (10 mL) of 4-cyanotetrahydro-2H-pyran-4-ylmethanol (500 mg, 3.58 mmol) was added and the mixture was stirred at the same temperature for 15 minutes. To this, triethylamine (2.40 mL, 17.2 mmol) was added and the mixture was stirred at room temperature for 3.0 minutes. The reaction was stopped by addition of water to the reaction mixture, and extraction with ethyl acetate was performed, followed by washing with brine and drying over anhydrous sodium sulfate. The solvent was evaporated off under reduced pressure, and thereby the crude product (263 mg) of 4-cyanotetrahydro-2H-pyran-4-ylmethanol carbaldehyde was obtained.

According to Reference Example 8-12, by use of the crude product dissolved in tetrahydrofuran (5.0 mL), a 1 mol/L solution of tetrabutylammonium fluoride in tetrahydrofuran (0.189 mL, 0.189 mmol) and (trifluoromethyl)trimethylsilane (0.419 mL, 2.83 mmol), the mixture was stirred and reacted at room temperature for 3 hours. Then, purification by silica gel column chromatography (hexane/ethyl acetate=7/3) was performed to give Compound EAO (167 mg, yield: 22%).

REFERENCE EXAMPLE 8-94

2,2,2-trifluoro-1-(4-hydroxytetrahydro-2H-pyran-4-yl)-ethanol (Compound EAP)

Step 1

A mixture of tetrahydro-4H-pyran-4-one (1.47 g, 14.7 mmol), trimethylsilyl cyanide (2.94 ml, 22.0 mmol) and zinc (II) iodide (46.9 mg, 0.147 mmol) was stirred at room temperature for 1 hour. Then, the reaction mixture was purified by silica gel column chromatography (hexane/ethyl acetate=4/1) to give 4-(trimethylsilyloxy)tetrahydro-2H-pyran-4-carbonitrile (2.56 g, yield: 90%).

Step 2

4-(Trimethylsilyloxy)tetrahydro-2H-pyran-4-carbonitrile (1.00 g, 5.02 mmol) was dissolved in dichloromethane (20 mL). To this, a 1 mol/L solution of diisopropylaluminum hydride in hexane (7.76 mL, 7.76 mmol) was added at −78° C. and the mixture was stirred at room temperature for 20 minutes. The reaction was stopped by addition of water (7.76 mL) at 0° C. The mixture was stirred at room temperature for 1 hour and then filtered through Celite. The solvent was evaporated off under reduced pressure and the residue was dissolved in tetrahydrofuran (10 mL). To this, a saturated aqueous ammonium chloride solution was added and the mixture was stirred at room temperature for 30 minutes. Then, extraction with ethyl acetate was performed, followed by washing with brine and drying over anhydrous sodium sulfate. The solvent was evaporated off under reduced pressure, and the residue was purified by silica gel column chromatography (hexane/ethyl acetate=9/1) to give 4-(trimethylsilyloxy)tetrahydro-2H-pyran-4-carbaldehyde (297 mg, yield: 29%).

Step 3

According to Reference Example 8-12, Compound EAP (230 mg, yield: 79%) was obtained from 4-(trimethylsilyloxy)tetrahydro-2H-pyran-4-carbaldehyde (295 mg, 1.46 mmol).

REFERENCE EXAMPLE 8-95

2,2,2-trifluoro-1-(4-methoxytetrahydro-2H-pyran-4-yl)-ethanol (Compound EAQ)

Step 1

Tetrahydro-4H-pyran-4-one (1.47 g, 14.7 mmol) was dissolved in methanol (60 mL). To this, 2,2-dimethoxypropane (11.1 mL, 90.0 mmol) and p-toluenesulfonic acid (285 mg, 1.50 mmol) were added and the mixture was heated to reflux for 1 hour. The solvent was evaporated off under reduced pressure, a saturated aqueous sodium bicarbonate solution was added to the residue, and extraction with ether was performed, followed by washing with brine and drying over anhydrous magnesium sulfate. The solvent was evaporated off under reduced pressure, and thereby the crude product (4.56 g) of 4,4-dimethoxytetrahydro-2H-pyran was obtained.

The crude product was dissolved in dichloromethane (45 mL). To this, tert-butyl isocyanide (3.73 ml, 33.0 mmol) and titanium tetrachloride (3.95 mL, 35.0 mmol) were added at −78° C. and the mixture was stirred at room temperature for 30 minutes. The reaction was stopped by addition of water to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=7/3) to give 4-methoxytetrahydro-2H-pyran-4-carbonitrile (2.85 g, yield: 67%).

Step 2

4-Methoxytetrahydro-2H-pyran-4-carbonitrile (1.00 g, 7.08 mmol) was dissolved in dichloromethane (20 mL). To this, a 1 mol/L solution of diisopropylaluminum hydride in hexane (10.9 mL, 10.9 mmol) was added at −78° C. and the mixture was stirred at room temperature for 30 minutes. The reaction was stopped by addition of water (10.9 mL) at 0° C. The mixture was stirred at room temperature for 1 hour and then filtered through Celite. The solvent was evaporated off under reduced pressure and the residue was dissolved in tetrahydrofuran (10 mL). To this, a 1 mol/L aqueous hydrogen chloride solution was added and the mixture was stirred at room temperature for 30 minutes. The reaction was stopped by addition of a saturated aqueous sodium bicarbonate solution to the reaction mixture, and extraction with ethyl acetate was performed, followed by washing with brine and drying over anhydrous sodium sulfate. The solvent was evaporated off under reduced pressure, and the residue was purified by silica gel column chromatography (hexane/ethyl acetate=9/1) to give 4-methoxytetrahydro-2H-pyran-4-carbaldehyde (195 mg, yield: 19%).

Step 3

According to Reference Example 8-12, Compound EAQ (221 mg, yield: 76%) was obtained from 4-methoxytetrahydro-2H-pyran-4-carbaldehyde (195 mg, 1.35 mmol).

REFERENCE EXAMPLE 8-96

1-acetyl-4-fluoro-4-(2,2,2-trifluoro-1-hydroxyethyl)-piperidine (Compound EAR)

According to Step 1 of Reference Example 8-92, benzyl 2-cyano-1-oxa-6-azaspiro[2.5]octane-6-carboxylate (4.86 g, yield: 83%) was obtained from 1-benzyloxycarbonylpiperidin-4-one (5.00 g, 21.4 mmol).

Step 2

According to Step 2 of Reference Example 8-92, 2-(1-benzyloxycarbonyl-4-piperidin-4-yl)-2-hydroxyacetonitrile (4.51 g, yield: 89%) was obtained from benzyl 2-cyano-1-oxa-6-azaspiro[2.5]octane-6-carboxylate (4.73 g, 17.4 mmol).

Step 3

According to Step 3 of Reference Example 8-92, 1-benzyloxy-4-fluoropiperidin-4-ylmethanol (3.53 g, yield: 86%) was obtained from 2-(1-benzyloxycarbonyl-4-piperidin-4-yl)-2-hydroxyacetonitrile (4.51 g, 15.4 mmol).

Step 4

According to Step 4 of Reference Example 8-92, the crude product (2.05 mg) of 1-benzyloxy-4-fluoropiperidin-4-ylcarbaldehyde was obtained from 1-benzyloxy-4-fluoropiperidin-4-ylmethanol (2.00 g, 7.48 mmol).

According to Reference Example 8-12, by use of the crude product dissolved in tetrahydrofuran (40 mL), a 1 mol/L solution of tetrabutylammonium fluoride in tetrahydrofuran (0.374 mL, 0.374 mmol) and (trifluoromethyl)trimethylsilane (1.72 mL, 11.2 mmol), the mixture was stirred and reacted at room temperature for 2 hours. Then, purification by silica gel column chromatography (hexane/ethyl acetate=7/3) was performed to give 2,2,2-trifluoro-1-(1-benzyloxy-4-fluoropiperidin-4-yl)-ethanol (1.09 g, yield: 43%).

Step 5

According to Step 1 of Reference Example 8-85, 1-benzyloxycarbonyl-4-fluoro-4-[2,2,2-trifluoro-1-(triethylsiloxy)ethyl]piperidine (1.67 g, yield: 97%) was obtained from 2,2,2-trifluoro-1-(1-benzyloxy-4-fluoropiperidin-4-yl)-ethanol (1.28 g, 3.82 mmol).

Step 6

According to Step 2 of Reference Example 8-85, 4-fluoro-4-[2,2,2-trifluoro-1-(triethylsiloxy)ethyl]-piperidine (1.28 g, yield: 100%) was obtained from 1-benzyloxycarbonyl-4-fluoro-4-[2,2,2-trifluoro-1-(triethylsiloxy)ethyl]piperidine (1.67 g, 3.71 mmol).

Step 7

4-Fluoro-4-[2,2,2-trifluoro-1-(triethylsiloxy)ethyl]-piperidine (300 mg, 0.951 mmol) was dissolved in dichloromethane (6 mL). To this, triethylamine (0.199 mL, 1.43 mmol) and acetic anhydride (0.134 mL, 1.43 mmol) were added and the mixture was stirred at room temperature for 30 minutes. The reaction was stopped by addition of water to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=1/1) to give 1-acetyl-4-fluoro-1-methanesulfonyl-4-[2,2,2-trifluoro-1-(triethylsiloxy)ethyl] piperidine (294 mg, yield: 86%).

Step 8

By use of 1-acetyl-4-fluoro-4-[2,2,2-trifluoro-1-(triethylsiloxy)-ethyl]piperidine (294 mg, 0.822 mmol) dissolved in tetrahydrofuran (5 mL) and a 1 mol/L solution of tetrabutylammonium fluoride in tetrahydrofuran (1.23 mL, 1.23 mmol), the mixture was stirred and reacted at room temperature for 30 minutes. The reaction was stopped by addition of water to the reaction mixture, and extraction with ethyl acetate was performed, followed by drying over anhydrous sodium sulfate.

The solvent was evaporated off under reduced pressure, and the residue was purified by silica gel column chromatography (hexane/ethyl acetate=1/1) to give Compound EAR (173 mg, yield: 86%).

REFERENCE EXAMPLE 8-97

4-fluoro-1-methanesulfonyl-4-(2,2,2-trifluoro-1-hydroxy-ethyl)piperidine (Compound EAS)

Step 1

4-Fluoro-4-[2,2,2-trifluoro-1-(triethylsiloxy)ethyl]-piperidine (300 mg, 0.951 mmol) was dissolved in dichloromethane (6 mL). To this, triethylamine (0.199 mL, 1.43 mmol) and methanesulfonyl chloride (0.140 mL, 1.43 mmol) were added and the mixture was stirred at room temperature for 30 minutes. The reaction was stopped by addition of water to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=7/3) to give 4-fluoro-1-methanesulfonyl-4-[2,2,2-trifluoro-1-(triethyl-siloxy)ethyl] piperidine (309 mg, yield: 83%).

Step 2

By use of 4-fluoro-1-methanesulfonyl-4-[2,2,2-trifluoro-1-(triethyl-siloxy)ethyl]piperidine (309 mg, 0.785 mmol) dissolved in tetrahydrofuran (5 mL) and a 1 mol/L solution of tetrabutylammonium fluoride in tetrahydrofuran (1.18 mL, 1.18 mmol), the mixture was stirred and reacted at room temperature for 30 minutes. The reaction was stopped by addition of water to the reaction mixture, and extraction with ethyl acetate was performed, followed by drying over anhydrous sodium sulfate. The solvent was evaporated off under reduced pressure, and the residue was purified by silica gel

291 column chromatography (hexane/ethyl acetate=1/1) to give Compound EAS (120 mg, yield: 55%).

REFERENCE EXAMPLE 8-98

1-tert-butoxycarbonyl-4-methyl-4-(2,2,2-trifluoro-1-hydroxyethyl)piperidine (Compound EAT)

Step 1

Methyl 1-tert-butoxycarbonyl-4-methylpiperidine-4-carboxylate (1.19 g, 4.39 mmol) was dissolved in tetrahydrofuran (10 mL). To this, lithium aluminum hydride (200 mg, 5.27 mmol) was added at 0° C. and the mixture was stirred at the same temperature for 30 minutes. The reaction was stopped by addition of sodium sulfate decahydrate to the reaction mixture, and 1 hour-stirring was performed at room temperature. After Celite-filtration, the mother liquid was concentrated, and thereby the crude product (1.19 g) of 1-tert-butoxycarbonyl-4-methylpiperidine-4-methanol was obtained.

According to Step 3 of Reference Example 8-93, by use of the crude product, oxalyl dichloride (0.902 mL, 10.3 mmol), dimethyl sulfoxide (1.46 mL, 20.6 mmol), triethylamine (4.33 mL, 31.1 mmol) and dichloromethane (20 mL), the mixture was stirred and reacted at room temperature for 30 minutes. Then, purification by silica gel column chromatography (hexane/ethyl acetate=1/1) was performed to give 1-tert-butoxycarbonyl-4-methylpiperidine-4-carbaldehyde (889 mg, yield: 89%).

Step 2

According to Reference Example 8-12, Compound EAT (1.12 g, yield: 96%) was obtained from 1-tert-butoxycarbonyl-4-methylpiperidine-4-carbaldehyde (889 mg, 3.91 mmol).

REFERENCE EXAMPLE 8-99

1-acetyl-4-methyl-4-(2,2,2-trifluoro-1-hydroxyethyl)-piperidine (Compound EAU)

Compound EAT (300 mg, 1.01 mmol) was dissolved in methanol (3.0 mL). To this, a 10% solution of hydrogen chloride in methanol (3.0 mL) was added and the mixture was stirred at 50° C. for 1.5 hours. The solvent was evaporated off under reduced pressure. Then, dichloromethane (6.0 mL), triethylamine (0.697 mmol, 5.05 mmol) and acetic anhydride (476 mL, 5.05 mmol) were added to the residue, and the mixture was stirred at room temperature for 1.5 hours. The reaction was stopped by addition of a saturated aqueous sodium bicarbonate solution to the reaction mixture, and extraction with dichloromethane was performed, followed by drying over anhydrous sodium sulfate. The solvent was evaporated off under reduced pressure, and the residue was purified by silica gel column chromatography (hexane/ethyl acetate=1/1) to give a mixture of Compound EAU and 1-acetyl-4-methyl-4-(2,2,2-trifluoro-1-acetoxyethyl)-piperidine.

The mixture was dissolved in methanol (5.0 mL). To this, potassium carbonate (294 mg, 2.13 mmol) was added and the mixture was stirred at room temperature for 1 hour. The reaction was stopped by addition of water to the reaction mixture, and extraction with ethyl acetate was performed, followed by drying over anhydrous sodium sulfate. The solvent was evaporated off under reduced pressure and thereby Compound EAU (182 mg, yield: 75%) was obtained.

292

REFERENCE EXAMPLE 9-1

Pyridine-3-sulfonamide (Compound FA)

A 25% aqueous ammonia solution (2 mL) was added to pyridine-3-sulfonyl chloride (300 mg, 1.7 mmol) and the mixture was stirred at room temperature for 2 hours. Then, a saturated aqueous ammonium chloride solution was added to the reaction mixture, and extraction with ethyl acetate was performed, followed by washing with brine and drying over anhydrous magnesium sulfate. The solvent was evaporated off under reduced pressure and thereby Compound FA (154 mg, yield: 58%) was obtained.

ESIMS m/z: 159 (M+H)$^+$; $^1$H-NMR (270 MHz, CDCl$_3$, δ): 4.95 (s, 2H), 7.48 (s, 1H), 8.21 (s, 1H), 8.82 (s, 1H), 9.16 (s, 1H).

REFERENCE EXAMPLE 9-2

5-chloro-3-methyl-1H-pyrazole-4-sulfonamide (Compound FB)

According to Reference Example 9-1, by use of 5-chloro-1,3-dimethyl-1H-pyrazole-4-sulfonyl chloride (300 mg, 1.3 mmol) and a 25% aqueous ammonia solution (2 mL), 5-chloro-3-methyl-1H-pyrazole-4-sulfonamide (Compound FB) (232 mg, yield: 85%) was obtained.

ESIMS m/z: 210 (M+H)$^+$.

REFERENCE EXAMPLE 9-3

3,5-dimethylisoxazole-4-sulfonamide (Compound FC)

According to Reference Example 9-1, by use of 3,5-dimethylisoxazole-4-sulfonyl chloride (200 mg, 1.0 mmol) and a 25% aqueous ammonia solution (2 mL), 3,5-dimethylisoxazole-4-sulfonamide (Compound FC) (156 mg, yield: 87%) was obtained.

ESIMS m/z: 177 (M+H)$^+$.

REFERENCE EXAMPLE 9-4

5-methyl-2-(trifluoromethyl)furan-3-sulfonamide (Compound FD)

According to Reference Example 9-1, by use of 5-methyl-2-(trifluoromethyl)furan-3-sulfonyl chloride (300 mg, 1.2 mmol) and a 25% aqueous ammonia solution (2 mL), 5-methyl-2-(trifluoromethyl)furan-3-sulfonamide (Compound FD) (235 mg, yield: 85%) was obtained.

ESIMS m/z: 230 (M+H)$^+$.

REFERENCE EXAMPLE 9-5

3,5-dichlorobenzenesulfonamide (Compound FE)

According to Reference Example 9-1, by use of 3,5-dichlorobenzene-1-sulfonyl chloride (300 mg, 1.2 mmol) and a 25% aqueous ammonia solution (2 mL), 3,5-dichlorobenzenesulfonamide (Compound FE) (268 mg, yield: 97%) was obtained.

ESIMS m/z: 227 (M+H)$^+$.

REFERENCE EXAMPLE 9-6

3,5-difluorobenzenesulfonamide (Compound FF)

According to Reference Example 9-1, by use of 3,5-difluorobenzene-1-sulfonyl chloride (300 mg, 1.4 mmol) and a 25% aqueous ammonia solution (2 mL), 3,5-difluorobenzenesulfonamide (Compound FF) (263 mg, yield: 97%) was obtained.

ESIMS m/z: 194 (M+H)$^+$.

REFERENCE EXAMPLE 9-7

1,2-dimethyl-1H-imidazole-4-sulfonamide (Compound FG)

A 7 mol/L solution of ammonia in methanol (2 mL) was added to 1,2-dimethyl-1H-imidazole-4-sulfonyl chloride (200 mg, 1.7 mmol) and the mixture was stirred at room temperature for 4 hours. The solvent in the reaction mixture was evaporated off under reduced pressure, and thereby 1,2-dimethyl-1H-imidazole-4-sulfonamide (Compound FG) (54 mg, yield: 60%) was obtained.

ESIMS m/z: 176 (M+H)$^+$.

REFERENCE EXAMPLE 9-8

2-methoxybenzenesulfonamide (Compound FH)

Diethyl ether (5 mL) was added to 2-bromoanisole (500 mg, 2.7 mmol) and the mixture was cooled to −78° C. by use of a dry ice bath. To this, n-butyllithium (a 1.56 mol/L solution in hexane, 2.6 mL, 4.0 mmol) was slowly added and the mixture was stirred at the same temperature for 30 minutes. To this, sulfuryl chloride (0.24 mL, 2.9 mmol) was added and the mixture was further stirred at the same temperature for 2 hours. After water was added to the reaction mixture, extraction with ethyl acetate was performed, followed by washing with brine and drying over anhydrous magnesium sulfate. The solvent was evaporated off under reduced pressure, a 7 mol/L solution of ammonia in methanol (2 mL) was added to the residue, and the mixture was stirred at room temperature for 2 hours. The solvent was evaporated off under reduced pressure, and slurry purification was performed using chloroform, to give 2-methoxybenzenesulfonamide (Compound FH) (70 mg, yield: 14%).

ESIMS m/z: 188 (M+H)$^+$.

REFERENCE EXAMPLE 9-9

Pyridine-2-sulfonamide (Compound FI)

According to Reference Example 9-8, by use of 2-bromopyridine (500 mg, 3.2 mmol), diethyl ether (5 mL), n-butyllithium (a 1.56 mol/L solution in hexane, 2.5 mL, 3.8 mmol), sulfuryl chloride (0.28 mL, 3.5 mmol) and a 7 mol/L solution of ammonia in methanol (2 mL), pyridine-2-sulfonamide (Compound FI) (77 mg, yield: 15%) was obtained.

ESIMS m/z: 159 (M+H)$^+$.

REFERENCE EXAMPLE 9-10

Thiophene-3-sulfonamide (Compound FJ)

According to Reference Example 9-1, by use of thiophene-3-sulfonyl chloride (200 mg, 1.1 mmol) and a 25% aqueous ammonia solution (2 mL), thiophene-3-sulfonamide (Compound FJ) (149 mg, yield: 84%) was obtained.

ESIMS m/z: 164 (M+H)$^+$.

REFERENCE EXAMPLE 9-11

2,5-dimethylthiophene-3-sulfonamide (Compound FK)

According to Reference Example 9-1, by use of 2,5-dimethylthiophene-3-sulfonyl chloride (200 mg, 1.0 mmol) and a 25% aqueous ammonia solution (2 mL), 2,5-dimethylthiophene-3-sulfonamide (Compound FK) (180 mg, yield: 99%) was obtained.

ESIMS m/z: 192 (M+H)$^+$.

REFERENCE EXAMPLE 9-12

2,4-dimethylthiazole-5-sulfonamide (Compound FL)

According to Reference Example 9-7, by use of 2,4-dimethylthiazole-5-sulfonyl chloride (250 mg, 1.1 mmol) and a 7 mol/L solution of ammonia in methanol (2 mL), the mixture was stirred and reacted at room temperature for 2 hours. Then, purification by silica gel column chromatography (chloroform/methanol=1/0 to 20/1) was performed to give 2,4-dimethylthiazole-5-sulfonamide (Compound FL) (60 mg, yield: 34%).

ESIMS m/z: 193 (M+H)$^+$.

REFERENCE EXAMPLE 9-13

Benzo[b]thiophene-2-sulfonamide (Compound FM)

According to Reference Example 9-1, by use of benzo[b]thiophene-2-sulfonyl chloride (200 mg, 0.86 mmol) and a 25% aqueous ammonia solution (2 mL), benzo[b]thiophene-2-sulfonamide (Compound FM) (167 mg, yield: 91%) was obtained.

ESIMS m/z: 214 (M+H)$^+$.

REFERENCE EXAMPLE 9-14

4-methyl-3,4-dihydro-2H-benzo[b][1,4]oxazine-7-sulfonamide (Compound FN)

According to Reference Example 9-1, by use of 4-methyl-3,4-dihydro-2H-benzo[b][1,4]oxazine-7-sulfonyl chloride (200 mg, 0.81 mmol) and a 25% aqueous ammonia solution (2 mL), 4-methyl-3,4-dihydro-2H-benzo[b][1,4]oxazine-7-sulfonamide (Compound FN) (106 mg, yield: 57%) was obtained.

ESIMS m/z: 229 (M+H)$^+$.

REFERENCE EXAMPLE 9-15

Propane-2-sulfonamide (Compound FO)

According to Reference Example 9-1, by use of propane-2-sulfonyl chloride (300 mg, 2.1 mmol) and a 25% aqueous ammonia solution (2 mL), propane-2-sulfonamide (Compound FO) (201 mg, yield: 78%) was obtained.

ESIMS m/z: 124 (M+H)$^+$.

REFERENCE EXAMPLE 9-16

Cyclopentanesulfonamide (Compound FP)

According to Reference Example 9-7, by use of cyclopentanesulfonyl chloride (300 mg, 1.8 mmol) and a 7 mol/L solution of ammonia in methanol (2 mL), the mixture was stirred and reacted at room temperature for 4 hours. After slurry purification using chloroform, purification by silica gel column chromatography (chloroform/methanol=1/0 to 20/1) was performed to give cyclopentanesulfonamide (Compound FP) (173 mg, yield: 66%).

ESIMS m/z: 149 (M+H)$^+$.

REFERENCE EXAMPLE 9-17

(2-chlorophenyl)methanesulfonamide (Compound FQ)

According to Reference Example 9-1, by use of (2-chlorophenyl)methanesulfonyl chloride (200 mg, 0.89 mmol) and a 25% aqueous ammonia solution (2 mL), (2-chlorophenyl) methanesulfonamide (Compound FQ) (180 mg, yield: 99%) was obtained.

ESIMS m/z: 206 (M+H)$^+$.

REFERENCE EXAMPLE 9-18

N,N-dimethylsulfuric diamide (Compound FR)

According to Reference Example 9-7, by use of dimethylsulfamoyl chloride (400 mg, 2.8 mmol) and a 7 mol/L solution of ammonia in methanol (2 mL), the mixture was stirred and reacted at room temperature for 5 hours. Thus, N,N-dimethylsulfuric diamide (Compound FR) (324 mg, yield: 81%) was obtained.

ESIMS m/z: 125 (M+H)$^+$.

REFERENCE EXAMPLE 9-19

Propane-1-sulfonamide (Compound FS)

A 25% aqueous ammonia solution (2 mL) was added to propane-1-sulfonyl chloride (300 mg, 2.1 mmol) and the mixture was stirred at room temperature for 12 hours. The solvent was evaporated off under reduced pressure, and the residue was purified by silica gel column chromatography (chloroform/methanol=1/0 to 10/1) to give propane-1-sulfonamide (Compound FS) (212 mg, yield: 82%).

ESIMS m/z: 124 (M+H)$^+$; $^1$H-NMR (270 MHz, CDCl$_3$, δ): 1.09 (t, J=7.4 Hz, 3H), 1.80-2.00 (m, 2H), 3.04-3.19 (m, 2H), 4.57 (br s, 2H).

REFERENCE EXAMPLE 9-20

2-methylpropane-1-sulfonamide (Compound FT)

According to Reference Example 9-19, by use of 2-methylpropane-1-sulfonyl chloride (300 mg, 1.9 mmol) and a 25% aqueous ammonia solution (2 mL), the mixture was stirred and reacted at room temperature for 14 hours. Then, purification by silica gel column chromatography (chloroform/methanol=1/0 to 10/1) was performed to give 2-methylpropane-1-sulfonamide (Compound FT) (183 mg, yield: 70%).

ESIMS m/z: 138 (M+H)$^+$; $^1$H-NMR (270 MHz, CDCl$_3$, δ): 1.13 (d, J=6.3 Hz, 6H), 2.31 (sept, J=6.3 Hz, 1H), 3.05 (d, J=6.3 Hz, 2H), 4.73 (br s, 2H).

REFERENCE EXAMPLE 9-21

3-chlorobenzenesulfonamide (Compound FU)

According to Reference Example 9-1, by use of 3-chlorobenzenesulfonyl chloride (200 mg, 0.95 mmol) and a 25% aqueous ammonia solution (2 mL), 3-chlorobenzenesulfonamide (Compound FU) (170 mg, yield: 93%) was obtained.

ESIMS m/z: 192 (M+H)$^+$.

REFERENCE EXAMPLE 9-22

4-chlorobenzenesulfonamide (Compound FV)

According to Reference Example 9-1, by use of 4-chlorobenzenesulfonyl chloride (200 mg, 0.95 mmol) and a 25% aqueous ammonia solution (2 mL), 4-chlorobenzenesulfonamide (Compound FV) (170 mg, yield: 93%) was obtained.

ESIMS m/z: 192 (M+H)$^+$.

REFERENCE EXAMPLE 9-23

Cyclohexanesulfonamide (Compound FW)

According to Reference Example 9-19, by use of cyclohexanesulfonyl chloride (300 mg, 1.6 mmol) and a 25% aqueous ammonia solution (2 mL), the mixture was stirred and reacted at room temperature for 18 hours. Then, purification by silica gel column chromatography (chloroform/methanol=1/0 to 20/1) was performed to give cyclohexanesulfonamide (Compound FW) (161 mg, yield: 60%).

ESIMS m/z: 164 (M+H)$^+$.

REFERENCE EXAMPLE 9-24

Butane-2-sulfonamide (Compound FX)

According to Reference Example 9-19, by use of butane-2-sulfonyl chloride (300 mg, 1.9 mmol) and a 25% aqueous ammonia solution (2 mL), the mixture was stirred and reacted at room temperature for 3 hours. Then, purification by silica gel column chromatography (chloroform/methanol=1/0 to 20/1) was performed to give butane-2-sulfonamide (Compound FX) (176 mg, yield: 67%).

ESIMS m/z: 138 (M+H)$^+$.

REFERENCE EXAMPLE 9-25

Morpholine-4-sulfonamide (Compound FY)

Tetrahydrofuran (3 mL) and morpholine (0.68 mL, 7.8 mmol) were added to sulfamide (500 mg, 5.2 mmol) and the mixture was stirred at 100° C. for 4 hours. The solvent was evaporated off under reduced pressure, and purification by silica gel column chromatography (chloroform/methanol=1/0 to 4/1) was performed to give morpholine-4-sulfonamide (Compound FY) (67 mg, yield: 8%).

ESIMS m/z: 167 (M+H)$^+$.

REFERENCE EXAMPLE 9-26

N-cyclopropylsulfuric diamide (Compound FZ)

Tetrahydrofuran (3 mL) and cyclopropylamine (0.54 mL, 7.8 mmol) were added to sulfamide (500 mg, 5.2 mmol) and the mixture was stirred by use of a microwave chemical reactor at 300 W at 100° C. for 10 minutes. The solvent was evaporated off under reduced pressure, and purification by silica gel column chromatography (chloroform/methanol=1/0 to 5/1) was performed to give N-cyclopropylsulfuric diamide (Compound FZ) (306 mg, yield: 43%).

ESIMS m/z: 137 (M+H)$^+$; $^1$H-NMR (270 MHz, CDCl$_3$, δ): 0.69-0.82 (m, 4H), 2.52-2.68 (m, 1H), 4.65 (br s, 2H), 4.83 (br s, 1H).

REFERENCE EXAMPLE 9-27

Ethanesulfonamide (Compound GA)

According to Reference Example 9-19, by use of ethanesulfonyl chloride (300 mg, 2.3 mmol) and a 25% aqueous ammonia solution (2 mL), the mixture was stirred and reacted at room temperature for 8 hours. Then, purification by silica gel column chromatography (chloroform/methanol=100/1 to 3/1) was performed to give ethanesulfonamide (Compound GA) (80 mg, yield: 31%).

ESIMS m/z: 110 (M+H)$^+$.

REFERENCE EXAMPLE 9-28

Butane-1-sulfonamide (Compound GB)

According to Reference Example 9-19, by use of butane-1-sulfonyl chloride (300 mg, 1.9 mmol) and a 25% aqueous ammonia solution (2 mL), the mixture was stirred and reacted at room temperature for 8 hours. Then, purification by silica gel column chromatography (chloroform/methanol=100/0 to 3/1) was performed to give butane-1-sulfonamide (Compound GB) (198 mg, yield: 76%).

ESIMS m/z: 138 (M+H)$^+$.

REFERENCE EXAMPLE 9-29

2,2,2-trifluoroethanesulfonamide (Compound GC)

Tetrahydrofuran (6 mL) was added to tert-butylamine (220 mg, 3.0 mmol), and 2,2,2-trifluoroethanesulfonyl chloride (300 mg, 1.6 mmol) was slowly added dropwise thereto. The mixture was stirred at room temperature for 30 minutes, and the solvent was evaporated off under reduced pressure. To the residue, trifluoroacetic acid (3.3 mL) was added and the mixture was stirred at room temperature for 15 hours. The solvent was evaporated off under reduced pressure, and purification by silica gel column chromatography (chloroform/methanol=100/0 to 5/1) was performed to give 2,2,2-trifluoroethanesulfonamide (Compound GC) (66 mg, yield: 25%).

ESIMS m/z: 164 (M+H)$^+$; $^1$H-NMR (270 MHz, CDCl$_3$, δ): 3.93 (q, J=8.8 Hz, 2H), 5.00 (br s, 2H).

REFERENCE EXAMPLE 9-30

N-propylsulfuric diamide (Compound GD)

According to Reference Example 9-26, tetrahydrofuran (3 mL) and propylamine (0.34 mL, 4.2 mmol) were added to sulfamide (400 mg, 4.2 mmol) and the mixture was stirred by use of a microwave chemical reactor at 300 W at 100° C. for 10 minutes. The solvent was evaporated off under reduced pressure, and purification by silica gel column chromatography (chloroform/methanol=1/0 to 10/1) was performed to give N-propylsulfuric diamide (Compound GD) (191 mg, yield: 33%).

ESIMS m/z: 139 (M+H)$^+$; $^1$H-NMR (270 MHz, CDCl$_3$, δ): 0.97 (t, J=7.3 Hz, 3H), 1.54-1.70 (m, 2H), 3.10 (td, J=6.3, 7.3 Hz, 2H), 4.46 (br s, 1H), 4.65 (br s, 2H).

REFERENCE EXAMPLE 9-31

N-ethylsulfuric diamide (Compound GE)

According to Reference Example 9-26, tetrahydrofuran (1 mL) and ethylamine (a 2 mol/L solution in tetrahydrofuran) (2.1 mL, 4.2 mmol) were added to sulfamide (400 mg, 4.2 mmol) and the mixture was stirred by use of a microwave chemical reactor at 300 W at 100° C. for 10 minutes. The solvent was evaporated off under reduced pressure, and purification by silica gel column chromatography (chloroform/methanol=1/0 to 10/1) was performed to give N-ethylsulfuric diamide (Compound GE) (230 mg, yield: 45%).

ESIMS m/z: 125 (M+H)$^+$.

REFERENCE EXAMPLE 9-32

N-(2-methoxyethyl) sulfuric diamide (Compound GF)

According to Reference Example 9-26, tetrahydrofuran (3 mL) and 2-methoxyethylamine (0.36 mL, 4.2 mmol) were added to sulfamide (400 mg, 4.2 mmol) and the mixture was stirred by use of a microwave chemical reactor at 300 W at 100° C. for 10 minutes. The solvent was evaporated off under reduced pressure, and purification by silica gel column chromatography (hexane/ethyl acetate=1/0 to 1/4) was performed to give N-(2-methoxyethyl)sulfuric diamide (Compound GF) (236 mg, yield: 37%).

ESIMS m/z: 155 (M+H)$^+$; $^1$H-NMR (270 MHz, CDCl$_3$, δ): 3.30-3.37 (m, 2H), 3.39 (s, 3H), 3.52-3.58 (m, 2H), 4.59 (br s, 2H), 4.68 (br s, 1H).

REFERENCE EXAMPLE 9-33

N-(3-methoxypropyl)sulfuric diamide (Compound GG)

According to Reference Example 9-26, tetrahydrofuran (3 mL) and 3-methoxypropylamine (0.42 mL, 4.2 mmol) were added to sulfamide (400 mg, 4.2 mmol) and the mixture was stirred by use of a microwave chemical reactor at 300 W at 100° C. for 10 minutes. The solvent was evaporated off under reduced pressure, and purification by silica gel column chromatography (hexane/ethyl acetate=1/0 to 1/1) was performed to give N-(3-methoxypropyl)sulfuric diamide (Compound GG) (165 mg, yield: 24%).

ESIMS m/z: 169 (M+H)$^+$; $^1$H-NMR (270 MHz, CDCl$_3$, δ): 1.87 (dt, J=5.6, 12.1 Hz, 2H), 3.28 (dd, J=5.6, 12.1 Hz, 2H), 3.34 (s, 3H), 3.52 (t, J=5.6 Hz, 2H), 4.49 (br s, 2H), 4.97 (br s, 1H).

REFERENCE EXAMPLE 9-34

N-(2-ethoxyethyl) sulfuric diamide (Compound GH)

According to Reference Example 9-26, tetrahydrofuran (3 mL) and 2-ethoxyethylamine (0.37 mL, 4.2 mmol) were added to sulfamide (400 mg, 4.2 mmol) and the mixture was stirred by use of a microwave chemical reactor at 300 W at 100° C. for 10 minutes. The solvent was evaporated off under reduced pressure, and purification by silica gel column chromatography (hexane/ethyl acetate=1/0 to 1/3) was performed to give N-(2-ethoxyethyl)sulfuric diamide (Compound GH) (296 mg, yield: 42%).
ESIMS m/z: 169 (M+H)$^+$; $^1$H-NMR (270 MHz, CDCl$_3$, δ): 1.21 (t, J=7.0 Hz, 3H), 3.33 (td, J=4.9, 5.8 Hz, 2H), 3.53 (q, J=7.1 Hz, 2H), 3.59 (t, J=4.9 Hz, 2H), 4.66 (br s, 2H), 4.76 (br s, 1H).

REFERENCE EXAMPLE 9-35 tert-butyl 4-sulfamoylphenethylcarbamate (Compound GI)

Dichloromethane (4 mL) and di-tert-butylcarboxylic acid (218 mg, 1.0 mmol) were added to 4-(2-aminoethyl)benzenesulfonamide (200 mg, 1.0 mmol) and the mixture was stirred at room temperature for 1.5 hours. Ethyl acetate (100 mL) was added to the reaction mixture and the solid was collected by filtration. Thus, tert-butyl 4-sulfamoylphenethylcarbamate (Compound GI) (160 mg, yield: 53%) was obtained.
ESIMS m/z: 301 (M+H)$^+$; $^1$H-NMR (270 MHz, CDCl$_3$, δ): 1.36 (s, 9H), 2.76 (t, J=7.2 Hz, 2H), 3.16 (q, J=7.2 Hz, 2H), 6.92 (br s, 1H), 7.28 (br s, 2H), 7.37 (d, J=8.1 Hz, 2H), 7.73 (d, J=8.1 Hz, 2H).

REFERENCE EXAMPLE 9-36

N-[2-(tert-butoxycarbonylamino)ethyl]-sulfuric diamide (Compound GJ)

According to Reference Example 9-26, tetrahydrofuran (3 mL) and N—BOC-ethylenediamine (0.66 mL, 4.2 mmol) were added to sulfamide (400 mg, 4.2 mmol) and the mixture was stirred by use of a microwave chemical reactor at 300 W at 100° C. for 10 minutes. The solvent was evaporated off under reduced pressure, and purification by silica gel column chromatography (chloroform/methanol=1/0 to 9/1) was performed to give N-[2-(tert-butoxycarbonylamino)ethyl]-sulfuric diamide (Compound GJ) (500 mg, yield: 50%).
ESIMS m/z: 240 (M+H)$^+$; $^1$H-NMR (270 MHz, CDCl$_3$, δ): 1.45 (s, 9H), 3.16-3.46 (m, 4H), 4.89 (br s, 2H), 4.97 (br s, 1H), 5.10 (br s, 1H).

REFERENCE EXAMPLE 9-37

N-(3,3-diethoxypropyl)-sulfuric diamide (Compound GK)

According to Reference Example 9-26, Compound GK (410 mg, yield: 44%) was obtained from sulfamide (400 mg, 4.16 mmol) and 3,3-diethoxypropan-1-amine (0.673 mL, 4.16 mmol).
ESIMS m/z: 227 (M+H)$^+$.

REFERENCE EXAMPLE 9-38

N-propargyl-sulfuric diamide (Compound GL)

According to Reference Example 9-26, Compound GL (103 mg, yield: 18%) was obtained from sulfamide (400 mg, 4.16 mmol) and propargylamine (0.285 mL, 4.16 mmol).
ESIMS m/z: 135 (M+H)$^+$.

REFERENCE EXAMPLE 9-39

Benzyl 4-sulfamoylbutanoate (Compound GM)

4-Sulfamoylbutanoic acid (1.00 g, 5.98 mmol) was dissolved in DMF (6.00 mL). To this, cesium carbonate (994 mg, 3.05 mmol) and benzyl bromide (0.711 mL, 5.98 mmol) were added and the mixture was stirred at room temperature for 18 hours. The reaction was stopped by addition of water, and the organic layer was extracted with dichloromethane, washed with a saturated aqueous sodium bicarbonate solution and dried over anhydrous magnesium sulfate. The solvent was evaporated off under reduced pressure, and the residue was subjected to slurry purification using diethyl ether, to give Compound GM (940 mg, yield: 61%).
ESIMS m/z: 258 (M+H)$^+$.

REFERENCE EXAMPLE 9-40

N-ethyl-N-methyl-sulfuric diamide (Compound GN)

According to Reference Example 9-26, Compound GN (345 mg, yield: 73%) was obtained from sulfamide (300 mg, 3.12 mmol) and N-methylpropan-1-amine (0.320 mL, 3.12 mmol).
ESIMS m/z: 153 (M+H)$^+$.

REFERENCE EXAMPLE 9-41

N,N-diethyl-sulfuric diamide (Compound GO)

According to Reference Example 9-26, Compound GO (260 mg, yield: 46%) was obtained from sulfamide (300 mg, 3.12 mmol) and dipropylamine (0.428 mL, 3.12 mmol).
ESIMS m/z: 181 (M+H)$^+$.

REFERENCE EXAMPLE 9-42

2-methoxyethanesulfonamide (Compound GP)

Sodium sulfite (1.47 g, 11.7 mmol) was dissolved in water (8.00 mL). To this, 1-bromo-2-methoxyethane (1.00 mL, 10.6 mmol) was added and the mixture was stirred with heat at 100° C. for 24 hours. The solvent in the reaction mixture was evaporated off under reduced pressure, and the residue was subjected to slurry purification using diisopropyl ether. To the obtained solid, thionyl chloride (7.80 mL, 106 mmol) and DMF (0.036 mL, 0.53 mmol) were added and the mixture was stirred with heat at 100° C. for 6 hours. The solvent in the reaction mixture was evaporated off under reduced pressure and chloroform was added to the residue. The insoluble matter was filtered off and the solvent in the filtrate was evaporated off under reduced pressure. An aqueous ammonia solution (3.00 mL) was added to the resulting oily compound and the mixture was stirred at room temperature for 14 hours. The solvent in the reaction mixture was evaporated off under reduced pressure, and purification by silica gel column chromatography (hexane/ethyl acetate=1/0 to 1/2) was performed to give Compound GP (245 mg, yield: 16%).
ESIMS m/z: 140 (M+H)$^+$.

REFERENCE EXAMPLE 9-43

3-methoxypropane-1-sulfonamide (Compound GQ)

Sodium sulfite (2.16 g, 17.2 mmol) was dissolved in water (33.0 mL). To this, 1-bromo-2-methoxypropane (2.5 g, 16.3 mmol) was added and the mixture was stirred with heat at 105° C. for 24 hours. The solvent in the reaction mixture was evaporated off under reduced pressure, and the residue was subjected to slurry purification using diisopropyl ether. To the obtained solid, thionyl chloride (12.0 mL, 163 mmol) and DMF (0.067 mL, 0.817 mmol) were added and the mixture was stirred with heat at 100° C. for 6 hours. The solvent in the reaction mixture was evaporated off under reduced pressure and chloroform was added to the residue. The insoluble matter was filtered off and the solvent in the filtrate was evaporated off under reduced pressure. An aqueous ammonia solution (18.7 mL) was added to the resulting oily compound and the mixture was stirred at room temperature for 18 hours. The solvent in the reaction mixture was evaporated off under reduced pressure and chloroform was added to the residue. The insoluble matter was filtered off and the solvent in the filtrate was evaporated off under reduced pressure. Thus, compound GQ (2.15 g, yield: 88%) was obtained.

ESIMS m/z: 154 (M+H)$^+$.

REFERENCE EXAMPLE 9-44

3-chloropropane-1-sulfonamide (Compound GR)

Sodium sulfite (4.60 g, 36.5 mmol) was dissolved in water (24.0 mL). To this, 3-bromo-propan-1-ol (3.00 mL, 33.2 mmol) was added and the mixture was stirred with heat at 105° C. for 24 hours. The solvent in the reaction mixture was evaporated off under reduced pressure, and the residue was subjected to slurry purification using diisopropyl ether. To the obtained solid, thionyl chloride (21.2 mL, 290 mmol) and DMF (0.141 mL, 1.81 mmol) were added and the mixture was stirred with heat at 100° C. for 6 hours. The solvent in the reaction mixture was evaporated off under reduced pressure and chloroform was added to the residue. The insoluble matter was filtered off and the solvent in the filtrate was evaporated off under reduced pressure. An aqueous ammonia solution (5.00 mL) was added to the resulting oily compound and the mixture was stirred at room temperature for 16 hours. The solvent in the reaction mixture was evaporated off under reduced pressure, and purification by silica gel column chromatography (hexane/ethyl acetate=1/0 to 1/2) was performed to give Compound GR (25.7 mg, yield: 0.5%).

ESIMS m/z: 158 (M+H)$^+$.

REFERENCE EXAMPLE 9-45

Cyclopropyl methanesulfonamide (Compound GS)

Step 1

Sodium sulfite (1.43 g, 11.3 mmol) was dissolved in water (8.00 mL). To this, (bromomethyl)cyclopropane (1.00 mL, 10.3 mmol) was added and the mixture was stirred with heat at 100° C. for 24 hours. The solvent in the reaction mixture was evaporated off under reduced pressure, and the residue was subjected to slurry purification using diisopropyl ether, to give sodium cyclopropanemethanesulfonate (2.10 g, yield: 99%).

Step 2

Phosphorus pentachloride (791 mg, 3.8 mmol) and 1,2-dichloroethane (1.50 mL) were added to sodium cyclopropanemethanesulfonate (300 mg, 1.90 mmol) obtained in Step 1 and the mixture was stirred with heat at 70° C. for 3 hours. After the reaction mixture was neutralized with an aqueous sodium bicarbonate solution, the organic layer was extracted with ethyl acetate, washed with brine and dried over anhydrous magnesium sulfate. The solvent was evaporated off under reduced pressure, an aqueous ammonia solution (2.00 mL) was added to the residue, and the mixture was stirred at room temperature for 1 hour. The solvent in the reaction mixture was evaporated off under reduced pressure, and purification by silica gel column chromatography (hexane/ethyl acetate=1/0 to 1/2) was performed to give Compound GS (44.6 mg, yield: 17%).

ESIMS m/z: 136 (M+H)$^+$.

REFERENCE EXAMPLE 9-46

2-propene-1-sulfonamide (Compound GT)

Step 1

Sodium sulfite (1.60 g, 12.7 mmol) was dissolved in water (8.00 mL). To this, allyl bromide (1.00 mL, 11.6 mmol) was added and the mixture was stirred with heat at 70° C. for 24 hours. The solvent in the reaction mixture was evaporated off under reduced pressure, and the residue was subjected to slurry purification using diisopropyl ether, to give sodium allylsulfonate (2.77 g, yield: 99%).

Step 2

Phosphorus pentachloride (3.6 g, 17.3 mmol), 1,2-dichloroethane (10.0 mL) and dichloromethane (4.00 mL) were added to sodium allylsulfonate (830 mg, 5.76 mmol) obtained in Step 1 and the mixture was stirred with heat at 80° C. for 4 hours. By addition of an aqueous sodium bicarbonate solution to neutralize the reaction mixture, the reaction was stopped. Then, extraction with ethyl acetate was performed, followed by washing with brine and drying over anhydrous magnesium sulfate. The solvent was evaporated off under reduced pressure, an aqueous ammonia solution (3.00 mL) was added to the residue, and the mixture was stirred at room temperature for 2 hours. The solvent in the reaction mixture was evaporated off under reduced pressure, and purification by silica gel column chromatography (hexane/ethyl acetate=1/0 to 1/2) was performed to give Compound GT (62.6 mg, yield: 9.0%).

ESIMS m/z: 122 (M+H)$^+$.

REFERENCE EXAMPLE 10-1

6-methoxy-2-[2,2,2-trifluoro-1-(pyridin-3-yl) ethoxy]-pyridin-3-amine (Compound HA)

Step 1

According to Example 90, by use of 60% sodium hydride (in oil) (85.0 mg, 2.12 mmol), tetrahydrofuran (8.0 mL), Compound CB (244 mg, 1.38 mmol) and 2-chloro-6-methoxy-3-nitropyridine (200 mg, 1.06 mmol), the mixture was stirred and reacted at room temperature for 3 hours. Then, purification by preparative thin-layer chromatography (hexane/ethyl acetate=1/1) was performed to give 6-methoxy-3-nitro-2-[2,2,2-trifluoro-1-(pyridin-3-yl)-ethoxy]pyridine (320 mg, yield: 92%).

ESIMS m/z: 330 (M+H)$^+$; $^1$H-NMR (270 MHz, CDCl$_3$, δ): 3.92 (s, 3H), 6.48 (d, J=8.6 Hz, 1H), 6.61 (q, J=6.4 Hz, 1H), 7.39 (dd, J=5.0, 7.9 Hz, 1H), 8.02 (d, J=7.9 Hz, 1H), 8.37 (d, J=8.6 Hz, 1H), 8.68 (dd, J=1.7, 5.0 Hz, 1H), 8.81 (d, J=2.0 Hz, 1H).

Step 2

6-Methoxy-3-nitro-2-[2,2,2-trifluoro-1-(pyridin-3-yl)-ethoxy]pyridine (243 mg, 0.738 mmol) was dissolved in acetic acid (3.6 mL) and water (3.6 mL). To this, reduced iron (124 mg, 2.21 mmol) was added under a nitrogen atmosphere at room temperature and the mixture was stirred for 1.7 hours. After water and brine were added to the reaction mixture, extraction with ethyl acetate was performed, followed by washing with saturated sodium bicarbonate and brine, and drying over anhydrous sodium sulfate. The solvent was evaporated off under reduced pressure, and the residue was purified by preparative thin-layer chromatography (chloroform/methanol=30/1) to give Compound HA (89.6 mg, yield: 41%).

ESIMS m/z: 300 (M+H)$^+$; $^1$H-NMR (300 MHz, CDCl$_3$, δ): 3.60 (br s, 2H), 3.70 (s, 3H), 6.26 (d, J=8.1 Hz, 1H), 6.48 (q, J=6.8 Hz, 1H), 7.02 (d, J=8.4 Hz, 1H), 7.34 (dd, J=4.9, 7.9 Hz, 1H), 7.89 (d, J=7.7 Hz, 1H), 8.64 (dd, J=1.5, 4.8 Hz, 1H), 8.82 (d, J=1.5 Hz, 1H).

REFERENCE EXAMPLE 10-2

2-chloro-3-[2,2,2-trifluoro-1-(pyridin-3-yl)ethoxy]-pyrido[3,2-b]pyrazine (Compound HB)

Step 1

Ytterbium(III) triflate [Yb(OTf)$_3$] (853 mg, 1.38 mmol) and diethyl malonate (7.5 mL, 55.0 mmol) were added to pyridine-2,3-diamine (3.00 g, 27.5 mmol) and the mixture was stirred at 80° C. for 2 hours. After water was added to the reaction mixture, the resulting solid was collected by filtration, washed with ethanol and dried under reduced pressure. Thus, pyrido[3,2-b]pyrazine-2,3(1H,4H)-dione (3.58 g, yield: 80%) was obtained.

Step 2

Phosphorus oxychloride (5.7 mL, 61 mmol) was added to pyrido[3,2-b]pyrazine-2,3(1H,4H)-dione (2.00 g, 12.3 mmol) and the mixture was stirred under reflux for 2 hours. After the reaction mixture was added to iced water, extraction with ethyl acetate was performed, followed by washing with brine and drying over anhydrous sodium sulfate. The solvent was evaporated off under reduced pressure, and thereby 2,3-dichloropyrido[3,2-b]pyrazine (1.90 g, yield: 77%) was obtained.

Step 3

According to Example 90, by use of 60% sodium hydride (in oil) (60.0 mg, 1.50 mmol), tetrahydrofuran (4.5 mL), Compound CB (146 mg, 0.825 mmol) and 2,3-dichloropyrido[3,2-b]pyrazine (150 mg, 0.750 mmol), the mixture was stirred and reacted at room temperature for 2 hours. Then, purification by preparative thin-layer chromatography (chloroform/methanol=15/1) was performed to give Compound HB (130 mg, yield: 51%).

ESIMS m/z: 343, 341 (M+H)$^+$; $^1$H-NMR (270 MHz, CDCl$_3$, δ): 7.04 (q, J=6.5 Hz, 1H), 7.40 (dd, J=4.8, 8.1"Hz, 1H), 7.64 (dd, J=4.6, 8.3 Hz, 1H), 8.03 (d, J=7.9 Hz, 1H), 8.35 (dd, J=2.0, 8.3 Hz, 1H), 8.69 (dd, J=1.7, 5.0 Hz, 1H), 8.94 (d, J=2.3 Hz, 1H), 9.03 (dd, J=2.0, 4.3 Hz, 1H).

REFERENCE EXAMPLE 10-3

2,3-dichloro-6,7-dimethylquinoxaline (Compound HC)

Step 1

Diethyl oxalate (4.0 mL, 29 mmol) and ytterbium trifluoromethanesulfonate (226 mg, 0.37 mmol) were added to 4,5-dimethyl-1,2-phenylenediamine (1.0 g, 7.3 mmol) and the mixture was stirred at 80° C. for 2 hours. After water was added to the reaction mixture, the precipitate was washed with ethanol. Thus, 6,7-dimethylquinoxaline-2,3(1H,4H)-dione (1.2 g, yield: 87%) was obtained.

ESIMS m/z: 191 (M+H)$^+$.

Step 2

Phosphorus oxychloride (2.9 mL, 31 mmol) was added to 6,7-dimethylquinoxaline-2,3(1H,4H)-dione (1.2 g, 6.2 mmol) obtained in Step 1 of Reference Example 10-3 and the mixture was stirred at 110° C. for 3 hours. After the reaction mixture was added to iced water, extraction with ethyl acetate was performed, followed by washing with brine and drying over anhydrous magnesium sulfate. The solvent was evaporated off under reduced pressure, and purification by silica gel column chromatography (chloroform/methanol=1/0 to 33/1) was performed to give Compound HC (840 mg, yield: 76%).

ESIMS m/z: 228 (M+H)$^+$; $^1$H-NMR (270 MHz, CDCl$_3$, δ): 2.49 (s, 6H), 7.77 (s, 2H).

REFERENCE EXAMPLE 10-4

2,3-dichlorobenzo[g]quinoxaline (Compound HD)

Step 1

According to Step 1 of Reference Example 10-3, diethyl oxalate (3.4 mL, 25 mmol) and ytterbium trifluoromethanesulfonate (196 mg, 0.32 mmol) were added to naphthalene-2,3-diamine (1.0 g, 6.3 mmol) and the mixture was stirred at 80° C. for 2 hours. After water was added to the reaction mixture, the precipitate was washed with ethanol. Thus, benzo[g]quinoxaline-2,3(1H,4H)-dione (1.4 g, yield: 99%) was obtained.

ESIMS m/z: 213 (M+H)

Step 2

According to Step 2 of Reference Example 10-3, phosphorus oxychloride (3.0 mL, 32 mmol) was added to benzo[g]quinoxaline-2,3(1H,4H)-dione (1.3 g, 6.3 mmol) obtained in Step 1 of Reference Example 10-4 and the mixture was stirred at 110° C. for 3 hours. After the reaction mixture was added to iced water, extraction with ethyl acetate was performed, followed by washing with brine and drying over anhydrous magnesium sulfate. The solvent was evaporated off under reduced pressure, and purification by silica gel column chromatography (chloroform/methanol=1/0 to 33/1) was performed to give 2,3-dichlorobenzo[g]quinoxaline (Compound HD) (920 mg, yield: 59%).

ESIMS m/z: 250 (M+H)$^+$; $^1$H-NMR (270 MHz, CDCl$_3$, δ): 7.73 (dd, J=3.3, 6.6 Hz, 2H), 8.28 (dd, J=3.3, 6.6 Hz, 2H), 8.76 (s, 2H).

REFERENCE EXAMPLE 10-5

2,3-dichloro-5-methylquinoxaline (Compound HE)

Step 1

According to Step 1 of Reference Example 10-3, diethyl oxalate (4.5 mL, 33 mmol) and ytterbium trifluoromethanesulfonate (254 mg, 0.41 mmol) were added to 2,3-diaminotoluene (1.0 g, 8.2 mmol) and the mixture was stirred at 80° C. for 2 hours. After water was added to the reaction mixture, the precipitate was washed with ethanol. Thus, 5-methylquinoxaline-2,3(1H,4H)-dione (1.1 g, yield: 78%) was obtained.

ESIMS m/z: 177 (M+H)$^+$.

Step 2

According to Step 2 of Reference Example 10-3, phosphorus oxychloride (3.0 mL, 32 mmol) was added to 5-methylquinoxaline-2,3(1H,4H)-dione (1.1 g, 6.4 mmol) obtained in Step 1 of Reference Example 10-5 and the mixture was stirred at 110° C. for 5 hours. After the reaction mixture was added to iced water, extraction with ethyl acetate was performed, followed by washing with brine and drying over anhydrous magnesium sulfate. The solvent was evaporated off under reduced pressure, and purification by silica gel column chromatography (chloroform/methanol=1/0 to 33/1) was performed to give Compound HE (830 mg, yield: 61%).

ESIMS m/z: 214 (M+H)$^+$; $^1$H-NMR (270 MHz, CDCl$_3$, δ): 2.76 (s, 3H), 7.60-7.76 (m, 2H), 7.82-7.92 (m, 1H)

REFERENCE EXAMPLE 10-6

2-[2,2,2-trifluoro-1-(pyridin-3-yl)ethoxy]quinolin-3-amine (Compound HF)

Step 1

2-Aminobenzaldehyde (1.75 g, 14.5 mmol) was dissolved in xylene (87.5 mL). To this, ethyl 2-nitroacetate (6.43 mL, 58.0 mmol) and piperidine (1.58 mL, 16.0 mmol) were added and the mixture was stirred with heat at 150° C. for 1.5 hours and successively stirred with cooling in an ice bath for 0.5 hour. The precipitate was collected by filtration and dried under reduced pressure. Thus, 3-nitroquinolin-2(1H)-one (1.40 g, yield: 51%) was obtained.

ESIMS m/z: 191 (M+H)$^+$.

Step 2

3-Nitroquinolin-2(1H)-one (1.40 g, 7.36 mmol) obtained in Step 1 was dissolved in phosphorus oxychloride (3.50 mL, 36.8 mmol) and the mixture was stirred with heat at 110° C. for 4 hours. The reaction mixture was poured into an ice bath and thereby the reaction was stopped. Then, extraction with ethyl acetate was performed, followed by washing with brine and drying over anhydrous magnesium sulfate. The solvent was evaporated off under reduced pressure, and the residue was purified by silica gel column chromatography (chloroform/methanol=1/0 to 50/1) to give 2-chloro-3-nitroquinoline (1.46 g, yield: 95%).

ESIMS m/z: 209 (M+H)$^+$.

Step 3

According to Example 90, by use of 60% sodium hydride (in oil) (115 mg, 2.88 mmol), tetrahydrofuran (12.0 mL), Compound CB (306 mg, 1.73 mmol) and 2-chloro-3-nitroquinoline (300 mg, 1.44 mmol) obtained in Step 2, the mixture was stirred and reacted at room temperature for 1 hour. The reaction was stopped by addition of water, and the organic layer was extracted with ethyl acetate, washed with brine and dried over anhydrous magnesium sulfate. The solvent was evaporated off under reduced pressure, and the residue was purified by silica gel column chromatography (hexane/ethyl acetate=1/0 to 1/1) to give 3-nitro-2-[2,2,2-trifluoro-1-(pyridin-3-yl)ethoxy]quinoline (375 mg, yield: 75%).

ESIMS m/z: 350 (M+H)$^+$.

Step 4

3-Nitro-2-[2,2,2-trifluoro-1-(pyridin-3-yl)ethoxy]quinoline (253 mg, 0.720 mmol) obtained in Step 3 was dissolved in ethanol (12.7 mL). To this, tin chloride dihydrate (817 mg, 3.62 mmol) was added and the mixture was stirred at 90° C. for 1 hour. By addition of an aqueous sodium bicarbonate solution to neutralize the reaction mixture, the reaction was stopped. Then, extraction with ethyl acetate was performed, followed by washing with brine and drying over anhydrous magnesium sulfate. The solvent was evaporated off under reduced pressure, and the residue was purified by silica gel column chromatography (hexane/ethyl acetate=1/0 to 3/1) to give Compound HF (182 mg, yield: 79%).

ESIMS m/z: 320 (M+H)$^+$.

REFERENCE EXAMPLE 10-7

2,3-dichloropyrido[3,4-b]pyrazine (Compound HG)

Step 1

Pyridine-3,4-diamine (2.00 g, 18.3 mmol) and oxalic acid (1.96 g, 20.2 mmol) were dissolved in an aqueous hydrochloric acid solution (2.00 M, 20.0 mL) and the mixture was stirred with heat at 100° C. for 24 hours. After the reaction mixture was cooled to room temperature, the precipitate was collected by filtration and dried under reduced pressure. Thus, pyrido[3,4-b]pyrazine-2,3(1H,4H)-dione (3.20 g, 74%) was obtained.

ESIMS m/z: 237 (M+H)$^+$.

Step 2

Pyrido[3,4-b]pyrazine-2,3(1H,4H)-dione (3.00 g, 18.4 mmol) obtained in Step 1 was dissolved in phosphorus oxychloride (8.50 mL, 91.9 mmol) and the mixture was stirred with heat at 110° C. for 24 hours. By addition of an aqueous sodium bicarbonate solution to neutralize the reaction mixture, the reaction was stopped. Then, extraction with ethyl acetate was performed, followed by washing with brine and drying over anhydrous magnesium sulfate. The solvent was evaporated off under reduced pressure, and the residue was purified by silica gel column chromatography (chloroform/methanol=1/0 to 33/1). Further, slurry purification was performed using diisopropyl ether, to give Compound HG (1.03 g, 29%).

ESIMS m/z: 201 (M+H)$^+$.

FORMULATION EXAMPLE 1

Tablets having the following composition are prepared in a usual manner. Compound 10 (40 g), 286.8 g of lactose and 60 g of potato starch are mixed, and to this mixture, 120 g of a 10% aqueous hydroxypropylcellulose solution is added. This mixture is kneaded, granulated, dried, and fine-granulated in a usual manner to prepare granules for tableting. 1.2 g of magnesium stearate is mixed with the granules, and tableting is performed by use of a tableting machine (Type RT-15, manufactured by Kikusui) having a pestle 8 mm in diameter to give tablets (containing 20 mg of the active ingredient per tablet).

| Formula | Compound 10 | 20 mg |
|---|---|---|
| | Lactose | 143.4 mg |
| | Potato starch | 30 mg |
| | Hydroxypropylcellulose | 6 mg |
| | Magnesium stearate | 0.6 mg |
| | | 200 mg |

FORMULATION EXAMPLE 2

Injections having the following composition are prepared in a usual manner. Compound 10 (1 g) and D-mannitol (5 g) are mixed with distilled water for injection. By addition of hydrochloric acid and an aqueous sodium hydroxide solution, the pH is adjusted to 6, and then the total volume is made up to 1,000 mL with distilled water for injection. 2 mL of the mixture is aseptically packed into each glass vial, and thus injections (containing 2 mg of the active ingredient per vial) are obtained.

| Formula | Compound 10 | 2 mg |
|---|---|---|
| | D-mannitol | 10 mg |
| | Hydrochloric acid | q.s. |
| | Aqueous sodium hydroxide solution | q.s. |
| | Distilled water for injection | q.s. |
| | | 2.00 ml |

INDUSTRIAL APPLICABILITY

The present invention provides a kynurenine production inhibitor, a nitrogen-containing heterocyclic compound or a pharmaceutically acceptable salt thereof having an inhibitory effect on kynurenine production, and the like.

The invention claimed is:
1. A nitrogen-containing heterocyclic compound represented by formula (II):

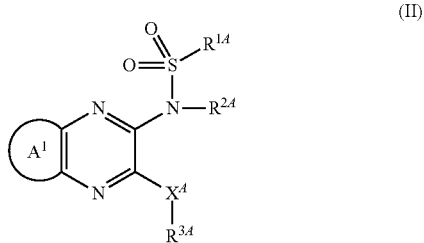

(II)

{wherein ring $A^1$ represents a benzene ring, a naphthalene ring or a pyridine ring (wherein the ring $A^1$ may have a substituent(s), the number of which is from 1 to the substitutable number, and the substituent(s) may be the same or different and each is halogen, optionally substituted lower alkyl or optionally substituted lower alkoxy), $X^A$ represents formula (IV):

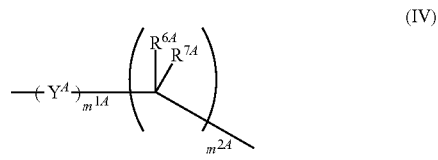

(IV)

[wherein $m^{1A}$ and $m^{2A}$ may be the same or different and each represent an integer of 0 or 1, $Y^A$ represents an oxygen atom, —S(O)$m^{3A}$- (wherein $m^{3A}$ represents an integer from 0 to 2) or —NR$^{8A}$— (wherein R$^{8A}$ represents a hydrogen atom or optionally substituted lower alkyl), and R$^{6A}$ and R$^{7A}$ may be the same or different and each represent a hydrogen atom, halogen, cyano, carboxy, optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{12A}$R$^{13A}$ (wherein R$^{12A}$ and R$^{13A}$ may be the same or different and each represent a hydrogen atom or optionally substituted lower alkyl, or R$^{12A}$ and R$^{13A}$ are combined together with the adjacent nitrogen atom to form an optionally substituted nitrogen-containing heterocyclic group)], R$^{1A}$ represents optionally substituted lower alkyl, optionally substituted lower alkenyl, optionally substituted lower alkynyl, or —NR$^{24A}$R$^{25A}$ (wherein R$^{24A}$ and R$^{25A}$ may be the same or different and each represent a hydrogen atom, optionally substituted lower alkyl, optionally substituted lower alkenyl, optionally substituted lower alkynyl or optionally substituted cycloalkyl), R$^{2A}$ represents a hydrogen atom or optionally substituted lower alkyl, or R$^{1A}$ and R$^{2A}$ are combined together with the adjacent sulfur atom and nitrogen atom to form an optionally substituted sulfur-containing and nitrogen-containing heterocyclic group, and R$^{3A}$ represents optionally substituted lower alkyl, optionally substituted cycloalkyl, an optionally substituted heterocyclic group, optionally substituted lower alkanoyl, optionally substituted lower alkoxycarbonyl or —CONR$^{28A}$R$^{29A}$ (wherein R$^{28A}$ and R$^{29A}$ may be the same or different and each represent a hydrogen atom or optionally substituted lower alkyl, or R$^{28A}$ and R$^{29A}$ are combined together with the adjacent nitrogen atom to form an optionally substituted nitrogen-containing heterocyclic group)}, or a pharmaceutically acceptable salt thereof.

2. The nitrogen-containing heterocyclic compound or a pharmaceutically acceptable salt thereof according to claim 1, wherein R$^{1A}$ is optionally substituted lower alkyl, optionally substituted lower alkenyl, optionally substituted lower alkynyl or —NR$^{24AA}$R$^{25AA}$ (wherein R$^{24AA}$ and R$^{25AA}$ may be the same or different and each represent a hydrogen atom, optionally substituted lower alkyl, optionally substituted lower alkenyl or optionally substituted lower alkynyl).

3. The nitrogen-containing heterocyclic compound or a pharmaceutically acceptable salt thereof according to claim 1, wherein ring $A^1$ is a benzene ring or a pyridine ring.

4. The nitrogen-containing heterocyclic compound or a pharmaceutically acceptable salt thereof according to claim 3, wherein $m^{2A}$ is 1.

5. The nitrogen-containing heterocyclic compound or a pharmaceutically acceptable salt thereof according to claim 4, wherein R$^{7A}$ is a hydrogen atom.

6. The nitrogen-containing heterocyclic compound or a pharmaceutically acceptable salt thereof according to claim 5, wherein R$^{6A}$ is halogen, cyano, carboxy, optionally substituted lower alkyl, optionally substituted cycloalkyl, optionally substituted aryl, an optionally substituted heterocyclic group, optionally substituted lower alkanoyl, optionally substituted lower alkoxycarbonyl or —CONR$^{12A}$R$^{13A}$ (wherein R$^{12A}$ and R$^{13A}$ have the same meanings as defined above, respectively).

7. The nitrogen-containing heterocyclic compound or a pharmaceutically acceptable salt thereof according to claim 5, wherein R$^{6A}$ is optionally substituted lower alkyl or an optionally substituted heterocyclic group.

8. The nitrogen-containing heterocyclic compound or a pharmaceutically acceptable salt thereof according to claim 5, wherein R$^{6A}$ is fluorine-substituted lower alkyl.

9. The nitrogen-containing heterocyclic compound or a pharmaceutically acceptable salt thereof according to claim 5, wherein R$^{6A}$ is trifluoromethyl.

10. The nitrogen-containing heterocyclic compound or a pharmaceutically acceptable salt thereof according to any one of claims 1, 2, and 5 to 9, wherein R$^{3A}$ is optionally substituted lower alkyl.

11. The nitrogen-containing heterocyclic compound or a pharmaceutically acceptable salt thereof according to any one of claims 1 or 5, wherein R$^{3A}$ is optionally substituted cycloalkyl, an optionally substituted heterocyclic group, optionally substituted lower alkanoyl, optionally substituted lower alkoxycarbonyl or —CONR$^{28A}$R$^{29A}$ (wherein R$^{28A}$ and R$^{29A}$ have the same meanings as defined above, respectively).

12. The nitrogen-containing heterocyclic compound or a pharmaceutically acceptable salt thereof according to any one of claims 1 or 5, wherein R$^{3A}$ is an optionally substituted heterocyclic group.

13. The nitrogen-containing heterocyclic compound or a pharmaceutically acceptable salt thereof according to any one of claim 1 or 5, wherein R$^{2A}$ is a hydrogen atom.

14. A pharmaceutical composition comprising, as an active ingredient, the nitrogen-containing heterocyclic compound or a pharmaceutically acceptable salt thereof described in any one of claims 1, 3, 4 and 5.

15. A method for inhibiting kynurenine production in a patient, comprising a step of administering to a patient in need thereof an effective amount of the nitrogen-containing heterocyclic compound or a pharmaceutically acceptable salt thereof described in any one of claims 1, 2, and 5 to 9.

16. The nitrogen-containing heterocyclic compound or a pharmaceutically acceptable salt thereof according to claim 3, wherein $m^{2.4}$ is 1, $R^{6.4}$ is optionally substituted lower alkyl, $R^{7.4}$ is a hydrogen atom, $R^{3.4}$ is an optionally substituted heterocyclic group, $R^{2.4}$ is a hydrogen atom, and $R^{1.4}$ is optionally substituted lower alkyl.

17. A pharmaceutical composition comprising, as an active ingredient, the nitrogen-containing heterocyclic compound or a pharmaceutically acceptable salt thereof described in claim 16.

* * * * *